United States Patent [19]
Chen et al.

[11] Patent Number: 6,160,092
[45] Date of Patent: Dec. 12, 2000

[54] CRYSTAL OF THE CORE PORTION OF A SIGNAL TRANSDUCER AND ACTIVATOR OF TRANSCRIPTION (STAT)

[75] Inventors: Xiaomin Chen; Uwe Vinkemeier; Yanxiang Zhao; David Jeruzalmi, all of New York; James E. Darnell, Jr., Larchmont; John Kuriyan, Riverdale, all of N.Y.

[73] Assignee: The Rockefeller University, New York, N.Y.

[21] Appl. No.: 09/087,465

[22] Filed: May 29, 1998

[51] Int. Cl.[7] .............................. C07K 14/00; A23J 1/00
[52] U.S. Cl. ......................... 530/350; 530/418; 530/420
[58] Field of Search ................................. 530/350, 418, 530/421; 702/19; 436/86

[56] References Cited

U.S. PATENT DOCUMENTS 6,030,780   2/2000   Vinkemeier et al. .................. 435/69.1

OTHER PUBLICATIONS

Becker et al. "Three–dimentional structure of the Stat3beta hmodimer bound to DNA" Nature 394, pp. 145–151, Jul. 1998.
Chen et al. "Crystal structure of a tyrosine phosphorelated STAT–1 dimer bound to DNA" Cell 93, 827–839, May 1998.
Abrahams et al., 1996, Acta Cryst, D53:30–42.
Baeuerle et al., 1994, Ann Rev Immunol, 12:141–79.
Bork et al., 1994, J Mol Biol, 242:309–320.
Briscoe et al., 1996, Phil Trans Royal Soc(London) B351:167–71.
Carson, 1991, Ribbons 2.0. J Appl Cryst, 24:958–61.
Cho et al., 1994, Science, 265:346–55.
Collaborative Computational Project, N, 1994, Acta Cryt, D50:760–3.
Darnell, 1997, Proc Natl Acad Sci USA, 94:11767–9.
Darnell, 1997, Science, 277:1630–5.
Esnouf, 1997, J Mol Graphics, 15:133–8.
Friend, 1994, Science, 265:334–5.
Fu, 1992, Cell, 70:323–5.
Fu et al., 1990, Proc Natl Acad Sci USA, 87:8555–9.
Fu et al., 1992, Proc Natl Acad Sci USA, 89:7840–3.
Ghosh et al., 1995, Nature, 373:303–10.
Holm et al., 1993, J Mol Biol, 233:123–38.
Hovath et al., 1995, Genes Dev, 9:984–94.
Ihle et al., 1995, Ann Rev Immunol, 13:369–98.
Jones et al., 1991, Acta Cryst, A47:110–9.
Kawata et al., 1997, Cell, 89:909–16.
Kuriyan et al., 1997, Ann Rev Biophys Biomol Struct, 26:259–88.
La Fortelle et al., 1997, Meth Enzymol, 276:472–94.
Leaman et al., 1996, FASEB J 10:1578–88.
Levy et al, 1990, New Biologist, 2:923–8.
Martinez–Moczygemba et al., 1997, J Biol Chem, 272(32):20070–6.
Merritt et al., 1997, Meth Enzymol, 277:503–24.
Meyer et al., 1997, J Biol Chem, 272:31821–8.
Muller et al., 1995, Nature, 373:311–7.
Nicholls et al, 1991, Proteins: Struct Funct and Genetics 11:281–96.
Otwinowski et al, 1997, Meth Enzymol, 276: 307–26.
Pawson, 1995, Nature, 373:573–80.

(List continued on next page.)

*Primary Examiner*—Nashaat T. Nashed
*Attorney, Agent, or Firm*—Klauber & Jackson

[57] ABSTRACT

The present invention provides a crystal of the core portion of the STAT protein in dimeric form with an 18-mer duplex DNA that contains a binding site for the STAT-dimer. The crystal is of sufficient quality to perform X-ray crystallographic studies. Methods of preparing the crystals are include in the invention. The present invention further discloses the three-dimensional structure of the crystal. The present invention also provides methods of using the structural information in drug discovery and drug development.

10 Claims, 13 Drawing Sheets

(7 of 13 Drawing Sheet(s) Filed in Color)

OTHER PUBLICATIONS

Schindler et al., 1992, Proc Natl Acad Sci USA, 89:7836–9.
Schindler et al., 1995, Immunity, 2:689–97.
Shuai et al., 1994, Cell, 76:821–8.
Shuai et al., 1993, Nature, 366:580–3.
Sicheri et al., 1997, Curr Op Struct Biol, 7:777–85.
Veals et al., 1992, Mol Cell Biol, 12:3315–24.
Vinkemeier et al., 1996, EMBO J, 15:5616–26.
Vinkemeier et al., 1998, Science, 279:1048–52.
Wagner et al., 1990, EMBO J, 9:4477–84.
Waksman et al., 1992, Nature, 358:646–53.
Xu et al., 1996, Science, 273:794–7.
Zhang et al., 1996, Proc Natl Acad Sci USA, 93:15092–6.

Alignment of v-src and STAT-1 SH2 Domains

Experimental MIR electron density map, calculated using SHARP and SOLOMON

Trp 495
Trp 504
Phe 506

CRYSTAL OF THE CORE PORTION OF A SIGNAL TRANSDUCER AND ACTIVATOR OF TRANSCRIPTION (STAT)

GOVERNMENTAL SUPPORT

The research leading to the present invention was supported, at least in part, by NIH Grant Nos. AI32489 and AI34420. Accordingly, the Government may have certain rights in the invention.

FIELD OF THE INVENTION

The present invention relates generally to structural studies of STAT proteins, modified STAT proteins and more particularly the core portion of STAT proteins. Included in the present invention is a crystal of the core portion of the STAT protein in dimeric form with an 18-mer duplex DNA that contains a binding site for the STAT-dimer. Corresponding structural information obtained by X-ray crystallography is also provided. The present invention further relates to methods of using the crystal and related structural information in drug screening assays.

BACKGROUND OF THE INVENTION

It has been established for more than a decade that gene transcription can be initiated within minutes after the activation of cell surface receptors by polypeptide ligands (reviewed in [Levy, D. E. and Darnell, J. E., *New Biologist* 2: 923–928 (1990)] and Darnell, J. E., *Proc. Natl. Acad. Sci.* (USA), 94:11767–11769 (1997)]. One of the most direct pathways of polypeptide stimulated gene activity is the so-called Jak-STAT pathway [Briscoe et al., *Phil. Trans. Royal Soc.* (London) B351: 167–171 (1996); [Darnell, 1997; Ihle et al., *Annu. Rev. Immunol.*, 13:369–398 (1995); Leaman et al., *FASEB J.*, 10:1578–1588 (1996)]. STATs are so named because they serve both as signal transducers in the cytoplasm and activators of transcription in the nucleus. Each STAT molecule contains a Src-homology 2 (SH2) domain, a modular unit that binds specifically to phosphotyrosine [Kuriyan, J. and Cowburn, D., *Annul. Rev. Biophys. Biomol. Struct.* 26:259–288 (1997); Pawson, T., *Nature*, 373:573–580 (1995)]. The STAT SH2 domain acts as a phosphorylation-dependent switch that controls receptor recognition and DNA binding, thus allowing the STATs to couple the activation of cell surface receptors to gene regulation in a direct manner [Darnell, J. E., *Proc. Natl. Acad. Sci.* (USA), 94:11767–11769 (1997)].

In animal cells, activation of the latent cytoplasmic STAT molecule is accomplished either through cell surface receptors for cytokines and their non-covalently associated Jak kinases, or by growth factor receptors with intrinsic tyrosine kinase activity [Ihle et al., *Annu. Rev. Immunol.*, 13:369–398 (1995)]. Binding of the cognate ligand to the cell surface receptor causes the phosphorylation of tyrosines in the cytoplasmic regions of the receptor, thus creating docking sites for the STAT SH2 domain. The consequent recruitment of the STATs to the receptor leads, in turn, to their phosphorylation on tyrosine by the Jak or receptor kinases. The phosphorylated STATs form SH2-mediated dimers and are then translocated to the nucleus, where they bind to DNA and direct specific transcriptional initiation [Darnell, J. E., *Proc. Natl. Acad. Sci.* (USA), 94:11767–11769 (1997)]. STAT-1 and STAT-2 were originally discovered as transcription factors that are activated by interferons α and γ [Fu, X.-Y. et al., *Proc. Natl. Acad. Sci.* (USA), 87:8555–8559 (1990); Fu, X.-Y et al., *Proc. Natl. Acad. Sci.* (USA) 89:7840–7843 (1992); Schindler, C. et al., *Proc. Natl. Acad. Sci.* (USA) 89:7836–7839 (1992); Veals, S. A. et al., *Mol. Cell Biol.*, 12:3315–3324 (1992)]. Seven mammalian STAT proteins have been discovered so far, and over 40 different polypeptides are now known to activate one or more STATs [reviewed in Darnell, J. E., *Proc. Natl. Acad. Sci.* (USA), 94:11767–11769 (1997)].

Several U.S. patents and pending U.S. patent applications describe structural features and functions of STAT proteins including, U.S. Pat. No. 5,716,622, and pending patent applications Ser. Nos: 08/820,754, filed Mar. 19, 1997; 08/951,130 filed Oct. 15, 1997; 09/012,710 filed Jan. 23, 1998, all of which are hearby incorporated by reference in their entireties. However, further efforts at dissecting the STATs into separable domains with distinct functions such as DNA binding have met with limited success. Molecular genetic experiments have, however, implicated specific regions of the protein in specific functions. A single phosphorylation site at Tyr 701 of STAT-1 was identified, and proven to be necessary for STAT activity [Shuai, K. et al., *Nature* 366:580–583 (1993)]. Just upstream from this residue is an SH2 domain, and biochemical experiments indicate that the SH2 domain and the phosphotyrosine in each of two STATs interact in a reciprocal manner to form a dimer [Shuai, K. et al., *Cell* 76:821–828 (1994)]. The potential DNA binding region of the STATs was shown to include residues in the 400–500 region [Horvath, C. M. et al., *Genes Dev.* 9:984–994 (1995); Schindler, U. et al., *Immunity* 2:689–697 (1995)]. However, the architecture and mechanism of this DNA binding region has not been fully elucidated.

Regions of STAT that are upstream from the DNA binding region appear to be involved in protein—protein interactions. An IRF family member, p48, has been shown to interact with a region around Lys 161 in the ISGF3 protein complex [Horvath, C. M. et al., *Mol. Cell. Biol.* 16:6957–6964 (1996); Martinez-Moczygemba, M. et al., *J. Biol. Chem.* 272:20070–20076 (1997)]. Furthermore, CBP interacts with the N-terminal 150 residues [Zhang, J. J. et al., *Proc. Natl. Acad. Sci.* 93:15092–15096 (1996)]. The amino-terminal 130 residues form a separable functional domain (N-Domain) that strengthens interactions between STAT dimers on adjacent DNA binding sites [Vinkemeier, U. et al., *EMBO J.* 15:5616–5626 (1996); Vinkemeier, U. et al., *Science* 279:1048–1052 (1998); Xu, X. et al., *Science* 273:794–797 (1996)].

A deeper understanding of the mechanism of transcriptional activation by the STATs and the role of tyrosine phosphorylation in controlling this activity is impeded greatly by the lack of three-dimensional structural information. Therefore, there is a need to obtain agonists and antagonists that can modulate the effect of STAT proteins during specific gene activation. In particular, there is a need to obtain drugs that will directly interact with the core portion of STAT proteins. Unfortunately, identification of such drugs have heretofore relied on serendipity and/or systematic screening of large numbers of natural and synthetic compounds. A far superior method of drug-screening relies on structure based drug design. In this case, the three dimensional structure of a protein or protein fragment is determined and potential agonists and/or potential antagonists are designed with the aid of computer modeling [Bugg et al., *Scientific American*, Dec. 92–98 (1993); West et al., *TIPS*, 16:67–74 (1995)]. However, heretofore the three-dimensional structure of a STAT protein or fragment thereof has remained unknown, essentially because no such protein crystals had been produced of sufficient quality to allow the required X-ray crystallographic data to be obtained.

Therefore, there is presently a need for obtaining a fragment of the core portion of the STAT protein that can be crystallized to form a crystal with sufficient quality to allow such crystallographic data to be obtained. Further, there is a need for such crystals. Furthermore there is a need for the determination of the three-dimensional structure of such crystals. Finally, there is a need for procedures for related structural based drug design based on such crystallographic data.

The citation of any reference herein should not be construed as an admission that such reference is available as "Prior Art" to the instant application.

SUMMARY OF THE INVENTION

One aspect of the present invention provides a crystal comprising a core portion of a STAT and a duplex DNA, in which the duplex DNA contains a binding site for a dimer of the STAT. In one such embodiment the crystal effectively diffracts X-rays and thereby allows the determination of the atomic coordinates of the core portion of the STAT and the duplex DNA to a resolution of greater than 5.0 Angstroms. In a preferred embodiment of this type the crystal effectively diffracts X-rays for the determination of the atomic coordinates of the core portion of the STAT and the duplex DNA to a resolution of greater than 3.0 Angstroms. In a particular embodiment, the core portion of the STAT contains four tandem structural domains: (I) an α-helical domain consisting of 4 long α-helices at the N-terminus of the core portion of the STAT; (ii) a DNA binding domain which contains an immunoglobulin-type fold, wherein the DNA binding domain is adjacent to the α-helical domain; (iii) a SH2 domain at the C-terminal end of the core portion of the STAT; and (iv) a linking domain that links the DNA binding domain to the SH2 domain. Each of the four domains is fused to the adjacent ones by the formation of a contiguous hydrophobic core. In another particular embodiment of the present invention the crystal of the core portion of a STAT and a duplex DNA has a space group of $C222_i$ with unit cell dimensions of a=76.6, b=148.2, and c=181.1 Å.

In one embodiment the core portion of the STAT is the core portion of STAT-1 comprising the amino acid sequence of SEQ ID NO:2. In another embodiment the core portion of the STAT is the core portion of STAT-2 comprising the amino acid sequence of SEQ ID NO:4. In still another embodiment the core portion of the STAT is the core portion of STAT-3 comprising the amino acid sequence of SEQ ID NO:6. In yet another embodiment the core portion of the STAT is the core portion of STAT-4 comprising the amino acid sequence of SEQ ID NO:8. In still another embodiment the core portion of the STAT is the core portion of STAT-5a comprising the amino acid sequence of SEQ ID NO:10. In yet another embodiment the core portion of the STAT is the core portion of STAT-6 comprising the amino acid sequence of SEQ ID NO:12.

In a particular embodiment of the present invention the duplex DNA is a 15mer. In another embodiment the duplex DNA is a 18mer. In a preferred embodiment of this type one strand of the duplex DNA has the nucleotide sequence of SEQ ID NO:13, and the other strand of the duplex DNA has the nucleotide sequence of SEQ ID NO:14. In still another embodiment the duplex DNA is a 24mer.

The present invention also provides a method of growing the crystals of the present invention. In one such embodiment, the method of making the crystal comprises placing an aliquot of a solution containing the core portion of the STAT and the duplex DNA on a cover slip as a hanging drop above a well containing a reservoir buffer that comprises 100 mM Na acetate, pH 5.0, 100 mM KCl, 20 mM $MgCl_2$, and 3% PEG400. Preferably a preservative e.g., azide, is added. Core portions of all STAT proteins of the present invention complexed with the appropriate DNA duplex may be handled in this manner to prepare such crystal, though one having skill in the art of growing crystals would readily understand that reasonable variations in the conditions may be necessary to optimize the procedure. In one specific embodiment the aliquot of a solution containing the core portion of the STAT-1 and the duplex DNA contains 1 part 0.10 mM protein:DNA complex and 1 part of the reservoir buffer.

The present invention also provides a data set that comprises the coordinates determined from the X-ray crystallographic analysis of the crystals of the present invention. One such data set is included in Table 2, below. The present invention further provides methods of using the data set in a drug screening assay. One such embodiment comprises selecting a potential drug by performing rational drug design with the three-dimensional structure defined by data set, wherein said selecting is performed in conjunction with computer modeling; contacting the potential drug with the STAT or a fragment thereof; and then detecting the binding of the potential drug with the STAT or fragment thereof; wherein a drug is selected that binds to the STAT or fragment thereof. In a particular embodiment the STAT or fragment thereof is labeled. In another embodiment the STAT or fragment thereof is bound to a solid support. For all of the drug screening methods described herein in which X-ray crystallographic determinations are made, such data sets can be employed instead, or in conjunction therewith.

Another aspect of the present invention includes a method of using a crystal of the present invention in a drug screening assay. One such embodiment comprises selecting a potential drug by performing rational drug design with the three-dimensional structure determined for the crystal, wherein said selecting is performed in conjunction with computer modeling; contacting the potential drug with the STAT or a fragment thereof; and detecting the binding of the potential drug with the STAT or fragment thereof; wherein a drug is selected that binds to the STAT or fragment thereof. In a particular embodiment the STAT or fragment thereof is labeled. In another embodiment the STAT or fragment thereof is bound to a solid support. In a preferred embodiment, the method further comprises growing a supplemental crystal containing a protein-drug complex formed between the core portion of the STAT and the duplex DNA and the candidate drug, wherein the crystal effectively diffracts X-rays for the determination of the atomic coordinates of the protein-ligand complex to a resolution of greater than 5.0 Angstroms; determining the three-dimensional structure of the supplemental crystal with molecular replacement analysis; and selecting a drug by performing rational drug design with the three-dimensional structure determined for the supplemental crystal, wherein said selecting is performed in conjunction with computer modeling.

In another embodiment the present invention provides a method for identifying a drug that enhances (e.g., an agonist) or diminishes (e.g., antagonist) the ability of a STAT to induce the expression of a gene operably under the control of a promoter containing a binding site for the STAT. Antagonists could be useful as drugs in the treatment of a variety of disease states, including inflammation, allergy, asthma, and leukemias. Agonists can be used as drugs that are useful in the treatment of anemias, neutropenias, thrombocytopenia, cancer, obesity, viral diseases and growth retardation, or other diseases characterized by an insufficient STAT activity.

One such embodiment comprises selecting a potential drug by performing rational drug design with the three-dimensional structure determined for a crystal of the present invention wherein said selecting is performed in conjunction with computer modeling; detecting the level of expression of a reporter gene contained by a host cell in the presence and absence of the potential drug; wherein the reporter gene is operably linked to a promoter containing a binding site for the STAT protein; wherein the binding of STAT to the binding site induces the expression of the reporter; and comparing the level of expression of the reporter gene in the presence and absence of the potential drug, wherein when the presence of the potential drug results in an increase in the level of expression of the reporter gene the potential drug is identified as a drug that enhances the ability of the STAT to induce the expression of a gene operably under the control of a promoter containing a binding site for the STAT, and wherein when the presence of the potential drug results in a decrease in the level of expression of the reporter gene, the potential drug is identified as a drug that diminishes the ability of the STAT to induce the expression of a gene under the control of a promoter containing a binding site for the STAT.

In a particular embodiment the host cell is a mammalian cell. In a preferred embodiment the method further comprises growing a supplemental crystal containing a protein-drug complex formed between the core portion of the STAT and the duplex DNA and the candidate drug, wherein the crystal effectively diffracts X-rays for the determination of the atomic coordinates of the protein-ligand complex to a resolution of greater than 5.0 Angstroms; determining the three-dimensional structure of the supplemental crystal with molecular replacement analysis; and selecting a drug by performing rational drug design with the three-dimensional structure determined for the supplemental crystal, wherein said selecting is performed in conjunction with computer modeling.

All of the STAT cores and fragments thereof of the present invention can be modified, placed in a fusion of chimeric peptide or protein, or labeled e.g., to have an N-terminal FLAG-tag. In a particular embodiment a DNA binding domain of a STAT can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties. The present invention also includes nucleic acids that encode all of the peptides, fragments including chimeric peptides and fragments of present invention.

The present invention also provides a peptide fragment of a core portion of a STAT that comprises an immunoglobulin-type fold of a DNA binding domain of the STAT. In one such embodiment, the peptide fragment consists of between 160 to 190 amino acid residues. In a preferred embodiment of this type, the fragment has an amino acid sequence corresponding to the sequence of the same number of amino acid residues from a DNA-binding domain of a STAT protein. In one such embodiment the peptide fragment is obtained from STAT-1. In another embodiment the peptide fragment is obtained from STAT-2. In yet another embodiment the peptide fragment is obtained from STAT-3. In still another embodiment the peptide fragment is obtained from STAT-4. In yet another embodiment the peptide fragment is obtained from STAT-5a. In still another embodiment the peptide fragment is obtained from STAT-6. In a more particular embodiment the peptide fragment has an amino acid sequence of SEQ ID NO:18. In another such embodiment the peptide fragment has an amino acid sequence of SEQ ID NO:24. In yet another such embodiment the peptide fragment has an amino acid sequence of SEQ ID NO:26. In still another such embodiment the peptide fragment has an amino acid sequence of SEQ ID NO:28. In yet another such embodiment the peptide fragment has an amino acid sequence of SEQ ID NO:30. In still another such embodiment the peptide fragment has an amino acid sequence of SEQ ID NO:32. In a preferred embodiment the peptide fragment of he STAT is a fragment of STAT-1 having the amino acid sequence of SEQ ID NO:18.

The present invention also provides fragments of the STAT cores that encode the coiled coil portion, (e.g., SEQ ID NO:16 for STAT-1), the linker domain (e.g., SEQ ID NO:20 for STAT-1), and the SH2 domain (e.g., SEQ ID NO:22 for STAT-1) as well as for the DNA binding domain. As is readily apparent from FIGS. 1A–1B, the present invention allows the facile identification of such domains in any STAT.

As mentioned above the present invention further provides chimeric proteins containing a fusion protein that comprises a DNA binding domain of a STAT and a fusion partner; wherein the DNA binding domain of the STAT consists of between 160 to 190 amino acid residues and comprises an immunoglobulin-type fold. In one such embodiment the chimeric protein the DNA binding protein has an amino acid sequence corresponding to the sequence of the same number of amino acid residues from a DNA-binding domain of a STAT protein. In another such embodiment the chimeric protein comprises a fragment of the core portion of STAT-1. In still another such embodiment the chimeric protein comprises a fragment of the core portion of STAT-2. In yet another such embodiment the chimeric protein comprises a fragment of the core portion of STAT-3. In still another such embodiment the chimeric protein comprises a fragment of the core portion of STAT-4. In yet another such embodiment the chimeric protein comprises a fragment of the core portion of STAT-5a. In still another such embodiment the chimeric protein comprises a fragment of the core portion of STAT-6.

These and other aspects of the present invention will be better appreciated by reference to the following drawings and Detailed Description.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1A is a schematic diagram showing the domains of STAT-1 of SEQ ID NO:2.

FIG. 1B shows the sequence alignment of the core regions of human STAT-1–STAT-6 (SEQ ID Nos:2, 4, 6, 8, and 12, respectively). The secondary structure deduced from the crystal structure is indicated with arrows for β strands and rectangles for α-helices. Buried residues that are in the hydrophobic core of the STAT-1 of SEQ ID NO:2 structure are highlighted in grey. A region in the DNA binding domain of STAT-5 of SEQ ID NO:10 and STAT-6 of SEQ ID NO:12 that cannot be reliably aligned with STAT-1 is shown in a hatched box. Residues mentioned in the Example 1, below are underlined. Tyr 701 is marked with an asterisk and disordered loops are indicated by broken lines.

FIG. 2A shows the ribbon diagram of the STAT-1 core dimer on DNA. The component domains are colored green (coiled coil domain), red (DNA binding domain), orange (linker domain), cyan (SH2 domain). The tail segments are shown in magenta and yellow. Disordered loops (one in the coiled coil domain, and one connecting the SH2 domain to the tail segment) are shown as dotted lines. The phosphotyrosine residue is shown in a stick representation. The N and C termini of STAT-1 core are indicated by 'N' and 'C'. The DNA backbone is shown in grey. This, and other ribbon diagrams were rendered using RIBBONS [Carson, J. Appl. Cryst. 24: 958–961 (1991)].

FIG. 2B shows the molecular surface of the STAT-1 dimer, in the same orientation as FIG. 2A. The surface was calculated using GRASP [Nicholls, A. et al., Proteins: Struct. Funct and Genetics 11:281–296 (1991)] and rendered using RASTER3D [Merritt, E. A. and Bacon, D. J., Meth. Enzyml. 277:503–524 (1997)]. The tail segments, shown in green and magenta, were not included in the surface generation. The surface is colored according to the local electrostatic potential, with blue and red representing positive and negative potential, respectively. The disordered linker connecting the C-terminus of the SH2 domain to the tyrosine-phosphorylated tail segment is shown as a green dotted line. DNA duplex is shown in yellow.

FIG. 2C is a view of the STAT-1 dimer looking at the DNA binding domains. Note that these domains do not contact each other.

In FIGS. 2C and 2D the crystallographic 2-fold rotation axis is perpendicular to the page.

FIG. 4A is a schematic representation of the immunoglobulin-like folds seen in STAT-1, NFkB [Ghosh, G. et al., Nature 373:303–310 (1995); Müller, C. W. et al., Nature 373:311–317 (1995)]; and p53 [Cho, Y. et al., Science 265:346–355 (1994)]. For STAT-1, the DNA binding segments are highlighted in grey. The secondary structure notation used in this paper is indicated, as are the residue numbers for the secondary structural boundaries. The lengths of the secondary structure elements and the connecting loops are not drawn to scale in these diagrams. The central strands of the immunoglobulin fold are labeled at the bottom of each diagram, using the standard notation for immunoglobulin-like domains [Bork, P. et al., J. Mol. Biol. 242:309–320 (1994)]. The DNA-binding loops of NFkB and p53 are indicated in grey.

FIG. 4B is the protein-DNA contact map for a STAT-1 core bound to DNA. Shown on the top of the panel is the sequence of the DNA oligonucleotide duplex (SEQ ID Nos:13 and 14) used in this study. The M67 site is underlined in the top strand. The numbering scheme used in the paper is indicated. In the bottom panel, the central C/G base pair at position 0 is at the center of the pseudo-twofold axis of the DNA duplex and is, therefore, a G/C base pair in one of the half-sites. Due to rotational averaging (see Example 1, below), electron density for base pairs at positions 2, 6, 7, and 8 corresponds to superpositions of the left and right halves of the duplex. The resulting ambiguity in the bases that contact the protein are indicated by circles around the relevant bases. Grey circles represent phosphates, and grey pentagons represent the ribose sugars. The DNA backbones are represented as straight lines connecting phosphates and sugars. Solid lines with black dots on both ends indicate potential hydrogen bonding interactions between protein residues and the DNA. Closed circles with "W?" inside represent possible water-mediated protein-DNA interactions. The indication of potential water-mediated interactions is not based on the direct observation of possible solvent sites in electron density maps but simply on the distances between the interacting groups, and their environment. Note that Segment 3, shown to interact in the minor groove, is partially disordered. This may be correlated with heterogeneity at position 7, since guanine is necessary for stabilization of Glu421 in the minor groove.

In FIG. 4C a ribbon representation of the structure of the DNA binding domain is shown in red, with the DNA interacting loops in cyan. The loops are denoted S1 to S4, corresponding to the segments 1 to 4 (see FIG. 4A). One of the two rotationally equivalent DNA duplexes is shown. The sidechains of Lys336, Glu420 and Asn460 are shown in blue.

FIG. 4D shows the surface representation of the STAT-1 dimer (left) and the NFkB dimer (right). The structure of NFkB shown here is that of [Müller, C. W. et al., Nature 373:311–317 (1995)]. The coiled coil domains of STAT-1 are not shown.

FIG. 5A shows the SH2 architecture and linkage to the DNA binding domain. At the top of the panel is shown an alignment of the sequences of the SH2 domains of v-Src and STAT-1. This alignment was generated by the DALI program [Holm, L. and Sander, C., J. Mol. Biol. 233:123–138 (1993)], based on the three dimensional structures of the Src SH2 domain (Waksman, G. et al., Nature 358:646–653 (1992)] and of STAT-1. The asterisks indicate residues that are considered by DALI to be equivalent in three dimensions. The secondary structure elements are indicated, using the standard SH2 notation. Identical residues are highlighted in yellow. The v-Src sequence shown spans the entire SH2 domain. Note that the structural conservation is maintained throughout this region of STAT-1. Ribbon diagrams for the SH2 domains, the linker region and part of the DNA binding domain are shown below. Two conserved tryptophan residues that pack tightly against the phosphate binding loop of the SH2 domain (green) and helix α6 of the DNA binding domain (red) are shown. Segment 4, which is crucial for DNA recognition, is shown in magenta. Also shown in magenta is the tail segment of the second SH2 domain (not shown) that binds to this SH2 domain via pTyr701. The tail segment of this SH2 domain, which interacts primarily with the other SH2 domain, is shown in yellow. The flexible connector to the tail is shown as a blue dotted line. The conserved arginine residue in the SH2 domain (Arg602) and three residues that interact with DNA are shown in blue. The phosphate backbone of the DNA is shown as a grey spiral.

FIG. 5B shows the SH2-dimer interface, colored similarly as in FIG. 5A. The second SH2 domain is shown, colored blue, while the DNA binding domain is not shown. Hydrophobic sidechains that pack at the dimer interface are shown in green, and residues found at 3 positions at the interface in STATs 1–6 are shown at the right.

DETAILED DESCRIPTION OF THE INVENTION

Figure 1A:
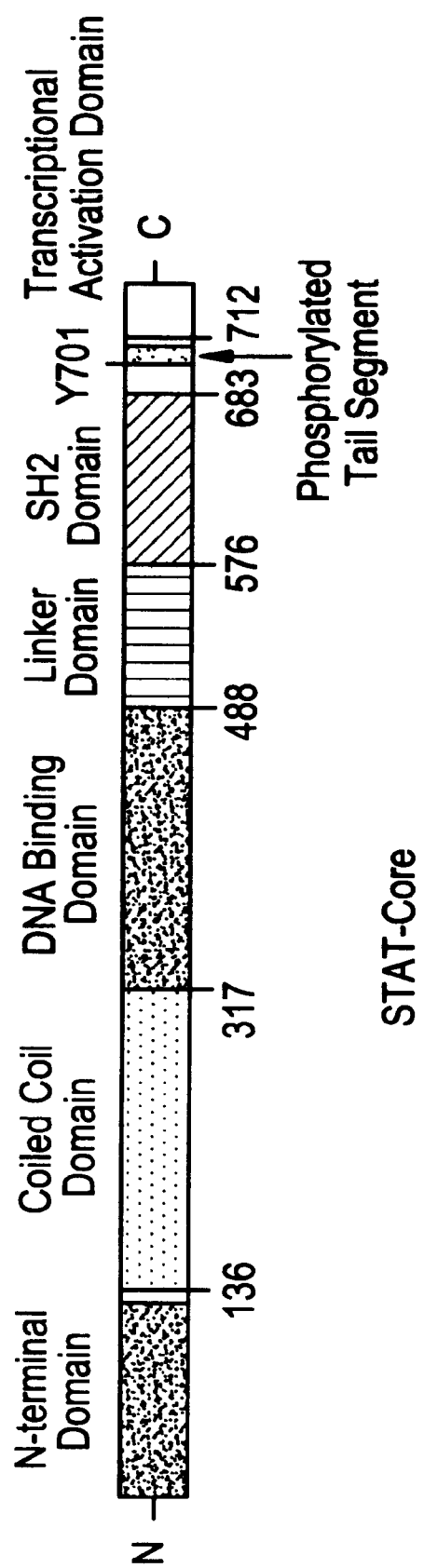
FIGS. 1A–1B show the domain structure and sequence alignment of STATs.

The present invention provides three-dimensional structural information regarding the important family of transcription factors known as STATS. More particularly, the present invention provides a crystalline form of the core portion of a STAT protein of sufficient quality to perform meaningful X-ray crystallographic measurements. In addition, the present invention provides a method of preparing such crystals.

In a particular embodiment of the present invention the crystal structure of the DNA complex of a STAT-1 homodimer is provide whcih has been determined at 2.9 A resolution. STAT-1 is disclosed as utilizing a DNA binding domain with an immunoglobulin fold, similar to that of NFkB and the p53 tumor suppressor protein. The STAT-1 dimer forms a contiguous C-shaped clamp around DNA that is stabilized by reciprocal and highly specific interactions between the SH2 domain of one monomer and the C-terminal segment, phosphorylated on tyrosine, of the other. The phosphotyrosine binding site of the SH2 domain in each monomer is coupled structurally to the DNA binding domain, indicating a potential role for the SH2-phosphotyrosine interaction in the stabilization of DNA interacting elements.

The present invention provides the identification of an important feature of the STATs, namely the presence of a SH2 domain which is fused into a contiguous structural element that includes the DNA binding domain. A STAT homolog has been found in the slime mold Dictyostelium discoideum [Kawata, T. et al., *Cell* 89:909–916 (1997)], suggesting a very ancient evolutionary origin for the utilization of the immunoglobulin fold to bind DNA, as well as for the interaction of SH2 domains with phosphotyrosines. The crystal structure of the STAT-1 DNA complex described herein reveals that dimeric interactions between two SH2 domains are crucial to the formation of a DNA-binding clamp that wraps almost entirely around the duplex. By limiting the dimer interaction to the SH2 domain, the STATs ensure that dephosphorylation of the tail segment will result in the rapid dissociation of the STAT-DNA complex.

In addition the present invention provides a method of using the crystals and the crystallographic measurements for drug discovery and development. These methods include procedures for screening drugs that either enhance or inhibit STATs, which can have a critical effect on the transcription of the specific genes under the control of STAT proteins. Drugs that are antagonists would be useful for the treatment of a variety of disease states, including but not limited to, inflammation, allergy, asthma, and leukemias. On the other hand, drugs that are found to be agonists will enhance this STAT function. Such drugs may therefore have utility in the treatment of anemias, neutropenias, thrombocytopenia, cancer, obesity, viral diseases and growth retardation, or other diseases characterized by a insufficient STAT activity.

Therefore, if appearing herein, the following terms shall have the definitions set out below. As used herein a the term "STAT protein" includes a particular family of transcription factor consisting of the Signal Transducers and Activators of Transcription proteins. These proteins have been defined in International Patent Publication No.s WO 93/19179 (Sep. 30, 1993, by James E. Darnell, Jr. et al.), WO 95/08629 (Mar. 30, 1995, by James E. Darnell, Jr. et al.) and United States application having a Ser. No. 08/212,184, filed on Mar. 11, 1994, entitled, "Interferon Associated Receptor Recognition Factors, Nucleic Acids Encoding the Same and Methods of Use Thereof" by James E. Darnell, Jr. et al., all of which are incorporated by reference in their entireties, herein. Currently, there are seven STAT family members which have been identified, numbered STAT 1, 2, 3, 4, 5A, 5B, and 6. STAT proteins include proteins derived from alternative splice sites such as Human STAT1α and STAT1β, i.e., STAT1β is a shorter protein than STAT1α and is translated from an alternatively spliced mRNA. Modified STAT proteins and functional fragments of STAT proteins are included in the present invention.

As used herein the terms "phosphorylated" and "nonphosphorylated" as used in conjunction with or in reference to a STAT protein denote the phosphorylation state of a particular tyrosine residue of the STAT proteins (e.g., Tyr 701 of STAT1). When STAT proteins are phosphorylated, they form homo- or heterodimeric structures in which the phosphotyrosine of one partner binds to the SRC homology domain (SH2) of the other. In their natural environment the newly formed dimer then translocates from the cytoplasm to the nucleus, binds to a palindromic GAS sequence, thereby activating transcription As used herein a "STAT core", "STAT core fragment", the "core portion of the STAT" and the like are used interchangeably and describe the portion of a STAT protein that comprises four tandem structural domains of a STAT protein (1) The first domain consists of several long helices (e.g., α1–4 of human STAT-1), and is referred to as the coiled coil domain, as exemplified below for human STAT-1; (2) the DNA binding domain follows next, and contains an immunoglobulin-type fold; (3) the next domain links the DNA binding domain to the SH2 domain, referred to as the linker domain as exemplified below for human STAT-1; and (4) the SH2 domain which is at the C-terminal end of the core structural unit. In addition it contains a C-terminal tail segment with a phosphorylatable tyrosine (e.g, residues 700 to 708 of human STAT-1 which is phosphorylated on Tyr 701) that is connected to the SH2 domain by a flexible linker (of 17 residues in human STAT-1). Each of the four domains is fused to the adjacent ones by the formation of a contiguous hydrophobic core. The "core" lacks only the N-terminal domain, defined below, and the C-terminal transcriptional domain of an intact STAT. As is readily apparent from FIG. 1B, a "STAT core" is a generalized STAT structural element that is merely exemplified by STAT-1 as disclosed herein.

The "N-terminal domain" of a STAT protein is used interchangeably herein with the "N-terminal cooperative domain" and refers to the N-terminal portion of a STAT protein involved in STAT protein dimer—dimer interaction at a weak STAT DNA binding site.

General Techniques for Constructing Nucleic Acids That Express Recombinant STAT Proteins In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

The term "corresponding to" is used herein to refer to homologous amino acid (or nucleotide) sequences in which the relative positions of the amino acid residues (or nucleotides) is equivalent though the numbering of the amino acid residues or nucleotide bases of the sequences may not be the same.

A gene encoding a STAT protein, whether genomic DNA or cDNA, can be isolated from any animal source, particularly from a mammal. Methods for obtaining the STAT protein gene are well known in the art, as described above (see, e.g., Sambrook et al., 1989, supra).

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide, sequence can comprise non-coding sequences including restriction sites, regulatory sites, promoters and the like.

The present invention also relates to cloning vectors containing genes encoding analogs and derivatives of the STAT protein, including modified STAT proteins of the invention, that have the same or homologous functional activity as STAT protein, and homologs thereof. The production and use of derivatives and analogs related to the STAT protein are within the scope of the present invention.

STAT protein derivatives and analogs as described above can be made by altering encoding nucleic acid sequences by substitutions, e.g. replacing threonine-459 of the crucial Segment 4 of the DNA binding domain of STAT-1 with a serine for example, or additions or deletions that provide for functionally equivalent or specifically modified molecules.

Due to the degeneracy of nucleotide coding sequences, other DNA sequences which encode substantially the same amino acid sequence as a nucleic acid encoding a modified STAT protein or more particularly a STAT core fragment of the present invention may be used in the practice of the present invention. These include but are not limited to allelic genes, homologous genes from other species, which are altered by the substitution of different codons that encode the same amino acid residue within the sequence, thus producing a silent change. Likewise, the modified STAT protein derivatives of the invention include, but are not limited to, those containing, as a primary amino acid sequence, all or part of the amino acid sequence of a STAT protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly preferred conserved amino acid exchanges are:

(a) Lys for His or for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained;

(e) Ile for Leu or for Val or vice versa as roughly equivalent hydrophobic amino acids; and (f) Phe for Tyr or vice versa as roughly equivalent aromatic amino acids.

Non-conserved amino acid substitutions may also be introduced to substitute an amino acid with a particularly preferable property. For example, a Cys may be introduced to provide a potential site for disulfide bridges with another Cys. A His may be introduced as a particular "catalytic" site (i.e., His can act as an acid or base and is the most common amino acid in biochemical catalysis). Pro may be introduced because of its particularly planar structure, which induces β-turns in the protein's structure.

The genes encoding STAT proteins, and derivatives and analogs thereof can be produced by various methods known in the art. The manipulations which result in their production can occur at the gene or protein level. For example, the cloned core of a STAT protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a STAT protein care should be taken to ensure that the modified gene remains within the same translational reading frame as the STAT protein gene, uninterrupted by translational stop signals, in the gene region where the desired activity is encoded.

Additionally, the STAT protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2µ plasmid.

In an alternative method, the desired gene may be identified and isolated after insertion into a suitable cloning vector in a "shot gun" approach. Enrichment for the desired gene, for example, by size fractionation, can be done before insertion into the cloning vector.
Expression of STAT Proteins The nucleotide sequence coding for a STAT protein, or functional fragment, including the core fragment of a STAT protein, derivatives or analogs thereof, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a STAT protein of the invention or functional fragment, including the core fragment of a STAT protein, derivatives or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector. As detailed below, all genetic manipulations described for the STAT gene in this section, may also be employed for genes encoding a core fragment, derivatives or analogs thereof, including a chimeric protein, thereof.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant STAT protein of the invention, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding STAT protein is cultured in an appropriate cell culture medium under conditions that provide for expression of STAT protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of STAT protein may be controlled by any promoter/enhancer element known in the art, but these regulatory elements must be functional in the host selected for expression.

Expression vectors containing a nucleic acid encoding a STAT protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding STAT protein is inserted within the "selection marker" gene sequence of the vector, recombinants containing the STAT protein insert can be identified by the absence of the STAT protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedron initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the present invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

In a specific embodiment, a fusion protein or peptide can be expressed. A STAT core fusion protein comprises at least a functionally active portion of a non-STAT protein joined via a peptide bond to a STAT core or a structural or functional domain of the core portion of the STAT as defined below. Alternatively, a fusion protein can contain structural or functional domains from two or more different STATs. All of these fusion proteins or peptides can be expressed. The non-STAT sequences can be amino- or carboxyl-terminal to the STAT sequences. A recombinant DNA molecule encoding such a fusion protein can comprise a sequence encoding a functionally active portion of a non-STAT protein or peptide joined in-frame to the coding sequence of the STAT core for example, and can encodes a cleavage site for a specific protease, e.g., thrombin or Factor Xa, preferably at the STAT-non-STAT juncture. In a specific embodiment, the fusion protein is expressed in *Escherichia coli*. An example of a fusion peptide or protein is a STAT binding domain fused to the maltose binding protein. An alternative example of a fusion protein or peptide is a an SH2 domain of a STAT joined with a green fluorescent protein or modified green fluorescent protein as described in U.S. Pat. No. 5,625,048, Issued Apr. 29, 1997 herein incorporated by reference in its entirety.

Such fusion proteins and peptides may also be classified as chimeric proteins or peptides which further include STATs having switched structural/functional domains such as a STAT core having a DNA binding domain from STAT-1 and an SH2 domain of STAT5. All of such chimeric STAT cores and fragments thereof including the fusion proteins and peptides are contemplated in the present invention.

Synthetic Polypeptides

The term "polypeptide" is used in its broadest sense to refer to a compound of two or more subunit amino acids, amino acid analogs, or peptidomimetics. The subunits are linked by peptide bonds. The STAT proteins and more particularly the core fragments thereof, of the present invention may be chemically synthesized.

More particularly, potential drugs that may be tested in the drug screening assays of the present invention may also be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine, and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); -helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

Crystals of the Core Portion of a STAT protein

Crystals of the core fragment of a STAT protein and its oligomer binding partner can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used. As exemplified below Protein-DNA complex was prepared by mixing the protein and DNA samples with a molar ratio of 1:1.04 (protein dimer: DNA duplex). As exemplified below, an initial crystal can be allowed to grow over several months at 4° C. from a hanging drop. Crystals then can be subsequently grown by macroseeding from the initial crystal.

Once a crystal of the present invention is grown, X-ray diffraction data can be collected. A MAR imaging plate detector for X-ray diffraction data collection can be used for example. Crystals can be characterized by using X-rays produced in a conventional source (such as a sealed tube or a rotating anode) or using a synchrotron source. In Example 1 below, diffraction data was measured at beamline A1 of Cornell High Energy Synchrotron Source using a CCD detector.

Methods of characterization include, but are not limited to, precision photography, oscillation photography and diffractometer data collection. As exemplified below, heavy atom derivatives can be obtained by soaking crystals in stabilization solution with 1 mM $Na_2OsCl_6$ for 12 hours, with 10 mM $KAu(CN)_2$ for 12 hours, with 10 mM $Pb(OAc)_2$ for 1 hour, and with 10 mM $UO_2(NO_3)_2$ for 4 hours. In this case, the crystals were frozen in freshly thawed liquid propane (temperature~–150° C.) after being serially transferred through the cryo-protection solutions with increasing concentrations of PEG400 (15% to 45%).

Alternatively, the STAT core fragment can be synthesized with selenium-methionine (Se-Met) in place of methionine, and the Se-Met multiwavelength anomalous dispersion data [Hendrickson, Science, 254:51–58 (1991)] can be collected on CHESS F2, using reverse-beam geometry to record Friedel pairs at four X-ray wavelengths, corresponding to two remote points above and below the Se absorption edge ($\lambda_1$ and $\lambda_4$) and the absorption edge inflection point ($\lambda_2$) and peak ($\lambda_3$). Selenium sites can be located using SHELXS-90 in Patterson search mode (G. M. Sheldrick). Experimental phases ($\alpha_{MAD}$) can be estimated via a multiple isomorphous replacement/anomalous scattering strategy using MLPHARE (Z. Otwinowski, Southwestern University of Texas, Dallas) with three of the wavelengths treated as derivatives and one ($\lambda_2$) treated as the parent for example.

Data processing and reduction can be carried out using programs such as HKL, DENZO, and SCALEPACK [Otwinowski and Minor, Meth. Enzymol. 276:307–326 (1997)]. In addition, X-PLOR, [Brüger, X-PLOR v.3.1 Manual, New Haven: Yale University, (1993B)] or Heavy [T. Terwilliger, Los Alamos National Laboratory] may be utilized for bulk solvent correction and B-factor scaling. Electron density maps can be calculated using SHARP [La Fortelle, E. D. and Bricogne, G., Methods in Enzymology 276:472–494 1997)] and SOLOMON as exemplified below. Molecular models can be built into this map using O [Jones, T. a. et al., ACTA Crystallogr. A47:110–119 (1991)]. A complete molecular model for the DNA can be built on the basis of the experimental electron density map. Model building interspersed with positional and simulated annealing refinement [Brünger, 1993B, supra] or with CNS, using a maximum likelihood residual [Brünger, A. T. et al., Acta Cryst. D:In Press (1998)] can permit an unambiguous trace and sequence assignment of the core fragment of the STAT protein.

Protein-Structure Based Design of Agonists and Antagonists of STAT Proteins

Once the three-dimensional structure of a crystal comprising a core portion of a STAT protein is determined, a potential ligand (antagonist or agonist) is examined through the use of computer modeling using a docking program such as GRAM, DOCK, or AUTODOCK [Dunbrack et al., 1997, supra]. This procedure can include computer fitting of potential ligands to the DNA binding domain for example to ascertain how well the shape and the chemical structure of the potential ligand will complement or interfere with the STAT-DNA binding [Bugg et al., Scientific American, Dec.:92–98 (1993); West et al., TIPS, 16:67–74 (1995)]. Computer programs can also be employed to estimate the attraction, repulsion, and steric hindrance of the ligand to the STAT-DNA binding domain. Generally the tighter the fit (e.g., the lower the steric hindrance, and/or the greater the attractive force) the more potent the potential drug will be since these properties are consistent with a tighter binding constant.

Furthermore, the more specificity in the design of a potential drug the more likely that the drug will not interfer with other properties of the STAT protein or other proteins (particularly proteins present in the nucleus). This will minimize potential side-effects due to unwanted interactions with other proteins.

Initially a potential ligand could be obtained by screening a random peptide library produced by recombinant bacteriophage for example, [Scott and Smith, Science, 249:386–390 (1990); Cwirla et al., Proc. Natl. Acad. Sci., 87:6378–6382 (1990); Devlin et al., Science, 249:404–406 (1990)] or a chemical library. A ligand selected in this manner could be then be systematically modified by computer modeling programs until one or more promising potential ligands are identified. Such analysis has been shown to be effective in the development of HIV protease inhibitors [Lam et al., Science 263:380–384 (1994); Wlodawer et al., Ann. Rev. Biochem. 62:543–585 (1993); Appelt, Perspectives in Drug Discovery and Design 1:23–48 (1993); Erickson, Perspectives in Drug Discovery and Design 1: 109–128 (1993)].

Such computer modeling allows the selection of a finite number of rational chemical modifications, as opposed to the countless number of essentially random chemical modifications that could be made, and of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structures disclosed herein (e.g. Table 2, below) and computer modeling, a large number of these compounds can be rapidly screened on the computer monitor screen, and a few likely candidates can be determined without the laborious synthesis of untold numbers of compounds.

Once a potential ligand (agonist or antagonist) is identified it can be either selected from a library of chemicals as are commercially available from most large chemical companies including Merck, Glaxo Welcome, Bristol Meyers Squib, Monsanto/Searle, Eli Lilly, Novartis and Pharmacia UpJohn, or alternatively the potential ligand may be synthesized de nov o. As mentioned above, the de novo synthesis of one or even a relatively small group of specific compounds is reasonable in the art of drug design. The prospective drug can be placed into any standard binding assay exemplified below to test its effect on any particular STAT function.

When a suitable drug is identified, a supplemental crystal can be grown which comprises a protein-ligand complex formed between the core portion of a STAT and a duplex DNA and the drug. Preferably the crystal effectively diffracts X-rays allowing the determination of the atomic coordinates of the protein-ligand complex to a resolution of greater than 5.0 Angstroms, more preferably greater than 3.0 Angstroms. The three-dimensional structure of the supplemental crystal can be determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR and AMORE [J. Navaza, *Acta Crystallographics ASO*, 157–163 (1994)]. Once the position and orientation are known an electron density map can be calculated using the search model to provide X-ray phases. Thereafter, the electron density is inspected for structural differences and the search model is modified to conform to the new structure. Using this approach, it will be possible to use the claimed structure to solve the three-dimensional structures of any such STAT core-DNA complex. Other computer programs that can be used to solve the structures of such STAT crystals include QUANTA, CHARMM; INSIGHT; SYBYL; MACROMODE; and ICM.

For all of the drug screening assays described herein further refinements to the structure of the drug will generally be necessary and can be made by the successive iterations of any and/or all of the steps provided by the particular drug screening assay.

Phage Libraries for Drug Screening

Phage libraries have been constructed which when infected into host *E. coli* produce random peptide sequences of approximately 10 to 15 amino acids [Parmley and Smith, Gene 73:305–318 (1988), Scott and Smith, Science 249:386–249(1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of the core portion of a STAT (e.g., a fragment having an amino acid sequence comprising SEQ ID NO:18). After a specified incubation period, the filters can be thoroughly washed and developed for autoradiography. Plaques containing the phage that bind to the radioactive fragment of the STAT can then be identified. These phages can be further cloned and then retested for their ability to bind to the fragment of a STAT protein as before. Once the phages have been purified, the binding sequence contained within the phage can be determined by standard DNA sequencing techniques. Once the DNA sequence is known, synthetic peptides can be generated which represents these sequences. These peptides can be tested, for example, for their ability to interfere with a STAT binding to a STAT DNA binding site for example.

The effective peptide(s) can be synthesized in large quantities for use in in vivo models and eventually in humans to modulate STAT signal transduction. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine 10:175–178 (1990)].

Binding Assays for Drug Screening Assays

The drug screening assays of the present invention may use any of a number of assays for measuring the functionality of a STAT, including for the ability for a STAT to become phosphorylated, to dimerize following activation and for the ability of the dimer to bind DNA.

In one binding assay, a nucleic acid containing a STAT binding site is placed on or coated onto a solid support. Methods for placing the nucleic acid on the solid support are well known in the art and include such things as linking biotin to the nucleic acid and linking avidin to the solid support. The STAT is allowed to equilibrate with the nucleic acid and drugs are tested to see if they disrupt or enhance the binding.

The STAT protein may be labeled as described below. For example, in one embodiment radiolabeled STAT proteins are used to measure the effect of a drug on binding. In another embodiment the natural ultraviolet absorbance of the STAT protein is used. In yet another embodiment, a Biocore chip (Pharmacia) coated with the nucleic acid is used and the change in surface conductivity can be measured.

In yet another embodiment, the affect of a prospective drug (a test compound) on interactions between STATs and their DNA binding sites are assayed in living cells that contain or can be induced to contain activated STAT proteins, i.e., STAT dimers. Cells containing a reporter gene, such as the heterologous gene for luciferase, green fluorescent protein, chloramphenicol acetyl transferase or 3-galactosidase and the like are operably linked to a promoter containing a STAT binding site. A prospective drug is then contacted with the cell in the presence of a cytokine which activates the STAT(s) of interest. The amount (and/or activity) of reporter produced in the absence and presence of prospective drug is determined and compared. Prospective drugs which reduce the amount (and/or activity) of reporter produced are candidate antagonists of the STAT-DNA interaction, whereas prospective drugs which increase the amount (and/or activity) of reporter produced are candidate agonists.

Although cells that naturally encode the STAT proteins may be used, preferably a cell is used that is transfected with a plasmid encoding the STAT protein. For example transient transfections can be performed with 50% confluent U3A cells using the calcium phosphate method as instructed by the manufacturer (Stratagene). In addition as mentioned above, the cells can also be modified to contain one or more reporter genes, a heterologous gene encoding a reporter such as luciferase, green fluorescent protein or derivative thereof, chloramphenicol acetyl transferase, β-galactosidase, etc. Such reporter genes can individually be operably linked to a promoter comprising a STAT binding site. Assays for detecting the reporter gene products are readily available in the literature. For example, luciferase assays can be performed according to the manufacturer's protocol (Promega), and β-galactosidase assays can be performed as described by Ausubel et al., [in *Current Protocols in Molecular Biology,* J. Wiley & Sons, Inc. (1994)].

In one example, the transfection reaction can comprise the transfection of a cell with a plasmid modified to contain a STAT protein, such as a pcDNA3 plasmid (Invitrogen), and a reporter plasmid that contains a reporter gene. Although the preparation of such plasmids is now routine in the art, many appropriate plasmids are commercially available e.g., a plasmid with β-galactosidase is available from Stratagene.

The reporter plasmids can contain specific restriction sites in which an enhancer element having a strong STAT binding site or alternatively two tandemly arranged "weak" STAT binding sites can be inserted. In one particular embodiment, thirty-six hours after transfection of the cells with a plasmid encoding STAT-1, the cells are treated with 5 ng/ml interferon-γ Amgen for ten hours. Protein expression and tyrosine phosphorylation (to monitor STAT activation) can be determined by e.g., gel shift experiments with whole cell extracts.

Labels:

Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419–439 (1980) and in U.S. Pat. No. 4,857,453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE 1

Crystal Structure of a Tyrosine Phosphorylated STAT-1 Dimer Bound to DNA

Introduction

The crystal structure of a DNA complex of a 67 kDa core fragment of STAT-1, lacking only the N-Domain and the C-terminal transcriptional activation domain is disclosed. The structure lays bare the molecular architecture of the STAT proteins and reveals the mechanism by which the STAT SH2 domain controls dimer formation and DNA binding.

Materials and Methods

Protein and DNA preparation and crystallization: Human STAT-1 core protein (residues 132 to 713) of SEQ ID NO:2 was over-expressed in *E. coli* and purified essentially as described [Vinkemeier, U. et al., *EMBO J.* 15:5616–5626 (1996)]. Oligonucleotides were synthesized by standard phosphoramidite chemistry on an Expedite Nucleic Acid Synthesis System (PerSeptive) and purified by preparative, denaturing polyacrylamide gel electrophoresis. Purified oligonucleotides were extracted from gel slices using electro-elution (Elutrap System, Schleicher & Schuell, Inc.) and desalted using a Resource RPC reverse phase column (Pharmacia) on HPLC at room temperature. Single stranded DNA was quantified by UV spectrophotometry, mixed with an equimolar amount of a complementary strand, and annealed in the presence of 100 mM KCl and 10 mM $MgCl_2$. Protein-DNA complex was prepared by mixing the protein and DNA samples with a molar ratio of 1:1.04 (protein dimer:DNA duplex). Crystals were obtained from a variety of oligonucleotide duplexes but suitable diffraction was only obtained from crystals of the 18-mer duplex (SEQ ID NOs:13 and 14) shown in FIG. 4B. One large crystal grew over several months at 4° C. from a hanging drop that had been set up by mixing 1 ml of 0.12 mM protein:DNA complex and 1 ml of the reservoir solution containing 100 mM Na acetate, pH 5.0, 100 mM KCl, 20 mM $MgCl_2$, 3%

PEG400, and 0.01% $NaN_3$. Crystals grown by macroseeding, originally from this crystal, reach a size of at least 0.25×0.2×0.1 $mm^3$ within 10 days. The crystals are in space group $C222_1$ with cell dimensions of a=76.6, b=148.2, c=181.1 Å, with one molecule of STAT-1 protein and a DNA half-site in the asymmetric unit.

The structure determination was carried out by multiple isomorphous replacement (MIR), using data collected at Cornell High Energy Synchrotron Source (CHESS) for native crystals and 4 heavy atom derivatives (Table 1). Heavy atom derivatives were obtained by soaking crystals in stabilization solution with 1 mM $Na_2OsCl_6$ for 12 hours, with 10 mM $KAu(CN)_2$ for 12 hours, with 10 mM $Pb(OAc)_2$ for 1 hour, and with 10 mM $UO_2(NO_3)_2$ for 4 hours. The crystals were frozen in freshly thawed liquid propane (temperature~–150° C.) after being serially transferred through the cryo-protection solutions with increasing concentrations of PEG400 (15% to 45%). Diffraction data were measured at beamline A1 of Cornell High Energy Synchrotron Source using a CCD detector. Data processing and reduction was carried out using programs DENZO, and SCALEPACK [Otwinowski and Minor, *Meth. Enzymol.* 276:307–326 (1997)].

held fixed at 0.5 during the refinement to account for the conformational averaging inherent in the symmetry of the crystallographic system. Almost all of the molecular model for the protein could also be built into the original experimental map, and the map continued to provide valuable guidance until the very end of the model refinement.

The final model for the protein extends from residue 136 to residue 710 of STAT-1. Two loops in the structure are disordered, and these span residues 183 to 196 in the coiled coil domain and residues 684 to 699 in the SH2 domain. The free R-value of the model to 2.9 Å is 29.4%, with a working R-value of 22.7%. The final model has 79% of the amino acid residues in the most favored regions of the Ramachandran plot. Only 6 residues are found in generously allowed regions with none in the disallowed regions. The relevant coordinates determined are included in Table 2.

Results

Structure Determination and General Architecture: The structure described here is that of STAT-1 core (residues 132 to 713, $M_r$=67.3 KDa), crystallized with an 18-mer duplex DNA containing a binding site for one STAT-1 dimer. The structure determination was carried out by multiple isomor-

TABLE 1

Summary of crystallographic analysis

| A. Multiple Isomorphous Replacement | | native | Na2OsCl6 | KAu(CN) | Pb(OAc)$_2$ | UO$_2$(NO$_3$)$_2$ |
|---|---|---|---|---|---|---|
| resolution (Å) | | 30.0–2.9 | 30.0–3.0 | 30.0–3.0 | 30.0–3.0 | 30.0–3.0 |
| number of sites | | — | 3 | 2 | 3 | 3 |
| reflections | measured(unique) | 261200(23301) | 174926(21229) | 324155(21315) | 209517(21008) | 158752(19573) |
| $R_{sym}$ (%) | overall(outer shell) | 7.5(19.8) | 7.7(19.2) | 9.4(19.4) | 7.9(17.3) | 9.9(14.2) |
| completeness | overall(outer shell) | 89.8(72.1) | 79.9(63.9) | 77.4(61.8) | 73.6(80.9) | 77.0(74.8) |
| (1 > 1σ(I)) | | | | | | |
| I/σ(I) | overall(outer shell) | 10.2(4.9) | 12.4(5.0) | 10.5(4.9) | 7.7(3.4) | 8.2(5.1) |
| $R_{iso}$(%) | overall(outer shell) | — | 18.0(22.1) | 15.1(24.8) | 15.7(18.8) | 42.1(35.9) |
| phasing power | centric/acentric | — | 0.89/1.33 | 1.05/1.29 | 0.78/0.89 | 0.63/0.69 |
| overall figure of merit | centric/acentric | — | | 0.32/0.28 | | |

| | resolution | number of reflec- | total number | $R_{working}/R_{free}$ | rms deviations | | |
|---|---|---|---|---|---|---|---|
| B. Refinement | range | tion (\|F\| > 2σ) | of atoms | (%) | bonds(Å) | angles(deg.) | B values (Å) |
| | 30.0–2.9 | 18485 | 5126 | 23.0/29.4 | 0.016 | 2.25 | 2.99 |

$R_{sym}$ % = 100 × Σ|I − <I>|ΣI, where I is the integrated intensity of a given reflection
$R_{iso}$ % = 100 × Σ|$F_{PH}$ − $F_p$|Σ$F_p$, where $F_{PH}$ and $F_P$ are the derivative and native structure factor amplitudes, respectively
Phasing power = Σ|$F_{PH(calc)}$|$^2$/Σ{|$F_{PH(obs)}$ − $F_{P\ (calc)}$|$^2$}$^{½}$
Figure of merit = cos<σΔφ>
The outershell for the native data is 3.0–2.9Å, and that for all of the derivatives is 3.11–3.0Å.

Figure 7:
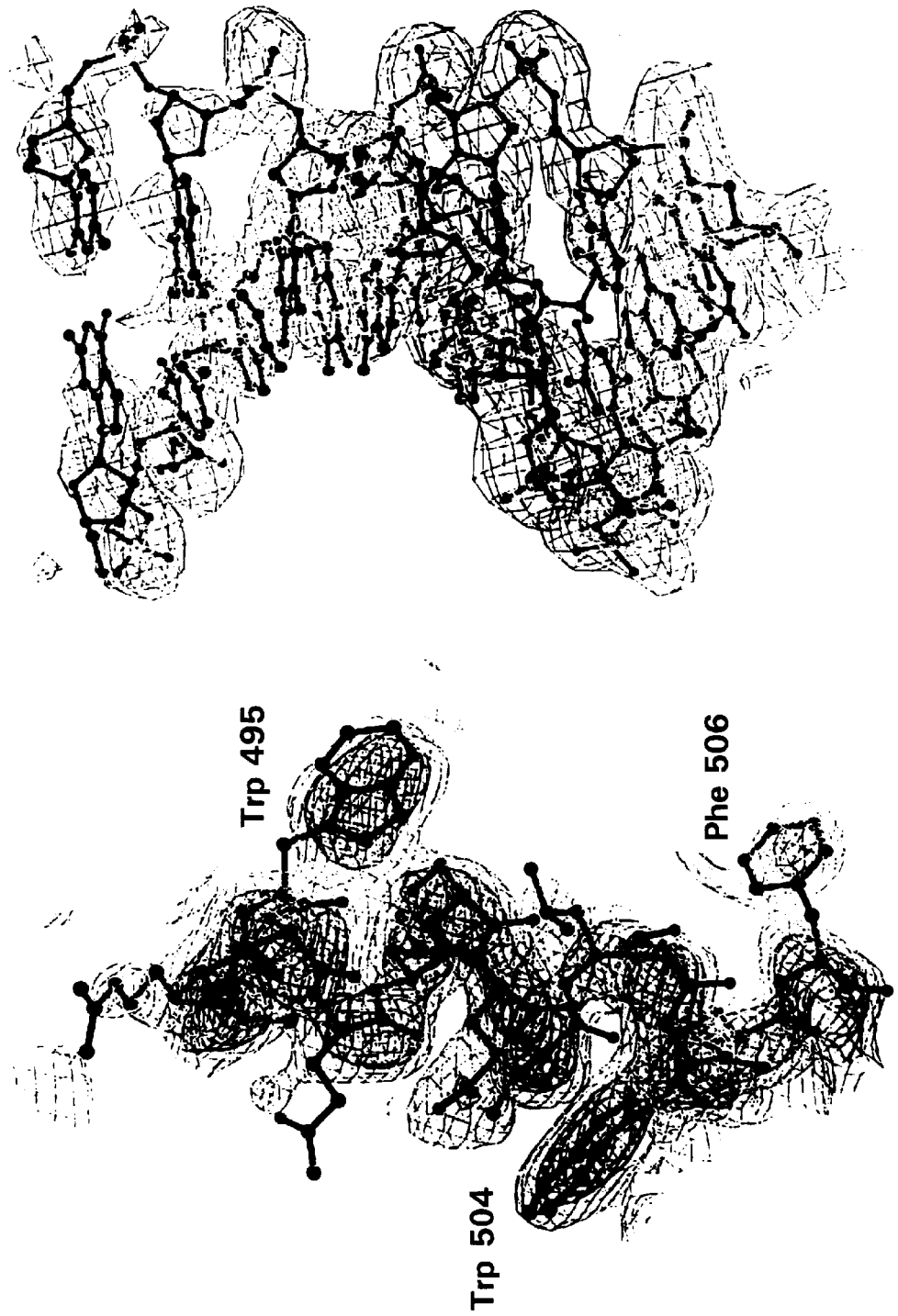
FIG. 7 shows the experimental MIR electron density maps at 3.0 Å resolution. The maps were calculated using phases from SHARP [La Fortelle, E. D. and Bricogne, G., *Enzymology* 276:472–494 (1997)] after density modification by SOLOMON [Abrahams, J. P. and Leslie, A. G., *Acta. Cryst.* D52:3042 (1996)]. Left, electron density at the 0.7 s and 2.0 s levels are shown for a region in the linker domain. The strong electron density seen here for the backbone and for aromatic sidechains is typical for the majority of the protein region, and greatly facilitated accurate model building. Right, electron density at 0.7 s and 2.5 s levels for the DNA. One half-site is shown. This figure was composed in BOBSCRIPT [Esnouf, R., *J. Mol. Graphics* 15:133–138 (1997)], and rendered with RASTER3D [Merritt, E. A. and Bacon, D. J., *Meth. Enzymol.* 277:503–524 (1997)].

Electron density maps calculated using phases derived from MLPHARE (Collaborative Computational Project, N., *Acta Cryst.* D50:760–763 (1994)] with density modification by SOLOMON [Abrahams, J. P. and Leslie, A. G., *Acta Cryst.* D52:30–42 (1996)] were of insufficient quality for model building. However, use of SHARP [La Fortelle, E. D. and Bricogne, G., *Methods in Enzymology* 276:472–494 1997)] and SOLOMON gave a map at 3.0 Å of excellent quality (FIG. 7). Molecular models were built into this map using O [Jones, T. a. et al., *ACTA Crystallogr.* A47: 110–119 (1991)] and refined with CNS, using a maximum likelihood residual [Brünger, A. T. et al., *Acta Cryst.* D:In Press (1998)]. A complete molecular model for the DNA was built on the basis of the experimental electron density map. Duplex DNA containing 17 basepairs and 1 overhang at each end was built to correspond to the sequence shown in FIG. 4B (SEQ ID NOs:13 and 14). A crystallographic two-fold axis passes through the central base pair of this duplex, as explained below. The occupancy of the DNA was phous replacement (MIR), and the structure has been refined using data to 2.9 Å resolution, with a free R-value of 29.4% and a conventional R-value of 22.7%. The crystallographic model contains one STAT-1 molecule per asymmetric unit, and includes residues 136 to 710 of SEQ ID NO:2 (of STAT-1).

STAT-1 core contains four tandem structural domains (FIGS. 1A, 2). The first domain (residues 136 to 317, SEQ ID NO:16) consists of 4 long helices (α1–4), and referred to herein as the coiled coil domain. The DNA binding domain follows next (residues 318 to 488, SEQ ID NO: 18), and contains an immunoglobulin-type fold. The next domain links the DNA binding domain to the SH2 domain, referred to herein as the linker domain (residues 488 to 576, SEQ ID NO:20). This region had been predicted to contain an SH3 domain [Fu X.-Y, *Cell* 70:323–335 (1992)], but the all β-sheet architecture of the SH3 domain is clearly missing. The SH2 domain (residues 577 to 683, SEQ ID NO:22) is at the C-terminal end of the core structural unit. The C-terminal tail segment (residues 700 to 708, SEQ ID NO:24) is phosphorylated on Tyr 701, and is connected to the SH2 domain by a flexible linker of 17 residues. Each of the four domains is fused to the adjacent ones by the formation of a contiguous hydrophobic core. The presence of extensive inter-domain interfaces explains why previous efforts at constructing smaller units encompassing the distinct functions of STATs have not been completely successful.

Two STAT-1 molecules bind to DNA as a dimer, with each monomer in the dimer related to the other by a crystallographic two-fold axis (FIG. 2). The DNA oligonucleotide used in this work contains 18 basepairs that encompass two half-sites, and the spacing of half-sites on the DNA is such that the two DNA binding domains are on opposite sides of the DNA and do not contact each other. The only protein—protein contacts between the monomers of the dimer occur between the SH2 domains, which exchange C-terminal segments in an intimate interaction. The C-terminal segments extend out of the SH2 domains of each monomer, bind to the SH2 domain of the other monomer, form an antiparallel β sheet arrangement with each other, and then return to make further interactions with the parent SH2 domain. This mutual handshake between SH2 domains seals the STAT dimer onto DNA in a closed embrace (FIG. 2B).

Figure 2A:
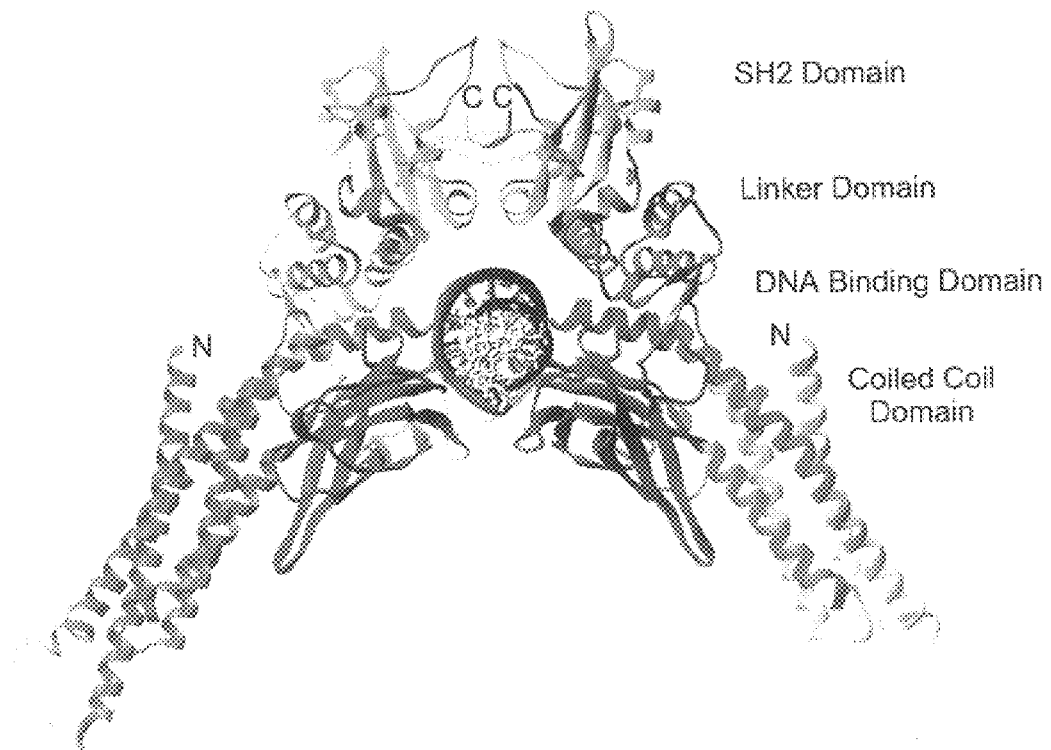
FIGS. 2A–2C show the structure of the STAT-1 DNA complex.
Figure 2B:
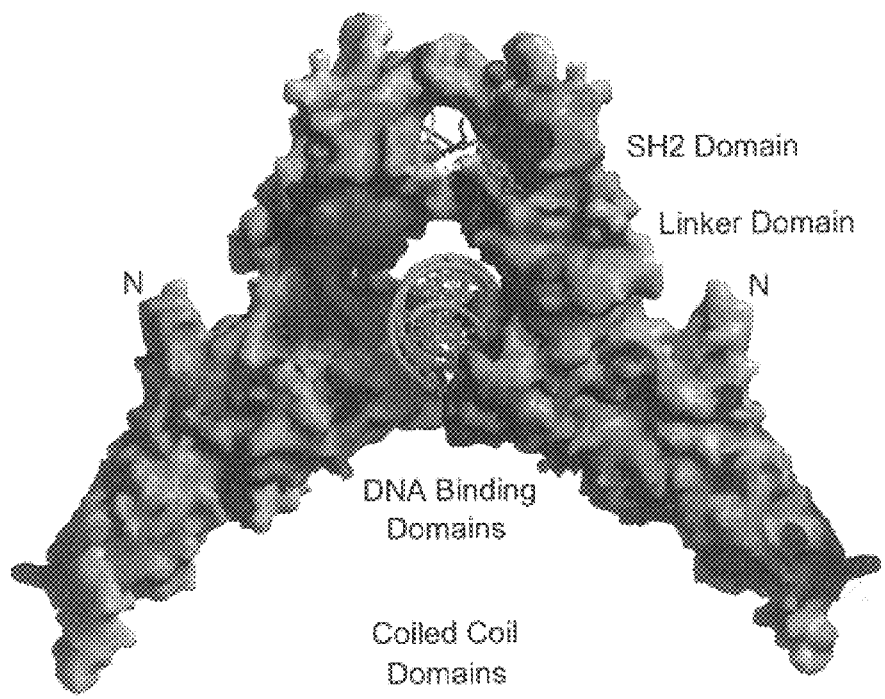
Figure 2C:
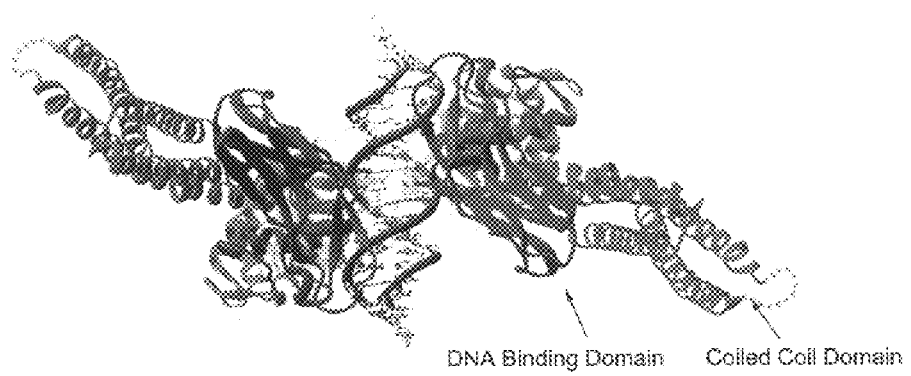
Figure 2D:
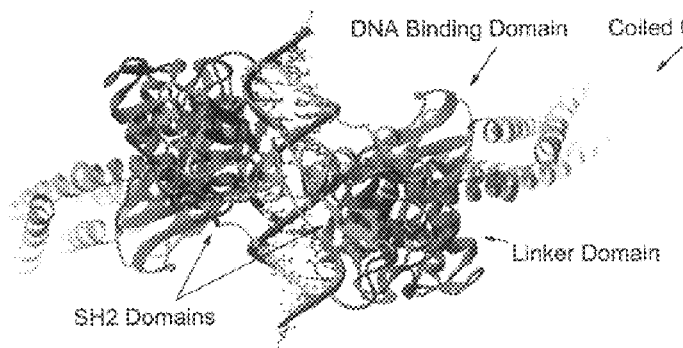
FIG. 2D is a view of the STAT-dimer, looking at the SH2 domains.
Figure 3:
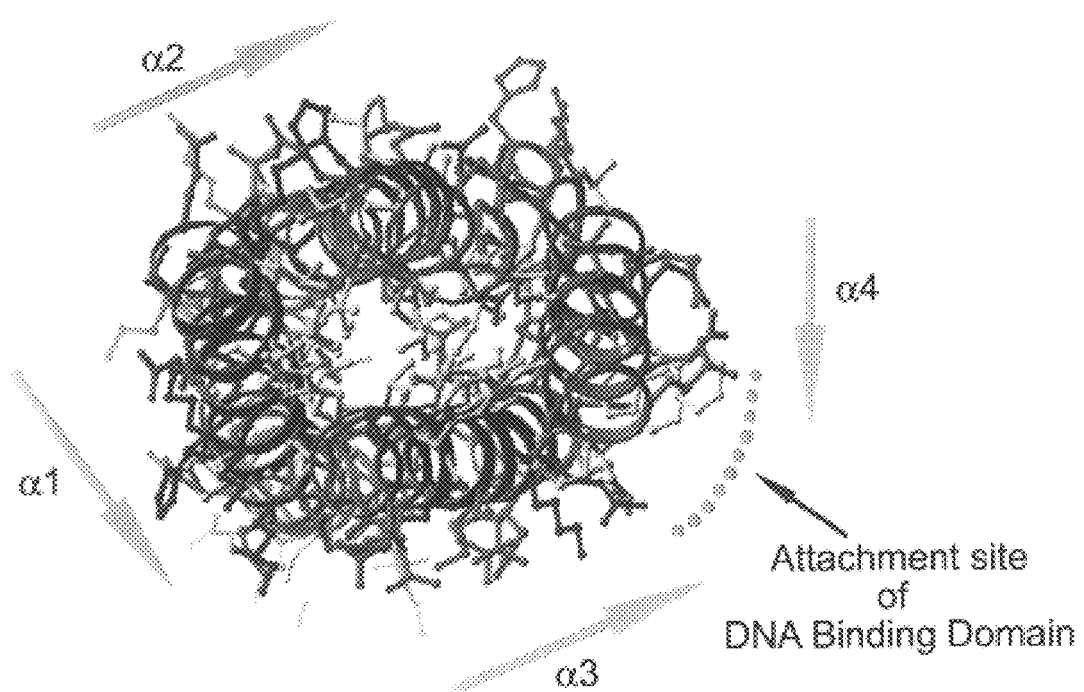
FIG. 3 shows the structure of the coiled coil domain of STAT-1. The polypeptide backbone of the four helices is shown as a grey ribbon. The directions of the helices are indicated by arrows. All the sidechains in the domain are depicted in the figure, and are colored red (acidic), blue (basic), orange (polar) and yellow (hydrophobic). Note the clusters of acidic and basic residues on the surface. The only significant cluster of hydrophobic sidechains on the surface corresponds to the site of attachment to the DNA binding domain, and is indicated by a dotted line.

The Coiled Coil Domain: The two coiled domains in the dimer project outwards from this C-shaped core, in opposite directions, and are not involved in interactions with the DNA or with the other monomer in the dimer (FIG. 2). The coiled-coil domain has four α-helices, two long ones (α1 and αc2, 50 residues, each) and two shorter ones (α3 and α4, 32 and 23 residues, respectively). The helices form a coiled coil structure that presents a predominantly hydrophilic surface area for interaction with other proteins (FIG. 3). A total of 11 aspartates, 16 glutamates, 7 arginines, 19 lysines and 4 histidines are on the surface of the structurally defined part of this domain. This suggests that the helices of this domain could participate in interactions with other helical proteins with specificity arising from the interdigitation of complementary charges.

Figure 4A:
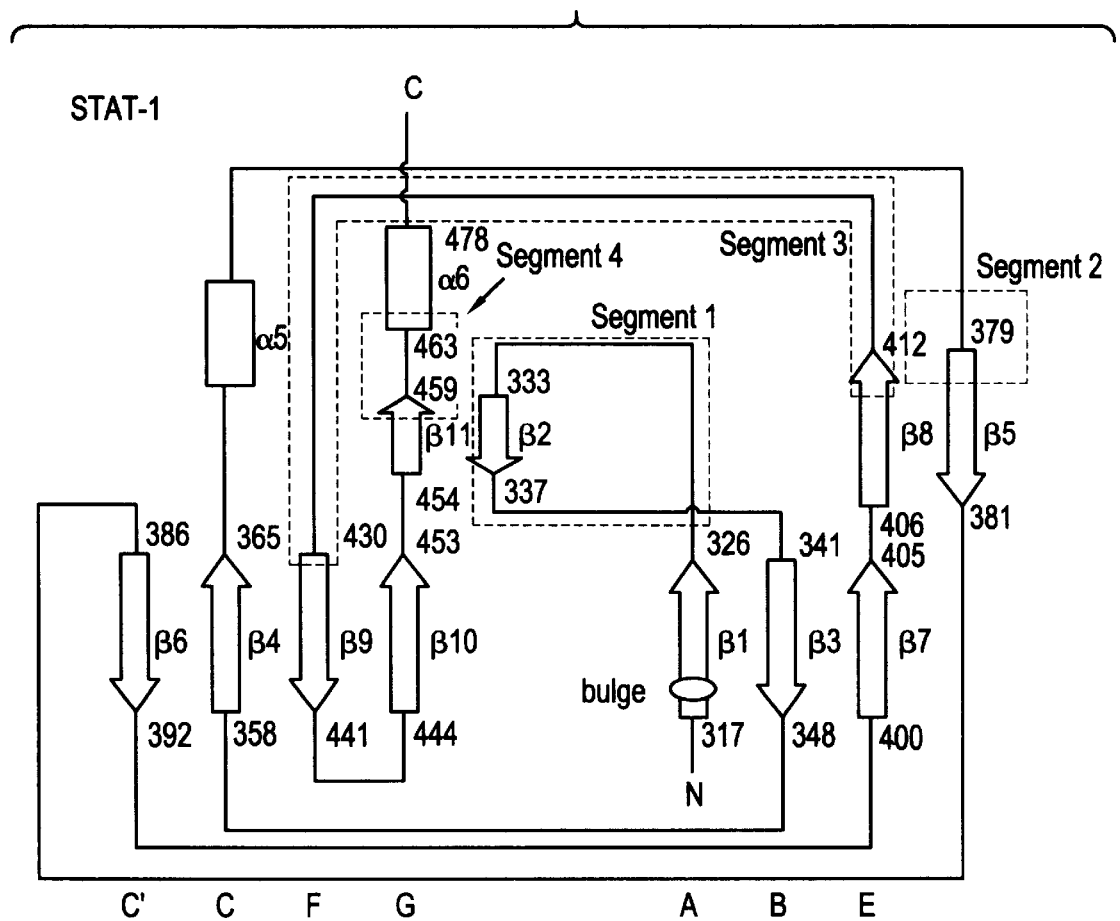
FIGS. 4A–4D show the structure of the STAT-1 DNA binding domain.
Figure 4A:
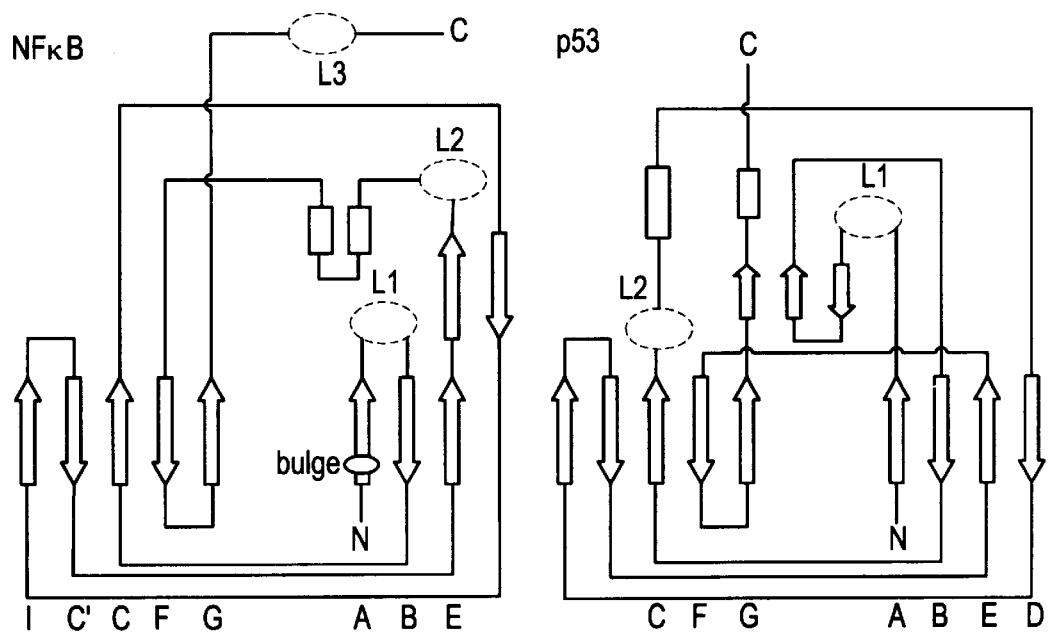

DNA Binding Mechanism: The general architecture of the domain is that of an immunoglobulin fold [Bork, P. et al., *J. Mol. Biol.* 242:309–320 (1994) (FIG. 4A)]. The β strands in the domain mainly run parallel to the major axis of the domain, and this axis is oriented perpendicular to the direction of the DNA axis (FIG. 4C). As a consequence, all of the loops at one end of the β sheet arrangement face the DNA, and amino acids in four segments make contacts with DNA (see FIGS. 4A and 4B for the notation used in this discussion). DNA binding Segment 1 includes two loops, between β1 and β2, and between β2 and β3. Segment 1 positions Lys 336 in the major groove and makes additional contact with the phosphate backbone of DNA. Segment 2, connecting α5 to β5, is the most distant from the DNA, but the sidechain of Arg 378 from this segment extends towards the DNA and makes contact with the phosphate backbone. Segment 3 is a long connector between strands β8 and β9, and it interacts with the minor groove and makes phosphate contacts in the major groove. The most important DNA recognition element is Segment 4, the connector between β11 and helix α6 at the C-terminal end of the DNA-binding domain. Asn 460 is positioned deep into the major groove by Segment 4, where it makes close contact with base pairs at positions 1 and 2 and can also interact, potentially via water molecules, with the A:T base pair at position 3. Segment 4 is coupled to the phosphotyrosine binding site via the linker domain, as discussed below.

Figure 4B:
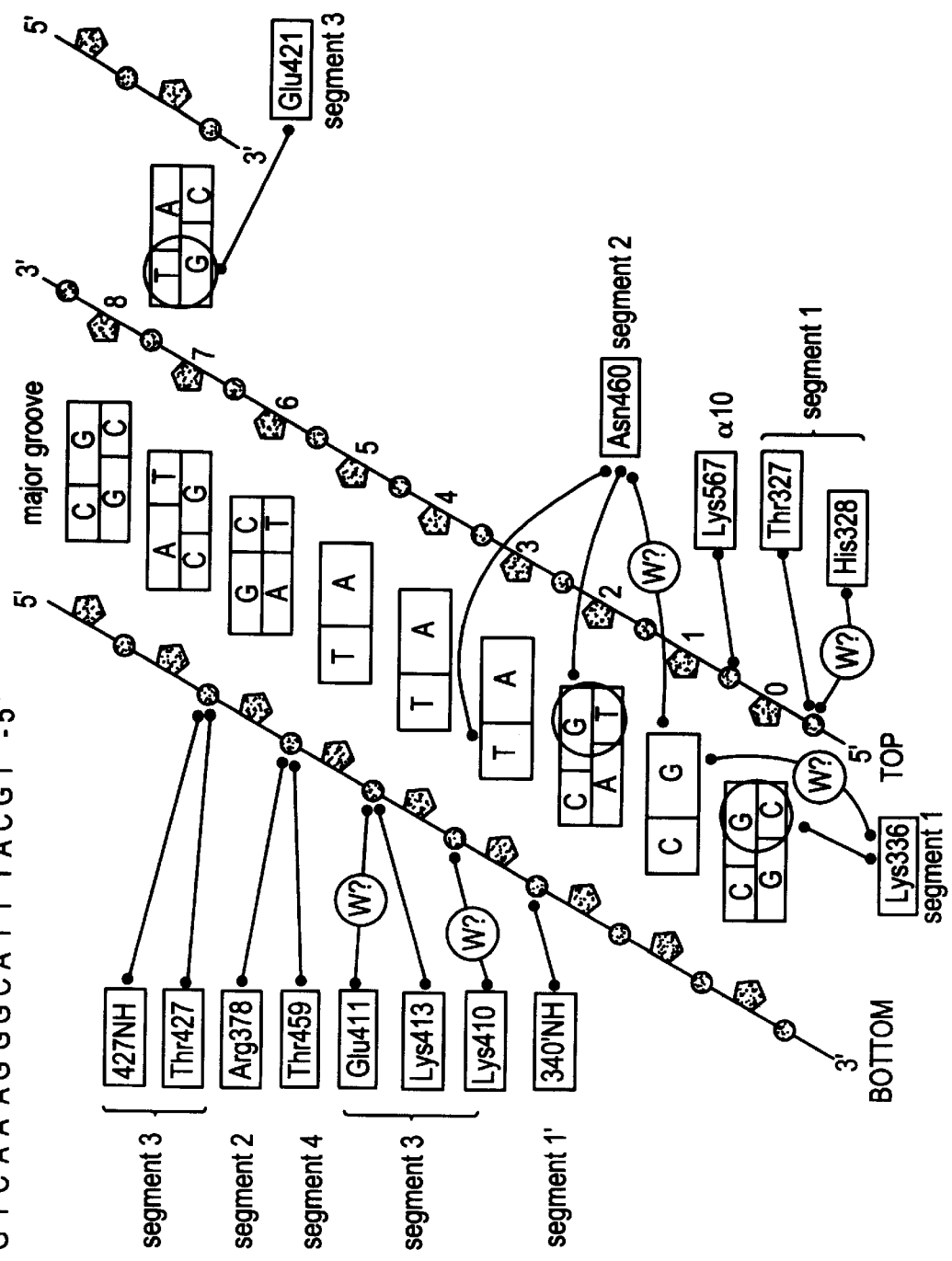
Figure 4C:
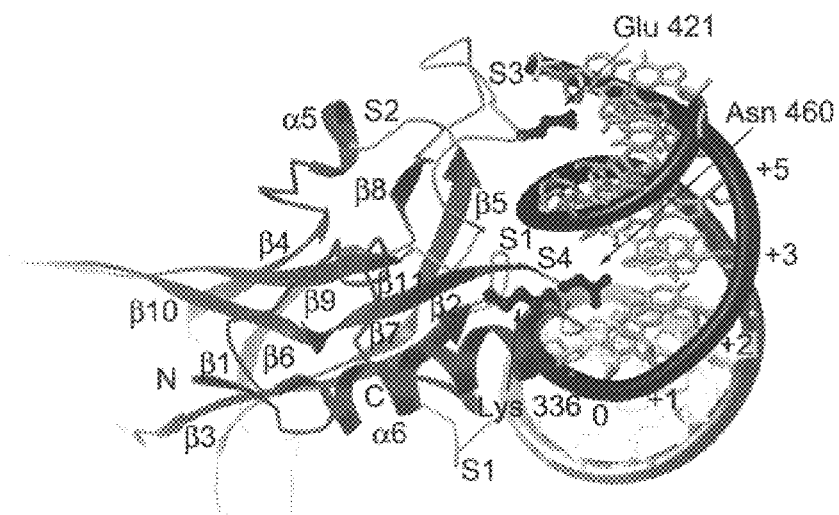

A crystallographic two-fold axis of symmetry passes through the center of the oligonucleotide in the crystals of STAT-1 core complexed to DNA (FIG. 4B). This two-fold axis also relates one STAT-1 monomer in the dimer to the other monomer, and thus each STAT-1 monomer in the crystallographic unit is bound to a 2-fold averaged DNA. However, the 18 basepair oligonucleotide that resulted in the best crystals of the STAT-1 DNA complex is not dyad symmetric (ACAGT<u>TTCCCGTAAA</u>TGC, (SEQ ID NO:33) the core sequence element is underlined and the central C/G is numbered 0, see FIG. 4B). This DNA corresponds to the so-called M67 variant of a region of the c-fos promoter [Wagner, B. J. et al., *EMBO J.* 9:4477–4484 (1990)]. The M67 site has been used widely in studies on STAT binding to DNA, and binds to STAT-1 strongly [Vinkemeier, U. et al., *EMBO J.* 15:5616–5626 (1996)]. The lack of dyad symmetry in the M67 site complicates the interpretation of sequence specific contacts between STAT-1 and DNA in this structure, since non-equivalent base pairs are superimposed at several positions in the crystallographic structure of the DNA.

Despite the asymmetry in the DNA sequence, the structure of the DNA binding domain and of the DNA is in general very well resolved in the electron density maps (see Material and Methods above). The temperature factors of atoms in the DNA binding domain (average value of 37 Å$^2$) and the DNA (average of 33 Å$^2$) are among the lowest in the STAT-1 core structure (average of 46 Å$^2$ over the whole protein, excluding the DNA binding domain). The heterogeneity in the DNA sequence does appear, however, to be correlated with localized regions of conformational disorder in the protein. For example, the region of Segment 3 that contacts DNA in the minor groove is very poorly resolved in the electron density. The most likely explanation of this is that Glu 421, which can interact with the exocyclic amino group of guanine at position 7 in the minor groove, is expelled from the minor groove in the half sites that contain thymine at this position instead (FIG. 4B).

The crystal structure shows that the STAT dimer contacts DNA over a 15 basepair region, consistent with studies on the sequence specificities of STAT-1 and -3 [Horvath, C. M. et al., *Genes Dev.* 9:984–994 (1995)]. The selection experiments for STAT-1 suggest the following consensus sequence for optimal DNA binding:

{G/A/C}A{A/C/T}<u>TTCC{C/G}GGAA</u>{G/A/T}TG (the core consensus element is underlined) [Horvath, C. M. et al., *Genes Dev.* 9:984–994 (1995)]. Selection for C:G or G:C basepairs at the 0, 1 and 2 positions are likely to be mediated by Asn 460 and Lys 336, which make direct (in the case of Asn 460) or potentially water mediated (in the case of both residues) interactions with these basepairs. The rotamer of the Asn 460 sidechain is defined by hydrogen bonding interactions between its terminal oxygen atom and the backbone amide group and the sidechain hydroxyl of Ser 462. The nitrogen atom of the asparagine sidechain is thus firmly positioned in the major groove, where it can donate hydrogen bonds to the O6 and N7 atoms of a guanine base of a G:C basepair at position 2.

Selection for the two A:T basepairs at positions 3 and 4 is likely to involve interactions with Asn 460 and may also be an indirect consequence of DNA deformation at these positions. The minor groove is significantly narrowed at these positions (the phosphate—phosphate distances across the groove is ~8 Å, in contrast to ~12 Å in B-form DNA). This deformation may help select for A:T base pairs, and a similar minor groove narrowing and associated selection for A:T basepairs has been noted for the for the p53-DNA interaction

[Cho, Y. et al., *Science* 265:346–355 (1994)] and for NFkB [Müller, C. W. et al., *Nature* 373:311–317 (1995)]. Finally, the structure suggests that selection for a G:C basepair at position 7 is likely to involve Glu 421 from Segment 3, which can accept hydrogen bonds from guanine in the minor groove.

The general aspects of the interface between the STAT-1 DNA binding domain and DNA suggest that relatively few direct contacts between STAT-1 sidechains and the DNA bases are likely to occur. This is consistent with the pattern of sequences in natural STAT binding sites, which do not show a sharply defined consensus sequence. Rather, specificity in DNA targeting is likely to arise from interactions between one STAT dimer on DNA and other proteins, particularly other STAT dimers bound to adjacent DNA sites [Vinkemeier, U. et al., *EMBO J.* 15:5616–5626 (1996); Xu, X. et al., *Science* 273:794–797 (1996)].

Similarities in the DNA binding domains of STAT, NFkB and p53: The utilization of immunoglobulin folds for the recognition of DNA was first seen in the tumor suppressor p53 [Cho, Y. et al., *Science* 265:346–355 (1994)] and in proteins that contain Rel homology domains, such as the p50 subunit of NFkB [Ghosh, G. et al., *Nature* 373:303–310 (1995); Müller, C. W. et al., *Nature* 373:311–317 (1995)]. A search of the protein database using the DALI server [Holm, L. and Sander, C., *J. Mol. Biol.* 233:123–138 (1993)] shows that the STAT-1 DNA binding domain is most closely related in structure to the DNA binding domains of p50-NFkB and p53. Structural alignments result in rms deviations of Cα positions of 3.0 Å over 106 residues and 3.4 Å over 1 13 residues for NFkB and p53, respectively.

NFkB and p53 are proteins that are unrelated except for their common immunoglobulin fold. NFkB is a member of the Rel family of transcription factors, and it plays an important role in cellular signal transduction in the immune system [Baeuerle, P. A. and Henkel, T., *Annul. Rev. Immunol.* 12:141–79 (1994)], while p53 is a tumor suppressor gene that is crucial for the control of DNA repair pathways [Friend, S., *Science* 265:334–335 (1994)]. Analysis of the strand connectivity shows that the particular variations on the general immunoglobulin fold that are seen in the STAT-1 DNA binding domain are similar to variations seen in either p53 or p50-NFkB (FIG. 4A). All three proteins bind to DNA using the same face of the immunoglobulin fold, using a similar set of loops. However, there are differences in the lengths and detailed structures of the loops in the three proteins, and consequently the orientation of DNA with respect to the protein is different in each of the three cases and the specific DNA sequences that are recognized are unrelated.

Given the close structural similarity between immunoglobin folds in general [Bork, P. et al., *J. Mol. Biol.* 242:309–320 (1994)], the significance of the structural correspondence between STAT-1, NFkB and p53 is of interest. The structural similarity between the three proteins is not reflected at the level of amino acid sequence, which makes it difficult to assign evolutionary significance to these relationships (sequence identity between STAT-1 and NFkB or p53 is 13% and 7%, respectively, for the structurally aligned regions). However, two aspects of the structural comparison are striking, and suggest functional correspondences that go well beyond just the utilization of a common fold. These involve comparison of the DNA recognition mechanism of STAT-1 to that of p53, and the mechanism of dimerization of STAT-1 to that of p50-NFkB.

The structural segments that recognize DNA in STAT-1 are remarkably similar in detail to the corresponding elements of p53. A distinctive aspect of the STAT-1-DNA interaction is the positioning of Asn 460 of Segment 4 in the major groove of DNA, which is brought about by strand β11 and the C-terminal helix α6 (FIG. 4C). An analogous interaction occurs in p53, where a C-terminal α-helix is important for positioning residues at the major groove [Cho, Y. et al., *Science* 265:346–355 (1994)]. Likewise, the interaction of Segment 2 of STAT-1 with the minor groove of DNA is mirrored in p53, which also interacts with the minor groove of DNA. Both these interactions are specific to the STAT-1-p53 comparison, since the p50 subunit of NFkB lacks the C-terminal α-helix and does not interact directly with the minor groove of DNA.

Figure 4D:
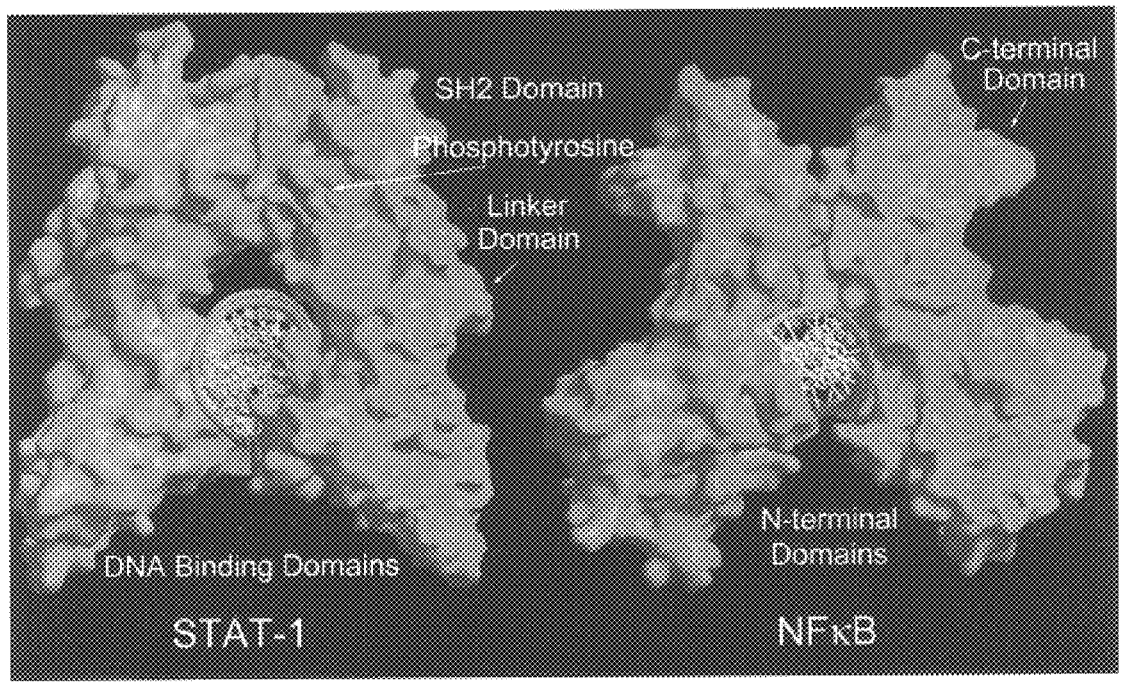

Dimer formation in both NFkB and STAT-1 results from interactions made by domains other than the DNA binding domain. The p50 subunit of NFkB contains two domains with immunoglobulin folds [Ghosh, G. et al., *Nature* 373:303–310 (1995); Müller, C. W. et al., *Nature* 373:311–317 (1995)]. The larger N-terminal domain makes sequence specific contacts with the DNA, while the C-terminal domain mediates dimerization and makes contact with the DNA backbone. Superposition of the N-terminal domain of p50-NFkB with the DNA binding domain of STAT-1 results in an overlay of the C-terminal dimerization domain of NFkB upon the linker and SH2 domains of STAT-1. These two STAT-1 domains are completely unrelated in structure to the C-terminal domain of p50-NFkB, but like the C-terminal domain of NFkB they are involved in forming the DNA-bound dimer (FIG. 4D).

Comparison of the p50-NFkB and STAT-1 dimers on DNA also emphasizes a key difference in the DNA binding properties of the two molecules. The p50-NFkB homodimer binds DNA tightly, with a dissociation constant in the picomolar range [Baeuerle, P. A. and Henkel, T., *Annu. Rev. Immunol.* 12:141–179 (1994)]. In contrast, STAT-1 binds to single DNA binding sites much more weakly, with a short half-life and dissociation constants in the nanomolar range [Vinkemeier, U. et al., *EMBO J.* 15:5616–5626 (1996)]. One structural difference between the NFkB and STAT-1 dimers on DNA is likely to underlie the difference in interaction strengths. The dimerization domain of p50-NFkB makes extensive direct contacts with the phosphate backbone of DNA [Ghosh G. et al., *Nature* 373:303–310 (1995); Müller, C. W. et al., *Nature* 373:311–317 (1995) (FIG. 4D)]. In contrast, the structure of the STAT-1 dimer holds the linker and SH2 domains at a greater distance from the DNA backbone, and restricts direct contacts with the DNA to the STAT-1 DNA binding domain (FIG. 4D). The clear separation in STAT-1 of the dimerization region from the region of direct DNA contact might explain the much weaker binding of the STATs to DNA.

Figure 5A:
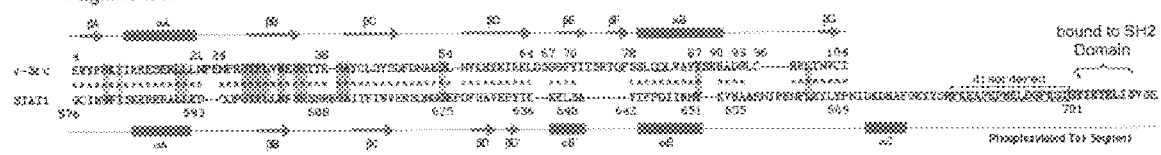
FIGS. 5A–5B show the structure of the STAT-1 SH2 domain.
Figure 5A:
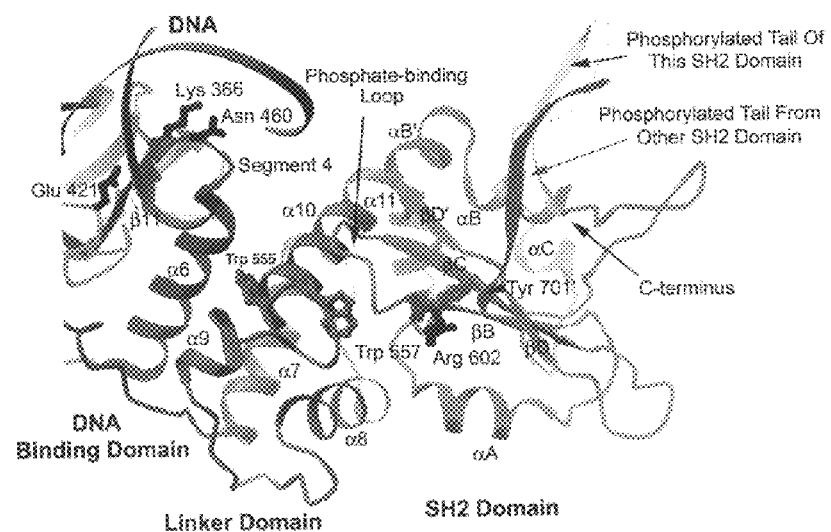

The STAT-1 SH2 domain: The STAT SH2 domains are quite divergent in sequence from most other SH2 domains, perhaps reflecting their appearance early in the evolution of phosphotyrosine signaling in eukaryotic cells. [Darnell, J. E., *Proc. Natl. Acad. Sci.* (USA) 94:11767–11769 (1997) and *Science* 277:1630–1635 (1997); Kawata, T. et al., *Cell* 89:909–916 (1997)]. Nevertheless, the basic architecture of the STAT SH2 domain and the mechanism for recognizing the phosphotyrosyl polypeptide are both fundamentally the same as that elucidated for other SH2 domains (reviewed in [Kuriyan, J. and Cowburn, D., *Annu. Rev. Biophys. Biomol. Struct.* 26:259–288 (1997)]. An antiparallel β sheet flanked by two α-helices forms the core of the domain, and the phosphorylated tail segment, emanating from the other monomer in the dimer, binds in an extended conformation in a direction orthogonal to that of the strands of the sheet (FIG. 5).

Figure 1B:
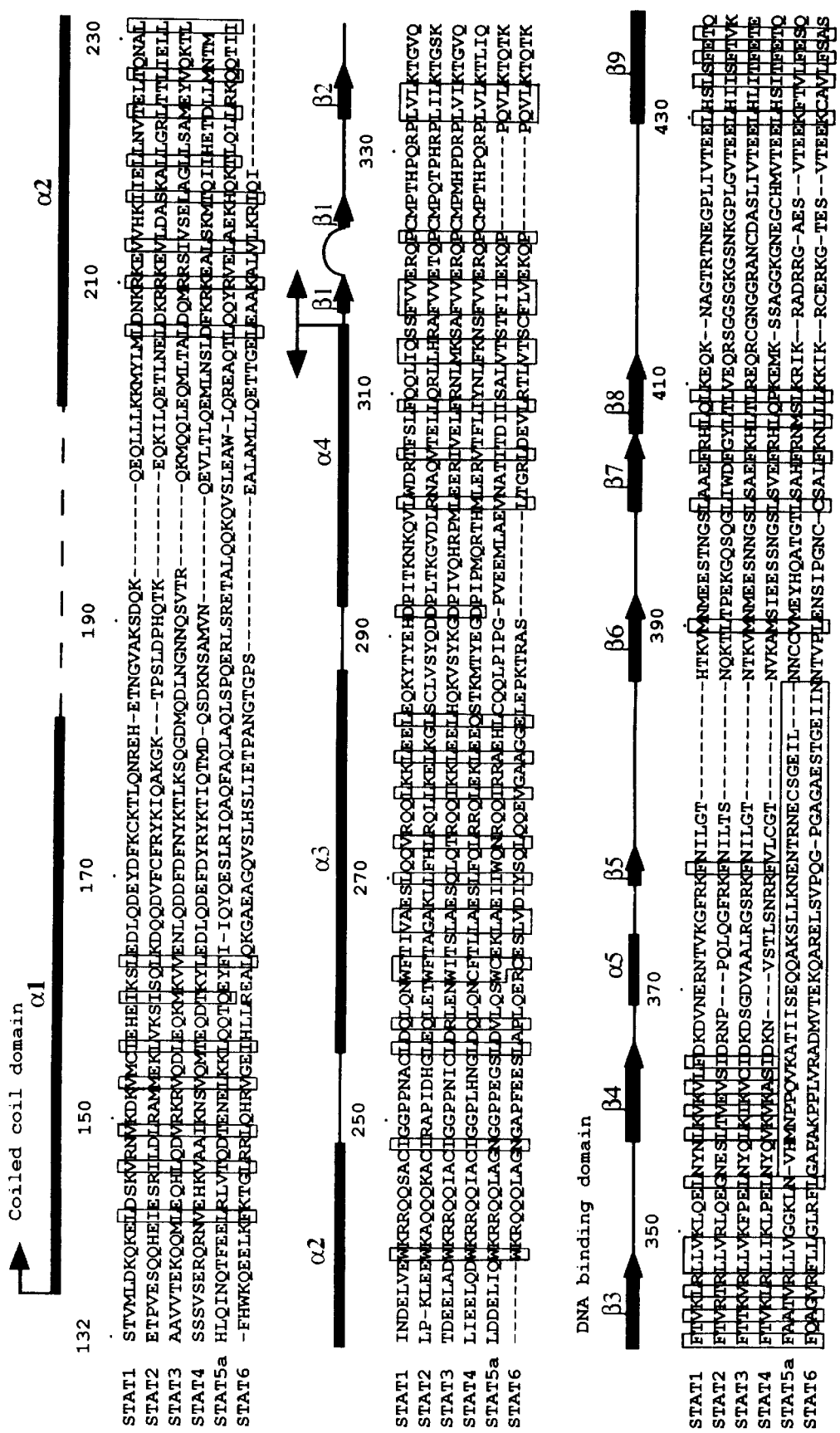
Figures 1, 1B:
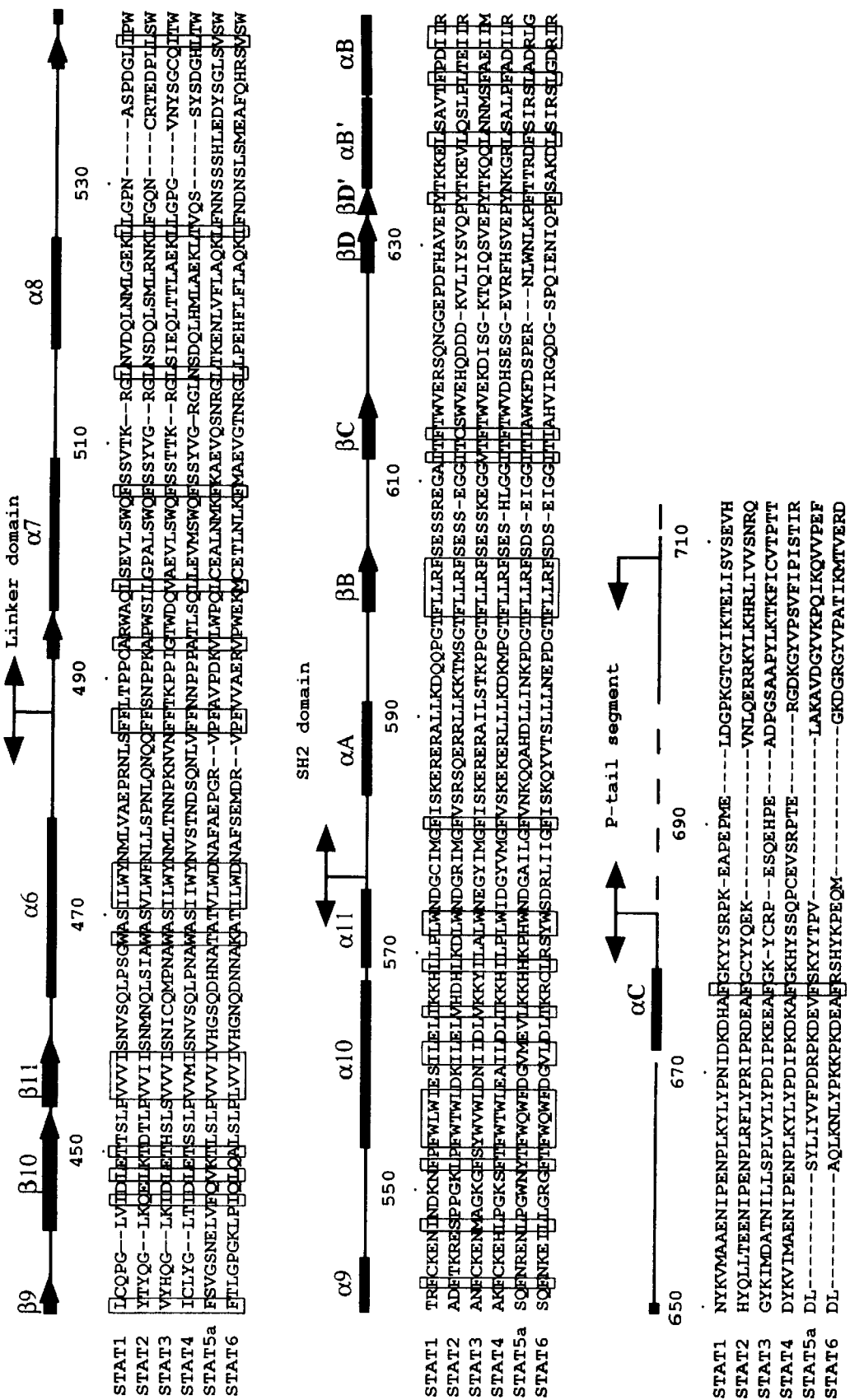

A defining aspect of the SH2-phosphotyrosine interaction is the recognition of the phosphate group of the phosphotyrosine by an arginine residue that rises up from the interior of the domain to engage the ligand. This arginine is strictly conserved in all known SH2 domains, and Arg 602 in strand βB of the STAT-1 SH2 domain plays this role (see FIG. 5 for the notation used) [Shuai, K. et al., Nature 366:580–583 (1993)]. Residues in the loop connecting strands βB and βC also coordinate the phosphate group, again with close similarity to the well known mechanism of phosphotyrosine recognition. In most SH2 domains helix αA provides another arginine sidechain that interacts with the phosphate group, the tyrosine ring and the polypeptide backbone of the ligand [Waksman, G. et al. Nature 358:646–653 (1992)]. This residue is missing in the STAT-1 SH2 domain, and its place is taken by Lys 584, which coordinates only the phosphate group and is conserved in the STATs (FIG. 1B).

The conservation in SH2 structure is particularly striking when one considers that only 16 residues are identical over the ~100 residue span of the SH2 domains of STAT1 and the prototypical one of the v-Src tyrosine kinase [Waksman, G. et al., Nature 358:646–653 (1992)]. An alignment of the three-dimensional structures of the Src and STAT-1 SH2 domains shows that the two chain folds are in register from the N-terminus of the Src SH2 domain through to the C-terminal boundary of the domain in v-Src (FIG. 5A). The DALI [Holm, L. and Sander, C., J. Mol. Biol. 233:123–138 (1993)] alignment of the two structures results in an rms deviation of 2.6 Å over 86 aligned residues, with quite limited insertions and deletions in the two sequences (FIG. 5A).

Mechanism of SH2-mediated Dimer Formation: The phosphotyrosine binding sites are at the distal edges of the inter-SH2 interface, and the C-terminal segment emanating from one SH2 domain has to cross the length of the other one before arriving at the binding site. The linker connecting the last structured residue in the STAT-1 SH2 domain (Arg 683) to pTyr 701 is not visible in the electron density maps. This linker has the sequence $^{684}$PKEAPEPMELDGPKGTK$^{700}$ (SEQ ID NO:35), and the preponderance of prolines, glycines and hydrophilic residues in this sequence is consistent with its role as a flexible tether that allows the phosphotyrosine to span the 18 Å distance to the binding site on the other SH2 domain. An inter-domain exchange of tail segments is enforced by the fact that the phosphotyrosine binding site on the same SH2 domain is located on the other side of the domain from Arg 683, and is therefore not accessible to the tail segment [Shuai, K. et al., Cell 76:821–828 (1994)].

Figure 5B:
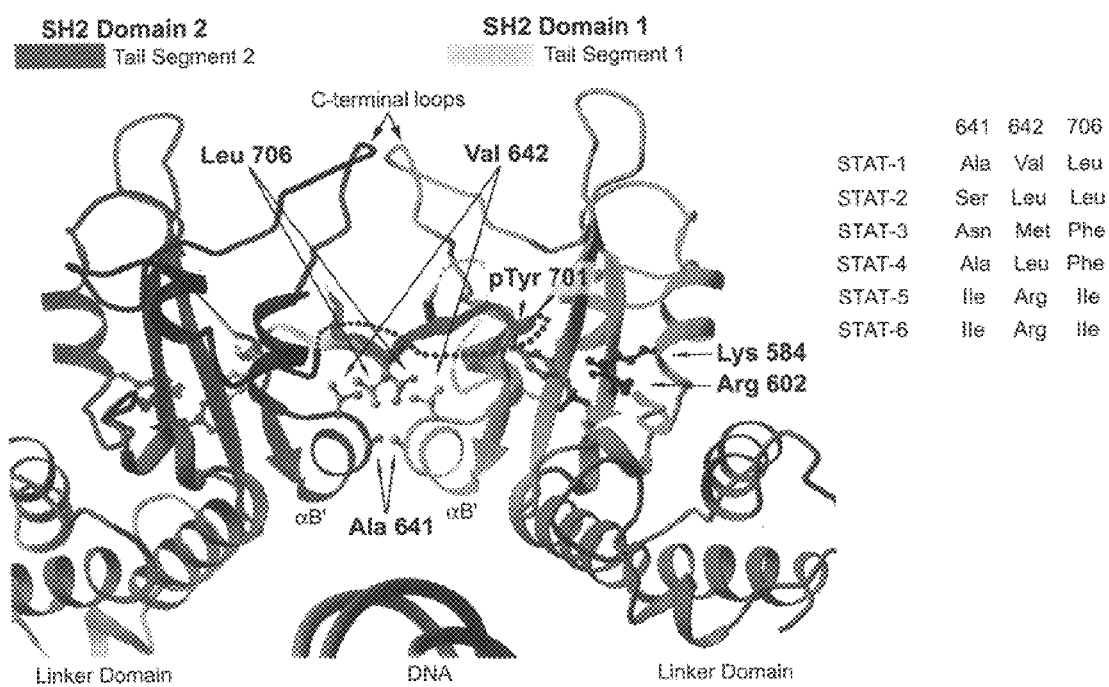

A characteristic aspect of SH2 domains that is preserved in STAT-1 is that interactions between the SH2 domain and its ligand are limited primarily to the residues that are C-terminal to the phosphotyrosine. This feature is a consequence of the geometry of phosphopeptide recognition, which occurs at one edge of the domain, and in STAT-1 it results in the formation of a pair of cross-over connections by the C-terminal segments of the two SH2 domains (FIG. 5B). The two tail segments form a 2-stranded anti-parallel β sheet that passes through a tunnel formed by the αB helix and the C-terminal extension of the SH2 domain (FIGS. 2B and 5B). This structural arrangement results in the tail segment being recognized by the SH2 domain over a 7 residue length subsequent to the phosphotyrosine.

The interaction between the two SH2 domains of the STAT-1 dimer is mediated almost exclusively by the phosphorylated tail segment (residues 701 to 708). This explains the ability of a peptide corresponding to STAT-1 residues 693 to 707 that is phosphorylated on Tyr 701 to break apart the DNA complexes formed by phosphorylated STAT-1 [Shuai, K. et al., Cell 76:821–828 (1994)]. The residues C-terminal to the phosphotyrosine are bound to the surface of the SH2 domain, with important interactions occuring at the +1, +3 and +5 positions of the tail segment, numbered relative to the phosphotyrosine. The residue at the +5 position is likely to be particularly crucial because it is at this point that the tail segment enters the tunnel formed by helices αB' at the base and the C-terminal loop connecting helix αC to the C-terminal end of the SH2 domain, at the top (see FIG. 5B). Consequently, sidechains at +5 (Leu 706), +6 (Ile 707) and +7 (Ser 708) are important mediators of the dimer interaction. In STAT-1 Leu 706 packs into a hydrophobic binding site that is formed by the close apposition of two symmetry related helices αB' (see FIG. 5B). The sidechains of Ala 641 and Val 642 (in the SH2 domain) are also brought into close contact at this site in STAT-1. Considerable variation in size and chemical properties are seen at these positions between various STATs (FIG. 5B). Subsequent to this point the tail emerges onto the surface of the parent SH2 domain, where it interacts with the tail from the partner SH2 domain.

Structural coupling between the phosphotyrosine binding site and the DNA binding domain: A notable feature of the STAT-1 SH2 domain is that the phosphate binding loop of the SH2 domain is buttressed by a number of interactions with elements of the linker domain, particularly with helix α10 (FIG. 5A). A series of hydrophobic sidechains presented by helix α10 pack into the hydrophobic core of the SH2 domain, right underneath the phosphate binding loop. The conformation of one of these, Trp 557, is likely to be sensitive to phosphotyrosine ligation since its sidechain forms a hydrogen bond with the backbone carbonyl of Ser 604, the sidechain of which is a phosphate ligand.

What is particularly intriguing about the interactions between the linker domain and the SH2 domain is that while one face of helix α10 interacts with the phosphate binding loop, the other face packs directly against helix α6 and Segment 4 of the DNA binding domain. Tip 555, located immediately before the tryptophan that packs under the phosphate binding loop (see FIG. 5B), is positioned so as to hydrogen bond with the carbonyl group of proline 465 in helix α6. Changes in the conformation of Trp 555 are likely to be communicated directly to Segment 4, which is at the base of this helix.

Segment 4 is the most crucial element of the DNA binding interface, and the one that is inserted most deeply into the major groove (FIG. 4C). The coupled interactions seen here between Segment 4 of the DNA binding domain and the phosphate binding loop of the SH2 domain raises the possibility that, in addition to the obvious effect of SH2 ligation upon dimerization, DNA binding in the STATs might be also be modulated directly by the SH2 domain. This feature could be an important aspect of the disassembly of DNA-bound STAT complexes by phosphatases.

Implications for STAT-1 dimer:dimer interaction on DNA: It is now clear that STAT proteins can achieve high affinity and specificity in their interactions with DNA by binding cooperatively to DNA sequences containing tandem arrays of multiple binding sites [Meyer, W. K. et al., J. Biol. Chem. 272:31821–31828 (1997); Vinkemeier, U. et al., EMBO J. 15:5616–5626 (1996); Xu, X. et al., Science 273:794–797 (1996)]. This synergistic recognition of DNA requires the presence of the N-terminal domain of the STATs, which is not required for the binding of STAT-1 core to a single DNA site [Vinkemeier, U. et al., EMBO J. 15:5616–5626 (1996); Xu, X. et al., Science 272:794–797 (1996)]. Recently the structure of the N-domain of STAT-4 has been determined, which is highly homologous to that of STAT-1, and have shown that it forms a dimer in the crystal [Vinkemeier, U. et al., Science 279:1048–1052 (1998)]. The determination of the structure of the STAT-1 dimer on DNA now allows us to construct a model for cooperative interactions between STATs on DNA.

An oligonucleotide containing two STAT binding sites that have an 18 basepair spacing between their centers (10 bp spacing between the ends of the core binding sites) exhibits cooperative binding by STAT-1 dimers [Vinkemeier, U. et al., *EMBO J.* 15:5616–5626 (1996)]. A computer model for this oligonucleotide has been generated by taking one DNA duplex from the STAT-1:DNA crystal structure, adding a 2 basepair B-form DNA extension to it, and then adding on a second DNA duplex from the crystal structure. A model for two STAT-1 core dimers bound to this oligonucleotide is shown in FIG. 6.

Figure 6:
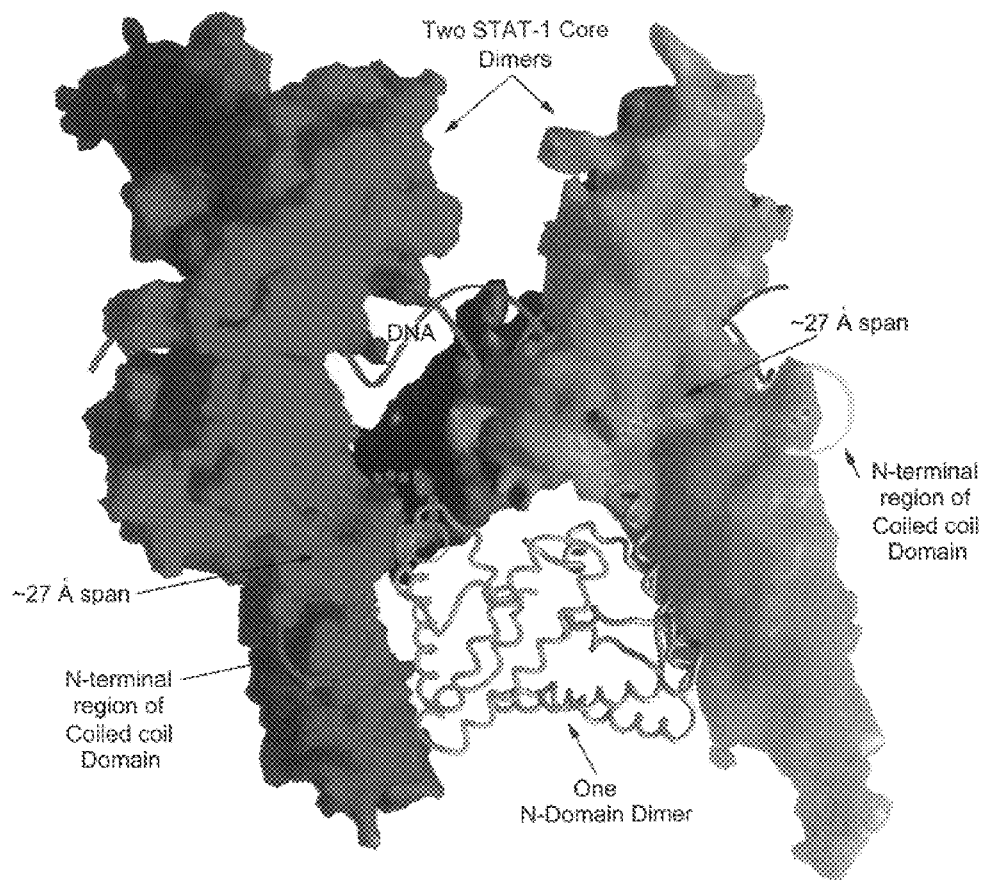
FIG. 6 shows a model for possible interaction between two STAT-1 dimers on DNA. A DNA duplex containing two STAT-1 binding sites with center to center spacing of 18 basepairs, was generated as described in Example 1, below. The DNA backbone is shown as blue and red ribbons. Two STAT-1 dimers (one blue, one purple) are shown bound to these two binding sites, based on the crystal structure of the STAT-1 DNA complex. One of the coiled coil domains from each dimer is extended towards the viewer, and the location of the N-terminal region of this domain is indicated by orange and green circles. The structure of the STAT-4 N-Domain dimer [Vinkemeier, U. et al., *Science* 279:1048–1052 (1998)] is shown in a ribbon representation, and this dimer has been docked so as to place the last helical residue in each monomer at an equal distance from the N-terminal region of the two coiled coil domains.

Each STAT-1 dimer extends out the coiled coil domains on either side of the DNA (FIG. 6). The spacing of 18 basepairs between the centers of the two DNA sites results in a rotation of the two dimers with respect to each other, in addition to the translation between the sites. The rotational offset between adjacent STAT-1 dimers results in the coiled coil extensions fanning out around the DNA, much like the blades of a screw propeller. The N-terminal region of the coiled coil domain is near the base of the domain, in close proximity to the DNA binding domain. The N-domain dimer was docked in between the coiled coil domains of two adjacent STAT-1 dimers, such that the C-terminal ends of each of the two monomers in the N-domain dimer are located at a minimal and equal distance (~27 Å) from the N-terminal ends of two adjacent coiled domains.

Can a ~27 Å distance be spanned by the linker between the N-domain and the coiled coil domain? There are 24 residues separating the last hydrophobic anchor residue of the C-terminal α-helix in the N-domain (Leu 116 in STAT4, corresponding to Leu 116 in STAT-1) and the first hydrophobic anchor residue in α1 of the coiled coil domain (Leu 142). In a fully extended conformation a 24 residue polypeptide can span ~60 Å. The 24 residues in this region of STAT-1 are predominantly hydrophilic, and are likely to be quite flexible in conformation ($^{117}$ENAQRFNQAQSGNQSTVMLDKQKE$^{141}$) SEQ ID NO:36. While the ~27 Å distance between the N-domains is not beyond the physical limit of extension of the polypeptide chain, in reality the distance is expected to be reduced significantly by conformational flexibility in the DNA and the protein, which was ignored in this simple model.

The model suggests that cooperativity in STAT binding to tandem sites on DNA does not result from direct interactions between the core regions of the STAT dimer. The N-terminal region of the coiled-coil domain of each STAT-1 core dimer is positioned so that the loosely tethered N-Domains can interact equally well with another STAT dimer that is on one side or the other of the parent dimer. This allows the formation of open ended complexes of STAT dimers on DNA, without particularly stringent requirements for site to site spacing.

Discussion

The STATs utilize an immunoglobulin fold to bind DNA, much like NFkB and p53. It is striking that the STATs and NFkB, two of the limited number of families of latent cytoplasmic transcription factors that are translocated to the nucleus upon activation, both use similar DNA-binding motifs. There are, however, basic differences in their mechanism. Sequestration of NFkB in the cytoplasm is achieved by binding to an inhibitor which upon release reveals a nuclear localization signal and nuclear translocation of NFkB follows. No nuclear localization signal for the STATs has been identified as yet, and the cytoplasmic unphosphorylated STATs are not bound to inhibitors. Rather, STAT activation requires tyrosine phosphorylation and dimerization, which somehow triggers nuclear translocation.

The SH2 domains first gained prominence because of their capacity to act as independently folded modular peptide binding units [Pawson, T., *Nature* 373:573–580 (1995)]. This concept holds true for the STATs, in that the phosphorylated tail segment interacts only with the SH2 domain, and does so in a conventional manner. However, the structure of STAT-1 makes clear that the SH2 module functions as a tightly integrated component of a complex signaling mechanism. This is reminiscent of the situation in the Src tyrosine kinases, which utilize the same conserved phosphopeptide binding mechanism of the SH2 domain to coordinate an internal ligand, resulting in the inactivation of the enzyme via a subtle mechanism [Sicheri, F. and Kuriyan, J., *Curr. Op. Struct. Biol.* 7:777–785 (1997)].

The following is a list of documents related to the above disclosure and particularly to the experimental procedures and discussions. These documents, and all others cited above, should be considered as incorporated by reference in their entirety.

References

Abrahams, J. P., and Leslie, A. G. (1996). Acta Cryst. D52, 30–42.
Baeuerle, P. A., and Henkel, T. (1994).. Annu. Rev. Immunol. 12, 141–79.
Bork et al. (1994). J. Mol. Biol. 242, 309–320.
Briscoe et al. (1996). Phil. Trans. Royal Soc. (London) B351, 167–171.
Brünger et al. (1998). Crystallography and NMR system: A new software system for macromolecular structure determination. Acta Cryst. D in press.
Carson, M. (1991). Ribbons 2.0. J. Appl. Cryst. 24, 958–961.
Cho et al. (1994). Science 265, 346–355.
Collaborative Computational Project, N. (1994). The CCP4 suite programs for protein crystallography. Acta Cryt. D50, 760–763.
Darnell, J. E., Jr. (1997) Proc. Natl. Acad. Sci. (USA) 94, 11767–11769.
Darnell, J. E., Jr. (1997) Science 277, 1630–1635.
Esnouf, R. (1997) J. Mol. Graphics 15, 133–138.
Friend, S. (1994) Science 265, 334–335.
Fu, X.-Y. (1992) Cell 70, 323–335.
Fu et al. (1990) Proc. Natl. Acad. Sci. (USA) 87, 8555–8559.
Fu et al (1992) Proc. Natl. Acad. Sci. (USA) 89, 7840–7843.
Ghosh et al. (1995) Nature 373, 303–310.
Holm, L., and Sander, C. (1993) J. Mol. Biol. 233, 123–138.
Horvath et al. (1996). Mol. Cell. Biol. 16, 6957–6964.
Horvath et al. (1995) Genes Dev. 9, 984–994.
Ihle et al. (1995) Annu. Rev. Immunol. 13, 369–398.
Jones et al. (1991) Acta Crystallogr. A47, 110–119.
Kawata et al. (1997) Cell 89, 909–916.
Kuriyan, J., and Cowburn, D. (1997) Annu. Rev. Biophys. Biomol. Struct. 26, 259–288.
La Fortelle, E. d., and Bricogne, G. (1997) Methods in Enzymology 276, 472–494.
Leaman et al. (1996) FASEB J. 10, 1578–1588.
Levy, D. E., and Darnell, J. E. (1990) New Biologist 2, 923–928.
Martinez-Moczygemba et al. (1997) J. Biol. Chem. 272, 20070–20076.
Merritt, E. A., and Bacon, D. J. (1997) Meth. Enzymol. 277, 503–524.
Meyer et al. (1997) J. Biol. Chem. 272, 31821–31828.
Müller et al. (1995) Nature 373, 311–317.
Nicholls et al. (1991) Proteins: Struct. Funct. and Genetics 11, 281–296.
Otwinowski, Z., and Minor, W. (1997) Meth. Enzymol. 276, 307–326.
Pawson, T. (1995. Nature 373, 573–580.
Schindler et al. (1992) Proc. Natl. Acad. Sci. (USA) 89, 7836–7839

Schindler et al. (1995) Immunity 2, 689–697.
Shuai et al. (1994) Cell 76, 821–828.
Shuai et al. (1993) Nature 366, 580–583.
Sicheri, F., and Kuriyan, J. (1997) Curr. Op. Struct. Biol. 7, 777–785.
Veals et al. (1992) Mol. Cell. Biol. 12, 3315–3324.
Vinkemeier et al. (1996) EMBO J. 15, 5616–5626.
Vinkemeier et al. Science 279, 1048–1052.
Wagner et al. (1990) EMBO J. 9, 4477–4484.
Waksman et al. (1992) Nature 358, 646–653.
Xu et al. (1996) Science 273, 794–797.
Zhang et al. (1996) Proc. Natl. Acad. Sci. 93, 15092–15096.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

SEQUENCE LISTING

```
<160> NUMBER OF SEQ ID NOS: 37

<210> SEQ ID NO 1
<211> LENGTH: 4003
<212> TYPE: DNA
<213> ORGANISM: Homo sapiens

<400> SEQUENCE: 1
attaaacctc tcgccgagcc cctccgcaga ctctgcgccg gaaagtttca tttgctgtat      60
gccatcctcg agagctgtct aggttaacgt tcgcactctg tgtatataac ctcgacagtc     120
ttggcaccta acgtgctgtg cgtagctgct cctttggttt aatccccagg cccttgttgg     180
ggcacaaggt ggcaggatgt ctcagtggta cgaacttcag cagcttgact caaaattcct     240
ggagcaggtt caccagcttt atgatgacag ttttcccatg gaaatcagac agtacctggc     300
acagtggtta gaaaagcaag actgggagca cgctgccaat gatgtttcat ttgccaccat     360 ccgtttcat gacctcctgt cacagctgga tgatcaatat agtcgctttt ctttggagaa      420
taacttcttg ctacagcata acataaggaa aagcaagcgt aatcttcagg ataattttca     480
ggaagaccca atccagatgt ctatgatcat ttacagctgt ctgaaggaag aaaggaaaat     540
tctggaaaac gcccagagat ttaatcaggc tcagtcgggg aatattcaga gcacagtgat     600
gttagacaaa cagaaagagc ttgacagtaa agtcagaaat gtgaaggaca aggttatgtg     660
tatagagcat gaaatcaaga gcctggaaga tttacaagat gaatatgact caaatgcaa      720 aaccttgcag aacagagaac acgagaccaa tggtgtggca aagagtgatc agaaacaaga     780
acagctgtta ctcaagaaga tgtatttaat gcttgacaat aagagaaagg aagtagttca     840 caaataata gagttgctga atgtcactga acttacccag aatgccctga ttaatgatga      900
actagtggag tggaagcgga gacagcagag cgcctgtatt ggggggccgc ccaatgcttg     960
cttggatcag ctgcagaact ggttcactat agttgcggag agtctgcagc aagttcggca    1020
gcagcttaaa agttggagg aattggaaca gaaatacacc tacgaacatg accctatcac     1080
aaaaaacaaa caagtgttat gggaccgcac cttcagtctt ttccagcagc tcattcagag    1140
ctcgtttgtg gtggaaagac agcctgcat gccaacgcac cctcagaggc cgctggtctt    1200
gaagacaggg gtccagttca ctgtgaagtt gagactgttg gtgaaattgc aagagctgaa    1260 ttataattg aaagtcaaag tcttatttga taaagatgtg aatgagagaa atacagtaaa     1320
aggatttagg aagttcaaca ttttgggcac gcacacaaaa gtgatgaaca tggaggagtc    1380
caccaatggc agtctggcgg ctgaatttcg gcacctgcaa ttgaaagaac agaaaaatgc    1440
tggcaccaga acgaatgagg gtcctctcat cgttactgaa gagcttcact cccttagttt    1500
tgaaacccaa ttgtgccagc ctggtttggt aattgacctc gagacgacct ctctgcccgt    1560
```

```
tgtggtgatc tccaacgtca gccagctccc gagcggttgg gcctccatcc tttggtacaa   1620
catgctggtg gcggaaccca ggaatctgtc cttcttcctg actccaccat gtgcacgatg   1680
ggctcagctt tcagaagtgc tgagttggca gttttcttct gtcaccaaaa gaggtctcaa   1740
tgtggaccag ctgaacatgt tgggagagaa gcttcttggt cctaacgcca gccccgatgg   1800
tctcattccg tggacgaggt tttgtaagga aatatataaat gataaaaatt ttcccttctg   1860
gctttggatt gaaagcatcc tagaactcat taaaaaacac ctgctccctc tctggaatga   1920
tgggtgcatc atgggcttca tcagcaagga gcgagagcgt gccctgttga aggaccagca   1980 gccgggacc ttcctgctgc ggttcagtga gagctcccgg aaggggcca tcacattcac   2040 atgggtggag cggtcccaga acggaggcga acctgacttc catgcggttg aaccctacac   2100
gaagaaagaa ctttctgctg ttactttccc tgacatcatt cgcaattaca agtcatggc   2160 tgctgagaat attcctgaga atcccctgaa gtatctgtat ccaaatattg acaaagacca   2220
tgcctttgga aagtattact ccaggccaaa ggaagcacca gagccaatgg aacttgatgg   2280
ccctaaagga actggatata tcaagactga gttgatttct gtgtctgaag ttcacccttc   2340
tagacttcag accacagaca acctgctccc catgtctcct gaggagtttg acgaggtgtc   2400
tcggatagtg ggctctgtag aattcgacag tatgatgaac acagtataga gcatgaattt   2460
ttttcatctt ctctggcgac agttttcctt ctcatctgtg attccctcct gctactctgt   2520
tccttcacat cctgtgtttc tagggaaatg aaagaaaggc cagcaaattc gctgcaacct   2580
gttgatagca agtgaatttt tctctaactc agaaacatca gttactctga agggcatcat   2640
gcatcttact gaaggtaaaa ttgaaaggca ttctctgaag agtgggtttc acaagtgaaa   2700
aacatccaga tacacccaaa gtatcaggac gagaatgagg gtcctttggg aaaggagaag   2760
ttaagcaaca tctagcaaat gttatgcata aagtcagtgc ccaactgtta taggttgttg   2820
gataaatcag tggttatta gggaactgct tgacgtagga acggtaaatt tctgtgggag   2880
aattcttaca tgttttcttt gctttaagtg taactggcag ttttccattg gtttacctgt   2940
gaaatagttc aaagccaagt ttatatacaa ttatatcagt cctctttcaa aggtagccat   3000
catggatctg gtaggggaa atgtgtatt ttattacatc tttcacattg gctatttaaa   3060
gacaaagaca aattctgttt cttgagaaga gaatattagc tttactgttt gttatggctt   3120
aatgacacta gctaatatca atagaaggat gtacatttcc aaattcacaa gttgtgtttg   3180
atatccaaag ctgaatacat tctgctttca tcttggtcac atacaattat ttttacagtt   3240
ctcccaaggg agttaggcta ttcacaacca ctcattcaaa agttgaaatt aaccatagat   3300
gtagataaac tcagaaattt aattcatgtt tcttaaatgg gctactttgt ccttttgtt   3360 attagggtgg tatttagtct attagccaca aaattgggaa aggagtagaa aaagcagtaa   3420
ctgacaactt gaataataca ccagagataa tatgagaatc agatcatttc aaaactcatt   3480
tcctatgtaa ctgcattgag aactgcatat gtttcgctga tatatgtgtt tttcacattt   3540
gcgaatggtt ccattctctc tcctgtactt tttccagaca cttttttgag tggatgatgt   3600
ttcgtgaagt atactgtatt tttaccttttt tccttcctta tcactgacac aaaaagtaga   3660
ttaagagatg ggtttgacaa ggttcttccc ttttacatac tgctgtctat gtggctgtat   3720 cttgttttc cactactgct accacaacta tattatcatg caaatgctgt attcttcttt   3780
ggtggagata aagatttctt gagttttgtt ttaaaattaa agctaaagta tctgtattgc   3840
attaaatata atatcgacac agtgctttcc gtggcactgc atacaatctg aggcctcctc   3900
```

```
tctcagtttt tatatagatg gcgagaacct aagtttcagt tgattttaca attgaaatga    3960
ctaaaaaaca aagaagacaa cattaaaaac aatattgttt cta                      4003
```

<210> SEQ ID NO 2
<211> LENGTH: 750
<212> TYPE: PRT
<213> ORGANISM: Homo sapiens

<400> SEQUENCE: 2

```
Met Ser Gln Trp Tyr Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
                20                  25                  30

Tyr Leu Ala Gln Trp Leu Glu Lys Gln Asp Trp Glu His Ala Ala Asn
            35                  40                  45

Asp Val Ser Phe Ala Thr Ile Arg Phe His Asp Leu Leu Ser Gln Leu
        50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
```

-continued

```
                355                 360                 365
Asn Glu Arg Asn Thr Val Lys Gly Phe Arg Lys Phe Asn Ile Leu Gly
            370                 375                 380
Thr His Thr Lys Val Met Asn Met Glu Glu Ser Thr Asn Gly Ser Leu
385                 390                 395                 400
Ala Ala Glu Phe Arg His Leu Gln Leu Lys Glu Gln Lys Asn Ala Gly
                405                 410                 415
Thr Arg Thr Asn Glu Gly Pro Leu Ile Val Thr Glu Leu His Ser
            420                 425                 430
Leu Ser Phe Glu Thr Gln Leu Cys Gln Pro Gly Leu Val Ile Asp Leu
                435                 440                 445
Glu Thr Thr Ser Leu Pro Val Val Ile Ser Asn Val Ser Gln Leu
            450                 455                 460
Pro Ser Gly Trp Ala Ser Ile Leu Trp Tyr Asn Met Leu Val Ala Glu
465                 470                 475                 480
Pro Arg Asn Leu Ser Phe Phe Leu Thr Pro Cys Ala Arg Trp Ala
                485                 490                 495
Gln Leu Ser Glu Val Leu Ser Trp Gln Phe Ser Ser Val Thr Lys Arg
            500                 505                 510
Gly Leu Asn Val Asp Gln Leu Asn Met Leu Gly Glu Lys Leu Leu Gly
            515                 520                 525
Pro Asn Ala Ser Pro Asp Gly Leu Ile Pro Trp Thr Arg Phe Cys Lys
            530                 535                 540
Glu Asn Ile Asn Asp Lys Asn Phe Pro Phe Trp Leu Trp Ile Glu Ser
545                 550                 555                 560
Ile Leu Glu Leu Ile Lys Lys His Leu Leu Pro Leu Trp Asn Asp Gly
            565                 570                 575
Cys Ile Met Gly Phe Ile Ser Lys Glu Arg Glu Arg Ala Leu Leu Lys
            580                 585                 590
Asp Gln Gln Pro Gly Thr Phe Leu Leu Arg Phe Ser Glu Ser Ser Arg
            595                 600                 605
Glu Gly Ala Ile Thr Phe Thr Trp Val Glu Arg Ser Gln Asn Gly Gly
            610                 615                 620
Glu Pro Asp Phe His Ala Val Glu Pro Tyr Thr Lys Lys Glu Leu Ser
625                 630                 635                 640
Ala Val Thr Phe Pro Asp Ile Ile Arg Asn Tyr Lys Val Met Ala Ala
                645                 650                 655
Glu Asn Ile Pro Glu Asn Pro Leu Lys Tyr Leu Tyr Pro Asn Ile Asp
                660                 665                 670
Lys Asp His Ala Phe Gly Lys Tyr Tyr Ser Arg Pro Lys Glu Ala Pro
                675                 680                 685
Glu Pro Met Glu Leu Asp Gly Pro Lys Gly Thr Gly Tyr Ile Lys Thr
            690                 695                 700
Glu Leu Ile Ser Val Ser Glu Val His Pro Ser Arg Leu Gln Thr Thr
705                 710                 715                 720
Asp Asn Leu Leu Pro Met Ser Pro Glu Glu Phe Asp Glu Val Ser Arg
                725                 730                 735
Ile Val Gly Ser Val Glu Phe Asp Ser Met Met Asn Thr Val
            740                 745                 750

<210> SEQ ID NO 3
<211> LENGTH: 17949
<212> TYPE: DNA
<213> ORGANISM: Homo sapiens
```

<400> SEQUENCE: 3

```
aagtcgcgac cagagccatt ggagggcgcg gggactgcaa ccctaatcag gtacgggccc      60
tgagagggtg tgctggggta ggggtggggg tgagagtgag agttcctccg agggaagggc     120
gactggccca ggggttaccc cctggagagg gtagcttcct tccccagatt gaaataggag     180
ctgtcgcctg ctcggtcctc gatcttcttc tgtccagcct atctccctaa ccctaatgcc     240
cctctcccaa aactgccctg cagcttccga gacccggaat ctggcattgt tatgttggtt     300
cggtatctga cgttttccc tctgctctgc attattttt atcttcacca aaaacgatg        360
ttcaaagata gataaatcta aaaacaaaga tagataaatc tattacccctt gtttcgtaaa    420
aagtataagc tactgaaaga tgaaacgatt gcctaaggtc acacacaaaa ttcagttcat     480
ttcagaaaag cttcttgagt gcaaatatg tgcctaagaa tgagagataa tgagaaaaaa     540
ttgtttcagc cccttaacct cagtgtttgc aatccatttg gggagaccag gttttttgtt    600
tttgttttca tatttgaatc tttgctgact tgctccttta atatcagaca cttaaatcct    660
cagatgggac tcatcatatt ttttttgaga tggaatcttc actatgttgc tcaagcttgg    720
tctgcaactc ctggctcaag ccatcctctc gtcttgttgg gcctctcgtc ttgtgggcct    780
gcacaaagtg ctgggattac aggcatgagc cattcatgcc ctgggcgcac cttggattgc    840
gatgtgtgtg tgttgtgaag ctttttttt tggtatcata aaagcaatac agatacatag     900
ttttaaaaat caagcagcta ctaaaagagt taaaatgaaa atagcccctc ccaatccctc     960
ccttgttcct gctggaggta gaaaggcagc tgatgttatt catgttagta aagactctc    1020
ccaccccaag catttctctt tattttgtaa taaaatcatg tgaccttttt agaccacaaa   1080
tatgcatgaa ttctgttctg ttaggctcag gctgcaacaa gataagtttc agtttcctaa   1140
atagacacca gctggcagtg agcagggaac agtggggaga aagatgcatg ggacagcctg   1200
cttggtgaca ggcaaaaacc ggtttgttgt tcttttagag acagagtctt gctttgtcac   1260
ccaggctgga gtgtagtgat gtgatctctg cttactgcaa ccctgcctct gggtacaagc   1320
cattctcctg cctcagcctc ttgagtagct gggattacag gcaacaattt taagtgaagt   1380
gaagtttcag gatctcgagc aaagttgtat aacctataat catattcaag attcacaggt   1440
cataaacgtg tcatattctt gggattgagc gacccattgc acagcattta gatgtgcttc   1500
tagaatggag ctcctccttc ctatatggag ggcagtttat atggtgtact acctgacca    1560
ccaaaaagat ttggctctaa aaaagcttca ggtggccggg catggtggtt caccctgta   1620
atccagcact ttgggaggca ggtgggcaga tcacctgagg tcagaagttc agacagctgg   1680
acatatggtg aaacctcatc tctactaaaa atacaaaaat tagactgggc atggtagtgg   1740
gcgcctgtaa tcccagctag tcgggaggct gaggcaggag aatcccttca actcggacgg   1800
cagagtttgc agtgaggccg agatcgtgtc actgcagtcc agcctgggtg acagagcaag   1860
actccatctc aaaaaagta aaaaaaaaa aagaaaaaa aaagcttca gagccagcag       1920
ggatcatgct gtaataaata cttaacatca acactgatct ttaaatgctt tagcacaatc   1980
aaatataaat aacaaacaca cacataaatg caaaataaat gaattaggga gatagatgaa   2040
ataagattgt ggaaatagta atgtttgtta agctggatgt gtgatccttg tactattcac   2100
tctactctag tgtgtatttg aaaattacca ttaggctggt tatggtggct catgcctgtt   2160
aatcccggca ttttggaagg ctgaggcagg cggattactt gagctcagga gtttagagtc   2220
tgcctgggca acatggcaaa atcccatctc tacaaaaaat tagctggcat gatggcacac   2280
```

```
tcctgtagtc ccagctcctt gaggggctga ggcagagaat ggcttgaacc tgagaggcta    2340
aagctgcagt gagccaagat catgccactg cactccagcc tgggtgacca agtgagaccc    2400
tgtctcaaaa aaaaaaaaaa aaaaaagaaa agaaaattcc cattaaagca caaaggccca    2460
cttattgaag ctattaaaat acaggttggg gccggctggg catcgcgtca cgcctgtaat    2520
cccagcactt tggaaggccg aggtaggcga gtcacgagtt caggagatcg agaccatcct    2580
ggctaacacg gtgaaacccc atctctacta aaatacaaa aaaaaaaatc agccgggcat    2640
ggtggcggga gcctatagtc ccagctactc gggaggctga ggcaggagaa tggcatgagc    2700
ccgggaggcg gagcttgcag tgagccaaaa tcacaccact gcactccagc ctgggcaaca    2760
gatcgagact ccatctgaag aaaaaaaaaa tacaggttgg gaccacagtg gctcatgcct    2820
gtaatcctag tactttggga gtccgaagta ggtggatcac ctgaggtcag gactttgaga    2880
ccagcctggc caacatggca aaccccatc tctactaaaa aatatacaaa aattagctgg    2940
gcgtggtggt gggtgcctgt aatcccagct actcaggagg ctgaggcaga agaatcacaa    3000
caaccagggg gatggtggtt gcaatgagcc aagatcatct ccacttcact ccggcccagg    3060
caaaagagtg agagtcatct taaaaaaaaa aaaaaaaaaa aaaaaaaat acagattagg    3120 cattcctaat ctgaaaaatt tggctccaaa atgctccagt cgagcatttc ctttgagtgt    3180
catgtgggtg ctcaaaaagt tagattttg gaccattttc agatttcaga gttttggatt    3240
agggatgctc gactggtaag taatcgagat attccaaaaa tctggacaaa tctgaaatcc    3300
aaaatgcttg gaatagcaga tactcaactg gtagcactcc ctggaagaat atgcaccaaa    3360
ctgatagcag tggttaccttc ctggtgagga ggggaaagaa ccaagattag cagtaggatc    3420
aacatatatt ttaatgtttt ctgtattttt attacttgta taatttaaac atttttaaatt    3480 agtaataatg aacaatcatg aaactatgga tgatttagtc cagcaaaata tccaattggg    3540
aaccctcatc cttctgcaga gcccaaatgg cgcagtggga aatgctgcag atcttgaca    3600 gccccttca ggatcagctg caccagcttt actcgcacag cctcctgcct gtggacattc    3660
gacagtactt ggctgtctgg attgaagacc agaactggtg aggccttcag gaagttgggg    3720
gaatgaaaaa ggtggccttc cacttctggg cccccgggat cctggaatca ttaatggcag    3780
gaaggggttg gaaagcctca ggactacagt aacactgcag agacactaat acttcttatt    3840
cctggtccca ggcaggaagc tgcacttggg agtgatgatt ccaaggctac catgctattc    3900
ttccacttct tggatcagct gaactatgag tgtggccgtt gcagccagga cccagagtcc    3960
ttgttgctgc agcacaattt gcggaaattc tgccgggaca ttcaggtact tggaacggtt    4020
gggagtgatg gggtagcact gggagcagag catagaggag taaggtttgg agaatagaat    4080
agtacctgga ggtggcaagg gagacgggaa caaatgtggg gaaaggagga cagagtctgg    4140
acttggggaa tcactagcag agagaagggt tgcatatacg tgacactgtt gggaggatgc    4200
tatggtgaaa agacaaaggg ctaagaaccc cgaaggagga ggaaatactg tggacattgg    4260
tggggagggt ctagggcaat aggtcattga gagtggttga attggatcaa tcctttctgt    4320
ttaccttcct gttagcccct ttcccaggat cctacccagt tggctgagat gatctttaac    4380
ctccttctgg aagaaaaaag aattttgatc caggctcaga gggcccaatt ggtgaggaca    4440
attcagtggt aatgttggaa actcctgaag tagagaggaa ccatggaaag gactcaggga    4500
gttgtctcag aacaggatcc ccccgacatc ctgtggtata atttcaggcc tgaacttaag    4560
gcatgaaagg ccagagttaa aacgtgctca gagcctcttt tttcaggaac aaggagagcc    4620
agttctcgaa acacctgtgg agagccagca acatgagatt gaatcccgga tcctggattt    4680
```

```
aagggctatg atggaggtta gtagatgtgg taggagttag ggttgacagt gttcagccta      4740
acacctccct gagaagcagc ctcatcgggg tcctctcccc tctgcagaag ctggtaaaat      4800
ccatcagcca actgaaagac cagcaggatg tcttctgctt ccgatataag atccaggcca      4860
aaggtaggaa gcacattgag gggctggaga aagataagtg cctgctgaga agccggagct      4920
ggaagtgaac aggagaaagc tccgatgagc agtagtcact gtcagacaca ccccactgac      4980
tacagtcctg ctgccgtgca aagctggaat cgtgctttgt ggaggctgag ctggaggtga      5040
cagctgagag acagtaaatt gttgaggaaa tgcatggaaa actaacagtg ttttatttga      5100
gggggtgtct ggtccaagat gaccacttca gaatttgcct ggagggtccc acaggtgcct      5160
gtgctttgct tggtttccct ttcttcctcc gccacaaaat tcctccttcc tgactctgac      5220
tgagacccca gtcaggaagg agaggaaaga accctggac tgactcctgt tcccaccatc      5280
cagggaagac accctctctg gaccccatc agaccaaaga gcagaagatt ctgcaggaaa      5340
ctctcaatga actggacaaa aggagaaagg tgggaggcag cagaacagaa catgtgggca      5400
acaaggacct gaaaaaatga gggatgttgg gaaccctggt aatctagcgc tggcttcttt      5460 cttctcttcat ccccagttgg gtggtggagg gtgaaaggga gagatgctca acactcacat      5520
tatctctttc caggaggtg ctggatgcct ccaaagcact gctaggccga ttaactaccc      5580
taatcgagct actgctgcca aagttggagg agtggaaggc ccagcagcaa aaagcctgca      5640
tcagagctcc cattgaccac gggttggaac agctggagac atggtgagag gtaccacccc      5700
aaccctcgtc ctcgccatgc gctgtgattt gtaagttgca gtgccctgca tatagcaaga      5760
gatactgttc tctatttgtc tctgctcccc agaatagagc cctgctccct gcctgactgc      5820
agctctattc tgcctcctca gcctcaccac gcagggaagc ccagaagtcc cagtctcctt      5880
cagggaaagg aatgaattaa cccacaatct ggttttgctt cttttttta atcacccaga      5940 aatatatata tatgtatttt ttttttactg caacgaatac aatgacaaga aaggaaggga      6000
aggaaggaag gaagagaaaa ttacctatta cctagcttat taaacaaaaa tggaatcata      6060
ttgtccatac tattttgaaa tccatggggt ttttttaag cttaacagta ttttatatat      6120
atatatatat atatatatat atatatatat atatatatat atatattttt tttttttttt      6180
tttttttttt tttttgagac ggagtctctc tctgttccct ggctggcgga gcggagtcgg      6240
cacgatctca gctcactgca acttccaact cccacggttc aagccaattc tcctgtctca      6300
gcctcccgag cctgggatta ccaggcacac accagcctgg ctagttttt tgattttta      6360 gtagagacga tgtttctcca tgttggccag gctggtctca aactcctgac ttcaggtgat      6420
ccacccaact tgggctccca aagtgctggg attacaggcg tgacgaccat gcccggccaa      6480
cagtatatta tatttatcca tgttatttct tatgtccaca caacagtccc ctatatggtg      6540
gtaacataat ttaattaatg aactcctatt ttcagctatt taggttattt tcaatttctt      6600 gttaccttt gccaggaaac gtatatttta tggtaattat attgtgttgt agaaaaatca      6660
ctagtctagt ccaacttgct tgaaaaatag ctacttttta actattttct catttaaaaa      6720
tttattataa tttagtcttt tagaaatata ccaggccagg catggcgtct catgcctgtt      6780
atcctagtac tttggaaggc tgaggacgga ggatcacttc agtcttgggg tttgagacca      6840
gcccgggaaa cataacaaga ccccatctct acaaaaaaaa aaaattgttt ttaattaggc      6900
atgtccgaca cagtggctca cacatgtggc cagcactgtg ggaaggccaa ggtgggtgga      6960
tcacttgagg gtcaggagtt caagaccagc ctggccaatg tggtgaaacc ccatctctac      7020
```

-continued

```
taaaaataca aaaatttgcc aggtgtggtg gcgcatgcct gtattcccag ctactcagga   7080
ggctaaggca ggaaatcact tgaactcgga ggcagaggtt gcagtgagct gtgacaatgc   7140
cactgtactc cagcctggt gacagagcga gctccgtctc aaaaaaaaaa aaaaaagatt    7200
aggcatggtg gcacacgcct gtagaccta gctactcagg aggctgaggt gggaggattg    7260
cttgagccca ggtgttggag gctgcagtga gccatgatta taccactgta gtccagcctg   7320
gacaacagaa cgagaccctg tctctaaaag tatatatgta cacataccat aatacccagc   7380
tactgaggag gctgaggcag aaagagtgct tgagtccagg agtttgatgt cagcctgagc   7440
aatatagcaa gaccctcacc tcttaaaaaa atttaaagta gattaaaaaa ataccacaat   7500
tgctcaggta gattaaaaaa ataccacaat tgctcaggta gattattgaa aaacaggcat   7560
atagtactta tggtacagga ccagcatgca tgcatgcatg cattgattga ttgattgatt   7620
gattgattga gacagggtct ctctctgtct cccaggctgg agtgcctggc cttaagtgat   7680
ctgcccacct ttgcttccca aagtgctgag attacaggtg tgagccacca tgtcagctgg   7740
cgaggctttt taaagatag ttccaagtgt tacagctctt ttaggatttg tctagcaggc    7800
tttcaggttt ttgccagaaa ccaccccac ccccaccaaa aaaaaaaaa aaaaaagat     7860 atgtacaagt tcccagatag tgttcccaac tgaatctatt tctcatgtgt agtgtatggt   7920
tgttttcctg tcaccacatt gctgattatt attattttta attatagaga cagtaaagta   7980
cagtagttaa aaatgtgagt tggggctggg tgcagtggct cacacctgta atcccagcac   8040
tttgggaggc caaggtgggc ggatcacctg aggtcaggag ttcaagacca gcttggccaa   8100
catggcaaaa ccccgtctcg actaaaaata tatatatata agttagccgg gcgtggtggc   8160
aacattacct gtaatcccag ctactcggga ggccaacagg caggagaatc tcttgaatcc   8220
aggaggtgga ggttgcagtg agccagatca caccattgca ctccagcctg gatgacaaga   8280
gagtgagact gtctaaaaaa aaaaaacaaa gtgtgagttg tacaatgaga ctgcctggga   8340
tcacatacaa gcttcatccc ttactagttg tattgaccct aaagcaagtc actaaccttt   8400
ctgtgccctc cagttttatc atctgtaatg tggggaaaat aatagtacct gcctcagagg   8460
gttgttttga ggattaaatg cattaatatg tggaaagggc ttaatataag ttgtacatag   8520
catatgaaaa ctgttatgtt aaatctatta gcagttttat atgtgaaaat agctttgatt   8580
ttcatttctt ggattatgaa tcatgttgaa taatcctta tatgcttcct ggattctttt    8640
tttttcttcc ccccagtcag tttctgactc ttctcatatt tatagagaga tcttggaacc   8700
tggatggggg aatccaggaa actcatggat tccttcttcc tgaattttat cacccaggtt   8760
cacagctgga gcaaagctgt tgtttcacct gaggcagctg ctgaaggagc tgaagggact   8820
gagttgcctg gttagctatc aggatgaccc tctgaccaaa ggggtggacc tacgcaacgc   8880
ccaggtcaca gagttgctac agcgtctgct ccacaggtct agaggccagg caggaaccct   8940
gggggaaaga aggaacaagg gaagccattc ttacacatac tgagctatat attctctcca   9000
cacctctctc tcctcgagcc tttgtggtag aaacccagcc ctgcatgccc caaactcccc   9060
atcgacccct catcctcaag actggcagca agttcaccgt ccgaacaagg ttggcattcc   9120
agaactcatt cccacttcct ttttccaacc ctgccactgt gtatttctg gctttacagc    9180 tactgcccac tcttggcttt ttcagtcttt cctgaatctc cctacctcgt tgataccca    9240 tcgtcctctt tttcaaacac ctagcctata caaaagccga ctccgaccac atttccctat   9300
accccttgac ttccccaggc tgctggtgag actccaggaa ggcaatgagt cactgactgt   9360
ggaagtctcc attgacaggt aaattggagc aggtgaaggg tggccaggac acgggctgct   9420
```

```
ggggtggagg agatactcac tcttcacaac agggccctag ggctatatcc ttcctccttc    9480
caatcctacc tcacagaaat tataattcat ttcttttgtt gaacacttac tttgtgacat    9540
gcagcatgtc agctactcat ttaattgtca caccaacccc atgaataaac tattaccagt    9600
gcactgtaca aacaaagata caggcttaga gagactgatt acatctcttc tcaaggccac    9660
atagctagtg agctcaagtc gggtttgaac cgaggtctgt ctgatcccaa agacgaaact    9720
cctaacttcc atactctttt gcccaatgat tttttttaaa tttatttctt ttcaggaatc    9780
ctcctcaatt acaagggtag gtgcttgaca aggacactgc aaacatctgt acagtgtatg    9840
acctgcagaa ccgggggatt tgggaaatgg acaagggag atggcgagat ctgaaatgga     9900
agtggaactt cagttttttt tttttctgct gagttttttac aataattcca ttccttgtct   9960
ccatgtatct tcctcctgga acagcttccg gaagttcaac attctgactt caaaccagaa   10020
aactttgacc cccgagaagg ggcagagtca gggtttgatt tgggactttg gttacctggt   10080
aagaatagtt tgtgacctat gcttttatta ctatttttat tttttcgaga cggagtctca   10140
ctctgtcccc caggctggag tgcagtggtg ccatcttggc tcacaggaac ctccgccctc   10200
cccggttcaa gcaattcttc tgtctcagcc tcctgagtac gtagagctat aggcagcaca   10260
ccaccatgcc cggctaattt ttgtattttt agtagagata gggtttcacc atattggtcg   10320
ggctggtctc gaactcctga cctcaggtga tccgacccgc ctcagcctcc caaagtgctg   10380
ggatcacagg catgagccac catagctggc ctgcttttag tccaaaggaa caggggttgg   10440
gggaagttcc cagggcttga gaggtcttga agccaaacag gggttccagg gagactaggg   10500
tgcccactct ggcattttct ctccttccct tcaattcaca gactctggtg gagcaacgtt   10560
caggtggttc aggaaagggc agcaataagg tgagatctgg acagaggact cgaggcaggg   10620
ggagcttgcc aaagagcctt ctgatgacta tgtctttgcc tgtcccagag gggccactag   10680
gtgtgacaga ggaactgcac atcatcagct tcacggtcaa atatacctac cagggtctga   10740
agcaggagct gaaagtgagt gaaaatggag ggcaaggaga gagaaagcag ctttggaaga   10800
aggcataaga agggggataaa cagaagcctc ttggggaggg ttagcactcc tttcctctaa   10860
caaatacctg cagctagaaa catcacatcc ctctctgtga ctcctgtctt ctccccacac   10920
acggacaccc tccctgtggt gattatttcc aacatgaacc agctctcaat tgcctgggct   10980
tcagttctct ggttcaattt gctcagccca aaccttcagg taggggagtg gggccgacag   11040
gtcccggcgc gagagcaggg gtgtggaagc ttggtgtgat aggttgcttc tgagccagcc   11100
tacactgctc ccaccctgc agaaccagca gttcttctcc aacccccca aggcccctg      11160 gagcttgctg ggccctgctc tcagttggca gttctcctcc tatgttggcc gaggcctcaa   11220
ctcagaccag ctgagcatgc tgagaaacaa gctgttcggt acagatttcc ttttctctca   11280 gccttcccc agccttagtc ttttctgtcc ctctgtccta tctatcccag gaccctggc     11340 ttccctcaca tatctgtggc tatctgtccc acagggcaga actgtaggac tgaggatcca   11400
ttattgtcct gggctgactt cactaaggta actccctgaa tcctgtggag ctgctggatc   11460
tagccccaca ttccaaatac tggccttccc acgtgccctc cttccctaca ccagaggcaa   11520
ctcctcagct tttgctacct ttccattcct ccagcgagag agccctcctg gcaagttacc   11580
attctggaca tggctggaca aaattctgga gttggtacat gaccacctga aggatctctg   11640
gaatgatggg taaggccttg gtcacccttc cctcatgggc ttgtgcttcc gggcttgaga   11700
gtggagtctc tgcaccctca cgtggcaagc agggagagag agcaaagcac ggtgcaggcc   11760
```

```
acgtctcctc acatttgtta agaataataa ggccgggtgt ggtggctcac acctgtaatc  11820
ccagcacttt gggaggccga ggcgggcgga tcatgaggtc aggagatcga gaccatcctg  11880
gctaacacgg tgaaacccccg tctctactct aaaaatacaa aaaattagcc gggcgtggag  11940
gcagacaccc tgtagtccca gctactcagg aggctgaggc aggaaaatgg cgtgaacctg  12000
ggagatggag cttgcagtga gccgagattg cgtcactgcc ctccagcctt ggggtgacgt  12060
agcaagactc cgtctcaaaa aaaaaaaaa aaacaacca ataatagcca taaacagtgt  12120
ttttgtgaag cactcctaca ttccagagct tgatgggtgc tcttcattaa ttctctcatc  12180
tcatccttac aaccatgctg agtggtgggt tttgccagct tcatttcatg tgaggaaact  12240
gagtttcaga gaagttaaag aacttaccca agggacacag ttgatattca aatccaggcc  12300
tatgtgactc caagcccatg ctctttccac cacactgcct accaacttgt gtagcatttg  12360
gcttttaaaa gtgctattca tgaccaggca cgatggctca cgccttgtaa tcccagcatt  12420
ttgggaggcc gaggtgggtg gatcacctga ggtcaggagt ttgagaccag cctggccaac  12480
atggcgaaac cccatctcta ttaaaaatac aaaaattagc cgggtgtggt ggtgggcgcc  12540
tgtaatccca gctactcagg aggctgagga ggagaatcgc ttgaatttag gagagaaggt  12600
tacagtgagc caagatcgtg ccattgcact ccagcctggg tgacagagca agactctgtc  12660
tcaaaacaaa accaaaaaaa agtgctattt gtggccaggc gtggttgctc atgcctgtaa  12720
tcctagcatt tttggggagg ctgaggagta cagatcactt gagcccagga gttcaaaact  12780
accctgggcc acgtggtgaa accccaaacc ccgtctctac gaaaaataca aaagttagcc  12840
aggatgggtg gtgtgcacct gtggtcccag ctactctgga ggctgagagg tgggaagat  12900 tgcttgagcc cgggaggtcg aggtggcagt gagctgtgat catgccacta ttctccagcc  12960
tgggtgacag aatacaccct gtctccctgt ctcccagaaa aaaaaaaag tgctgttcat  13020 ctgtgtgatc tcactgaatc ttcgtacttc aaaccctcgg aaggtggcta ttgtcagcaa  13080
agtgaagtga cttgtaaaag ataaaaaaaa gctaagtggc agggcttggt ccaaagcctg  13140
gattccaaac ctgggctgtt tctccataca aggggagcag ggaggcaggg gcctgggggg  13200
gcagggtgtt gggcggtgtc acacgtgaca cactgtgctc cagacgcatc atgggctttg  13260
tgagtcggag ccaggagcgc cggctgctga agaagaccat gtctggcacc tttctactgc  13320
gcttcagtga atcgtcagaa gggggcatta cctgctcctg ggtggagcac caggatgatg  13380
gtagctgctc tgccctgcca ttcccacagc ctctcctttc tgcctggctc tcctctggcc  13440
cctctgcctg ccttgcttcg ctggctctga actgaatgct cagtggtttg ggactgggca  13500
gccagagagt cagagagctc caaggcccgg cctcttccct caagcccgcc tgttcctgca  13560
ttcactctcc agacaaggtg ctcatctact ctgtgcaacc gtacacgaag gaggtgctgc  13620
agtcactccc gctgactgaa atcatccgcc attaccagtt gctcactgag gagaatatac  13680
ctgaaaaccc actgcgcttc ctctatcccc gaatcccccg ggatgaagct tttgggtgct  13740
actaccagga gaaaggtggg aatcgttgac atacttcatt gctagattgc agagatctac  13800
cagacatcca tagatcccac tccttccttt aaagcatggg aaaactgata tctagaggaa  13860
ttaagggatt cgtccatggg atactgctgg ttactatggg gatgagactg ccaggaccat  13920
ctgcactagg ggaaaacctc aggctatatg tctggcccac tgatcttctc tgcttcttgt  13980
atatgttcct cacagttaat ctccaggaac ggaggaaata cctgaaacac aggctcattg  14040
tggtctctaa tagagtgaga tatgaactgt tcattcatcc tccctaatcc ttattggctc  14100
tgcttcagtg aatcgtcaaa agggggcatt accttctcct gggtggagca ccaggatgat  14160
```

```
ggtcagctgc tctgccctgc cattcccaca gcctctcctt tctgccttct cctaagctgc    14220
ccctattcca gtctccccag ccttccctcc ctcctagccc cactctagtt ttttctggtt    14280
ctagtctctc ctatctcata ttttttctgct gccatcctta ggttgtctcc acaggggttt    14340
ctggataata atgatcataa tcactggtgt taagggtac ctacttgatg caagcatgga    14400 gcttttttt tttccagaca gggttttgtt ctgtcgccca ggctggagtg cagtggtgtg    14460
atcctggctc actgcagcct cgacctcctg agctcaagca atacaggcat gcatcaccaa    14520
actcagctaa tttttttgt attttttgta gagatgggt cttaccatgt tgacgcatca    14580
ggctgttctg aactcctgga ctcaagcaat ccacccacct tggcctccca aaagtcaggg    14640
attacaggcg tgcgaccaca ccccgcatat atatatttt tttttttttt tttttttttt    14700 tttttgaga cagggtctct gttatccagg ctggagttgc agtggataat atgactacga    14760
gccttgacct aggggttgaa gcaatgctcc tgcctcagcc accaagtgct gagactcag    14820 gcacacgcca atctacactc aatcacactc agctaatttt ttaaattttt tgtagggatg    14880
gggtatcact gtgtttgccc aggctggtct tgaactcctg gcctcaagca gtctcctgcc    14940
ttggcctccc aaaattgccgg gattgtagga atgagccatg gcacttggct gggggataga    15000
attttttttt tttttttttt tttttttttt tttgagacag tctcactctc attgcccggg    15060
ctggagtgca gtggtgcaat ttcagctcac tgcaacctct gcctcccagg ctcaagcaat    15120
tctcctgcct cagcctatag agtagctggg attacaggcg agcgccaccc atgcctggtt    15180 aattttttgtt ttttttttga cacagagtct cgccctgttg cccaggctgg agtgcagtgg    15240
cacgatctca gctcactgca acctctgcct cccaggctca agcaattctc ctgcctcagc    15300
ctcctgagta ctgggactac aagcgcgcac aaccaccaca cctggtaatt tttgtatttt    15360
tagtagagac agggttttac catattggcc aggctggtct caaactcctg acctcatgat    15420
ccgacccacc ttggcctccc aaagtgcagg gattacaggc gtgagcctct gcacccggcc    15480
taacttttgt atttttagta gaaacagggt ttcaccatgt tggccaggct ggtcatgagc    15540
tcctggcctc aagtgatctg cccgcctcag cctcccaaag tgcttggatt acaggtgtga    15600
gccacctggc ctgagagttt attatgcgcc aggcactagg caaatggttt gcatttattt    15660 tctcattta ttgaatctac aaaatagtcc tgtgaagtaa acactgttac tgttttcagc    15720
taaggaactg gatttagagt agtcaagttt tgtacctaag gtacgtggct aatgatacag    15780
gtctgttaga ttccgtagcc ctgattttaa ccaccctact gcctctcaag aattactagg    15840
tattgttctc atttatagat gataaatctg aggctcagaa aagttaggcc acttgcctaa    15900
ggtcccccag ccaggattca aactccagga ggcctgattc caaacccatg ctctttagcc    15960
ctccgcccta ctgccttctt agactagctt ctgcttattc taccattcct gatttcattt    16020
gaaccactga gccctgcccc tttgtctgtc tttgggtatc caggcaggtg gatgaactgc    16080
aacaaccgct ggagcttaag ccagagccag agctggagtc attagagctg aactagggc    16140 tggtgccaga gccagagctc agcctggact tagagccact gctgaaggca gggctggatc    16200
tggggccaga gctagagtct gtgctggagt ccactctgga gcctgtgata gagcccacac    16260
tatgcatggt atcacaaaca gtgccagagc cagaccaagg acctgtatca cagccagtgc    16320
cagagccaga tttgccctgt gatctgagac atttgaacac tgagccaatg gaaagtaagt    16380
gatgagatgc agtggcacac attcccttc ctacctcttc tccctctccc attacagaaa    16440
aagctgaact ccaagctcct cattggagag aggtccatct gtgattcctt ttttaggaa    16500
```

-continued

```
ttacacatgc cttcccccac ctccctgctc tttcatccca caagttccca ctcaggctct    16560
tcccaggcct ttcctgccat cctccctccc ttgggctgct gggttgggaa ctcctaacta    16620 agatcgggc ctcacttttc tctctggatt acctagtctt cagaaactgt gtaaagattg     16680
aagaaatcat gccgaatggt gacccactgt tggctggcca aacaccgtg gatgaggttt     16740 acgtctcccg ccccagccac ttctacactg atggacccatt gatgccttct gacttctagg   16800
aaccacattt cctctgttct tttcatatct ctttgccctt cctactcctc atagcatgat    16860
attgttctcc aaggatggga atcaggcatg tgtcccttcc aagctgtgtt aactgttcaa    16920
actcaggcct gtgtgactcc attggggtga gaggtgaaag cataacatgg gtacagaggg    16980
gacaacaatg aatcagaaca gatgctgagc cataggtcta aataggatcc tggaggctgc    17040
ctgctgtgct gggaggtata ggggtcctgg gggcaggcca gggcagttga caggtacttg    17100
gagggctcag ggcagtggct tctttccagt atggaaggat ttcaacattt taatagttgg    17160
ttaggctaaa ctggtgcata ctggcattgg ccttggtggg gagcacagac acaggatagg    17220
actccatttc tttcttccat tccttcatgt ctaggataac ttgctttctt ctttccttta    17280
ctcctggctc aagccctgaa tttcttcttt tcctgcaggg gttgagagct ttctgcctta    17340
gcctaccatg tgaaactcta ccctgaagaa agggatggat aggaagtaga cctctttttc    17400
ttaccagtct cctcccctac tctgcccct aagctggctg tacctgttcc tcccccataa     17460
aatgatcctg ccaatctaat gtgagtgtga agtttgcaca ctagtttatg ctacctagtc    17520
tccactttct caatgcttag gagacagatc actcctggag gctggggatg gtaggattgc    17580
tggggatttt ttttttttta aagagggtct cactctgttg cccaggctag agtgcaatgg    17640
tgcaatcaca gctcactgca gcctcaacct cctgggttca agcaatcctc ctacctcagc    17700
ctcctgggta gctagcacca tggcatcgcc accatgccct atttttttt tttaaagaca     17760 gggtcttgct atattgccca ggctggtctt gaactgggct caagtgatcc tcacgccttg    17820
cctcccaaag tgctgggatt ataggcatga gccactgtgc ttggccagga ttttttttt    17880 ttttttttg agatggagtt tctctcttgt tgtccaggct ggagtgcaat ggtgtgatcc     17940
ggggaattc                                                            17949
```

```
<210> SEQ ID NO 4
<211> LENGTH: 851
<212> TYPE: PRT
<213> ORGANISM: Homo sapiens

<400> SEQUENCE: 4

Met Ala Gln Trp Glu Met Leu Gln Asn Leu Asp Ser Pro Phe Gln Asp
 1               5                  10                  15

Gln Leu His Gln Leu Tyr Ser His Ser Leu Leu Pro Val Asp Ile Arg
                20                  25                  30

Gln Tyr Leu Ala Val Trp Ile Glu Asp Gln Asn Trp Gln Glu Ala Ala
            35                  40                  45

Leu Gly Ser Asp Asp Ser Lys Ala Thr Met Leu Phe Phe His Phe Leu
        50                  55                  60

Asp Gln Leu Asn Tyr Glu Cys Gly Arg Cys Ser Gln Asp Pro Glu Ser
    65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
               100                 105                 110
```

```
Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
        130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
210                 215                 220

Thr Thr Leu Ile Glu Leu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
            260                 265                 270

Arg Gln Leu Leu Lys Glu Leu Lys Gly Leu Ser Cys Leu Val Ser Tyr
        275                 280                 285

Gln Asp Asp Pro Leu Thr Lys Gly Val Asp Leu Arg Asn Ala Gln Val
        290                 295                 300

Thr Glu Leu Leu Gln Arg Leu Leu His Arg Ala Phe Val Val Glu Thr
305                 310                 315                 320

Gln Pro Cys Met Pro Gln Thr Pro His Arg Pro Leu Ile Leu Lys Thr
                325                 330                 335

Gly Ser Lys Phe Thr Val Arg Thr Arg Leu Leu Val Arg Leu Gln Glu
            340                 345                 350

Gly Asn Glu Ser Leu Thr Val Glu Val Ser Ile Asp Arg Asn Pro Pro
        355                 360                 365

Gln Leu Gln Gly Phe Arg Lys Phe Asn Ile Leu Thr Ser Asn Gln Lys
        370                 375                 380

Thr Leu Thr Pro Glu Lys Gly Gln Ser Gln Gly Leu Ile Trp Asp Phe
385                 390                 395                 400

Gly Tyr Leu Thr Leu Val Glu Gln Arg Ser Gly Gly Ser Gly Lys Gly
                405                 410                 415

Ser Asn Lys Gly Pro Leu Gly Val Thr Glu Glu Leu His Ile Ile Ser
            420                 425                 430

Phe Thr Val Lys Tyr Thr Tyr Gln Gly Leu Lys Gln Glu Leu Lys Thr
        435                 440                 445

Asp Thr Leu Pro Val Val Ile Ile Ser Asn Met Asn Gln Leu Ser Ile
        450                 455                 460

Ala Trp Ala Ser Val Leu Trp Phe Asn Leu Leu Ser Pro Asn Leu Gln
465                 470                 475                 480

Asn Gln Gln Phe Phe Ser Asn Pro Pro Lys Ala Pro Trp Ser Leu Leu
                485                 490                 495

Gly Pro Ala Leu Ser Trp Gln Phe Ser Ser Tyr Val Gly Arg Gly Leu
            500                 505                 510

Asn Ser Asp Gln Leu Ser Met Leu Arg Asn Lys Leu Phe Gly Gln Asn
        515                 520                 525

Cys Arg Thr Glu Asp Pro Leu Leu Ser Trp Ala Asp Phe Thr Lys Arg
```

```
            530                 535                 540
Glu Ser Pro Pro Gly Lys Leu Pro Phe Trp Thr Trp Leu Asp Lys Ile
545                 550                 555                 560

Leu Glu Leu Val His Asp His Leu Lys Asp Leu Trp Asn Asp Gly Arg
                565                 570                 575

Ile Met Gly Phe Val Ser Arg Ser Gln Glu Arg Arg Leu Leu Lys Lys
            580                 585                 590

Thr Met Ser Gly Thr Phe Leu Leu Arg Phe Ser Glu Ser Ser Glu Gly
            595                 600                 605

Gly Ile Thr Cys Ser Trp Val Glu His Gln Asp Asp Lys Val Leu
            610                 615                 620

Ile Tyr Ser Val Gln Pro Tyr Thr Lys Glu Val Leu Gln Ser Leu Pro
625                 630                 635                 640

Leu Thr Glu Ile Ile Arg His Tyr Gln Leu Leu Thr Glu Glu Asn Ile
                645                 650                 655

Pro Glu Asn Pro Leu Arg Phe Leu Tyr Pro Arg Ile Pro Arg Asp Glu
                660                 665                 670

Ala Phe Gly Cys Tyr Tyr Gln Glu Lys Val Asn Leu Gln Glu Arg Arg
            675                 680                 685

Lys Tyr Leu Lys His Arg Leu Ile Val Val Ser Asn Arg Gln Val Asp
690                 695                 700

Glu Leu Gln Gln Pro Leu Glu Leu Lys Pro Glu Pro Glu Leu Glu Ser
705                 710                 715                 720

Leu Glu Leu Glu Leu Gly Leu Val Pro Glu Pro Glu Leu Ser Leu Asp
                725                 730                 735

Leu Glu Pro Leu Leu Lys Ala Gly Leu Asp Leu Gly Pro Glu Leu Glu
                740                 745                 750

Ser Val Leu Glu Ser Thr Leu Glu Pro Val Ile Glu Pro Thr Leu Cys
                755                 760                 765

Met Val Ser Gln Thr Val Pro Glu Pro Asp Gln Gly Pro Val Ser Gln
770                 775                 780

Pro Val Pro Glu Pro Asp Leu Pro Cys Asp Leu Arg His Leu Asn Thr
785                 790                 795                 800

Glu Pro Met Glu Ile Phe Arg Asn Cys Val Lys Ile Glu Glu Ile Met
                805                 810                 815

Pro Asn Gly Asp Pro Leu Leu Ala Gly Gln Asn Thr Val Asp Glu Val
            820                 825                 830

Tyr Val Ser Arg Pro Ser His Phe Tyr Thr Asp Gly Pro Leu Met Pro
            835                 840                 845

Ser Asp Phe
    850

<210> SEQ ID NO 5
<211> LENGTH: 2787
<212> TYPE: DNA
<213> ORGANISM: Homo sapiens

<400> SEQUENCE: 5
cagctggaat tcgggcggc ggcgcagact gggaggggga gccggggtt ccgacgtcgc      60 agccgaggga acaagcccca accggatcct ggacaggcac cccggcttgg cgctgtctct    120 cccctcggc tcgagaggc ccttcggcct gagggagcct cgccgcccgt ccccggcaca    180
cgcgcagccc cggcctctcg gcctctgccg gagaaacagg atggcccaat ggaatcagct    240
acagcagctt gacacacggt acctggagca gctccatcag ctctacagtg acagcttccc    300
```

-continued

```
aatggagctg cggcagtttc tggcccttg  gattgagagt caagattggg catatgcggc  360
cagcaaagaa tcacatgcca ctttggtgtt tcataatctc ctgggagaga ttgaccagca  420
gtatagccgc ttcctgcaag agtcgaatgt tctctatcag cacaatctac gaagaatcaa  480
gcagtttctt cagagcaggt atcttgaaga gccaatggag attgcccgga ttgtggcccg  540
gtgcctgtgg gaagaatcac gccttctaca gactgcagcc actgcggccc agcaaggggg  600
ccaggccaac caccccacag cagccgtggt gacggagaag cagcagatgc tggagcagca  660
ccttcaggat gtccggaaga gagtgcagga tctagaacaa aaaatgaaag tggtagagaa  720
tctccaggat gactttgatt tcaactataa acccctcaag agtcaaggag acatgcaaga  780
tctgaatgga acaaccagt  cagtgaccag gcagaagatg cagcagctgg aacagatgct  840
cactgcgctg gaccagatgc ggagaagcat cgtgagtgag ctggcggggc ttttgtcagc  900
gatggagtac gtgcagaaaa ctctcacgga cgaggagctg gctgactgga gaggcggca   960
acagattgcc tgcattggag gcccgcccaa catctgccta gatcggctag aaaactggat  1020
aacgtcatta gcagaatctc aacttcagac ccgtcaacaa attaagaaac tggaggagtt  1080
gcaccaaaaa gtttcctaca aggggaccc  cattgtacag caccggccga tgctggagga  1140
gaggatcgtg gagctgttca gaaacttaat gaaaagtgcc tttgtggtgg agcggcagcc  1200
ctgcatgccc atgcatcctg accggcccct cgtcatcaag accggcgtcc agttcactac  1260
taaagtcagg ttgctggtca agttccctga gttgaattat cagcttaaaa ttaaagtgtg  1320
cattgacaaa gactctgggg acgttgcagc tctcagagga tcccggaaat ttaacattct  1380
gggcacaaac acaaaagtga tgaacatgga agaatccaac aacggcagcc tctctgcaga  1440
attcaaacac ttgaccctga gggagcagag atgtgggaat gggggccgag ccaattgtga  1500
tgcttccctg attgtgactg aggagctgca cctgatcacc tttgagaccg aggtgtatca  1560
ccaaggtctc aagattgacc tagagaccca ctccttgtca gttgtggtga tctccaacat  1620
ctgtcagatg ccaaatgcct gggcgtccat cctgtggtac aacatgctga ccaacaatcc  1680
caagaatgtg aacttcttca ctaagccgcc aattggaacc tgggaccaag tggccgaggt  1740
gctcagctgg cagttctcgt ccaccaccaa gcgggggctg agcatcgagc agctgacaac  1800
gctggctgag aagctcctag gcctggtgt  gaactactca gggtgtcaga tcacatgggc  1860
taacttctgc aaagaaaaca tggctggcaa gggcttctcc tactgggtct ggctagacaa  1920
tatcatcgac cttgtgaaaa agtatatctt ggccctttgg aatgaagggt acatcatggg  1980
tttcatcagc aaggagcggg agcgggccat cttgagcact aagcccccag gcaccttcct  2040
gctgcgcttc agtgaaagca gcaaagaagg aggcgtcact ttcacttggg tggagaagga  2100
catcagcggt aagacccaga tccagtccgt ggaaccatac acaaagcagc agctgaacaa  2160
catgtcattt gctgaaatca tcatgggcta taagatcatg gatgctacca atatcctgtt  2220
gtctccactt gtctatctct atcctgacat tcccaaggag gaggcattcg ggaagtattg  2280
tcggccagag agccaggagc atcctgaagc tgacccaggt agcgctgccc catacctgaa  2340
gaccaagttt atctgtgtga caccaacgac ctgcagcaat accattgacc tgccgatgtc  2400
cccccgcgct ttagattcat tgatgcagtt tggaaataat ggtgaaggtg ctgaaccctc  2460
agcaggaggg cagtttgagt ccctcacctt tgacatggag ttgacctcgg agtgcgctac  2520
ctcccccatg tgaggagctg agaacggaag ctgcagaaag atacgactga ggcgcctacc  2580
tgcattctgc cacccctcac acagccaaac cccagatcat ctgaaactac taactttgtg  2640
```

-continued

```
gttccagatt ttttttaatc tcctacttct gctatctttg agcaatctgg gcacttttaa     2700
aaatagagaa atgagtgaat gtgggtgatc tgcttttatc taaatgcaaa taaggatgtg     2760
ttctctgaga cccatgatca ggggatg                                         2787
```

<210> SEQ ID NO 6
<211> LENGTH: 770
<212> TYPE: PRT
<213> ORGANISM: Homo sapiens

<400> SEQUENCE: 6

```
Met Ala Gln Trp Asn Gln Leu Gln Gln Leu Asp Thr Arg Tyr Leu Glu
  1               5                  10                  15

Gln Leu His Gln Leu Tyr Ser Asp Ser Phe Pro Met Glu Leu Arg Gln
                 20                  25                  30

Phe Leu Ala Pro Trp Ile Glu Ser Gln Asp Trp Ala Tyr Ala Ala Ser
             35                  40                  45

Lys Glu Ser His Ala Thr Leu Val Phe His Asn Leu Leu Gly Glu Ile
         50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu His
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350
```

```
Val Lys Phe Pro Glu Leu Asn Tyr Gln Leu Lys Ile Lys Val Cys Ile
    355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Ser Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Asn Phe Cys Lys Glu Asn Met Ala Gly Lys Gly Phe Ser
545                 550                 555                 560

Tyr Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
    595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Leu Ser Pro Leu Val Tyr
            660                 665                 670

Leu Tyr Pro Asp Ile Pro Lys Glu Glu Ala Phe Gly Lys Tyr Cys Arg
    675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Ala Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
    755                 760                 765
```

Pro Met
    770

<210> SEQ ID NO 7
<211> LENGTH: 2588
<212> TYPE: DNA
<213> ORGANISM: Homo sapiens

<400> SEQUENCE: 7

| | | | | |
|---|---|---|---|---|
| gctttctcct | agggactgtg | agggcgctt | ctgactttgg | acttgagcac | tgcctgggac | 60 |
| ctgtgctgag | agagcgctag | catgtctcag | tggaatcaag | tccaacagtt | agaaatcaag | 120 |
| ttttggagc | aggtggatca | attctatgat | gacaactttc | ccatggaaat | tcggcatctg | 180 |
| ttggcccaat | ggattgaaaa | tcaagactgg | gaggcagctt | ctaacaatga | aaccatggca | 240 |
| acgattcttc | ttcaaaactt | gttaatacaa | ctggatgaac | agttaggtcg | tgtttccaaa | 300 |
| gagaaaaacc | tactcttgat | acacaatcta | aaagaatta | ggaaggtcct | tcagggaaaa | 360 |
| tttcatggaa | atccaatgca | tgtagctgtg | gttatttcaa | actgtttaag | ggaagagagg | 420 |
| agaatattgg | ctgcagccaa | catgcctgtc | caggggcctc | tagagaaatc | cttacaaagt | 480 |
| tcttcagttt | cagaaagaca | gaggaatgtg | gagcacaaag | tggctgccat | taaaaacagt | 540 |
| gtgcagatga | cagaacaaga | taccaaatac | ttagaagatc | tgcaagacga | atttgactac | 600 |
| aggtataaaa | caattcagac | aatggatcag | agtgacaaga | atagtgccat | ggtgaatcag | 660 |
| gaagttttga | cactgcagga | aatgcttaac | agcctcgatt | tcaagagaaa | ggaggctctc | 720 |
| agtaaaatga | cccaaatcat | ccatgagaca | gacctgttaa | tgaacaccat | gctcatagaa | 780 |
| gagctgcaag | actggaagcg | gcggcagcaa | atcgcctgca | tcgggggtcc | actccacaat | 840 |
| gggctcgacc | agcttcagaa | ctgctttaca | ctattggcag | aaagtctttt | ccaactgaga | 900 |
| aggcaattgg | agaaactaga | ggagcaatct | accaaaatga | catatgaagg | tgatcccatt | 960 |
| ccaatgcaaa | gaactcacat | gctagaaaga | gtcaccttct | tgatctacaa | ccttttcaag | 1020 |
| aactcatttg | tggttgagcg | acagccatgt | atgccaaccc | accctcagag | gccgttggta | 1080 |
| cttaaaaccc | taattcagtt | cactgtaaaa | ctaaggctac | taataaaatt | gccagaacta | 1140 |
| aactatcagg | taaaggttaa | ggcatcaatt | gacaagaatg | tttcaactct | aagcaaccga | 1200 |
| agatttgtac | tttgtggaac | taatgtcaaa | gccatgtcta | ttgaagaatc | ttccaatggg | 1260 |
| agtctctcag | tagaatttcg | acatttgcaa | ccaaaggaaa | tgaagtccag | tgctggaggt | 1320 |
| aaaggaaatg | agggctgtca | catggtgact | gaagaacttc | attccataac | gtttgaaaca | 1380 |
| cagatctgcc | tctatggcct | gaccatagat | ttggagacca | gctcattgcc | tgtggtgatg | 1440 |
| atttccaatg | tcagtcagtt | acctaatgct | tgggcatcca | tcatttggta | caacgtgtca | 1500 |
| accaacgatt | cccagaactt | ggttttcttt | aataatcctc | cacctgccac | attgagtcaa | 1560 |
| ctactggagg | tgatgagctg | gcagttttca | tcgtacgttg | gtcgtggtct | taactcagat | 1620 |
| caactccata | tgctggcaga | gaagcttaca | gtccaatcta | gctacagtga | tggtcacctc | 1680 |
| acctgggcca | agtctgcaa | ggaacattta | cctggtaaat | catttacctt | ttggacatgg | 1740 |
| cttgaagcaa | tattggatct | aattaagaaa | cacattcttc | cccttggat | tgatgggtat | 1800 |
| gtcatgggct | ttgttagcaa | agagaaggaa | cggctgttgc | taaggataa | aatgcctggc | 1860 |
| accttttat | taagattcag | tgaaagccat | ctcggaggaa | taactttcac | ctgggtggac | 1920 |
| cattctgaaa | gtgggaagt | gagattccac | tctgtagaac | cctacaataa | aggccggttg | 1980 |
| tctgctctgc | cattcgctga | catcctgcga | gactacaaag | ttattatggc | tgaaaacatt | 2040 |

-continued

```
cctgaaaacc ctctgaagta cctatatcct gacattccca aagacaaagc cttcggtaaa    2100
cactacagct ctcagccttg cgaagtttca agaccaacag aaagggtga caaaggttat    2160 gttccttctg tttttatccc catctcaaca atccgaagtg attcaacaga gccacattct    2220
ccatcagacc ttcttcccat gtctccaagt gtgtatgcgg tgttgagaga aaacctgagt    2280
cccacaacaa ttgaaactgc aatgaagtct ccttattctg ctgaatgaca ggataaactc    2340
tgacgcacca agaaaggaag caaatgaaaa agtttaaaga ctgttctttg cccaataacc    2400
acattttatt tcttcagctt tgtaaatacc aggttctagg aaatgtttga catctgaagc    2460
tctcttcaca ctcccgtggc actcctcaat tgggagtgtt gtgactgaaa tgcttgaaac    2520
caaagcttca gataaacttg caagataaga caactttaag aaaccagtgt taataacaat    2580
attaacag                                                             2588
```

<210> SEQ ID NO 8
<211> LENGTH: 748
<212> TYPE: PRT
<213> ORGANISM: Homo sapiens

<400> SEQUENCE: 8

```
Met Ser Gln Trp Asn Gln Val Gln Gln Leu Glu Ile Lys Phe Leu Glu
 1               5                  10                  15

Gln Val Asp Gln Phe Tyr Asp Asp Asn Phe Pro Met Glu Ile Arg His
                20                  25                  30

Leu Leu Ala Gln Trp Ile Glu Asn Gln Asp Trp Glu Ala Ala Ser Asn
            35                  40                  45

Asn Glu Thr Met Ala Thr Ile Leu Leu Gln Asn Leu Leu Ile Gln Leu
        50                  55                  60

Asp Glu Gln Leu Gly Arg Val Ser Lys Glu Lys Asn Leu Leu Leu Ile
 65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Val Gln Gly Pro Leu Glu
        115                 120                 125

Lys Ser Leu Gln Ser Ser Ser Val Ser Glu Arg Gln Arg Asn Val Glu
    130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
        195                 200                 205

Arg Lys Glu Ala Leu Ser Lys Met Thr Gln Ile Ile His Glu Thr Asp
    210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270
```

-continued

```
Arg Arg Gln Leu Glu Lys Leu Glu Glu Gln Ser Thr Lys Met Thr Tyr
            275                 280                 285

Glu Gly Asp Pro Ile Pro Met Gln Arg Thr His Met Leu Glu Arg Val
290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
            355                 360                 365

Thr Leu Ser Asn Arg Arg Phe Val Leu Cys Gly Thr Asn Val Lys Ala
370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
                405                 410                 415

Glu Gly Cys His Met Val Thr Glu Glu Leu His Ser Ile Thr Phe Glu
                420                 425                 430

Thr Gln Ile Cys Leu Tyr Gly Leu Thr Ile Asp Leu Glu Thr Ser Ser
            435                 440                 445

Leu Pro Val Val Met Ile Ser Asn Val Ser Gln Leu Pro Asn Ala Trp
450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ala Thr Leu Ser Gln Leu Leu Glu
                485                 490                 495

Val Met Ser Trp Gln Phe Ser Ser Tyr Val Gly Arg Gly Leu Asn Ser
                500                 505                 510

Asp Gln Leu His Met Leu Ala Glu Lys Leu Thr Val Gln Ser Ser Tyr
            515                 520                 525

Ser Asp Gly His Leu Thr Trp Ala Lys Phe Cys Lys Glu His Leu Pro
530                 535                 540

Gly Lys Ser Phe Thr Phe Trp Thr Trp Leu Glu Ala Ile Leu Asp Leu
545                 550                 555                 560

Ile Lys Lys His Ile Leu Pro Leu Trp Ile Asp Gly Tyr Val Met Gly
                565                 570                 575

Phe Val Ser Lys Glu Lys Glu Arg Leu Leu Leu Lys Asp Lys Met Pro
            580                 585                 590

Gly Thr Phe Leu Leu Arg Phe Ser Glu Ser His Leu Gly Gly Ile Thr
            595                 600                 605

Phe Thr Trp Val Asp His Ser Glu Ser Gly Glu Val Arg Phe His Ser
610                 615                 620

Val Glu Pro Tyr Asn Lys Gly Arg Leu Ser Ala Leu Pro Phe Ala Asp
625                 630                 635                 640

Ile Leu Arg Asp Tyr Lys Val Ile Met Ala Glu Asn Ile Pro Glu Asn
                645                 650                 655

Pro Leu Lys Tyr Leu Tyr Pro Asp Ile Pro Lys Asp Lys Ala Phe Gly
                660                 665                 670

Lys His Tyr Ser Ser Gln Pro Cys Glu Val Ser Arg Pro Thr Glu Arg
            675                 680                 685

Gly Asp Lys Gly Tyr Val Pro Ser Val Phe Ile Pro Ile Ser Thr Ile
```

-continued

```
                690                 695                 700
Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
            740                 745
```

<210> SEQ ID NO 9
<211> LENGTH: 3714
<212> TYPE: DNA
<213> ORGANISM: Homo sapiens

<400> SEQUENCE: 9

| | | | | | |
|---|---|---|---|---|---|
| gcggggcgca | gagccggccc | ggctgccgga | cggtgcggcc | ccaccaggtg | aacggccatg | 60 |
| gcgggctgga | tccaggccca | gcagctgcag | ggagacgcgc | tgcgccagat | gcaggtgctg | 120 |
| tacggccagc | acttccccat | cgaggtccgg | cactacttgg | cccagtggat | tgagagccag | 180 |
| ccatgggatg | ccattgactt | ggacaatccc | caggacagag | cccaagccac | ccagctcctg | 240 |
| gagggcctgg | tgcaggagct | gcagaagaag | gcggagcacc | aggtggggga | agatgggttt | 300 |
| ttactgaaga | tcaagctggg | gcactacgcc | acgcagctcc | agaaaacata | tgaccgctgc | 360 |
| cccctggagc | tggtccgctg | catccggcac | attctgtaca | atgaacagag | gctggtccga | 420 |
| gaagccaaca | attgcagctc | tccggctggg | atcctggttg | acgccatgtc | ccagaagcac | 480 |
| cttcagatca | accagacatt | tgaggagctg | cgactggtca | cgcaggacac | agagaatgag | 540 |
| ctgaagaaac | tgcagcagac | tcaggagtac | ttcatcatcc | agtaccagga | gagcctgagg | 600 |
| atccaagctc | agtttgccca | gctggcccag | ctgagccccc | aggagcgtct | gagccgggag | 660 |
| acggccctcc | agcagaagca | ggtgtctctg | gaggcctggt | tgcagcgtga | ggcacagaca | 720 |
| ctgcagcagt | accgcgtgga | gctggccgag | aagcaccaga | agaccctgca | gctgctgcgg | 780 |
| aagcagcaga | ccatcatcct | ggatgacgag | ctgatccagt | ggaagcggcg | gcagcagctg | 840 |
| gccgggaacg | gcgggccccc | cgagggcagc | ctggacgtgc | tacagtcctg | gtgtgagaag | 900 |
| ttggccgaga | tcatctggca | gaaccggcag | cagatccgca | gggctgagca | cctctgccag | 960 |
| cagctgccca | tccccggccc | agtggaggag | atgctggccg | aggtcaacgc | caccatcacg | 1020 |
| gacattatct | cagccctggt | gaccagcaca | ttcatcattg | agaagcagcc | tcctcaggtc | 1080 |
| ctgaagaccc | agaccaagtt | tgcagccacc | gtacgcctgc | tggtgggcgg | aagctgaac | 1140 |
| gtgcacatga | atcccccca | ggtgaaggcc | accatcatca | gtgagcagca | ggccaagtct | 1200 |
| ctgcttaaaa | atgagaacac | ccgcaacgag | tgcagtggtg | agatcctgaa | caactgctgc | 1260 |
| gtgatggagt | accaccaagc | cacgggcacc | ctcagtgccc | acttcaggaa | catgtcactg | 1320 |
| aagaggatca | agcgtgctga | ccggcggggt | gcagagtccg | tgacagagga | gaagttcaca | 1380 |
| gtcctgtttg | agtctcagtt | cagtgttggc | agcaatgagc | ttgtgttcca | ggtgaagact | 1440 |
| ctgtccctac | ctgtggttgt | catcgtccac | ggcagccagg | accacaatgc | cacggctact | 1500 |
| gtgctgtggg | acaatgcctt | tgctgagccg | ggcagggtgc | catttgccgt | gcctgacaaa | 1560 |
| gtgctgtggc | cgcagctgtg | tgaggcgctc | aacatgaaat | tcaaggccga | agtgcagagc | 1620 |
| aaccgggggcc | tgaccaagga | gaacctcgtg | ttcctggcgc | agaaactgtt | caacaacagc | 1680 |
| agcagccacc | tggaggacta | cagtggcctg | tccgtgtcct | ggtcccagtt | caacagggag | 1740 |
| aacttgccgg | gctggaacta | caccttctgg | cagtggtttg | acgggtgat | ggaggtgttg | 1800 |

-continued

```
aagaagcacc acaagcccca ctggaatgat ggggccatcc taggttttgt gaataagcaa    1860
caggcccacg acctgctcat caacaagccc gacgggacct tcttgttgcg ctttagtgac    1920
tcagaaatcg ggggcatcac catcgcctgg aagtttgact ccccggaacg caacctgtgg    1980
aacctgaaac cattcaccac gcgggatttc tccatcaggt ccctggctga ccggctgggg    2040
gacctgagct atctcatcta tgtgtttcct gaccgcccca aggatgaggt cttctccaag    2100
tactacactc ctgtgctggc taaagctgtt gatggatatg tgaaaccaca gatcaagcaa    2160
gtggtccctg agtttgtgaa tgcatctgca gatgctgggg gcagcagcgc cacgtacatg    2220
gaccaggccc cctccccagc tgtgtgcccc caggctccct ataacatgta cccacagaac    2280
cctgaccatg tactcgatca ggatggagaa ttcgacctgg atgagaccat ggatgtggcc    2340
aggcacgtgg aggaactctt acgccgacca atggacagtc ttgactcccg cctctcgccc    2400
cctgccggtc ttttcacctc tgccagaggc tccctctcat gaatgtttga atcccacgct    2460
tctctttgga aacaatatgc aatgtgaagc ggtcgtgttg tgagtttagt aaggttgtgt    2520
acactgacac ctttgcaggc atgcatgtgc ttgtgtgtgt gtgtgtgtgt gtgtccttgt    2580
gcatgagcta cgcctgcctc ccctgtgcag tcctgggatg tggctgcagc agcggtggcc    2640
tcttttcaga tcatggcatc caagagtgcg ccgagtctgt ctctgtcatg gtagagaccg    2700
agcctctgtc actgcaggca ctcaatgcag ccagacctat tcctcctggg cccctcatct    2760
gctcagcagc tatttgaatg agatgattca aaggggagg ggagacaggt aacgtctgta    2820
agctgaagtt tcactccgga gtgagaagct ttgccctcct aagagagaga gacagagaga    2880
cagagagaga gaaagagaga gtgtgtgggt ctatgtaaat gcatctgtcc tcatgtgttg    2940
atgtaaccga ttcatctctc agaagggagg ctggggttc attttcgagt agtattttat    3000
actttagtga acgtggactc cagactctct gtgaaccta tgagagcgcg tctgggcccg    3060
gccatgtcct tagcacaggg gggccgccgg tttgagtgag ggtttctgag ctgctctgaa    3120
ttagtccttg cttggctgct tggccttggg cttcattcaa gtctatgatg ctgttgccca    3180
cgtttcccgg gatatatatt ctctcccctc cgttgggccc cagccttctt tgcttgcctc    3240
tctgtttgta accttgtcga caaagaggta gaaaagattg ggtctaggat atggtgggtg    3300
gacaggggcc ccgggacttg gagggttggt cctcttgcct cctggaaaaa acaaaaacaa    3360
aaaactgcag tgaaagacaa gctgcaaatc agccatgtgc tgcgtgcctg tggaatctgg    3420 agtgagggt aaaagctgat ctggtttgac tccgctggag gtggggcctg gagcaggcct    3480
tgcgctgttg cgtaactggc tgtgttctgg tgaggccttg ctcccaaccc cacacgctcc    3540
tccctctgag gctgtaggac tcgcagtcag gggcagctga ccatggaaga ttgagagccc    3600
aaggtttaaa cttctctgaa gggaggtggg gatgagaaga ggggtttttt tgtactttgt    3660
acaaagacca cacatttgtg taaacagtgt tttggaataa aatatttttt tcat         3714
```

<210> SEQ ID NO 10
<211> LENGTH: 794
<212> TYPE: PRT
<213> ORGANISM: Homo sapiens

<400> SEQUENCE: 10

```
Met Ala Gly Trp Ile Gln Ala Gln Gln Leu Gln Gly Asp Ala Leu Arg
  1               5                  10                  15

Gln Met Gln Val Leu Tyr Gly Gln His Phe Pro Ile Glu Val Arg His
                 20                  25                  30

Tyr Leu Ala Gln Trp Ile Glu Ser Gln Pro Trp Asp Ala Ile Asp Leu
```

```
                  35                  40                  45
Asp Asn Pro Gln Asp Arg Ala Gln Ala Thr Gln Leu Leu Glu Gly Leu
        50                  55                  60
Val Gln Glu Leu Gln Lys Lys Ala Glu His Gln Val Gly Glu Asp Gly
 65                  70                  75                  80
Phe Leu Leu Lys Ile Lys Leu Gly His Tyr Ala Thr Gln Leu Gln Lys
                85                  90                  95
Thr Tyr Asp Arg Cys Pro Leu Glu Leu Val Arg Cys Ile Arg His Ile
            100                 105                 110
Leu Tyr Asn Glu Gln Arg Leu Val Arg Glu Ala Asn Asn Cys Ser Ser
            115                 120                 125
Pro Ala Gly Ile Leu Val Asp Ala Met Ser Gln Lys His Leu Gln Ile
        130                 135                 140
Asn Gln Thr Phe Glu Glu Leu Arg Leu Val Thr Gln Asp Thr Glu Asn
145                 150                 155                 160
Glu Leu Lys Lys Leu Gln Gln Thr Gln Glu Tyr Phe Ile Ile Gln Tyr
                165                 170                 175
Gln Glu Ser Leu Arg Ile Gln Ala Gln Phe Ala Gln Leu Ala Gln Leu
            180                 185                 190
Ser Pro Gln Glu Arg Leu Ser Arg Glu Thr Ala Leu Gln Gln Lys Gln
            195                 200                 205
Val Ser Leu Glu Ala Trp Leu Gln Arg Glu Ala Gln Thr Leu Gln Gln
        210                 215                 220
Tyr Arg Val Glu Leu Ala Glu Lys His Gln Lys Thr Leu Gln Leu Leu
225                 230                 235                 240
Arg Lys Gln Gln Thr Ile Ile Leu Asp Asp Glu Leu Ile Gln Trp Lys
                245                 250                 255
Arg Arg Gln Gln Leu Ala Gly Asn Gly Gly Pro Pro Glu Gly Ser Leu
            260                 265                 270
Asp Val Leu Gln Ser Trp Cys Glu Lys Leu Ala Glu Ile Ile Trp Gln
        275                 280                 285
Asn Arg Gln Gln Ile Arg Arg Ala Glu His Leu Cys Gln Gln Leu Pro
        290                 295                 300
Ile Pro Gly Pro Val Glu Glu Met Leu Ala Glu Val Asn Ala Thr Ile
305                 310                 315                 320
Thr Asp Ile Ile Ser Ala Leu Val Thr Ser Thr Phe Ile Ile Glu Lys
                325                 330                 335
Gln Pro Pro Gln Val Leu Lys Thr Gln Thr Lys Phe Ala Ala Thr Val
            340                 345                 350
Arg Leu Leu Val Gly Gly Lys Leu Asn Val His Met Asn Pro Pro Gln
            355                 360                 365
Val Lys Ala Thr Ile Ile Ser Glu Gln Gln Ala Lys Ser Leu Leu Lys
        370                 375                 380
Asn Glu Asn Thr Arg Asn Glu Cys Ser Gly Glu Ile Leu Asn Asn Cys
385                 390                 395                 400
Cys Val Met Glu Tyr His Gln Ala Thr Gly Thr Leu Ser Ala His Phe
                405                 410                 415
Arg Asn Met Ser Leu Lys Arg Ile Lys Arg Ala Asp Arg Arg Gly Ala
            420                 425                 430
Glu Ser Val Thr Glu Glu Lys Phe Thr Val Leu Phe Glu Ser Gln Phe
            435                 440                 445
Ser Val Gly Ser Asn Glu Leu Val Phe Gln Val Lys Thr Leu Ser Leu
        450                 455                 460
```

```
Pro Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
            485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
            515                 520                 525

Asn Leu Val Phe Leu Ala Gln Lys Leu Phe Asn Ser Ser Ser His
    530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Ser Tyr Leu Ile Tyr Val Phe Pro Asp
            660                 665                 670

Arg Pro Lys Asp Glu Val Phe Ser Lys Tyr Tyr Thr Pro Val Leu Ala
            675                 680                 685

Lys Ala Val Asp Gly Tyr Val Lys Pro Gln Ile Lys Gln Val Val Pro
            690                 695                 700

Glu Phe Val Asn Ala Ser Ala Asp Ala Gly Gly Ser Ser Ala Thr Tyr
705                 710                 715                 720

Met Asp Gln Ala Pro Ser Pro Ala Val Cys Pro Gln Ala Pro Tyr Asn
            725                 730                 735

Met Tyr Pro Gln Asn Pro Asp His Val Leu Asp Gln Asp Gly Glu Phe
            740                 745                 750

Asp Leu Asp Glu Thr Met Asp Val Ala Arg His Val Glu Glu Leu Leu
            755                 760                 765

Arg Arg Pro Met Asp Ser Leu Asp Ser Arg Leu Ser Pro Pro Ala Gly
770                 775                 780

Leu Phe Thr Ser Ala Arg Gly Ser Leu Ser
785                 790

<210> SEQ ID NO 11
<211> LENGTH: 3046
<212> TYPE: DNA
<213> ORGANISM: Homo sapiens

<400> SEQUENCE: 11
atcttatttt tcttttggt ggtggtggtg aaggggggga ggtgctagca gggccagcct    60
tgaactcgct ggacagagct acagacctat ggggcctgga agtgcccgct gagaaaggga   120
gaagacagca gaggggttgc cgaggcaacc tccaagtccc agatcatgtc tctgtggggt   180
ctggtctcca agatgccccc agaaaaagtg cagcggctct atgtcgactt tcccaacac    240
```

```
ctgcggcatc ttctgggtga ctggctggag agccagccct gggagttcct ggtcggctcc      300
gacgccttct gctgcaactt ggctagtgcc ctactttcag acactgtcca gcaccttcag      360
gcctcggtgg gagagcaggg ggaggggagc accatcttgc aacacatcag cacccttgag      420
agcatatatc agagggaccc cctgaagctg gtggccactt tcagacaaat acttcaagga      480
gagaaaaaag ctgttatgga acagttccgc cacttgccaa tgcctttcca ctggaagcag      540
gaagaactca gtttaagac aggcttgcgg aggctgcagc accgagtagg ggagatccac       600
cttctccgag aagccctgca aaggggggct gaggctggcc aagtgtctct gcacagcttg      660
atagaaactc ctgctaatgg gactgggcca agtgaggccc tggccatgct actgcaggag      720
accactggag agctagaggc agccaaagcc ctagtgctga agaggatcca gatttggaaa      780
cggcagcagc agctggcagg gaatggcgca ccgtttgagg agagcctggc cccactccag      840
gagaggtgtg aaagcctggt ggacatttat tcccagctac agcaggaggt aggggcggct      900
ggtggggagc ttgagcccaa acccgggca tcgctgactg gccggctgga tgaagtcctg       960
agaaccctcg tcaccagttg cttcctggtg gagaagcagc cccccaggt actgaagact      1020 cagaccaagt tccaggctgg agttcgattc ctgttgggct tgaggttcct gggggcccca     1080
gccaagcctc cgctggtcag ggccgacatg gtgacagaga agcaggcgcg ggagctgagt     1140
gtgcctcagg gtcctggggc tggagcagaa agcactggag aaatcatcaa caacactgtg     1200
cccttggaga acagcattcc tgggaactgc tgctctgccc tgttcaagaa cctgcttctc     1260
aagaagatca agcggtgtga gcggaagggc actgagtctg tcacagagga gaagtgcgct     1320
gtgctcttct ctgccagctt cacacttggc cccggcaaac tccccatcca gctccaggcc     1380
ctgtctctgc ccctggtggt catcgtccat ggcaaccaag acaacaatgc caaagccact     1440
atcctgtggg acaatgcctt ctctgagatg accgcgtgc cctttgtggt ggctgagcgg      1500
gtgccctggg agaagatgtg tgaaactctg aacctgaagt tcatggctga ggtggggacc     1560
aaccgggggc tgctcccaga gcacttcctc ttcctggccc agaagatctt caatgacaac     1620
agcctcagta tggaggcctt ccagcaccgt tctgtgtcct ggtcgcagtt caacaaggag     1680
atcctgctgg gccgtggctt caccttttgg cagtggtttg atggtgtcct ggacctcacc     1740
aaacgctgtc tccggagcta ctggtctgac cggctgatca ttggcttcat cagcaaacag     1800
tacgttacta gccttcttct caatgagccc gacggaacct ttctcctccg cttcagcgac     1860
tcagagattg ggggcatcac cattgcccat gtcatccggg gccaggatgg ctctccacag     1920
atagagaaca tccagccatt ctctgccaaa gacctgtcca ttcgctcact ggggaccga     1980 atccgggatc ttgctcagct caaaaatctc tatcccaaga agcccaagga tgaggctttc     2040
cggagccact acaagcctga acagatgggt aaggatggca ggggttatgt cccagctacc     2100
atcaagatga ccgtggaaag ggaccaacca cttcctaccc cagagctcca gatgcctacc     2160
atggtgcctt cttatgacct tggaatggcc cctgattcct ccatgagcat gcagcttggc     2220
ccagatatgt gccccaggt gtacccacca cactctcact ccatcccccc gtatcaaggc      2280
ctctccccag aagaatcagt caacgtgttg tcagccttcc aggagcctca cctgcagatg     2340 cccccagcc tggccagat gagcctgccc tttgaccagc tcacccccca gggcctgctg      2400
ccgtgccagc ctcaggagca tgctgtgtcc agccctgacc cctgctctg ctcagatgtg      2460 accatggtgg aagacagctg cctgagccag ccagtgacag cgtttcctca gggcacttgg     2520
attggtgaag acatattccc tcctctgctg cctcccactg aacaggacct cactaagctt     2580
```

-continued

```
ctcctggagg ggcaagggga gtcgggggga gggtccttgg gggcacagcc cctcctgcag    2640
ccctcccact atgggcaatc tgggatctca atgtcccaca tggacctaag ggccaacccc    2700
agttggtgat cccagctgga gggagaaccc aaagagacag ctcttctact accccacag    2760 acctgctctg acacttgct catgccctgc caagcagcag atggggaggg tgccctccta    2820 tcccccaccta ctcctgggtc aggaggaaaa gactaacagg agaatgcaca gtgggtggag    2880
ccaatccact ccttcctttc tatcattccc ctgcccacct ccttccagca ctgactggaa    2940
gggaagttca ggctctgaga cacgccccaa catgcctgca cctgcagcgc gcacacgcac    3000
gcacacacac atacagagct ctctgagggt gatggggctg agcagg                   3046
```

<210> SEQ ID NO 12
<211> LENGTH: 847
<212> TYPE: PRT
<213> ORGANISM: Homo sapiens

<400> SEQUENCE: 12

```
Met Ser Leu Trp Gly Leu Val Ser Lys Met Pro Pro Glu Lys Val Gln
  1               5                  10                  15

Arg Leu Tyr Val Asp Phe Pro Gln His Leu Arg His Leu Leu Gly Asp
             20                  25                  30

Trp Leu Glu Ser Gln Pro Trp Glu Phe Leu Val Gly Ser Asp Ala Phe
         35                  40                  45

Cys Cys Asn Leu Ala Ser Ala Leu Leu Ser Asp Thr Val Gln His Leu
     50                  55                  60

Gln Ala Ser Val Gly Glu Gln Gly Glu Gly Ser Thr Ile Leu Gln His
 65                  70                  75                  80

Ile Ser Thr Leu Glu Ser Ile Tyr Gln Arg Asp Pro Leu Lys Leu Val
                 85                  90                  95

Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
```

-continued

```
            290                 295                 300
Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
                355                 360                 365

Lys Arg Cys Glu Arg Lys Gly Thr Glu Ser Val Thr Glu Glu Lys Cys
        370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
530                 535                 540

Gln Tyr Val Thr Ser Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Pro Lys Asp Glu Ala
610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
        675                 680                 685

Val Pro Gln Val Tyr Pro Pro His Ser His Ser Ile Pro Pro Tyr Gln
690                 695                 700

Gly Leu Ser Pro Glu Glu Ser Val Asn Val Leu Ser Ala Phe Gln Glu
705                 710                 715                 720
```

```
Pro His Leu Gln Met Pro Pro Ser Leu Gly Gln Met Ser Leu Pro Phe
            725                 730                 735

Asp Gln Pro His Pro Gln Gly Leu Leu Pro Cys Gln Pro Gln Glu His
        740                 745                 750

Ala Val Ser Ser Pro Asp Pro Leu Leu Cys Ser Asp Val Thr Met Val
        755                 760                 765

Glu Asp Ser Cys Leu Ser Gln Pro Val Thr Ala Phe Pro Gln Gly Thr
    770                 775                 780

Trp Ile Gly Glu Asp Ile Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
            820                 825                 830

Gly Ile Ser Met Ser His Met Asp Leu Arg Ala Asn Pro Ser Trp
            835                 840                 845
```

<210> SEQ ID NO 13
<211> LENGTH: 18
<212> TYPE: DNA
<213> ORGANISM: Homo sapiens

<400> SEQUENCE: 13
acagtttccc gtaaatgc                                                18

<210> SEQ ID NO 14
<211> LENGTH: 18
<212> TYPE: DNA
<213> ORGANISM: Homo sapiens

<400> SEQUENCE: 14
tgcatttacg ggaaactg                                                18

<210> SEQ ID NO 15
<211> LENGTH: 543
<212> TYPE: DNA
<213> ORGANISM: Homo sapiens

<400> SEQUENCE: 15
ttagacaaac agaaagagct tgacagtaaa gtcagaaatg tgaaggacaa ggttatgtgt      60
atagagcatg aaatcaagag cctggaagat ttacaagatg aatatgactt caaatgcaaa     120
accttgcaga acagagaaca cgagaccaat ggtgtggcaa agagtgatca gaaacaagaa     180
cagctgttac tcaagaagat gtatttaatg cttgacaata gagaaaagga agtagttcac     240
aaaataatag agttgctgaa tgtcactgaa cttacccaga atgccctgat taatgatgaa     300 ctagtgggagt ggaagcggag acagcagagc gcctgtattg ggggccgcc caatgcttgc     360 ttggatcagc tgcagaactg gttcactata gttgcggaga gtctgcagca agttcggcag     420
cagcttaaaa agttggagga attggaacag aaatacacct acgaacatga ccctatcaca     480
aaaaacaaac aagtgttatg ggaccgcacc ttcagtcttt tccagcagct cattcagagc     540
tcg                                                                  543

<210> SEQ ID NO 16
<211> LENGTH: 181
<212> TYPE: PRT
<213> ORGANISM: Homo sapiens

```
<400> SEQUENCE: 16

Leu Asp Lys Gln Lys Glu Leu Asp Ser Lys Val Arg Asn Val Lys Asp
  1               5                  10                  15

Lys Val Met Cys Ile Glu His Glu Ile Lys Ser Leu Glu Asp Leu Gln
             20                  25                  30

Asp Glu Tyr Asp Phe Lys Cys Lys Thr Leu Gln Asn Arg Glu His Glu
         35                  40                  45

Thr Asn Gly Val Ala Lys Ser Asp Gln Lys Gln Glu Gln Leu Leu Leu
     50                  55                  60

Lys Lys Met Tyr Leu Met Leu Asp Asn Lys Arg Lys Glu Val Val His
 65                  70                  75                  80

Lys Ile Ile Glu Leu Leu Asn Val Thr Glu Leu Thr Gln Asn Ala Leu
                 85                  90                  95

Ile Asn Asp Glu Leu Val Glu Trp Lys Arg Arg Gln Gln Ser Ala Cys
            100                 105                 110

Ile Gly Gly Pro Pro Asn Ala Cys Leu Asp Gln Leu Gln Asn Trp Phe
        115                 120                 125

Thr Ile Val Ala Glu Ser Leu Gln Gln Val Arg Gln Gln Leu Lys Lys
    130                 135                 140

Leu Glu Glu Leu Glu Gln Lys Tyr Thr Tyr Glu His Asp Pro Ile Thr
145                 150                 155                 160

Lys Asn Lys Gln Val Leu Trp Asp Arg Thr Phe Ser Leu Phe Gln Gln
                165                 170                 175

Leu Ile Gln Ser Ser
            180

<210> SEQ ID NO 17
<211> LENGTH: 513
<212> TYPE: DNA
<213> ORGANISM: Homo sapiens

<400> SEQUENCE: 17
tttgtggtgg aaagacagcc ctgcatgcca acgcaccctc agaggccgct ggtcttgaag      60 acagggtcc agttcactgt gaagttgaga ctgttggtga aattgcaaga gctgaattat      120
aatttgaaag tcaaagtctt atttgataaa gatgtgaatg agagaaatac agtaaaagga      180
tttaggaagt tcaacatttt gggcacgcac acaaaagtga tgaacatgga ggagtccacc      240
aatggcagtc tggcggctga atttcggcac ctgcaattga agaacagaa aaatgctggc      300 accagaacga atgagggtcc tctcatcgtt actgaagagc ttcactccct tagttttgaa      360
acccaattgt gccagcctgg tttggtaatt gacctcgaga cgacctctct gcccgttgtg      420
gtgatctcca acgtcagcca gctcccgagc ggttgggcct ccatcctttg gtacaacatg      480
ctggtggcgg aacccaggaa tctgtccttc ttc                                  513

<210> SEQ ID NO 18
<211> LENGTH: 171
<212> TYPE: PRT
<213> ORGANISM: Homo sapiens

<400> SEQUENCE: 18

Phe Val Val Glu Arg Gln Pro Cys Met Pro Thr His Pro Gln Arg Pro
  1               5                  10                  15

Leu Val Leu Lys Thr Gly Val Gln Phe Thr Val Lys Leu Arg Leu Leu
             20                  25                  30

Val Lys Leu Gln Glu Leu Asn Tyr Asn Leu Lys Val Lys Val Leu Phe
```

```
                35                  40                  45
Asp Lys Asp Val Asn Glu Arg Asn Thr Val Lys Gly Phe Arg Lys Phe
        50                  55                  60

Asn Ile Leu Gly Thr His Thr Lys Val Met Asn Met Glu Glu Ser Thr
65                  70                  75                  80

Asn Gly Ser Leu Ala Ala Glu Phe Arg His Leu Gln Leu Lys Glu Gln
                85                  90                  95

Lys Asn Ala Gly Thr Arg Thr Asn Glu Gly Pro Leu Ile Val Thr Glu
            100                 105                 110

Glu Leu His Ser Leu Ser Phe Glu Thr Gln Leu Cys Gln Pro Gly Leu
        115                 120                 125

Val Ile Asp Leu Glu Thr Thr Ser Leu Pro Val Val Ile Ser Asn
    130                 135                 140

Val Ser Gln Leu Pro Ser Gly Trp Ala Ser Ile Leu Trp Tyr Asn Met
145                 150                 155                 160

Leu Val Ala Glu Pro Arg Asn Leu Ser Phe Phe
                165                 170

<210> SEQ ID NO 19
<211> LENGTH: 267
<212> TYPE: DNA
<213> ORGANISM: Homo sapiens

<400> SEQUENCE: 19
ctgactccac catgtgcacg atgggctcag ctttcagaag tgctgagttg gcagttttct       60
tctgtcacca aaagaggtct caatgtggac cagctgaaca tgttgggaga gaagcttctt     120
ggtcctaacg ccagccccga tggtctcatt ccgtggacga ggttttgtaa ggaaaatata     180
aatgataaaa attttccctt ctggctttgg attgaaagca tcctagaact cattaaaaaa     240
cacctgctcc ctctctggaa tgatggg                                         267

<210> SEQ ID NO 20
<211> LENGTH: 89
<212> TYPE: PRT
<213> ORGANISM: Homo sapiens

<400> SEQUENCE: 20

Leu Thr Pro Pro Cys Ala Arg Trp Ala Gln Leu Ser Glu Val Leu Ser
1               5                   10                  15

Trp Gln Phe Ser Ser Val Thr Lys Arg Gly Leu Asn Val Asp Gln Leu
            20                  25                  30

Asn Met Leu Gly Glu Lys Leu Leu Gly Pro Asn Ala Ser Pro Asp Gly
        35                  40                  45

Leu Ile Pro Trp Thr Arg Phe Cys Lys Glu Asn Ile Asn Asp Lys Asn
    50                  55                  60

Phe Pro Phe Trp Leu Trp Ile Glu Ser Ile Leu Glu Leu Ile Lys Lys
65                  70                  75                  80

His Leu Leu Pro Leu Trp Asn Asp Gly
                85

<210> SEQ ID NO 21
<211> LENGTH: 321
<212> TYPE: DNA
<213> ORGANISM: Homo sapiens

<400> SEQUENCE: 21
tgcatcatgg gcttcatcag caaggagcga gagcgtgccc tgttgaagga ccagcagccg       60
```

```
gggaccttcc tgctgcggtt cagtgagagc tcccgggaag gggccatcac attcacatgg    120
gtggagcggt cccagaacgg aggcgaacct gacttccatg cggttgaacc ctacacgaag    180
aaagaacttt ctgctgttac tttccctgac atcattcgca attacaaagt catggctgct    240
gagaatattc ctgagaatcc cctgaagtat ctgtatccaa atattgacaa agaccatgcc    300 tttgaaagt attactccag g                                              321
```

```
<210> SEQ ID NO 22
<211> LENGTH: 107
<212> TYPE: PRT
<213> ORGANISM: Homo sapiens

<400> SEQUENCE: 22
```

Cys Ile Met Gly Phe Ile Ser Lys Glu Arg Glu Arg Ala Leu Leu Lys
 1               5                  10                  15

Asp Gln Gln Pro Gly Thr Phe Leu Leu Arg Phe Ser Glu Ser Ser Arg
            20                  25                  30

Glu Gly Ala Ile Thr Phe Thr Trp Val Glu Arg Ser Gln Asn Gly Gly
        35                  40                  45

Glu Pro Asp Phe His Ala Val Glu Pro Tyr Thr Lys Lys Glu Leu Ser
    50                  55                  60

Ala Val Thr Phe Pro Asp Ile Ile Arg Asn Tyr Lys Val Met Ala Ala
65                  70                  75                  80

Glu Asn Ile Pro Glu Asn Pro Leu Lys Tyr Leu Tyr Pro Asn Ile Asp
                85                  90                  95

Lys Asp His Ala Phe Gly Lys Tyr Tyr Ser Arg
            100                 105

```
<210> SEQ ID NO 23
<211> LENGTH: 316
<212> TYPE: DNA
<213> ORGANISM: Homo sapiens

<400> SEQUENCE: 23
aagtcgcgac cagagccatt ggagggcgcg gggactgcaa ccctaatcag agcccaaatg     60
gcgcagtggg aaatgctgca gaatcttgac agcccctttc aggatcagct gcaccagctt    120
tactcgcaca gcctcctgcc tgtggacatt cgacagtact tggctgtctg gattgaagac    180
cagaactggc aggaagctgc acttgggagt gatgattcca aggctaccat gctattcttc    240
cacttcttgg atcagctgaa ctatgagtgt ggccgttgca gccaggaccc agagtccttg    300
ttgctgcagc acaatt                                                    316
```

```
<210> SEQ ID NO 24
<211> LENGTH: 170
<212> TYPE: PRT
<213> ORGANISM: Homo sapiens

<400> SEQUENCE: 24
```

Phe Val Val Glu Thr Gln Pro Cys Met Pro Gln Thr Pro His Arg Pro
 1               5                  10                  15

Leu Ile Leu Lys Thr Gly Ser Lys Phe Thr Val Arg Thr Arg Leu Leu
            20                  25                  30

Val Arg Leu Gln Glu Gly Asn Glu Ser Leu Thr Val Glu Val Ser Ile
        35                  40                  45

Asp Arg Asn Pro Pro Gln Leu Gln Gly Phe Arg Lys Phe Asn Ile Leu
    50                  55                  60

```
Thr Ser Asn Gln Lys Thr Leu Thr Pro Glu Lys Gly Gln Ser Gln Gly
 65                  70                  75                  80

Leu Ile Trp Asp Phe Gly Tyr Leu Thr Leu Val Glu Gln Arg Ser Gly
                 85                  90                  95

Gly Ser Gly Lys Gly Ser Asn Lys Gly Pro Leu Gly Val Thr Glu Glu
            100                 105                 110

Leu His Ile Ile Ser Phe Thr Val Lys Tyr Thr Tyr Gln Gly Leu Lys
            115                 120                 125

Gln Glu Leu Lys Thr Asp Thr Leu Pro Val Val Ile Ile Ser Asn Met
        130                 135                 140

Asn Gln Leu Ser Ile Ala Trp Ala Ser Val Leu Trp Phe Asn Leu Leu
145                 150                 155                 160

Ser Pro Asn Leu Gln Asn Gln Gln Phe Phe
                165                 170

<210> SEQ ID NO 25
<211> LENGTH: 519
<212> TYPE: DNA
<213> ORGANISM: Homo sapiens

<400> SEQUENCE: 25
tttgtggtgg agcggcagcc ctgcatgccc atgcatcctg accggcccct cgtcatcaag     60
accggcgtcc agttcactac taaagtcagg ttgctggtca agttccctga gttgaattat    120
cagcttaaaa ttaaagtgtg cattgacaaa gactctgggg acgttgcagc tctcagagga    180
tcccggaaat ttaacattct gggcacaaac acaaaagtga tgaacatgga agaatccaac    240
aacggcagcc tctctgcaga attcaaacac ttgaccctga gggagcagag atgtgggaat    300
gggggccgag ccaattgtga tgcttccctg attgtgactg aggagctgca cctgatcacc    360
tttgagaccg aggtgtatca ccaaggtctc aagattgacc tagagaccca ctccttgtca    420
gttgtggtga tctccaacat ctgtcagatg ccaaatgcct gggcgtccat cctgtggtac    480
aacatgctga ccaacaatcc caagaatgtg aacttcttc                           519

<210> SEQ ID NO 26
<211> LENGTH: 173
<212> TYPE: PRT
<213> ORGANISM: Homo sapiens

<400> SEQUENCE: 26

Phe Val Val Glu Arg Gln Pro Cys Met Pro Met His Pro Asp Arg Pro
 1               5                  10                  15

Leu Val Ile Lys Thr Gly Val Gln Phe Thr Thr Lys Val Arg Leu Leu
             20                  25                  30

Val Lys Phe Pro Glu Leu Asn Tyr Gln Leu Lys Ile Lys Val Cys Ile
         35                  40                  45

Asp Lys Asp Ser Gly Asp Val Ala Ala Leu Arg Gly Ser Arg Lys Phe
     50                  55                  60

Asn Ile Leu Gly Thr Asn Thr Lys Val Met Asn Met Glu Glu Ser Asn
 65                  70                  75                  80

Asn Gly Ser Leu Ser Ala Glu Phe Lys His Leu Thr Leu Arg Glu Gln
                 85                  90                  95

Arg Cys Gly Asn Gly Gly Arg Ala Asn Cys Asp Ala Ser Leu Ile Val
            100                 105                 110

Thr Glu Glu Leu His Leu Ile Thr Phe Glu Thr Glu Val Tyr His Gln
            115                 120                 125
```

-continued

```
Gly Leu Lys Ile Asp Leu Glu Thr His Ser Leu Ser Val Val Ile
    130                 135                 140

Ser Asn Ile Cys Gln Met Pro Asn Ala Trp Ala Ser Ile Leu Trp Tyr
145                 150                 155                 160

Asn Met Leu Thr Asn Asn Pro Lys Asn Val Asn Phe Phe
                165                 170
```

<210> SEQ ID NO 27
<211> LENGTH: 504
<212> TYPE: DNA
<213> ORGANISM: Homo sapiens

<400> SEQUENCE: 27

```
tttgtggttg agcgacagcc atgtatgcca acccaccctc agaggccgtt ggtacttaaa      60
accctaattc agttcactgt aaaactaagg ctactaataa aattgccaga actaaactat     120
caggtaaagg ttaaggcatc aattgacaag aatgtttcaa ctctaagcaa ccgaagattt     180
gtactttgtg gaactaatgt caaagccatg tctattgaag aatcttccaa tgggagtctc     240
tcagtagaat ttcgacattt gcaaccaaag gaaatgaagt ccagtgctgg aggtaaagga     300
aatgagggct gtcacatggt gactgaagaa cttcattcca taacgtttga aacacagatc     360
tgcctctatg gcctgaccat agatttggag accagctcat gcctgtggt gatgatttcc      420
aatgtcagtc agttacctaa tgcttgggca tccatcattt ggtacaacgt gtcaaccaac     480
gattcccaga acttggtttt cttt                                            504
```

<210> SEQ ID NO 28
<211> LENGTH: 168
<212> TYPE: PRT
<213> ORGANISM: Homo sapiens

<400> SEQUENCE: 28

```
Phe Val Val Glu Arg Gln Pro Cys Met Pro Thr His Pro Gln Arg Pro
  1               5                  10                  15

Leu Val Leu Lys Thr Leu Ile Gln Phe Thr Val Lys Leu Arg Leu Leu
                 20                  25                  30

Ile Lys Leu Pro Glu Leu Asn Tyr Gln Val Lys Val Lys Ala Ser Ile
             35                  40                  45

Asp Lys Asn Val Ser Thr Leu Ser Asn Arg Arg Phe Val Leu Cys Gly
     50                  55                  60

Thr Asn Val Lys Ala Met Ser Ile Glu Glu Ser Ser Asn Gly Ser Leu
 65                  70                  75                  80

Ser Val Glu Phe Arg His Leu Gln Pro Lys Glu Met Lys Ser Ser Ala
                 85                  90                  95

Gly Gly Lys Gly Asn Glu Gly Cys His Met Val Thr Glu Glu Leu His
            100                 105                 110

Ser Ile Thr Phe Glu Thr Gln Ile Cys Leu Tyr Gly Leu Thr Ile Asp
        115                 120                 125

Leu Glu Thr Ser Ser Leu Pro Val Val Met Ile Ser Asn Val Ser Gln
    130                 135                 140

Leu Pro Asn Ala Trp Ala Ser Ile Ile Trp Tyr Asn Val Ser Thr Asn
145                 150                 155                 160

Asp Ser Gln Asn Leu Val Phe Phe
                165
```

<210> SEQ ID NO 29

<211> LENGTH: 495
<212> TYPE: DNA
<213> ORGANISM: Homo sapiens

<400> SEQUENCE: 29

```
ttcatcattg agaagcagcc tcctcaggtc ctgaagaccc agaccaagtt tgcagccacc      60
gtacgcctgc tggtgggcgg gaagctgaac gtgcacatga atcccccca ggtgaaggcc     120
accatcatca gtgagcagca ggccaagtct ctgcttaaaa atgagaacac ccgcaacgag    180
tgcagtggtg agatcctgaa caactgctgc gtgatggagt accaccaagc cacgggcacc    240
ctcagtgccc acttcaggaa catgtcactg aagaggatca agcgtgctga ccggcggggt    300
gcagagtccg tgacagagga gaagttcaca gtcctgtttg agtctcagtt cagtgttggc    360
agcaatgagc ttgtgttcca ggtgaagact ctgtccctac ctgtggttgt catcgtccac    420
ggcagccagg accacaatgc cacggctact gtgctgtggg acaatgcctt tgctgagccg    480
ggcagggtgc cattt                                                     495
```

<210> SEQ ID NO 30
<211> LENGTH: 165
<212> TYPE: PRT
<213> ORGANISM: Homo sapiens

<400> SEQUENCE: 30

```
Phe Ile Ile Glu Lys Gln Pro Pro Gln Val Leu Lys Thr Gln Thr Lys
  1               5                  10                  15
Phe Ala Ala Thr Val Arg Leu Leu Val Gly Gly Lys Leu Asn Val His
                 20                  25                  30
Met Asn Pro Pro Gln Val Lys Ala Thr Ile Ile Ser Glu Gln Gln Ala
             35                  40                  45
Lys Ser Leu Leu Lys Asn Glu Asn Thr Arg Asn Glu Cys Ser Gly Glu
         50                  55                  60
Ile Leu Asn Asn Cys Cys Val Met Glu Tyr His Gln Ala Thr Gly Thr
 65                  70                  75                  80
Leu Ser Ala His Phe Arg Asn Met Ser Leu Lys Arg Ile Lys Arg Ala
                 85                  90                  95
Asp Arg Arg Gly Ala Glu Ser Val Thr Glu Glu Lys Phe Thr Val Leu
            100                 105                 110
Phe Glu Ser Gln Phe Ser Val Gly Ser Asn Glu Leu Val Phe Gln Val
            115                 120                 125
Lys Thr Leu Ser Leu Pro Val Val Val Ile Val His Gly Ser Gln Asp
        130                 135                 140
His Asn Ala Thr Ala Thr Val Leu Trp Asp Asn Ala Phe Ala Glu Pro
145                 150                 155                 160
Gly Arg Val Pro Phe
            165
```

<210> SEQ ID NO 31
<211> LENGTH: 504
<212> TYPE: DNA
<213> ORGANISM: Homo sapiens

<400> SEQUENCE: 31

```
ttcctggtgg agaagcagcc cccccaggta ctgaagactc agaccaagtt ccaggctgga     60
gttcgattcc tgttgggctt gaggttcctg ggggccccag ccaagcctcc gctggtcagg    120
gccgacatgg tgacagagaa gcaggcgcgg gagctgagtg tgcctcaggg tcctggggct    180
```

-continued

```
ggagcagaaa gcactggaga aatcatcaac aacactgtgc ccttggagaa cagcattcct    240
gggaactgct gctctgccct gttcaagaac ctgcttctca agaagatcaa gcggtgtgag    300
cggaagggca ctgagtctgt cacagaggag aagtgcgctg tgctcttctc tgccagcttc    360
acacttggcc ccggcaaact ccccatccag ctccaggccc tgtctctgcc cctggtggtc    420
atcgtccatg gcaaccaaga caacaatgcc aaagccacta tcctgtggga caatgccttc    480
tctgagatgg accgcgtgcc cttt                                           504
```

```
<210> SEQ ID NO 32
<211> LENGTH: 168
<212> TYPE: PRT
<213> ORGANISM: Homo sapiens

<400> SEQUENCE: 32
```

Phe Leu Val Glu Lys Gln Pro Pro Gln Val Leu Lys Thr Gln Thr Lys
 1               5                  10                  15

Phe Gln Ala Gly Val Arg Phe Leu Gly Leu Arg Phe Leu Gly Ala
            20                  25                  30

Pro Ala Lys Pro Pro Leu Val Arg Ala Asp Met Val Thr Glu Lys Gln
        35                  40                  45

Ala Arg Glu Leu Ser Val Pro Gln Gly Pro Gly Ala Gly Ala Glu Ser
    50                  55                  60

Thr Gly Glu Ile Ile Asn Asn Thr Val Pro Leu Glu Asn Ser Ile Pro
65                  70                  75                  80

Gly Asn Cys Cys Ser Ala Leu Phe Lys Asn Leu Leu Leu Lys Lys Ile
                85                  90                  95

Lys Arg Cys Glu Arg Lys Gly Thr Glu Ser Val Thr Glu Glu Lys Cys
            100                 105                 110

Ala Val Leu Phe Ser Ala Ser Phe Thr Leu Gly Pro Gly Lys Leu Pro
        115                 120                 125

Ile Gln Leu Gln Ala Leu Ser Leu Pro Leu Val Val Ile Val His Gly
    130                 135                 140

Asn Gln Asp Asn Asn Ala Lys Ala Thr Ile Leu Trp Asp Asn Ala Phe
145                 150                 155                 160

Ser Glu Met Asp Arg Val Pro Phe
                165

```
<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Consensus

<400> SEQUENCE: 33
acagtttccc gtaaatgc                                                   18
```

```
<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Consensus
<220> FEATURE:
<221> NAME/KEY: misc_difference
<222> LOCATION: (1)
<223> OTHER INFORMATION: This n could be G, A, or C.
<220> FEATURE:
<221> NAME/KEY: misc_difference
<222> LOCATION: (3)
```

```
<223> OTHER INFORMATION: This n could be A, C, or T
<220> FEATURE:
<221> NAME/KEY: misc_difference
<222> LOCATION: (8)
<223> OTHER INFORMATION: This n could be C or G.
<220> FEATURE:
<221> NAME/KEY: misc_difference
<222> LOCATION: (13)
<223> OTHER INFORMATION: This n could be G, A or T.

<400> SEQUENCE: 34
nanttccngg aantg                                                   15

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Linker

<400> SEQUENCE: 35

Pro Lys Glu Ala Pro Glu Pro Met Glu Leu Asp Gly Pro Lys Gly Thr
  1               5                  10                  15

Lys

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Linker

<400> SEQUENCE: 36

Glu Asn Ala Gln Arg Phe Asn Gln Ala Gln Ser Gly Asn Gln Ser Thr
  1               5                  10                  15

Val Met Leu Asp Lys Gln Lys Glu
                 20

<210> SEQ ID NO 37
<211> LENGTH: 100
<212> TYPE: PRT
<213> ORGANISM: Rous sarcoma virus

<400> SEQUENCE: 37

Glu Trp Tyr Phe Gly Lys Ile Thr Arg Arg Glu Ser Glu Arg Leu Leu
  1               5                  10                  15

Leu Asn Pro Glu Asn Pro Arg Gly Thr Phe Leu Val Arg Glu Ser Glu
                 20                  25                  30

Thr Thr Lys Gly Ala Tyr Cys Leu Ser Val Ser Asp Phe Asp Asn Ala
             35                  40                  45

Lys Gly Leu Asn Val Lys His Tyr Lys Ile Arg Lys Leu Asp Ser Gly
         50                  55                  60

Gly Phe Tyr Ile Thr Ser Arg Thr Gln Phe Ser Ser Leu Gln Gln Leu
 65                  70                  75                  80

Val Ala Tyr Tyr Ser Lys His Ala Asp Gly Leu Cys His Arg Leu Thr
                 85                  90                  95

Asn Val Cys Thr
             100
```

54

Table 2

The crystals contain 1 STAT-1 monomer and one DNA half-site in
the asymmetric unit.For convenience, these coordinates contain
one STAT-1 DIMER and one full 18 bp DNA site
generated using crystallographic operators)

Resolution: 2.9 Angstroms.
R-value: 22.7%   R-free: 29.3%

```
ATOM     1  CB  LEU  136    75.391  32.177  64.288  1.00  78.90
ATOM     2  CG  LEU  136    76.404  33.321  64.374  1.00  80.10
ATOM     3  CD1 LEU  136    76.714  33.820  62.963  1.00  76.67
ATOM     4  CD2 LEU  136    75.840  34.453  65.231  1.00  78.56
ATOM     5  C   LEU  136    73.863  30.470  65.246  1.00  78.60
ATOM     6  O   LEU  136    72.741  30.715  64.802  1.00  78.79
ATOM     7  N   LEU  136    75.936  31.082  66.449  1.00  76.89
ATOM     8  CA  LEU  136    74.831  31.591  65.589  1.00  78.14
ATOM     9  N   ASP  137    74.312  29.239  65.451  1.00  80.35
ATOM    10  CA  ASP  137    73.508  28.057  65.159  1.00  80.53
ATOM    11  CB  ASP  137    74.149  26.824  65.794  1.00  81.03
ATOM    12  CG  ASP  137    73.305  25.589  65.625  1.00  81.50
ATOM    13  OD1 ASP  137    73.048  25.201  64.467  1.00  83.62
ATOM    14  OD2 ASP  137    72.890  25.012  66.652  1.00  82.58
ATOM    15  C   ASP  137    72.057  28.171  65.621  1.00  79.98
ATOM    16  O   ASP  137    71.141  28.199  64.797  1.00  81.29
ATOM    17  N   LYS  138    71.852  28.226  66.936  1.00  77.77
ATOM    18  CA  LYS  138    70.509  28.337  67.496  1.00  74.77
ATOM    19  CB  LYS  138    70.556  28.574  69.012  1.00  78.12
ATOM    20  CG  LYS  138    71.041  27.379  69.828  1.00  80.83
ATOM    21  CD  LYS  138    70.876  27.621  71.325  1.00  81.18
ATOM    22  CE  LYS  138    71.282  26.393  72.131  1.00  82.16
ATOM    23  NZ  LYS  138    71.086  26.603  73.592  1.00  82.40
ATOM    24  C   LYS  138    69.721  29.457  66.841  1.00  71.05
ATOM    25  O   LYS  138    68.535  29.305  66.559  1.00  70.94
ATOM    26  N   GLN  139    70.374  30.585  66.603  1.00  66.84
ATOM    27  CA  GLN  139    69.692  31.700  65.968  1.00  65.35
ATOM    28  CB  GLN  139    70.655  32.874  65.780  1.00  64.57
ATOM    29  CG  GLN  139    71.302  33.348  67.073  1.00  63.28
ATOM    30  CD  GLN  139    71.936  34.720  66.940  1.00  64.52
ATOM    31  OE1 GLN  139    72.808  34.942  66.098  1.00  61.50
ATOM    32  NE2 GLN  139    71.498  35.652  67.780  1.00  63.79
ATOM    33  C   GLN  139    69.142  31.246  64.617  1.00  64.51
ATOM    34  O   GLN  139    67.934  31.282  64.372  1.00  63.29
ATOM    35  N   LYS  140    70.048  30.801  63.754  1.00  64.02
ATOM    36  CA  LYS  140    69.704  30.325  62.422  1.00  62.28
ATOM    37  CB  LYS  140    70.937  29.665  61.806  1.00  66.09
ATOM    38  CG  LYS  140    72.163  30.579  61.832  1.00  72.92
ATOM    39  CD  LYS  140    73.440  29.882  61.359  1.00  75.96
ATOM    40  CE  LYS  140    74.647  30.825  61.449  1.00  77.62
ATOM    41  NZ  LYS  140    75.937  30.193  61.032  1.00  74.46
ATOM    42  C   LYS  140    68.528  29.348  62.433  1.00  59.26
ATOM    43  O   LYS  140    67.693  29.363  61.534  1.00  55.98
ATOM    44  N   GLU  141    68.454  28.505  63.453  1.00  58.71
ATOM    45  CA  GLU  141    67.369  27.538  63.538  1.00  61.13
ATOM    46  CB  GLU  141    67.705  26.440  64.549  1.00  67.33
ATOM    47  CG  GLU  141    66.652  25.337  64.627  1.00  75.25
ATOM    48  CD  GLU  141    67.086  24.166  65.492  1.00  80.17
ATOM    49  OE1 GLU  141    67.310  24.363  66.706  1.00  84.23
ATOM    50  OE2 GLU  141    67.209  23.045  64.953  1.00  81.08
ATOM    51  C   GLU  141    66.051  28.193  63.916  1.00  59.26
ATOM    52  O   GLU  141    64.987  27.758  63.484  1.00  60.74
ATOM    53  N   LEU  142    66.117  29.230  64.737  1.00  56.93
ATOM    54  CA  LEU  142    64.909  29.932  65.141  1.00  53.72
ATOM    55  CB  LEU  142    65.204  30.872  66.310  1.00  51.75
ATOM    56  CG  LEU  142    64.114  31.884  66.657  1.00  48.29
ATOM    57  CD1 LEU  142    62.808  31.182  66.973  1.00  43.64
```

55

| ATOM | 58 | CD2 | LEU | 142 | 64.583 | 32.715 | 67.823 | 1.00 | 47.35 |
| ATOM | 59 | C | LEU | 142 | 64.433 | 30.735 | 63.950 | 1.00 | 53.73 |
| ATOM | 60 | O | LEU | 142 | 63.261 | 31.081 | 63.838 | 1.00 | 53.89 |
| ATOM | 61 | N | ASP | 143 | 65.359 | 31.024 | 63.049 | 1.00 | 54.01 |
| ATOM | 62 | CA | ASP | 143 | 65.038 | 31.800 | 61.864 | 1.00 | 54.22 |
| ATOM | 63 | CB | ASP | 143 | 66.322 | 32.137 | 61.115 | 1.00 | 56.24 |
| ATOM | 64 | CG | ASP | 143 | 66.326 | 33.544 | 60.594 | 1.00 | 59.81 |
| ATOM | 65 | OD1 | ASP | 143 | 65.446 | 33.885 | 59.775 | 1.00 | 64.14 |
| ATOM | 66 | OD2 | ASP | 143 | 67.212 | 34.313 | 61.018 | 1.00 | 65.27 |
| ATOM | 67 | C | ASP | 143 | 64.089 | 31.021 | 60.952 | 1.00 | 52.41 |
| ATOM | 68 | O | ASP | 143 | 63.178 | 31.589 | 60.352 | 1.00 | 51.12 |
| ATOM | 69 | N | SER | 144 | 64.306 | 29.715 | 60.855 | 1.00 | 50.96 |
| ATOM | 70 | CA | SER | 144 | 63.466 | 28.882 | 60.017 | 1.00 | 48.47 |
| ATOM | 71 | CB | SER | 144 | 64.148 | 27.544 | 59.724 | 1.00 | 49.53 |
| ATOM | 72 | OG | SER | 144 | 64.211 | 26.734 | 60.885 | 1.00 | 53.41 |
| ATOM | 73 | C | SER | 144 | 62.127 | 28.638 | 60.698 | 1.00 | 46.34 |
| ATOM | 74 | O | SER | 144 | 61.096 | 28.574 | 60.037 | 1.00 | 49.82 |
| ATOM | 75 | N | LYS | 145 | 62.130 | 28.489 | 62.017 | 1.00 | 42.15 |
| ATOM | 76 | CA | LYS | 145 | 60.873 | 28.263 | 62.706 | 1.00 | 38.82 |
| ATOM | 77 | CB | LYS | 145 | 61.069 | 28.135 | 64.214 | 1.00 | 40.16 |
| ATOM | 78 | CG | LYS | 145 | 61.670 | 26.841 | 64.681 | 1.00 | 41.21 |
| ATOM | 79 | CD | LYS | 145 | 61.642 | 26.829 | 66.196 | 1.00 | 50.07 |
| ATOM | 80 | CE | LYS | 145 | 62.154 | 25.524 | 66.777 | 1.00 | 53.11 |
| ATOM | 81 | NZ | LYS | 145 | 62.104 | 25.555 | 68.268 | 1.00 | 54.84 |
| ATOM | 82 | C | LYS | 145 | 59.943 | 29.423 | 62.423 | 1.00 | 35.62 |
| ATOM | 83 | O | LYS | 145 | 58.732 | 29.233 | 62.319 | 1.00 | 36.54 |
| ATOM | 84 | N | VAL | 146 | 60.507 | 30.624 | 62.301 | 1.00 | 31.82 |
| ATOM | 85 | CA | VAL | 146 | 59.699 | 31.804 | 62.020 | 1.00 | 32.33 |
| ATOM | 86 | CB | VAL | 146 | 60.455 | 33.104 | 62.337 | 1.00 | 28.44 |
| ATOM | 87 | CG1 | VAL | 146 | 59.680 | 34.297 | 61.821 | 1.00 | 27.77 |
| ATOM | 88 | CG2 | VAL | 146 | 60.634 | 33.234 | 63.834 | 1.00 | 25.92 |
| ATOM | 89 | C | VAL | 146 | 59.252 | 31.816 | 60.564 | 1.00 | 34.07 |
| ATOM | 90 | O | VAL | 146 | 58.100 | 32.109 | 60.277 | 1.00 | 33.32 |
| ATOM | 91 | N | ARG | 147 | 60.152 | 31.511 | 59.639 | 1.00 | 36.78 |
| ATOM | 92 | CA | ARG | 147 | 59.749 | 31.461 | 58.242 | 1.00 | 44.42 |
| ATOM | 93 | CB | ARG | 147 | 60.942 | 31.123 | 57.341 | 1.00 | 50.03 |
| ATOM | 94 | CG | ARG | 147 | 61.784 | 32.349 | 56.972 | 1.00 | 60.30 |
| ATOM | 95 | CD | ARG | 147 | 62.150 | 33.193 | 58.195 | 1.00 | 66.59 |
| ATOM | 96 | NE | ARG | 147 | 62.776 | 34.461 | 57.820 | 1.00 | 75.47 |
| ATOM | 97 | CZ | ARG | 147 | 63.121 | 35.418 | 58.682 | 1.00 | 77.95 |
| ATOM | 98 | NH1 | ARG | 147 | 62.897 | 35.256 | 59.980 | 1.00 | 78.19 |
| ATOM | 99 | NH2 | ARG | 147 | 63.681 | 36.543 | 58.245 | 1.00 | 77.84 |
| ATOM | 100 | C | ARG | 147 | 58.658 | 30.467 | 58.121 | 1.00 | 44.14 |
| ATOM | 101 | O | ARG | 147 | 57.668 | 30.604 | 57.420 | 1.00 | 45.79 |
| ATOM | 102 | N | ASN | 148 | 58.826 | 29.298 | 58.834 | 1.00 | 43.39 |
| ATOM | 103 | CA | ASN | 148 | 57.837 | 28.225 | 58.815 | 1.00 | 43.36 |
| ATOM | 104 | CB | ASN | 148 | 58.231 | 27.093 | 59.758 | 1.00 | 45.08 |
| ATOM | 105 | CG | ASN | 148 | 57.236 | 25.957 | 59.729 | 1.00 | 45.85 |
| ATOM | 106 | OD1 | ASN | 148 | 57.066 | 25.307 | 58.704 | 1.00 | 51.32 |
| ATOM | 107 | ND2 | ASN | 148 | 56.558 | 25.723 | 60.846 | 1.00 | 45.98 |
| ATOM | 108 | C | ASN | 148 | 56.471 | 28.746 | 59.233 | 1.00 | 40.02 |
| ATOM | 109 | O | ASN | 148 | 55.462 | 28.421 | 58.617 | 1.00 | 40.50 |
| ATOM | 110 | N | VAL | 149 | 56.437 | 29.540 | 60.296 | 1.00 | 36.79 |
| ATOM | 111 | CA | VAL | 149 | 55.181 | 30.101 | 60.757 | 1.00 | 36.35 |
| ATOM | 112 | CB | VAL | 149 | 55.370 | 30.994 | 62.019 | 1.00 | 34.77 |
| ATOM | 113 | CG1 | VAL | 149 | 54.035 | 31.633 | 62.420 | 1.00 | 32.94 |
| ATOM | 114 | CG2 | VAL | 149 | 55.906 | 30.155 | 63.171 | 1.00 | 33.68 |
| ATOM | 115 | C | VAL | 149 | 54.564 | 30.928 | 59.635 | 1.00 | 37.24 |
| ATOM | 116 | O | VAL | 149 | 53.409 | 30.703 | 59.274 | 1.00 | 40.54 |
| ATOM | 117 | N | LYS | 150 | 55.328 | 31.868 | 59.074 | 1.00 | 35.32 |
| ATOM | 118 | CA | LYS | 150 | 54.817 | 32.706 | 57.991 | 1.00 | 34.77 |
| ATOM | 119 | CB | LYS | 150 | 55.894 | 33.652 | 57.446 | 1.00 | 37.25 |
| ATOM | 120 | CG | LYS | 150 | 55.381 | 34.487 | 56.256 | 1.00 | 47.77 |
| ATOM | 121 | CD | LYS | 150 | 56.432 | 35.395 | 55.603 | 1.00 | 50.00 |
| ATOM | 122 | CE | LYS | 150 | 56.816 | 36.577 | 56.481 | 1.00 | 50.86 |
| ATOM | 123 | NZ | LYS | 150 | 57.809 | 37.464 | 55.807 | 1.00 | 51.16 |
| ATOM | 124 | C | LYS | 150 | 54.266 | 31.852 | 56.846 | 1.00 | 35.60 |
| ATOM | 125 | O | LYS | 150 | 53.170 | 32.118 | 56.357 | 1.00 | 35.76 |
| ATOM | 126 | N | ASP | 151 | 55.012 | 30.835 | 56.411 | 1.00 | 34.33 |
| ATOM | 127 | CA | ASP | 151 | 54.513 | 29.979 | 55.343 | 1.00 | 36.68 |

56

| ATOM | 128 | CB | ASP | 151 | 55.434 | 28.784 | 55.073 | 1.00 | 40.49 |
| ATOM | 129 | CG | ASP | 151 | 56.786 | 29.191 | 54.513 | 1.00 | 46.68 |
| ATOM | 130 | OD1 | ASP | 151 | 56.854 | 30.233 | 53.818 | 1.00 | 43.58 |
| ATOM | 131 | OD2 | ASP | 151 | 57.772 | 28.448 | 54.742 | 1.00 | 47.75 |
| ATOM | 132 | C | ASP | 151 | 53.136 | 29.448 | 55.714 | 1.00 | 37.74 |
| ATOM | 133 | O | ASP | 151 | 52.155 | 29.740 | 55.035 | 1.00 | 40.86 |
| ATOM | 134 | N | LYS | 152 | 53.058 | 28.680 | 56.798 | 1.00 | 37.37 |
| ATOM | 135 | CA | LYS | 152 | 51.782 | 28.113 | 57.227 | 1.00 | 35.11 |
| ATOM | 136 | CB | LYS | 152 | 51.895 | 27.444 | 58.599 | 1.00 | 34.51 |
| ATOM | 137 | CG | LYS | 152 | 52.754 | 26.200 | 58.626 | 1.00 | 35.87 |
| ATOM | 138 | CD | LYS | 152 | 52.334 | 25.260 | 59.746 | 1.00 | 36.70 |
| ATOM | 139 | CE | LYS | 152 | 53.149 | 23.973 | 59.708 | 1.00 | 42.21 |
| ATOM | 140 | NZ | LYS | 152 | 52.617 | 22.917 | 60.630 | 1.00 | 46.74 |
| ATOM | 141 | C | LYS | 152 | 50.615 | 29.088 | 57.266 | 1.00 | 35.71 |
| ATOM | 142 | O | LYS | 152 | 49.484 | 28.693 | 57.020 | 1.00 | 36.33 |
| ATOM | 143 | N | VAL | 153 | 50.869 | 30.353 | 57.576 | 1.00 | 33.21 |
| ATOM | 144 | CA | VAL | 153 | 49.778 | 31.319 | 57.640 | 1.00 | 33.70 |
| ATOM | 145 | CB | VAL | 153 | 50.209 | 32.613 | 58.361 | 1.00 | 36.62 |
| ATOM | 146 | CG1 | VAL | 153 | 48.987 | 33.491 | 58.627 | 1.00 | 36.64 |
| ATOM | 147 | CG2 | VAL | 153 | 50.908 | 33.276 | 59.652 | 1.00 | 38.90 |
| ATOM | 148 | C | VAL | 153 | 49.271 | 31.684 | 56.243 | 1.00 | 32.20 |
| ATOM | 149 | O | VAL | 153 | 48.059 | 31.822 | 56.029 | 1.00 | 28.40 |
| ATOM | 150 | N | MET | 154 | 50.199 | 31.854 | 55.304 | 1.00 | 30.18 |
| ATOM | 151 | CA | MET | 154 | 49.833 | 32.184 | 53.936 | 1.00 | 31.44 |
| ATOM | 152 | CB | MET | 154 | 51.059 | 32.647 | 53.146 | 1.00 | 30.24 |
| ATOM | 153 | CG | MET | 154 | 51.596 | 33.983 | 53.633 | 1.00 | 43.57 |
| ATOM | 154 | SD | MET | 154 | 53.057 | 34.607 | 52.760 | 1.00 | 58.55 |
| ATOM | 155 | CE | MET | 154 | 54.267 | 33.325 | 53.056 | 1.00 | 52.24 |
| ATOM | 156 | C | MET | 154 | 49.220 | 30.948 | 53.307 | 1.00 | 30.49 |
| ATOM | 157 | O | MET | 154 | 48.182 | 31.017 | 52.650 | 1.00 | 30.45 |
| ATOM | 158 | N | CYS | 155 | 49.854 | 29.807 | 53.537 | 1.00 | 29.98 |
| ATOM | 159 | CA | CYS | 155 | 49.352 | 28.567 | 52.996 | 1.00 | 31.39 |
| ATOM | 160 | CB | CYS | 155 | 50.181 | 27.395 | 53.510 | 1.00 | 36.24 |
| ATOM | 161 | SG | CYS | 155 | 49.769 | 25.794 | 52.753 | 1.00 | 58.18 |
| ATOM | 162 | C | CYS | 155 | 47.909 | 28.444 | 53.453 | 1.00 | 29.83 |
| ATOM | 163 | O | CYS | 155 | 47.027 | 28.123 | 52.672 | 1.00 | 34.32 |
| ATOM | 164 | N | ILE | 156 | 47.663 | 28.730 | 54.721 | 1.00 | 31.51 |
| ATOM | 165 | CA | ILE | 156 | 46.314 | 28.645 | 55.258 | 1.00 | 31.07 |
| ATOM | 166 | CB | ILE | 156 | 46.291 | 28.804 | 56.795 | 1.00 | 28.44 |
| ATOM | 167 | CG2 | ILE | 156 | 44.858 | 28.851 | 57.293 | 1.00 | 25.04 |
| ATOM | 168 | CG1 | ILE | 156 | 47.018 | 27.627 | 57.449 | 1.00 | 30.51 |
| ATOM | 169 | CD1 | ILE | 156 | 47.071 | 27.702 | 58.954 | 1.00 | 34.46 |
| ATOM | 170 | C | ILE | 156 | 45.360 | 29.671 | 54.673 | 1.00 | 32.31 |
| ATOM | 171 | O | ILE | 156 | 44.167 | 29.402 | 54.552 | 1.00 | 34.94 |
| ATOM | 172 | N | GLU | 157 | 45.846 | 30.846 | 54.304 | 1.00 | 35.80 |
| ATOM | 173 | CA | GLU | 157 | 44.902 | 31.813 | 53.765 | 1.00 | 41.03 |
| ATOM | 174 | CB | GLU | 157 | 45.477 | 33.233 | 53.779 | 1.00 | 45.85 |
| ATOM | 175 | CG | GLU | 157 | 44.425 | 34.303 | 53.466 | 1.00 | 53.60 |
| ATOM | 176 | CD | GLU | 157 | 44.846 | 35.691 | 53.925 | 1.00 | 61.45 |
| ATOM | 177 | OE1 | GLU | 157 | 44.083 | 36.659 | 53.691 | 1.00 | 63.05 |
| ATOM | 178 | OE2 | GLU | 157 | 45.937 | 35.808 | 54.530 | 1.00 | 62.31 |
| ATOM | 179 | C | GLU | 157 | 44.443 | 31.423 | 52.367 | 1.00 | 40.56 |
| ATOM | 180 | O | GLU | 157 | 43.324 | 31.751 | 51.970 | 1.00 | 42.93 |
| ATOM | 181 | N | HIS | 158 | 45.300 | 30.715 | 51.627 | 1.00 | 38.68 |
| ATOM | 182 | CA | HIS | 158 | 44.942 | 30.269 | 50.284 | 1.00 | 33.97 |
| ATOM | 183 | CB | HIS | 158 | 46.118 | 29.585 | 49.593 | 1.00 | 28.31 |
| ATOM | 184 | CG | HIS | 158 | 47.147 | 30.535 | 49.076 | 1.00 | 29.87 |
| ATOM | 185 | CD2 | HIS | 158 | 48.476 | 30.626 | 49.308 | 1.00 | 30.45 |
| ATOM | 186 | ND1 | HIS | 158 | 46.842 | 31.543 | 48.187 | 1.00 | 30.53 |
| ATOM | 187 | CE1 | HIS | 158 | 47.940 | 32.215 | 47.894 | 1.00 | 31.17 |
| ATOM | 188 | NE2 | HIS | 158 | 48.946 | 31.679 | 48.561 | 1.00 | 33.12 |
| ATOM | 189 | C | HIS | 158 | 43.797 | 29.284 | 50.390 | 1.00 | 34.66 |
| ATOM | 190 | O | HIS | 158 | 42.756 | 29.460 | 49.764 | 1.00 | 36.53 |
| ATOM | 191 | N | GLU | 159 | 43.990 | 28.249 | 51.194 | 1.00 | 31.59 |
| ATOM | 192 | CA | GLU | 159 | 42.960 | 27.247 | 51.367 | 1.00 | 34.13 |
| ATOM | 193 | CB | GLU | 159 | 43.405 | 26.197 | 52.386 | 1.00 | 39.12 |
| ATOM | 194 | CG | GLU | 159 | 44.619 | 25.393 | 51.959 | 1.00 | 47.51 |
| ATOM | 195 | CD | GLU | 159 | 44.969 | 24.307 | 52.955 | 1.00 | 55.28 |
| ATOM | 196 | OE1 | GLU | 159 | 44.097 | 23.446 | 53.214 | 1.00 | 57.63 |
| ATOM | 197 | OE2 | GLU | 159 | 46.111 | 24.316 | 53.475 | 1.00 | 60.95 |

57

| ATOM | 198 | C | GLU | 159 | 41.629 | 27.842 | 51.803 | 1.00 | 33.97 |
| --- | --- | --- | --- | --- | --- | --- | --- | --- | --- |
| ATOM | 199 | O | GLU | 159 | 40.581 | 27.225 | 51.614 | 1.00 | 34.45 |
| ATOM | 200 | N | ILE | 160 | 41.655 | 29.035 | 52.384 | 1.00 | 33.50 |
| ATOM | 201 | CA | ILE | 160 | 40.413 | 29.643 | 52.838 | 1.00 | 33.77 |
| ATOM | 202 | CB | ILE | 160 | 40.660 | 30.558 | 54.059 | 1.00 | 33.81 |
| ATOM | 203 | CG2 | ILE | 160 | 39.476 | 31.487 | 54.302 | 1.00 | 33.51 |
| ATOM | 204 | CG1 | ILE | 160 | 40.912 | 29.670 | 55.283 | 1.00 | 33.36 |
| ATOM | 205 | CD1 | ILE | 160 | 41.059 | 30.410 | 56.573 | 1.00 | 39.69 |
| ATOM | 206 | C | ILE | 160 | 39.642 | 30.359 | 51.742 | 1.00 | 34.77 |
| ATOM | 207 | O | ILE | 160 | 38.413 | 30.304 | 51.725 | 1.00 | 36.67 |
| ATOM | 208 | N | LYS | 161 | 40.338 | 31.026 | 50.823 | 1.00 | 35.79 |
| ATOM | 209 | CA | LYS | 161 | 39.640 | 31.682 | 49.720 | 1.00 | 32.72 |
| ATOM | 210 | CB | LYS | 161 | 40.612 | 32.435 | 48.808 | 1.00 | 34.10 |
| ATOM | 211 | CG | LYS | 161 | 41.289 | 33.568 | 49.528 | 1.00 | 43.45 |
| ATOM | 212 | CD | LYS | 161 | 42.075 | 34.513 | 48.640 | 1.00 | 48.40 |
| ATOM | 213 | CE | LYS | 161 | 42.613 | 35.641 | 49.525 | 1.00 | 54.45 |
| ATOM | 214 | NZ | LYS | 161 | 43.338 | 36.725 | 48.816 | 1.00 | 58.40 |
| ATOM | 215 | C | LYS | 161 | 39.000 | 30.537 | 48.969 | 1.00 | 31.33 |
| ATOM | 216 | O | LYS | 161 | 37.828 | 30.591 | 48.612 | 1.00 | 32.86 |
| ATOM | 217 | N | SER | 162 | 39.785 | 29.481 | 48.776 | 1.00 | 27.67 |
| ATOM | 218 | CA | SER | 162 | 39.338 | 28.284 | 48.083 | 1.00 | 28.87 |
| ATOM | 219 | CB | SER | 162 | 40.482 | 27.283 | 47.980 | 1.00 | 25.30 |
| ATOM | 220 | OG | SER | 162 | 41.603 | 27.886 | 47.367 | 1.00 | 29.25 |
| ATOM | 221 | C | SER | 162 | 38.171 | 27.626 | 48.793 | 1.00 | 32.12 |
| ATOM | 222 | O | SER | 162 | 37.420 | 26.870 | 48.195 | 1.00 | 38.83 |
| ATOM | 223 | N | LEU | 163 | 38.019 | 27.898 | 50.077 | 1.00 | 34.61 |
| ATOM | 224 | CA | LEU | 163 | 36.925 | 27.299 | 50.815 | 1.00 | 35.03 |
| ATOM | 225 | CB | LEU | 163 | 37.272 | 27.227 | 52.302 | 1.00 | 38.37 |
| ATOM | 226 | CG | LEU | 163 | 36.517 | 26.232 | 53.188 | 1.00 | 38.57 |
| ATOM | 227 | CD1 | LEU | 163 | 36.777 | 26.608 | 54.628 | 1.00 | 40.24 |
| ATOM | 228 | CD2 | LEU | 163 | 35.018 | 26.266 | 52.927 | 1.00 | 45.38 |
| ATOM | 229 | C | LEU | 163 | 35.718 | 28.201 | 50.597 | 1.00 | 34.24 |
| ATOM | 230 | O | LEU | 163 | 34.616 | 27.724 | 50.353 | 1.00 | 31.18 |
| ATOM | 231 | N | GLU | 164 | 35.951 | 29.510 | 50.676 | 1.00 | 38.30 |
| ATOM | 232 | CA | GLU | 164 | 34.905 | 30.517 | 50.491 | 1.00 | 44.78 |
| ATOM | 233 | CB | GLU | 164 | 35.466 | 31.921 | 50.714 | 1.00 | 44.04 |
| ATOM | 234 | CG | GLU | 164 | 35.945 | 32.165 | 52.119 | 1.00 | 52.45 |
| ATOM | 235 | CD | GLU | 164 | 36.380 | 33.597 | 52.347 | 1.00 | 58.43 |
| ATOM | 236 | OE1 | GLU | 164 | 37.335 | 34.047 | 51.673 | 1.00 | 60.52 |
| ATOM | 237 | OE2 | GLU | 164 | 35.761 | 34.270 | 53.204 | 1.00 | 60.51 |
| ATOM | 238 | C | GLU | 164 | 34.258 | 30.464 | 49.113 | 1.00 | 47.43 |
| ATOM | 239 | O | GLU | 164 | 33.033 | 30.408 | 48.994 | 1.00 | 49.24 |
| ATOM | 240 | N | ASP | 165 | 35.076 | 30.496 | 48.070 | 1.00 | 49.08 |
| ATOM | 241 | CA | ASP | 165 | 34.543 | 30.445 | 46.722 | 1.00 | 50.66 |
| ATOM | 242 | CB | ASP | 165 | 35.655 | 30.648 | 45.692 | 1.00 | 52.68 |
| ATOM | 243 | CG | ASP | 165 | 36.414 | 31.937 | 45.906 | 1.00 | 56.95 |
| ATOM | 244 | OD1 | ASP | 165 | 35.771 | 33.004 | 46.047 | 1.00 | 56.77 |
| ATOM | 245 | OD2 | ASP | 165 | 37.660 | 31.883 | 45.921 | 1.00 | 59.48 |
| ATOM | 246 | C | ASP | 165 | 33.877 | 29.099 | 46.485 | 1.00 | 50.27 |
| ATOM | 247 | O | ASP | 165 | 32.714 | 29.033 | 46.092 | 1.00 | 51.73 |
| ATOM | 248 | N | LEU | 166 | 34.614 | 28.025 | 46.742 | 1.00 | 47.88 |
| ATOM | 249 | CA | LEU | 166 | 34.089 | 26.689 | 46.523 | 1.00 | 48.17 |
| ATOM | 250 | CB | LEU | 166 | 35.124 | 25.650 | 46.954 | 1.00 | 49.54 |
| ATOM | 251 | CG | LEU | 166 | 34.920 | 24.175 | 46.600 | 1.00 | 51.03 |
| ATOM | 252 | CD1 | LEU | 166 | 36.247 | 23.452 | 46.744 | 1.00 | 52.85 |
| ATOM | 253 | CD2 | LEU | 166 | 33.861 | 23.538 | 47.482 | 1.00 | 51.91 |
| ATOM | 254 | C | LEU | 166 | 32.764 | 26.460 | 47.232 | 1.00 | 50.26 |
| ATOM | 255 | O | LEU | 166 | 32.044 | 25.524 | 46.910 | 1.00 | 50.62 |
| ATOM | 256 | N | GLN | 167 | 32.422 | 27.317 | 48.187 | 1.00 | 53.90 |
| ATOM | 257 | CA | GLN | 167 | 31.153 | 27.143 | 48.888 | 1.00 | 56.44 |
| ATOM | 258 | CB | GLN | 167 | 31.245 | 27.606 | 50.343 | 1.00 | 58.07 |
| ATOM | 259 | CG | GLN | 167 | 29.984 | 27.284 | 51.133 | 1.00 | 61.99 |
| ATOM | 260 | CD | GLN | 167 | 30.005 | 27.814 | 52.553 | 1.00 | 63.54 |
| ATOM | 261 | OE1 | GLN | 167 | 30.028 | 29.024 | 52.780 | 1.00 | 63.55 |
| ATOM | 262 | NE2 | GLN | 167 | 29.996 | 26.904 | 53.519 | 1.00 | 66.37 |
| ATOM | 263 | C | GLN | 167 | 30.048 | 27.915 | 48.180 | 1.00 | 56.68 |
| ATOM | 264 | O | GLN | 167 | 28.957 | 27.384 | 47.970 | 1.00 | 57.48 |
| ATOM | 265 | N | ASP | 168 | 30.325 | 29.167 | 47.817 | 1.00 | 55.93 |
| ATOM | 266 | CA | ASP | 168 | 29.337 | 29.978 | 47.111 | 1.00 | 57.13 |
| ATOM | 267 | CB | ASP | 168 | 29.843 | 31.414 | 46.911 | 1.00 | 62.02 |

58

| | | | | | | | | |
|---|---|---|---|---|---|---|---|---|
| ATOM | 268 | CG | ASP | 168 | 30.133 | 32.126 | 48.231 | 1.00 71.07 |
| ATOM | 269 | OD1 | ASP | 168 | 29.243 | 32.178 | 49.110 | 1.00 74.06 |
| ATOM | 270 | OD2 | ASP | 168 | 31.256 | 32.649 | 48.391 | 1.00 77.41 |
| ATOM | 271 | C | ASP | 168 | 29.032 | 29.335 | 45.755 | 1.00 55.08 |
| ATOM | 272 | O | ASP | 168 | 28.079 | 29.712 | 45.082 | 1.00 54.17 |
| ATOM | 273 | N | GLU | 169 | 29.856 | 28.365 | 45.364 | 1.00 53.00 |
| ATOM | 274 | CA | GLU | 169 | 29.671 | 27.639 | 44.113 | 1.00 51.20 |
| ATOM | 275 | CB | GLU | 169 | 30.967 | 26.938 | 43.695 | 1.00 48.94 |
| ATOM | 276 | CG | GLU | 169 | 30.873 | 26.184 | 42.372 | 1.00 43.86 |
| ATOM | 277 | CD | GLU | 169 | 32.089 | 25.311 | 42.095 | 1.00 45.23 |
| ATOM | 278 | OE1 | GLU | 169 | 33.228 | 25.809 | 42.206 | 1.00 46.47 |
| ATOM | 279 | OE2 | GLU | 169 | 31.910 | 24.123 | 41.751 | 1.00 42.32 |
| ATOM | 280 | C | GLU | 169 | 28.608 | 26.588 | 44.392 | 1.00 52.23 |
| ATOM | 281 | O | GLU | 169 | 27.562 | 26.550 | 43.749 | 1.00 52.91 |
| ATOM | 282 | N | TYR | 170 | 28.897 | 25.735 | 45.367 | 1.00 53.92 |
| ATOM | 283 | CA | TYR | 170 | 27.983 | 24.679 | 45.776 | 1.00 55.91 |
| ATOM | 284 | CB | TYR | 170 | 28.622 | 23.837 | 46.879 | 1.00 58.27 |
| ATOM | 285 | CG | TYR | 170 | 29.680 | 22.858 | 46.407 | 1.00 62.28 |
| ATOM | 286 | CD1 | TYR | 170 | 30.670 | 23.234 | 45.496 | 1.00 61.31 |
| ATOM | 287 | CE1 | TYR | 170 | 31.690 | 22.345 | 45.130 | 1.00 61.41 |
| ATOM | 288 | CD2 | TYR | 170 | 29.733 | 21.572 | 46.933 | 1.00 63.83 |
| ATOM | 289 | CE2 | TYR | 170 | 30.743 | 20.679 | 46.578 | 1.00 65.13 |
| ATOM | 290 | CZ | TYR | 170 | 31.720 | 21.068 | 45.681 | 1.00 64.58 |
| ATOM | 291 | OH | TYR | 170 | 32.731 | 20.183 | 45.365 | 1.00 61.68 |
| ATOM | 292 | C | TYR | 170 | 26.650 | 25.236 | 46.268 | 1.00 55.20 |
| ATOM | 293 | O | TYR | 170 | 25.607 | 24.626 | 46.055 | 1.00 53.55 |
| ATOM | 294 | N | ASP | 171 | 26.679 | 26.390 | 46.928 | 1.00 56.30 |
| ATOM | 295 | CA | ASP | 171 | 25.442 | 26.979 | 47.425 | 1.00 60.40 |
| ATOM | 296 | CB | ASP | 171 | 25.724 | 28.164 | 48.350 | 1.00 66.08 |
| ATOM | 297 | CG | ASP | 171 | 24.449 | 28.741 | 48.962 | 1.00 71.70 |
| ATOM | 298 | OD1 | ASP | 171 | 23.780 | 28.019 | 49.739 | 1.00 71.00 |
| ATOM | 299 | OD2 | ASP | 171 | 24.113 | 29.911 | 48.661 | 1.00 74.51 |
| ATOM | 300 | C | ASP | 171 | 24.592 | 27.445 | 46.251 | 1.00 60.50 |
| ATOM | 301 | O | ASP | 171 | 23.367 | 27.291 | 46.259 | 1.00 59.90 |
| ATOM | 302 | N | PHE | 172 | 25.245 | 28.021 | 45.245 | 1.00 59.52 |
| ATOM | 303 | CA | PHE | 172 | 24.546 | 28.497 | 44.057 | 1.00 58.11 |
| ATOM | 304 | CB | PHE | 172 | 25.519 | 29.195 | 43.110 | 1.00 57.74 |
| ATOM | 305 | CG | PHE | 172 | 24.860 | 29.804 | 41.906 | 1.00 58.18 |
| ATOM | 306 | CD1 | PHE | 172 | 24.077 | 30.946 | 42.029 | 1.00 57.84 |
| ATOM | 307 | CD2 | PHE | 172 | 25.012 | 29.228 | 40.649 | 1.00 57.54 |
| ATOM | 308 | CE1 | PHE | 172 | 23.459 | 31.507 | 40.918 | 1.00 55.18 |
| ATOM | 309 | CE2 | PHE | 172 | 24.397 | 29.779 | 39.535 | 1.00 55.67 |
| ATOM | 310 | CZ | PHE | 172 | 23.620 | 30.923 | 39.669 | 1.00 56.82 |
| ATOM | 311 | C | PHE | 172 | 23.926 | 27.298 | 43.342 | 1.00 57.85 |
| ATOM | 312 | O | PHE | 172 | 22.754 | 27.322 | 42.966 | 1.00 57.10 |
| ATOM | 313 | N | LYS | 173 | 24.720 | 26.248 | 43.157 | 1.00 54.82 |
| ATOM | 314 | CA | LYS | 173 | 24.230 | 25.055 | 42.491 | 1.00 54.64 |
| ATOM | 315 | CB | LYS | 173 | 25.350 | 24.026 | 42.338 | 1.00 49.04 |
| ATOM | 316 | CG | LYS | 173 | 26.517 | 24.529 | 41.513 | 1.00 46.83 |
| ATOM | 317 | CD | LYS | 173 | 27.494 | 23.418 | 41.183 | 1.00 48.12 |
| ATOM | 318 | CE | LYS | 173 | 28.634 | 23.930 | 40.307 | 1.00 50.32 |
| ATOM | 319 | NZ | LYS | 173 | 29.562 | 22.834 | 39.884 | 1.00 47.21 |
| ATOM | 320 | C | LYS | 173 | 23.055 | 24.446 | 43.244 | 1.00 59.04 |
| ATOM | 321 | O | LYS | 173 | 22.240 | 23.742 | 42.658 | 1.00 62.42 |
| ATOM | 322 | N | CYS | 174 | 22.963 | 24.711 | 44.543 | 1.00 62.37 |
| ATOM | 323 | CA | CYS | 174 | 21.856 | 24.180 | 45.330 | 1.00 65.61 |
| ATOM | 324 | CB | CYS | 174 | 22.153 | 24.248 | 46.830 | 1.00 71.42 |
| ATOM | 325 | SG | CYS | 174 | 23.373 | 23.058 | 47.442 | 1.00 81.22 |
| ATOM | 326 | C | CYS | 174 | 20.594 | 24.964 | 45.042 | 1.00 65.22 |
| ATOM | 327 | O | CYS | 174 | 19.585 | 24.393 | 44.641 | 1.00 64.31 |
| ATOM | 328 | N | LYS | 175 | 20.648 | 26.275 | 45.247 | 1.00 65.77 |
| ATOM | 329 | CA | LYS | 175 | 19.483 | 27.110 | 45.001 | 1.00 69.68 |
| ATOM | 330 | CB | LYS | 175 | 19.846 | 28.597 | 45.069 | 1.00 68.45 |
| ATOM | 331 | CG | LYS | 175 | 18.658 | 29.511 | 44.776 | 1.00 70.19 |
| ATOM | 332 | CD | LYS | 175 | 19.040 | 30.982 | 44.705 | 1.00 71.48 |
| ATOM | 333 | CE | LYS | 175 | 17.837 | 31.818 | 44.281 | 1.00 73.98 |
| ATOM | 334 | NZ | LYS | 175 | 18.167 | 33.255 | 44.115 | 1.00 74.17 |
| ATOM | 335 | C | LYS | 175 | 18.857 | 26.806 | 43.642 | 1.00 72.93 |
| ATOM | 336 | O | LYS | 175 | 17.649 | 26.587 | 43.546 | 1.00 73.15 |
| ATOM | 337 | N | THR | 176 | 19.675 | 26.787 | 42.593 | 1.00 76.15 |

59

| ATOM | 338 | CA   | THR | 176 | 19.158 | 26.513 | 41.258 | 1.00 | 78.83  |
|------|-----|------|-----|-----|--------|--------|--------|------|--------|
| ATOM | 339 | CB   | THR | 176 | 20.282 | 26.498 | 40.189 | 1.00 | 79.52  |
| ATOM | 340 | OG1  | THR | 176 | 21.233 | 25.474 | 40.501 | 1.00 | 84.06  |
| ATOM | 341 | CG2  | THR | 176 | 20.985 | 27.850 | 40.131 | 1.00 | 77.87  |
| ATOM | 342 | C    | THR | 176 | 18.411 | 25.182 | 41.228 | 1.00 | 80.20  |
| ATOM | 343 | O    | THR | 176 | 17.204 | 25.164 | 41.003 | 1.00 | 83.46  |
| ATOM | 344 | N    | LEU | 177 | 19.111 | 24.075 | 41.466 | 1.00 | 79.17  |
| ATOM | 345 | CA   | LEU | 177 | 18.467 | 22.763 | 41.451 | 1.00 | 78.30  |
| ATOM | 346 | CB   | LEU | 177 | 19.409 | 21.690 | 42.009 | 1.00 | 78.05  |
| ATOM | 347 | CG   | LEU | 177 | 20.482 | 21.101 | 41.081 | 1.00 | 77.56  |
| ATOM | 348 | CD1  | LEU | 177 | 21.336 | 22.190 | 40.458 | 1.00 | 77.06  |
| ATOM | 349 | CD2  | LEU | 177 | 21.340 | 20.134 | 41.880 | 1.00 | 76.82  |
| ATOM | 350 | C    | LEU | 177 | 17.138 | 22.721 | 42.200 | 1.00 | 79.80  |
| ATOM | 351 | O    | LEU | 177 | 16.307 | 21.863 | 41.926 | 1.00 | 77.60  |
| ATOM | 352 | N    | GLN | 178 | 16.932 | 23.644 | 43.138 | 1.00 | 84.01  |
| ATOM | 353 | CA   | GLN | 178 | 15.680 | 23.693 | 43.894 | 1.00 | 89.15  |
| ATOM | 354 | CB   | GLN | 178 | 15.868 | 24.457 | 45.218 | 1.00 | 90.44  |
| ATOM | 355 | CG   | GLN | 178 | 16.711 | 23.682 | 46.231 | 1.00 | 96.59  |
| ATOM | 356 | CD   | GLN | 178 | 16.777 | 24.384 | 47.575 | 1.00 | 99.76  |
| ATOM | 357 | OE1  | GLN | 178 | 15.747 | 24.666 | 48.191 | 1.00 | 102.75 |
| ATOM | 358 | NE2  | GLN | 178 | 17.991 | 24.661 | 48.041 | 1.00 | 100.55 |
| ATOM | 359 | C    | GLN | 178 | 14.564 | 24.356 | 43.096 | 1.00 | 91.62  |
| ATOM | 360 | O    | GLN | 178 | 13.427 | 23.881 | 43.085 | 1.00 | 92.05  |
| ATOM | 361 | N    | ASN | 179 | 14.886 | 25.460 | 42.433 | 1.00 | 94.74  |
| ATOM | 362 | CA   | ASN | 179 | 13.897 | 26.154 | 41.622 | 1.00 | 97.73  |
| ATOM | 363 | CB   | ASN | 179 | 14.210 | 27.651 | 41.557 | 1.00 | 98.06  |
| ATOM | 364 | CG   | ASN | 179 | 14.170 | 28.309 | 42.928 | 1.00 | 98.79  |
| ATOM | 365 | OD1  | ASN | 179 | 13.173 | 28.209 | 43.647 | 1.00 | 97.71  |
| ATOM | 366 | ND2  | ASN | 179 | 15.254 | 28.987 | 43.296 | 1.00 | 98.47  |
| ATOM | 367 | C    | ASN | 179 | 13.846 | 25.541 | 40.223 | 1.00 | 99.54  |
| ATOM | 368 | O    | ASN | 179 | 12.861 | 25.710 | 39.506 | 1.00 | 100.58 |
| ATOM | 369 | N    | ARG | 180 | 14.908 | 24.831 | 39.837 | 1.00 | 101.87 |
| ATOM | 370 | CA   | ARG | 180 | 14.947 | 24.154 | 38.540 | 1.00 | 103.70 |
| ATOM | 371 | CB   | ARG | 180 | 16.391 | 23.939 | 38.040 | 1.00 | 104.10 |
| ATOM | 372 | CG   | ARG | 180 | 17.038 | 25.173 | 37.401 | 1.00 | 106.21 |
| ATOM | 373 | CD   | ARG | 180 | 18.368 | 24.869 | 36.678 | 1.00 | 109.06 |
| ATOM | 374 | NE   | ARG | 180 | 19.477 | 24.525 | 37.573 | 1.00 | 111.46 |
| ATOM | 375 | CZ   | ARG | 180 | 20.734 | 24.330 | 37.171 | 1.00 | 110.99 |
| ATOM | 376 | NH1  | ARG | 180 | 21.051 | 24.445 | 35.887 | 1.00 | 110.57 |
| ATOM | 377 | NH2  | ARG | 180 | 21.682 | 24.032 | 38.053 | 1.00 | 108.06 |
| ATOM | 378 | C    | ARG | 180 | 14.240 | 22.808 | 38.690 | 1.00 | 104.86 |
| ATOM | 379 | O    | ARG | 180 | 14.654 | 21.797 | 38.119 | 1.00 | 103.98 |
| ATOM | 380 | N    | GLU | 181 | 13.171 | 22.817 | 39.480 | 1.00 | 106.61 |
| ATOM | 381 | CA   | GLU | 181 | 12.363 | 21.632 | 39.732 | 1.00 | 108.71 |
| ATOM | 382 | CB   | GLU | 181 | 12.843 | 20.920 | 41.001 | 1.00 | 109.87 |
| ATOM | 383 | CG   | GLU | 181 | 14.200 | 20.238 | 40.853 | 1.00 | 112.25 |
| ATOM | 384 | CD   | GLU | 181 | 14.680 | 19.583 | 42.140 | 1.00 | 113.31 |
| ATOM | 385 | OE1  | GLU | 181 | 15.733 | 18.905 | 42.109 | 1.00 | 112.54 |
| ATOM | 386 | OE2  | GLU | 181 | 14.009 | 19.752 | 43.182 | 1.00 | 114.07 |
| ATOM | 387 | C    | GLU | 181 | 10.894 | 22.018 | 39.870 | 1.00 | 109.38 |
| ATOM | 388 | O    | GLU | 181 | 10.080 | 21.710 | 38.995 | 1.00 | 108.91 |
| ATOM | 389 | N    | HIS | 182 | 10.564 | 22.701 | 40.964 | 1.00 | 110.53 |
| ATOM | 390 | CA   | HIS | 182 | 9.192  | 23.133 | 41.223 | 1.00 | 111.09 |
| ATOM | 391 | CB   | HIS | 182 | 9.155  | 24.150 | 42.373 | 1.00 | 112.09 |
| ATOM | 392 | CG   | HIS | 182 | 9.615  | 23.601 | 43.690 | 1.00 | 112.78 |
| ATOM | 393 | CD2  | HIS | 182 | 10.570 | 24.031 | 44.551 | 1.00 | 112.20 |
| ATOM | 394 | ND1  | HIS | 182 | 9.043  | 22.494 | 44.278 | 1.00 | 112.38 |
| ATOM | 395 | CE1  | HIS | 182 | 9.624  | 22.264 | 45.443 | 1.00 | 112.09 |
| ATOM | 396 | NE2  | HIS | 182 | 10.554 | 23.184 | 45.631 | 1.00 | 112.22 |
| ATOM | 397 | C    | HIS | 182 | 8.551  | 23.748 | 39.980 | 1.00 | 110.27 |
| ATOM | 398 | O    | HIS | 182 | 8.633  | 24.987 | 39.846 | 1.00 | 108.96 |
| ATOM | 399 | N    | LEU | 197 | 27.706 | 14.082 | 41.351 | 1.00 | 102.45 |
| ATOM | 400 | CA   | LEU | 197 | 26.585 | 13.857 | 42.292 | 1.00 | 102.82 |
| ATOM | 401 | CB   | LEU | 197 | 26.893 | 12.661 | 43.196 | 1.00 | 100.97 |
| ATOM | 405 | C    | LEU | 197 | 26.385 | 15.116 | 43.156 | 1.00 | 102.70 |
| ATOM | 406 | O    | LEU | 197 | 27.183 | 15.343 | 44.068 | 1.00 | 104.63 |
| ATOM | 407 | N    | LEU | 198 | 25.359 | 15.927 | 42.860 | 1.00 | 101.78 |
| ATOM | 408 | CA   | LEU | 198 | 24.988 | 17.123 | 43.603 | 1.00 | 101.64 |
| ATOM | 409 | CB   | LEU | 198 | 23.558 | 17.484 | 43.291 | 1.00 | 102.31 |
| ATOM | 413 | C    | LEU | 198 | 25.150 | 16.952 | 45.107 | 1.00 | 101.60 |

60

| ATOM | 414 | O | LEU | 198 | 26.017 | 17.600 | 45.744 | 1.00 | 101.14 |
|---|---|---|---|---|---|---|---|---|---|
| ATOM | 415 | N | LEU | 199 | 24.289 | 16.090 | 45.661 | 1.00 | 101.22 |
| ATOM | 416 | CA | LEU | 199 | 24.231 | 15.834 | 47.092 | 1.00 | 100.20 |
| ATOM | 417 | CB | LEU | 199 | 23.206 | 14.735 | 47.403 | 1.00 | 100.68 |
| ATOM | 421 | C | LEU | 199 | 25.590 | 15.488 | 47.686 | 1.00 | 99.95 |
| ATOM | 422 | O | LEU | 199 | 26.047 | 16.179 | 48.599 | 1.00 | 99.72 |
| ATOM | 423 | N | LYS | 200 | 26.220 | 14.421 | 47.194 | 1.00 | 99.53 |
| ATOM | 424 | CA | LYS | 200 | 27.502 | 13.985 | 47.710 | 1.00 | 97.60 |
| ATOM | 425 | CB | LYS | 200 | 28.040 | 12.814 | 46.901 | 1.00 | 98.24 |
| ATOM | 426 | CG | LYS | 200 | 27.236 | 11.534 | 47.063 | 1.00 | 100.55 |
| ATOM | 427 | CD | LYS | 200 | 27.926 | 10.335 | 46.434 | 1.00 | 101.35 |
| ATOM | 428 | CE | LYS | 200 | 27.135 | 9.065 | 46.706 | 1.00 | 102.29 |
| ATOM | 429 | NZ | LYS | 200 | 27.818 | 7.839 | 46.214 | 1.00 | 101.38 |
| ATOM | 430 | C | LYS | 200 | 28.555 | 15.084 | 47.773 | 1.00 | 95.79 |
| ATOM | 431 | O | LYS | 200 | 29.084 | 15.370 | 48.840 | 1.00 | 95.57 |
| ATOM | 432 | N | LYS | 201 | 28.868 | 15.680 | 46.627 | 1.00 | 94.70 |
| ATOM | 433 | CA | LYS | 201 | 29.874 | 16.737 | 46.570 | 1.00 | 94.46 |
| ATOM | 434 | CB | LYS | 201 | 29.784 | 17.520 | 45.251 | 1.00 | 97.08 |
| ATOM | 435 | CG | LYS | 201 | 30.178 | 16.750 | 43.998 | 1.00 | 98.09 |
| ATOM | 436 | CD | LYS | 201 | 30.164 | 17.664 | 42.778 | 1.00 | 97.68 |
| ATOM | 437 | CE | LYS | 201 | 30.618 | 16.932 | 41.522 | 1.00 | 98.51 |
| ATOM | 438 | NZ | LYS | 201 | 30.629 | 17.829 | 40.330 | 1.00 | 98.01 |
| ATOM | 439 | C | LYS | 201 | 29.749 | 17.712 | 47.733 | 1.00 | 92.03 |
| ATOM | 440 | O | LYS | 201 | 30.588 | 17.732 | 48.633 | 1.00 | 90.97 |
| ATOM | 441 | N | MET | 202 | 28.696 | 18.522 | 47.695 | 1.00 | 89.18 |
| ATOM | 442 | CA | MET | 202 | 28.429 | 19.516 | 48.731 | 1.00 | 86.67 |
| ATOM | 443 | CB | MET | 202 | 26.944 | 19.929 | 48.691 | 1.00 | 82.65 |
| ATOM | 444 | CG | MET | 202 | 26.665 | 21.329 | 48.126 | 1.00 | 77.06 |
| ATOM | 445 | SD | MET | 202 | 26.745 | 22.729 | 49.308 | 1.00 | 69.57 |
| ATOM | 446 | CE | MET | 202 | 25.240 | 22.503 | 50.233 | 1.00 | 66.97 |
| ATOM | 447 | C | MET | 202 | 28.784 | 19.047 | 50.132 | 1.00 | 86.80 |
| ATOM | 448 | O | MET | 202 | 29.944 | 19.075 | 50.541 | 1.00 | 88.33 |
| ATOM | 449 | N | TYR | 203 | 27.761 | 18.607 | 50.849 | 1.00 | 85.72 |
| ATOM | 450 | CA | TYR | 203 | 27.877 | 18.157 | 52.220 | 1.00 | 84.20 |
| ATOM | 451 | CB | TYR | 203 | 26.570 | 17.473 | 52.602 | 1.00 | 87.98 |
| ATOM | 452 | CG | TYR | 203 | 25.366 | 18.318 | 52.241 | 1.00 | 92.68 |
| ATOM | 453 | CD1 | TYR | 203 | 25.235 | 19.618 | 52.728 | 1.00 | 94.71 |
| ATOM | 454 | CE1 | TYR | 203 | 24.150 | 20.418 | 52.377 | 1.00 | 95.63 |
| ATOM | 455 | CD2 | TYR | 203 | 24.371 | 17.831 | 51.391 | 1.00 | 95.53 |
| ATOM | 456 | CE2 | TYR | 203 | 23.278 | 18.626 | 51.032 | 1.00 | 97.27 |
| ATOM | 457 | CZ | TYR | 203 | 23.178 | 19.918 | 51.531 | 1.00 | 97.38 |
| ATOM | 458 | OH | TYR | 203 | 22.112 | 20.715 | 51.180 | 1.00 | 98.13 |
| ATOM | 459 | C | TYR | 203 | 29.069 | 17.278 | 52.595 | 1.00 | 82.26 |
| ATOM | 460 | O | TYR | 203 | 29.316 | 17.063 | 53.779 | 1.00 | 83.66 |
| ATOM | 461 | N | LEU | 204 | 29.820 | 16.775 | 51.620 | 1.00 | 78.88 |
| ATOM | 462 | CA | LEU | 204 | 30.955 | 15.929 | 51.967 | 1.00 | 75.00 |
| ATOM | 463 | CB | LEU | 204 | 30.904 | 14.597 | 51.216 | 1.00 | 76.04 |
| ATOM | 464 | CG | LEU | 204 | 32.085 | 13.658 | 51.521 | 1.00 | 77.21 |
| ATOM | 465 | CD1 | LEU | 204 | 32.139 | 13.365 | 53.020 | 1.00 | 75.86 |
| ATOM | 466 | CD2 | LEU | 204 | 31.953 | 12.364 | 50.723 | 1.00 | 76.84 |
| ATOM | 467 | C | LEU | 204 | 32.332 | 16.540 | 51.779 | 1.00 | 72.47 |
| ATOM | 468 | O | LEU | 204 | 33.193 | 16.368 | 52.635 | 1.00 | 72.78 |
| ATOM | 469 | N | MET | 205 | 32.574 | 17.243 | 50.680 | 1.00 | 70.46 |
| ATOM | 470 | CA | MET | 205 | 33.905 | 17.804 | 50.518 | 1.00 | 69.43 |
| ATOM | 471 | CB | MET | 205 | 34.244 | 18.057 | 49.056 | 1.00 | 71.51 |
| ATOM | 472 | CG | MET | 205 | 35.708 | 18.416 | 48.889 | 1.00 | 77.83 |
| ATOM | 473 | SD | MET | 205 | 36.234 | 18.610 | 47.196 | 1.00 | 87.99 |
| ATOM | 474 | CE | MET | 205 | 35.789 | 17.007 | 46.522 | 1.00 | 86.47 |
| ATOM | 475 | C | MET | 205 | 34.100 | 19.078 | 51.311 | 1.00 | 67.12 |
| ATOM | 476 | O | MET | 205 | 35.153 | 19.268 | 51.915 | 1.00 | 67.42 |
| ATOM | 477 | N | LEU | 206 | 33.101 | 19.955 | 51.311 | 1.00 | 64.45 |
| ATOM | 478 | CA | LEU | 206 | 33.203 | 21.193 | 52.081 | 1.00 | 63.33 |
| ATOM | 479 | CB | LEU | 206 | 31.861 | 21.927 | 52.140 | 1.00 | 60.81 |
| ATOM | 480 | CG | LEU | 206 | 31.264 | 22.528 | 50.872 | 1.00 | 60.06 |
| ATOM | 481 | CD1 | LEU | 206 | 29.969 | 23.243 | 51.226 | 1.00 | 61.25 |
| ATOM | 482 | CD2 | LEU | 206 | 32.241 | 23.507 | 50.255 | 1.00 | 60.13 |
| ATOM | 483 | C | LEU | 206 | 33.624 | 20.837 | 53.502 | 1.00 | 63.39 |
| ATOM | 484 | O | LEU | 206 | 34.491 | 21.481 | 54.090 | 1.00 | 63.88 |
| ATOM | 485 | N | ASP | 207 | 32.994 | 19.798 | 54.040 | 1.00 | 64.17 |
| ATOM | 486 | CA | ASP | 207 | 33.275 | 19.323 | 55.386 | 1.00 | 62.35 |

```
ATOM  487  CB   ASP  207   32.386  18.115  55.694  1.00 67.59
ATOM  488  CG   ASP  207   32.410  17.724  57.158  1.00 72.93
ATOM  489  OD1  ASP  207   31.979  18.547  57.993  1.00 74.92
ATOM  490  OD2  ASP  207   32.854  16.595  57.475  1.00 73.67
ATOM  491  C    ASP  207   34.750  18.936  55.471  1.00 59.66
ATOM  492  O    ASP  207   35.463  19.380  56.365  1.00 59.80
ATOM  493  N    ASN  208   35.207  18.109  54.535  1.00 56.54
ATOM  494  CA   ASN  208   36.604  17.693  54.518  1.00 53.72
ATOM  495  CB   ASN  208   36.873  16.733  53.366  1.00 54.57
ATOM  496  CG   ASN  208   36.546  15.302  53.724  1.00 59.31
ATOM  497  OD1  ASN  208   35.442  14.994  54.185  1.00 58.75
ATOM  498  ND2  ASN  208   37.511  14.412  53.516  1.00 62.01
ATOM  499  C    ASN  208   37.516  18.884  54.403  1.00 52.25
ATOM  500  O    ASN  208   38.632  18.861  54.904  1.00 52.47
ATOM  501  N    LYS  209   37.035  19.926  53.736  1.00 51.81
ATOM  502  CA   LYS  209   37.808  21.146  53.572  1.00 48.31
ATOM  503  CB   LYS  209   37.312  21.928  52.356  1.00 45.89
ATOM  504  CG   LYS  209   37.765  21.319  51.049  1.00 48.85
ATOM  505  CD   LYS  209   39.284  21.278  51.011  1.00 58.03
ATOM  506  CE   LYS  209   39.821  20.748  49.695  1.00 62.03
ATOM  507  NZ   LYS  209   41.314  20.699  49.726  1.00 67.26
ATOM  508  C    LYS  209   37.766  22.007  54.834  1.00 46.17
ATOM  509  O    LYS  209   38.775  22.608  55.210  1.00 44.93
ATOM  510  N    ARG  210   36.610  22.070  55.490  1.00 41.19
ATOM  511  CA   ARG  210   36.511  22.837  56.720  1.00 37.52
ATOM  512  CB   ARG  210   35.079  22.838  57.269  1.00 38.78
ATOM  513  CG   ARG  210   34.087  23.598  56.410  1.00 42.81
ATOM  514  CD   ARG  210   32.759  23.837  57.127  1.00 43.77
ATOM  515  NE   ARG  210   31.991  24.877  56.443  1.00 47.57
ATOM  516  CZ   ARG  210   30.940  25.507  56.960  1.00 45.02
ATOM  517  NH1  ARG  210   30.514  25.207  58.173  1.00 49.15
ATOM  518  NH2  ARG  210   30.330  26.462  56.274  1.00 47.84
ATOM  519  C    ARG  210   37.445  22.165  57.714  1.00 35.99
ATOM  520  O    ARG  210   38.401  22.773  58.194  1.00 35.36
ATOM  521  N    LYS  211   37.171  20.900  58.006  1.00 35.56
ATOM  522  CA   LYS  211   38.003  20.147  58.925  1.00 38.38
ATOM  523  CB   LYS  211   37.632  18.667  58.892  1.00 36.29
ATOM  524  CG   LYS  211   36.233  18.371  59.374  1.00 41.09
ATOM  525  CD   LYS  211   36.016  16.872  59.483  1.00 44.11
ATOM  526  CE   LYS  211   34.666  16.550  60.096  1.00 43.20
ATOM  527  NZ   LYS  211   34.536  15.088  60.332  1.00 48.32
ATOM  528  C    LYS  211   39.466  20.304  58.541  1.00 40.38
ATOM  529  O    LYS  211   40.324  20.528  59.392  1.00 43.38
ATOM  530  N    GLU  212   39.744  20.196  57.251  1.00 40.10
ATOM  531  CA   GLU  212   41.107  20.318  56.772  1.00 42.53
ATOM  532  CB   GLU  212   41.143  20.303  55.242  1.00 50.94
ATOM  533  CG   GLU  212   42.242  19.424  54.646  1.00 55.66
ATOM  534  CD   GLU  212   43.608  19.700  55.242  1.00 60.12
ATOM  535  OE1  GLU  212   43.784  19.476  56.459  1.00 62.48
ATOM  536  OE2  GLU  212   44.508  20.142  54.497  1.00 66.37
ATOM  537  C    GLU  212   41.712  21.618  57.272  1.00 40.06
ATOM  538  O    GLU  212   42.751  21.617  57.922  1.00 41.22
ATOM  539  N    VAL  213   41.061  22.733  56.970  1.00 39.20
ATOM  540  CA   VAL  213   41.580  24.021  57.403  1.00 41.29
ATOM  541  CB   VAL  213   40.681  25.197  56.948  1.00 42.26
ATOM  542  CG1  VAL  213   41.186  26.494  57.550  1.00 47.91
ATOM  543  CG2  VAL  213   40.718  25.326  55.443  1.00 42.17
ATOM  544  C    VAL  213   41.748  24.079  58.911  1.00 40.12
ATOM  545  O    VAL  213   42.858  24.268  59.395  1.00 39.94
ATOM  546  N    VAL  214   40.654  23.914  59.650  1.00 38.93
ATOM  547  CA   VAL  214   40.720  23.959  61.110  1.00 38.47
ATOM  548  CB   VAL  214   39.457  23.361  61.760  1.00 35.05
ATOM  549  CG1  VAL  214   39.719  23.062  63.216  1.00 31.34
ATOM  550  CG2  VAL  214   38.313  24.347  61.655  1.00 29.44
ATOM  551  C    VAL  214   41.941  23.218  61.632  1.00 39.58
ATOM  552  O    VAL  214   42.756  23.779  62.372  1.00 40.95
ATOM  553  N    HIS  215   42.069  21.958  61.246  1.00 39.71
ATOM  554  CA   HIS  215   43.210  21.179  61.680  1.00 40.81
ATOM  555  CB   HIS  215   43.226  19.833  60.951  1.00 43.75
ATOM  556  CG   HIS  215   44.451  19.013  61.209  1.00 48.64
```

62

```
ATOM  557  CD2 HIS  215  44.633  17.890  61.944  1.00  52.38
ATOM  558  ND1 HIS  215  45.684  19.331  60.681  1.00  49.91
ATOM  559  CE1 HIS  215  46.574  18.438  61.077  1.00  49.29
ATOM  560  NE2 HIS  215  45.963  17.553  61.845  1.00  54.44
ATOM  561  C   HIS  215  44.489  21.977  61.415  1.00  40.50
ATOM  562  O   HIS  215  45.292  22.181  62.321  1.00  40.60
ATOM  563  N   LYS  216  44.665  22.459  60.189  1.00  37.85
ATOM  564  CA  LYS  216  45.860  23.230  59.864  1.00  35.62
ATOM  565  CB  LYS  216  45.914  23.565  58.374  1.00  34.81
ATOM  566  CG  LYS  216  46.538  22.474  57.539  1.00  38.79
ATOM  567  CD  LYS  216  47.005  23.045  56.229  1.00  40.33
ATOM  568  CE  LYS  216  47.926  22.085  55.520  1.00  45.99
ATOM  569  NZ  LYS  216  48.497  22.706  54.287  1.00  51.76
ATOM  570  C   LYS  216  46.084  24.507  60.667  1.00  33.87
ATOM  571  O   LYS  216  47.224  24.936  60.833  1.00  31.70
ATOM  572  N   ILE  217  45.015  25.132  61.146  1.00  30.80
ATOM  573  CA  ILE  217  45.176  26.338  61.948  1.00  32.33
ATOM  574  CB  ILE  217  43.832  27.079  62.163  1.00  33.66
ATOM  575  CG2 ILE  217  43.972  28.133  63.262  1.00  31.33
ATOM  576  CG1 ILE  217  43.383  27.721  60.850  1.00  35.35
ATOM  577  CD1 ILE  217  42.039  28.423  60.936  1.00  39.43
ATOM  578  C   ILE  217  45.708  25.862  63.288  1.00  33.62
ATOM  579  O   ILE  217  46.693  26.391  63.802  1.00  31.48
ATOM  580  N   ILE  218  45.044  24.849  63.839  1.00  32.18
ATOM  581  CA  ILE  218  45.440  24.260  65.110  1.00  29.82
ATOM  582  CB  ILE  218  44.623  23.004  65.413  1.00  25.16
ATOM  583  CG2 ILE  218  45.262  22.225  66.528  1.00  15.90
ATOM  584  CG1 ILE  218  43.190  23.391  65.742  1.00  25.93
ATOM  585  CD1 ILE  218  42.283  22.212  65.946  1.00  27.70
ATOM  586  C   ILE  218  46.900  23.855  65.064  1.00  32.59
ATOM  587  O   ILE  218  47.587  23.871  66.077  1.00  36.79
ATOM  588  N   GLU  219  47.374  23.500  63.881  1.00  35.00
ATOM  589  CA  GLU  219  48.748  23.070  63.738  1.00  38.94
ATOM  590  CB  GLU  219  48.879  22.185  62.502  1.00  46.30
ATOM  591  CG  GLU  219  49.851  21.036  62.680  1.00  58.14
ATOM  592  CD  GLU  219  49.619  19.921  61.676  1.00  67.39
ATOM  593  OE1 GLU  219  50.218  18.835  61.842  1.00  72.57
ATOM  594  OE2 GLU  219  48.840  20.128  60.718  1.00  73.48
ATOM  595  C   GLU  219  49.697  24.249  63.657  1.00  37.29
ATOM  596  O   GLU  219  50.853  24.140  64.055  1.00  36.67
ATOM  597  N   LEU  220  49.201  25.376  63.150  1.00  38.39
ATOM  598  CA  LEU  220  50.004  26.598  63.012  1.00  36.23
ATOM  599  CB  LEU  220  49.279  27.617  62.125  1.00  35.63
ATOM  600  CG  LEU  220  50.068  28.764  61.479  1.00  35.00
ATOM  601  CD1 LEU  220  49.079  29.710  60.803  1.00  36.26
ATOM  602  CD2 LEU  220  50.893  29.520  62.500  1.00  31.56
ATOM  603  C   LEU  220  50.205  27.194  64.404  1.00  34.88
ATOM  604  O   LEU  220  51.315  27.582  64.779  1.00  35.93
ATOM  605  N   LEU  221  49.119  27.267  65.165  1.00  30.59
ATOM  606  CA  LEU  221  49.189  27.792  66.513  1.00  27.66
ATOM  607  CB  LEU  221  47.813  27.774  67.174  1.00  21.88
ATOM  608  CG  LEU  221  46.820  28.750  66.544  1.00  25.44
ATOM  609  CD1 LEU  221  45.484  28.722  67.283  1.00  25.33
ATOM  610  CD2 LEU  221  47.411  30.144  66.594  1.00  24.29
ATOM  611  C   LEU  221  50.178  26.993  67.349  1.00  32.90
ATOM  612  O   LEU  221  50.919  27.570  68.143  1.00  39.66
ATOM  613  N   ASN  222  50.207  25.673  67.184  1.00  33.56
ATOM  614  CA  ASN  222  51.156  24.883  67.962  1.00  34.88
ATOM  615  CB  ASN  222  51.050  23.380  67.657  1.00  34.83
ATOM  616  CG  ASN  222  49.693  22.796  67.993  1.00  34.15
ATOM  617  OD1 ASN  222  49.058  23.174  68.975  1.00  30.54
ATOM  618  ND2 ASN  222  49.261  21.833  67.190  1.00  40.22
ATOM  619  C   ASN  222  52.579  25.347  67.648  1.00  34.03
ATOM  620  O   ASN  222  53.333  25.730  68.542  1.00  37.86
ATOM  621  N   VAL  223  52.944  25.306  66.374  1.00  30.07
ATOM  622  CA  VAL  223  54.271  25.715  65.952  1.00  28.48
ATOM  623  CB  VAL  223  54.415  25.594  64.424  1.00  26.36
ATOM  624  CG1 VAL  223  55.794  26.044  63.983  1.00  27.80
ATOM  625  CG2 VAL  223  54.176  24.171  64.009  1.00  30.05
ATOM  626  C   VAL  223  54.550  27.154  66.372  1.00  30.60
```

63

| | | | | | | | | |
|---|---|---|---|---|---|---|---|---|
| ATOM | 627 | O | VAL | 223 | 55.689 | 27.501 | 66.690 | 1.00 29.20 |
| ATOM | 628 | N | THR | 224 | 53.521 | 27.996 | 66.369 | 1.00 28.91 |
| ATOM | 629 | CA | THR | 224 | 53.717 | 29.387 | 66.763 | 1.00 32.64 |
| ATOM | 630 | CB | THR | 224 | 52.419 | 30.192 | 66.685 | 1.00 33.32 |
| ATOM | 631 | OG1 | THR | 224 | 51.887 | 30.106 | 65.362 | 1.00 36.51 |
| ATOM | 632 | CG2 | THR | 224 | 52.687 | 31.648 | 67.003 | 1.00 33.90 |
| ATOM | 633 | C | THR | 224 | 54.210 | 29.405 | 68.198 | 1.00 31.57 |
| ATOM | 634 | O | THR | 224 | 55.116 | 30.155 | 68.543 | 1.00 32.32 |
| ATOM | 635 | N | GLU | 225 | 53.600 | 28.566 | 69.027 | 1.00 31.14 |
| ATOM | 636 | CA | GLU | 225 | 53.974 | 28.446 | 70.424 | 1.00 31.18 |
| ATOM | 637 | CB | GLU | 225 | 53.116 | 27.379 | 71.092 | 1.00 36.51 |
| ATOM | 638 | CG | GLU | 225 | 53.455 | 27.172 | 72.537 | 1.00 50.34 |
| ATOM | 639 | CD | GLU | 225 | 53.411 | 28.469 | 73.310 | 1.00 60.77 |
| ATOM | 640 | OE1 | GLU | 225 | 52.337 | 29.109 | 73.317 | 1.00 62.50 |
| ATOM | 641 | OE2 | GLU | 225 | 54.448 | 28.846 | 73.904 | 1.00 69.42 |
| ATOM | 642 | C | GLU | 225 | 55.458 | 28.086 | 70.537 | 1.00 29.76 |
| ATOM | 643 | O | GLU | 225 | 56.228 | 28.822 | 71.147 | 1.00 30.47 |
| ATOM | 644 | N | LEU | 226 | 55.860 | 26.960 | 69.952 | 1.00 27.58 |
| ATOM | 645 | CA | LEU | 226 | 57.264 | 26.545 | 69.982 | 1.00 28.56 |
| ATOM | 646 | CB | LEU | 226 | 57.521 | 25.369 | 69.040 | 1.00 31.03 |
| ATOM | 647 | CG | LEU | 226 | 57.167 | 23.940 | 69.423 | 1.00 33.55 |
| ATOM | 648 | CD1 | LEU | 226 | 57.619 | 22.994 | 68.320 | 1.00 39.71 |
| ATOM | 649 | CD2 | LEU | 226 | 57.876 | 23.578 | 70.687 | 1.00 31.73 |
| ATOM | 650 | C | LEU | 226 | 58.200 | 27.667 | 69.560 | 1.00 29.87 |
| ATOM | 651 | O | LEU | 226 | 59.258 | 27.862 | 70.151 | 1.00 34.20 |
| ATOM | 652 | N | THR | 227 | 57.818 | 28.383 | 68.513 | 1.00 27.74 |
| ATOM | 653 | CA | THR | 227 | 58.630 | 29.473 | 67.999 | 1.00 25.52 |
| ATOM | 654 | CB | THR | 227 | 58.039 | 30.008 | 66.685 | 1.00 26.99 |
| ATOM | 655 | OG1 | THR | 227 | 57.812 | 28.913 | 65.794 | 1.00 26.00 |
| ATOM | 656 | CG2 | THR | 227 | 58.988 | 30.997 | 66.028 | 1.00 17.48 |
| ATOM | 657 | C | THR | 227 | 58.672 | 30.609 | 69.011 | 1.00 25.17 |
| ATOM | 658 | O | THR | 227 | 59.742 | 31.041 | 69.445 | 1.00 23.44 |
| ATOM | 659 | N | GLN | 228 | 57.487 | 31.076 | 69.387 | 1.00 23.92 |
| ATOM | 660 | CA | GLN | 228 | 57.346 | 32.174 | 70.329 | 1.00 26.12 |
| ATOM | 661 | CB | GLN | 228 | 55.879 | 32.332 | 70.721 | 1.00 19.67 |
| ATOM | 662 | CG | GLN | 228 | 55.399 | 33.761 | 70.677 | 1.00 19.87 |
| ATOM | 663 | CD | GLN | 228 | 53.915 | 33.901 | 70.962 | 1.00 24.68 |
| ATOM | 664 | OE1 | GLN | 228 | 53.437 | 33.531 | 72.028 | 1.00 26.90 |
| ATOM | 665 | NE2 | GLN | 228 | 53.184 | 34.443 | 70.007 | 1.00 22.55 |
| ATOM | 666 | C | GLN | 228 | 58.205 | 31.911 | 71.550 | 1.00 25.91 |
| ATOM | 667 | O | GLN | 228 | 59.085 | 32.701 | 71.879 | 1.00 26.06 |
| ATOM | 668 | N | ASN | 229 | 57.961 | 30.789 | 72.212 | 1.00 27.79 |
| ATOM | 669 | CA | ASN | 229 | 58.733 | 30.435 | 73.390 | 1.00 29.44 |
| ATOM | 670 | CB | ASN | 229 | 58.373 | 29.018 | 73.856 | 1.00 37.01 |
| ATOM | 671 | CG | ASN | 229 | 59.397 | 28.445 | 74.834 | 1.00 45.60 |
| ATOM | 672 | OD1 | ASN | 229 | 60.534 | 28.132 | 74.454 | 1.00 41.84 |
| ATOM | 673 | ND2 | ASN | 229 | 59.006 | 28.323 | 76.100 | 1.00 51.47 |
| ATOM | 674 | C | ASN | 229 | 60.246 | 30.550 | 73.197 | 1.00 23.90 |
| ATOM | 675 | O | ASN | 229 | 60.956 | 30.889 | 74.130 | 1.00 22.56 |
| ATOM | 676 | N | ALA | 230 | 60.750 | 30.261 | 72.006 | 1.00 19.65 |
| ATOM | 677 | CA | ALA | 230 | 62.190 | 30.362 | 71.782 | 1.00 21.38 |
| ATOM | 678 | CB | ALA | 230 | 62.578 | 29.640 | 70.507 | 1.00 23.67 |
| ATOM | 679 | C | ALA | 230 | 62.537 | 31.837 | 71.672 | 1.00 23.45 |
| ATOM | 680 | O | ALA | 230 | 63.570 | 32.307 | 72.156 | 1.00 20.60 |
| ATOM | 681 | N | LEU | 231 | 61.650 | 32.564 | 71.016 | 1.00 24.75 |
| ATOM | 682 | CA | LEU | 231 | 61.818 | 33.984 | 70.842 | 1.00 25.02 |
| ATOM | 683 | CB | LEU | 231 | 60.646 | 34.520 | 70.030 | 1.00 25.42 |
| ATOM | 684 | CG | LEU | 231 | 60.675 | 36.002 | 69.713 | 1.00 25.84 |
| ATOM | 685 | CD1 | LEU | 231 | 61.973 | 36.314 | 68.993 | 1.00 24.29 |
| ATOM | 686 | CD2 | LEU | 231 | 59.463 | 36.378 | 68.867 | 1.00 26.07 |
| ATOM | 687 | C | LEU | 231 | 61.856 | 34.639 | 72.230 | 1.00 31.15 |
| ATOM | 688 | O | LEU | 231 | 62.919 | 35.056 | 72.702 | 1.00 32.01 |
| ATOM | 689 | N | ILE | 232 | 60.693 | 34.693 | 72.883 | 1.00 31.34 |
| ATOM | 690 | CA | ILE | 232 | 60.544 | 35.299 | 74.206 | 1.00 29.73 |
| ATOM | 691 | CB | ILE | 232 | 59.095 | 35.158 | 74.723 | 1.00 26.16 |
| ATOM | 692 | CG2 | ILE | 232 | 58.961 | 35.821 | 76.077 | 1.00 27.46 |
| ATOM | 693 | CG1 | ILE | 232 | 58.118 | 35.829 | 73.752 | 1.00 23.94 |
| ATOM | 694 | CD1 | ILE | 232 | 56.671 | 35.753 | 74.194 | 1.00 16.77 |
| ATOM | 695 | C | ILE | 232 | 61.476 | 34.779 | 75.303 | 1.00 34.77 |
| ATOM | 696 | O | ILE | 232 | 62.301 | 35.535 | 75.828 | 1.00 39.59 |

64

| ATOM | 697 | N | ASN | 233 | 61.354 | 33.498 | 75.649 | 1.00 | 36.31 |
| ATOM | 698 | CA | ASN | 233 | 62.167 | 32.911 | 76.723 | 1.00 | 33.23 |
| ATOM | 699 | CB | ASN | 233 | 61.552 | 31.604 | 77.185 | 1.00 | 27.79 |
| ATOM | 700 | CG | ASN | 233 | 60.132 | 31.768 | 77.618 | 1.00 | 30.93 |
| ATOM | 701 | OD1 | ASN | 233 | 59.802 | 32.683 | 78.370 | 1.00 | 35.73 |
| ATOM | 702 | ND2 | ASN | 233 | 59.271 | 30.873 | 77.161 | 1.00 | 35.50 |
| ATOM | 703 | C | ASN | 233 | 63.665 | 32.681 | 76.551 | 1.00 | 34.17 |
| ATOM | 704 | O | ASN | 233 | 64.380 | 32.625 | 77.541 | 1.00 | 40.81 |
| ATOM | 705 | N | ASP | 234 | 64.162 | 32.523 | 75.336 | 1.00 | 35.33 |
| ATOM | 706 | CA | ASP | 234 | 65.592 | 32.307 | 75.194 | 1.00 | 38.16 |
| ATOM | 707 | CB | ASP | 234 | 65.871 | 31.029 | 74.398 | 1.00 | 42.22 |
| ATOM | 708 | CG | ASP | 234 | 67.365 | 30.788 | 74.172 | 1.00 | 50.98 |
| ATOM | 709 | OD1 | ASP | 234 | 68.043 | 31.689 | 73.627 | 1.00 | 55.41 |
| ATOM | 710 | OD2 | ASP | 234 | 67.866 | 29.694 | 74.527 | 1.00 | 57.31 |
| ATOM | 711 | C | ASP | 234 | 66.278 | 33.494 | 74.528 | 1.00 | 40.03 |
| ATOM | 712 | O | ASP | 234 | 67.278 | 33.993 | 75.031 | 1.00 | 43.70 |
| ATOM | 713 | N | GLU | 235 | 65.750 | 33.954 | 73.400 | 1.00 | 37.89 |
| ATOM | 714 | CA | GLU | 235 | 66.375 | 35.074 | 72.711 | 1.00 | 36.19 |
| ATOM | 715 | CB | GLU | 235 | 65.844 | 35.199 | 71.281 | 1.00 | 41.28 |
| ATOM | 716 | CG | GLU | 235 | 66.309 | 34.098 | 70.355 | 1.00 | 45.65 |
| ATOM | 717 | CD | GLU | 235 | 67.819 | 34.064 | 70.204 | 1.00 | 51.95 |
| ATOM | 718 | OE1 | GLU | 235 | 68.400 | 35.079 | 69.757 | 1.00 | 55.11 |
| ATOM | 719 | OE2 | GLU | 235 | 68.426 | 33.020 | 70.533 | 1.00 | 54.63 |
| ATOM | 720 | C | GLU | 235 | 66.237 | 36.414 | 73.419 | 1.00 | 31.92 |
| ATOM | 721 | O | GLU | 235 | 67.226 | 37.119 | 73.585 | 1.00 | 29.05 |
| ATOM | 722 | N | LEU | 236 | 65.026 | 36.777 | 73.834 | 1.00 | 29.07 |
| ATOM | 723 | CA | LEU | 236 | 64.847 | 38.057 | 74.505 | 1.00 | 23.14 |
| ATOM | 724 | CB | LEU | 236 | 63.375 | 38.357 | 74.760 | 1.00 | 20.01 |
| ATOM | 725 | CG | LEU | 236 | 62.971 | 39.838 | 74.826 | 1.00 | 23.50 |
| ATOM | 726 | CD1 | LEU | 236 | 61.582 | 39.922 | 75.441 | 1.00 | 23.51 |
| ATOM | 727 | CD2 | LEU | 236 | 63.939 | 40.648 | 75.659 | 1.00 | 22.21 |
| ATOM | 728 | C | LEU | 236 | 65.568 | 37.952 | 75.830 | 1.00 | 24.11 |
| ATOM | 729 | O | LEU | 236 | 66.413 | 38.782 | 76.149 | 1.00 | 26.68 |
| ATOM | 730 | N | VAL | 237 | 65.244 | 36.919 | 76.602 | 1.00 | 22.14 |
| ATOM | 731 | CA | VAL | 237 | 65.885 | 36.725 | 77.897 | 1.00 | 18.63 |
| ATOM | 732 | CB | VAL | 237 | 65.429 | 35.417 | 78.540 | 1.00 | 13.56 |
| ATOM | 733 | CG1 | VAL | 237 | 66.247 | 35.125 | 79.764 | 1.00 | 7.56 |
| ATOM | 734 | CG2 | VAL | 237 | 63.972 | 35.540 | 78.930 | 1.00 | 13.70 |
| ATOM | 735 | C | VAL | 237 | 67.406 | 36.756 | 77.794 | 1.00 | 19.25 |
| ATOM | 736 | O | VAL | 237 | 68.084 | 37.281 | 78.669 | 1.00 | 21.33 |
| ATOM | 737 | N | GLU | 238 | 67.953 | 36.217 | 76.718 | 1.00 | 21.11 |
| ATOM | 738 | CA | GLU | 238 | 69.391 | 36.243 | 76.563 | 1.00 | 23.82 |
| ATOM | 739 | CB | GLU | 238 | 69.820 | 35.254 | 75.484 | 1.00 | 28.31 |
| ATOM | 740 | CG | GLU | 238 | 71.303 | 34.964 | 75.476 | 1.00 | 42.03 |
| ATOM | 741 | CD | GLU | 238 | 71.697 | 34.010 | 74.360 | 1.00 | 53.11 |
| ATOM | 742 | OE1 | GLU | 238 | 71.666 | 34.399 | 73.165 | 1.00 | 54.64 |
| ATOM | 743 | OE2 | GLU | 238 | 72.029 | 32.852 | 74.687 | 1.00 | 64.50 |
| ATOM | 744 | C | GLU | 238 | 69.839 | 37.673 | 76.206 | 1.00 | 23.45 |
| ATOM | 745 | O | GLU | 238 | 70.827 | 38.174 | 76.742 | 1.00 | 26.06 |
| ATOM | 746 | N | TRP | 239 | 69.109 | 38.343 | 75.320 | 1.00 | 18.69 |
| ATOM | 747 | CA | TRP | 239 | 69.478 | 39.699 | 74.953 | 1.00 | 17.31 |
| ATOM | 748 | CB | TRP | 239 | 68.453 | 40.322 | 74.010 | 1.00 | 17.97 |
| ATOM | 749 | CG | TRP | 239 | 68.893 | 41.659 | 73.503 | 1.00 | 15.86 |
| ATOM | 750 | CD2 | TRP | 239 | 68.524 | 42.940 | 74.033 | 1.00 | 14.64 |
| ATOM | 751 | CE2 | TRP | 239 | 69.271 | 43.908 | 73.331 | 1.00 | 17.23 |
| ATOM | 752 | CE3 | TRP | 239 | 67.636 | 43.360 | 75.033 | 1.00 | 15.89 |
| ATOM | 753 | CD1 | TRP | 239 | 69.817 | 41.900 | 72.529 | 1.00 | 12.12 |
| ATOM | 754 | NE1 | TRP | 239 | 70.050 | 43.245 | 72.421 | 1.00 | 17.41 |
| ATOM | 755 | CZ2 | TRP | 239 | 69.157 | 45.281 | 73.600 | 1.00 | 17.49 |
| ATOM | 756 | CZ3 | TRP | 239 | 67.524 | 44.722 | 75.299 | 1.00 | 17.19 |
| ATOM | 757 | CH2 | TRP | 239 | 68.280 | 45.665 | 74.586 | 1.00 | 16.55 |
| ATOM | 758 | C | TRP | 239 | 69.549 | 40.549 | 76.215 | 1.00 | 22.10 |
| ATOM | 759 | O | TRP | 239 | 70.454 | 41.376 | 76.381 | 1.00 | 23.47 |
| ATOM | 760 | N | LYS | 240 | 68.584 | 40.350 | 77.106 | 1.00 | 21.51 |
| ATOM | 761 | CA | LYS | 240 | 68.559 | 41.096 | 78.346 | 1.00 | 20.13 |
| ATOM | 762 | CB | LYS | 240 | 67.277 | 40.815 | 79.116 | 1.00 | 16.93 |
| ATOM | 763 | CG | LYS | 240 | 66.030 | 41.302 | 78.428 | 1.00 | 10.86 |
| ATOM | 764 | CD | LYS | 240 | 64.941 | 41.532 | 79.447 | 1.00 | 4.21 |
| ATOM | 765 | CE | LYS | 240 | 63.765 | 42.214 | 78.808 | 1.00 | 19.29 |
| ATOM | 766 | NZ | LYS | 240 | 62.833 | 42.799 | 79.802 | 1.00 | 26.58 |

65

| ATOM | 767 | C | LYS | 240 | 69.773 | 40.804 | 79.231 | 1.00 | 25.62 |
| ATOM | 768 | O | LYS | 240 | 70.382 | 41.739 | 79.763 | 1.00 | 26.77 |
| ATOM | 769 | N | ARG | 241 | 70.138 | 39.533 | 79.402 | 1.00 | 23.86 |
| ATOM | 770 | CA | ARG | 241 | 71.308 | 39.242 | 80.228 | 1.00 | 26.60 |
| ATOM | 771 | CB | ARG | 241 | 71.628 | 37.742 | 80.267 | 1.00 | 26.03 |
| ATOM | 772 | CG | ARG | 241 | 70.579 | 36.879 | 80.962 | 1.00 | 34.52 |
| ATOM | 773 | CD | ARG | 241 | 70.440 | 37.211 | 82.442 | 1.00 | 38.22 |
| ATOM | 774 | NE | ARG | 241 | 69.300 | 36.526 | 83.057 | 1.00 | 41.98 |
| ATOM | 775 | CZ | ARG | 241 | 68.021 | 36.748 | 82.744 | 1.00 | 45.51 |
| ATOM | 776 | NH1 | ARG | 241 | 67.695 | 37.641 | 81.811 | 1.00 | 44.01 |
| ATOM | 777 | NH2 | ARG | 241 | 67.057 | 36.080 | 83.372 | 1.00 | 44.45 |
| ATOM | 778 | C | ARG | 241 | 72.515 | 40.001 | 79.686 | 1.00 | 29.11 |
| ATOM | 779 | O | ARG | 241 | 73.260 | 40.620 | 80.447 | 1.00 | 31.10 |
| ATOM | 780 | N | ARG | 242 | 72.709 | 39.972 | 78.371 | 1.00 | 27.92 |
| ATOM | 781 | CA | ARG | 242 | 73.845 | 40.671 | 77.791 | 1.00 | 26.83 |
| ATOM | 782 | CB | ARG | 242 | 73.940 | 40.402 | 76.298 | 1.00 | 28.49 |
| ATOM | 783 | CG | ARG | 242 | 74.224 | 38.973 | 75.953 | 1.00 | 31.61 |
| ATOM | 784 | CD | ARG | 242 | 74.210 | 38.838 | 74.454 | 1.00 | 46.69 |
| ATOM | 785 | NE | ARG | 242 | 74.139 | 37.449 | 74.014 | 1.00 | 60.12 |
| ATOM | 786 | CZ | ARG | 242 | 73.779 | 37.084 | 72.786 | 1.00 | 66.42 |
| ATOM | 787 | NH1 | ARG | 242 | 73.463 | 38.014 | 71.886 | 1.00 | 69.02 |
| ATOM | 788 | NH2 | ARG | 242 | 73.720 | 35.794 | 72.462 | 1.00 | 68.04 |
| ATOM | 789 | C | ARG | 242 | 73.765 | 42.169 | 78.038 | 1.00 | 26.93 |
| ATOM | 790 | O | ARG | 242 | 74.796 | 42.835 | 78.160 | 1.00 | 30.81 |
| ATOM | 791 | N | GLN | 243 | 72.547 | 42.705 | 78.103 | 1.00 | 23.38 |
| ATOM | 792 | CA | GLN | 243 | 72.373 | 44.135 | 78.361 | 1.00 | 17.91 |
| ATOM | 793 | CB | GLN | 243 | 70.891 | 44.516 | 78.268 | 1.00 | 6.83 |
| ATOM | 794 | CG | GLN | 243 | 70.608 | 45.963 | 78.537 | 1.00 | 4.06 |
| ATOM | 795 | CD | GLN | 243 | 69.138 | 46.322 | 78.389 | 1.00 | 10.99 |
| ATOM | 796 | OE1 | GLN | 243 | 68.264 | 45.695 | 78.979 | 1.00 | 15.68 |
| ATOM | 797 | NE2 | GLN | 243 | 68.863 | 47.351 | 77.607 | 1.00 | 14.12 |
| ATOM | 798 | C | GLN | 243 | 72.943 | 44.429 | 79.756 | 1.00 | 18.76 |
| ATOM | 799 | O | GLN | 243 | 73.749 | 45.349 | 79.925 | 1.00 | 12.38 |
| ATOM | 800 | N | GLN | 244 | 72.543 | 43.630 | 80.748 | 1.00 | 16.93 |
| ATOM | 801 | CA | GLN | 244 | 73.058 | 43.819 | 82.097 | 1.00 | 16.61 |
| ATOM | 802 | CB | GLN | 244 | 72.743 | 42.632 | 83.020 | 1.00 | 16.76 |
| ATOM | 803 | CG | GLN | 244 | 71.278 | 42.446 | 83.361 | 1.00 | 24.00 |
| ATOM | 804 | CD | GLN | 244 | 71.063 | 41.391 | 84.427 | 1.00 | 24.92 |
| ATOM | 805 | OE1 | GLN | 244 | 71.629 | 41.489 | 85.503 | 1.00 | 30.66 |
| ATOM | 806 | NE2 | GLN | 244 | 70.236 | 40.387 | 84.137 | 1.00 | 24.31 |
| ATOM | 807 | C | GLN | 244 | 74.558 | 43.957 | 82.022 | 1.00 | 15.57 |
| ATOM | 808 | O | GLN | 244 | 75.117 | 44.973 | 82.413 | 1.00 | 21.96 |
| ATOM | 809 | N | SER | 245 | 75.211 | 42.934 | 81.496 | 1.00 | 9.97 |
| ATOM | 810 | CA | SER | 245 | 76.653 | 42.957 | 81.417 | 1.00 | 9.59 |
| ATOM | 811 | CB | SER | 245 | 77.155 | 41.677 | 80.788 | 1.00 | 7.59 |
| ATOM | 812 | OG | SER | 245 | 78.563 | 41.677 | 80.810 | 1.00 | 13.51 |
| ATOM | 813 | C | SER | 245 | 77.221 | 44.147 | 80.662 | 1.00 | 12.38 |
| ATOM | 814 | O | SER | 245 | 78.325 | 44.600 | 80.937 | 1.00 | 10.90 |
| ATOM | 815 | N | ALA | 246 | 76.472 | 44.661 | 79.703 | 1.00 | 14.99 |
| ATOM | 816 | CA | ALA | 246 | 76.957 | 45.798 | 78.939 | 1.00 | 15.16 |
| ATOM | 817 | CB | ALA | 246 | 76.041 | 46.054 | 77.759 | 1.00 | 17.67 |
| ATOM | 818 | C | ALA | 246 | 77.021 | 47.025 | 79.846 | 1.00 | 14.92 |
| ATOM | 819 | O | ALA | 246 | 78.028 | 47.724 | 79.867 | 1.00 | 18.29 |
| ATOM | 820 | N | CYS | 247 | 75.946 | 47.272 | 80.595 | 1.00 | 12.05 |
| ATOM | 821 | CA | CYS | 247 | 75.871 | 48.403 | 81.510 | 1.00 | 10.68 |
| ATOM | 822 | CB | CYS | 247 | 74.588 | 48.342 | 82.344 | 1.00 | 13.62 |
| ATOM | 823 | SG | CYS | 247 | 73.043 | 48.551 | 81.416 | 1.00 | 23.51 |
| ATOM | 824 | C | CYS | 247 | 77.054 | 48.477 | 82.455 | 1.00 | 9.59 |
| ATOM | 825 | O | CYS | 247 | 77.477 | 49.566 | 82.837 | 1.00 | 14.75 |
| ATOM | 826 | N | ILE | 248 | 77.594 | 47.325 | 82.858 | 1.00 | 7.77 |
| ATOM | 827 | CA | ILE | 248 | 78.730 | 47.390 | 83.765 | 1.00 | 9.41 |
| ATOM | 828 | CB | ILE | 248 | 78.609 | 46.369 | 84.925 | 1.00 | 8.01 |
| ATOM | 829 | CG2 | ILE | 248 | 77.494 | 46.794 | 85.883 | 1.00 | 5.66 |
| ATOM | 830 | CG1 | ILE | 248 | 78.352 | 44.978 | 84.372 | 1.00 | 8.56 |
| ATOM | 831 | CD1 | ILE | 248 | 78.201 | 43.941 | 85.425 | 1.00 | 6.71 |
| ATOM | 832 | C | ILE | 248 | 80.072 | 47.233 | 83.059 | 1.00 | 11.69 |
| ATOM | 833 | O | ILE | 248 | 81.051 | 46.817 | 83.664 | 1.00 | 15.86 |
| ATOM | 834 | N | GLY | 249 | 80.110 | 47.562 | 81.771 | 1.00 | 9.77 |
| ATOM | 835 | CA | GLY | 249 | 81.356 | 47.522 | 81.029 | 1.00 | 4.22 |
| ATOM | 836 | C | GLY | 249 | 81.788 | 46.272 | 80.308 | 1.00 | 9.80 |

66

| ATOM | 837 | O | GLY | 249 | 82.944 | 46.190 | 79.899 | 1.00 | 13.59 |
| ATOM | 838 | N | GLY | 250 | 80.893 | 45.305 | 80.141 | 1.00 | 11.42 |
| ATOM | 839 | CA | GLY | 250 | 81.256 | 44.081 | 79.445 | 1.00 | 12.90 |
| ATOM | 840 | C | GLY | 250 | 81.129 | 44.226 | 77.939 | 1.00 | 14.31 |
| ATOM | 841 | O | GLY | 250 | 81.204 | 45.342 | 77.419 | 1.00 | 13.11 |
| ATOM | 842 | N | PRO | 251 | 80.930 | 43.122 | 77.200 | 1.00 | 15.35 |
| ATOM | 843 | CD | PRO | 251 | 80.785 | 41.719 | 77.614 | 1.00 | 9.56 |
| ATOM | 844 | CA | PRO | 251 | 80.801 | 43.215 | 75.746 | 1.00 | 17.19 |
| ATOM | 845 | CB | PRO | 251 | 80.633 | 41.760 | 75.338 | 1.00 | 10.14 |
| ATOM | 846 | CG | PRO | 251 | 81.355 | 41.028 | 76.430 | 1.00 | 3.82 |
| ATOM | 847 | C | PRO | 251 | 79.593 | 44.075 | 75.372 | 1.00 | 23.21 |
| ATOM | 848 | O | PRO | 251 | 78.642 | 44.185 | 76.142 | 1.00 | 28.63 |
| ATOM | 849 | N | PRO | 252 | 79.615 | 44.694 | 74.181 | 1.00 | 28.61 |
| ATOM | 850 | CD | PRO | 252 | 80.696 | 44.648 | 73.179 | 1.00 | 34.98 |
| ATOM | 851 | CA | PRO | 252 | 78.535 | 45.552 | 73.693 | 1.00 | 32.69 |
| ATOM | 852 | CB | PRO | 252 | 79.203 | 46.271 | 72.537 | 1.00 | 32.18 |
| ATOM | 853 | CG | PRO | 252 | 79.983 | 45.123 | 71.927 | 1.00 | 34.05 |
| ATOM | 854 | C | PRO | 252 | 77.313 | 44.752 | 73.237 | 1.00 | 36.23 |
| ATOM | 855 | O | PRO | 252 | 77.444 | 43.712 | 72.587 | 1.00 | 35.51 |
| ATOM | 856 | N | ASN | 253 | 76.127 | 45.241 | 73.583 | 1.00 | 36.93 |
| ATOM | 857 | CA | ASN | 253 | 74.897 | 44.576 | 73.188 | 1.00 | 40.43 |
| ATOM | 858 | CB | ASN | 253 | 73.675 | 45.344 | 73.697 | 1.00 | 46.95 |
| ATOM | 859 | CG | ASN | 253 | 72.891 | 44.578 | 74.740 | 1.00 | 58.55 |
| ATOM | 860 | OD1 | ASN | 253 | 72.658 | 43.364 | 74.609 | 1.00 | 58.85 |
| ATOM | 861 | ND2 | ASN | 253 | 72.443 | 45.291 | 75.776 | 1.00 | 61.95 |
| ATOM | 862 | C | ASN | 253 | 74.793 | 44.499 | 71.671 | 1.00 | 40.82 |
| ATOM | 863 | O | ASN | 253 | 75.258 | 45.390 | 70.951 | 1.00 | 39.37 |
| ATOM | 864 | N | ALA | 254 | 74.177 | 43.431 | 71.185 | 1.00 | 39.77 |
| ATOM | 865 | CA | ALA | 254 | 73.968 | 43.280 | 69.761 | 1.00 | 35.09 |
| ATOM | 866 | CB | ALA | 254 | 73.694 | 41.831 | 69.422 | 1.00 | 38.63 |
| ATOM | 867 | C | ALA | 254 | 72.745 | 44.137 | 69.464 | 1.00 | 32.69 |
| ATOM | 868 | O | ALA | 254 | 71.955 | 44.428 | 70.349 | 1.00 | 28.43 |
| ATOM | 869 | N | CYS | 255 | 72.603 | 44.556 | 68.219 | 1.00 | 33.12 |
| ATOM | 870 | CA | CYS | 255 | 71.476 | 45.373 | 67.815 | 1.00 | 34.09 |
| ATOM | 871 | CB | CYS | 255 | 71.682 | 45.817 | 66.368 | 1.00 | 38.05 |
| ATOM | 872 | SG | CYS | 255 | 70.307 | 46.714 | 65.643 | 1.00 | 44.25 |
| ATOM | 873 | C | CYS | 255 | 70.203 | 44.544 | 67.931 | 1.00 | 34.22 |
| ATOM | 874 | O | CYS | 255 | 70.223 | 43.342 | 67.678 | 1.00 | 38.32 |
| ATOM | 875 | N | LEU | 256 | 69.100 | 45.184 | 68.307 | 1.00 | 31.19 |
| ATOM | 876 | CA | LEU | 256 | 67.819 | 44.499 | 68.433 | 1.00 | 30.86 |
| ATOM | 877 | CB | LEU | 256 | 66.875 | 45.276 | 69.349 | 1.00 | 31.13 |
| ATOM | 878 | CG | LEU | 256 | 66.948 | 45.237 | 70.872 | 1.00 | 30.14 |
| ATOM | 879 | CD1 | LEU | 256 | 65.830 | 46.097 | 71.416 | 1.00 | 23.16 |
| ATOM | 880 | CD2 | LEU | 256 | 66.782 | 43.819 | 71.370 | 1.00 | 27.45 |
| ATOM | 881 | C | LEU | 256 | 67.075 | 44.270 | 67.117 | 1.00 | 34.88 |
| ATOM | 882 | O | LEU | 256 | 65.926 | 43.832 | 67.140 | 1.00 | 37.02 |
| ATOM | 883 | N | ASP | 257 | 67.688 | 44.572 | 65.974 | 1.00 | 37.67 |
| ATOM | 884 | CA | ASP | 257 | 66.991 | 44.370 | 64.706 | 1.00 | 35.09 |
| ATOM | 885 | CB | ASP | 257 | 67.773 | 44.941 | 63.528 | 1.00 | 37.14 |
| ATOM | 886 | CG | ASP | 257 | 67.764 | 46.450 | 63.508 | 1.00 | 47.17 |
| ATOM | 887 | OD1 | ASP | 257 | 66.708 | 47.047 | 63.815 | 1.00 | 46.78 |
| ATOM | 888 | OD2 | ASP | 257 | 68.803 | 47.044 | 63.159 | 1.00 | 51.54 |
| ATOM | 889 | C | ASP | 257 | 66.695 | 42.914 | 64.450 | 1.00 | 32.00 |
| ATOM | 890 | O | ASP | 257 | 65.579 | 42.560 | 64.062 | 1.00 | 30.45 |
| ATOM | 891 | N | GLN | 258 | 67.686 | 42.062 | 64.667 | 1.00 | 28.83 |
| ATOM | 892 | CA | GLN | 258 | 67.463 | 40.649 | 64.450 | 1.00 | 28.39 |
| ATOM | 893 | CB | GLN | 258 | 68.645 | 39.842 | 64.967 | 1.00 | 30.08 |
| ATOM | 894 | CG | GLN | 258 | 68.531 | 38.365 | 64.684 | 1.00 | 39.12 |
| ATOM | 895 | CD | GLN | 258 | 69.730 | 37.590 | 65.185 | 1.00 | 46.31 |
| ATOM | 896 | OE1 | GLN | 258 | 70.041 | 37.602 | 66.382 | 1.00 | 47.18 |
| ATOM | 897 | NE2 | GLN | 258 | 70.416 | 36.907 | 64.269 | 1.00 | 48.63 |
| ATOM | 898 | C | GLN | 258 | 66.178 | 40.268 | 65.192 | 1.00 | 28.43 |
| ATOM | 899 | O | GLN | 258 | 65.233 | 39.750 | 64.585 | 1.00 | 30.75 |
| ATOM | 900 | N | LEU | 259 | 66.142 | 40.556 | 66.495 | 1.00 | 23.97 |
| ATOM | 901 | CA | LEU | 259 | 64.979 | 40.264 | 67.334 | 1.00 | 17.77 |
| ATOM | 902 | CB | LEU | 259 | 65.186 | 40.791 | 68.755 | 1.00 | 16.83 |
| ATOM | 903 | CG | LEU | 259 | 65.861 | 39.879 | 69.763 | 1.00 | 16.56 |
| ATOM | 904 | CD1 | LEU | 259 | 66.011 | 40.598 | 71.084 | 1.00 | 18.10 |
| ATOM | 905 | CD2 | LEU | 259 | 65.016 | 38.635 | 69.937 | 1.00 | 12.88 |
| ATOM | 906 | C | LEU | 259 | 63.676 | 40.841 | 66.813 | 1.00 | 16.86 |

67

| | | | | | | | | |
|---|---|---|---|---|---|---|---|---|
| ATOM | 907 | O | LEU | 259 | 62.643 | 40.167 | 66.794 | 1.00 15.26 |
| ATOM | 908 | N | GLN | 260 | 63.721 | 42.102 | 66.416 | 1.00 16.83 |
| ATOM | 909 | CA | GLN | 260 | 62.537 | 42.767 | 65.919 | 1.00 18.12 |
| ATOM | 910 | CB | GLN | 260 | 62.868 | 44.200 | 65.563 | 1.00 14.58 |
| ATOM | 911 | CG | GLN | 260 | 61.681 | 45.023 | 65.223 | 1.00 21.89 |
| ATOM | 912 | CD | GLN | 260 | 62.044 | 46.474 | 65.202 | 1.00 31.24 |
| ATOM | 913 | OE1 | GLN | 260 | 62.930 | 46.889 | 64.448 | 1.00 35.38 |
| ATOM | 914 | NE2 | GLN | 260 | 61.377 | 47.267 | 66.039 | 1.00 34.50 |
| ATOM | 915 | C | GLN | 260 | 61.966 | 42.051 | 64.708 | 1.00 21.13 |
| ATOM | 916 | O | GLN | 260 | 60.746 | 41.921 | 64.567 | 1.00 19.79 |
| ATOM | 917 | N | ASN | 261 | 62.835 | 41.564 | 63.835 | 1.00 21.58 |
| ATOM | 918 | CA | ASN | 261 | 62.326 | 40.882 | 62.665 | 1.00 26.76 |
| ATOM | 919 | CB | ASN | 261 | 63.454 | 40.459 | 61.743 | 1.00 34.20 |
| ATOM | 920 | CG | ASN | 261 | 62.933 | 39.959 | 60.424 | 1.00 37.70 |
| ATOM | 921 | OD1 | ASN | 261 | 62.160 | 40.659 | 59.759 | 1.00 41.37 |
| ATOM | 922 | ND2 | ASN | 261 | 63.334 | 38.752 | 60.034 | 1.00 40.06 |
| ATOM | 923 | C | ASN | 261 | 61.507 | 39.661 | 63.052 | 1.00 25.98 |
| ATOM | 924 | O | ASN | 261 | 60.372 | 39.494 | 62.614 | 1.00 23.66 |
| ATOM | 925 | N | TRP | 262 | 62.091 | 38.797 | 63.872 | 1.00 28.58 |
| ATOM | 926 | CA | TRP | 262 | 61.381 | 37.612 | 64.316 | 1.00 28.27 |
| ATOM | 927 | CB | TRP | 262 | 62.235 | 36.845 | 65.324 | 1.00 25.55 |
| ATOM | 928 | CG | TRP | 262 | 63.495 | 36.385 | 64.705 | 1.00 28.40 |
| ATOM | 929 | CD2 | TRP | 262 | 64.680 | 35.950 | 65.372 | 1.00 34.05 |
| ATOM | 930 | CE2 | TRP | 262 | 65.585 | 35.514 | 64.377 | 1.00 35.88 |
| ATOM | 931 | CE3 | TRP | 262 | 65.069 | 35.884 | 66.710 | 1.00 38.07 |
| ATOM | 932 | CD1 | TRP | 262 | 63.721 | 36.203 | 63.372 | 1.00 35.97 |
| ATOM | 933 | NE1 | TRP | 262 | 64.973 | 35.679 | 63.165 | 1.00 37.26 |
| ATOM | 934 | CZ2 | TRP | 262 | 66.850 | 35.018 | 64.681 | 1.00 32.17 |
| ATOM | 935 | CZ3 | TRP | 262 | 66.331 | 35.391 | 67.011 | 1.00 42.33 |
| ATOM | 936 | CH2 | TRP | 262 | 67.206 | 34.966 | 65.998 | 1.00 34.45 |
| ATOM | 937 | C | TRP | 262 | 60.029 | 37.998 | 64.913 | 1.00 27.63 |
| ATOM | 938 | O | TRP | 262 | 58.980 | 37.539 | 64.449 | 1.00 31.14 |
| ATOM | 939 | N | PHE | 263 | 60.052 | 38.859 | 65.924 | 1.00 23.56 |
| ATOM | 940 | CA | PHE | 263 | 58.823 | 39.300 | 66.554 | 1.00 19.80 |
| ATOM | 941 | CB | PHE | 263 | 59.097 | 40.412 | 67.573 | 1.00 19.87 |
| ATOM | 942 | CG | PHE | 263 | 59.390 | 39.917 | 68.965 | 1.00 18.61 |
| ATOM | 943 | CD1 | PHE | 263 | 60.654 | 39.465 | 69.316 | 1.00 18.39 |
| ATOM | 944 | CD2 | PHE | 263 | 58.384 | 39.900 | 69.926 | 1.00 13.65 |
| ATOM | 945 | CE1 | PHE | 263 | 60.911 | 39.003 | 70.609 | 1.00 19.90 |
| ATOM | 946 | CE2 | PHE | 263 | 58.626 | 39.441 | 71.216 | 1.00 13.16 |
| ATOM | 947 | CZ | PHE | 263 | 59.891 | 38.992 | 71.560 | 1.00 19.24 |
| ATOM | 948 | C | PHE | 263 | 57.736 | 39.776 | 65.587 | 1.00 20.14 |
| ATOM | 949 | O | PHE | 263 | 56.658 | 39.185 | 65.548 | 1.00 17.90 |
| ATOM | 950 | N | THR | 264 | 57.994 | 40.819 | 64.795 | 1.00 19.21 |
| ATOM | 951 | CA | THR | 264 | 56.924 | 41.306 | 63.913 | 1.00 19.63 |
| ATOM | 952 | CB | THR | 264 | 57.314 | 42.608 | 63.127 | 1.00 17.63 |
| ATOM | 953 | OG1 | THR | 264 | 57.571 | 42.291 | 61.763 | 1.00 26.32 |
| ATOM | 954 | CG2 | THR | 264 | 58.535 | 43.272 | 63.724 | 1.00 9.38 |
| ATOM | 955 | C | THR | 264 | 56.419 | 40.251 | 62.926 | 1.00 16.21 |
| ATOM | 956 | O | THR | 264 | 55.230 | 40.179 | 62.641 | 1.00 15.01 |
| ATOM | 957 | N | ILE | 265 | 57.312 | 39.419 | 62.420 | 1.00 14.05 |
| ATOM | 958 | CA | ILE | 265 | 56.906 | 38.390 | 61.480 | 1.00 20.91 |
| ATOM | 959 | CB | ILE | 265 | 58.105 | 37.580 | 61.006 | 1.00 24.10 |
| ATOM | 960 | CG2 | ILE | 265 | 57.632 | 36.347 | 60.258 | 1.00 22.40 |
| ATOM | 961 | CG1 | ILE | 265 | 59.017 | 38.470 | 60.164 | 1.00 27.02 |
| ATOM | 962 | CD1 | ILE | 265 | 60.328 | 37.804 | 59.800 | 1.00 36.93 |
| ATOM | 963 | C | ILE | 265 | 55.897 | 37.426 | 62.091 | 1.00 22.62 |
| ATOM | 964 | O | ILE | 265 | 54.963 | 36.977 | 61.416 | 1.00 24.37 |
| ATOM | 965 | N | VAL | 266 | 56.097 | 37.083 | 63.359 | 1.00 22.40 |
| ATOM | 966 | CA | VAL | 266 | 55.174 | 36.178 | 64.015 | 1.00 23.32 |
| ATOM | 967 | CB | VAL | 266 | 55.860 | 35.454 | 65.203 | 1.00 20.75 |
| ATOM | 968 | CG1 | VAL | 266 | 56.390 | 36.458 | 66.176 | 1.00 28.47 |
| ATOM | 969 | CG2 | VAL | 266 | 54.882 | 34.523 | 65.897 | 1.00 21.30 |
| ATOM | 970 | C | VAL | 266 | 53.977 | 37.014 | 64.478 | 1.00 22.96 |
| ATOM | 971 | O | VAL | 266 | 52.855 | 36.518 | 64.593 | 1.00 25.37 |
| ATOM | 972 | N | ALA | 267 | 54.220 | 38.298 | 64.709 | 1.00 21.40 |
| ATOM | 973 | CA | ALA | 267 | 53.166 | 39.205 | 65.143 | 1.00 22.46 |
| ATOM | 974 | CB | ALA | 267 | 53.774 | 40.549 | 65.543 | 1.00 24.76 |
| ATOM | 975 | C | ALA | 267 | 52.139 | 39.399 | 64.024 | 1.00 24.77 |
| ATOM | 976 | O | ALA | 267 | 50.941 | 39.554 | 64.272 | 1.00 24.94 |

68

| ATOM | 977 | N | GLU | 268 | 52.618 | 39.395 | 62.787 | 1.00 | 29.65 |
| ATOM | 978 | CA | GLU | 268 | 51.744 | 39.568 | 61.630 | 1.00 | 32.38 |
| ATOM | 979 | CB | GLU | 268 | 52.579 | 39.990 | 60.419 | 1.00 | 31.97 |
| ATOM | 980 | CG | GLU | 268 | 53.391 | 41.251 | 60.669 | 1.00 | 36.14 |
| ATOM | 981 | CD | GLU | 268 | 54.290 | 41.625 | 59.501 | 1.00 | 40.44 |
| ATOM | 982 | OE1 | GLU | 268 | 55.009 | 40.740 | 58.987 | 1.00 | 44.50 |
| ATOM | 983 | OE2 | GLU | 268 | 54.297 | 42.809 | 59.109 | 1.00 | 42.27 |
| ATOM | 984 | C | GLU | 268 | 50.970 | 38.266 | 61.342 | 1.00 | 32.22 |
| ATOM | 985 | O | GLU | 268 | 49.796 | 38.292 | 60.958 | 1.00 | 33.27 |
| ATOM | 986 | N | SER | 269 | 51.625 | 37.129 | 61.540 | 1.00 | 27.06 |
| ATOM | 987 | CA | SER | 269 | 50.967 | 35.857 | 61.321 | 1.00 | 24.86 |
| ATOM | 988 | CB | SER | 269 | 51.948 | 34.710 | 61.518 | 1.00 | 27.07 |
| ATOM | 989 | OG | SER | 269 | 52.963 | 34.771 | 60.534 | 1.00 | 35.50 |
| ATOM | 990 | C | SER | 269 | 49.781 | 35.695 | 62.254 | 1.00 | 23.07 |
| ATOM | 991 | O | SER | 269 | 48.712 | 35.294 | 61.826 | 1.00 | 27.29 |
| ATOM | 992 | N | LEU | 270 | 49.949 | 35.993 | 63.533 | 1.00 | 26.85 |
| ATOM | 993 | CA | LEU | 270 | 48.814 | 35.854 | 64.428 | 1.00 | 28.53 |
| ATOM | 994 | CB | LEU | 270 | 49.218 | 36.067 | 65.888 | 1.00 | 32.73 |
| ATOM | 995 | CG | LEU | 270 | 49.865 | 34.889 | 66.616 | 1.00 | 31.19 |
| ATOM | 996 | CD1 | LEU | 270 | 51.119 | 34.439 | 65.911 | 1.00 | 36.64 |
| ATOM | 997 | CD2 | LEU | 270 | 50.197 | 35.317 | 68.015 | 1.00 | 36.90 |
| ATOM | 998 | C | LEU | 270 | 47.722 | 36.833 | 64.031 | 1.00 | 27.53 |
| ATOM | 999 | O | LEU | 270 | 46.546 | 36.477 | 64.044 | 1.00 | 26.35 |
| ATOM | 1000 | N | GLN | 271 | 48.088 | 38.060 | 63.671 | 1.00 | 28.39 |
| ATOM | 1001 | CA | GLN | 271 | 47.056 | 39.010 | 63.269 | 1.00 | 34.57 |
| ATOM | 1002 | CB | GLN | 271 | 47.640 | 40.366 | 62.861 | 1.00 | 39.19 |
| ATOM | 1003 | CG | GLN | 271 | 48.185 | 41.198 | 63.996 | 1.00 | 43.77 |
| ATOM | 1004 | CD | GLN | 271 | 48.526 | 42.602 | 63.544 | 1.00 | 48.50 |
| ATOM | 1005 | OE1 | GLN | 271 | 49.293 | 42.791 | 62.599 | 1.00 | 54.27 |
| ATOM | 1006 | NE2 | GLN | 271 | 47.960 | 43.599 | 64.219 | 1.00 | 46.44 |
| ATOM | 1007 | C | GLN | 271 | 46.291 | 38.438 | 62.089 | 1.00 | 32.21 |
| ATOM | 1008 | O | GLN | 271 | 45.092 | 38.669 | 61.936 | 1.00 | 28.44 |
| ATOM | 1009 | N | GLN | 272 | 46.998 | 37.680 | 61.263 | 1.00 | 32.40 |
| ATOM | 1010 | CA | GLN | 272 | 46.402 | 37.084 | 60.084 | 1.00 | 32.65 |
| ATOM | 1011 | CB | GLN | 272 | 47.508 | 36.572 | 59.165 | 1.00 | 34.39 |
| ATOM | 1012 | CG | GLN | 272 | 47.120 | 36.531 | 57.709 | 1.00 | 42.31 |
| ATOM | 1013 | CD | GLN | 272 | 48.291 | 36.193 | 56.808 | 1.00 | 49.15 |
| ATOM | 1014 | OE1 | GLN | 272 | 49.335 | 36.859 | 56.837 | 1.00 | 44.87 |
| ATOM | 1015 | NE2 | GLN | 272 | 48.122 | 35.157 | 55.989 | 1.00 | 56.41 |
| ATOM | 1016 | C | GLN | 272 | 45.441 | 35.958 | 60.479 | 1.00 | 31.95 |
| ATOM | 1017 | O | GLN | 272 | 44.271 | 35.970 | 60.093 | 1.00 | 32.84 |
| ATOM | 1018 | N | VAL | 273 | 45.923 | 34.992 | 61.255 | 1.00 | 28.72 |
| ATOM | 1019 | CA | VAL | 273 | 45.071 | 33.890 | 61.690 | 1.00 | 29.08 |
| ATOM | 1020 | CB | VAL | 273 | 45.739 | 33.059 | 62.797 | 1.00 | 20.32 |
| ATOM | 1021 | CG1 | VAL | 273 | 44.778 | 32.022 | 63.316 | 1.00 | 10.59 |
| ATOM | 1022 | CG2 | VAL | 273 | 46.973 | 32.387 | 62.257 | 1.00 | 21.82 |
| ATOM | 1023 | C | VAL | 273 | 43.754 | 34.433 | 62.231 | 1.00 | 34.63 |
| ATOM | 1024 | O | VAL | 273 | 42.695 | 33.818 | 62.081 | 1.00 | 35.61 |
| ATOM | 1025 | N | ARG | 274 | 43.829 | 35.605 | 62.848 | 1.00 | 39.11 |
| ATOM | 1026 | CA | ARG | 274 | 42.658 | 36.239 | 63.433 | 1.00 | 42.58 |
| ATOM | 1027 | CB | ARG | 274 | 43.081 | 37.515 | 64.155 | 1.00 | 46.56 |
| ATOM | 1028 | CG | ARG | 274 | 42.100 | 37.993 | 65.185 | 1.00 | 55.63 |
| ATOM | 1029 | CD | ARG | 274 | 42.609 | 39.254 | 65.842 | 1.00 | 65.50 |
| ATOM | 1030 | NE | ARG | 274 | 41.663 | 39.749 | 66.834 | 1.00 | 72.14 |
| ATOM | 1031 | CZ | ARG | 274 | 41.610 | 41.012 | 67.238 | 1.00 | 73.62 |
| ATOM | 1032 | NH1 | ARG | 274 | 42.453 | 41.901 | 66.728 | 1.00 | 74.54 |
| ATOM | 1033 | NH2 | ARG | 274 | 40.708 | 41.388 | 68.136 | 1.00 | 73.76 |
| ATOM | 1034 | C | ARG | 274 | 41.637 | 36.548 | 62.347 | 1.00 | 42.27 |
| ATOM | 1035 | O | ARG | 274 | 40.450 | 36.290 | 62.522 | 1.00 | 37.56 |
| ATOM | 1036 | N | GLN | 275 | 42.119 | 37.088 | 61.223 | 1.00 | 46.69 |
| ATOM | 1037 | CA | GLN | 275 | 41.280 | 37.437 | 60.067 | 1.00 | 45.79 |
| ATOM | 1038 | CB | GLN | 275 | 42.112 | 38.108 | 58.971 | 1.00 | 48.14 |
| ATOM | 1039 | CG | GLN | 275 | 43.044 | 39.194 | 59.457 | 1.00 | 57.45 |
| ATOM | 1040 | CD | GLN | 275 | 42.321 | 40.315 | 60.168 | 1.00 | 64.73 |
| ATOM | 1041 | OE1 | GLN | 275 | 41.583 | 40.085 | 61.135 | 1.00 | 66.02 |
| ATOM | 1042 | NE2 | GLN | 275 | 42.535 | 41.544 | 59.700 | 1.00 | 67.93 |
| ATOM | 1043 | C | GLN | 275 | 40.708 | 36.148 | 59.502 | 1.00 | 44.45 |
| ATOM | 1044 | O | GLN | 275 | 39.497 | 36.006 | 59.343 | 1.00 | 45.72 |
| ATOM | 1045 | N | GLN | 276 | 41.601 | 35.214 | 59.186 | 1.00 | 42.91 |
| ATOM | 1046 | CA | GLN | 276 | 41.200 | 33.912 | 58.653 | 1.00 | 42.79 |

69

| | | | | | | | | |
|---|---|---|---|---|---|---|---|---|
| ATOM | 1047 | CB | GLN | 276 | 42.409 | 32.991 | 58.602 | 1.00 44.87 |
| ATOM | 1048 | CG | GLN | 276 | 43.505 | 32.522 | 57.697 | 1.00 50.88 |
| ATOM | 1049 | CD | GLN | 276 | 44.818 | 32.789 | 57.871 | 1.00 56.17 |
| ATOM | 1050 | OE1 | GLN | 276 | 45.362 | 32.726 | 58.974 | 1.00 56.88 |
| ATOM | 1051 | NE2 | GLN | 276 | 45.344 | 32.240 | 56.778 | 1.00 58.75 |
| ATOM | 1052 | C | GLN | 276 | 40.115 | 33.359 | 59.557 | 1.00 40.96 |
| ATOM | 1053 | O | GLN | 276 | 39.169 | 32.729 | 59.090 | 1.00 36.31 |
| ATOM | 1054 | N | LEU | 277 | 40.245 | 33.609 | 60.857 | 1.00 42.71 |
| ATOM | 1055 | CA | LEU | 277 | 39.247 | 33.143 | 61.809 | 1.00 44.26 |
| ATOM | 1056 | CB | LEU | 277 | 39.757 | 33.285 | 63.243 | 1.00 43.55 |
| ATOM | 1057 | CG | LEU | 277 | 40.689 | 32.147 | 63.673 | 1.00 43.77 |
| ATOM | 1058 | CD1 | LEU | 277 | 41.258 | 32.409 | 65.063 | 1.00 44.35 |
| ATOM | 1059 | CD2 | LEU | 277 | 39.905 | 30.844 | 63.644 | 1.00 39.07 |
| ATOM | 1060 | C | LEU | 277 | 37.926 | 33.878 | 61.636 | 1.00 43.83 |
| ATOM | 1061 | O | LEU | 277 | 36.860 | 33.284 | 61.819 | 1.00 43.53 |
| ATOM | 1062 | N | LYS | 278 | 37.994 | 35.162 | 61.284 | 1.00 43.08 |
| ATOM | 1063 | CA | LYS | 278 | 36.787 | 35.955 | 61.053 | 1.00 44.18 |
| ATOM | 1064 | CB | LYS | 278 | 37.125 | 37.435 | 60.859 | 1.00 48.32 |
| ATOM | 1065 | CG | LYS | 278 | 37.738 | 38.133 | 62.064 | 1.00 55.31 |
| ATOM | 1066 | CD | LYS | 278 | 38.023 | 39.605 | 61.748 | 1.00 59.91 |
| ATOM | 1067 | CE | LYS | 278 | 38.650 | 40.335 | 62.929 | 1.00 63.40 |
| ATOM | 1068 | NZ | LYS | 278 | 38.923 | 41.764 | 62.608 | 1.00 64.87 |
| ATOM | 1069 | C | LYS | 278 | 36.101 | 35.430 | 59.790 | 1.00 42.39 |
| ATOM | 1070 | O | LYS | 278 | 34.877 | 35.294 | 59.752 | 1.00 39.17 |
| ATOM | 1071 | N | LYS | 279 | 36.898 | 35.136 | 58.762 | 1.00 39.67 |
| ATOM | 1072 | CA | LYS | 279 | 36.364 | 34.609 | 57.510 | 1.00 38.21 |
| ATOM | 1073 | CB | LYS | 279 | 37.477 | 34.344 | 56.491 | 1.00 36.85 |
| ATOM | 1074 | CG | LYS | 279 | 38.122 | 34.585 | 55.905 | 1.00 41.29 |
| ATOM | 1075 | CD | LYS | 279 | 39.035 | 35.203 | 54.742 | 1.00 48.66 |
| ATOM | 1076 | CE | LYS | 279 | 39.588 | 36.420 | 53.993 | 1.00 48.48 |
| ATOM | 1077 | NZ | LYS | 279 | 40.305 | 36.032 | 52.725 | 1.00 45.47 |
| ATOM | 1078 | C | LYS | 279 | 35.604 | 33.315 | 57.756 | 1.00 37.99 |
| ATOM | 1079 | O | LYS | 279 | 34.478 | 33.152 | 57.281 | 1.00 39.89 |
| ATOM | 1080 | N | LEU | 280 | 36.217 | 32.392 | 58.492 | 1.00 36.65 |
| ATOM | 1081 | CA | LEU | 280 | 35.560 | 31.126 | 58.776 | 1.00 37.27 |
| ATOM | 1082 | CB | LEU | 280 | 36.429 | 30.236 | 59.658 | 1.00 32.83 |
| ATOM | 1083 | CG | LEU | 280 | 37.680 | 29.660 | 58.998 | 1.00 32.26 |
| ATOM | 1084 | CD1 | LEU | 280 | 38.306 | 28.622 | 59.912 | 1.00 32.06 |
| ATOM | 1085 | CD2 | LEU | 280 | 37.312 | 29.009 | 57.694 | 1.00 27.52 |
| ATOM | 1086 | C | LEU | 280 | 34.214 | 31.336 | 59.440 | 1.00 39.68 |
| ATOM | 1087 | O | LEU | 280 | 33.234 | 30.695 | 59.080 | 1.00 39.84 |
| ATOM | 1088 | N | GLU | 281 | 34.147 | 32.230 | 60.415 | 1.00 44.46 |
| ATOM | 1089 | CA | GLU | 281 | 32.866 | 32.449 | 61.048 | 1.00 50.60 |
| ATOM | 1090 | CB | GLU | 281 | 32.990 | 33.420 | 62.231 | 1.00 51.66 |
| ATOM | 1091 | CG | GLU | 281 | 33.699 | 32.784 | 63.431 | 1.00 58.50 |
| ATOM | 1092 | CD | GLU | 281 | 33.557 | 33.580 | 64.719 | 1.00 61.34 |
| ATOM | 1093 | OE1 | GLU | 281 | 32.405 | 33.807 | 65.148 | 1.00 62.78 |
| ATOM | 1094 | OE2 | GLU | 281 | 34.593 | 33.967 | 65.309 | 1.00 61.12 |
| ATOM | 1095 | C | GLU | 281 | 31.874 | 32.947 | 60.006 | 1.00 52.45 |
| ATOM | 1096 | O | GLU | 281 | 30.705 | 32.561 | 60.016 | 1.00 50.47 |
| ATOM | 1097 | N | GLU | 282 | 32.347 | 33.775 | 59.080 | 1.00 57.39 |
| ATOM | 1098 | CA | GLU | 282 | 31.466 | 34.291 | 58.040 | 1.00 59.19 |
| ATOM | 1099 | CB | GLU | 282 | 32.212 | 35.274 | 57.121 | 1.00 61.86 |
| ATOM | 1100 | CG | GLU | 282 | 32.548 | 35.621 | 57.797 | 1.00 69.91 |
| ATOM | 1101 | CD | GLU | 282 | 33.182 | 37.649 | 56.851 | 1.00 71.52 |
| ATOM | 1102 | OE1 | GLU | 282 | 32.556 | 37.988 | 55.822 | 1.00 71.14 |
| ATOM | 1103 | OE2 | GLU | 282 | 34.302 | 38.127 | 57.143 | 1.00 70.65 |
| ATOM | 1104 | C | GLU | 282 | 30.843 | 33.160 | 57.226 | 1.00 57.33 |
| ATOM | 1105 | O | GLU | 282 | 29.708 | 33.284 | 56.765 | 1.00 57.47 |
| ATOM | 1106 | N | LEU | 283 | 31.568 | 32.053 | 57.067 | 1.00 54.00 |
| ATOM | 1107 | CA | LEU | 283 | 31.044 | 30.925 | 56.309 | 1.00 51.80 |
| ATOM | 1108 | CB | LEU | 283 | 32.142 | 29.941 | 55.909 | 1.00 49.82 |
| ATOM | 1109 | CG | LEU | 283 | 33.306 | 30.354 | 55.013 | 1.00 52.56 |
| ATOM | 1110 | CD1 | LEU | 283 | 33.997 | 29.076 | 54.546 | 1.00 49.11 |
| ATOM | 1111 | CD2 | LEU | 283 | 32.820 | 31.144 | 53.806 | 1.00 51.58 |
| ATOM | 1112 | C | LEU | 283 | 29.988 | 30.153 | 57.071 | 1.00 53.49 |
| ATOM | 1113 | O | LEU | 283 | 29.058 | 29.630 | 56.466 | 1.00 55.33 |
| ATOM | 1114 | N | GLU | 284 | 30.118 | 30.059 | 58.391 | 1.00 55.71 |
| ATOM | 1115 | CA | GLU | 284 | 29.120 | 29.308 | 59.144 | 1.00 55.38 |
| ATOM | 1116 | CB | GLU | 284 | 29.569 | 29.046 | 60.583 | 1.00 54.03 |

70

```
ATOM   1117  CG   GLU   284      29.444  30.227  61.512  1.00 59.81
ATOM   1118  CD   GLU   284      29.762  29.857  62.947  1.00 62.29
ATOM   1119  OE1  GLU   284      29.112  28.927  63.477  1.00 59.90
ATOM   1120  OE2  GLU   284      30.657  30.497  63.542  1.00 61.42
ATOM   1121  C    GLU   284      27.798  30.064  59.139  1.00 55.09
ATOM   1122  O    GLU   284      26.736  29.454  59.110  1.00 54.36
ATOM   1123  N    GLN   285      27.854  31.391  59.166  1.00 55.63
ATOM   1124  CA   GLN   285      26.625  32.169  59.129  1.00 58.23
ATOM   1125  CB   GLN   285      26.913  33.666  59.290  1.00 60.15
ATOM   1126  CG   GLN   285      27.279  34.068  60.718  1.00 67.28
ATOM   1127  CD   GLN   285      27.480  35.571  60.880  1.00 74.12
ATOM   1128  OE1  GLN   285      26.594  36.366  60.565  1.00 74.60
ATOM   1129  NE2  GLN   285      28.647  35.963  61.384  1.00 78.26
ATOM   1130  C    GLN   285      25.909  31.895  57.810  1.00 57.70
ATOM   1131  O    GLN   285      24.677  31.871  57.755  1.00 57.35
ATOM   1132  N    LYS   286      26.685  31.684  56.750  1.00 56.09
ATOM   1133  CA   LYS   286      26.112  31.376  55.444  1.00 54.68
ATOM   1134  CB   LYS   286      27.113  31.647  54.314  1.00 54.58
ATOM   1135  CG   LYS   286      27.448  33.114  54.106  1.00 55.54
ATOM   1136  CD   LYS   286      28.496  33.300  53.018  1.00 56.56
ATOM   1137  CE   LYS   286      28.886  34.766  52.884  1.00 57.05
ATOM   1138  NZ   LYS   286      29.992  34.965  51.912  1.00 57.24
ATOM   1139  C    LYS   286      25.717  29.910  55.418  1.00 53.45
ATOM   1140  O    LYS   286      24.761  29.535  54.751  1.00 55.29
ATOM   1141  N    TYR   287      26.453  29.079  56.146  1.00 54.61
ATOM   1142  CA   TYR   287      26.146  27.656  56.189  1.00 57.52
ATOM   1143  CB   TYR   287      26.581  26.985  54.882  1.00 54.70
ATOM   1144  CG   TYR   287      26.311  25.501  54.864  1.00 54.09
ATOM   1145  CD1  TYR   287      25.036  25.011  55.138  1.00 51.95
ATOM   1146  CE1  TYR   287      24.786  23.652  55.177  1.00 54.94
ATOM   1147  CD2  TYR   287      27.335  24.585  54.617  1.00 52.31
ATOM   1148  CE2  TYR   287      27.096  23.219  54.653  1.00 53.29
ATOM   1149  CZ   TYR   287      25.817  22.759  54.939  1.00 56.41
ATOM   1150  OH   TYR   287      25.567  21.410  55.031  1.00 58.71
ATOM   1151  C    TYR   287      26.770  26.918  57.375  1.00 60.67
ATOM   1152  O    TYR   287      27.965  27.054  57.650  1.00 61.53
ATOM   1153  N    THR   288      25.948  26.128  58.066  1.00 61.23
ATOM   1154  CA   THR   288      26.400  25.357  59.220  1.00 61.97
ATOM   1155  CB   THR   288      26.030  26.047  60.530  1.00 59.99
ATOM   1156  OG1  THR   288      26.420  27.419  60.460  1.00 65.21
ATOM   1157  CG2  THR   288      26.763  25.395  61.696  1.00 62.23
ATOM   1158  C    THR   288      25.762  23.973  59.223  1.00 61.64
ATOM   1159  O    THR   288      25.033  23.612  58.298  1.00 60.84
ATOM   1160  N    TYR   289      26.037  23.201  60.271  1.00 61.94
ATOM   1161  CA   TYR   289      25.490  21.861  60.377  1.00 61.03
ATOM   1162  CB   TYR   289      25.773  21.100  59.078  1.00 54.72
ATOM   1163  CG   TYR   289      27.233  21.019  58.705  1.00 51.15
ATOM   1164  CD1  TYR   289      28.032  19.969  59.153  1.00 51.78
ATOM   1165  CE1  TYR   289      29.377  19.890  58.805  1.00 51.28
ATOM   1166  CD2  TYR   289      27.820  21.994  57.901  1.00 48.79
ATOM   1167  CE2  TYR   289      29.162  21.926  57.551  1.00 47.85
ATOM   1168  CZ   TYR   289      29.932  20.869  58.003  1.00 50.10
ATOM   1169  OH   TYR   289      31.255  20.778  57.637  1.00 51.14
ATOM   1170  C    TYR   289      26.023  21.101  61.584  1.00 63.74
ATOM   1171  O    TYR   289      27.117  21.369  62.072  1.00 62.92
ATOM   1172  N    GLU   290      25.217  20.153  62.051  1.00 69.67
ATOM   1173  CA   GLU   290      25.511  19.309  63.209  1.00 75.22
ATOM   1174  CB   GLU   290      24.869  17.930  63.009  1.00 79.97
ATOM   1175  CG   GLU   290      23.346  17.970  63.116  1.00 89.27
ATOM   1176  CD   GLU   290      22.675  16.642  62.804  1.00 93.57
ATOM   1177  OE1  GLU   290      23.020  15.623  63.446  1.00 95.68
ATOM   1178  OE2  GLU   290      21.790  16.627  61.918  1.00 94.24
ATOM   1179  C    GLU   290      26.961  19.137  63.655  1.00 73.60
ATOM   1180  O    GLU   290      27.287  19.425  64.809  1.00 74.26
ATOM   1181  N    HIS   291      27.826  18.660  62.768  1.00 71.52
ATOM   1182  CA   HIS   291      29.218  18.458  63.146  1.00 71.29
ATOM   1183  CB   HIS   291      29.601  16.994  62.972  1.00 73.52
ATOM   1184  CG   HIS   291      28.672  16.061  63.673  1.00 75.86
ATOM   1185  CD2  HIS   291      28.025  14.952  63.245  1.00 76.81
ATOM   1186  ND1  HIS   291      28.285  16.251  64.982  1.00 77.44
```

| | | | | | | | | |
|---|---|---|---|---|---|---|---|---|
| ATOM | 1187 | CE1 | HIS | 291 | 27.438 | 15.300 | 65.329 | 1.00 79.81 |
| ATOM | 1188 | NE2 | HIS | 291 | 27.263 | 14.499 | 64.293 | 1.00 80.07 |
| ATOM | 1189 | C | HIS | 291 | 30.153 | 19.354 | 62.368 | 1.00 69.94 |
| ATOM | 1190 | O | HIS | 291 | 31.217 | 18.939 | 61.896 | 1.00 68.71 |
| ATOM | 1191 | N | ASP | 292 | 29.725 | 20.601 | 62.244 | 1.00 67.87 |
| ATOM | 1192 | CA | ASP | 292 | 30.486 | 21.622 | 61.556 | 1.00 64.42 |
| ATOM | 1193 | CB | ASP | 292 | 29.566 | 22.810 | 61.259 | 1.00 65.32 |
| ATOM | 1194 | CG | ASP | 292 | 30.320 | 24.045 | 60.862 | 1.00 67.16 |
| ATOM | 1195 | OD1 | ASP | 292 | 31.349 | 23.910 | 60.168 | 1.00 69.00 |
| ATOM | 1196 | OD2 | ASP | 292 | 29.869 | 25.151 | 61.227 | 1.00 67.27 |
| ATOM | 1197 | C | ASP | 292 | 31.663 | 22.018 | 62.445 | 1.00 59.74 |
| ATOM | 1198 | O | ASP | 292 | 31.490 | 22.672 | 63.475 | 1.00 56.46 |
| ATOM | 1199 | N | PRO | 293 | 32.880 | 21.602 | 62.054 | 1.00 55.91 |
| ATOM | 1200 | CD | PRO | 293 | 33.162 | 20.835 | 60.832 | 1.00 54.69 |
| ATOM | 1201 | CA | PRO | 293 | 34.137 | 21.866 | 62.759 | 1.00 56.99 |
| ATOM | 1202 | CB | PRO | 293 | 35.178 | 21.236 | 61.830 | 1.00 55.86 |
| ATOM | 1203 | CG | PRO | 293 | 34.525 | 21.368 | 60.473 | 1.00 55.06 |
| ATOM | 1204 | C | PRO | 293 | 34.382 | 23.348 | 62.976 | 1.00 57.25 |
| ATOM | 1205 | O | PRO | 293 | 34.892 | 23.777 | 64.014 | 1.00 59.39 |
| ATOM | 1206 | N | ILE | 294 | 33.999 | 24.127 | 61.978 | 1.00 55.40 |
| ATOM | 1207 | CA | ILE | 294 | 34.170 | 25.564 | 62.013 | 1.00 52.29 |
| ATOM | 1208 | CB | ILE | 294 | 33.732 | 26.162 | 60.643 | 1.00 51.13 |
| ATOM | 1209 | CG2 | ILE | 294 | 32.303 | 26.664 | 60.710 | 1.00 54.38 |
| ATOM | 1210 | CG1 | ILE | 294 | 34.642 | 27.314 | 60.247 | 1.00 46.91 |
| ATOM | 1211 | CD1 | ILE | 294 | 34.387 | 27.787 | 58.842 | 1.00 47.38 |
| ATOM | 1212 | C | ILE | 294 | 33.351 | 26.137 | 63.176 | 1.00 49.76 |
| ATOM | 1213 | O | ILE | 294 | 33.360 | 27.334 | 63.420 | 1.00 50.69 |
| ATOM | 1214 | N | THR | 295 | 32.653 | 25.267 | 63.899 | 1.00 49.07 |
| ATOM | 1215 | CA | THR | 295 | 31.833 | 25.693 | 65.034 | 1.00 51.16 |
| ATOM | 1216 | CB | THR | 295 | 30.367 | 25.245 | 64.871 | 1.00 50.59 |
| ATOM | 1217 | OG1 | THR | 295 | 29.822 | 25.807 | 63.674 | 1.00 51.83 |
| ATOM | 1218 | CG2 | THR | 295 | 29.541 | 25.720 | 66.048 | 1.00 48.78 |
| ATOM | 1219 | C | THR | 295 | 32.346 | 25.157 | 66.377 | 1.00 49.90 |
| ATOM | 1220 | O | THR | 295 | 32.281 | 25.844 | 67.393 | 1.00 48.03 |
| ATOM | 1221 | N | LYS | 296 | 32.840 | 23.926 | 66.382 | 1.00 49.13 |
| ATOM | 1222 | CA | LYS | 296 | 33.360 | 23.338 | 67.598 | 1.00 51.93 |
| ATOM | 1223 | CB | LYS | 296 | 33.472 | 21.816 | 67.438 | 1.00 52.82 |
| ATOM | 1224 | CG | LYS | 296 | 32.104 | 21.166 | 67.149 | 1.00 59.11 |
| ATOM | 1225 | CD | LYS | 296 | 32.114 | 19.624 | 67.069 | 1.00 55.65 |
| ATOM | 1226 | CE | LYS | 296 | 30.687 | 19.073 | 66.849 | 1.00 45.24 |
| ATOM | 1227 | NZ | LYS | 296 | 30.590 | 17.586 | 66.866 | 1.00 37.02 |
| ATOM | 1228 | C | LYS | 296 | 34.714 | 23.983 | 67.884 | 1.00 55.06 |
| ATOM | 1229 | O | LYS | 296 | 34.872 | 24.678 | 68.893 | 1.00 56.63 |
| ATOM | 1230 | N | ASN | 297 | 35.681 | 23.780 | 66.992 | 1.00 53.08 |
| ATOM | 1231 | CA | ASN | 297 | 37.008 | 24.370 | 67.168 | 1.00 52.15 |
| ATOM | 1232 | CB | ASN | 297 | 37.945 | 23.877 | 66.071 | 1.00 53.86 |
| ATOM | 1233 | CG | ASN | 297 | 38.093 | 22.375 | 66.061 | 1.00 55.78 |
| ATOM | 1234 | OD1 | ASN | 297 | 38.561 | 21.780 | 67.029 | 1.00 61.09 |
| ATOM | 1235 | ND2 | ASN | 297 | 37.699 | 21.749 | 64.958 | 1.00 59.41 |
| ATOM | 1236 | C | ASN | 297 | 36.920 | 25.902 | 67.110 | 1.00 51.83 |
| ATOM | 1237 | O | ASN | 297 | 37.849 | 26.621 | 67.487 | 1.00 50.24 |
| ATOM | 1238 | N | LYS | 298 | 35.787 | 26.381 | 66.618 | 1.00 49.72 |
| ATOM | 1239 | CA | LYS | 298 | 35.510 | 27.801 | 66.471 | 1.00 47.90 |
| ATOM | 1240 | CB | LYS | 298 | 33.997 | 27.986 | 66.378 | 1.00 48.66 |
| ATOM | 1241 | CG | LYS | 298 | 33.485 | 29.397 | 66.261 | 1.00 44.51 |
| ATOM | 1242 | CD | LYS | 298 | 31.964 | 29.349 | 66.248 | 1.00 45.88 |
| ATOM | 1243 | CE | LYS | 298 | 31.341 | 30.732 | 66.294 | 1.00 47.28 |
| ATOM | 1244 | NZ | LYS | 298 | 29.853 | 30.642 | 66.383 | 1.00 47.12 |
| ATOM | 1245 | C | LYS | 298 | 36.074 | 28.640 | 67.608 | 1.00 47.79 |
| ATOM | 1246 | O | LYS | 298 | 37.046 | 29.368 | 67.424 | 1.00 42.57 |
| ATOM | 1247 | N | GLN | 299 | 35.464 | 28.520 | 68.785 | 1.00 51.79 |
| ATOM | 1248 | CA | GLN | 299 | 35.876 | 29.291 | 69.964 | 1.00 51.88 |
| ATOM | 1249 | CB | GLN | 299 | 34.891 | 29.080 | 71.100 | 1.00 51.10 |
| ATOM | 1250 | CG | GLN | 299 | 35.163 | 29.993 | 72.270 | 1.00 50.56 |
| ATOM | 1251 | CD | GLN | 299 | 34.856 | 31.435 | 71.947 | 1.00 50.22 |
| ATOM | 1252 | OE1 | GLN | 299 | 33.708 | 31.786 | 71.666 | 1.00 53.87 |
| ATOM | 1253 | NE2 | GLN | 299 | 35.875 | 32.281 | 71.978 | 1.00 51.50 |
| ATOM | 1254 | C | GLN | 299 | 37.280 | 29.015 | 70.502 | 1.00 49.96 |
| ATOM | 1255 | O | GLN | 299 | 38.013 | 29.939 | 70.835 | 1.00 49.68 |
| ATOM | 1256 | N | VAL | 300 | 37.642 | 27.745 | 70.618 | 1.00 47.84 |

72

| ATOM | 1257 | CA | VAL | 300 | 38.963 | 27.384 | 71.113 | 1.00 | 44.58 |
| ATOM | 1258 | CB | VAL | 300 | 39.241 | 25.886 | 70.905 | 1.00 | 45.76 |
| ATOM | 1259 | CG1 | VAL | 300 | 40.581 | 25.526 | 71.508 | 1.00 | 48.32 |
| ATOM | 1260 | CG2 | VAL | 300 | 38.131 | 25.057 | 71.508 | 1.00 | 49.81 |
| ATOM | 1261 | C | VAL | 300 | 40.073 | 28.154 | 70.394 | 1.00 | 41.93 |
| ATOM | 1262 | O | VAL | 300 | 40.872 | 28.844 | 71.019 | 1.00 | 38.98 |
| ATOM | 1263 | N | LEU | 301 | 40.104 | 28.015 | 69.072 | 1.00 | 41.05 |
| ATOM | 1264 | CA | LEU | 301 | 41.105 | 28.647 | 68.221 | 1.00 | 38.62 |
| ATOM | 1265 | CB | LEU | 301 | 40.837 | 28.306 | 66.757 | 1.00 | 43.99 |
| ATOM | 1266 | CG | LEU | 301 | 40.949 | 26.839 | 66.352 | 1.00 | 49.80 |
| ATOM | 1267 | CD1 | LEU | 301 | 40.626 | 26.698 | 64.867 | 1.00 | 53.48 |
| ATOM | 1268 | CD2 | LEU | 301 | 42.360 | 26.337 | 66.652 | 1.00 | 49.99 |
| ATOM | 1269 | C | LEU | 301 | 41.215 | 30.151 | 68.348 | 1.00 | 35.75 |
| ATOM | 1270 | O | LEU | 301 | 42.310 | 30.707 | 68.272 | 1.00 | 34.40 |
| ATOM | 1271 | N | TRP | 302 | 40.087 | 30.822 | 68.518 | 1.00 | 34.20 |
| ATOM | 1272 | CA | TRP | 302 | 40.140 | 32.267 | 68.633 | 1.00 | 35.36 |
| ATOM | 1273 | CB | TRP | 302 | 38.740 | 32.862 | 68.754 | 1.00 | 39.06 |
| ATOM | 1274 | CG | TRP | 302 | 38.714 | 34.283 | 68.317 | 1.00 | 48.72 |
| ATOM | 1275 | CD2 | TRP | 302 | 38.762 | 35.437 | 69.158 | 1.00 | 52.89 |
| ATOM | 1276 | CE2 | TRP | 302 | 38.824 | 36.571 | 68.313 | 1.00 | 56.67 |
| ATOM | 1277 | CE3 | TRP | 302 | 38.763 | 35.627 | 70.545 | 1.00 | 57.89 |
| ATOM | 1278 | CD1 | TRP | 302 | 38.743 | 34.747 | 67.026 | 1.00 | 51.22 |
| ATOM | 1279 | NE1 | TRP | 302 | 38.809 | 36.120 | 67.016 | 1.00 | 54.53 |
| ATOM | 1280 | CZ2 | TRP | 302 | 38.885 | 37.873 | 68.809 | 1.00 | 59.53 |
| ATOM | 1281 | CZ3 | TRP | 302 | 38.825 | 36.922 | 71.041 | 1.00 | 62.01 |
| ATOM | 1282 | CH2 | TRP | 302 | 38.884 | 38.030 | 70.172 | 1.00 | 63.70 |
| ATOM | 1283 | C | TRP | 302 | 40.948 | 32.611 | 69.880 | 1.00 | 32.82 |
| ATOM | 1284 | O | TRP | 302 | 42.032 | 33.203 | 69.791 | 1.00 | 32.64 |
| ATOM | 1285 | N | ASP | 303 | 40.414 | 32.216 | 71.036 | 1.00 | 28.45 |
| ATOM | 1286 | CA | ASP | 303 | 41.055 | 32.466 | 72.316 | 1.00 | 25.59 |
| ATOM | 1287 | CB | ASP | 303 | 40.352 | 31.705 | 73.433 | 1.00 | 26.25 |
| ATOM | 1288 | CG | ASP | 303 | 38.930 | 32.159 | 73.642 | 1.00 | 29.72 |
| ATOM | 1289 | OD1 | ASP | 303 | 38.665 | 33.374 | 73.525 | 1.00 | 36.14 |
| ATOM | 1290 | OD2 | ASP | 303 | 38.079 | 31.307 | 73.958 | 1.00 | 35.81 |
| ATOM | 1291 | C | ASP | 303 | 42.520 | 32.096 | 72.330 | 1.00 | 21.28 |
| ATOM | 1292 | O | ASP | 303 | 43.350 | 32.841 | 72.829 | 1.00 | 19.18 |
| ATOM | 1293 | N | ARG | 304 | 42.839 | 30.936 | 71.788 | 1.00 | 20.05 |
| ATOM | 1294 | CA | ARG | 304 | 44.218 | 30.509 | 71.759 | 1.00 | 23.99 |
| ATOM | 1295 | CB | ARG | 304 | 44.328 | 29.113 | 71.160 | 1.00 | 22.62 |
| ATOM | 1296 | CG | ARG | 304 | 45.729 | 28.568 | 71.248 | 1.00 | 31.09 |
| ATOM | 1297 | CD | ARG | 304 | 45.848 | 27.199 | 70.628 | 1.00 | 31.88 |
| ATOM | 1298 | NE | ARG | 304 | 47.242 | 26.781 | 70.618 | 1.00 | 36.98 |
| ATOM | 1299 | CZ | ARG | 304 | 47.702 | 25.724 | 69.963 | 1.00 | 37.21 |
| ATOM | 1300 | NH1 | ARG | 304 | 46.878 | 24.967 | 69.253 | 1.00 | 36.05 |
| ATOM | 1301 | NH2 | ARG | 304 | 48.993 | 25.431 | 70.017 | 1.00 | 41.44 |
| ATOM | 1302 | C | ARG | 304 | 45.088 | 31.489 | 70.967 | 1.00 | 28.59 |
| ATOM | 1303 | O | ARG | 304 | 46.292 | 31.592 | 71.214 | 1.00 | 31.48 |
| ATOM | 1304 | N | THR | 305 | 44.486 | 32.215 | 70.022 | 1.00 | 29.81 |
| ATOM | 1305 | CA | THR | 305 | 45.242 | 33.178 | 69.217 | 1.00 | 24.21 |
| ATOM | 1306 | CB | THR | 305 | 44.622 | 33.387 | 67.812 | 1.00 | 24.88 |
| ATOM | 1307 | OG1 | THR | 305 | 44.696 | 32.162 | 67.070 | 1.00 | 27.85 |
| ATOM | 1308 | CG2 | THR | 305 | 45.388 | 34.454 | 67.046 | 1.00 | 25.54 |
| ATOM | 1309 | C | THR | 305 | 45.352 | 34.516 | 69.918 | 1.00 | 18.37 |
| ATOM | 1310 | O | THR | 305 | 46.128 | 35.367 | 69.515 | 1.00 | 16.94 |
| ATOM | 1311 | N | PHE | 306 | 44.570 | 34.708 | 70.970 | 1.00 | 15.94 |
| ATOM | 1312 | CA | PHE | 306 | 44.657 | 35.946 | 71.717 | 1.00 | 12.60 |
| ATOM | 1313 | CB | PHE | 306 | 43.398 | 36.166 | 72.543 | 1.00 | 15.38 |
| ATOM | 1314 | CG | PHE | 306 | 43.445 | 37.410 | 73.373 | 1.00 | 21.76 |
| ATOM | 1315 | CD1 | PHE | 306 | 43.363 | 38.660 | 72.775 | 1.00 | 20.33 |
| ATOM | 1316 | CD2 | PHE | 306 | 43.650 | 37.334 | 74.755 | 1.00 | 24.10 |
| ATOM | 1317 | CE1 | PHE | 306 | 43.489 | 39.812 | 73.535 | 1.00 | 23.91 |
| ATOM | 1318 | CE2 | PHE | 306 | 43.778 | 38.479 | 75.523 | 1.00 | 23.52 |
| ATOM | 1319 | CZ | PHE | 306 | 43.699 | 39.723 | 74.912 | 1.00 | 29.73 |
| ATOM | 1320 | C | PHE | 306 | 45.873 | 35.789 | 72.640 | 1.00 | 17.73 |
| ATOM | 1321 | O | PHE | 306 | 46.724 | 36.690 | 72.739 | 1.00 | 16.46 |
| ATOM | 1322 | N | SER | 307 | 45.959 | 34.631 | 73.296 | 1.00 | 15.11 |
| ATOM | 1323 | CA | SER | 307 | 47.074 | 34.328 | 74.184 | 1.00 | 19.06 |
| ATOM | 1324 | CB | SER | 307 | 46.977 | 32.893 | 74.684 | 1.00 | 20.89 |
| ATOM | 1325 | OG | SER | 307 | 45.818 | 32.711 | 75.468 | 1.00 | 36.23 |
| ATOM | 1326 | C | SER | 307 | 48.429 | 34.514 | 73.500 | 1.00 | 22.29 |

73

```
ATOM   1327  O    SER  307      49.188  35.426  73.850  1.00 26.36
ATOM   1328  N    LEU  308      48.739  33.636  72.540  1.00 20.60
ATOM   1329  CA   LEU  308      50.002  33.720  71.820  1.00 15.77
ATOM   1330  CB   LEU  308      49.974  32.931  70.516  1.00 15.80
ATOM   1331  CG   LEU  308      50.096  31.414  70.376  1.00 21.98
ATOM   1332  CD1  LEU  308      51.462  30.972  70.859  1.00 26.62
ATOM   1333  CD2  LEU  308      48.985  30.720  71.122  1.00 28.90
ATOM   1334  C    LEU  308      50.291  35.159  71.466  1.00 18.96
ATOM   1335  O    LEU  308      51.421  35.625  71.624  1.00 22.93
ATOM   1336  N    PHE  309      49.270  35.866  70.989  1.00 16.59
ATOM   1337  CA   PHE  309      49.452  37.250  70.576  1.00 20.11
ATOM   1338  CB   PHE  309      48.283  37.723  69.722  1.00 19.00
ATOM   1339  CG   PHE  309      48.475  39.100  69.176  1.00 15.63
ATOM   1340  CD1  PHE  309      49.401  39.330  68.165  1.00 17.24
ATOM   1341  CD2  PHE  309      47.794  40.185  69.732  1.00 12.36
ATOM   1342  CE1  PHE  309      49.654  40.629  67.714  1.00 16.15
ATOM   1343  CE2  PHE  309      48.033  41.477  69.294  1.00 15.43
ATOM   1344  CZ   PHE  309      48.968  41.703  68.283  1.00 17.87
ATOM   1345  C    PHE  309      49.642  38.213  71.736  1.00 20.97
ATOM   1346  O    PHE  309      50.449  39.154  71.656  1.00 17.52
ATOM   1347  N    GLN  310      48.890  37.995  72.808  1.00 22.10
ATOM   1348  CA   GLN  310      49.031  38.853  73.984  1.00 23.33
ATOM   1349  CB   GLN  310      48.036  38.480  75.073  1.00 22.77
ATOM   1350  CG   GLN  310      48.283  39.236  76.346  1.00 18.76
ATOM   1351  CD   GLN  310      47.731  38.518  77.540  1.00 23.39
ATOM   1352  OE1  GLN  310      46.525  38.284  77.638  1.00 26.24
ATOM   1353  NE2  GLN  310      48.612  38.149  78.461  1.00 25.99
ATOM   1354  C    GLN  310      50.425  38.656  74.543  1.00 17.79
ATOM   1355  O    GLN  310      51.175  39.598  74.734  1.00 14.86
ATOM   1356  N    GLN  311      50.759  37.404  74.799  1.00 17.15
ATOM   1357  CA   GLN  311      52.059  37.075  75.343  1.00 21.88
ATOM   1358  CB   GLN  311      52.254  35.564  75.334  1.00 18.60
ATOM   1359  CG   GLN  311      53.470  35.125  76.085  1.00 25.56
ATOM   1360  CD   GLN  311      53.565  33.624  76.160  1.00 35.33
ATOM   1361  OE1  GLN  311      53.793  32.945  75.148  1.00 34.54
ATOM   1362  NE2  GLN  311      53.372  33.083  77.365  1.00 36.66
ATOM   1363  C    GLN  311      53.150  37.740  74.529  1.00 21.31
ATOM   1364  O    GLN  311      53.939  38.530  75.052  1.00 20.60
ATOM   1365  N    LEU  312      53.170  37.410  73.241  1.00 25.30
ATOM   1366  CA   LEU  312      54.143  37.935  72.303  1.00 24.96
ATOM   1367  CB   LEU  312      53.801  37.472  70.884  1.00 21.27
ATOM   1368  CG   LEU  312      54.647  38.072  69.752  1.00 24.65
ATOM   1369  CD1  LEU  312      56.075  37.574  69.855  1.00 21.92
ATOM   1370  CD2  LEU  312      54.064  37.688  68.406  1.00 19.02
ATOM   1371  C    LEU  312      54.246  39.457  72.335  1.00 25.75
ATOM   1372  O    LEU  312      55.342  40.003  72.374  1.00 27.98
ATOM   1373  N    ILE  313      53.122  40.158  72.329  1.00 26.58
ATOM   1374  CA   ILE  313      53.212  41.610  72.326  1.00 29.08
ATOM   1375  CB   ILE  313      51.876  42.265  71.982  1.00 32.07
ATOM   1376  CG2  ILE  313      50.801  41.776  72.927  1.00 33.25
ATOM   1377  CG1  ILE  313      52.048  43.786  72.025  1.00 34.12
ATOM   1378  CD1  ILE  313      50.776  44.564  71.868  1.00 44.95
ATOM   1379  C    ILE  313      53.715  42.192  73.637  1.00 25.17
ATOM   1380  O    ILE  313      54.443  43.178  73.644  1.00 25.38
ATOM   1381  N    GLN  314      53.321  41.592  74.751  1.00 26.88
ATOM   1382  CA   GLN  314      53.771  42.077  76.047  1.00 25.48
ATOM   1383  CB   GLN  314      53.015  41.373  77.173  1.00 25.30
ATOM   1384  CG   GLN  314      51.515  41.551  77.083  1.00 29.08
ATOM   1385  CD   GLN  314      50.776  40.922  78.240  1.00 33.89
ATOM   1386  OE1  GLN  314      50.999  39.762  78.581  1.00 37.04
ATOM   1387  NE2  GLN  314      49.871  41.680  78.838  1.00 37.72
ATOM   1388  C    GLN  314      55.270  41.839  76.185  1.00 23.31
ATOM   1389  O    GLN  314      55.992  42.676  76.725  1.00 25.97
ATOM   1390  N    SER  315      55.746  40.704  75.689  1.00 16.45
ATOM   1391  CA   SER  315      57.167  40.416  75.767  1.00 17.76
ATOM   1392  CB   SER  315      57.444  38.960  75.396  1.00 17.64
ATOM   1393  OG   SER  315      56.862  38.069  76.324  1.00 22.55
ATOM   1394  C    SER  315      57.990  41.323  74.859  1.00 19.65
ATOM   1395  O    SER  315      59.136  41.628  75.173  1.00 20.54
ATOM   1396  N    SER  316      57.408  41.756  73.740  1.00 20.68
```

74

| ATOM | 1397 | CA | SER | 316 | 58.107 | 42.613 | 72.775 | 1.00 | 19.70 |
| ATOM | 1398 | CB | SER | 316 | 57.307 | 42.726 | 71.478 | 1.00 | 23.63 |
| ATOM | 1399 | OG | SER | 316 | 56.097 | 43.436 | 71.685 | 1.00 | 27.17 |
| ATOM | 1400 | C | SER | 316 | 58.416 | 44.024 | 73.271 | 1.00 | 19.03 |
| ATOM | 1401 | O | SER | 316 | 59.306 | 44.684 | 72.727 | 1.00 | 17.75 |
| ATOM | 1402 | N | PHE | 317 | 57.661 | 44.488 | 74.270 | 1.00 | 15.52 |
| ATOM | 1403 | CA | PHE | 317 | 57.852 | 45.809 | 74.875 | 1.00 | 12.66 |
| ATOM | 1404 | CB | PHE | 317 | 56.709 | 46.103 | 75.833 | 1.00 | 11.88 |
| ATOM | 1405 | CG | PHE | 317 | 56.647 | 47.528 | 76.302 | 1.00 | 10.16 |
| ATOM | 1406 | CD1 | PHE | 317 | 56.099 | 47.832 | 77.532 | 1.00 | 9.59 |
| ATOM | 1407 | CD2 | PHE | 317 | 57.018 | 48.573 | 75.466 | 1.00 | 6.40 |
| ATOM | 1408 | CE1 | PHE | 317 | 55.916 | 49.158 | 77.917 | 1.00 | 14.26 |
| ATOM | 1409 | CE2 | PHE | 317 | 56.830 | 49.904 | 75.852 | 1.00 | 6.42 |
| ATOM | 1410 | CZ | PHE | 317 | 56.280 | 50.193 | 77.069 | 1.00 | 6.01 |
| ATOM | 1411 | C | PHE | 317 | 59.128 | 45.724 | 75.706 | 1.00 | 14.67 |
| ATOM | 1412 | O | PHE | 317 | 59.147 | 45.043 | 76.728 | 1.00 | 15.55 |
| ATOM | 1413 | N | VAL | 318 | 60.187 | 46.409 | 75.305 | 1.00 | 11.03 |
| ATOM | 1414 | CA | VAL | 318 | 61.417 | 46.321 | 76.080 | 1.00 | 9.10 |
| ATOM | 1415 | CB | VAL | 318 | 62.420 | 45.371 | 75.418 | 1.00 | 5.34 |
| ATOM | 1416 | CG1 | VAL | 318 | 63.001 | 46.020 | 74.172 | 1.00 | 3.09 |
| ATOM | 1417 | CG2 | VAL | 318 | 63.510 | 45.000 | 76.403 | 1.00 | 11.83 |
| ATOM | 1418 | C | VAL | 318 | 62.127 | 47.645 | 76.298 | 1.00 | 10.78 |
| ATOM | 1419 | O | VAL | 318 | 61.901 | 48.628 | 75.592 | 1.00 | 16.70 |
| ATOM | 1420 | N | VAL | 319 | 62.994 | 47.666 | 77.296 | 1.00 | 10.44 |
| ATOM | 1421 | CA | VAL | 319 | 63.754 | 48.862 | 77.585 | 1.00 | 13.74 |
| ATOM | 1422 | CB | VAL | 319 | 64.033 | 48.993 | 79.078 | 1.00 | 14.50 |
| ATOM | 1423 | CG1 | VAL | 319 | 64.956 | 50.162 | 79.326 | 1.00 | 7.96 |
| ATOM | 1424 | CG2 | VAL | 319 | 62.719 | 49.180 | 79.816 | 1.00 | 14.78 |
| ATOM | 1425 | C | VAL | 319 | 65.052 | 48.747 | 76.826 | 1.00 | 14.67 |
| ATOM | 1426 | O | VAL | 319 | 66.021 | 48.203 | 77.329 | 1.00 | 18.28 |
| ATOM | 1427 | N | GLU | 320 | 65.042 | 49.252 | 75.597 | 1.00 | 20.34 |
| ATOM | 1428 | CA | GLU | 320 | 66.199 | 49.221 | 74.721 | 1.00 | 20.70 |
| ATOM | 1429 | CB | GLU | 320 | 65.865 | 49.887 | 73.392 | 1.00 | 23.22 |
| ATOM | 1430 | CG | GLU | 320 | 67.069 | 50.172 | 72.541 | 1.00 | 31.29 |
| ATOM | 1431 | CD | GLU | 320 | 66.689 | 50.487 | 71.123 | 1.00 | 37.84 |
| ATOM | 1432 | OE1 | GLU | 320 | 65.721 | 51.247 | 70.922 | 1.00 | 42.42 |
| ATOM | 1433 | OE2 | GLU | 320 | 67.368 | 49.983 | 70.207 | 1.00 | 41.32 |
| ATOM | 1434 | C | GLU | 320 | 67.411 | 49.871 | 75.348 | 1.00 | 20.66 |
| ATOM | 1435 | O | GLU | 320 | 68.486 | 49.275 | 75.376 | 1.00 | 23.40 |
| ATOM | 1436 | N | ARG | 321 | 67.271 | 51.101 | 75.822 | 1.00 | 18.81 |
| ATOM | 1437 | CA | ARG | 321 | 68.408 | 51.696 | 76.489 | 1.00 | 18.32 |
| ATOM | 1438 | CB | ARG | 321 | 68.967 | 52.911 | 75.743 | 1.00 | 15.82 |
| ATOM | 1439 | CG | ARG | 321 | 70.346 | 53.222 | 76.288 | 1.00 | 31.43 |
| ATOM | 1440 | CD | ARG | 321 | 70.931 | 51.852 | 76.719 | 1.00 | 45.04 |
| ATOM | 1441 | NE | ARG | 321 | 72.152 | 51.849 | 77.519 | 1.00 | 53.48 |
| ATOM | 1442 | CZ | ARG | 321 | 72.499 | 50.832 | 78.308 | 1.00 | 49.21 |
| ATOM | 1443 | NH1 | ARG | 321 | 71.707 | 49.769 | 78.399 | 1.00 | 31.36 |
| ATOM | 1444 | NH2 | ARG | 321 | 73.642 | 50.867 | 78.986 | 1.00 | 51.91 |
| ATOM | 1445 | C | ARG | 321 | 68.092 | 52.053 | 77.937 | 1.00 | 18.19 |
| ATOM | 1446 | O | ARG | 321 | 67.304 | 52.953 | 78.212 | 1.00 | 18.03 |
| ATOM | 1447 | N | GLN | 322 | 68.704 | 51.318 | 78.860 | 1.00 | 13.67 |
| ATOM | 1448 | CA | GLN | 322 | 68.481 | 51.536 | 80.280 | 1.00 | 14.31 |
| ATOM | 1449 | CB | GLN | 322 | 69.454 | 50.698 | 81.104 | 1.00 | 20.99 |
| ATOM | 1450 | CG | GLN | 322 | 69.185 | 49.195 | 81.069 | 1.00 | 19.96 |
| ATOM | 1451 | CD | GLN | 322 | 67.775 | 48.876 | 81.503 | 1.00 | 18.89 |
| ATOM | 1452 | OE1 | GLN | 322 | 67.287 | 49.401 | 82.512 | 1.00 | 17.94 |
| ATOM | 1453 | NE2 | GLN | 322 | 67.110 | 48.010 | 80.753 | 1.00 | 22.92 |
| ATOM | 1454 | C | GLN | 322 | 68.607 | 52.990 | 80.680 | 1.00 | 12.66 |
| ATOM | 1455 | O | GLN | 322 | 69.260 | 53.778 | 79.988 | 1.00 | 15.23 |
| ATOM | 1456 | N | PRO | 323 | 67.983 | 53.368 | 81.812 | 1.00 | 12.52 |
| ATOM | 1457 | CD | PRO | 323 | 67.231 | 52.496 | 82.724 | 1.00 | 13.20 |
| ATOM | 1458 | CA | PRO | 323 | 67.998 | 54.736 | 82.344 | 1.00 | 14.43 |
| ATOM | 1459 | CB | PRO | 323 | 67.310 | 54.582 | 83.692 | 1.00 | 8.87 |
| ATOM | 1460 | CG | PRO | 323 | 66.319 | 53.504 | 83.388 | 1.00 | 15.57 |
| ATOM | 1461 | C | PRO | 323 | 69.434 | 55.141 | 82.483 | 1.00 | 15.26 |
| ATOM | 1462 | O | PRO | 323 | 70.279 | 54.287 | 82.607 | 1.00 | 19.74 |
| ATOM | 1463 | N | CYS | 324 | 69.716 | 56.432 | 82.441 | 1.00 | 18.60 |
| ATOM | 1464 | CA | CYS | 324 | 71.084 | 56.903 | 82.554 | 1.00 | 17.16 |
| ATOM | 1465 | CB | CYS | 324 | 71.928 | 56.293 | 81.438 | 1.00 | 11.98 |
| ATOM | 1466 | SG | CYS | 324 | 73.688 | 56.630 | 81.586 | 1.00 | 25.84 |

75

| ATOM | 1467 | C | CYS | 324 | 71.172 | 58.429 | 82.473 | 1.00 | 18.58 |
| ATOM | 1468 | O | CYS | 324 | 70.306 | 59.086 | 81.881 | 1.00 | 18.19 |
| ATOM | 1469 | N | MET | 325 | 72.208 | 58.989 | 83.096 | 1.00 | 22.00 |
| ATOM | 1470 | CA | MET | 325 | 72.435 | 60.424 | 83.040 | 1.00 | 20.26 |
| ATOM | 1471 | CB | MET | 325 | 73.067 | 60.914 | 84.338 | 1.00 | 12.79 |
| ATOM | 1472 | CG | MET | 325 | 72.170 | 60.670 | 85.512 | 1.00 | 18.48 |
| ATOM | 1473 | SD | MET | 325 | 72.735 | 61.360 | 87.047 | 1.00 | 18.16 |
| ATOM | 1474 | CE | MET | 325 | 72.857 | 63.012 | 86.606 | 1.00 | 26.16 |
| ATOM | 1475 | C | MET | 325 | 73.367 | 60.660 | 81.849 | 1.00 | 21.05 |
| ATOM | 1476 | O | MET | 325 | 74.395 | 60.000 | 81.721 | 1.00 | 24.07 |
| ATOM | 1477 | N | PRO | 326 | 72.994 | 61.579 | 80.941 | 1.00 | 19.98 |
| ATOM | 1478 | CD | PRO | 326 | 71.765 | 62.388 | 80.987 | 1.00 | 22.16 |
| ATOM | 1479 | CA | PRO | 326 | 73.762 | 61.927 | 79.743 | 1.00 | 14.08 |
| ATOM | 1480 | CB | PRO | 326 | 72.919 | 63.025 | 79.123 | 1.00 | 15.91 |
| ATOM | 1481 | CG | PRO | 326 | 71.518 | 62.605 | 79.532 | 1.00 | 21.82 |
| ATOM | 1482 | C | PRO | 326 | 75.172 | 62.387 | 80.045 | 1.00 | 11.07 |
| ATOM | 1483 | O | PRO | 326 | 76.029 | 62.332 | 79.188 | 1.00 | 10.10 |
| ATOM | 1484 | N | THR | 327 | 75.406 | 62.835 | 81.271 | 1.00 | 12.84 |
| ATOM | 1485 | CA | THR | 327 | 76.726 | 63.296 | 81.678 | 1.00 | 16.26 |
| ATOM | 1486 | CB | THR | 327 | 76.633 | 64.321 | 82.850 | 1.00 | 23.95 |
| ATOM | 1487 | OG1 | THR | 327 | 75.784 | 65.415 | 82.486 | 1.00 | 31.77 |
| ATOM | 1488 | CG2 | THR | 327 | 78.013 | 64.872 | 83.187 | 1.00 | 30.49 |
| ATOM | 1489 | C | THR | 327 | 77.545 | 62.107 | 82.168 | 1.00 | 14.38 |
| ATOM | 1490 | O | THR | 327 | 78.727 | 62.235 | 82.469 | 1.00 | 13.07 |
| ATOM | 1491 | N | HIS | 328 | 76.904 | 60.950 | 82.254 | 1.00 | 13.70 |
| ATOM | 1492 | CA | HIS | 328 | 77.551 | 59.738 | 82.746 | 1.00 | 18.04 |
| ATOM | 1493 | CB | HIS | 328 | 77.045 | 59.441 | 84.153 | 1.00 | 16.17 |
| ATOM | 1494 | CG | HIS | 328 | 77.405 | 60.494 | 85.144 | 1.00 | 14.08 |
| ATOM | 1495 | CD2 | HIS | 328 | 76.671 | 61.488 | 85.693 | 1.00 | 17.57 |
| ATOM | 1496 | ND1 | HIS | 328 | 78.690 | 60.657 | 85.614 | 1.00 | 14.41 |
| ATOM | 1497 | CE1 | HIS | 328 | 78.730 | 61.709 | 86.411 | 1.00 | 19.23 |
| ATOM | 1498 | NE2 | HIS | 328 | 77.519 | 62.230 | 86.475 | 1.00 | 19.92 |
| ATOM | 1499 | C | HIS | 328 | 77.288 | 58.538 | 81.857 | 1.00 | 21.79 |
| ATOM | 1500 | O | HIS | 328 | 76.810 | 57.497 | 82.318 | 1.00 | 26.54 |
| ATOM | 1501 | N | PRO | 329 | 77.602 | 58.660 | 80.565 | 1.00 | 23.69 |
| ATOM | 1502 | CD | PRO | 329 | 78.206 | 59.806 | 79.874 | 1.00 | 22.07 |
| ATOM | 1503 | CA | PRO | 329 | 77.388 | 57.568 | 79.617 | 1.00 | 21.25 |
| ATOM | 1504 | CB | PRO | 329 | 78.072 | 58.096 | 78.351 | 1.00 | 26.68 |
| ATOM | 1505 | CG | PRO | 329 | 79.108 | 59.094 | 78.912 | 1.00 | 22.05 |
| ATOM | 1506 | C | PRO | 329 | 77.918 | 56.208 | 80.064 | 1.00 | 15.61 |
| ATOM | 1507 | O | PRO | 329 | 77.415 | 55.182 | 79.624 | 1.00 | 16.90 |
| ATOM | 1508 | N | GLN | 330 | 78.927 | 56.195 | 80.931 | 1.00 | 14.91 |
| ATOM | 1509 | CA | GLN | 330 | 79.480 | 54.928 | 81.405 | 1.00 | 16.77 |
| ATOM | 1510 | CB | GLN | 330 | 81.014 | 54.938 | 81.346 | 1.00 | 23.52 |
| ATOM | 1511 | CG | GLN | 330 | 81.565 | 54.740 | 79.937 | 1.00 | 30.89 |
| ATOM | 1512 | CD | GLN | 330 | 81.024 | 55.765 | 78.973 | 1.00 | 35.36 |
| ATOM | 1513 | OE1 | GLN | 330 | 81.393 | 56.937 | 79.019 | 1.00 | 37.43 |
| ATOM | 1514 | NE2 | GLN | 330 | 80.112 | 55.334 | 78.109 | 1.00 | 39.25 |
| ATOM | 1515 | C | GLN | 330 | 79.039 | 54.502 | 82.790 | 1.00 | 14.39 |
| ATOM | 1516 | O | GLN | 330 | 79.661 | 53.637 | 53.390 | 1.00 | 12.12 |
| ATOM | 1517 | N | ARG | 331 | 77.972 | 55.118 | 83.293 | 1.00 | 14.51 |
| ATOM | 1518 | CA | ARG | 331 | 77.419 | 54.789 | 84.601 | 1.00 | 13.34 |
| ATOM | 1519 | CB | ARG | 331 | 78.102 | 55.602 | 85.693 | 1.00 | 5.87 |
| ATOM | 1520 | CG | ARG | 331 | 79.510 | 55.059 | 85.827 | 1.00 | 9.37 |
| ATOM | 1521 | CD | ARG | 331 | 80.226 | 55.511 | 87.047 | 1.00 | 14.50 |
| ATOM | 1522 | NE | ARG | 331 | 81.588 | 54.991 | 87.015 | 1.00 | 21.06 |
| ATOM | 1523 | CZ | ARG | 331 | 82.524 | 55.307 | 87.904 | 1.00 | 31.08 |
| ATOM | 1524 | NH1 | ARG | 331 | 82.251 | 56.142 | 88.911 | 1.00 | 29.86 |
| ATOM | 1525 | NH2 | ARG | 331 | 83.741 | 54.794 | 87.779 | 1.00 | 30.75 |
| ATOM | 1526 | C | ARG | 331 | 75.921 | 54.986 | 84.585 | 1.00 | 15.33 |
| ATOM | 1527 | O | ARG | 331 | 75.379 | 55.904 | 85.206 | 1.00 | 18.05 |
| ATOM | 1528 | N | PRO | 332 | 75.230 | 54.096 | 83.852 | 1.00 | 14.69 |
| ATOM | 1529 | CD | PRO | 332 | 75.921 | 53.042 | 83.083 | 1.00 | 12.19 |
| ATOM | 1530 | CA | PRO | 332 | 73.792 | 54.003 | 83.611 | 1.00 | 11.26 |
| ATOM | 1531 | CB | PRO | 332 | 73.716 | 52.970 | 82.488 | 1.00 | 9.21 |
| ATOM | 1532 | CG | PRO | 332 | 74.811 | 52.028 | 82.868 | 1.00 | 12.86 |
| ATOM | 1533 | C | PRO | 332 | 72.738 | 53.727 | 84.692 | 1.00 | 9.94 |
| ATOM | 1534 | O | PRO | 332 | 71.589 | 54.140 | 84.535 | 1.00 | 23.57 |
| ATOM | 1535 | N | LEU | 333 | 72.991 | 53.072 | 85.793 | 1.00 | 2.99 |
| ATOM | 1536 | CA | LEU | 333 | 71.758 | 52.940 | 86.550 | 1.00 | 8.02 |

76

| ATOM | 1537 | CB | LEU | 333 | 71.507 | 51.457 | 86.830 | 1.00 | 11.16 |
| ATOM | 1538 | CG | LEU | 333 | 71.246 | 50.659 | 85.537 | 1.00 | 10.53 |
| ATOM | 1539 | CD1 | LEU | 333 | 71.486 | 49.193 | 85.757 | 1.00 | 14.50 |
| ATOM | 1540 | CD2 | LEU | 333 | 69.845 | 50.879 | 85.054 | 1.00 | 6.72 |
| ATOM | 1541 | C | LEU | 333 | 71.662 | 53.836 | 87.787 | 1.00 | 11.16 |
| ATOM | 1542 | O | LEU | 333 | 70.778 | 53.678 | 88.639 | 1.00 | 9.95 |
| ATOM | 1543 | N | VAL | 334 | 72.569 | 54.813 | 87.836 | 1.00 | 8.01 |
| ATOM | 1544 | CA | VAL | 334 | 72.642 | 55.760 | 88.927 | 1.00 | 5.93 |
| ATOM | 1545 | CB | VAL | 334 | 74.063 | 55.877 | 89.393 | 1.00 | 2.99 |
| ATOM | 1546 | CG1 | VAL | 334 | 74.161 | 56.827 | 90.573 | 1.00 | 2.99 |
| ATOM | 1547 | CG2 | VAL | 334 | 74.552 | 54.505 | 89.742 | 1.00 | 2.99 |
| ATOM | 1548 | C | VAL | 334 | 72.116 | 57.134 | 88.531 | 1.00 | 8.65 |
| ATOM | 1549 | O | VAL | 334 | 72.802 | 57.923 | 87.887 | 1.00 | 2.99 |
| ATOM | 1550 | N | LEU | 335 | 70.880 | 57.395 | 88.947 | 1.00 | 9.14 |
| ATOM | 1551 | CA | LEU | 335 | 70.175 | 58.633 | 88.672 | 1.00 | 7.34 |
| ATOM | 1552 | CB | LEU | 335 | 68.716 | 58.316 | 88.414 | 1.00 | 6.12 |
| ATOM | 1553 | CG | LEU | 335 | 68.562 | 57.246 | 87.348 | 1.00 | 8.54 |
| ATOM | 1554 | CD1 | LEU | 335 | 67.080 | 57.002 | 87.087 | 1.00 | 5.51 |
| ATOM | 1555 | CD2 | LEU | 335 | 69.285 | 57.696 | 86.075 | 1.00 | 6.66 |
| ATOM | 1556 | C | LEU | 335 | 70.263 | 59.636 | 89.808 | 1.00 | 10.02 |
| ATOM | 1557 | O | LEU | 335 | 69.981 | 59.323 | 90.966 | 1.00 | 13.30 |
| ATOM | 1558 | N | LYS | 336 | 70.641 | 60.858 | 89.475 | 1.00 | 13.10 |
| ATOM | 1559 | CA | LYS | 336 | 70.742 | 61.886 | 90.492 | 1.00 | 15.85 |
| ATOM | 1560 | CB | LYS | 336 | 72.034 | 62.682 | 90.358 | 1.00 | 14.82 |
| ATOM | 1561 | CG | LYS | 336 | 72.036 | 63.941 | 91.194 | 1.00 | 15.90 |
| ATOM | 1562 | CD | LYS | 336 | 73.230 | 64.799 | 90.849 | 1.00 | 26.88 |
| ATOM | 1563 | CE | LYS | 336 | 73.100 | 66.216 | 91.388 | 1.00 | 25.68 |
| ATOM | 1564 | NZ | LYS | 336 | 74.276 | 67.043 | 90.967 | 1.00 | 25.22 |
| ATOM | 1565 | C | LYS | 336 | 69.583 | 62.842 | 90.413 | 1.00 | 14.65 |
| ATOM | 1566 | O | LYS | 336 | 69.234 | 63.349 | 89.342 | 1.00 | 18.98 |
| ATOM | 1567 | N | THR | 337 | 69.001 | 63.082 | 91.576 | 1.00 | 13.01 |
| ATOM | 1568 | CA | THR | 337 | 67.887 | 63.994 | 91.745 | 1.00 | 11.01 |
| ATOM | 1569 | CB | THR | 337 | 67.648 | 64.179 | 93.237 | 1.00 | 5.42 |
| ATOM | 1570 | OG1 | THR | 337 | 66.758 | 63.160 | 93.679 | 1.00 | 13.87 |
| ATOM | 1571 | CG2 | THR | 337 | 67.091 | 65.533 | 93.554 | 1.00 | 16.08 |
| ATOM | 1572 | C | THR | 337 | 68.145 | 65.339 | 91.070 | 1.00 | 11.71 |
| ATOM | 1573 | O | THR | 337 | 69.282 | 65.802 | 91.004 | 1.00 | 14.89 |
| ATOM | 1574 | N | GLY | 338 | 67.091 | 65.958 | 90.554 | 1.00 | 13.28 |
| ATOM | 1575 | CA | GLY | 338 | 67.250 | 67.249 | 89.918 | 1.00 | 18.27 |
| ATOM | 1576 | C | GLY | 338 | 67.725 | 67.193 | 88.483 | 1.00 | 23.39 |
| ATOM | 1577 | O | GLY | 338 | 67.233 | 67.953 | 87.648 | 1.00 | 29.63 |
| ATOM | 1578 | N | VAL | 339 | 68.686 | 66.314 | 88.197 | 1.00 | 26.48 |
| ATOM | 1579 | CA | VAL | 339 | 69.218 | 66.144 | 86.842 | 1.00 | 26.27 |
| ATOM | 1580 | CB | VAL | 339 | 70.568 | 65.408 | 86.859 | 1.00 | 28.07 |
| ATOM | 1581 | CG1 | VAL | 339 | 71.170 | 65.430 | 85.482 | 1.00 | 25.58 |
| ATOM | 1582 | CG2 | VAL | 339 | 71.513 | 66.034 | 87.874 | 1.00 | 27.61 |
| ATOM | 1583 | C | VAL | 339 | 68.226 | 65.284 | 86.052 | 1.00 | 27.29 |
| ATOM | 1584 | O | VAL | 339 | 67.527 | 64.447 | 86.631 | 1.00 | 31.21 |
| ATOM | 1585 | N | GLN | 340 | 68.160 | 65.472 | 84.737 | 1.00 | 28.29 |
| ATOM | 1586 | CA | GLN | 340 | 67.213 | 64.690 | 83.935 | 1.00 | 31.56 |
| ATOM | 1587 | CB | GLN | 340 | 66.362 | 65.612 | 83.044 | 1.00 | 30.25 |
| ATOM | 1588 | CG | GLN | 340 | 67.121 | 66.580 | 82.170 | 1.00 | 34.97 |
| ATOM | 1589 | CD | GLN | 340 | 66.197 | 67.637 | 81.548 | 1.00 | 40.83 |
| ATOM | 1590 | OE1 | GLN | 340 | 65.463 | 68.335 | 82.254 | 1.00 | 36.53 |
| ATOM | 1591 | NE2 | GLN | 340 | 66.243 | 67.762 | 80.226 | 1.00 | 42.24 |
| ATOM | 1592 | C | GLN | 340 | 67.848 | 63.591 | 83.105 | 1.00 | 30.61 |
| ATOM | 1593 | O | GLN | 340 | 68.654 | 63.853 | 82.219 | 1.00 | 38.09 |
| ATOM | 1594 | N | PHE | 341 | 67.463 | 62.353 | 83.392 | 1.00 | 22.02 |
| ATOM | 1595 | CA | PHE | 341 | 68.014 | 61.209 | 82.691 | 1.00 | 17.36 |
| ATOM | 1596 | CB | PHE | 341 | 68.030 | 59.994 | 83.622 | 1.00 | 19.30 |
| ATOM | 1597 | CG | PHE | 341 | 66.692 | 59.681 | 84.216 | 1.00 | 17.64 |
| ATOM | 1598 | CD1 | PHE | 341 | 65.864 | 58.739 | 83.636 | 1.00 | 16.16 |
| ATOM | 1599 | CD2 | PHE | 341 | 66.232 | 60.390 | 85.318 | 1.00 | 17.37 |
| ATOM | 1600 | CE1 | PHE | 341 | 64.594 | 58.508 | 84.140 | 1.00 | 19.86 |
| ATOM | 1601 | CE2 | PHE | 341 | 64.974 | 60.166 | 85.824 | 1.00 | 18.07 |
| ATOM | 1602 | CZ | PHE | 341 | 64.148 | 59.223 | 85.234 | 1.00 | 21.56 |
| ATOM | 1603 | C | PHE | 341 | 67.263 | 60.883 | 81.425 | 1.00 | 14.47 |
| ATOM | 1604 | O | PHE | 341 | 66.226 | 61.477 | 81.130 | 1.00 | 6.78 |
| ATOM | 1605 | N | THR | 342 | 67.799 | 59.905 | 80.701 | 1.00 | 13.34 |
| ATOM | 1606 | CA | THR | 342 | 67.248 | 59.448 | 79.436 | 1.00 | 14.79 |

| | | | | | | | | |
|---|---|---|---|---|---|---|---|---|
| ATOM | 1607 | CB | THR | 342 | 68.178 | 59.822 | 78.287 | 1.00 16.93 |
| ATOM | 1608 | OG1 | THR | 342 | 68.238 | 61.247 | 78.169 | 1.00 30.91 |
| ATOM | 1609 | CG2 | THR | 342 | 67.694 | 59.225 | 76.999 | 1.00 26.33 |
| ATOM | 1610 | C | THR | 342 | 67.083 | 57.940 | 79.401 | 1.00 15.95 |
| ATOM | 1611 | O | THR | 342 | 68.019 | 57.196 | 79.718 | 1.00 17.12 |
| ATOM | 1612 | N | VAL | 343 | 65.901 | 57.484 | 79.008 | 1.00 9.97 |
| ATOM | 1613 | CA | VAL | 343 | 65.675 | 56.058 | 78.909 | 1.00 8.23 |
| ATOM | 1614 | CB | VAL | 343 | 64.634 | 55.579 | 79.892 | 1.00 6.73 |
| ATOM | 1615 | CG1 | VAL | 343 | 64.733 | 54.077 | 80.033 | 1.00 4.54 |
| ATOM | 1616 | CG2 | VAL | 343 | 64.807 | 56.279 | 81.211 | 1.00 10.57 |
| ATOM | 1617 | C | VAL | 343 | 65.123 | 55.844 | 77.524 | 1.00 9.38 |
| ATOM | 1618 | O | VAL | 343 | 64.559 | 56.770 | 76.952 | 1.00 12.92 |
| ATOM | 1619 | N | LYS | 344 | 65.291 | 54.648 | 76.965 | 1.00 9.18 |
| ATOM | 1620 | CA | LYS | 344 | 64.735 | 54.393 | 75.646 | 1.00 11.90 |
| ATOM | 1621 | CB | LYS | 344 | 65.814 | 54.326 | 74.566 | 1.00 10.50 |
| ATOM | 1622 | CG | LYS | 344 | 65.193 | 54.357 | 73.163 | 1.00 14.67 |
| ATOM | 1623 | CD | LYS | 344 | 66.184 | 54.148 | 72.046 | 1.00 12.69 |
| ATOM | 1624 | CE | LYS | 344 | 65.461 | 54.137 | 70.708 | 1.00 22.94 |
| ATOM | 1625 | NZ | LYS | 344 | 66.288 | 53.653 | 69.555 | 1.00 23.90 |
| ATOM | 1626 | C | LYS | 344 | 63.934 | 53.101 | 75.623 | 1.00 17.52 |
| ATOM | 1627 | O | LYS | 344 | 64.460 | 52.022 | 75.928 | 1.00 14.12 |
| ATOM | 1628 | N | LEU | 345 | 62.658 | 53.222 | 75.260 | 1.00 17.99 |
| ATOM | 1629 | CA | LEU | 345 | 61.766 | 52.069 | 75.184 | 1.00 20.73 |
| ATOM | 1630 | CB | LEU | 345 | 60.401 | 52.403 | 75.786 | 1.00 21.64 |
| ATOM | 1631 | CG | LEU | 345 | 60.416 | 52.876 | 77.240 | 1.00 24.52 |
| ATOM | 1632 | CD1 | LEU | 345 | 58.986 | 53.069 | 77.669 | 1.00 26.85 |
| ATOM | 1633 | CD2 | LEU | 345 | 61.118 | 51.870 | 78.149 | 1.00 26.03 |
| ATOM | 1634 | C | LEU | 345 | 61.586 | 51.657 | 73.737 | 1.00 20.69 |
| ATOM | 1635 | O | LEU | 345 | 61.937 | 52.400 | 72.833 | 1.00 24.69 |
| ATOM | 1636 | N | ARG | 346 | 61.028 | 50.477 | 73.520 | 1.00 17.11 |
| ATOM | 1637 | CA | ARG | 346 | 60.825 | 49.996 | 72.173 | 1.00 17.28 |
| ATOM | 1638 | CB | ARG | 346 | 62.168 | 49.667 | 71.546 | 1.00 22.31 |
| ATOM | 1639 | CG | ARG | 346 | 62.066 | 49.013 | 70.185 | 1.00 22.31 |
| ATOM | 1640 | CD | ARG | 346 | 63.447 | 48.939 | 69.601 | 1.00 22.62 |
| ATOM | 1641 | NE | ARG | 346 | 63.474 | 48.346 | 68.279 | 1.00 23.75 |
| ATOM | 1642 | CZ | ARG | 346 | 64.597 | 48.137 | 67.608 | 1.00 30.44 |
| ATOM | 1643 | NH1 | ARG | 346 | 65.760 | 48.479 | 68.147 | 1.00 26.88 |
| ATOM | 1644 | NH2 | ARG | 346 | 64.566 | 47.560 | 66.414 | 1.00 39.09 |
| ATOM | 1645 | C | ARG | 346 | 59.923 | 48.783 | 72.076 | 1.00 18.61 |
| ATOM | 1646 | O | ARG | 346 | 59.997 | 47.871 | 72.891 | 1.00 21.79 |
| ATOM | 1647 | N | LEU | 347 | 59.070 | 48.771 | 71.063 | 1.00 19.26 |
| ATOM | 1648 | CA | LEU | 347 | 58.166 | 47.654 | 70.874 | 1.00 25.09 |
| ATOM | 1649 | CB | LEU | 347 | 56.755 | 48.161 | 70.575 | 1.00 17.62 |
| ATOM | 1650 | CG | LEU | 347 | 55.649 | 47.123 | 70.744 | 1.00 16.64 |
| ATOM | 1651 | CD1 | LEU | 347 | 55.711 | 46.533 | 72.135 | 1.00 13.31 |
| ATOM | 1652 | CD2 | LEU | 347 | 54.309 | 47.774 | 70.520 | 1.00 17.42 |
| ATOM | 1653 | C | LEU | 347 | 58.726 | 46.873 | 69.700 | 1.00 29.76 |
| ATOM | 1654 | O | LEU | 347 | 58.734 | 47.365 | 68.567 | 1.00 38.29 |
| ATOM | 1655 | N | LEU | 348 | 59.202 | 45.662 | 69.973 | 1.00 28.09 |
| ATOM | 1656 | CA | LEU | 348 | 59.812 | 44.830 | 68.942 | 1.00 28.01 |
| ATOM | 1657 | CB | LEU | 348 | 60.593 | 43.693 | 69.599 | 1.00 23.79 |
| ATOM | 1658 | CG | LEU | 348 | 61.731 | 44.092 | 70.539 | 1.00 19.13 |
| ATOM | 1659 | CD1 | LEU | 348 | 62.225 | 42.886 | 71.283 | 1.00 22.21 |
| ATOM | 1660 | CD2 | LEU | 348 | 62.855 | 44.729 | 69.751 | 1.00 19.26 |
| ATOM | 1661 | C | LEU | 348 | 58.822 | 44.253 | 67.952 | 1.00 31.91 |
| ATOM | 1662 | O | LEU | 348 | 59.183 | 43.405 | 67.144 | 1.00 33.58 |
| ATOM | 1663 | N | VAL | 349 | 57.580 | 44.724 | 68.004 | 1.00 39.93 |
| ATOM | 1664 | CA | VAL | 349 | 56.539 | 44.216 | 67.120 | 1.00 46.27 |
| ATOM | 1665 | CB | VAL | 349 | 55.199 | 44.121 | 67.871 | 1.00 45.89 |
| ATOM | 1666 | CG1 | VAL | 349 | 54.067 | 43.828 | 66.914 | 1.00 44.52 |
| ATOM | 1667 | CG2 | VAL | 349 | 55.278 | 42.995 | 68.889 | 1.00 47.72 |
| ATOM | 1668 | C | VAL | 349 | 56.309 | 44.899 | 65.771 | 1.00 50.99 |
| ATOM | 1669 | O | VAL | 349 | 55.866 | 44.243 | 64.835 | 1.00 59.93 |
| ATOM | 1670 | N | LYS | 350 | 56.595 | 46.186 | 65.635 | 1.00 52.31 |
| ATOM | 1671 | CA | LYS | 350 | 56.385 | 46.838 | 64.337 | 1.00 54.71 |
| ATOM | 1672 | CB | LYS | 350 | 57.466 | 46.436 | 63.332 | 1.00 56.20 |
| ATOM | 1673 | CG | LYS | 350 | 58.796 | 47.135 | 63.443 | 1.00 62.56 |
| ATOM | 1674 | CD | LYS | 350 | 59.692 | 46.614 | 62.334 | 1.00 71.44 |
| ATOM | 1675 | CE | LYS | 350 | 61.049 | 47.283 | 62.319 | 1.00 76.32 |
| ATOM | 1676 | NZ | LYS | 350 | 61.957 | 46.704 | 61.277 | 1.00 79.68 |

| | | | | | | | |
|---|---|---|---|---|---|---|---|
| ATOM | 1677 | C   | LYS | 350 | 55.044 | 46.540 | 63.670 | 1.00 54.60 |
| ATOM | 1678 | O   | LYS | 350 | 54.939 | 45.631 | 62.854 | 1.00 55.66 |
| ATOM | 1679 | N   | LEU | 351 | 54.018 | 47.298 | 64.006 | 1.00 54.06 |
| ATOM | 1680 | CA  | LEU | 351 | 52.736 | 47.098 | 63.367 | 1.00 56.28 |
| ATOM | 1681 | CB  | LEU | 351 | 51.749 | 46.428 | 64.323 | 1.00 55.45 |
| ATOM | 1682 | CG  | LEU | 351 | 52.084 | 44.965 | 64.631 | 1.00 52.96 |
| ATOM | 1683 | CD1 | LEU | 351 | 50.974 | 44.353 | 65.459 | 1.00 51.94 |
| ATOM | 1684 | CD2 | LEU | 351 | 52.244 | 44.188 | 63.336 | 1.00 52.53 |
| ATOM | 1685 | C   | LEU | 351 | 52.245 | 48.460 | 62.911 | 1.00 59.74 |
| ATOM | 1686 | O   | LEU | 351 | 51.863 | 49.293 | 63.720 | 1.00 60.51 |
| ATOM | 1687 | N   | GLN | 352 | 52.286 | 48.680 | 61.602 | 1.00 64.18 |
| ATOM | 1688 | CA  | GLN | 352 | 51.880 | 49.946 | 61.008 | 1.00 68.94 |
| ATOM | 1689 | CB  | GLN | 352 | 51.502 | 49.729 | 59.535 | 1.00 74.42 |
| ATOM | 1690 | CG  | GLN | 352 | 51.284 | 51.015 | 58.742 | 1.00 78.27 |
| ATOM | 1691 | CD  | GLN | 352 | 52.526 | 51.890 | 58.704 | 1.00 80.26 |
| ATOM | 1692 | OE1 | GLN | 352 | 53.572 | 51.485 | 58.190 | 1.00 82.60 |
| ATOM | 1693 | NE2 | GLN | 352 | 52.417 | 53.094 | 59.257 | 1.00 81.28 |
| ATOM | 1694 | C   | GLN | 352 | 50.725 | 50.608 | 61.761 | 1.00 69.59 |
| ATOM | 1695 | O   | GLN | 352 | 50.874 | 51.703 | 62.304 | 1.00 69.75 |
| ATOM | 1696 | N   | GLU | 353 | 49.578 | 49.938 | 61.798 | 1.00 68.82 |
| ATOM | 1697 | CA  | GLU | 353 | 48.409 | 50.474 | 62.482 | 1.00 69.95 |
| ATOM | 1698 | CB  | GLU | 353 | 47.159 | 49.665 | 62.102 | 1.00 73.68 |
| ATOM | 1699 | CG  | GLU | 353 | 47.363 | 48.151 | 62.000 | 1.00 77.45 |
| ATOM | 1700 | CD  | GLU | 353 | 47.877 | 47.516 | 63.282 | 1.00 77.47 |
| ATOM | 1701 | OE1 | GLU | 353 | 47.200 | 47.637 | 64.327 | 1.00 75.56 |
| ATOM | 1702 | OE2 | GLU | 353 | 48.957 | 46.886 | 63.238 | 1.00 77.93 |
| ATOM | 1703 | C   | GLU | 353 | 48.561 | 50.531 | 63.996 | 1.00 68.69 |
| ATOM | 1704 | O   | GLU | 353 | 47.575 | 50.465 | 64.732 | 1.00 72.13 |
| ATOM | 1705 | N   | LEU | 354 | 49.799 | 50.680 | 64.455 | 1.00 65.01 |
| ATOM | 1706 | CA  | LEU | 354 | 50.101 | 50.736 | 65.886 | 1.00 60.44 |
| ATOM | 1707 | CB  | LEU | 354 | 50.836 | 49.458 | 66.313 | 1.00 56.77 |
| ATOM | 1708 | CG  | LEU | 354 | 51.112 | 49.198 | 67.788 | 1.00 50.13 |
| ATOM | 1709 | CD1 | LEU | 354 | 49.804 | 49.081 | 68.527 | 1.00 50.28 |
| ATOM | 1710 | CD2 | LEU | 354 | 51.897 | 47.920 | 67.937 | 1.00 48.83 |
| ATOM | 1711 | C   | LEU | 354 | 50.978 | 51.950 | 66.170 | 1.00 59.94 |
| ATOM | 1712 | O   | LEU | 354 | 51.461 | 52.134 | 67.281 | 1.00 60.64 |
| ATOM | 1713 | N   | ASN | 355 | 51.180 | 52.774 | 65.151 | 1.00 58.76 |
| ATOM | 1714 | CA  | ASN | 355 | 51.993 | 53.972 | 65.279 | 1.00 55.53 |
| ATOM | 1715 | CB  | ASN | 355 | 52.627 | 54.268 | 63.915 | 1.00 57.49 |
| ATOM | 1716 | CG  | ASN | 355 | 53.597 | 55.451 | 63.942 | 1.00 59.14 |
| ATOM | 1717 | OD1 | ASN | 355 | 54.389 | 55.590 | 64.873 | 1.00 61.95 |
| ATOM | 1718 | ND2 | ASN | 355 | 53.568 | 56.231 | 62.889 | 1.00 59.56 |
| ATOM | 1719 | C   | ASN | 355 | 51.097 | 55.113 | 65.785 | 1.00 53.11 |
| ATOM | 1720 | O   | ASN | 355 | 49.979 | 55.302 | 65.315 | 1.00 53.96 |
| ATOM | 1721 | N   | TYR | 356 | 51.597 | 55.845 | 66.774 | 1.00 54.40 |
| ATOM | 1722 | CA  | TYR | 356 | 50.881 | 56.949 | 67.417 | 1.00 55.90 |
| ATOM | 1723 | CB  | TYR | 356 | 50.474 | 58.036 | 66.411 | 1.00 56.40 |
| ATOM | 1724 | CG  | TYR | 356 | 51.635 | 58.711 | 65.718 | 1.00 59.31 |
| ATOM | 1725 | CD1 | TYR | 356 | 52.304 | 58.080 | 64.676 | 1.00 61.31 |
| ATOM | 1726 | CE1 | TYR | 356 | 53.388 | 58.678 | 64.042 | 1.00 57.61 |
| ATOM | 1727 | CD2 | TYR | 356 | 52.082 | 59.970 | 66.119 | 1.00 59.91 |
| ATOM | 1728 | CE2 | TYR | 356 | 53.172 | 60.580 | 65.490 | 1.00 59.50 |
| ATOM | 1729 | CZ  | TYR | 356 | 53.817 | 59.921 | 64.447 | 1.00 58.37 |
| ATOM | 1730 | OH  | TYR | 356 | 54.879 | 60.496 | 63.787 | 1.00 57.81 |
| ATOM | 1731 | C   | TYR | 356 | 49.643 | 56.502 | 68.194 | 1.00 53.74 |
| ATOM | 1732 | O   | TYR | 356 | 48.705 | 57.279 | 68.363 | 1.00 54.38 |
| ATOM | 1733 | N   | ASN | 357 | 49.642 | 55.259 | 68.669 | 1.00 50.64 |
| ATOM | 1734 | CA  | ASN | 357 | 48.512 | 54.747 | 69.440 | 1.00 52.33 |
| ATOM | 1735 | CB  | ASN | 357 | 47.907 | 53.519 | 68.765 | 1.00 52.50 |
| ATOM | 1736 | CG  | ASN | 357 | 47.132 | 53.872 | 67.546 | 1.00 52.86 |
| ATOM | 1737 | OD1 | ASN | 357 | 46.155 | 54.651 | 67.625 | 1.00 51.37 |
| ATOM | 1738 | ND2 | ASN | 357 | 47.464 | 53.298 | 66.409 | 1.00 55.42 |
| ATOM | 1739 | C   | ASN | 357 | 48.886 | 54.396 | 70.871 | 1.00 52.73 |
| ATOM | 1740 | O   | ASN | 357 | 48.108 | 54.623 | 71.807 | 1.00 51.42 |
| ATOM | 1741 | N   | LEU | 358 | 50.080 | 53.838 | 71.038 | 1.00 49.89 |
| ATOM | 1742 | CA  | LEU | 358 | 50.550 | 53.455 | 72.358 | 1.00 44.67 |
| ATOM | 1743 | CB  | LEU | 358 | 51.626 | 52.387 | 72.231 | 1.00 43.24 |
| ATOM | 1744 | CG  | LEU | 358 | 51.130 | 51.151 | 71.495 | 1.00 41.27 |
| ATOM | 1745 | CD1 | LEU | 358 | 52.279 | 50.192 | 71.276 | 1.00 43.21 |
| ATOM | 1746 | CD2 | LEU | 358 | 50.017 | 50.503 | 72.295 | 1.00 44.97 |

| | | | | | | | | |
|---|---|---|---|---|---|---|---|---|
| ATOM | 1747 | C | LEU | 358 | 51.092 | 54.647 | 73.127 | 1.00 41.77 |
| ATOM | 1748 | O | LEU | 358 | 52.091 | 55.251 | 72.749 | 1.00 43.56 |
| ATOM | 1749 | N | LYS | 359 | 50.412 | 54.984 | 74.210 | 1.00 41.02 |
| ATOM | 1750 | CA | LYS | 359 | 50.818 | 56.091 | 75.048 | 1.00 38.85 |
| ATOM | 1751 | CB | LYS | 359 | 49.572 | 56.823 | 75.533 | 1.00 42.51 |
| ATOM | 1752 | CG | LYS | 359 | 49.818 | 58.131 | 76.245 | 1.00 51.75 |
| ATOM | 1753 | CD | LYS | 359 | 48.490 | 58.801 | 76.539 | 1.00 57.82 |
| ATOM | 1754 | CE | LYS | 359 | 48.675 | 60.176 | 77.140 | 1.00 62.48 |
| ATOM | 1755 | NZ | LYS | 359 | 47.350 | 60.811 | 77.386 | 1.00 68.22 |
| ATOM | 1756 | C | LYS | 359 | 51.584 | 55.475 | 76.220 | 1.00 39.79 |
| ATOM | 1757 | O | LYS | 359 | 51.042 | 54.640 | 76.952 | 1.00 44.17 |
| ATOM | 1758 | N | VAL | 360 | 52.848 | 55.860 | 76.384 | 1.00 34.84 |
| ATOM | 1759 | CA | VAL | 360 | 53.652 | 55.318 | 77.465 | 1.00 26.87 |
| ATOM | 1760 | CB | VAL | 360 | 55.077 | 55.067 | 77.013 | 1.00 22.94 |
| ATOM | 1761 | CG1 | VAL | 360 | 55.892 | 54.488 | 78.167 | 1.00 16.57 |
| ATOM | 1762 | CG2 | VAL | 360 | 55.074 | 54.129 | 75.823 | 1.00 18.83 |
| ATOM | 1763 | C | VAL | 360 | 53.688 | 56.260 | 78.650 | 1.00 27.93 |
| ATOM | 1764 | O | VAL | 360 | 53.816 | 57.469 | 78.479 | 1.00 29.28 |
| ATOM | 1765 | N | LYS | 361 | 53.579 | 55.696 | 79.851 | 1.00 28.24 |
| ATOM | 1766 | CA | LYS | 361 | 53.594 | 56.472 | 81.087 | 1.00 26.64 |
| ATOM | 1767 | CB | LYS | 361 | 52.279 | 56.293 | 81.839 | 1.00 33.43 |
| ATOM | 1768 | CG | LYS | 361 | 51.077 | 56.039 | 80.959 | 1.00 46.46 |
| ATOM | 1769 | CD | LYS | 361 | 49.942 | 55.492 | 81.805 | 1.00 51.10 |
| ATOM | 1770 | CE | LYS | 361 | 48.803 | 54.954 | 80.958 | 1.00 54.54 |
| ATOM | 1771 | NZ | LYS | 361 | 47.780 | 54.296 | 81.828 | 1.00 56.08 |
| ATOM | 1772 | C | LYS | 361 | 54.701 | 55.891 | 81.953 | 1.00 21.39 |
| ATOM | 1773 | O | LYS | 361 | 54.753 | 54.671 | 82.138 | 1.00 20.87 |
| ATOM | 1774 | N | VAL | 362 | 55.565 | 56.752 | 82.495 | 1.00 18.92 |
| ATOM | 1775 | CA | VAL | 362 | 56.666 | 56.308 | 83.357 | 1.00 10.25 |
| ATOM | 1776 | CB | VAL | 362 | 57.888 | 57.218 | 83.257 | 1.00 5.35 |
| ATOM | 1777 | CG1 | VAL | 362 | 59.035 | 56.580 | 83.957 | 1.00 11.99 |
| ATOM | 1778 | CG2 | VAL | 362 | 58.247 | 57.479 | 81.831 | 1.00 8.53 |
| ATOM | 1779 | C | VAL | 362 | 56.223 | 56.377 | 84.801 | 1.00 9.21 |
| ATOM | 1780 | O | VAL | 362 | 55.725 | 57.400 | 85.236 | 1.00 12.58 |
| ATOM | 1781 | N | LEU | 363 | 56.398 | 55.288 | 85.542 | 1.00 13.08 |
| ATOM | 1782 | CA | LEU | 363 | 56.029 | 55.247 | 86.962 | 1.00 13.14 |
| ATOM | 1783 | CB | LEU | 363 | 54.977 | 54.182 | 87.228 | 1.00 14.01 |
| ATOM | 1784 | CG | LEU | 363 | 53.566 | 54.551 | 86.792 | 1.00 20.44 |
| ATOM | 1785 | CD1 | LEU | 363 | 53.526 | 54.839 | 85.309 | 1.00 19.51 |
| ATOM | 1786 | CD2 | LEU | 363 | 52.635 | 53.414 | 87.144 | 1.00 25.52 |
| ATOM | 1787 | C | LEU | 363 | 57.235 | 54.946 | 87.818 | 1.00 17.48 |
| ATOM | 1788 | O | LEU | 363 | 58.190 | 54.322 | 87.350 | 1.00 15.89 |
| ATOM | 1789 | N | PHE | 364 | 57.211 | 55.393 | 89.071 | 1.00 21.53 |
| ATOM | 1790 | CA | PHE | 364 | 58.343 | 55.114 | 89.940 | 1.00 23.17 |
| ATOM | 1791 | CB | PHE | 364 | 58.909 | 56.388 | 90.528 | 1.00 18.87 |
| ATOM | 1792 | CG | PHE | 364 | 60.354 | 56.272 | 90.888 | 1.00 16.83 |
| ATOM | 1793 | CD1 | PHE | 364 | 61.305 | 56.057 | 89.895 | 1.00 14.05 |
| ATOM | 1794 | CD2 | PHE | 364 | 60.777 | 56.389 | 92.202 | 1.00 12.42 |
| ATOM | 1795 | CE1 | PHE | 364 | 62.651 | 55.968 | 90.206 | 1.00 13.05 |
| ATOM | 1796 | CE2 | PHE | 364 | 62.128 | 56.298 | 92.521 | 1.00 15.07 |
| ATOM | 1797 | CZ | PHE | 364 | 63.064 | 56.090 | 91.522 | 1.00 9.70 |
| ATOM | 1798 | C | PHE | 364 | 57.982 | 54.152 | 91.060 | 1.00 25.21 |
| ATOM | 1799 | O | PHE | 364 | 56.925 | 54.264 | 91.671 | 1.00 28.66 |
| ATOM | 1800 | N | ASP | 365 | 58.880 | 53.207 | 91.317 | 1.00 28.53 |
| ATOM | 1801 | CA | ASP | 365 | 58.691 | 52.174 | 92.335 | 1.00 31.89 |
| ATOM | 1802 | CB | ASP | 365 | 59.001 | 52.711 | 93.738 | 1.00 31.91 |
| ATOM | 1803 | CG | ASP | 365 | 60.457 | 53.131 | 93.900 | 1.00 37.15 |
| ATOM | 1804 | OD1 | ASP | 365 | 61.348 | 52.409 | 93.396 | 1.00 32.82 |
| ATOM | 1805 | OD2 | ASP | 365 | 60.712 | 54.173 | 94.554 | 1.00 42.62 |
| ATOM | 1806 | C | ASP | 365 | 57.315 | 51.493 | 92.336 | 1.00 32.21 |
| ATOM | 1807 | O | ASP | 365 | 56.742 | 51.238 | 93.393 | 1.00 31.36 |
| ATOM | 1808 | N | LYS | 366 | 56.794 | 51.188 | 91.150 | 1.00 34.07 |
| ATOM | 1809 | CA | LYS | 366 | 55.509 | 50.507 | 91.037 | 1.00 35.19 |
| ATOM | 1810 | CB | LYS | 366 | 55.075 | 50.415 | 89.574 | 1.00 32.45 |
| ATOM | 1811 | CG | LYS | 366 | 53.786 | 49.634 | 89.365 | 1.00 26.06 |
| ATOM | 1812 | CD | LYS | 366 | 53.534 | 49.325 | 87.896 | 1.00 30.87 |
| ATOM | 1813 | CE | LYS | 366 | 52.314 | 48.429 | 87.723 | 1.00 30.66 |
| ATOM | 1814 | NZ | LYS | 366 | 52.048 | 48.122 | 86.294 | 1.00 36.42 |
| ATOM | 1815 | C | LYS | 366 | 55.681 | 49.094 | 91.592 | 1.00 42.03 |
| ATOM | 1816 | O | LYS | 366 | 56.609 | 48.383 | 91.201 | 1.00 44.46 |

80

```
ATOM   1817  N    ASP  367      54.792  48.685  92.496  1.00 46.03
ATOM   1818  CA   ASP  367      54.866  47.352  93.089  1.00 48.28
ATOM   1819  CB   ASP  367      54.656  46.271  92.024  1.00 46.87
ATOM   1820  CG   ASP  367      53.334  46.411  91.300  1.00 47.26
ATOM   1821  OD1  ASP  367      52.279  46.489  91.967  1.00 45.49
ATOM   1822  OD2  ASP  367      53.356  46.426  90.051  1.00 48.05
ATOM   1823  C    ASP  367      56.220  47.127  93.759  1.00 50.33
ATOM   1824  O    ASP  367      56.924  46.155  93.471  1.00 53.11
ATOM   1825  N    VAL  368      56.590  48.037  94.646  1.00 50.69
ATOM   1826  CA   VAL  368      57.852  47.922  95.346  1.00 50.06
ATOM   1827  CB   VAL  368      58.770  49.117  95.034  1.00 46.12
ATOM   1828  CG1  VAL  368      60.007  49.069  95.911  1.00 47.56
ATOM   1829  CG2  VAL  368      59.177  49.077  93.576  1.00 39.85
ATOM   1830  C    VAL  368      57.556  47.857  96.829  1.00 53.94
ATOM   1831  O    VAL  368      57.358  48.876  97.486  1.00 54.08
ATOM   1832  N    ASN  369      57.516  46.638  97.347  1.00 58.96
ATOM   1833  CA   ASN  369      57.225  46.415  98.750  1.00 62.71
ATOM   1834  CB   ASN  369      57.103  44.914  99.006  1.00 64.34
ATOM   1835  CG   ASN  369      55.998  44.282  98.180  1.00 69.13
ATOM   1836  OD1  ASN  369      54.821  44.620  98.336  1.00 72.28
ATOM   1837  ND2  ASN  369      56.371  43.373  97.284  1.00 70.37
ATOM   1838  C    ASN  369      58.253  47.042  99.683  1.00 63.40
ATOM   1839  O    ASN  369      57.928  47.404 100.813  1.00 65.70
ATOM   1840  N    GLU  370      59.488  47.181  99.210  1.00 62.50
ATOM   1841  CA   GLU  370      60.541  47.774 100.024  1.00 62.56
ATOM   1842  CB   GLU  370      61.820  47.954  99.202  1.00 61.79
ATOM   1843  CG   GLU  370      62.580  46.667  98.884  1.00 64.67
ATOM   1844  CD   GLU  370      61.749  45.618  98.154  1.00 65.82
ATOM   1845  OE1  GLU  370      61.104  45.956  97.140  1.00 67.32
ATOM   1846  OE2  GLU  370      61.758  44.443  98.584  1.00 64.04
ATOM   1847  C    GLU  370      60.089  49.122 100.581  1.00 62.89
ATOM   1848  O    GLU  370      60.674  49.634 101.534  1.00 60.42
ATOM   1849  N    ARG  371      59.048  49.689  99.978  1.00 64.29
ATOM   1850  CA   ARG  371      58.501  50.971 100.418  1.00 65.30
ATOM   1851  CB   ARG  371      57.295  51.370  99.569  1.00 67.73
ATOM   1852  CG   ARG  371      57.548  51.693  98.112  1.00 67.61
ATOM   1853  CD   ARG  371      56.209  52.023  97.490  1.00 72.25
ATOM   1854  NE   ARG  371      56.292  52.495  96.117  1.00 81.24
ATOM   1855  CZ   ARG  371      55.244  52.932  95.420  1.00 87.21
ATOM   1856  NH1  ARG  371      54.037  52.952  95.975  1.00 88.15
ATOM   1857  NH2  ARG  371      55.401  53.359  94.172  1.00 91.06
ATOM   1858  C    ARG  371      58.036  50.863 101.863  1.00 64.60
ATOM   1859  O    ARG  371      58.336  51.721 102.694  1.00 63.97
ATOM   1860  N    ASN  372      57.282  49.805 102.145  1.00 62.72
ATOM   1861  CA   ASN  372      56.759  49.561 103.483  1.00 61.95
ATOM   1862  CB   ASN  372      55.442  48.792 103.398  1.00 63.07
ATOM   1863  CG   ASN  372      54.474  49.419 102.429  1.00 63.91
ATOM   1864  OD1  ASN  372      54.125  50.589 102.566  1.00 64.48
ATOM   1865  ND2  ASN  372      54.035  48.644 101.436  1.00 61.34
ATOM   1866  C    ASN  372      57.765  48.733 104.270  1.00 60.95
ATOM   1867  O    ASN  372      58.301  49.177 105.290  1.00 63.68
ATOM   1868  N    THR  373      58.017  47.527 103.774  1.00 57.61
ATOM   1869  CA   THR  373      58.941  46.601 104.406  1.00 53.62
ATOM   1870  CB   THR  373      59.198  45.394 103.495  1.00 53.88
ATOM   1871  OG1  THR  373      57.998  44.613 103.407  1.00 54.31
ATOM   1872  CG2  THR  373      60.343  44.539 104.033  1.00 54.97
ATOM   1873  C    THR  373      60.275  47.190 104.837  1.00 48.96
ATOM   1874  O    THR  373      60.778  46.852 105.902  1.00 51.44
ATOM   1875  N    VAL  374      60.859  48.066 104.032  1.00 43.88
ATOM   1876  CA   VAL  374      62.140  48.634 104.422  1.00 40.92
ATOM   1877  CB   VAL  374      63.079  48.809 103.210  1.00 41.09
ATOM   1878  CG1  VAL  374      64.449  49.307 103.681  1.00 37.84
ATOM   1879  CG2  VAL  374      63.220  47.487 102.467  1.00 37.11
ATOM   1880  C    VAL  374      62.021  49.964 105.165  1.00 39.43
ATOM   1881  O    VAL  374      61.318  50.883 104.739  1.00 36.07
ATOM   1882  N    LYS  375      62.728  50.040 106.287  1.00 37.35
ATOM   1883  CA   LYS  375      62.740  51.216 107.140  1.00 36.81
ATOM   1884  CB   LYS  375      63.281  50.818 108.513  1.00 40.06
ATOM   1885  CG   LYS  375      63.255  51.892 109.592  1.00 42.28
ATOM   1886  CD   LYS  375      63.764  51.284 110.892  1.00 47.85
```

| | | | | | | | | |
|---|---|---|---|---|---|---|---|---|
| ATOM | 1887 | CE | LYS | 375 | 63.795 | 52.256 | 112.055 | 1.00 50.57 |
| ATOM | 1888 | NZ | LYS | 375 | 64.338 | 51.574 | 113.274 | 1.00 51.16 |
| ATOM | 1889 | C | LYS | 375 | 63.612 | 52.287 | 106.504 | 1.00 35.26 |
| ATOM | 1890 | O | LYS | 375 | 64.551 | 51.968 | 105.786 | 1.00 36.20 |
| ATOM | 1891 | N | GLY | 376 | 63.287 | 53.551 | 106.760 | 1.00 35.25 |
| ATOM | 1892 | CA | GLY | 376 | 64.047 | 54.659 | 106.208 | 1.00 32.11 |
| ATOM | 1893 | C | GLY | 376 | 63.913 | 54.846 | 104.704 | 1.00 33.07 |
| ATOM | 1894 | O | GLY | 376 | 64.199 | 55.921 | 104.182 | 1.00 36.31 |
| ATOM | 1895 | N | PHE | 377 | 63.477 | 53.797 | 104.015 | 1.00 30.18 |
| ATOM | 1896 | CA | PHE | 377 | 63.298 | 53.788 | 102.562 | 1.00 29.04 |
| ATOM | 1897 | CB | PHE | 377 | 62.401 | 52.607 | 102.202 | 1.00 29.63 |
| ATOM | 1898 | CG | PHE | 377 | 62.509 | 52.166 | 100.779 | 1.00 29.50 |
| ATOM | 1899 | CD1 | PHE | 377 | 63.661 | 51.538 | 100.323 | 1.00 21.28 |
| ATOM | 1900 | CD2 | PHE | 377 | 61.449 | 52.365 | 99.891 | 1.00 31.91 |
| ATOM | 1901 | CE1 | PHE | 377 | 63.756 | 51.114 | 99.007 | 1.00 27.42 |
| ATOM | 1902 | CE2 | PHE | 377 | 61.534 | 51.945 | 98.561 | 1.00 28.74 |
| ATOM | 1903 | CZ | PHE | 377 | 62.689 | 51.318 | 98.121 | 1.00 28.78 |
| ATOM | 1904 | C | PHE | 377 | 62.666 | 55.091 | 102.046 | 1.00 32.87 |
| ATOM | 1905 | O | PHE | 377 | 61.566 | 55.454 | 102.474 | 1.00 35.87 |
| ATOM | 1906 | N | ARG | 378 | 63.338 | 55.787 | 101.124 | 1.00 29.24 |
| ATOM | 1907 | CA | ARG | 378 | 62.803 | 57.044 | 100.580 | 1.00 27.11 |
| ATOM | 1908 | CB | ARG | 378 | 63.941 | 58.025 | 100.331 | 1.00 22.72 |
| ATOM | 1909 | CG | ARG | 378 | 65.182 | 57.340 | 99.906 | 1.00 28.51 |
| ATOM | 1910 | CD | ARG | 378 | 66.314 | 58.272 | 99.577 | 1.00 28.35 |
| ATOM | 1911 | NE | ARG | 378 | 67.387 | 57.461 | 99.024 | 1.00 38.26 |
| ATOM | 1912 | CZ | ARG | 378 | 68.374 | 57.923 | 98.275 | 1.00 43.91 |
| ATOM | 1913 | NH1 | ARG | 378 | 68.439 | 59.209 | 97.978 | 1.00 46.76 |
| ATOM | 1914 | NH2 | ARG | 378 | 69.281 | 57.087 | 97.793 | 1.00 50.80 |
| ATOM | 1915 | C | ARG | 378 | 61.948 | 56.893 | 99.321 | 1.00 25.36 |
| ATOM | 1916 | O | ARG | 378 | 62.092 | 55.926 | 98.591 | 1.00 24.57 |
| ATOM | 1917 | N | LYS | 379 | 61.047 | 57.853 | 99.100 | 1.00 28.34 |
| ATOM | 1918 | CA | LYS | 379 | 60.121 | 57.870 | 97.961 | 1.00 26.00 |
| ATOM | 1919 | CB | LYS | 379 | 58.697 | 58.107 | 98.430 | 1.00 27.01 |
| ATOM | 1920 | CG | LYS | 379 | 58.156 | 57.186 | 99.489 | 1.00 34.28 |
| ATOM | 1921 | CD | LYS | 379 | 56.738 | 57.676 | 99.824 | 1.00 46.71 |
| ATOM | 1922 | CE | LYS | 379 | 55.962 | 56.753 | 100.767 | 1.00 54.74 |
| ATOM | 1923 | NZ | LYS | 379 | 54.564 | 57.255 | 100.971 | 1.00 50.35 |
| ATOM | 1924 | C | LYS | 379 | 60.435 | 59.018 | 97.019 | 1.00 26.76 |
| ATOM | 1925 | O | LYS | 379 | 60.823 | 60.092 | 97.458 | 1.00 29.98 |
| ATOM | 1926 | N | PHE | 380 | 60.247 | 58.818 | 95.724 | 1.00 26.63 |
| ATOM | 1927 | CA | PHE | 380 | 60.501 | 59.910 | 94.790 | 1.00 26.29 |
| ATOM | 1928 | CB | PHE | 380 | 61.834 | 59.731 | 94.057 | 1.00 18.88 |
| ATOM | 1929 | CG | PHE | 380 | 63.014 | 59.584 | 94.961 | 1.00 13.37 |
| ATOM | 1930 | CD1 | PHE | 380 | 63.233 | 58.405 | 95.657 | 1.00 11.67 |
| ATOM | 1931 | CD2 | PHE | 380 | 63.924 | 60.627 | 95.108 | 1.00 16.55 |
| ATOM | 1932 | CE1 | PHE | 380 | 64.348 | 58.264 | 96.487 | 1.00 12.69 |
| ATOM | 1933 | CE2 | PHE | 380 | 65.043 | 60.495 | 95.936 | 1.00 11.78 |
| ATOM | 1934 | CZ | PHE | 380 | 65.252 | 59.306 | 96.626 | 1.00 11.17 |
| ATOM | 1935 | C | PHE | 380 | 59.387 | 60.019 | 93.759 | 1.00 28.67 |
| ATOM | 1936 | O | PHE | 380 | 58.580 | 59.107 | 93.595 | 1.00 31.55 |
| ATOM | 1937 | N | ASN | 381 | 59.343 | 61.146 | 93.067 | 1.00 30.25 |
| ATOM | 1938 | CA | ASN | 381 | 58.343 | 61.354 | 92.042 | 1.00 31.33 |
| ATOM | 1939 | CB | ASN | 381 | 57.470 | 62.550 | 92.375 | 1.00 33.57 |
| ATOM | 1940 | CG | ASN | 381 | 56.725 | 62.384 | 93.655 | 1.00 38.93 |
| ATOM | 1941 | OD1 | ASN | 381 | 55.884 | 61.493 | 93.784 | 1.00 36.52 |
| ATOM | 1942 | ND2 | ASN | 381 | 57.020 | 63.248 | 94.624 | 1.00 40.24 |
| ATOM | 1943 | C | ASN | 381 | 59.077 | 61.670 | 90.766 | 1.00 33.90 |
| ATOM | 1944 | O | ASN | 381 | 60.089 | 62.375 | 90.792 | 1.00 36.66 |
| ATOM | 1945 | N | ILE | 382 | 58.582 | 61.151 | 89.647 | 1.00 36.07 |
| ATOM | 1946 | CA | ILE | 382 | 59.197 | 61.464 | 88.371 | 1.00 36.19 |
| ATOM | 1947 | CB | ILE | 382 | 58.669 | 60.578 | 87.266 | 1.00 33.46 |
| ATOM | 1948 | CG2 | ILE | 382 | 59.435 | 60.845 | 86.000 | 1.00 32.20 |
| ATOM | 1949 | CG1 | ILE | 382 | 58.867 | 59.118 | 87.668 | 1.00 32.92 |
| ATOM | 1950 | CD1 | ILE | 382 | 58.217 | 58.131 | 86.754 | 1.00 38.75 |
| ATOM | 1951 | C | ILE | 382 | 58.705 | 62.889 | 88.226 | 1.00 38.26 |
| ATOM | 1952 | O | ILE | 382 | 57.838 | 63.314 | 88.985 | 1.00 39.98 |
| ATOM | 1953 | N | LEU | 383 | 59.209 | 63.649 | 87.272 | 1.00 39.32 |
| ATOM | 1954 | CA | LEU | 383 | 58.761 | 65.028 | 87.254 | 1.00 39.96 |
| ATOM | 1955 | CB | LEU | 383 | 59.793 | 65.856 | 88.009 | 1.00 35.43 |
| ATOM | 1956 | CG | LEU | 383 | 59.476 | 67.221 | 88.578 | 1.00 28.20 |

| | | | | | | | | |
|---|---|---|---|---|---|---|---|---|
| ATOM | 1957 | CD1 | LEU | 383 | 58.457 | 67.063 | 89.671 | 1.00 30.05 |
| ATOM | 1958 | CD2 | LEU | 383 | 60.745 | 67.821 | 89.143 | 1.00 25.53 |
| ATOM | 1959 | C | LEU | 383 | 58.521 | 65.622 | 85.885 | 1.00 45.09 |
| ATOM | 1960 | O | LEU | 383 | 57.413 | 66.090 | 85.607 | 1.00 48.97 |
| ATOM | 1961 | N | GLY | 384 | 59.559 | 65.601 | 85.046 | 1.00 46.02 |
| ATOM | 1962 | CA | GLY | 384 | 59.487 | 66.161 | 83.700 | 1.00 50.15 |
| ATOM | 1963 | C | GLY | 384 | 58.280 | 65.803 | 82.848 | 1.00 53.37 |
| ATOM | 1964 | O | GLY | 384 | 57.182 | 66.335 | 83.043 | 1.00 55.71 |
| ATOM | 1965 | N | THR | 385 | 58.478 | 64.918 | 81.879 | 1.00 53.98 |
| ATOM | 1966 | CA | THR | 385 | 57.378 | 64.496 | 81.018 | 1.00 58.55 |
| ATOM | 1967 | CB | THR | 385 | 57.742 | 64.708 | 79.518 | 1.00 57.59 |
| ATOM | 1968 | OG1 | THR | 385 | 57.957 | 66.106 | 79.265 | 1.00 53.16 |
| ATOM | 1969 | CG2 | THR | 385 | 56.621 | 64.227 | 78.626 | 1.00 59.42 |
| ATOM | 1970 | C | THR | 385 | 57.024 | 63.023 | 81.298 | 1.00 61.02 |
| ATOM | 1971 | O | THR | 385 | 57.591 | 62.109 | 80.704 | 1.00 60.96 |
| ATOM | 1972 | N | HIS | 386 | 56.081 | 62.807 | 82.213 | 1.00 61.46 |
| ATOM | 1973 | CA | HIS | 386 | 55.671 | 61.461 | 82.603 | 1.00 61.45 |
| ATOM | 1974 | CB | HIS | 386 | 54.494 | 61.510 | 83.575 | 1.00 68.04 |
| ATOM | 1975 | CG | HIS | 386 | 54.674 | 62.444 | 84.726 | 1.00 77.37 |
| ATOM | 1976 | CD2 | HIS | 386 | 55.698 | 63.260 | 85.073 | 1.00 81.75 |
| ATOM | 1977 | ND1 | HIS | 386 | 53.687 | 62.650 | 85.671 | 1.00 82.22 |
| ATOM | 1978 | CE1 | HIS | 386 | 54.094 | 63.550 | 86.543 | 1.00 83.92 |
| ATOM | 1979 | NE2 | HIS | 386 | 55.312 | 63.939 | 86.206 | 1.00 85.42 |
| ATOM | 1980 | C | HIS | 386 | 55.228 | 60.592 | 81.430 | 1.00 59.77 |
| ATOM | 1981 | O | HIS | 386 | 55.257 | 59.362 | 81.524 | 1.00 59.09 |
| ATOM | 1982 | N | THR | 387 | 54.797 | 61.224 | 80.339 | 1.00 55.81 |
| ATOM | 1983 | CA | THR | 387 | 54.289 | 60.483 | 79.183 | 1.00 51.63 |
| ATOM | 1984 | CB | THR | 387 | 52.773 | 60.691 | 79.020 | 1.00 51.51 |
| ATOM | 1985 | OG1 | THR | 387 | 52.095 | 60.250 | 80.201 | 1.00 54.34 |
| ATOM | 1986 | CG2 | THR | 387 | 52.255 | 59.912 | 77.829 | 1.00 55.32 |
| ATOM | 1987 | C | THR | 387 | 54.915 | 60.861 | 77.860 | 1.00 48.89 |
| ATOM | 1988 | O | THR | 387 | 55.344 | 61.992 | 77.677 | 1.00 52.20 |
| ATOM | 1989 | N | LYS | 388 | 54.942 | 59.910 | 76.931 | 1.00 46.57 |
| ATOM | 1990 | CA | LYS | 388 | 55.490 | 60.149 | 75.601 | 1.00 45.76 |
| ATOM | 1991 | CB | LYS | 388 | 57.015 | 60.178 | 75.649 | 1.00 41.96 |
| ATOM | 1992 | CG | LYS | 388 | 57.664 | 60.854 | 74.457 | 1.00 35.19 |
| ATOM | 1993 | CD | LYS | 388 | 59.150 | 61.018 | 74.706 | 1.00 34.53 |
| ATOM | 1994 | CE | LYS | 388 | 59.769 | 61.995 | 73.733 | 1.00 37.59 |
| ATOM | 1995 | NZ | LYS | 388 | 59.583 | 61.566 | 72.325 | 1.00 42.90 |
| ATOM | 1996 | C | LYS | 388 | 55.019 | 59.052 | 74.653 | 1.00 48.59 |
| ATOM | 1997 | O | LYS | 388 | 55.283 | 57.870 | 74.875 | 1.00 53.42 |
| ATOM | 1998 | N | VAL | 389 | 54.310 | 59.459 | 73.603 | 1.00 46.90 |
| ATOM | 1999 | CA | VAL | 389 | 53.771 | 58.550 | 72.594 | 1.00 42.32 |
| ATOM | 2000 | CB | VAL | 389 | 52.837 | 59.311 | 71.646 | 1.00 41.35 |
| ATOM | 2001 | CG1 | VAL | 389 | 52.186 | 58.350 | 70.678 | 1.00 43.11 |
| ATOM | 2002 | CG2 | VAL | 389 | 51.800 | 60.075 | 72.450 | 1.00 41.17 |
| ATOM | 2003 | C | VAL | 389 | 54.861 | 57.884 | 71.753 | 1.00 41.51 |
| ATOM | 2004 | O | VAL | 389 | 55.852 | 58.514 | 71.386 | 1.00 43.60 |
| ATOM | 2005 | N | MET | 390 | 54.679 | 56.608 | 71.436 | 1.00 38.14 |
| ATOM | 2006 | CA | MET | 390 | 55.669 | 55.911 | 70.636 | 1.00 39.84 |
| ATOM | 2007 | CB | MET | 390 | 55.632 | 54.416 | 70.935 | 1.00 39.79 |
| ATOM | 2008 | CG | MET | 390 | 56.259 | 54.066 | 72.276 | 1.00 42.83 |
| ATOM | 2009 | SD | MET | 390 | 56.520 | 52.302 | 72.548 | 1.00 39.18 |
| ATOM | 2010 | CE | MET | 390 | 54.848 | 51.749 | 72.599 | 1.00 34.80 |
| ATOM | 2011 | C | MET | 390 | 55.504 | 56.148 | 69.147 | 1.00 41.88 |
| ATOM | 2012 | O | MET | 390 | 54.393 | 56.100 | 68.631 | 1.00 45.14 |
| ATOM | 2013 | N | ASN | 391 | 56.619 | 56.410 | 68.467 | 1.00 44.60 |
| ATOM | 2014 | CA | ASN | 391 | 56.630 | 56.663 | 67.026 | 1.00 48.82 |
| ATOM | 2015 | CB | ASN | 391 | 57.211 | 58.039 | 66.699 | 1.00 54.79 |
| ATOM | 2016 | CG | ASN | 391 | 56.590 | 59.153 | 67.489 | 1.00 60.64 |
| ATOM | 2017 | OD1 | ASN | 391 | 55.379 | 59.382 | 67.432 | 1.00 65.87 |
| ATOM | 2018 | ND2 | ASN | 391 | 57.425 | 59.877 | 68.228 | 1.00 61.10 |
| ATOM | 2019 | C | ASN | 391 | 57.558 | 55.681 | 66.346 | 1.00 50.32 |
| ATOM | 2020 | O | ASN | 391 | 58.079 | 54.753 | 66.957 | 1.00 50.01 |
| ATOM | 2021 | N | MET | 392 | 57.766 | 55.928 | 65.060 | 1.00 54.16 |
| ATOM | 2022 | CA | MET | 392 | 58.689 | 55.164 | 64.237 | 1.00 60.31 |
| ATOM | 2023 | CB | MET | 392 | 57.959 | 54.368 | 63.151 | 1.00 56.19 |
| ATOM | 2024 | CG | MET | 392 | 57.230 | 53.149 | 63.684 | 1.00 56.19 |
| ATOM | 2025 | SD | MET | 392 | 56.598 | 52.065 | 62.403 | 1.00 52.44 |
| ATOM | 2026 | CE | MET | 392 | 55.515 | 53.210 | 61.556 | 1.00 56.97 |

83

| ATOM | 2027 | C | MET | 392 | 59.563 | 56.240 | 63.613 | 1.00 | 64.97 |
|---|---|---|---|---|---|---|---|---|---|
| ATOM | 2028 | O | MET | 392 | 60.567 | 55.961 | 62.960 | 1.00 | 65.93 |
| ATOM | 2029 | N | GLU | 393 | 59.164 | 57.485 | 63.858 | 1.00 | 73.18 |
| ATOM | 2030 | CA | GLU | 393 | 59.861 | 58.656 | 63.349 | 1.00 | 80.67 |
| ATOM | 2031 | CB | GLU | 393 | 58.918 | 59.866 | 63.361 | 1.00 | 80.78 |
| ATOM | 2032 | CG | GLU | 393 | 58.507 | 60.318 | 64.756 | 1.00 | 86.43 |
| ATOM | 2033 | CD | GLU | 393 | 57.511 | 61.467 | 64.751 | 1.00 | 89.63 |
| ATOM | 2034 | OE1 | GLU | 393 | 57.777 | 62.503 | 64.101 | 1.00 | 92.89 |
| ATOM | 2035 | OE2 | GLU | 393 | 56.461 | 61.339 | 65.414 | 1.00 | 90.77 |
| ATOM | 2036 | C | GLU | 393 | 61.105 | 58.957 | 64.185 | 1.00 | 85.11 |
| ATOM | 2037 | O | GLU | 393 | 62.183 | 59.193 | 63.637 | 1.00 | 86.94 |
| ATOM | 2038 | N | GLU | 394 | 60.954 | 58.942 | 65.509 | 1.00 | 90.05 |
| ATOM | 2039 | CA | GLU | 394 | 62.067 | 59.225 | 66.416 | 1.00 | 94.23 |
| ATOM | 2040 | CB | GLU | 394 | 61.709 | 58.836 | 67.858 | 1.00 | 98.44 |
| ATOM | 2041 | CG | GLU | 394 | 60.713 | 59.765 | 68.543 | 1.00 | 101.69 |
| ATOM | 2042 | CD | GLU | 394 | 60.553 | 59.459 | 70.025 | 1.00 | 102.20 |
| ATOM | 2043 | OE1 | GLU | 394 | 60.021 | 58.381 | 70.368 | 1.00 | 103.73 |
| ATOM | 2044 | OE2 | GLU | 394 | 60.974 | 60.297 | 70.849 | 1.00 | 101.48 |
| ATOM | 2045 | C | GLU | 394 | 63.382 | 58.549 | 66.037 | 1.00 | 94.97 |
| ATOM | 2046 | O | GLU | 394 | 64.416 | 59.209 | 65.923 | 1.00 | 93.34 |
| ATOM | 2047 | N | SER | 395 | 63.342 | 57.233 | 65.850 | 1.00 | 96.41 |
| ATOM | 2048 | CA | SER | 395 | 64.541 | 56.480 | 65.504 | 1.00 | 96.15 |
| ATOM | 2049 | CB | SER | 395 | 64.554 | 55.148 | 66.262 | 1.00 | 97.26 |
| ATOM | 2050 | OG | SER | 395 | 64.564 | 55.367 | 67.665 | 1.00 | 96.01 |
| ATOM | 2051 | C | SER | 395 | 64.689 | 56.230 | 64.007 | 1.00 | 94.96 |
| ATOM | 2052 | O | SER | 395 | 63.831 | 55.601 | 63.382 | 1.00 | 92.90 |
| ATOM | 2053 | N | THR | 396 | 65.789 | 56.732 | 63.445 | 1.00 | 95.40 |
| ATOM | 2054 | CA | THR | 396 | 66.090 | 56.576 | 62.023 | 1.00 | 94.03 |
| ATOM | 2055 | CB | THR | 396 | 67.533 | 57.000 | 61.736 | 1.00 | 92.59 |
| ATOM | 2058 | C | THR | 396 | 65.885 | 55.116 | 61.652 | 1.00 | 92.43 |
| ATOM | 2059 | O | THR | 396 | 65.397 | 54.794 | 60.564 | 1.00 | 92.62 |
| ATOM | 2060 | N | ASN | 397 | 66.268 | 54.236 | 62.570 | 1.00 | 90.08 |
| ATOM | 2061 | CA | ASN | 397 | 66.095 | 52.814 | 62.358 | 1.00 | 87.52 |
| ATOM | 2062 | CB | ASN | 397 | 66.661 | 52.036 | 63.541 | 1.00 | 84.94 |
| ATOM | 2066 | C | ASN | 397 | 64.586 | 52.609 | 62.255 | 1.00 | 86.47 |
| ATOM | 2067 | O | ASN | 397 | 63.847 | 52.963 | 63.177 | 1.00 | 86.04 |
| ATOM | 2068 | N | GLY | 398 | 64.130 | 52.077 | 61.122 | 1.00 | 84.13 |
| ATOM | 2069 | CA | GLY | 398 | 62.706 | 51.820 | 60.917 | 1.00 | 80.51 |
| ATOM | 2070 | C | GLY | 398 | 62.252 | 50.909 | 62.048 | 1.00 | 79.00 |
| ATOM | 2071 | O | GLY | 398 | 62.274 | 49.685 | 61.902 | 1.00 | 82.87 |
| ATOM | 2072 | N | SER | 399 | 61.855 | 51.507 | 63.171 | 1.00 | 70.42 |
| ATOM | 2073 | CA | SER | 399 | 61.423 | 50.746 | 64.342 | 1.00 | 58.90 |
| ATOM | 2074 | CB | SER | 399 | 62.651 | 50.246 | 65.116 | 1.00 | 52.07 |
| ATOM | 2076 | C | SER | 399 | 60.538 | 51.595 | 65.252 | 1.00 | 51.76 |
| ATOM | 2077 | O | SER | 399 | 60.676 | 52.817 | 65.313 | 1.00 | 48.55 |
| ATOM | 2078 | N | LEU | 400 | 59.628 | 50.940 | 65.962 | 1.00 | 43.97 |
| ATOM | 2079 | CA | LEU | 400 | 58.729 | 51.653 | 66.860 | 1.00 | 36.40 |
| ATOM | 2080 | CB | LEU | 400 | 57.435 | 50.862 | 67.029 | 1.00 | 30.85 |
| ATOM | 2081 | CG | LEU | 400 | 56.315 | 51.633 | 67.713 | 1.00 | 22.35 |
| ATOM | 2082 | CD1 | LEU | 400 | 55.780 | 52.660 | 66.755 | 1.00 | 23.86 |
| ATOM | 2083 | CD2 | LEU | 400 | 55.206 | 50.689 | 68.106 | 1.00 | 25.54 |
| ATOM | 2084 | C | LEU | 400 | 59.418 | 51.829 | 68.216 | 1.00 | 33.63 |
| ATOM | 2085 | O | LEU | 400 | 59.835 | 50.848 | 68.833 | 1.00 | 34.51 |
| ATOM | 2086 | N | ALA | 401 | 59.539 | 53.073 | 68.675 | 1.00 | 29.44 |
| ATOM | 2087 | CA | ALA | 401 | 60.199 | 53.359 | 69.948 | 1.00 | 24.05 |
| ATOM | 2088 | CB | ALA | 401 | 61.698 | 53.515 | 69.724 | 1.00 | 16.73 |
| ATOM | 2089 | C | ALA | 401 | 59.658 | 54.580 | 70.699 | 1.00 | 23.24 |
| ATOM | 2090 | O | ALA | 401 | 58.623 | 55.131 | 70.357 | 1.00 | 27.02 |
| ATOM | 2091 | N | ALA | 402 | 60.371 | 54.979 | 71.743 | 1.00 | 25.82 |
| ATOM | 2092 | CA | ALA | 402 | 59.999 | 56.128 | 72.569 | 1.00 | 26.79 |
| ATOM | 2093 | CB | ALA | 402 | 58.747 | 55.824 | 73.390 | 1.00 | 23.55 |
| ATOM | 2094 | C | ALA | 402 | 61.177 | 56.429 | 73.491 | 1.00 | 27.15 |
| ATOM | 2095 | O | ALA | 402 | 61.571 | 55.607 | 74.324 | 1.00 | 27.53 |
| ATOM | 2096 | N | GLU | 403 | 61.752 | 57.608 | 73.324 | 1.00 | 29.72 |
| ATOM | 2097 | CA | GLU | 403 | 62.890 | 57.970 | 74.131 | 1.00 | 31.33 |
| ATOM | 2098 | CB | GLU | 403 | 64.082 | 58.357 | 73.257 | 1.00 | 33.23 |
| ATOM | 2099 | CG | GLU | 403 | 65.375 | 58.477 | 74.038 | 1.00 | 37.15 |
| ATOM | 2100 | CD | GLU | 403 | 66.545 | 58.885 | 73.179 | 1.00 | 42.62 |
| ATOM | 2101 | OE1 | GLU | 403 | 66.772 | 58.244 | 72.132 | 1.00 | 49.23 |
| ATOM | 2102 | OE2 | GLU | 403 | 67.261 | 59.840 | 73.554 | 1.00 | 46.03 |

84

| ATOM | 2103 | C | GLU | 403 | 62.529 | 59.124 | 75.019 | 1.00 | 32.67 |
| ATOM | 2104 | O | GLU | 403 | 62.013 | 60.137 | 74.560 | 1.00 | 34.12 |
| ATOM | 2105 | N | PHE | 404 | 62.790 | 58.951 | 76.306 | 1.00 | 34.31 |
| ATOM | 2106 | CA | PHE | 404 | 62.516 | 59.991 | 77.264 | 1.00 | 30.64 |
| ATOM | 2107 | CB | PHE | 404 | 61.921 | 59.430 | 78.555 | 1.00 | 25.42 |
| ATOM | 2108 | CG | PHE | 404 | 60.633 | 58.707 | 78.357 | 1.00 | 21.09 |
| ATOM | 2109 | CD1 | PHE | 404 | 60.612 | 57.455 | 77.753 | 1.00 | 20.91 |
| ATOM | 2110 | CD2 | PHE | 404 | 59.432 | 59.301 | 78.721 | 1.00 | 10.39 |
| ATOM | 2111 | CE1 | PHE | 404 | 59.399 | 56.805 | 77.511 | 1.00 | 15.51 |
| ATOM | 2112 | CE2 | PHE | 404 | 58.228 | 58.672 | 78.488 | 1.00 | 14.07 |
| ATOM | 2113 | CZ | PHE | 404 | 58.203 | 57.419 | 77.880 | 1.00 | 19.09 |
| ATOM | 2114 | C | PHE | 404 | 63.803 | 60.693 | 77.591 | 1.00 | 33.68 |
| ATOM | 2115 | O | PHE | 404 | 64.877 | 60.089 | 77.699 | 1.00 | 31.58 |
| ATOM | 2116 | N | ARG | 405 | 63.664 | 61.997 | 77.725 | 1.00 | 37.56 |
| ATOM | 2117 | CA | ARG | 405 | 64.740 | 62.894 | 78.089 | 1.00 | 36.57 |
| ATOM | 2118 | CB | ARG | 405 | 65.243 | 63.608 | 76.847 | 1.00 | 31.06 |
| ATOM | 2119 | CG | ARG | 405 | 65.820 | 62.625 | 75.843 | 1.00 | 31.70 |
| ATOM | 2120 | CD | ARG | 405 | 66.020 | 63.257 | 74.492 | 1.00 | 37.04 |
| ATOM | 2121 | NE | ARG | 405 | 66.510 | 62.303 | 73.502 | 1.00 | 44.10 |
| ATOM | 2122 | CZ | ARG | 405 | 66.112 | 62.286 | 72.229 | 1.00 | 50.59 |
| ATOM | 2123 | NH1 | ARG | 405 | 65.223 | 63.178 | 71.800 | 1.00 | 49.49 |
| ATOM | 2124 | NH2 | ARG | 405 | 66.598 | 61.378 | 71.382 | 1.00 | 48.92 |
| ATOM | 2125 | C | ARG | 405 | 63.955 | 63.807 | 79.008 | 1.00 | 36.23 |
| ATOM | 2126 | O | ARG | 405 | 62.720 | 63.804 | 78.972 | 1.00 | 42.67 |
| ATOM | 2127 | N | HIS | 406 | 64.632 | 64.552 | 79.856 | 1.00 | 32.61 |
| ATOM | 2128 | CA | HIS | 406 | 63.921 | 65.439 | 80.763 | 1.00 | 37.89 |
| ATOM | 2129 | CB | HIS | 406 | 62.835 | 66.224 | 80.005 | 1.00 | 36.24 |
| ATOM | 2130 | CG | HIS | 406 | 63.249 | 66.628 | 78.622 | 1.00 | 37.87 |
| ATOM | 2131 | CD2 | HIS | 406 | 62.648 | 66.446 | 77.423 | 1.00 | 35.78 |
| ATOM | 2132 | ND1 | HIS | 406 | 64.463 | 67.225 | 78.355 | 1.00 | 37.50 |
| ATOM | 2133 | CE1 | HIS | 406 | 64.595 | 67.388 | 77.050 | 1.00 | 33.63 |
| ATOM | 2134 | NE2 | HIS | 406 | 63.508 | 66.923 | 76.463 | 1.00 | 33.52 |
| ATOM | 2135 | C | HIS | 406 | 63.305 | 64.688 | 81.956 | 1.00 | 39.83 |
| ATOM | 2136 | O | HIS | 406 | 62.456 | 65.251 | 82.654 | 1.00 | 45.48 |
| ATOM | 2137 | N | LEU | 407 | 63.702 | 63.433 | 82.198 | 1.00 | 37.15 |
| ATOM | 2138 | CA | LEU | 407 | 62.714 | 62.611 | 83.062 | 1.00 | 28.54 |
| ATOM | 2139 | CB | LEU | 407 | 62.935 | 61.117 | 82.921 | 1.00 | 26.43 |
| ATOM | 2140 | CG | LEU | 407 | 61.933 | 60.326 | 82.102 | 1.00 | 27.62 |
| ATOM | 2141 | CD1 | LEU | 407 | 62.466 | 58.932 | 81.912 | 1.00 | 27.73 |
| ATOM | 2142 | CD2 | LEU | 407 | 60.583 | 60.308 | 82.806 | 1.00 | 28.36 |
| ATOM | 2143 | C | LEU | 407 | 63.516 | 63.114 | 84.243 | 1.00 | 29.36 |
| ATOM | 2144 | O | LEU | 407 | 64.705 | 63.389 | 84.117 | 1.00 | 30.18 |
| ATOM | 2145 | N | GLN | 408 | 62.899 | 63.208 | 85.405 | 1.00 | 26.44 |
| ATOM | 2146 | CA | GLN | 408 | 63.636 | 63.764 | 86.513 | 1.00 | 24.32 |
| ATOM | 2147 | CB | GLN | 408 | 63.637 | 65.261 | 86.281 | 1.00 | 22.71 |
| ATOM | 2148 | CG | GLN | 408 | 64.374 | 66.130 | 87.229 | 1.00 | 23.57 |
| ATOM | 2149 | CD | GLN | 408 | 64.192 | 67.566 | 86.818 | 1.00 | 21.23 |
| ATOM | 2150 | OE1 | GLN | 408 | 64.601 | 67.961 | 85.725 | 1.00 | 18.17 |
| ATOM | 2151 | NE2 | GLN | 408 | 63.544 | 68.350 | 87.669 | 1.00 | 22.44 |
| ATOM | 2152 | C | GLN | 408 | 63.042 | 63.387 | 87.866 | 1.00 | 24.35 |
| ATOM | 2153 | O | GLN | 408 | 61.830 | 63.395 | 88.050 | 1.00 | 24.75 |
| ATOM | 2154 | N | LEU | 409 | 63.901 | 63.054 | 88.818 | 1.00 | 24.67 |
| ATOM | 2155 | CA | LEU | 409 | 63.433 | 62.657 | 90.138 | 1.00 | 26.17 |
| ATOM | 2156 | CB | LEU | 409 | 64.122 | 61.350 | 90.551 | 1.00 | 24.46 |
| ATOM | 2157 | CG | LEU | 409 | 63.638 | 60.013 | 89.982 | 1.00 | 25.49 |
| ATOM | 2158 | CD1 | LEU | 409 | 63.049 | 60.176 | 88.603 | 1.00 | 28.34 |
| ATOM | 2159 | CD2 | LEU | 409 | 64.807 | 59.039 | 89.982 | 1.00 | 30.52 |
| ATOM | 2160 | C | LEU | 409 | 63.631 | 63.697 | 91.236 | 1.00 | 26.03 |
| ATOM | 2161 | O | LEU | 409 | 64.647 | 64.399 | 91.280 | 1.00 | 21.11 |
| ATOM | 2162 | N | LYS | 410 | 62.647 | 63.784 | 92.124 | 1.00 | 28.79 |
| ATOM | 2163 | CA | LYS | 410 | 62.711 | 64.699 | 93.260 | 1.00 | 33.51 |
| ATOM | 2164 | CB | LYS | 410 | 61.908 | 65.972 | 92.980 | 1.00 | 33.69 |
| ATOM | 2165 | CG | LYS | 410 | 62.017 | 66.997 | 94.088 | 1.00 | 39.52 |
| ATOM | 2166 | CD | LYS | 410 | 61.243 | 68.256 | 93.771 | 1.00 | 43.40 |
| ATOM | 2167 | CE | LYS | 410 | 61.459 | 69.339 | 94.835 | 1.00 | 45.99 |
| ATOM | 2168 | NZ | LYS | 410 | 62.879 | 69.815 | 94.920 | 1.00 | 45.95 |
| ATOM | 2169 | C | LYS | 410 | 62.123 | 63.961 | 94.464 | 1.00 | 33.40 |
| ATOM | 2170 | O | LYS | 410 | 61.199 | 63.159 | 94.298 | 1.00 | 30.07 |
| ATOM | 2171 | N | GLU | 411 | 62.663 | 64.202 | 95.660 | 1.00 | 33.27 |
| ATOM | 2172 | CA | GLU | 411 | 62.142 | 63.540 | 96.861 | 1.00 | 37.76 |

85

```
ATOM   2173  CB  GLU  411      62.984  63.817  98.094  1.00 33.42
ATOM   2174  CG  GLU  411      64.102  62.878  98.333  1.00 35.86
ATOM   2175  CD  GLU  411      64.209  62.551  99.790  1.00 37.11
ATOM   2176  OE1 GLU  411      63.310  61.848 100.306  1.00 33.84
ATOM   2177  OE2 GLU  411      65.178  63.009 100.421  1.00 44.21
ATOM   2178  C   GLU  411      60.750  63.962  97.237  1.00 43.64
ATOM   2179  O   GLU  411      60.343  65.099  96.993  1.00 48.12
ATOM   2180  N   GLN  412      60.033  63.042  97.869  1.00 48.96
ATOM   2181  CA  GLN  412      58.694  63.323  98.338  1.00 55.18
ATOM   2182  CB  GLN  412      57.782  62.129  98.082  1.00 57.76
ATOM   2183  CG  GLN  412      56.308  62.442  98.255  1.00 66.63
ATOM   2184  CD  GLN  412      55.424  61.213  98.112  1.00 70.64
ATOM   2185  OE1 GLN  412      55.463  60.300  98.946  1.00 69.65
ATOM   2186  NE2 GLN  412      54.624  61.181  97.047  1.00 71.58
ATOM   2187  C   GLN  412      58.872  63.558  99.840  1.00 61.73
ATOM   2188  O   GLN  412      58.340  62.821 100.675  1.00 61.03
ATOM   2189  N   LYS  413      59.667  64.579 100.162  1.00 68.95
ATOM   2190  CA  LYS  413      59.968  64.971 101.542  1.00 74.24
ATOM   2191  CB  LYS  413      60.552  66.385 101.564  1.00 72.95
ATOM   2192  CG  LYS  413      61.811  66.598 100.747  1.00 69.38
ATOM   2193  CD  LYS  413      62.998  65.897 101.372  1.00 69.79
ATOM   2194  CE  LYS  413      64.275  66.253 100.643  1.00 65.82
ATOM   2195  NZ  LYS  413      65.464  65.653 101.286  1.00 63.52
ATOM   2196  C   LYS  413      58.685  64.976 102.361  1.00 80.17
ATOM   2197  O   LYS  413      57.793  65.782 102.095  1.00 81.79
ATOM   2198  N   ASN  414      58.586  64.105 103.359  1.00 87.09
ATOM   2199  CA  ASN  414      57.375  64.057 104.174  1.00 95.52
ATOM   2200  CB  ASN  414      56.267  63.305 103.428  1.00100.40
ATOM   2201  CG  ASN  414      55.695  64.098 102.269  1.00104.68
ATOM   2202  OD1 ASN  414      55.143  65.187 102.458  1.00106.92
ATOM   2203  ND2 ASN  414      55.819  63.557 101.061  1.00106.48
ATOM   2204  C   ASN  414      57.515  63.449 105.562  1.00 98.71
ATOM   2205  O   ASN  414      58.604  63.074 106.000  1.00 98.34
ATOM   2206  N   ALA  415      56.377  63.361 106.243  1.00102.54
ATOM   2207  CA  ALA  415      56.301  62.796 107.579  1.00106.90
ATOM   2208  CB  ALA  415      55.309  63.592 108.425  1.00105.30
ATOM   2209  C   ALA  415      55.853  61.340 107.469  1.00110.34
ATOM   2210  O   ALA  415      56.150  60.525 108.345  1.00111.70
ATOM   2211  N   GLY  416      55.142  61.025 106.384  1.00114.20
ATOM   2212  CA  GLY  416      54.635  59.670 106.128  1.00117.21
ATOM   2213  C   GLY  416      55.755  58.635 106.234  1.00118.21
ATOM   2214  O   GLY  416      55.625  57.625 106.933  1.00118.02
ATOM   2215  N   THR  417      56.851  58.896 105.526  1.00118.19
ATOM   2216  CA  THR  417      58.012  58.017 105.536  1.00117.02
ATOM   2217  CB  THR  417      58.298  57.508 104.124  1.00115.07
ATOM   2220  C   THR  417      59.199  58.816 106.069  1.00116.53
ATOM   2221  O   THR  417      60.183  59.038 105.359  1.00117.74
ATOM   2222  N   ARG  418      59.092  59.255 107.322  1.00114.62
ATOM   2223  CA  ARG  418      60.142  60.042 107.962  1.00112.22
ATOM   2224  CB  ARG  418      59.797  60.264 109.434  1.00109.92
ATOM   2231  C   ARG  418      61.509  59.368 107.837  1.00110.79
ATOM   2232  O   ARG  418      61.611  58.141 107.842  1.00111.08
ATOM   2233  N   THR  419      62.558  60.176 107.718  1.00109.21
ATOM   2234  CA  THR  419      63.916  59.658 107.601  1.00107.88
ATOM   2235  CB  THR  419      64.894  60.803 107.368  1.00106.18
ATOM   2238  C   THR  419      64.294  58.890 108.861  1.00108.21
ATOM   2239  O   THR  419      63.684  59.071 109.916  1.00109.97
ATOM   2240  N   ASN  420      65.304  58.035 108.755  1.00107.63
ATOM   2241  CA  ASN  420      65.756  57.242 109.893  1.00106.37
ATOM   2242  CB  ASN  420      65.252  55.806 109.773  1.00106.51
ATOM   2246  C   ASN  420      67.280  57.262 109.939  1.00105.90
ATOM   2247  O   ASN  420      67.879  56.966 110.971  1.00105.84
ATOM   2248  N   GLU  421      67.887  57.608 108.797  1.00105.25
ATOM   2249  CA  GLU  421      69.347  57.698 108.621  1.00104.83
ATOM   2250  CB  GLU  421      69.903  58.958 109.260  1.00106.61
ATOM   2251  CG  GLU  421      69.693  59.019 110.763  1.00109.77
ATOM   2252  CD  GLU  421      70.321  60.239 111.357  1.00110.95
ATOM   2253  OE1 GLU  421      71.544  60.428 111.183  1.00111.97
ATOM   2254  OE2 GLU  421      69.584  61.014 111.980  1.00112.24
ATOM   2255  C   GLU  421      70.089  56.511 109.226  1.00103.23
```

86

```
ATOM   2256  O    GLU  421      71.189  56.668 109.800  1.00105.43
ATOM   2257  N    GLY  422      69.476  55.346 109.140  1.00 99.96
ATOM   2258  CA   GLY  422      69.939  54.514 110.523  1.00 93.92
ATOM   2259  C    GLY  422      69.086  53.326 110.163  1.00 90.85
ATOM   2260  O    GLY  422      69.177  52.285 110.831  1.00 90.27
ATOM   2261  N    PRO  423      68.206  53.471 109.142  1.00 87.96
ATOM   2262  CD   PRO  423      67.823  54.632 108.307  1.00 87.40
ATOM   2263  CA   PRO  423      67.387  52.319 108.780  1.00 81.12
ATOM   2264  CB   PRO  423      66.407  52.906 107.774  1.00 84.06
ATOM   2265  CG   PRO  423      67.219  53.954 107.079  1.00 86.90
ATOM   2266  C    PRO  423      68.225  51.202 108.180  1.00 73.80
ATOM   2267  O    PRO  423      69.440  51.311 107.989  1.00 72.15
ATOM   2268  N    LEU  424      67.525  50.134 107.854  1.00 64.98
ATOM   2269  CA   LEU  424      68.103  48.928 107.300  1.00 57.94
ATOM   2270  CB   LEU  424      66.971  48.116 106.670  1.00 60.84
ATOM   2271  CG   LEU  424      65.753  48.073 107.613  1.00 64.48
ATOM   2272  CD1  LEU  424      64.595  47.321 106.963  1.00 68.52
ATOM   2273  CD2  LEU  424      66.142  47.424 108.944  1.00 69.23
ATOM   2274  C    LEU  424      69.279  49.053 106.317  1.00 52.33
ATOM   2275  O    LEU  424      70.154  48.189 106.299  1.00 52.98
ATOM   2276  N    ILE  425      69.330  50.119 105.523  1.00 45.49
ATOM   2277  CA   ILE  425      70.412  50.244 104.542  1.00 38.92
ATOM   2278  CB   ILE  425      70.045  49.465 103.243  1.00 39.10
ATOM   2279  CG2  ILE  425      70.129  47.960 103.469  1.00 43.38
ATOM   2280  CG1  ILE  425      68.636  49.857 102.785  1.00 34.56
ATOM   2281  CD1  ILE  425      68.132  49.053 101.609  1.00 21.80
ATOM   2282  C    ILE  425      70.824  51.663 104.129  1.00 34.34
ATOM   2283  O    ILE  425      70.013  52.581 104.138  1.00 35.19
ATOM   2284  N    VAL  426      72.095  51.818 103.766  1.00 28.78
ATOM   2285  CA   VAL  426      72.658  53.087 103.299  1.00 27.42
ATOM   2286  CB   VAL  426      74.129  52.875 102.836  1.00 24.91
ATOM   2287  CG1  VAL  426      74.654  51.094 102.113  1.00 35.41
ATOM   2288  CG2  VAL  426      74.996  52.581 104.026  1.00 26.66
ATOM   2289  C    VAL  426      71.787  53.517 102.112  1.00 28.82
ATOM   2290  O    VAL  426      71.054  52.680 101.577  1.00 30.49
ATOM   2291  N    THR  427      71.854  54.783 101.682  1.00 22.96
ATOM   2292  CA   THR  427      71.005  55.215 100.574  1.00 20.32
ATOM   2293  CB   THR  427      71.087  56.744 100.288  1.00 19.13
ATOM   2294  OG1  THR  427      72.435  57.116 100.015  1.00 30.96
ATOM   2295  CG2  THR  427      70.575  57.539 101.447  1.00 11.08
ATOM   2296  C    THR  427      71.196  54.453  99.265  1.00 23.55
ATOM   2297  O    THR  427      70.658  54.864  98.229  1.00 22.45
ATOM   2298  N    GLU  428      71.971  53.361  99.299  1.00 28.67
ATOM   2299  CA   GLU  428      72.129  52.491  98.118  1.00 28.03
ATOM   2300  CB   GLU  428      73.571  52.061  97.896  1.00 22.20
ATOM   2301  CG   GLU  428      74.399  53.108  97.169  1.00 29.62
ATOM   2302  CD   GLU  428      74.437  54.445  97.883  1.00 25.78
ATOM   2303  OE1  GLU  428      73.370  55.074  98.012  1.00 24.10
ATOM   2304  OE2  GLU  428      75.534  54.862  98.318  1.00 29.09
ATOM   2305  C    GLU  428      71.199  51.270  98.264  1.00 27.16
ATOM   2306  O    GLU  428      71.590  50.145  98.569  1.00 27.25
ATOM   2307  N    GLU  429      69.935  51.598  98.053  1.00 27.46
ATOM   2308  CA   GLU  429      68.769  50.751  98.078  1.00 24.68
ATOM   2309  CB   GLU  429      67.712  51.484  98.384  1.00 25.82
ATOM   2310  CG   GLU  429      67.788  52.974  98.586  1.00 27.46
ATOM   2311  CD   GLU  429      66.854  53.820  99.409  1.00 32.85
ATOM   2312  OE1  GLU  429      66.829  53.659 100.646  1.00 30.36
ATOM   2313  OE2  GLU  429      66.162  54.669  98.811  1.00 28.94
ATOM   2314  C    GLU  429      68.411  50.792  96.604  1.00 26.74
ATOM   2315  O    GLU  429      68.774  51.739  95.910  1.00 30.95
ATOM   2316  N    LEU  430      67.681  49.807  96.116  1.00 23.65
ATOM   2317  CA   LEU  430      67.370  49.795  94.703  1.00 19.05
ATOM   2318  CB   LEU  430      67.717  48.429  94.143  1.00 12.62
ATOM   2319  CG   LEU  430      69.150  48.019  94.485  1.00  9.85
ATOM   2320  CD1  LEU  430      69.308  46.536  94.235  1.00  7.62
ATOM   2321  CD2  LEU  430      70.162  48.849  93.695  1.00  7.97
ATOM   2322  C    LEU  430      65.920  50.133  94.410  1.00 24.17
ATOM   2323  O    LEU  430      65.010  49.681  95.102  1.00 24.79
ATOM   2324  N    HIS  431      65.729  50.941  93.372  1.00 21.35
ATOM   2325  CA   HIS  431      64.417  51.364  92.922  1.00 18.35
```

87

```
ATOM   2326  CB   HIS   431     64.357  52.878  92.922  1.00  18.74
ATOM   2327  CG   HIS   431     64.408  53.474  94.288  1.00  21.07
ATOM   2328  CD2  HIS   431     65.415  54.080  94.960  1.00  21.32
ATOM   2329  ND1  HIS   431     63.339  53.434  95.154  1.00  26.33
ATOM   2330  CE1  HIS   431     63.683  53.991  96.301  1.00  23.42
ATOM   2331  NE2  HIS   431     64.938  54.390  96.209  1.00  18.11
ATOM   2332  C    HIS   431     64.194  50.839  91.510  1.00  18.73
ATOM   2333  O    HIS   431     65.081  50.213  90.936  1.00  16.10
ATOM   2334  N    SER   432     63.005  51.078  90.957  1.00  19.42
ATOM   2335  CA   SER   432     62.710  50.636  89.601  1.00  18.24
ATOM   2336  CB   SER   432     61.922  49.319  89.599  1.00  16.89
ATOM   2337  OG   SER   432     60.559  49.526  89.943  1.00  14.21
ATOM   2338  C    SER   432     61.891  51.693  88.879  1.00  19.37
ATOM   2339  O    SER   432     61.162  52.463  89.506  1.00  22.52
ATOM   2340  N    LEU   433     62.043  51.730  87.559  1.00  20.78
ATOM   2341  CA   LEU   433     61.300  52.636  86.691  1.00  19.96
ATOM   2342  CB   LEU   433     62.240  53.379  85.757  1.00  21.54
ATOM   2343  CG   LEU   433     63.122  54.489  86.298  1.00  27.14
ATOM   2344  CD1  LEU   433     64.296  54.633  85.369  1.00  26.40
ATOM   2345  CD2  LEU   433     62.330  55.801  86.430  1.00  24.72
ATOM   2346  C    LEU   433     60.443  51.708  85.857  1.00  22.93
ATOM   2347  O    LEU   433     60.967  50.911  85.088  1.00  30.49
ATOM   2348  N    SER   434     59.133  51.786  86.010  1.00  24.71
ATOM   2349  CA   SER   434     58.258  50.918  85.239  1.00  20.49
ATOM   2350  CB   SER   434     57.156  50.353  86.134  1.00  24.34
ATOM   2351  OG   SER   434     57.692  49.840  87.347  1.00  35.39
ATOM   2352  C    SER   434     57.652  51.755  84.127  1.00  20.33
ATOM   2353  O    SER   434     57.433  52.958  84.281  1.00  24.04
ATOM   2354  N    PHE   435     57.396  51.114  82.998  1.00  20.71
ATOM   2355  CA   PHE   435     56.813  51.776  81.837  1.00  14.99
ATOM   2356  CB   PHE   435     57.811  51.747  80.693  1.00   7.92
ATOM   2357  CG   PHE   435     59.088  52.437  81.038  1.00   8.03
ATOM   2358  CD1  PHE   435     59.180  53.820  80.973  1.00  12.20
ATOM   2359  CD2  PHE   435     60.153  51.722  81.558  1.00   2.99
ATOM   2360  CE1  PHE   435     60.311  54.481  81.424  1.00  11.05
ATOM   2361  CE2  PHE   435     61.282  52.366  82.013  1.00   5.78
ATOM   2362  CZ   PHE   435     61.365  53.754  81.947  1.00  11.62
ATOM   2363  C    PHE   435     55.571  51.003  81.528  1.00  15.41
ATOM   2364  O    PHE   435     55.596  49.785  81.389  1.00  14.60
ATOM   2365  N    GLU   436     54.474  51.731  81.445  1.00  19.88
ATOM   2366  CA   GLU   436     53.182  51.129  81.218  1.00  23.43
ATOM   2367  CB   GLU   436     52.364  51.319  82.485  1.00  23.87
ATOM   2368  CG   GLU   436     51.125  50.505  82.602  1.00  29.77
ATOM   2369  CD   GLU   436     50.556  50.619  83.992  1.00  38.96
ATOM   2370  OE1  GLU   436     50.147  51.740  84.362  1.00  40.11
ATOM   2371  OE2  GLU   436     50.540  49.601  84.719  1.00  40.64
ATOM   2372  C    GLU   436     52.465  51.752  80.042  1.00  22.62
ATOM   2373  O    GLU   436     52.488  52.964  79.862  1.00  23.51
ATOM   2374  N    THR   437     51.848  50.916  79.224  1.00  23.27
ATOM   2375  CA   THR   437     51.078  51.416  78.094  1.00  26.10
ATOM   2376  CB   THR   437     51.938  51.626  76.827  1.00  30.22
ATOM   2377  OG1  THR   437     51.115  52.151  75.778  1.00  22.74
ATOM   2378  CG2  THR   437     52.571  50.313  76.376  1.00  30.56
ATOM   2379  C    THR   437     49.980  50.419  77.802  1.00  25.90
ATOM   2380  O    THR   437     49.935  49.339  78.397  1.00  24.31
ATOM   2381  N    GLN   438     49.091  50.771  76.889  1.00  25.40
ATOM   2382  CA   GLN   438     47.994  49.876  76.581  1.00  29.19
ATOM   2383  CB   GLN   438     46.845  50.147  77.555  1.00  27.69
ATOM   2384  CG   GLN   438     45.534  49.548  77.140  1.00  35.65
ATOM   2385  CD   GLN   438     44.453  49.733  78.184  1.00  41.29
ATOM   2386  OE1  GLN   438     44.273  50.827  78.740  1.00  44.99
ATOM   2387  NE2  GLN   438     43.706  48.666  78.443  1.00  43.69
ATOM   2388  C    GLN   438     47.499  49.909  75.139  1.00  28.67
ATOM   2389  O    GLN   438     47.115  50.952  74.606  1.00  28.27
ATOM   2390  N    LEU   439     47.526  48.740  74.514  1.00  30.10
ATOM   2391  CA   LEU   439     47.065  48.583  73.147  1.00  32.18
ATOM   2392  CB   LEU   439     47.656  47.308  72.545  1.00  27.24
ATOM   2393  CG   LEU   439     47.091  46.937  71.184  1.00  24.61
ATOM   2394  CD1  LEU   439     47.178  48.129  70.277  1.00  30.43
ATOM   2395  CD2  LEU   439     47.830  45.756  70.617  1.00  23.82
```

88

```
ATOM  2396  C    LEU  439    45.542  48.505  73.157  1.00  35.48
ATOM  2397  O    LEU  439    44.956  47.484  73.523  1.00  34.80
ATOM  2398  N    CYS  440    44.894  49.592  72.765  1.00  42.32
ATOM  2399  CA   CYS  440    43.445  49.602  72.754  1.00  47.98
ATOM  2400  CB   CYS  440    42.900  50.855  73.434  1.00  49.90
ATOM  2401  SG   CYS  440    41.087  50.878  73.513  1.00  63.76
ATOM  2402  C    CYS  440    42.901  49.524  71.348  1.00  47.45
ATOM  2403  O    CYS  440    43.156  50.402  70.530  1.00  45.50
ATOM  2404  N    GLN  441    42.144  48.463  71.090  1.00  50.88
ATOM  2405  CA   GLN  441    41.522  48.219  69.794  1.00  54.22
ATOM  2406  CB   GLN  441    42.454  47.372  68.918  1.00  54.30
ATOM  2407  CG   GLN  441    43.386  48.195  68.037  1.00  52.75
ATOM  2408  CD   GLN  441    44.453  47.359  67.355  1.00  52.28
ATOM  2409  OE1  GLN  441    44.213  46.216  66.959  1.00  53.22
ATOM  2410  NE2  GLN  441    45.634  47.938  67.188  1.00  52.50
ATOM  2411  C    GLN  441    40.164  47.529  69.947  1.00  55.33
ATOM  2412  O    GLN  441    39.865  46.955  70.995  1.00  55.43
ATOM  2413  N    PRO  442    39.309  47.606  68.908  1.00  57.84
ATOM  2414  CD   PRO  442    39.497  48.305  67.624  1.00  58.02
ATOM  2415  CA   PRO  442    37.981  46.981  68.938  1.00  56.57
ATOM  2416  CB   PRO  442    37.357  47.481  67.642  1.00  56.69
ATOM  2417  CG   PRO  442    38.566  47.523  66.718  1.00  56.85
ATOM  2418  C    PRO  442    38.114  45.455  68.972  1.00  56.52
ATOM  2419  O    PRO  442    38.599  44.842  68.015  1.00  56.90
ATOM  2420  N    GLY  443    37.692  44.846  70.076  1.00  56.31
ATOM  2421  CA   GLY  443    37.798  43.403  70.193  1.00  54.86
ATOM  2422  C    GLY  443    39.146  42.991  70.756  1.00  53.06
ATOM  2423  O    GLY  443    39.381  41.812  71.023  1.00  54.62
ATOM  2424  N    LEU  444    40.035  43.970  70.916  1.00  49.03
ATOM  2425  CA   LEU  444    41.368  43.748  71.474  1.00  44.32
ATOM  2426  CB   LEU  444    42.467  43.850  70.417  1.00  40.97
ATOM  2427  CG   LEU  444    43.070  42.604  69.782  1.00  36.92
ATOM  2428  CD1  LEU  444    44.221  43.055  68.911  1.00  40.25
ATOM  2429  CD2  LEU  444    43.577  41.641  70.831  1.00  33.69
ATOM  2430  C    LEU  444    41.685  44.778  72.526  1.00  42.42
ATOM  2431  O    LEU  444    41.287  45.927  72.424  1.00  43.94
ATOM  2432  N    VAL  445    42.419  44.356  73.538  1.00  41.36
ATOM  2433  CA   VAL  445    42.834  45.243  74.606  1.00  38.38
ATOM  2434  CB   VAL  445    41.742  45.476  75.669  1.00  33.59
ATOM  2435  CG1  VAL  445    42.133  46.647  76.533  1.00  30.85
ATOM  2436  CG2  VAL  445    40.407  45.708  75.029  1.00  35.52
ATOM  2437  C    VAL  445    43.966  44.511  75.287  1.00  37.27
ATOM  2438  O    VAL  445    43.806  43.365  75.722  1.00  40.30
ATOM  2439  N    ILE  446    45.119  45.149  75.366  1.00  31.70
ATOM  2440  CA   ILE  446    46.230  44.512  76.028  1.00  28.68
ATOM  2441  CB   ILE  446    47.164  43.800  75.030  1.00  26.97
ATOM  2442  CG2  ILE  446    48.173  42.971  75.804  1.00  26.27
ATOM  2443  CG1  ILE  446    46.363  42.886  74.093  1.00  25.44
ATOM  2444  CD1  ILE  446    47.210  42.201  73.044  1.00  20.66
ATOM  2445  C    ILE  446    47.010  45.593  76.740  1.00  28.63
ATOM  2446  O    ILE  446    47.129  46.710  76.240  1.00  29.22
ATOM  2447  N    ASP  447    47.521  45.273  77.921  1.00  28.33
ATOM  2448  CA   ASP  447    48.319  46.237  78.662  1.00  27.00
ATOM  2449  CB   ASP  447    47.870  46.323  80.120  1.00  31.71
ATOM  2450  CG   ASP  447    46.418  46.738  80.261  1.00  34.84
ATOM  2451  OD1  ASP  447    46.066  47.841  79.789  1.00  38.90
ATOM  2452  OD2  ASP  447    45.633  45.959  80.845  1.00  37.39
ATOM  2453  C    ASP  447    49.745  45.743  78.601  1.00  23.98
ATOM  2454  O    ASP  447    50.015  44.590  78.923  1.00  23.21
ATOM  2455  N    LEU  448    50.650  46.606  78.162  1.00  20.39
ATOM  2456  CA   LEU  448    52.058  46.254  78.068  1.00  19.56
ATOM  2457  CB   LEU  448    52.621  46.739  76.733  1.00  16.66
ATOM  2458  CG   LEU  448    51.820  46.280  75.513  1.00  21.42
ATOM  2459  CD1  LEU  448    52.180  47.121  74.298  1.00  28.41
ATOM  2460  CD2  LEU  448    52.070  44.808  75.260  1.00  27.98
ATOM  2461  C    LEU  448    52.789  46.940  79.225  1.00  21.05
ATOM  2462  O    LEU  448    52.502  48.091  79.573  1.00  21.65
ATOM  2463  N    GLU  449    53.729  46.231  79.825  1.00  18.78
ATOM  2464  CA   GLU  449    54.496  46.776  80.929  1.00  18.21
ATOM  2465  CB   GLU  449    53.795  46.463  82.250  1.00  21.06
```

89

| ATOM | 2466 | CG | GLU | 449 | 54.602 | 46.830 | 83.483 | 1.00 | 34.45 |
|------|------|-----|-----|-----|--------|--------|--------|------|-------|
| ATOM | 2467 | CD | GLU | 449 | 53.875 | 46.464 | 84.760 | 1.00 | 42.97 |
| ATOM | 2468 | OE1 | GLU | 449 | 54.435 | 46.700 | 85.855 | 1.00 | 45.69 |
| ATOM | 2469 | OE2 | GLU | 449 | 52.738 | 45.939 | 84.667 | 1.00 | 43.49 |
| ATOM | 2470 | C | GLU | 449 | 55.892 | 46.177 | 80.937 | 1.00 | 14.54 |
| ATOM | 2471 | O | GLU | 449 | 56.083 | 45.009 | 80.584 | 1.00 | 15.88 |
| ATOM | 2472 | N | THR | 450 | 56.867 | 46.976 | 81.334 | 1.00 | 8.28 |
| ATOM | 2473 | CA | THR | 450 | 58.244 | 46.502 | 81.399 | 1.00 | 10.97 |
| ATOM | 2474 | CB | THR | 450 | 58.926 | 46.518 | 80.006 | 1.00 | 12.50 |
| ATOM | 2475 | OG1 | THR | 450 | 60.300 | 46.151 | 80.136 | 1.00 | 9.41 |
| ATOM | 2476 | CG2 | THR | 450 | 58.859 | 47.894 | 79.389 | 1.00 | 17.23 |
| ATOM | 2477 | C | THR | 450 | 58.971 | 47.444 | 82.328 | 1.00 | 9.84 |
| ATOM | 2478 | O | THR | 450 | 58.573 | 48.590 | 82.461 | 1.00 | 14.29 |
| ATOM | 2479 | N | THR | 451 | 60.016 | 46.988 | 82.999 | 1.00 | 3.94 |
| ATOM | 2480 | CA | THR | 451 | 60.698 | 47.910 | 83.879 | 1.00 | 5.14 |
| ATOM | 2481 | CB | THR | 451 | 60.393 | 47.621 | 85.382 | 1.00 | 11.97 |
| ATOM | 2482 | OG1 | THR | 451 | 61.164 | 46.505 | 85.830 | 1.00 | 8.83 |
| ATOM | 2483 | CG2 | THR | 451 | 58.913 | 47.306 | 85.575 | 1.00 | 9.56 |
| ATOM | 2484 | C | THR | 451 | 62.197 | 47.886 | 83.658 | 1.00 | 5.03 |
| ATOM | 2485 | O | THR | 451 | 62.755 | 46.926 | 83.127 | 1.00 | 4.94 |
| ATOM | 2486 | N | SER | 452 | 62.850 | 48.970 | 84.046 | 1.00 | 7.72 |
| ATOM | 2487 | CA | SER | 452 | 64.287 | 49.050 | 83.902 | 1.00 | 7.53 |
| ATOM | 2488 | CB | SER | 452 | 64.759 | 50.470 | 84.132 | 1.00 | 2.99 |
| ATOM | 2489 | OG | SER | 452 | 64.402 | 50.870 | 85.443 | 1.00 | 7.13 |
| ATOM | 2490 | C | SER | 452 | 64.885 | 48.167 | 84.977 | 1.00 | 6.89 |
| ATOM | 2491 | O | SER | 452 | 64.177 | 47.669 | 85.860 | 1.00 | 8.33 |
| ATOM | 2492 | N | LEU | 453 | 66.190 | 47.959 | 84.880 | 1.00 | 5.76 |
| ATOM | 2493 | CA | LEU | 453 | 66.898 | 47.184 | 85.870 | 1.00 | 5.54 |
| ATOM | 2494 | CB | LEU | 453 | 68.346 | 46.973 | 85.427 | 1.00 | 7.29 |
| ATOM | 2495 | CG | LEU | 453 | 68.681 | 46.158 | 84.179 | 1.00 | 2.99 |
| ATOM | 2496 | CD1 | LEU | 453 | 70.077 | 46.500 | 83.711 | 1.00 | 2.99 |
| ATOM | 2497 | CD2 | LEU | 453 | 68.570 | 44.680 | 84.484 | 1.00 | 2.99 |
| ATOM | 2498 | C | LEU | 453 | 66.860 | 48.102 | 87.100 | 1.00 | 10.51 |
| ATOM | 2499 | O | LEU | 453 | 66.633 | 49.311 | 86.990 | 1.00 | 9.59 |
| ATOM | 2500 | N | PRO | 454 | 67.070 | 47.546 | 88.289 | 1.00 | 13.03 |
| ATOM | 2501 | CD | PRO | 454 | 67.373 | 46.170 | 88.690 | 1.00 | 16.37 |
| ATOM | 2502 | CA | PRO | 454 | 67.040 | 48.414 | 89.461 | 1.00 | 13.53 |
| ATOM | 2503 | CB | PRO | 454 | 67.491 | 47.479 | 90.577 | 1.00 | 19.76 |
| ATOM | 2504 | CG | PRO | 454 | 68.326 | 46.440 | 89.821 | 1.00 | 24.39 |
| ATOM | 2505 | C | PRO | 454 | 67.961 | 49.616 | 89.302 | 1.00 | 9.03 |
| ATOM | 2506 | O | PRO | 454 | 69.066 | 49.508 | 88.772 | 1.00 | 10.84 |
| ATOM | 2507 | N | VAL | 455 | 67.478 | 50.751 | 89.788 | 1.00 | 13.10 |
| ATOM | 2508 | CA | VAL | 455 | 68.159 | 52.046 | 89.757 | 1.00 | 11.90 |
| ATOM | 2509 | CB | VAL | 455 | 67.161 | 53.116 | 89.211 | 1.00 | 10.38 |
| ATOM | 2510 | CG1 | VAL | 455 | 67.604 | 54.508 | 89.557 | 1.00 | 20.03 |
| ATOM | 2511 | CG2 | VAL | 455 | 67.051 | 52.987 | 87.710 | 1.00 | 18.72 |
| ATOM | 2512 | C | VAL | 455 | 68.662 | 52.463 | 91.157 | 1.00 | 8.60 |
| ATOM | 2513 | O | VAL | 455 | 68.222 | 51.928 | 92.172 | 1.00 | 10.89 |
| ATOM | 2514 | N | VAL | 456 | 69.600 | 53.398 | 91.202 | 1.00 | 6.74 |
| ATOM | 2515 | CA | VAL | 456 | 70.122 | 53.926 | 92.461 | 1.00 | 8.39 |
| ATOM | 2516 | CB | VAL | 456 | 71.627 | 53.594 | 92.639 | 1.00 | 6.61 |
| ATOM | 2517 | CG1 | VAL | 456 | 72.257 | 54.461 | 93.733 | 1.00 | 2.99 |
| ATOM | 2518 | CG2 | VAL | 456 | 71.769 | 52.145 | 93.003 | 1.00 | 4.38 |
| ATOM | 2519 | C | VAL | 456 | 69.945 | 55.441 | 92.416 | 1.00 | 9.81 |
| ATOM | 2520 | O | VAL | 456 | 70.521 | 56.099 | 91.554 | 1.00 | 13.27 |
| ATOM | 2521 | N | VAL | 457 | 69.158 | 56.005 | 93.331 | 1.00 | 9.21 |
| ATOM | 2522 | CA | VAL | 457 | 68.938 | 57.454 | 93.312 | 1.00 | 8.57 |
| ATOM | 2523 | CB | VAL | 457 | 67.462 | 57.800 | 93.668 | 1.00 | 6.82 |
| ATOM | 2524 | CG1 | VAL | 457 | 67.242 | 59.295 | 93.590 | 1.00 | 5.32 |
| ATOM | 2525 | CG2 | VAL | 457 | 66.503 | 57.078 | 92.720 | 1.00 | 9.52 |
| ATOM | 2526 | C | VAL | 457 | 69.859 | 58.218 | 94.256 | 1.00 | 7.61 |
| ATOM | 2527 | O | VAL | 457 | 69.891 | 57.924 | 95.445 | 1.00 | 8.74 |
| ATOM | 2528 | N | ILE | 458 | 70.607 | 59.192 | 93.734 | 1.00 | 8.04 |
| ATOM | 2529 | CA | ILE | 458 | 71.500 | 59.998 | 94.582 | 1.00 | 10.91 |
| ATOM | 2530 | CB | ILE | 458 | 72.976 | 59.865 | 94.187 | 1.00 | 10.01 |
| ATOM | 2531 | CG2 | ILE | 458 | 73.487 | 58.486 | 94.539 | 1.00 | 6.77 |
| ATOM | 2532 | CG1 | ILE | 458 | 73.149 | 60.247 | 92.718 | 1.00 | 9.10 |
| ATOM | 2533 | CD1 | ILE | 458 | 74.599 | 60.306 | 92.302 | 1.00 | 5.34 |
| ATOM | 2534 | C | ILE | 458 | 71.179 | 61.493 | 94.533 | 1.00 | 13.93 |
| ATOM | 2535 | O | ILE | 458 | 70.474 | 61.943 | 93.630 | 1.00 | 21.61 |

90

```
ATOM   2536  N   SER   459      71.697  62.266  95.490  1.00 13.16
ATOM   2537  CA  SER   459      71.439  63.704  95.488  1.00 13.83
ATOM   2538  CB  SER   459      70.878  64.176  96.836  1.00 16.68
ATOM   2539  OG  SER   459      71.827  64.052  97.874  1.00 17.40
ATOM   2540  C   SER   459      72.686  64.502  95.157  1.00 12.46
ATOM   2541  O   SER   459      72.603  65.661  94.786  1.00 14.57
ATOM   2542  N   ASN   460      73.848  63.885  95.289  1.00 14.66
ATOM   2543  CA  ASN   460      75.088  64.576  94.981  1.00 18.40
ATOM   2544  CB  ASN   460      75.737  65.076  96.261  1.00 17.64
ATOM   2545  CG  ASN   460      76.798  66.118  95.991  1.00 25.74
ATOM   2546  OD1 ASN   460      77.793  65.861  95.292  1.00 26.74
ATOM   2547  ND2 ASN   460      76.586  67.318  96.532  1.00 25.46
ATOM   2548  C   ASN   460      76.059  63.661  94.227  1.00 19.49
ATOM   2549  O   ASN   460      76.253  62.501  94.594  1.00 18.25
ATOM   2550  N   VAL   461      76.685  64.183  93.180  1.00 19.41
ATOM   2551  CA  VAL   461      77.590  63.365  92.395  1.00 20.99
ATOM   2552  CB  VAL   461      78.245  64.167  91.249  1.00 21.32
ATOM   2553  CG1 VAL   461      78.935  63.218  90.292  1.00 26.23
ATOM   2554  CG2 VAL   461      77.189  64.963  90.485  1.00 34.86
ATOM   2555  C   VAL   461      78.672  62.762  93.266  1.00 18.92
ATOM   2556  O   VAL   461      79.446  61.918  92.811  1.00 22.30
ATOM   2557  N   SER   462      78.731  63.173  94.528  1.00 16.27
ATOM   2558  CA  SER   462      79.755  62.623  95.412  1.00 17.66
ATOM   2559  CB  SER   462      79.921  63.483  96.644  1.00 14.55
ATOM   2560  OG  SER   462      78.730  63.447  97.397  1.00 24.91
ATOM   2561  C   SER   462      79.315  61.244  95.836  1.00 16.50
ATOM   2562  O   SER   462      80.113  60.436  96.290  1.00 22.25
ATOM   2563  N   GLN   463      78.024  60.988  95.680  1.00 19.76
ATOM   2564  CA  GLN   463      77.433  59.707  96.032  1.00 18.42
ATOM   2565  CB  GLN   463      75.996  59.910  96.499  1.00  8.90
ATOM   2566  CG  GLN   463      75.842  60.894  97.603  1.00  8.83
ATOM   2567  CD  GLN   463      74.426  60.934  98.116  1.00 14.77
ATOM   2568  OE1 GLN   463      73.492  61.176  97.346  1.00 12.51
ATOM   2569  NE2 GLN   463      74.248  60.693  99.427  1.00 14.36
ATOM   2570  C   GLN   463      77.400  58.771  94.825  1.00 20.75
ATOM   2571  O   GLN   463      76.786  57.710  94.880  1.00 24.19
ATOM   2572  N   LEU   464      78.045  59.154  93.733  1.00 20.05
ATOM   2573  CA  LEU   464      77.988  58.322  92.551  1.00 19.85
ATOM   2574  CB  LEU   464      78.155  59.200  91.309  1.00 21.18
ATOM   2575  CG  LEU   464      78.237  58.569  89.922  1.00 23.31
ATOM   2576  CD1 LEU   464      77.848  59.603  88.886  1.00 23.93
ATOM   2577  CD2 LEU   464      79.658  58.048  89.669  1.00 26.18
ATOM   2578  C   LEU   464      78.958  57.146  92.567  1.00 20.90
ATOM   2579  O   LEU   464      78.574  56.011  92.263  1.00 22.06
ATOM   2580  N   PRO   465      80.225  57.386  92.925  1.00 19.34
ATOM   2581  CD  PRO   465      80.938  58.597  93.337  1.00 19.16
ATOM   2582  CA  PRO   465      81.141  56.252  92.944  1.00 16.62
ATOM   2583  CB  PRO   465      82.428  56.873  93.475  1.00  4.24
ATOM   2584  CG  PRO   465      81.918  57.998  94.316  1.00 18.18
ATOM   2585  C   PRO   465      80.603  55.138  93.838  1.00 18.12
ATOM   2586  O   PRO   465      80.751  53.956  93.529  1.00 23.17
ATOM   2587  N   SER   466      79.953  55.508  94.932  1.00 19.30
ATOM   2588  CA  SER   466      79.421  54.498  95.839  1.00 21.24
ATOM   2589  CB  SER   466      79.062  55.141  97.177  1.00 21.39
ATOM   2590  OG  SER   466      78.644  54.162  98.106  1.00 30.76
ATOM   2591  C   SER   466      78.195  53.817  95.223  1.00 20.72
ATOM   2592  O   SER   466      77.988  52.602  95.361  1.00 19.04
ATOM   2593  N   GLY   467      77.381  54.611  94.543  1.00 20.30
ATOM   2594  CA  GLY   467      76.202  54.071  93.904  1.00 18.36
ATOM   2595  C   GLY   467      76.602  53.100  92.809  1.00 16.20
ATOM   2596  O   GLY   467      75.980  52.044  92.642  1.00 17.52
ATOM   2597  N   TRP   468      77.648  53.445  92.064  1.00 11.82
ATOM   2598  CA  TRP   468      78.098  52.585  90.986  1.00 11.12
ATOM   2599  CB  TRP   468      79.284  53.221  90.265  1.00 12.38
ATOM   2600  CG  TRP   468      79.745  52.437  89.071  1.00 12.58
ATOM   2601  CD2 TRP   468      78.963  52.071  87.937  1.00 11.82
ATOM   2602  CE2 TRP   468      79.793  51.322  87.080  1.00 13.53
ATOM   2603  CE3 TRP   468      77.638  52.298  87.559  1.00 13.59
ATOM   2604  CD1 TRP   468      80.988  51.912  88.864  1.00  7.83
ATOM   2605  NE1 TRP   468      81.026  51.242  87.675  1.00  8.07
```

91

```
ATOM   2606  CZ2 TRP   468      79.342  50.797  85.860  1.00 14.54
ATOM   2607  CZ3 TRP   468      77.189  51.776  86.345  1.00 18.05
ATOM   2608  CH2 TRP   468      78.041  51.034  85.513  1.00 14.64
ATOM   2609  C   TRP   468      78.493  51.238  91.566  1.00 10.44
ATOM   2610  O   TRP   468      78.132  50.185  91.043  1.00 14.09
ATOM   2611  N   ALA   469      79.237  51.271  92.661  1.00 13.55
ATOM   2612  CA  ALA   469      79.664  50.037  93.298  1.00 15.28
ATOM   2613  CB  ALA   469      80.238  50.329  94.678  1.00  9.42
ATOM   2614  C   ALA   469      78.497  49.061  93.414  1.00 12.95
ATOM   2615  O   ALA   469      78.640  47.886  93.106  1.00 13.69
ATOM   2616  N   SER   470      77.341  49.564  93.838  1.00 12.21
ATOM   2617  CA  SER   470      76.153  48.734  94.029  1.00 10.10
ATOM   2618  CB  SER   470      75.041  49.547  94.683  1.00  7.12
ATOM   2619  OG  SER   470      75.390  49.904  96.008  1.00 16.69
ATOM   2620  C   SER   470      75.622  48.099  92.764  1.00 11.73
ATOM   2621  O   SER   470      75.195  46.945  92.776  1.00  9.84
ATOM   2622  N   ILE   471      75.637  48.859  91.676  1.00 15.27
ATOM   2623  CA  ILE   471      75.158  48.374  90.389  1.00 13.31
ATOM   2624  CB  ILE   471      74.870  49.568  89.465  1.00 10.04
ATOM   2625  CG2 ILE   471      74.496  49.119  88.072  1.00  9.87
ATOM   2626  CG1 ILE   471      73.716  50.349  90.066  1.00 11.74
ATOM   2627  CD1 ILE   471      73.308  51.524  89.288  1.00 20.79
ATOM   2628  C   ILE   471      76.145  47.379  89.764  1.00 17.11
ATOM   2629  O   ILE   471      75.744  46.503  88.980  1.00 22.71
ATOM   2630  N   LEU   472      77.429  47.499  90.101  1.00 15.66
ATOM   2631  CA  LEU   472      78.389  46.534  89.585  1.00 19.04
ATOM   2632  CB  LEU   472      79.829  46.893  89.955  1.00 18.23
ATOM   2633  CG  LEU   472      80.512  48.135  89.393  1.00 23.42
ATOM   2634  CD1 LEU   472      81.981  48.126  89.822  1.00 23.19
ATOM   2635  CD2 LEU   472      80.428  48.133  87.879  1.00 26.02
ATOM   2636  C   LEU   472      78.039  45.237  90.296  1.00 20.24
ATOM   2637  O   LEU   472      77.856  44.192  89.683  1.00 25.84
ATOM   2638  N   TRP   473      77.918  45.342  91.612  1.00 17.57
ATOM   2639  CA  TRP   473      77.638  44.212  92.469  1.00 14.10
ATOM   2640  CB  TRP   473      77.713  44.671  93.912  1.00  9.58
ATOM   2641  CG  TRP   473      78.047  43.597  94.856  1.00 11.53
ATOM   2642  CD2 TRP   473      79.359  43.160  95.204  1.00  9.32
ATOM   2643  CE2 TRP   473      79.220  42.130  96.164  1.00  7.60
ATOM   2644  CE3 TRP   473      80.645  43.543  94.801  1.00  5.25
ATOM   2645  CD1 TRP   473      77.182  42.836  95.582  1.00 14.14
ATOM   2646  NE1 TRP   473      77.877  41.950  96.376  1.00 15.87
ATOM   2647  CZ2 TRP   473      80.316  41.475  96.733  1.00  6.93
ATOM   2648  CZ3 TRP   473      81.736  42.898  95.363  1.00  8.03
ATOM   2649  CH2 TRP   473      81.565  41.873  96.322  1.00  6.63
ATOM   2650  C   TRP   473      76.293  43.592  92.177  1.00 16.96
ATOM   2651  O   TRP   473      76.114  42.370  92.234  1.00 20.32
ATOM   2652  N   TYR   474      75.332  44.428  91.846  1.00 18.22
ATOM   2653  CA  TYR   474      74.023  43.894  91.552  1.00 18.53
ATOM   2654  CB  TYR   474      73.031  45.005  91.298  1.00 22.21
ATOM   2655  CG  TYR   474      71.660  44.449  91.132  1.00 22.29
ATOM   2656  CD1 TYR   474      70.958  44.005  92.235  1.00 23.56
ATOM   2657  CE1 TYR   474      69.740  43.410  92.096  1.00 26.50
ATOM   2658  CD2 TYR   474      71.100  44.279  89.866  1.00 19.61
ATOM   2659  CE2 TYR   474      69.874  43.678  89.708  1.00 16.55
ATOM   2660  CZ  TYR   474      69.206  43.244  90.832  1.00 25.96
ATOM   2661  OH  TYR   474      68.012  42.616  90.733  1.00 25.10
ATOM   2662  C   TYR   474      74.075  43.034  90.306  1.00 19.18
ATOM   2663  O   TYR   474      73.887  41.822  90.364  1.00 22.90
ATOM   2664  N   ASN   475      74.334  43.688  89.178  1.00 15.02
ATOM   2665  CA  ASN   475      74.394  43.034  87.881  1.00 14.76
ATOM   2666  CB  ASN   475      74.592  44.097  86.818  1.00 16.93
ATOM   2667  CG  ASN   475      73.459  45.095  86.793  1.00 16.74
ATOM   2668  OD1 ASN   475      72.391  44.816  86.259  1.00 17.75
ATOM   2669  ND2 ASN   475      73.674  46.255  87.402  1.00 13.07
ATOM   2670  C   ASN   475      75.476  41.968  87.776  1.00 19.28
ATOM   2671  O   ASN   475      75.405  41.063  86.939  1.00 15.61
ATOM   2672  N   MET   476      76.485  42.065  88.627  1.00 20.59
ATOM   2673  CA  MET   476      77.537  41.083  88.605  1.00 18.15
ATOM   2674  CB  MET   476      78.731  41.564  89.416  1.00 18.72
ATOM   2675  CG  MET   476      79.997  40.789  89.131  1.00 24.27
```

| ATOM | 2676 | SD | MET | 476 | 81.292 | 41.109 | 90.326 | 1.00 | 34.28 |
|------|------|-----|-----|-----|--------|--------|--------|------|-------|
| ATOM | 2677 | CE | MET | 476 | 81.311 | 42.898 | 90.316 | 1.00 | 28.63 |
| ATOM | 2678 | C | MET | 476 | 76.966 | 39.809 | 89.227 | 1.00 | 20.87 |
| ATOM | 2679 | O | MET | 476 | 77.350 | 38.703 | 86.855 | 1.00 | 22.54 |
| ATOM | 2680 | N | LEU | 477 | 76.026 | 39.949 | 90.155 | 1.00 | 22.91 |
| ATOM | 2681 | CA | LEU | 477 | 75.479 | 38.759 | 90.797 | 1.00 | 28.10 |
| ATOM | 2682 | CB | LEU | 477 | 75.886 | 38.744 | 92.271 | 1.00 | 24.65 |
| ATOM | 2683 | CG | LEU | 477 | 77.396 | 38.778 | 92.515 | 1.00 | 24.07 |
| ATOM | 2684 | CD1 | LEU | 477 | 77.697 | 38.774 | 93.997 | 1.00 | 21.65 |
| ATOM | 2685 | CD2 | LEU | 477 | 78.029 | 37.591 | 91.851 | 1.00 | 19.29 |
| ATOM | 2686 | C | LEU | 477 | 73.983 | 38.489 | 90.698 | 1.00 | 32.48 |
| ATOM | 2687 | O | LEU | 477 | 73.459 | 37.709 | 91.486 | 1.00 | 32.84 |
| ATOM | 2688 | N | VAL | 478 | 73.291 | 39.106 | 89.742 | 1.00 | 39.03 |
| ATOM | 2689 | CA | VAL | 478 | 71.846 | 38.885 | 89.584 | 1.00 | 44.63 |
| ATOM | 2690 | CB | VAL | 478 | 71.048 | 40.021 | 90.246 | 1.00 | 40.69 |
| ATOM | 2691 | CG1 | VAL | 478 | 69.561 | 39.803 | 90.055 | 1.00 | 40.11 |
| ATOM | 2692 | CG2 | VAL | 478 | 71.374 | 40.080 | 91.717 | 1.00 | 36.70 |
| ATOM | 2693 | C | VAL | 478 | 71.435 | 38.768 | 88.108 | 1.00 | 50.69 |
| ATOM | 2694 | O | VAL | 478 | 72.178 | 39.181 | 87.224 | 1.00 | 53.37 |
| ATOM | 2695 | N | ALA | 479 | 70.262 | 38.192 | 87.845 | 1.00 | 57.24 |
| ATOM | 2696 | CA | ALA | 479 | 69.765 | 38.022 | 86.476 | 1.00 | 63.60 |
| ATOM | 2697 | CB | ALA | 479 | 70.207 | 36.679 | 85.928 | 1.00 | 58.03 |
| ATOM | 2698 | C | ALA | 479 | 68.244 | 38.120 | 86.417 | 1.00 | 70.27 |
| ATOM | 2699 | O | ALA | 479 | 67.655 | 38.212 | 85.343 | 1.00 | 74.30 |
| ATOM | 2700 | N | GLU | 480 | 67.621 | 38.092 | 87.586 | 1.00 | 77.20 |
| ATOM | 2701 | CA | GLU | 480 | 66.483 | 36.606 | 87.816 | 1.00 | 81.95 |
| ATOM | 2702 | CB | GLU | 480 | 66.437 | 35.862 | 89.153 | 1.00 | 83.92 |
| ATOM | 2703 | CG | GLU | 480 | 67.827 | 35.476 | 89.635 | 1.00 | 87.80 |
| ATOM | 2704 | CD | GLU | 480 | 67.837 | 34.912 | 91.029 | 1.00 | 90.76 |
| ATOM | 2705 | OE1 | GLU | 480 | 67.263 | 35.559 | 91.934 | 1.00 | 92.09 |
| ATOM | 2706 | OE2 | GLU | 480 | 68.436 | 33.832 | 91.222 | 1.00 | 92.61 |
| ATOM | 2707 | C | GLU | 480 | 65.539 | 37.800 | 87.884 | 1.00 | 83.13 |
| ATOM | 2708 | O | GLU | 480 | 65.984 | 38.943 | 87.743 | 1.00 | 83.93 |
| ATOM | 2709 | N | PRO | 481 | 64.218 | 37.559 | 88.062 | 1.00 | 83.98 |
| ATOM | 2710 | CD | PRO | 481 | 63.422 | 36.334 | 88.222 | 1.00 | 83.97 |
| ATOM | 2711 | CA | PRO | 481 | 63.342 | 38.733 | 88.152 | 1.00 | 82.98 |
| ATOM | 2712 | CB | PRO | 481 | 61.991 | 38.114 | 88.521 | 1.00 | 83.21 |
| ATOM | 2713 | CG | PRO | 481 | 62.399 | 36.809 | 89.212 | 1.00 | 84.59 |
| ATOM | 2714 | C | PRO | 481 | 64.051 | 39.418 | 89.316 | 1.00 | 80.27 |
| ATOM | 2715 | O | PRO | 481 | 64.472 | 38.744 | 90.264 | 1.00 | 80.00 |
| ATOM | 2716 | N | ARG | 482 | 64.203 | 40.730 | 89.280 | 1.00 | 74.38 |
| ATOM | 2717 | CA | ARG | 482 | 65.021 | 41.289 | 90.326 | 1.00 | 68.21 |
| ATOM | 2718 | CB | ARG | 482 | 66.094 | 42.178 | 89.692 | 1.00 | 74.75 |
| ATOM | 2719 | CG | ARG | 482 | 65.778 | 41.944 | 88.421 | 1.00 | 75.98 |
| ATOM | 2720 | CD | ARG | 482 | 65.643 | 42.016 | 87.235 | 1.00 | 76.94 |
| ATOM | 2721 | NE | ARG | 482 | 66.107 | 42.651 | 86.009 | 1.00 | 80.59 |
| ATOM | 2722 | CZ | ARG | 482 | 66.030 | 42.098 | 84.801 | 1.00 | 83.27 |
| ATOM | 2723 | NH1 | ARG | 482 | 65.500 | 40.889 | 84.652 | 1.00 | 85.13 |
| ATOM | 2724 | NH2 | ARG | 482 | 66.510 | 42.740 | 83.741 | 1.00 | 83.46 |
| ATOM | 2725 | C | ARG | 482 | 64.592 | 41.895 | 91.641 | 1.00 | 61.78 |
| ATOM | 2726 | O | ARG | 482 | 63.682 | 42.724 | 91.743 | 1.00 | 65.17 |
| ATOM | 2727 | N | ASN | 483 | 65.369 | 41.446 | 92.628 | 1.00 | 50.99 |
| ATOM | 2728 | CA | ASN | 483 | 65.312 | 41.756 | 94.057 | 1.00 | 42.36 |
| ATOM | 2729 | CB | ASN | 483 | 66.133 | 40.660 | 94.764 | 1.00 | 43.27 |
| ATOM | 2730 | CG | ASN | 483 | 66.282 | 40.899 | 96.251 | 1.00 | 46.70 |
| ATOM | 2731 | OD1 | ASN | 483 | 67.069 | 40.215 | 96.908 | 1.00 | 50.86 |
| ATOM | 2732 | ND2 | ASN | 483 | 65.524 | 41.847 | 96.795 | 1.00 | 43.91 |
| ATOM | 2733 | C | ASN | 483 | 65.808 | 43.102 | 94.519 | 1.00 | 34.50 |
| ATOM | 2734 | O | ASN | 483 | 67.009 | 43.304 | 94.680 | 1.00 | 32.10 |
| ATOM | 2735 | N | LEU | 484 | 64.881 | 44.011 | 94.795 | 1.00 | 28.52 |
| ATOM | 2736 | CA | LEU | 484 | 65.237 | 45.349 | 95.247 | 1.00 | 24.56 |
| ATOM | 2737 | CB | LEU | 484 | 64.058 | 46.294 | 95.065 | 1.00 | 23.03 |
| ATOM | 2738 | CG | LEU | 484 | 63.433 | 46.399 | 93.678 | 1.00 | 18.83 |
| ATOM | 2739 | CD1 | LEU | 484 | 62.331 | 47.465 | 93.677 | 1.00 | 11.34 |
| ATOM | 2740 | CD2 | LEU | 484 | 64.505 | 46.755 | 92.693 | 1.00 | 22.14 |
| ATOM | 2741 | C | LEU | 484 | 65.681 | 45.395 | 96.710 | 1.00 | 24.68 |
| ATOM | 2742 | O | LEU | 484 | 65.890 | 46.475 | 97.265 | 1.00 | 21.85 |
| ATOM | 2743 | N | SER | 485 | 65.805 | 44.228 | 97.339 | 1.00 | 26.46 |
| ATOM | 2744 | CA | SER | 485 | 66.247 | 44.135 | 98.742 | 1.00 | 24.10 |
| ATOM | 2745 | CB | SER | 485 | 65.259 | 43.335 | 99.597 | 1.00 | 26.60 |

93

| ATOM | 2746 | OG | SER | 485 | 63.976 | 43.927 | 99.600 | 1.00 | 24.78 |
| ATOM | 2747 | C | SER | 485 | 67.588 | 43.420 | 98.735 | 1.00 | 21.38 |
| ATOM | 2748 | O | SER | 485 | 68.079 | 42.972 | 99.763 | 1.00 | 18.51 |
| ATOM | 2749 | N | PHE | 486 | 68.160 | 43.322 | 97.543 | 1.00 | 19.23 |
| ATOM | 2750 | CA | PHE | 486 | 69.440 | 42.681 | 97.332 | 1.00 | 18.70 |
| ATOM | 2751 | CB | PHE | 486 | 70.035 | 43.138 | 96.011 | 1.00 | 14.88 |
| ATOM | 2752 | CG | PHE | 486 | 71.313 | 42.443 | 95.642 | 1.00 | 12.45 |
| ATOM | 2753 | CD1 | PHE | 486 | 71.295 | 41.149 | 95.130 | 1.00 | 2.99 |
| ATOM | 2754 | CD2 | PHE | 486 | 72.529 | 43.108 | 95.742 | 1.00 | 9.82 |
| ATOM | 2755 | CE1 | PHE | 486 | 72.456 | 40.534 | 94.709 | 1.00 | 2.99 |
| ATOM | 2756 | CE2 | PHE | 486 | 73.707 | 42.496 | 95.321 | 1.00 | 10.70 |
| ATOM | 2757 | CZ | PHE | 486 | 73.667 | 41.208 | 94.800 | 1.00 | 9.95 |
| ATOM | 2758 | C | PHE | 486 | 70.434 | 42.984 | 98.433 | 1.00 | 20.87 |
| ATOM | 2759 | O | PHE | 486 | 70.981 | 42.078 | 99.042 | 1.00 | 24.94 |
| ATOM | 2760 | N | PHE | 487 | 70.669 | 44.276 | 98.703 | 1.00 | 22.81 |
| ATOM | 2761 | CA | PHE | 487 | 71.649 | 44.632 | 99.731 | 1.00 | 25.79 |
| ATOM | 2762 | CB | PHE | 487 | 72.132 | 46.078 | 99.541 | 1.00 | 17.94 |
| ATOM | 2763 | CG | PHE | 487 | 72.868 | 46.273 | 98.263 | 1.00 | 20.22 |
| ATOM | 2764 | CD1 | PHE | 487 | 72.232 | 46.794 | 97.146 | 1.00 | 19.37 |
| ATOM | 2765 | CD2 | PHE | 487 | 74.172 | 45.808 | 98.131 | 1.00 | 22.89 |
| ATOM | 2766 | CE1 | PHE | 487 | 72.880 | 46.845 | 95.908 | 1.00 | 21.04 |
| ATOM | 2767 | CE2 | PHE | 487 | 74.829 | 45.853 | 96.900 | 1.00 | 19.94 |
| ATOM | 2768 | CZ | PHE | 487 | 74.176 | 46.374 | 95.786 | 1.00 | 20.07 |
| ATOM | 2769 | C | PHE | 487 | 71.307 | 44.361 | 101.195 | 1.00 | 23.78 |
| ATOM | 2770 | O | PHE | 487 | 72.107 | 44.654 | 102.080 | 1.00 | 21.23 |
| ATOM | 2771 | N | LEU | 488 | 70.135 | 43.804 | 101.464 | 1.00 | 20.84 |
| ATOM | 2772 | CA | LEU | 488 | 69.829 | 42.466 | 102.840 | 1.00 | 24.73 |
| ATOM | 2773 | CB | LEU | 488 | 68.349 | 43.158 | 103.015 | 1.00 | 17.11 |
| ATOM | 2774 | CG | LEU | 488 | 67.467 | 44.397 | 103.050 | 1.00 | 17.56 |
| ATOM | 2775 | CD1 | LEU | 488 | 66.024 | 43.950 | 103.012 | 1.00 | 19.95 |
| ATOM | 2776 | CD2 | LEU | 488 | 67.782 | 45.251 | 104.300 | 1.00 | 9.73 |
| ATOM | 2777 | C | LEU | 488 | 70.658 | 42.231 | 103.173 | 1.00 | 28.27 |
| ATOM | 2778 | O | LEU | 488 | 70.859 | 41.890 | 104.341 | 1.00 | 29.34 |
| ATOM | 2779 | N | THR | 489 | 71.151 | 41.577 | 102.128 | 1.00 | 31.30 |
| ATOM | 2780 | CA | THR | 489 | 71.950 | 40.373 | 102.265 | 1.00 | 33.91 |
| ATOM | 2781 | CB | THR | 489 | 71.050 | 39.151 | 102.410 | 1.00 | 37.88 |
| ATOM | 2782 | OG1 | THR | 489 | 70.362 | 39.214 | 103.666 | 1.00 | 40.91 |
| ATOM | 2783 | CG2 | THR | 489 | 71.870 | 37.864 | 102.336 | 1.00 | 44.83 |
| ATOM | 2784 | C | THR | 489 | 72.814 | 40.218 | 101.030 | 1.00 | 34.22 |
| ATOM | 2785 | O | THR | 489 | 72.593 | 39.326 | 100.206 | 1.00 | 37.77 |
| ATOM | 2786 | N | PRO | 490 | 73.815 | 41.097 | 100.885 | 1.00 | 32.24 |
| ATOM | 2787 | CD | PRO | 490 | 74.155 | 42.184 | 101.812 | 1.00 | 33.46 |
| ATOM | 2788 | CA | PRO | 490 | 74.746 | 41.115 | 99.765 | 1.00 | 30.98 |
| ATOM | 2789 | CB | PRO | 490 | 75.591 | 42.346 | 100.063 | 1.00 | 32.33 |
| ATOM | 2790 | CG | PRO | 490 | 75.637 | 42.326 | 101.562 | 1.00 | 32.30 |
| ATOM | 2791 | C | PRO | 490 | 75.578 | 39.856 | 99.668 | 1.00 | 29.67 |
| ATOM | 2792 | O | PRO | 490 | 76.497 | 39.645 | 100.460 | 1.00 | 31.94 |
| ATOM | 2793 | N | PRO | 491 | 75.266 | 38.997 | 98.693 | 1.00 | 27.50 |
| ATOM | 2794 | CD | PRO | 491 | 74.203 | 39.121 | 97.693 | 1.00 | 25.89 |
| ATOM | 2795 | CA | PRO | 491 | 75.990 | 37.748 | 98.480 | 1.00 | 27.98 |
| ATOM | 2796 | CB | PRO | 491 | 75.265 | 37.159 | 97.284 | 1.00 | 28.82 |
| ATOM | 2797 | CG | PRO | 491 | 74.820 | 38.390 | 96.554 | 1.00 | 27.12 |
| ATOM | 2798 | C | PRO | 491 | 77.443 | 38.083 | 98.171 | 1.00 | 30.90 |
| ATOM | 2799 | O | PRO | 491 | 77.722 | 39.129 | 97.589 | 1.00 | 35.20 |
| ATOM | 2800 | N | CYS | 492 | 78.371 | 37.218 | 98.566 | 1.00 | 30.10 |
| ATOM | 2801 | CA | CYS | 492 | 79.780 | 37.482 | 98.306 | 1.00 | 25.57 |
| ATOM | 2802 | CB | CYS | 492 | 80.653 | 36.451 | 99.021 | 1.00 | 33.58 |
| ATOM | 2803 | SG | CYS | 492 | 80.363 | 36.321 | 100.807 | 1.00 | 50.28 |
| ATOM | 2804 | C | CYS | 492 | 79.991 | 37.397 | 96.804 | 1.00 | 22.84 |
| ATOM | 2805 | O | CYS | 492 | 79.078 | 37.007 | 96.075 | 1.00 | 23.93 |
| ATOM | 2806 | N | ALA | 493 | 81.183 | 37.770 | 96.341 | 1.00 | 19.09 |
| ATOM | 2807 | CA | ALA | 493 | 81.510 | 37.721 | 94.920 | 1.00 | 15.11 |
| ATOM | 2808 | CB | ALA | 493 | 81.703 | 39.112 | 94.383 | 1.00 | 9.51 |
| ATOM | 2809 | C | ALA | 493 | 82.777 | 36.917 | 94.707 | 1.00 | 17.34 |
| ATOM | 2810 | O | ALA | 493 | 83.765 | 37.108 | 95.418 | 1.00 | 18.16 |
| ATOM | 2811 | N | ARG | 494 | 82.761 | 36.025 | 93.723 | 1.00 | 23.22 |
| ATOM | 2812 | CA | ARG | 494 | 83.941 | 35.211 | 93.427 | 1.00 | 27.33 |
| ATOM | 2813 | CB | ARG | 494 | 83.520 | 34.045 | 92.554 | 1.00 | 34.43 |
| ATOM | 2814 | CG | ARG | 494 | 84.593 | 33.050 | 92.285 | 1.00 | 48.98 |
| ATOM | 2815 | CD | ARG | 494 | 84.021 | 31.979 | 91.408 | 1.00 | 56.03 |

94

| ATOM | 2816 | NE | ARG | 494 | 85.064 | 31.191 | 90.775 | 1.00 | 65.90 |
| ATOM | 2817 | CZ | ARG | 494 | 84.820 | 30.286 | 89.838 | 1.00 | 76.49 |
| ATOM | 2818 | NH1 | ARG | 494 | 83.569 | 30.067 | 89.446 | 1.00 | 80.94 |
| ATOM | 2819 | NH2 | ARG | 494 | 85.820 | 29.605 | 89.292 | 1.00 | 83.01 |
| ATOM | 2820 | C | ARG | 494 | 84.984 | 36.106 | 92.737 | 1.00 | 22.71 |
| ATOM | 2821 | O | ARG | 494 | 84.637 | 36.978 | 91.945 | 1.00 | 21.71 |
| ATOM | 2822 | N | TRP | 495 | 86.263 | 35.908 | 93.018 | 1.00 | 21.21 |
| ATOM | 2823 | CA | TRP | 495 | 87.229 | 36.827 | 92.440 | 1.00 | 22.62 |
| ATOM | 2824 | CB | TRP | 495 | 88.534 | 36.838 | 93.225 | 1.00 | 26.65 |
| ATOM | 2825 | CG | TRP | 495 | 89.352 | 38.039 | 92.842 | 1.00 | 35.87 |
| ATOM | 2826 | CD2 | TRP | 495 | 90.694 | 38.046 | 92.379 | 1.00 | 32.98 |
| ATOM | 2827 | CE2 | TRP | 495 | 91.041 | 39.390 | 92.104 | 1.00 | 38.42 |
| ATOM | 2828 | CE3 | TRP | 495 | 91.643 | 37.047 | 92.160 | 1.00 | 37.62 |
| ATOM | 2829 | CD1 | TRP | 495 | 88.939 | 39.354 | 92.841 | 1.00 | 38.63 |
| ATOM | 2830 | NE1 | TRP | 495 | 89.951 | 40.172 | 92.398 | 1.00 | 37.12 |
| ATOM | 2831 | CZ2 | TRP | 495 | 92.296 | 39.756 | 91.630 | 1.00 | 45.27 |
| ATOM | 2832 | CZ3 | TRP | 495 | 92.895 | 37.408 | 91.687 | 1.00 | 46.34 |
| ATOM | 2833 | CH2 | TRP | 495 | 93.210 | 38.750 | 91.424 | 1.00 | 49.63 |
| ATOM | 2834 | C | TRP | 495 | 87.544 | 36.695 | 90.976 | 1.00 | 18.98 |
| ATOM | 2835 | O | TRP | 495 | 87.928 | 37.665 | 90.332 | 1.00 | 16.68 |
| ATOM | 2836 | N | ALA | 496 | 87.400 | 35.504 | 90.438 | 1.00 | 16.97 |
| ATOM | 2837 | CA | ALA | 496 | 87.651 | 35.344 | 89.024 | 1.00 | 21.54 |
| ATOM | 2838 | CB | ALA | 496 | 87.383 | 33.908 | 88.625 | 1.00 | 22.40 |
| ATOM | 2839 | C | ALA | 496 | 86.679 | 36.304 | 88.308 | 1.00 | 24.63 |
| ATOM | 2840 | O | ALA | 496 | 86.962 | 36.849 | 87.237 | 1.00 | 24.91 |
| ATOM | 2841 | N | GLN | 497 | 85.536 | 36.531 | 88.939 | 1.00 | 24.31 |
| ATOM | 2842 | CA | GLN | 497 | 84.521 | 37.405 | 88.390 | 1.00 | 22.55 |
| ATOM | 2843 | CB | GLN | 497 | 83.157 | 36.915 | 88.860 | 1.00 | 21.74 |
| ATOM | 2844 | CG | GLN | 497 | 82.014 | 37.835 | 88.539 | 1.00 | 32.36 |
| ATOM | 2845 | CD | GLN | 497 | 80.712 | 37.311 | 89.091 | 1.00 | 42.04 |
| ATOM | 2846 | OE1 | GLN | 497 | 80.643 | 36.893 | 90.256 | 1.00 | 47.49 |
| ATOM | 2847 | NE2 | GLN | 497 | 79.660 | 37.337 | 88.268 | 1.00 | 44.24 |
| ATOM | 2848 | C | GLN | 497 | 84.702 | 38.900 | 88.718 | 1.00 | 26.25 |
| ATOM | 2849 | O | GLN | 497 | 84.509 | 39.758 | 87.848 | 1.00 | 27.25 |
| ATOM | 2850 | N | LEU | 498 | 85.074 | 39.224 | 89.955 | 1.00 | 23.97 |
| ATOM | 2851 | CA | LEU | 498 | 85.250 | 40.633 | 90.328 | 1.00 | 19.85 |
| ATOM | 2852 | CB | LEU | 498 | 85.432 | 40.763 | 91.839 | 1.00 | 13.34 |
| ATOM | 2853 | CG | LEU | 498 | 85.112 | 42.088 | 92.527 | 1.00 | 7.91 |
| ATOM | 2854 | CD1 | LEU | 498 | 85.651 | 42.013 | 93.935 | 1.00 | 7.38 |
| ATOM | 2855 | CD2 | LEU | 498 | 85.743 | 43.249 | 91.818 | 1.00 | 7.59 |
| ATOM | 2856 | C | LEU | 498 | 86.474 | 41.223 | 89.612 | 1.00 | 20.34 |
| ATOM | 2857 | O | LEU | 498 | 86.417 | 42.323 | 89.050 | 1.00 | 23.49 |
| ATOM | 2858 | N | SER | 499 | 87.586 | 40.495 | 89.645 | 1.00 | 18.97 |
| ATOM | 2859 | CA | SER | 499 | 88.808 | 40.943 | 88.984 | 1.00 | 17.08 |
| ATOM | 2860 | CB | SER | 499 | 89.801 | 39.801 | 88.929 | 1.00 | 9.85 |
| ATOM | 2861 | OG | SER | 499 | 89.173 | 38.692 | 88.329 | 1.00 | 15.60 |
| ATOM | 2862 | C | SER | 499 | 88.495 | 41.395 | 87.558 | 1.00 | 18.66 |
| ATOM | 2863 | O | SER | 499 | 88.972 | 42.432 | 87.097 | 1.00 | 17.98 |
| ATOM | 2864 | N | GLU | 500 | 87.687 | 40.601 | 86.863 | 1.00 | 17.37 |
| ATOM | 2865 | CA | GLU | 500 | 87.312 | 40.916 | 85.501 | 1.00 | 13.88 |
| ATOM | 2866 | CB | GLU | 500 | 86.437 | 39.810 | 84.938 | 1.00 | 18.52 |
| ATOM | 2867 | CG | GLU | 500 | 86.149 | 39.989 | 83.468 | 1.00 | 31.79 |
| ATOM | 2868 | CD | GLU | 500 | 85.400 | 38.820 | 82.883 | 1.00 | 39.48 |
| ATOM | 2869 | OE1 | GLU | 500 | 84.311 | 38.494 | 83.402 | 1.00 | 50.72 |
| ATOM | 2870 | OE2 | GLU | 500 | 85.898 | 38.229 | 81.904 | 1.00 | 42.38 |
| ATOM | 2871 | C | GLU | 500 | 86.581 | 42.242 | 85.469 | 1.00 | 11.99 |
| ATOM | 2872 | O | GLU | 500 | 87.037 | 43.195 | 84.856 | 1.00 | 13.68 |
| ATOM | 2873 | N | VAL | 501 | 85.445 | 42.293 | 86.126 | 1.00 | 14.41 |
| ATOM | 2874 | CA | VAL | 501 | 84.695 | 43.534 | 86.188 | 1.00 | 12.58 |
| ATOM | 2875 | CB | VAL | 501 | 83.552 | 43.436 | 87.214 | 1.00 | 8.10 |
| ATOM | 2876 | CG1 | VAL | 501 | 83.011 | 44.804 | 87.489 | 1.00 | 2.99 |
| ATOM | 2877 | CG2 | VAL | 501 | 82.405 | 42.497 | 86.659 | 1.00 | 6.71 |
| ATOM | 2878 | C | VAL | 501 | 85.624 | 44.689 | 86.572 | 1.00 | 14.63 |
| ATOM | 2879 | O | VAL | 501 | 85.486 | 45.797 | 86.062 | 1.00 | 14.80 |
| ATOM | 2880 | N | LEU | 502 | 86.574 | 44.454 | 87.469 | 1.00 | 13.92 |
| ATOM | 2881 | CA | LEU | 502 | 87.442 | 45.545 | 87.798 | 1.00 | 20.31 |
| ATOM | 2882 | CB | LEU | 502 | 88.468 | 45.153 | 88.844 | 1.00 | 22.10 |
| ATOM | 2883 | CG | LEU | 502 | 87.754 | 45.044 | 90.203 | 1.00 | 26.90 |
| ATOM | 2884 | CD1 | LEU | 502 | 88.740 | 44.731 | 91.289 | 1.00 | 31.51 |
| ATOM | 2885 | CD2 | LEU | 502 | 87.104 | 46.350 | 90.556 | 1.00 | 27.47 |

```
ATOM  2886  C    LEU  502    88.089  46.013  86.521  1.00  23.21
ATOM  2887  O    LEU  502    87.960  47.184  86.146  1.00  29.47
ATOM  2888  N    SER  503    88.738  45.110  85.814  1.00  20.82
ATOM  2889  CA   SER  503    89.380  45.490  84.573  1.00  21.69
ATOM  2890  CB   SER  503    89.959  44.247  83.904  1.00  20.75
ATOM  2891  OG   SER  503    90.778  44.611  82.819  1.00  27.50
ATOM  2892  C    SER  503    88.387  46.214  83.625  1.00  20.79
ATOM  2893  O    SER  503    88.731  47.228  82.991  1.00  19.45
ATOM  2894  N    TRP  504    87.159  45.711  83.521  1.00  17.20
ATOM  2895  CA   TRP  504    86.202  46.378  82.654  1.00  14.16
ATOM  2896  CB   TRP  504    84.789  45.809  82.793  1.00   7.81
ATOM  2897  CG   TRP  504    84.659  44.425  82.277  1.00   7.87
ATOM  2898  CD2  TRP  504    83.477  43.597  82.274  1.00   7.23
ATOM  2899  CE2  TRP  504    83.792  42.412  81.557  1.00   5.70
ATOM  2900  CE3  TRP  504    82.175  43.742  82.803  1.00  11.63
ATOM  2901  CD1  TRP  504    85.609  43.730  81.597  1.00   7.56
ATOM  2902  NE1  TRP  504    85.098  42.521  81.158  1.00   7.99
ATOM  2903  CZ2  TRP  504    82.871  41.368  81.355  1.00   2.99
ATOM  2904  CZ3  TRP  504    81.233  42.694  82.606  1.00   9.00
ATOM  2905  CH2  TRP  504    81.603  41.522  81.879  1.00   7.59
ATOM  2906  C    TRP  504    86.173  47.835  83.033  1.00  15.20
ATOM  2907  O    TRP  504    86.292  48.694  82.188  1.00  20.75
ATOM  2908  N    GLN  505    86.049  48.128  84.314  1.00  15.02
ATOM  2909  CA   GLN  505    85.950  49.506  84.710  1.00  12.05
ATOM  2910  CB   GLN  505    86.022  49.634  86.215  1.00  10.86
ATOM  2911  CG   GLN  505    84.905  48.868  86.889  1.00  15.10
ATOM  2912  CD   GLN  505    83.617  48.838  86.041  1.00  17.04
ATOM  2913  OE1  GLN  505    83.352  47.843  85.390  1.00  16.48
ATOM  2914  NE2  GLN  505    82.850  49.937  86.025  1.00   9.06
ATOM  2915  C    GLN  505    86.966  50.363  84.035  1.00  14.64
ATOM  2916  O    GLN  505    86.602  51.389  83.493  1.00  16.27
ATOM  2917  N    PHE  506    88.235  49.954  84.054  1.00  15.74
ATOM  2918  CA   PHE  506    89.296  50.699  83.377  1.00  12.60
ATOM  2919  CB   PHE  506    90.640  50.109  83.716  1.00  11.05
ATOM  2920  CG   PHE  506    91.067  50.395  85.110  1.00  20.20
ATOM  2921  CD1  PHE  506    90.431  49.750  86.188  1.00  18.84
ATOM  2922  CD2  PHE  506    92.089  51.331  95.364  1.00  19.41
ATOM  2923  CE1  PHE  506    90.817  50.117  87.512  1.00  19.60
ATOM  2924  CE2  PHE  506    92.470  51.657  86.676  1.00  12.39
ATOM  2925  CZ   PHE  506    91.839  51.053  87.745  1.00  13.45
ATOM  2926  C    PHE  506    89.114  50.656  81.865  1.00  13.80
ATOM  2927  O    PHE  506    89.299  51.637  81.155  1.00  13.49
ATOM  2928  N    SER  507    88.736  49.521  81.334  1.00  15.47
ATOM  2929  CA   SER  507    88.590  49.556  79.914  1.00  19.24
ATOM  2930  CB   SER  507    88.686  48.153  79.276  1.00  13.66
ATOM  2931  OG   SER  507    87.860  47.237  79.902  1.00  22.24
ATOM  2932  C    SER  507    87.345  50.277  79.492  1.00  20.25
ATOM  2933  O    SER  507    87.017  50.265  78.303  1.00  27.99
ATOM  2934  N    SER  508    86.675  50.946  80.430  1.00  19.51
ATOM  2935  CA   SER  508    85.439  51.674  80.110  1.00  22.13
ATOM  2936  CB   SER  508    84.341  51.269  81.057  1.00  26.57
ATOM  2937  OG   SER  508    84.236  49.858  81.042  1.00  44.13
ATOM  2938  C    SER  508    85.628  53.181  80.171  1.00  26.02
ATOM  2939  O    SER  508    84.927  53.930  79.499  1.00  30.85
ATOM  2940  N    VAL  509    86.574  53.636  80.987  1.00  27.32
ATOM  2941  CA   VAL  509    86.895  55.046  81.086  1.00  21.98
ATOM  2942  CB   VAL  509    87.093  55.422  82.507  1.00  17.99
ATOM  2943  CG1  VAL  509    87.392  56.903  82.658  1.00  14.86
ATOM  2944  CG2  VAL  509    85.860  55.079  83.216  1.00  17.66
ATOM  2945  C    VAL  509    88.171  55.348  80.306  1.00  23.50
ATOM  2946  O    VAL  509    88.488  56.515  80.094  1.00  26.47
ATOM  2947  N    THR  510    88.883  54.303  79.876  1.00  21.43
ATOM  2948  CA   THR  510    90.125  54.443  79.125  1.00  18.80
ATOM  2949  CB   THR  510    91.362  54.195  79.952  1.00  18.71
ATOM  2950  OG1  THR  510    91.453  52.792  80.273  1.00  10.43
ATOM  2951  CG2  THR  510    91.323  55.062  81.212  1.00  15.16
ATOM  2952  C    THR  510    90.196  53.426  78.056  1.00  20.92
ATOM  2953  O    THR  510    89.238  52.710  77.816  1.00  24.65
ATOM  2954  N    LYS  511    91.378  53.328  77.459  1.00  25.14
ATOM  2955  CA   LYS  511    91.654  52.426  76.333  1.00  28.07
```

96

| | | | | | | | | |
|---|---|---|---|---|---|---|---|---|
| ATOM | 2956 | CB | LYS | 511 | 92.535 | 52.151 | 75.295 | 1.00 30.82 |
| ATOM | 2957 | CG | LYS | 511 | 92.067 | 54.521 | 74.766 | 1.00 36.78 |
| ATOM | 2958 | CD | LYS | 511 | 93.187 | 55.113 | 73.901 | 1.00 46.24 |
| ATOM | 2959 | CE | LYS | 511 | 92.860 | 56.475 | 73.301 | 1.00 54.23 |
| ATOM | 2960 | NZ | LYS | 511 | 94.055 | 57.060 | 72.597 | 1.00 54.82 |
| ATOM | 2961 | C | LYS | 511 | 92.333 | 51.086 | 76.681 | 1.00 28.17 |
| ATOM | 2962 | O | LYS | 511 | 92.571 | 50.265 | 75.790 | 1.00 28.97 |
| ATOM | 2963 | N | ARG | 512 | 92.694 | 50.872 | 77.945 | 1.00 28.53 |
| ATOM | 2964 | CA | ARG | 512 | 93.301 | 49.598 | 78.323 | 1.00 27.04 |
| ATOM | 2965 | CB | ARG | 512 | 94.804 | 49.648 | 78.188 | 1.00 23.09 |
| ATOM | 2966 | CG | ARG | 512 | 95.499 | 50.299 | 79.304 | 1.00 30.57 |
| ATOM | 2967 | CD | ARG | 512 | 96.916 | 50.581 | 78.908 | 1.00 30.40 |
| ATOM | 2968 | NE | ARG | 512 | 97.604 | 49.343 | 78.636 | 1.00 34.55 |
| ATOM | 2969 | CZ | ARG | 512 | 98.616 | 49.232 | 77.787 | 1.00 37.28 |
| ATOM | 2970 | NH1 | ARG | 512 | 99.054 | 50.293 | 77.129 | 1.00 31.86 |
| ATOM | 2971 | NH2 | ARG | 512 | 99.173 | 48.041 | 77.583 | 1.00 44.11 |
| ATOM | 2972 | C | ARG | 512 | 92.905 | 49.204 | 79.737 | 1.00 25.71 |
| ATOM | 2973 | O | ARG | 512 | 92.926 | 50.031 | 80.648 | 1.00 27.58 |
| ATOM | 2974 | N | GLY | 513 | 92.513 | 47.937 | 79.888 | 1.00 24.86 |
| ATOM | 2975 | CA | GLY | 513 | 92.069 | 47.416 | 81.163 | 1.00 19.29 |
| ATOM | 2976 | C | GLY | 513 | 93.240 | 47.116 | 82.056 | 1.00 19.73 |
| ATOM | 2977 | O | GLY | 513 | 94.296 | 47.780 | 82.019 | 1.00 16.98 |
| ATOM | 2978 | N | LEU | 514 | 93.053 | 46.094 | 82.873 | 1.00 20.54 |
| ATOM | 2979 | CA | LEU | 514 | 94.079 | 45.694 | 83.800 | 1.00 23.37 |
| ATOM | 2980 | CB | LEU | 514 | 93.462 | 45.419 | 85.168 | 1.00 23.53 |
| ATOM | 2981 | CG | LEU | 514 | 92.748 | 46.559 | 85.881 | 1.00 21.53 |
| ATOM | 2982 | CD1 | LEU | 514 | 92.299 | 46.104 | 87.261 | 1.00 11.24 |
| ATOM | 2983 | CD2 | LEU | 514 | 93.732 | 47.751 | 85.949 | 1.00 16.80 |
| ATOM | 2984 | C | LEU | 514 | 94.590 | 44.412 | 83.248 | 1.00 26.45 |
| ATOM | 2985 | O | LEU | 514 | 93.797 | 43.654 | 82.712 | 1.00 26.37 |
| ATOM | 2986 | N | ASN | 515 | 95.897 | 44.165 | 83.379 | 1.00 28.94 |
| ATOM | 2987 | CA | ASN | 515 | 96.516 | 42.921 | 82.909 | 1.00 28.53 |
| ATOM | 2988 | CB | ASN | 515 | 97.935 | 43.189 | 82.439 | 1.00 28.65 |
| ATOM | 2989 | CG | ASN | 515 | 98.826 | 43.717 | 83.570 | 1.00 28.10 |
| ATOM | 2990 | OD1 | ASN | 515 | 98.816 | 43.198 | 84.679 | 1.00 25.58 |
| ATOM | 2991 | ND2 | ASN | 515 | 99.600 | 44.736 | 83.280 | 1.00 31.85 |
| ATOM | 2992 | C | ASN | 515 | 96.602 | 42.027 | 84.143 | 1.00 32.26 |
| ATOM | 2993 | O | ASN | 515 | 96.182 | 42.428 | 85.240 | 1.00 34.24 |
| ATOM | 2994 | N | VAL | 516 | 97.180 | 40.840 | 83.985 | 1.00 31.17 |
| ATOM | 2995 | CA | VAL | 516 | 97.341 | 39.948 | 85.114 | 1.00 31.12 |
| ATOM | 2996 | CB | VAL | 516 | 97.823 | 38.575 | 84.607 | 1.00 31.42 |
| ATOM | 2997 | CG1 | VAL | 516 | 98.199 | 37.657 | 85.757 | 1.00 34.40 |
| ATOM | 2998 | CG2 | VAL | 516 | 96.690 | 37.917 | 83.876 | 1.00 34.04 |
| ATOM | 2999 | C | VAL | 516 | 98.230 | 40.473 | 86.296 | 1.00 33.16 |
| ATOM | 3000 | O | VAL | 516 | 97.869 | 40.293 | 87.451 | 1.00 34.62 |
| ATOM | 3001 | N | ASP | 517 | 99.358 | 41.132 | 86.060 | 1.00 34.19 |
| ATOM | 3002 | CA | ASP | 517 | 100.155 | 41.555 | 87.213 | 1.00 38.41 |
| ATOM | 3003 | CB | ASP | 517 | 101.437 | 42.310 | 86.785 | 1.00 43.24 |
| ATOM | 3004 | CG | ASP | 517 | 102.384 | 41.404 | 86.024 | 1.00 50.92 |
| ATOM | 3005 | OD1 | ASP | 517 | 102.928 | 40.495 | 86.683 | 1.00 55.11 |
| ATOM | 3006 | OD2 | ASP | 517 | 102.579 | 41.586 | 84.782 | 1.00 52.69 |
| ATOM | 3007 | C | ASP | 517 | 99.398 | 42.550 | 88.097 | 1.00 36.86 |
| ATOM | 3008 | O | ASP | 517 | 99.459 | 42.475 | 89.320 | 1.00 38.49 |
| ATOM | 3009 | N | GLN | 518 | 98.712 | 43.479 | 87.461 | 1.00 35.50 |
| ATOM | 3010 | CA | GLN | 518 | 97.939 | 44.478 | 88.164 | 1.00 34.33 |
| ATOM | 3011 | CB | GLN | 518 | 97.387 | 45.460 | 87.137 | 1.00 34.56 |
| ATOM | 3012 | CG | GLN | 518 | 98.529 | 46.054 | 86.357 | 1.00 34.52 |
| ATOM | 3013 | CD | GLN | 518 | 98.126 | 46.963 | 85.230 | 1.00 34.14 |
| ATOM | 3014 | OE1 | GLN | 518 | 97.435 | 46.554 | 84.263 | 1.00 31.83 |
| ATOM | 3015 | NE2 | GLN | 518 | 98.572 | 48.223 | 85.330 | 1.00 33.92 |
| ATOM | 3016 | C | GLN | 518 | 96.823 | 43.784 | 88.947 | 1.00 34.07 |
| ATOM | 3017 | O | GLN | 518 | 96.549 | 44.087 | 90.116 | 1.00 34.11 |
| ATOM | 3018 | N | LEU | 519 | 96.186 | 42.830 | 88.305 | 1.00 31.41 |
| ATOM | 3019 | CA | LEU | 519 | 95.128 | 42.129 | 88.972 | 1.00 30.24 |
| ATOM | 3020 | CB | LEU | 519 | 94.372 | 41.261 | 87.989 | 1.00 25.38 |
| ATOM | 3021 | CG | LEU | 519 | 93.639 | 42.099 | 86.972 | 1.00 20.93 |
| ATOM | 3022 | CD1 | LEU | 519 | 92.944 | 41.177 | 86.061 | 1.00 16.15 |
| ATOM | 3023 | CD2 | LEU | 519 | 92.650 | 43.040 | 87.680 | 1.00 15.83 |
| ATOM | 3024 | C | LEU | 519 | 95.577 | 41.281 | 90.137 | 1.00 32.22 |
| ATOM | 3025 | O | LEU | 519 | 94.787 | 41.095 | 91.050 | 1.00 38.55 |

97

| | | | | | | | | | |
|---|---|---|---|---|---|---|---|---|---|
| ATOM | 3026 | N | ASN | 520 | 96.801 | 40.755 | 90.142 | 1.00 | 31.01 |
| ATOM | 3027 | CA | ASN | 520 | 97.203 | 39.915 | 91.284 | 1.00 | 34.46 |
| ATOM | 3028 | CB | ASN | 520 | 98.428 | 39.027 | 90.969 | 1.00 | 35.43 |
| ATOM | 3029 | CG | ASN | 520 | 98.174 | 37.981 | 89.839 | 1.00 | 40.99 |
| ATOM | 3030 | OD1 | ASN | 520 | 97.139 | 37.294 | 89.799 | 1.00 | 34.28 |
| ATOM | 3031 | ND2 | ASN | 520 | 99.163 | 37.839 | 88.939 | 1.00 | 41.37 |
| ATOM | 3032 | C | ASN | 520 | 97.550 | 40.806 | 92.480 | 1.00 | 34.60 |
| ATOM | 3033 | O | ASN | 520 | 97.417 | 40.396 | 93.638 | 1.00 | 32.29 |
| ATOM | 3034 | N | MET | 521 | 97.991 | 42.030 | 92.166 | 1.00 | 32.92 |
| ATOM | 3035 | CA | MET | 521 | 98.401 | 43.035 | 93.146 | 1.00 | 27.06 |
| ATOM | 3036 | CB | MET | 521 | 99.027 | 44.213 | 92.401 | 1.00 | 27.89 |
| ATOM | 3037 | CG | MET | 521 | 99.411 | 45.410 | 93.237 | 1.00 | 30.72 |
| ATOM | 3038 | SD | MET | 521 | 98.028 | 46.354 | 93.921 | 1.00 | 38.43 |
| ATOM | 3039 | CE | MET | 521 | 98.920 | 47.742 | 94.538 | 1.00 | 28.87 |
| ATOM | 3040 | C | MET | 521 | 97.163 | 43.454 | 93.893 | 1.00 | 24.60 |
| ATOM | 3041 | O | MET | 521 | 97.164 | 43.584 | 95.108 | 1.00 | 23.37 |
| ATOM | 3042 | N | LEU | 522 | 96.093 | 43.659 | 93.146 | 1.00 | 22.69 |
| ATOM | 3043 | CA | LEU | 522 | 94.833 | 44.023 | 93.739 | 1.00 | 21.37 |
| ATOM | 3044 | CB | LEU | 522 | 93.874 | 44.511 | 92.669 | 1.00 | 17.76 |
| ATOM | 3045 | CG | LEU | 522 | 94.252 | 45.831 | 91.983 | 1.00 | 20.29 |
| ATOM | 3046 | CD1 | LEU | 522 | 93.273 | 46.075 | 90.866 | 1.00 | 15.93 |
| ATOM | 3047 | CD2 | LEU | 522 | 94.274 | 47.031 | 92.979 | 1.00 | 14.50 |
| ATOM | 3048 | C | LEU | 522 | 94.265 | 42.805 | 94.447 | 1.00 | 22.37 |
| ATOM | 3049 | O | LEU | 522 | 93.649 | 42.914 | 95.504 | 1.00 | 26.13 |
| ATOM | 3050 | N | GLY | 523 | 94.473 | 41.638 | 93.866 | 1.00 | 23.71 |
| ATOM | 3051 | CA | GLY | 523 | 93.983 | 40.419 | 94.474 | 1.00 | 25.05 |
| ATOM | 3052 | C | GLY | 523 | 94.582 | 40.113 | 95.832 | 1.00 | 28.15 |
| ATOM | 3053 | O | GLY | 523 | 93.857 | 39.776 | 96.739 | 1.00 | 30.48 |
| ATOM | 3054 | N | GLU | 524 | 95.888 | 40.229 | 96.015 | 1.00 | 32.20 |
| ATOM | 3055 | CA | GLU | 524 | 96.430 | 39.892 | 97.322 | 1.00 | 37.80 |
| ATOM | 3056 | CB | GLU | 524 | 97.950 | 39.645 | 97.246 | 1.00 | 46.32 |
| ATOM | 3057 | CG | GLU | 524 | 98.309 | 38.340 | 96.474 | 1.00 | 60.81 |
| ATOM | 3058 | CD | GLU | 524 | 99.836 | 38.080 | 96.291 | 1.00 | 69.00 |
| ATOM | 3059 | OE1 | GLU | 524 | 100.570 | 38.954 | 95.749 | 1.00 | 74.99 |
| ATOM | 3060 | OE2 | GLU | 524 | 100.302 | 36.978 | 96.671 | 1.00 | 68.23 |
| ATOM | 3061 | C | GLU | 524 | 96.103 | 41.017 | 98.270 | 1.00 | 36.94 |
| ATOM | 3062 | O | GLU | 524 | 96.552 | 41.069 | 99.419 | 1.00 | 42.11 |
| ATOM | 3063 | N | LYS | 525 | 95.288 | 41.924 | 97.778 | 1.00 | 33.36 |
| ATOM | 3064 | CA | LYS | 525 | 94.912 | 43.077 | 98.562 | 1.00 | 29.49 |
| ATOM | 3065 | CB | LYS | 525 | 95.046 | 44.314 | 97.687 | 1.00 | 30.54 |
| ATOM | 3066 | CG | LYS | 525 | 94.833 | 45.578 | 98.406 | 1.00 | 35.97 |
| ATOM | 3067 | CD | LYS | 525 | 95.509 | 46.719 | 97.673 | 1.00 | 39.11 |
| ATOM | 3068 | CE | LYS | 525 | 95.313 | 47.992 | 98.463 | 1.00 | 42.69 |
| ATOM | 3069 | NZ | LYS | 525 | 96.308 | 48.978 | 98.038 | 1.00 | 52.57 |
| ATOM | 3070 | C | LYS | 525 | 93.500 | 42.914 | 99.078 | 1.00 | 25.91 |
| ATOM | 3071 | O | LYS | 525 | 93.104 | 43.568 | 100.017 | 1.00 | 24.13 |
| ATOM | 3072 | N | LEU | 526 | 92.762 | 42.006 | 98.461 | 1.00 | 21.67 |
| ATOM | 3073 | CA | LEU | 526 | 91.398 | 41.743 | 98.825 | 1.00 | 21.03 |
| ATOM | 3074 | CB | LEU | 526 | 90.492 | 41.845 | 97.603 | 1.00 | 24.10 |
| ATOM | 3075 | CG | LEU | 526 | 90.167 | 43.211 | 97.013 | 1.00 | 28.95 |
| ATOM | 3076 | CD1 | LEU | 526 | 89.232 | 43.039 | 95.837 | 1.00 | 27.89 |
| ATOM | 3077 | CD2 | LEU | 526 | 89.494 | 44.086 | 98.091 | 1.00 | 29.55 |
| ATOM | 3078 | C | LEU | 526 | 91.261 | 40.358 | 99.395 | 1.00 | 22.60 |
| ATOM | 3079 | O | LEU | 526 | 90.297 | 40.046 | 100.085 | 1.00 | 27.01 |
| ATOM | 3080 | N | LEU | 527 | 92.214 | 39.501 | 99.101 | 1.00 | 19.41 |
| ATOM | 3081 | CA | LEU | 527 | 92.097 | 38.173 | 99.612 | 1.00 | 17.02 |
| ATOM | 3082 | CB | LEU | 527 | 91.777 | 37.242 | 98.491 | 1.00 | 19.69 |
| ATOM | 3083 | CG | LEU | 527 | 90.460 | 37.395 | 97.762 | 1.00 | 26.99 |
| ATOM | 3084 | CD1 | LEU | 527 | 90.491 | 36.498 | 96.466 | 1.00 | 28.28 |
| ATOM | 3085 | CD2 | LEU | 527 | 89.316 | 36.997 | 98.697 | 1.00 | 24.50 |
| ATOM | 3086 | C | LEU | 527 | 93.378 | 37.744 | 100.263 | 1.00 | 18.46 |
| ATOM | 3087 | O | LEU | 527 | 93.429 | 36.700 | 100.902 | 1.00 | 24.77 |
| ATOM | 3088 | N | GLY | 528 | 94.426 | 38.531 | 100.103 | 1.00 | 15.65 |
| ATOM | 3089 | CA | GLY | 528 | 95.677 | 38.137 | 100.709 | 1.00 | 17.90 |
| ATOM | 3090 | C | GLY | 528 | 96.430 | 37.075 | 99.917 | 1.00 | 20.93 |
| ATOM | 3091 | O | GLY | 528 | 96.029 | 36.680 | 98.807 | 1.00 | 16.96 |
| ATOM | 3092 | N | PRO | 529 | 97.568 | 36.625 | 100.456 | 1.00 | 19.80 |
| ATOM | 3093 | CD | PRO | 529 | 98.176 | 37.124 | 101.690 | 1.00 | 23.68 |
| ATOM | 3094 | CA | PRO | 529 | 98.440 | 35.614 | 99.880 | 1.00 | 18.74 |
| ATOM | 3095 | CB | PRO | 529 | 99.431 | 35.346 | 101.013 | 1.00 | 19.83 |

| | | | | | | | | |
|---|---|---|---|---|---|---|---|---|
| ATOM | 3096 | CG | PRO | 529 | 98.723 | 30.865 | 102.235 | 1.00 25.57 |
| ATOM | 3097 | C | PRO | 529 | 97.795 | 34.351 | 99.304 | 1.00 17.05 |
| ATOM | 3098 | O | PRO | 529 | 98.324 | 33.763 | 98.373 | 1.00 21.62 |
| ATOM | 3099 | N | ASN | 530 | 96.683 | 33.899 | 99.838 | 1.00 13.32 |
| ATOM | 3100 | CA | ASN | 530 | 96.077 | 32.742 | 99.227 | 1.00 10.40 |
| ATOM | 3101 | CB | ASN | 530 | 95.406 | 31.843 | 100.277 | 1.00 12.78 |
| ATOM | 3102 | CG | ASN | 530 | 96.399 | 31.174 | 101.191 | 1.00 16.08 |
| ATOM | 3103 | OD1 | ASN | 530 | 97.446 | 30.685 | 100.755 | 1.00 15.39 |
| ATOM | 3104 | ND2 | ASN | 530 | 96.060 | 31.108 | 102.464 | 1.00 20.34 |
| ATOM | 3105 | C | ASN | 530 | 95.036 | 33.240 | 98.222 | 1.00 9.36 |
| ATOM | 3106 | O | ASN | 530 | 94.032 | 32.575 | 97.978 | 1.00 12.07 |
| ATOM | 3107 | N | ALA | 531 | 95.244 | 34.429 | 97.676 | 1.00 9.11 |
| ATOM | 3108 | CA | ALA | 531 | 94.312 | 34.973 | 96.690 | 1.00 16.24 |
| ATOM | 3109 | CB | ALA | 531 | 94.884 | 36.240 | 96.085 | 1.00 15.66 |
| ATOM | 3110 | C | ALA | 531 | 94.137 | 33.885 | 95.620 | 1.00 20.32 |
| ATOM | 3111 | O | ALA | 531 | 95.126 | 33.277 | 95.186 | 1.00 23.70 |
| ATOM | 3112 | N | SER | 532 | 92.900 | 33.662 | 95.191 | 1.00 20.26 |
| ATOM | 3113 | CA | SER | 532 | 92.562 | 32.587 | 94.268 | 1.00 23.52 |
| ATOM | 3114 | CB | SER | 532 | 92.271 | 31.325 | 95.115 | 1.00 20.83 |
| ATOM | 3115 | OG | SER | 532 | 91.618 | 30.278 | 94.403 | 1.00 21.44 |
| ATOM | 3116 | C | SER | 532 | 91.318 | 32.952 | 93.460 | 1.00 29.15 |
| ATOM | 3117 | O | SER | 532 | 90.414 | 33.582 | 93.980 | 1.00 33.79 |
| ATOM | 3118 | N | PRO | 533 | 91.225 | 32.524 | 92.189 | 1.00 30.94 |
| ATOM | 3119 | CD | PRO | 533 | 92.102 | 31.692 | 91.382 | 1.00 31.79 |
| ATOM | 3120 | CA | PRO | 533 | 90.042 | 32.866 | 91.394 | 1.00 30.69 |
| ATOM | 3121 | CB | PRO | 533 | 90.267 | 32.079 | 90.122 | 1.00 30.00 |
| ATOM | 3122 | CG | PRO | 533 | 91.045 | 30.939 | 90.619 | 1.00 32.94 |
| ATOM | 3123 | C | PRO | 533 | 88.756 | 32.484 | 92.090 | 1.00 29.74 |
| ATOM | 3124 | O | PRO | 533 | 87.755 | 33.197 | 92.012 | 1.00 32.67 |
| ATOM | 3125 | N | ASP | 534 | 88.786 | 31.360 | 92.786 | 1.00 30.43 |
| ATOM | 3126 | CA | ASP | 534 | 87.605 | 30.909 | 93.532 | 1.00 28.51 |
| ATOM | 3127 | CB | ASP | 534 | 87.709 | 29.403 | 93.812 | 1.00 33.67 |
| ATOM | 3128 | CG | ASP | 534 | 87.462 | 28.577 | 92.576 | 1.00 41.12 |
| ATOM | 3129 | OD1 | ASP | 534 | 86.350 | 28.689 | 92.024 | 1.00 47.49 |
| ATOM | 3130 | OD2 | ASP | 534 | 88.357 | 27.822 | 92.144 | 1.00 46.20 |
| ATOM | 3131 | C | ASP | 534 | 87.352 | 31.658 | 94.847 | 1.00 17.83 |
| ATOM | 3132 | O | ASP | 534 | 86.281 | 31.600 | 95.398 | 1.00 13.32 |
| ATOM | 3133 | N | GLY | 535 | 88.332 | 32.366 | 95.349 | 1.00 12.79 |
| ATOM | 3134 | CA | GLY | 535 | 88.105 | 33.054 | 96.604 | 1.00 16.58 |
| ATOM | 3135 | C | GLY | 535 | 86.890 | 33.961 | 96.709 | 1.00 17.53 |
| ATOM | 3136 | O | GLY | 535 | 86.615 | 34.730 | 95.805 | 1.00 21.34 |
| ATOM | 3137 | N | LEU | 536 | 86.154 | 33.891 | 97.814 | 1.00 14.15 |
| ATOM | 3138 | CA | LEU | 536 | 85.004 | 34.769 | 97.961 | 1.00 13.54 |
| ATOM | 3139 | CB | LEU | 536 | 83.924 | 34.050 | 98.753 | 1.00 9.02 |
| ATOM | 3140 | CG | LEU | 536 | 83.178 | 32.999 | 97.939 | 1.00 2.99 |
| ATOM | 3141 | CD1 | LEU | 536 | 82.166 | 32.373 | 58.783 | 1.00 2.99 |
| ATOM | 3142 | CD2 | LEU | 536 | 82.506 | 33.619 | 96.733 | 1.00 7.27 |
| ATOM | 3143 | C | LEU | 536 | 85.345 | 36.151 | 98.586 | 1.00 17.67 |
| ATOM | 3144 | O | LEU | 536 | 86.195 | 36.261 | 99.465 | 1.00 21.34 |
| ATOM | 3145 | N | ILE | 537 | 84.690 | 37.203 | 98.114 | 1.00 16.53 |
| ATOM | 3146 | CA | ILE | 537 | 84.966 | 38.568 | 98.575 | 1.00 16.70 |
| ATOM | 3147 | CB | ILE | 537 | 85.533 | 39.427 | 97.419 | 1.00 9.12 |
| ATOM | 3148 | CG2 | ILE | 537 | 85.847 | 40.794 | 97.908 | 1.00 6.56 |
| ATOM | 3149 | CG1 | ILE | 537 | 86.750 | 38.741 | 96.820 | 1.00 12.41 |
| ATOM | 3150 | CD1 | ILE | 537 | 87.638 | 39.627 | 95.928 | 1.00 12.78 |
| ATOM | 3151 | C | ILE | 537 | 83.704 | 39.283 | 99.097 | 1.00 19.54 |
| ATOM | 3152 | O | ILE | 537 | 82.898 | 39.787 | 98.340 | 1.00 17.95 |
| ATOM | 3153 | N | PRO | 538 | 83.548 | 39.376 | 100.405 | 1.00 21.87 |
| ATOM | 3154 | CD | PRO | 538 | 84.404 | 38.967 | 101.526 | 1.00 25.30 |
| ATOM | 3155 | CA | PRO | 538 | 82.363 | 40.053 | 100.900 | 1.00 19.92 |
| ATOM | 3156 | CB | PRO | 538 | 82.590 | 40.036 | 102.396 | 1.00 23.53 |
| ATOM | 3157 | CG | PRO | 538 | 83.370 | 38.748 | 102.582 | 1.00 24.29 |
| ATOM | 3158 | C | PRO | 538 | 82.166 | 41.489 | 100.367 | 1.00 19.86 |
| ATOM | 3159 | O | PRO | 538 | 83.124 | 42.254 | 100.149 | 1.00 15.94 |
| ATOM | 3160 | N | TRP | 539 | 80.890 | 41.822 | 100.159 | 1.00 20.34 |
| ATOM | 3161 | CA | TRP | 539 | 80.454 | 43.133 | 99.707 | 1.00 17.93 |
| ATOM | 3162 | CB | TRP | 539 | 78.939 | 43.217 | 99.878 | 1.00 14.96 |
| ATOM | 3163 | CG | TRP | 539 | 78.373 | 44.577 | 99.836 | 1.00 17.80 |
| ATOM | 3164 | CD2 | TRP | 539 | 78.481 | 45.546 | 98.780 | 1.00 23.05 |
| ATOM | 3165 | CE2 | TRP | 539 | 77.693 | 46.659 | 99.141 | 1.00 20.91 |

99

| | | | | | | | | |
|---|---|---|---|---|---|---|---|---|
| ATOM | 3166 | CE3 | TRP | 539 | 79.161 | 45.580 | 97.557 | 1.00 20.35 |
| ATOM | 3167 | CD1 | TRP | 539 | 77.551 | 45.141 | 100.767 | 1.00 20.91 |
| ATOM | 3168 | NE1 | TRP | 539 | 77.136 | 46.386 | 100.363 | 1.00 16.86 |
| ATOM | 3169 | CZ2 | TRP | 539 | 77.572 | 47.772 | 98.347 | 1.00 20.78 |
| ATOM | 3170 | CZ3 | TRP | 539 | 79.034 | 46.674 | 96.780 | 1.00 22.02 |
| ATOM | 3171 | CH2 | TRP | 539 | 78.246 | 47.760 | 97.167 | 1.00 21.44 |
| ATOM | 3172 | C | TRP | 539 | 81.189 | 44.090 | 100.631 | 1.00 18.97 |
| ATOM | 3173 | O | TRP | 539 | 81.889 | 45.011 | 100.212 | 1.00 20.76 |
| ATOM | 3174 | N | THR | 540 | 81.056 | 43.806 | 101.911 | 1.00 22.49 |
| ATOM | 3175 | CA | THR | 540 | 81.704 | 44.545 | 102.976 | 1.00 24.76 |
| ATOM | 3176 | CB | THR | 540 | 81.512 | 43.742 | 104.227 | 1.00 25.48 |
| ATOM | 3177 | OG1 | THR | 540 | 80.159 | 43.255 | 104.196 | 1.00 30.38 |
| ATOM | 3178 | CG2 | THR | 540 | 81.758 | 44.586 | 105.479 | 1.00 18.07 |
| ATOM | 3179 | C | THR | 540 | 83.204 | 44.812 | 102.733 | 1.00 24.53 |
| ATOM | 3180 | O | THR | 540 | 83.648 | 45.934 | 102.802 | 1.00 22.92 |
| ATOM | 3181 | N | ARG | 541 | 84.014 | 43.793 | 102.441 | 1.00 26.20 |
| ATOM | 3182 | CA | ARG | 541 | 85.427 | 44.038 | 102.202 | 1.00 24.35 |
| ATOM | 3183 | CB | ARG | 541 | 86.226 | 42.717 | 102.026 | 1.00 26.91 |
| ATOM | 3184 | CG | ARG | 541 | 87.763 | 42.863 | 102.332 | 1.00 28.98 |
| ATOM | 3185 | CD | ARG | 541 | 88.445 | 41.554 | 102.405 | 1.00 33.22 |
| ATOM | 3186 | NE | ARG | 541 | 87.828 | 40.682 | 103.400 | 1.00 45.72 |
| ATOM | 3187 | CZ | ARG | 541 | 88.054 | 39.359 | 103.515 | 1.00 50.69 |
| ATOM | 3188 | NH1 | ARG | 541 | 88.914 | 38.729 | 102.703 | 1.00 49.15 |
| ATOM | 3189 | NH2 | ARG | 541 | 87.439 | 38.651 | 104.477 | 1.00 50.60 |
| ATOM | 3190 | C | ARG | 541 | 85.584 | 44.884 | 100.967 | 1.00 24.31 |
| ATOM | 3191 | O | ARG | 541 | 86.618 | 45.484 | 100.761 | 1.00 24.09 |
| ATOM | 3192 | N | PHE | 542 | 84.537 | 45.000 | 100.161 | 1.00 23.81 |
| ATOM | 3193 | CA | PHE | 542 | 84.662 | 45.741 | 98.932 | 1.00 22.27 |
| ATOM | 3194 | CB | PHE | 542 | 83.786 | 45.068 | 97.888 | 1.00 18.66 |
| ATOM | 3195 | CG | PHE | 542 | 83.938 | 45.609 | 96.483 | 1.00 20.13 |
| ATOM | 3196 | CD1 | PHE | 542 | 85.112 | 45.461 | 95.773 | 1.00 17.86 |
| ATOM | 3197 | CD2 | PHE | 542 | 82.900 | 46.330 | 95.877 | 1.00 16.68 |
| ATOM | 3198 | CE1 | PHE | 542 | 85.213 | 46.046 | 94.489 | 1.00 17.80 |
| ATOM | 3199 | CE2 | PHE | 542 | 83.036 | 46.889 | 94.627 | 1.00 11.59 |
| ATOM | 3200 | CZ | PHE | 542 | 84.190 | 46.756 | 93.938 | 1.00 8.87 |
| ATOM | 3201 | C | PHE | 542 | 84.362 | 47.208 | 98.987 | 1.00 27.35 |
| ATOM | 3202 | O | PHE | 542 | 85.135 | 47.973 | 98.443 | 1.00 28.66 |
| ATOM | 3203 | N | CYS | 543 | 83.242 | 47.611 | 99.626 | 1.00 32.72 |
| ATOM | 3204 | CA | CYS | 543 | 82.770 | 49.018 | 99.659 | 1.00 34.68 |
| ATOM | 3205 | CB | CYS | 543 | 81.431 | 49.192 | 98.818 | 1.00 35.45 |
| ATOM | 3206 | SG | CYS | 543 | 80.742 | 51.096 | 98.361 | 1.00 57.09 |
| ATOM | 3207 | C | CYS | 543 | 82.570 | 49.529 | 101.094 | 1.00 34.86 |
| ATOM | 3208 | O | CYS | 543 | 82.102 | 50.630 | 101.294 | 1.00 37.10 |
| ATOM | 3209 | N | LYS | 544 | 82.956 | 48.767 | 102.101 | 1.00 35.70 |
| ATOM | 3210 | CA | LYS | 544 | 82.766 | 49.207 | 103.479 | 1.00 34.21 |
| ATOM | 3211 | CB | LYS | 544 | 81.618 | 48.427 | 104.084 | 1.00 28.25 |
| ATOM | 3212 | CG | LYS | 544 | 80.421 | 48.683 | 103.330 | 1.00 29.41 |
| ATOM | 3213 | CD | LYS | 544 | 79.244 | 48.169 | 104.055 | 1.00 31.35 |
| ATOM | 3214 | CE | LYS | 544 | 78.032 | 48.763 | 103.434 | 1.00 30.59 |
| ATOM | 3215 | NZ | LYS | 544 | 76.944 | 48.557 | 104.339 | 1.00 30.23 |
| ATOM | 3216 | C | LYS | 544 | 83.980 | 49.139 | 104.403 | 1.00 37.46 |
| ATOM | 3217 | O | LYS | 544 | 84.323 | 50.101 | 105.070 | 1.00 38.19 |
| ATOM | 3218 | N | GLU | 545 | 84.634 | 47.998 | 104.469 | 1.00 43.22 |
| ATOM | 3219 | CA | GLU | 545 | 85.784 | 47.854 | 105.332 | 1.00 51.22 |
| ATOM | 3220 | CB | GLU | 545 | 86.294 | 46.443 | 105.201 | 1.00 53.28 |
| ATOM | 3221 | CG | GLU | 545 | 87.217 | 46.018 | 106.253 | 1.00 63.18 |
| ATOM | 3222 | CD | GLU | 545 | 88.065 | 44.856 | 105.765 | 1.00 70.60 |
| ATOM | 3223 | OE1 | GLU | 545 | 89.071 | 45.107 | 105.018 | 1.00 71.06 |
| ATOM | 3224 | OE2 | GLU | 545 | 87.701 | 43.688 | 106.100 | 1.00 74.69 |
| ATOM | 3225 | C | GLU | 545 | 86.805 | 48.877 | 104.823 | 1.00 55.82 |
| ATOM | 3226 | O | GLU | 545 | 86.727 | 49.315 | 103.685 | 1.00 62.58 |
| ATOM | 3227 | N | ASN | 546 | 87.752 | 49.272 | 105.656 | 1.00 57.63 |
| ATOM | 3228 | CA | ASN | 546 | 88.754 | 50.263 | 105.316 | 1.00 57.40 |
| ATOM | 3229 | CB | ASN | 546 | 89.170 | 50.882 | 106.598 | 1.00 59.88 |
| ATOM | 3230 | CG | ASN | 546 | 90.239 | 51.891 | 106.442 | 1.00 65.28 |
| ATOM | 3231 | OD1 | ASN | 546 | 90.030 | 52.990 | 105.918 | 1.00 66.76 |
| ATOM | 3232 | ND2 | ASN | 546 | 91.424 | 51.540 | 106.941 | 1.00 66.15 |
| ATOM | 3233 | C | ASN | 546 | 89.746 | 49.284 | 104.815 | 1.00 58.23 |
| ATOM | 3234 | O | ASN | 546 | 89.755 | 48.180 | 105.282 | 1.00 58.91 |
| ATOM | 3235 | N | ILE | 547 | 90.616 | 49.626 | 103.869 | 1.00 62.18 |

100

```
ATOM   3236  CA   ILE  547      91.466  48.518 103.380  1.00 63.55
ATOM   3237  CB   ILE  547      91.119  48.154 101.873  1.00 63.13
ATOM   3238  CG2  ILE  547      91.563  49.213 100.913  1.00 58.54
ATOM   3239  CG1  ILE  547      91.601  46.740 101.491  1.00 66.35
ATOM   3240  CD1  ILE  547      90.730  46.147 100.343  1.00 70.43
ATOM   3241  C    ILE  547      92.935  48.357 103.966  1.00 65.14
ATOM   3242  O    ILE  547      93.263  48.860 104.986  1.00 69.33
ATOM   3243  N    ASN  548      93.826  47.662 103.309  1.00 68.68
ATOM   3244  CA   ASN  548      95.169  47.298 103.939  1.00 70.68
ATOM   3245  CB   ASN  548      96.226  47.117 102.839  1.00 64.95
ATOM   3246  CG   ASN  548      95.686  46.294 101.764  1.00 62.95
ATOM   3247  OD1  ASN  548      94.906  45.351 102.029  1.00 66.19
ATOM   3248  ND2  ASN  548      95.910  46.710 100.573  1.00 65.73
ATOM   3249  C    ASN  548      95.698  48.045 105.276  1.00 72.35
ATOM   3250  O    ASN  548      96.071  47.316 106.196  1.00 77.17
ATOM   3251  N    ASP  549      95.579  49.351 105.467  1.00 70.24
ATOM   3252  CA   ASP  549      96.049  49.894 106.759  1.00 66.17
ATOM   3253  CB   ASP  549      97.581  49.904 106.850  1.00 67.12
ATOM   3254  CG   ASP  549      98.238  51.057 106.111  1.00 73.35
ATOM   3255  OD1  ASP  549      97.692  51.412 105.071  1.00 83.98
ATOM   3256  OD2  ASP  549      99.283  51.610 106.563  1.00 74.95
ATOM   3257  C    ASP  549      95.520  51.381 106.732  1.00 65.37
ATOM   3258  O    ASP  549      95.883  52.160 107.587  1.00 65.29
ATOM   3259  N    LYS  550      94.684  51.669 105.775  1.00 63.59
ATOM   3260  CA   LYS  550      94.099  53.059 105.558  1.00 61.82
ATOM   3261  CB   LYS  550      93.931  53.128 104.057  1.00 61.71
ATOM   3262  CG   LYS  550      95.151  52.493 103.383  1.00 63.31
ATOM   3263  CD   LYS  550      94.724  52.119 101.975  1.00 69.77
ATOM   3264  CE   LYS  550      95.767  51.452 100.993  1.00 69.50
ATOM   3265  NZ   LYS  550      95.241  51.331  99.511  1.00 61.63
ATOM   3266  C    LYS  550      92.808  53.695 106.251  1.00 61.84
ATOM   3267  O    LYS  550      92.477  53.489 107.386  1.00 63.76
ATOM   3268  N    ASN  551      92.200  54.681 105.550  1.00 61.82
ATOM   3269  CA   ASN  551      90.987  55.397 106.046  1.00 60.51
ATOM   3270  CB   ASN  551      91.294  56.832 106.465  1.00 66.42
ATOM   3271  CG   ASN  551      92.211  56.876 107.579  1.00 72.41
ATOM   3272  OD1  ASN  551      91.926  56.336 108.657  1.00 76.65
ATOM   3273  ND2  ASN  551      93.361  57.483 107.356  1.00 76.33
ATOM   3274  C    ASN  551      89.953  55.521 104.938  1.00 56.75
ATOM   3275  O    ASN  551      89.244  56.567 104.854  1.00 57.11
ATOM   3276  N    PHE  552      89.912  54.494 104.070  1.00 48.02
ATOM   3277  CA   PHE  552      88.960  54.397 102.951  1.00 38.19
ATOM   3278  CB   PHE  552      89.409  55.257 101.769  1.00 39.00
ATOM   3279  CG   PHE  552      90.887  55.197 101.490  1.00 41.98
ATOM   3280  CD1  PHE  552      91.420  54.194 100.677  1.00 42.87
ATOM   3281  CD2  PHE  552      91.764  56.036 102.176  1.00 39.73
ATOM   3282  CE1  PHE  552      92.778  54.041 100.571  1.00 42.60
ATOM   3283  CE2  PHE  552      93.141  55.892 102.077  1.00 39.57
ATOM   3284  CZ   PHE  552      93.654  54.901 101.294  1.00 41.84
ATOM   3285  C    PHE  552      88.901  52.963 102.564  1.00 31.48
ATOM   3286  O    PHE  552      89.843  52.234 102.858  1.00 30.14
ATOM   3287  N    PRO  553      87.778  52.533 101.962  1.00 25.59
ATOM   3288  CD   PRO  553      86.618  53.394 101.701  1.00 24.90
ATOM   3289  CA   PRO  553      87.488  51.183 101.473  1.00 20.27
ATOM   3290  CB   PRO  553      85.960  51.198 101.232  1.00 17.37
ATOM   3291  CG   PRO  553      85.505  52.409 101.875  1.00 21.71
ATOM   3292  C    PRO  553      88.228  50.958 100.129  1.00 16.68
ATOM   3293  O    PRO  553      88.615  51.886  99.460  1.00  9.69
ATOM   3294  N    PHE  554      88.348  49.693  99.744  1.00 19.06
ATOM   3295  CA   PHE  554      88.974  49.296  98.534  1.00 16.66
ATOM   3296  CB   PHE  554      88.764  47.840  98.345  1.00 14.57
ATOM   3297  CG   PHE  554      89.288  47.316  97.030  1.00 23.60
ATOM   3298  CD1  PHE  554      90.662  47.263  96.783  1.00 23.97
ATOM   3299  CD2  PHE  554      88.408  46.844  96.023  1.00 23.65
ATOM   3300  CE1  PHE  554      91.187  46.751  95.578  1.00 21.44
ATOM   3301  CE2  PHE  554      88.919  46.334  94.812  1.00 24.09
ATOM   3302  CZ   PHE  554      90.319  46.288  94.589  1.00 21.53
ATOM   3303  C    PHE  554      88.339  50.050  97.380  1.00 18.69
ATOM   3304  O    PHE  554      89.012  50.740  96.625  1.00 18.91
ATOM   3305  N    TRP  555      87.024  49.919  97.260  1.00 18.51
```

101

| ATOM | 3306 | CA | TRP | 555 | 86.395 | 50.503 | 96.069 | 1.00 | 20.70 |
| ATOM | 3307 | CB | TRP | 555 | 84.885 | 50.123 | 95.939 | 1.00 | 18.54 |
| ATOM | 3308 | CG | TRP | 555 | 84.254 | 50.803 | 94.742 | 1.00 | 15.36 |
| ATOM | 3309 | CD2 | TRP | 555 | 84.585 | 50.621 | 93.369 | 1.00 | 17.70 |
| ATOM | 3310 | CE2 | TRP | 555 | 83.860 | 51.553 | 92.661 | 1.00 | 22.49 |
| ATOM | 3311 | CE3 | TRP | 555 | 85.448 | 49.755 | 92.672 | 1.00 | 21.95 |
| ATOM | 3312 | CD1 | TRP | 555 | 83.375 | 51.771 | 94.786 | 1.00 | 15.17 |
| ATOM | 3313 | NE1 | TRP | 555 | 83.115 | 52.241 | 93.570 | 1.00 | 20.97 |
| ATOM | 3314 | CZ2 | TRP | 555 | 83.944 | 51.673 | 91.259 | 1.00 | 24.57 |
| ATOM | 3315 | CZ3 | TRP | 555 | 85.551 | 49.852 | 91.320 | 1.00 | 20.00 |
| ATOM | 3316 | CH2 | TRP | 555 | 84.804 | 50.812 | 90.615 | 1.00 | 23.36 |
| ATOM | 3317 | C | TRP | 555 | 86.596 | 51.987 | 95.794 | 1.00 | 22.83 |
| ATOM | 3318 | O | TRP | 555 | 86.896 | 52.360 | 94.650 | 1.00 | 23.95 |
| ATOM | 3319 | N | LEU | 556 | 86.477 | 52.825 | 96.820 | 1.00 | 21.86 |
| ATOM | 3320 | CA | LEU | 556 | 86.652 | 54.231 | 96.597 | 1.00 | 20.24 |
| ATOM | 3321 | CB | LEU | 556 | 86.241 | 55.013 | 97.818 | 1.00 | 28.70 |
| ATOM | 3322 | CG | LEU | 556 | 84.850 | 54.499 | 98.302 | 1.00 | 37.28 |
| ATOM | 3323 | CD1 | LEU | 556 | 84.705 | 54.973 | 99.771 | 1.00 | 38.52 |
| ATOM | 3324 | CD2 | LEU | 556 | 83.625 | 54.925 | 97.367 | 1.00 | 33.03 |
| ATOM | 3325 | C | LEU | 556 | 88.047 | 54.523 | 96.243 | 1.00 | 18.28 |
| ATOM | 3326 | O | LEU | 556 | 88.297 | 55.539 | 95.602 | 1.00 | 22.74 |
| ATOM | 3327 | N | TRP | 557 | 88.983 | 53.664 | 96.624 | 1.00 | 15.99 |
| ATOM | 3328 | CA | TRP | 557 | 90.418 | 53.893 | 96.275 | 1.00 | 14.69 |
| ATOM | 3329 | CB | TRP | 557 | 91.308 | 52.947 | 97.098 | 1.00 | 13.79 |
| ATOM | 3330 | CG | TRP | 557 | 92.702 | 52.796 | 96.696 | 1.00 | 15.32 |
| ATOM | 3331 | CD2 | TRP | 557 | 93.271 | 51.642 | 96.127 | 1.00 | 17.15 |
| ATOM | 3332 | CE2 | TRP | 557 | 94.657 | 51.905 | 95.931 | 1.00 | 19.14 |
| ATOM | 3333 | CE3 | TRP | 557 | 92.750 | 50.393 | 95.751 | 1.00 | 18.98 |
| ATOM | 3334 | CD1 | TRP | 557 | 93.739 | 53.713 | 96.815 | 1.00 | 18.59 |
| ATOM | 3335 | NE1 | TRP | 557 | 94.920 | 53.180 | 96.355 | 1.00 | 12.98 |
| ATOM | 3336 | CZ2 | TRP | 557 | 95.502 | 50.963 | 95.394 | 1.00 | 19.30 |
| ATOM | 3337 | CZ3 | TRP | 557 | 93.583 | 49.466 | 95.219 | 1.00 | 18.38 |
| ATOM | 3338 | CH2 | TRP | 557 | 94.951 | 49.749 | 95.044 | 1.00 | 22.88 |
| ATOM | 3339 | C | TRP | 557 | 90.568 | 53.632 | 94.758 | 1.00 | 15.98 |
| ATOM | 3340 | O | TRP | 557 | 91.120 | 54.428 | 94.039 | 1.00 | 13.10 |
| ATOM | 3341 | N | ILE | 558 | 90.059 | 52.511 | 94.277 | 1.00 | 14.66 |
| ATOM | 3342 | CA | ILE | 558 | 90.126 | 52.293 | 92.898 | 1.00 | 15.31 |
| ATOM | 3343 | CB | ILE | 558 | 89.652 | 50.892 | 92.556 | 1.00 | 14.44 |
| ATOM | 3344 | CG2 | ILE | 558 | 88.991 | 50.834 | 91.240 | 1.00 | 11.57 |
| ATOM | 3345 | CG1 | ILE | 558 | 90.864 | 50.051 | 92.300 | 1.00 | 17.32 |
| ATOM | 3346 | CD1 | ILE | 558 | 90.635 | 48.581 | 92.478 | 1.00 | 21.17 |
| ATOM | 3347 | C | ILE | 558 | 89.294 | 53.385 | 92.202 | 1.00 | 15.98 |
| ATOM | 3348 | O | ILE | 558 | 89.741 | 53.978 | 91.211 | 1.00 | 20.25 |
| ATOM | 3349 | N | GLU | 559 | 88.125 | 53.717 | 92.722 | 1.00 | 14.89 |
| ATOM | 3350 | CA | GLU | 559 | 87.331 | 54.742 | 92.016 | 1.00 | 18.27 |
| ATOM | 3351 | CB | GLU | 559 | 86.004 | 55.107 | 92.664 | 1.00 | 23.11 |
| ATOM | 3352 | CG | GLU | 559 | 84.747 | 54.891 | 91.838 | 1.00 | 33.51 |
| ATOM | 3353 | CD | GLU | 559 | 84.800 | 55.661 | 90.546 | 1.00 | 43.95 |
| ATOM | 3354 | OE1 | GLU | 559 | 85.069 | 54.953 | 89.537 | 1.00 | 48.11 |
| ATOM | 3355 | OE2 | GLU | 559 | 84.611 | 56.929 | 90.546 | 1.00 | 44.84 |
| ATOM | 3356 | C | GLU | 559 | 88.022 | 56.006 | 91.932 | 1.00 | 16.22 |
| ATOM | 3357 | O | GLU | 559 | 87.752 | 56.748 | 91.051 | 1.00 | 16.29 |
| ATOM | 3358 | N | SER | 560 | 88.929 | 56.274 | 92.838 | 1.00 | 15.24 |
| ATOM | 3359 | CA | SER | 560 | 89.537 | 57.547 | 92.741 | 1.00 | 18.10 |
| ATOM | 3360 | CB | SER | 560 | 89.806 | 58.074 | 94.147 | 1.00 | 15.45 |
| ATOM | 3361 | OG | SER | 560 | 90.779 | 57.304 | 94.779 | 1.00 | 27.44 |
| ATOM | 3362 | C | SER | 560 | 90.765 | 57.542 | 91.837 | 1.00 | 18.35 |
| ATOM | 3363 | O | SER | 560 | 91.210 | 58.586 | 91.359 | 1.00 | 20.60 |
| ATOM | 3364 | N | ILE | 561 | 91.317 | 56.372 | 91.578 | 1.00 | 16.98 |
| ATOM | 3365 | CA | ILE | 561 | 92.456 | 56.357 | 90.735 | 1.00 | 17.36 |
| ATOM | 3366 | CB | ILE | 561 | 93.194 | 54.998 | 90.862 | 1.00 | 21.77 |
| ATOM | 3367 | CG2 | ILE | 561 | 94.179 | 54.792 | 89.685 | 1.00 | 18.44 |
| ATOM | 3368 | CG1 | ILE | 561 | 93.890 | 54.959 | 92.205 | 1.00 | 18.15 |
| ATOM | 3369 | CD1 | ILE | 561 | 94.729 | 53.719 | 92.473 | 1.00 | 25.08 |
| ATOM | 3370 | C | ILE | 561 | 91.860 | 56.503 | 89.361 | 1.00 | 18.32 |
| ATOM | 3371 | O | ILE | 561 | 92.408 | 57.227 | 88.524 | 1.00 | 17.23 |
| ATOM | 3372 | N | LEU | 562 | 90.734 | 55.831 | 89.132 | 1.00 | 16.68 |
| ATOM | 3373 | CA | LEU | 562 | 90.065 | 55.969 | 87.856 | 1.00 | 17.63 |
| ATOM | 3374 | CB | LEU | 562 | 88.731 | 55.239 | 87.840 | 1.00 | 10.34 |
| ATOM | 3375 | CG | LEU | 562 | 88.590 | 53.823 | 87.337 | 1.00 | 10.62 |

102

```
ATOM   3376  CD1 LEU   562      87.277  53.976  86.736  1.00 18.40
ATOM   3377  CD2 LEU   562      89.491  53.350  86.251  1.00  7.89
ATOM   3378  C   LEU   562      89.806  57.456  87.602  1.00 20.04
ATOM   3379  O   LEU   562      90.104  58.013  86.538  1.00 21.18
ATOM   3380  N   GLU   563      89.216  58.099  88.585  1.00 22.52
ATOM   3381  CA  GLU   563      88.927  59.461  88.388  1.00 25.41
ATOM   3382  CB  GLU   563      88.209  60.029  89.596  1.00 31.72
ATOM   3383  CG  GLU   563      86.665  59.831  89.485  1.00 44.56
ATOM   3384  CD  GLU   563      85.826  60.630  90.549  1.00 51.48
ATOM   3385  OE1 GLU   563      86.029  61.904  90.665  1.00 54.55
ATOM   3386  OE2 GLU   563      84.966  59.960  91.226  1.00 48.03
ATOM   3387  C   GLU   563      90.207  60.163  88.142  1.00 25.52
ATOM   3388  O   GLU   563      90.226  61.147  87.458  1.00 26.81
ATOM   3389  N   LEU   564      91.299  59.651  88.690  1.00 26.30
ATOM   3390  CA  LEU   564      92.585  60.325  88.502  1.00 26.55
ATOM   3391  CB  LEU   564      93.594  59.929  89.580  1.00 22.99
ATOM   3392  CG  LEU   564      94.922  60.553  89.195  1.00 23.73
ATOM   3393  CD1 LEU   564      94.857  62.038  89.570  1.00 25.89
ATOM   3394  CD2 LEU   564      96.064  59.831  89.881  1.00 22.00
ATOM   3395  C   LEU   564      93.158  60.105  87.094  1.00 24.51
ATOM   3396  O   LEU   564      93.736  61.013  86.502  1.00 24.95
ATOM   3397  N   ILE   565      92.975  58.905  86.574  1.00 22.72
ATOM   3398  CA  ILE   565      93.405  58.562  85.215  1.00 22.30
ATOM   3399  CB  ILE   565      93.134  57.096  84.893  1.00 15.85
ATOM   3400  CG2 ILE   565      93.370  56.825  83.436  1.00 13.00
ATOM   3401  CG1 ILE   565      94.051  56.279  85.755  1.00 12.16
ATOM   3402  CD1 ILE   565      93.646  54.978  85.919  1.00 20.64
ATOM   3403  C   ILE   565      92.671  59.400  84.200  1.00 24.08
ATOM   3404  O   ILE   565      93.326  60.107  83.429  1.00 26.27
ATOM   3405  N   LYS   566      91.333  59.306  84.237  1.00 24.44
ATOM   3406  CA  LYS   566      90.396  59.997  83.357  1.00 26.09
ATOM   3407  CB  LYS   566      88.950  59.698  83.775  1.00 31.14
ATOM   3408  CG  LYS   566      87.867  60.358  82.961  1.00 30.15
ATOM   3409  CD  LYS   566      86.471  60.192  83.610  1.00 37.38
ATOM   3410  CE  LYS   566      85.431  61.196  82.904  1.00 42.47
ATOM   3411  NZ  LYS   566      83.929  61.235  83.218  1.00 39.57
ATOM   3412  C   LYS   566      90.571  61.491  83.238  1.00 26.81
ATOM   3413  O   LYS   566      90.270  62.017  82.193  1.00 27.37
ATOM   3414  N   LYS   567      91.035  62.180  84.282  1.00 26.95
ATOM   3415  CA  LYS   567      91.283  63.636  84.218  1.00 27.90
ATOM   3416  CB  LYS   567      90.714  64.368  85.436  1.00 29.88
ATOM   3417  CG  LYS   567      89.255  64.175  85.803  1.00 38.26
ATOM   3418  CD  LYS   567      89.171  64.569  87.297  1.00 47.74
ATOM   3419  CE  LYS   567      87.783  64.485  87.984  1.00 50.15
ATOM   3420  NZ  LYS   567      87.815  65.371  89.247  1.00 44.36
ATOM   3421  C   LYS   567      92.790  64.054  84.171  1.00 30.15
ATOM   3422  O   LYS   567      93.081  65.255  84.213  1.00 31.17
ATOM   3423  N   HIS   568      93.766  63.137  84.082  1.00 29.59
ATOM   3424  CA  HIS   568      95.165  63.600  84.127  1.00 26.57
ATOM   3425  CB  HIS   568      95.594  63.980  85.548  1.00 25.77
ATOM   3426  CG  HIS   568      94.837  65.099  86.162  1.00 22.03
ATOM   3427  CD2 HIS   568      93.865  65.103  87.106  1.00 21.98
ATOM   3428  ND1 HIS   568      95.096  66.414  85.861  1.00 23.44
ATOM   3429  CE1 HIS   568      94.315  67.182  86.606  1.00 26.47
ATOM   3430  NE2 HIS   568      93.559  66.408  87.371  1.00 20.39
ATOM   3431  C   HIS   568      96.211  62.610  83.685  1.00 26.51
ATOM   3432  O   HIS   568      97.411  62.926  83.715  1.00 26.87
ATOM   3433  N   LEU   569      95.816  61.395  83.349  1.00 24.93
ATOM   3434  CA  LEU   569      96.856  60.484  82.909  1.00 23.36
ATOM   3435  CB  LEU   569      97.197  59.572  84.055  1.00 17.29
ATOM   3436  CG  LEU   569      97.526  60.288  85.341  1.00 13.67
ATOM   3437  CD1 LEU   569      97.559  59.265  86.561  1.00  7.24
ATOM   3438  CD2 LEU   569      98.844  61.060  85.115  1.00 10.46
ATOM   3439  C   LEU   569      96.500  59.635  81.673  1.00 25.58
ATOM   3440  O   LEU   569      97.297  58.751  81.286  1.00 27.82
ATOM   3441  N   LEU   570      95.361  59.917  81.028  1.00 24.66
ATOM   3442  CA  LEU   570      94.929  59.068  79.934  1.00 24.53
ATOM   3443  CB  LEU   570      93.753  59.635  79.194  1.00 23.12
ATOM   3444  CG  LEU   570      92.420  59.157  79.713  1.00 20.59
ATOM   3445  CD1 LEU   570      91.346  59.847  79.009  1.00 16.74
```

103

| ATOM | 3446 | CD2 | LEU | 570 | 92.296 | 57.653 | 79.537 | 1.00 | 18.05 |
| --- | --- | --- | --- | --- | --- | --- | --- | --- | --- |
| ATOM | 3447 | C | LEU | 570 | 95.967 | 58.659 | 78.953 | 1.00 | 26.99 |
| ATOM | 3448 | O | LEU | 570 | 96.191 | 57.439 | 78.711 | 1.00 | 28.67 |
| ATOM | 3449 | N | PRO | 571 | 96.593 | 59.647 | 78.311 | 1.00 | 26.85 |
| ATOM | 3450 | CD | PRO | 571 | 96.379 | 61.091 | 78.286 | 1.00 | 23.77 |
| ATOM | 3451 | CA | PRO | 571 | 97.633 | 59.255 | 77.351 | 1.00 | 25.58 |
| ATOM | 3452 | CB | PRO | 571 | 98.116 | 60.590 | 76.837 | 1.00 | 21.80 |
| ATOM | 3453 | CG | PRO | 571 | 97.715 | 61.511 | 77.991 | 1.00 | 24.73 |
| ATOM | 3454 | C | PRO | 571 | 98.732 | 58.331 | 77.965 | 1.00 | 24.46 |
| ATOM | 3455 | O | PRO | 571 | 98.977 | 57.221 | 77.419 | 1.00 | 19.72 |
| ATOM | 3456 | N | LEU | 572 | 99.336 | 58.734 | 79.096 | 1.00 | 24.04 |
| ATOM | 3457 | CA | LEU | 572 | 100.374 | 57.893 | 79.713 | 1.00 | 24.92 |
| ATOM | 3458 | CB | LEU | 572 | 100.829 | 58.407 | 81.066 | 1.00 | 25.01 |
| ATOM | 3459 | CG | LEU | 572 | 101.328 | 59.788 | 81.328 | 1.00 | 22.76 |
| ATOM | 3460 | CD1 | LEU | 572 | 101.702 | 59.770 | 82.771 | 1.00 | 18.35 |
| ATOM | 3461 | CD2 | LEU | 572 | 102.494 | 60.154 | 80.445 | 1.00 | 22.35 |
| ATOM | 3462 | C | LEU | 572 | 99.782 | 56.529 | 80.010 | 1.00 | 26.81 |
| ATOM | 3463 | O | LEU | 572 | 100.434 | 55.455 | 79.740 | 1.00 | 25.43 |
| ATOM | 3464 | N | TRP | 573 | 98.561 | 56.576 | 80.596 | 1.00 | 24.17 |
| ATOM | 3465 | CA | TRP | 573 | 97.881 | 55.332 | 81.003 | 1.00 | 24.15 |
| ATOM | 3466 | CB | TRP | 573 | 96.534 | 55.556 | 81.685 | 1.00 | 18.70 |
| ATOM | 3467 | CG | TRP | 573 | 95.757 | 54.287 | 81.892 | 1.00 | 9.45 |
| ATOM | 3468 | CD2 | TRP | 573 | 96.068 | 53.221 | 82.775 | 1.00 | 3.81 |
| ATOM | 3469 | CE2 | TRP | 573 | 95.178 | 52.157 | 82.489 | 1.00 | 3.68 |
| ATOM | 3470 | CE3 | TRP | 573 | 97.001 | 53.047 | 83.764 | 1.00 | 6.58 |
| ATOM | 3471 | CD1 | TRP | 573 | 94.727 | 53.857 | 81.138 | 1.00 | 8.55 |
| ATOM | 3472 | NE1 | TRP | 573 | 94.367 | 52.573 | 81.472 | 1.00 | 5.71 |
| ATOM | 3473 | CZ2 | TRP | 573 | 95.194 | 50.949 | 83.169 | 1.00 | 2.99 |
| ATOM | 3474 | CZ3 | TRP | 573 | 97.029 | 51.788 | 84.456 | 1.00 | 10.21 |
| ATOM | 3475 | CH2 | TRP | 573 | 96.134 | 50.783 | 84.149 | 1.00 | 5.63 |
| ATOM | 3476 | C | TRP | 573 | 97.637 | 54.454 | 79.858 | 1.00 | 25.90 |
| ATOM | 3477 | O | TRP | 573 | 98.070 | 53.338 | 79.844 | 1.00 | 24.35 |
| ATOM | 3478 | N | ASN | 574 | 96.913 | 54.994 | 78.899 | 1.00 | 29.35 |
| ATOM | 3479 | CA | ASN | 574 | 96.629 | 54.223 | 77.726 | 1.00 | 34.97 |
| ATOM | 3480 | CB | ASN | 574 | 95.900 | 55.021 | 76.667 | 1.00 | 36.78 |
| ATOM | 3481 | CG | ASN | 574 | 94.516 | 55.439 | 77.098 | 1.00 | 36.61 |
| ATOM | 3482 | OD1 | ASN | 574 | 93.795 | 54.652 | 77.732 | 1.00 | 34.44 |
| ATOM | 3483 | ND2 | ASN | 574 | 94.115 | 56.665 | 76.723 | 1.00 | 34.02 |
| ATOM | 3484 | C | ASN | 574 | 97.886 | 53.684 | 77.130 | 1.00 | 36.99 |
| ATOM | 3485 | O | ASN | 574 | 97.921 | 52.484 | 76.938 | 1.00 | 40.76 |
| ATOM | 3486 | N | ASP | 575 | 98.910 | 54.506 | 76.834 | 1.00 | 36.98 |
| ATOM | 3487 | CA | ASP | 575 | 100.155 | 53.935 | 76.247 | 1.00 | 38.81 |
| ATOM | 3488 | CB | ASP | 575 | 101.007 | 54.975 | 75.476 | 1.00 | 39.37 |
| ATOM | 3489 | CG | ASP | 575 | 100.200 | 55.852 | 74.527 | 1.00 | 38.82 |
| ATOM | 3490 | OD1 | ASP | 575 | 99.294 | 55.351 | 73.857 | 1.00 | 39.09 |
| ATOM | 3491 | OD2 | ASP | 575 | 100.491 | 57.064 | 74.428 | 1.00 | 40.02 |
| ATOM | 3492 | C | ASP | 575 | 101.084 | 53.241 | 77.267 | 1.00 | 38.65 |
| ATOM | 3493 | O | ASP | 575 | 102.287 | 53.453 | 77.258 | 1.00 | 38.81 |
| ATOM | 3494 | N | GLY | 576 | 100.492 | 52.420 | 78.135 | 1.00 | 40.50 |
| ATOM | 3495 | CA | GLY | 576 | 101.176 | 51.615 | 79.156 | 1.00 | 38.10 |
| ATOM | 3496 | C | GLY | 576 | 102.465 | 52.052 | 79.820 | 1.00 | 37.23 |
| ATOM | 3497 | O | GLY | 576 | 103.370 | 51.257 | 79.979 | 1.00 | 34.47 |
| ATOM | 3498 | N | CYS | 577 | 102.537 | 53.300 | 80.247 | 1.00 | 39.92 |
| ATOM | 3499 | CA | CYS | 577 | 103.741 | 53.822 | 80.884 | 1.00 | 38.82 |
| ATOM | 3500 | CB | CYS | 577 | 104.019 | 55.257 | 80.354 | 1.00 | 36.66 |
| ATOM | 3501 | SG | CYS | 577 | 103.663 | 55.510 | 78.521 | 1.00 | 43.25 |
| ATOM | 3502 | C | CYS | 577 | 103.448 | 53.798 | 82.419 | 1.00 | 40.69 |
| ATOM | 3503 | O | CYS | 577 | 104.282 | 54.210 | 83.241 | 1.00 | 40.40 |
| ATOM | 3504 | N | ILE | 578 | 102.267 | 53.316 | 82.831 | 1.00 | 40.27 |
| ATOM | 3505 | CA | ILE | 578 | 101.985 | 53.291 | 84.268 | 1.00 | 38.34 |
| ATOM | 3506 | CB | ILE | 578 | 100.735 | 54.018 | 84.635 | 1.00 | 34.86 |
| ATOM | 3507 | CG2 | ILE | 578 | 100.598 | 54.054 | 86.073 | 1.00 | 28.64 |
| ATOM | 3508 | CG1 | ILE | 578 | 100.756 | 55.420 | 84.051 | 1.00 | 35.63 |
| ATOM | 3509 | CD1 | ILE | 578 | 99.430 | 56.138 | 84.077 | 1.00 | 28.97 |
| ATOM | 3510 | C | ILE | 578 | 101.706 | 51.882 | 84.570 | 1.00 | 42.26 |
| ATOM | 3511 | O | ILE | 578 | 100.953 | 51.243 | 83.847 | 1.00 | 44.13 |
| ATOM | 3512 | N | MET | 579 | 102.325 | 51.404 | 85.637 | 1.00 | 45.96 |
| ATOM | 3513 | CA | MET | 579 | 102.183 | 50.055 | 86.140 | 1.00 | 47.73 |
| ATOM | 3514 | CB | MET | 579 | 103.549 | 49.484 | 86.412 | 1.00 | 49.49 |
| ATOM | 3515 | CG | MET | 579 | 104.164 | 49.009 | 85.129 | 1.00 | 57.86 |

| ATOM | 3516 | SD   | MET | 579 | 105.674 | 48.015 | 85.157  | 1.00 | 59.50 |
| ---- | ---- | ---- | --- | --- | ------- | ------ | ------- | ---- | ----- |
| ATOM | 3517 | CE   | MET | 579 | 105.633 | 47.572 | 83.098  | 1.00 | 48.98 |
| ATOM | 3518 | C    | MET | 579 | 101.511 | 50.198 | 87.440  | 1.00 | 49.56 |
| ATOM | 3519 | O    | MET | 579 | 101.655 | 49.348 | 88.264  | 1.00 | 55.19 |
| ATOM | 3520 | N    | GLY | 580 | 100.823 | 51.319 | 87.630  | 1.00 | 50.38 |
| ATOM | 3521 | CA   | GLY | 580 | 100.143 | 51.690 | 88.875  | 1.00 | 46.04 |
| ATOM | 3522 | C    | GLY | 580 | 99.980  | 50.745 | 90.037  | 1.00 | 44.50 |
| ATOM | 3523 | O    | GLY | 580 | 100.277 | 51.067 | 91.181  | 1.00 | 45.20 |
| ATOM | 3524 | N    | PHE | 581 | 99.497  | 49.560 | 89.774  | 1.00 | 41.55 |
| ATOM | 3525 | CA   | PHE | 581 | 99.318  | 48.699 | 90.875  | 1.00 | 41.39 |
| ATOM | 3526 | CB   | PHE | 581 | 98.039  | 47.970 | 90.672  | 1.00 | 42.54 |
| ATOM | 3527 | CG   | PHE | 581 | 96.875  | 48.859 | 90.411  | 1.00 | 39.74 |
| ATOM | 3528 | CD1  | PHE | 581 | 96.648  | 49.354 | 89.165  | 1.00 | 37.08 |
| ATOM | 3529 | CD2  | PHE | 581 | 95.941  | 49.100 | 91.401  | 1.00 | 40.16 |
| ATOM | 3530 | CE1  | PHE | 581 | 95.531  | 50.063 | 88.911  | 1.00 | 34.99 |
| ATOM | 3531 | CE2  | PHE | 581 | 94.826  | 49.810 | 91.141  | 1.00 | 38.52 |
| ATOM | 3532 | CZ   | PHE | 581 | 94.616  | 50.284 | 89.886  | 1.00 | 36.68 |
| ATOM | 3533 | C    | PHE | 581 | 100.447 | 47.722 | 91.104  | 1.00 | 42.95 |
| ATOM | 3534 | O    | PHE | 581 | 100.430 | 46.591 | 90.619  | 1.00 | 40.91 |
| ATOM | 3535 | N    | ILE | 582 | 101.446 | 48.103 | 91.850  | 1.00 | 46.89 |
| ATOM | 3536 | CA   | ILE | 582 | 102.563 | 47.284 | 92.161  | 1.00 | 50.28 |
| ATOM | 3537 | CB   | ILE | 582 | 103.863 | 47.663 | 91.511  | 1.00 | 49.03 |
| ATOM | 3538 | CG2  | ILE | 582 | 104.859 | 46.548 | 91.761  | 1.00 | 47.83 |
| ATOM | 3539 | CG1  | ILE | 582 | 103.727 | 47.729 | 90.011  | 1.00 | 51.15 |
| ATOM | 3540 | CD1  | ILE | 582 | 105.068 | 47.837 | 89.338  | 1.00 | 52.88 |
| ATOM | 3541 | C    | ILE | 582 | 102.908 | 47.181 | 93.625  | 1.00 | 52.98 |
| ATOM | 3542 | O    | ILE | 582 | 103.256 | 48.174 | 94.291  | 1.00 | 54.41 |
| ATOM | 3543 | N    | SER | 583 | 102.843 | 45.941 | 94.080  | 1.00 | 53.36 |
| ATOM | 3544 | CA   | SER | 583 | 103.149 | 45.531 | 95.426  | 1.00 | 55.22 |
| ATOM | 3545 | CB   | SER | 583 | 103.478 | 44.036 | 95.290  | 1.00 | 57.27 |
| ATOM | 3546 | OG   | SER | 583 | 103.465 | 43.331 | 96.504  | 1.00 | 62.93 |
| ATOM | 3547 | C    | SER | 583 | 104.368 | 46.382 | 95.672  | 1.00 | 55.20 |
| ATOM | 3548 | O    | SER | 583 | 105.060 | 46.590 | 94.723  | 1.00 | 55.16 |
| ATOM | 3549 | N    | LYS | 584 | 104.641 | 46.928 | 96.866  | 1.00 | 59.07 |
| ATOM | 3550 | CA   | LYS | 584 | 105.907 | 47.738 | 97.049  | 1.00 | 59.61 |
| ATOM | 3551 | CB   | LYS | 584 | 105.940 | 48.550 | 98.351  | 1.00 | 57.32 |
| ATOM | 3552 | CG   | LYS | 584 | 104.884 | 49.593 | 98.442  | 1.00 | 61.01 |
| ATOM | 3553 | CD   | LYS | 584 | 105.327 | 50.756 | 99.325  | 1.00 | 64.39 |
| ATOM | 3554 | CE   | LYS | 584 | 104.196 | 51.779 | 99.594  | 1.00 | 64.69 |
| ATOM | 3555 | NZ   | LYS | 584 | 104.663 | 52.868 | 100.499 | 1.00 | 64.59 |
| ATOM | 3556 | C    | LYS | 584 | 107.165 | 46.844 | 97.024  | 1.00 | 61.21 |
| ATOM | 3557 | O    | LYS | 584 | 108.277 | 47.315 | 96.793  | 1.00 | 60.52 |
| ATOM | 3558 | N    | GLU | 585 | 106.970 | 45.550 | 97.296  | 1.00 | 63.34 |
| ATOM | 3559 | CA   | GLU | 585 | 108.035 | 44.579 | 97.244  | 1.00 | 62.62 |
| ATOM | 3560 | CB   | GLU | 585 | 107.534 | 43.208 | 97.528  | 1.00 | 64.94 |
| ATOM | 3561 | CG   | GLU | 585 | 107.025 | 43.037 | 98.848  | 1.00 | 70.80 |
| ATOM | 3562 | CD   | GLU | 585 | 106.964 | 41.563 | 99.138  | 1.00 | 76.32 |
| ATOM | 3563 | OE1  | GLU | 585 | 107.826 | 40.773 | 98.598  | 1.00 | 70.90 |
| ATOM | 3564 | OE2  | GLU | 585 | 106.052 | 41.230 | 99.927  | 1.00 | 79.84 |
| ATOM | 3565 | C    | GLU | 585 | 108.513 | 44.518 | 95.846  | 1.00 | 61.32 |
| ATOM | 3566 | O    | GLU | 585 | 109.580 | 44.964 | 95.563  | 1.00 | 61.30 |
| ATOM | 3567 | N    | ARG | 586 | 107.691 | 43.940 | 94.978  | 1.00 | 61.92 |
| ATOM | 3568 | CA   | ARG | 586 | 108.049 | 43.762 | 93.598  | 1.00 | 61.55 |
| ATOM | 3569 | CB   | ARG | 586 | 106.922 | 43.169 | 92.783  | 1.00 | 64.40 |
| ATOM | 3570 | CG   | ARG | 586 | 107.430 | 42.794 | 91.398  | 1.00 | 67.33 |
| ATOM | 3571 | CD   | ARG | 586 | 106.398 | 42.935 | 90.279  | 1.00 | 68.76 |
| ATOM | 3572 | NE   | ARG | 586 | 105.259 | 42.063 | 90.430  | 1.00 | 70.50 |
| ATOM | 3573 | CZ   | ARG | 586 | 104.362 | 41.864 | 89.473  | 1.00 | 75.50 |
| ATOM | 3574 | NH1  | ARG | 586 | 104.483 | 42.485 | 88.307  | 1.00 | 72.10 |
| ATOM | 3575 | NH2  | ARG | 586 | 103.341 | 41.031 | 89.686  | 1.00 | 80.24 |
| ATOM | 3576 | C    | ARG | 586 | 108.521 | 45.016 | 92.957  | 1.00 | 61.66 |
| ATOM | 3577 | O    | ARG | 586 | 109.281 | 44.936 | 91.995  | 1.00 | 63.22 |
| ATOM | 3578 | N    | GLU | 587 | 108.078 | 46.173 | 93.439  | 1.00 | 61.75 |
| ATOM | 3579 | CA   | GLU | 587 | 108.606 | 47.439 | 92.904  | 1.00 | 64.12 |
| ATOM | 3580 | CB   | GLU | 587 | 108.094 | 48.639 | 93.705  | 1.00 | 63.94 |
| ATOM | 3581 | CG   | GLU | 587 | 108.798 | 49.956 | 93.401  | 1.00 | 67.04 |
| ATOM | 3582 | CD   | GLU | 587 | 108.311 | 51.173 | 94.240  | 1.00 | 67.88 |
| ATOM | 3583 | OE1  | GLU | 587 | 108.299 | 51.066 | 95.501  | 1.00 | 69.40 |
| ATOM | 3584 | OE2  | GLU | 587 | 107.960 | 52.143 | 93.620  | 1.00 | 67.44 |
| ATOM | 3585 | C    | GLU | 587 | 110.122 | 47.265 | 93.124  | 1.00 | 67.19 |

| | | | | | | | | |
|---|---|---|---|---|---|---|---|---|
| ATOM | 3586 | O | GLU | 587 | 110.850 | 46.996 | 92.185 | 1.00 67.95 |
| ATOM | 3587 | N | ARG | 588 | 110.578 | 47.380 | 94.375 | 1.00 70.16 |
| ATOM | 3588 | CA | ARG | 588 | 111.974 | 47.145 | 94.772 | 1.00 71.97 |
| ATOM | 3589 | CB | ARG | 588 | 112.004 | 46.654 | 96.242 | 1.00 75.25 |
| ATOM | 3590 | CG | ARG | 588 | 111.332 | 47.550 | 97.315 | 1.00 78.25 |
| ATOM | 3591 | CD | ARG | 588 | 111.378 | 46.923 | 98.763 | 1.00 79.69 |
| ATOM | 3592 | NE | ARG | 588 | 111.172 | 47.953 | 99.798 | 1.00 81.26 |
| ATOM | 3593 | CZ | ARG | 588 | 111.496 | 47.824 | 101.090 | 1.00 83.00 |
| ATOM | 3594 | NH1 | ARG | 588 | 112.054 | 46.704 | 101.531 | 1.00 83.21 |
| ATOM | 3595 | NH2 | ARG | 588 | 111.301 | 48.830 | 101.943 | 1.00 82.76 |
| ATOM | 3596 | C | ARG | 588 | 112.635 | 46.044 | 93.874 | 1.00 72.13 |
| ATOM | 3597 | O | ARG | 588 | 113.567 | 46.325 | 93.097 | 1.00 72.00 |
| ATOM | 3598 | N | ALA | 589 | 112.151 | 44.801 | 94.017 | 1.00 71.62 |
| ATOM | 3599 | CA | ALA | 589 | 112.622 | 43.623 | 93.275 | 1.00 72.59 |
| ATOM | 3600 | CB | ALA | 589 | 111.594 | 42.542 | 93.326 | 1.00 73.21 |
| ATOM | 3601 | C | ALA | 589 | 112.986 | 43.865 | 91.837 | 1.00 73.38 |
| ATOM | 3602 | O | ALA | 589 | 114.069 | 43.496 | 91.384 | 1.00 73.26 |
| ATOM | 3603 | N | LEU | 590 | 112.083 | 44.482 | 91.109 | 1.00 74.19 |
| ATOM | 3604 | CA | LEU | 590 | 112.373 | 44.730 | 89.735 | 1.00 77.99 |
| ATOM | 3605 | CB | LEU | 590 | 111.092 | 44.980 | 88.985 | 1.00 79.14 |
| ATOM | 3606 | CG | LEU | 590 | 111.156 | 45.408 | 87.511 | 1.00 79.98 |
| ATOM | 3607 | CD1 | LEU | 590 | 112.349 | 44.788 | 86.689 | 1.00 78.22 |
| ATOM | 3608 | CD2 | LEU | 590 | 109.761 | 45.016 | 86.975 | 1.00 77.30 |
| ATOM | 3609 | C | LEU | 590 | 113.322 | 45.865 | 89.477 | 1.00 80.76 |
| ATOM | 3610 | O | LEU | 590 | 113.701 | 46.107 | 88.326 | 1.00 80.36 |
| ATOM | 3611 | N | LEU | 591 | 113.758 | 46.554 | 90.520 | 1.00 84.85 |
| ATOM | 3612 | CA | LEU | 591 | 114.610 | 47.688 | 90.220 | 1.00 89.58 |
| ATOM | 3613 | CB | LEU | 591 | 114.131 | 48.966 | 90.925 | 1.00 89.75 |
| ATOM | 3614 | CG | LEU | 591 | 112.819 | 49.526 | 90.328 | 1.00 88.63 |
| ATOM | 3615 | CD1 | LEU | 591 | 112.441 | 50.809 | 91.023 | 1.00 91.20 |
| ATOM | 3616 | CD2 | LEU | 591 | 112.963 | 49.769 | 86.854 | 1.00 86.04 |
| ATOM | 3617 | C | LEU | 591 | 116.098 | 47.572 | 90.299 | 1.00 92.12 |
| ATOM | 3618 | O | LEU | 591 | 116.786 | 48.563 | 90.158 | 1.00 93.19 |
| ATOM | 3619 | N | LYS | 592 | 116.621 | 46.387 | 90.547 | 1.00 94.82 |
| ATOM | 3620 | CA | LYS | 592 | 118.049 | 46.283 | 90.429 | 1.00 96.18 |
| ATOM | 3621 | CB | LYS | 592 | 118.594 | 45.123 | 91.231 | 1.00 97.72 |
| ATOM | 3622 | CG | LYS | 592 | 118.513 | 45.358 | 92.737 | 1.00 98.39 |
| ATOM | 3623 | CD | LYS | 592 | 119.317 | 44.274 | 93.427 | 1.00 99.59 |
| ATOM | 3624 | CE | LYS | 592 | 119.709 | 44.641 | 94.845 | 1.00100.32 |
| ATOM | 3625 | NZ | LYS | 592 | 120.673 | 43.659 | 95.428 | 1.00 99.60 |
| ATOM | 3626 | C | LYS | 592 | 118.008 | 45.961 | 88.950 | 1.00 97.07 |
| ATOM | 3627 | O | LYS | 592 | 117.964 | 44.807 | 88.570 | 1.00 96.96 |
| ATOM | 3628 | N | ASP | 593 | 117.854 | 47.012 | 88.146 | 1.00 98.38 |
| ATOM | 3629 | CA | ASP | 593 | 117.823 | 46.949 | 86.684 | 1.00 99.07 |
| ATOM | 3630 | CB | ASP | 593 | 116.575 | 47.584 | 86.089 | 1.00 94.43 |
| ATOM | 3631 | CG | ASP | 593 | 116.393 | 47.218 | 84.650 | 1.00 90.60 |
| ATOM | 3632 | OD1 | ASP | 593 | 116.714 | 46.061 | 84.349 | 1.00 86.87 |
| ATOM | 3633 | OD2 | ASP | 593 | 115.909 | 48.036 | 83.836 | 1.00 88.75 |
| ATOM | 3634 | C | ASP | 593 | 118.981 | 47.868 | 86.468 | 1.00102.18 |
| ATOM | 3635 | O | ASP | 593 | 119.385 | 48.144 | 85.353 | 1.00103.40 |
| ATOM | 3636 | N | GLN | 594 | 119.472 | 48.359 | 87.602 | 1.00105.49 |
| ATOM | 3637 | CA | GLN | 594 | 120.633 | 49.214 | 87.668 | 1.00109.29 |
| ATOM | 3638 | CB | GLN | 594 | 121.828 | 48.367 | 88.120 | 1.00112.41 |
| ATOM | 3639 | CG | GLN | 594 | 123.193 | 48.969 | 87.783 | 1.00114.35 |
| ATOM | 3640 | CD | GLN | 594 | 124.226 | 47.929 | 87.345 | 1.00115.68 |
| ATOM | 3641 | OE1 | GLN | 594 | 123.922 | 46.983 | 86.587 | 1.00113.90 |
| ATOM | 3642 | NE2 | GLN | 594 | 125.470 | 48.125 | 87.793 | 1.00116.89 |
| ATOM | 3643 | C | GLN | 594 | 120.955 | 49.915 | 86.360 | 1.00110.02 |
| ATOM | 3644 | O | GLN | 594 | 122.074 | 49.884 | 85.863 | 1.00112.42 |
| ATOM | 3645 | N | GLN | 595 | 119.955 | 50.482 | 85.745 | 1.00109.21 |
| ATOM | 3646 | CA | GLN | 595 | 120.207 | 51.255 | 84.567 | 1.00109.77 |
| ATOM | 3647 | CB | GLN | 595 | 119.363 | 50.701 | 83.440 | 1.00110.74 |
| ATOM | 3648 | CG | GLN | 595 | 119.805 | 49.298 | 83.158 | 1.00110.79 |
| ATOM | 3649 | CD | GLN | 595 | 118.929 | 48.555 | 82.207 | 1.00111.93 |
| ATOM | 3650 | OE1 | GLN | 595 | 117.713 | 48.444 | 82.402 | 1.00114.95 |
| ATOM | 3651 | NE2 | GLN | 595 | 119.538 | 48.012 | 81.169 | 1.00111.61 |
| ATOM | 3652 | C | GLN | 595 | 119.584 | 52.343 | 85.390 | 1.00110.27 |
| ATOM | 3653 | O | GLN | 595 | 118.368 | 52.574 | 85.319 | 1.00111.25 |
| ATOM | 3654 | N | PRO | 596 | 120.425 | 52.996 | 86.237 | 1.00109.67 |
| ATOM | 3655 | CD | PRO | 596 | 121.887 | 52.807 | 86.175 | 1.00110.11 |

106

| ATOM | 3656 | CA | PRO | 596 | 120.141 | 54.071 | 87.190 | 1.00 | 108.52 |
| --- | --- | --- | --- | --- | --- | --- | --- | --- | --- |
| ATOM | 3657 | CB | PRO | 596 | 121.510 | 54.694 | 87.391 | 1.00 | 109.39 |
| ATOM | 3658 | CG | PRO | 596 | 122.351 | 53.469 | 87.466 | 1.00 | 109.50 |
| ATOM | 3659 | C | PRO | 596 | 119.037 | 55.072 | 86.907 | 1.00 | 107.19 |
| ATOM | 3660 | O | PRO | 596 | 118.698 | 55.843 | 87.802 | 1.00 | 106.40 |
| ATOM | 3661 | N | GLY | 597 | 118.482 | 55.037 | 85.684 | 1.00 | 105.83 |
| ATOM | 3662 | CA | GLY | 597 | 117.376 | 55.897 | 85.268 | 1.00 | 101.00 |
| ATOM | 3663 | C | GLY | 597 | 116.298 | 54.924 | 85.594 | 1.00 | 98.36 |
| ATOM | 3664 | O | GLY | 597 | 115.718 | 54.250 | 84.771 | 1.00 | 97.98 |
| ATOM | 3665 | N | THR | 598 | 116.095 | 54.791 | 86.876 | 1.00 | 96.76 |
| ATOM | 3666 | CA | THR | 598 | 115.118 | 53.853 | 87.336 | 1.00 | 94.35 |
| ATOM | 3667 | CB | THR | 598 | 115.642 | 53.091 | 88.556 | 1.00 | 96.85 |
| ATOM | 3668 | OG1 | THR | 598 | 116.743 | 52.245 | 88.163 | 1.00 | 96.70 |
| ATOM | 3669 | CG2 | THR | 598 | 114.533 | 52.266 | 89.138 | 1.00 | 98.37 |
| ATOM | 3670 | C | THR | 598 | 113.745 | 54.441 | 87.615 | 1.00 | 90.12 |
| ATOM | 3671 | O | THR | 598 | 113.434 | 54.895 | 88.717 | 1.00 | 90.84 |
| ATOM | 3672 | N | PHE | 599 | 112.930 | 54.396 | 86.572 | 1.00 | 84.26 |
| ATOM | 3673 | CA | PHE | 599 | 111.566 | 54.867 | 86.572 | 1.00 | 75.24 |
| ATOM | 3674 | CB | PHE | 599 | 111.302 | 55.545 | 85.267 | 1.00 | 79.32 |
| ATOM | 3675 | CG | PHE | 599 | 111.364 | 56.969 | 85.337 | 1.00 | 82.12 |
| ATOM | 3676 | CD1 | PHE | 599 | 112.110 | 57.585 | 86.322 | 1.00 | 86.02 |
| ATOM | 3677 | CD2 | PHE | 599 | 110.667 | 57.719 | 84.424 | 1.00 | 84.26 |
| ATOM | 3678 | CE1 | PHE | 599 | 112.172 | 58.992 | 86.403 | 1.00 | 90.74 |
| ATOM | 3679 | CE2 | PHE | 599 | 110.703 | 59.087 | 84.468 | 1.00 | 90.38 |
| ATOM | 3680 | CZ | PHE | 599 | 111.458 | 59.751 | 85.472 | 1.00 | 92.07 |
| ATOM | 3681 | C | PHE | 599 | 110.526 | 53.768 | 86.730 | 1.00 | 68.29 |
| ATOM | 3682 | O | PHE | 599 | 110.596 | 52.694 | 86.115 | 1.00 | 62.77 |
| ATOM | 3683 | N | LEU | 600 | 109.528 | 54.113 | 87.530 | 1.00 | 62.22 |
| ATOM | 3684 | CA | LEU | 600 | 108.367 | 53.278 | 87.822 | 1.00 | 55.02 |
| ATOM | 3685 | CB | LEU | 600 | 108.730 | 52.181 | 88.812 | 1.00 | 56.98 |
| ATOM | 3686 | CG | LEU | 600 | 107.577 | 51.230 | 89.111 | 1.00 | 54.45 |
| ATOM | 3687 | CD1 | LEU | 600 | 107.379 | 50.349 | 87.902 | 1.00 | 56.85 |
| ATOM | 3688 | CD2 | LEU | 600 | 107.876 | 50.382 | 90.323 | 1.00 | 55.06 |
| ATOM | 3689 | C | LEU | 600 | 107.231 | 54.107 | 88.417 | 1.00 | 50.57 |
| ATOM | 3690 | O | LEU | 600 | 107.282 | 54.487 | 89.592 | 1.00 | 52.08 |
| ATOM | 3691 | N | LEU | 601 | 106.210 | 54.374 | 87.610 | 1.00 | 41.07 |
| ATOM | 3692 | CA | LEU | 601 | 105.049 | 55.147 | 88.041 | 1.00 | 30.95 |
| ATOM | 3693 | CB | LEU | 601 | 104.412 | 55.812 | 86.829 | 1.00 | 21.58 |
| ATOM | 3694 | CG | LEU | 601 | 105.385 | 56.488 | 85.849 | 1.00 | 16.19 |
| ATOM | 3695 | CD1 | LEU | 601 | 104.618 | 57.027 | 84.671 | 1.00 | 10.48 |
| ATOM | 3696 | CD2 | LEU | 601 | 106.167 | 57.581 | 86.519 | 1.00 | 14.08 |
| ATOM | 3697 | C | LEU | 601 | 104.061 | 54.166 | 88.671 | 1.00 | 30.95 |
| ATOM | 3698 | O | LEU | 601 | 103.562 | 53.279 | 87.999 | 1.00 | 31.11 |
| ATOM | 3699 | N | ARG | 602 | 103.808 | 54.305 | 89.969 | 1.00 | 33.37 |
| ATOM | 3700 | CA | ARG | 602 | 102.882 | 53.426 | 90.704 | 1.00 | 31.57 |
| ATOM | 3701 | CB | ARG | 602 | 103.593 | 52.750 | 91.892 | 1.00 | 26.78 |
| ATOM | 3702 | CG | ARG | 602 | 102.652 | 51.893 | 92.722 | 1.00 | 37.34 |
| ATOM | 3703 | CD | ARG | 602 | 103.262 | 51.155 | 93.950 | 1.00 | 41.62 |
| ATOM | 3704 | NE | ARG | 602 | 103.319 | 51.940 | 95.184 | 1.00 | 40.96 |
| ATOM | 3705 | CZ | ARG | 602 | 104.170 | 52.939 | 95.401 | 1.00 | 44.17 |
| ATOM | 3706 | NH1 | ARG | 602 | 105.046 | 53.275 | 94.460 | 1.00 | 44.25 |
| ATOM | 3707 | NH2 | ARG | 602 | 104.159 | 53.596 | 96.563 | 1.00 | 40.54 |
| ATOM | 3708 | C | ARG | 602 | 101.765 | 54.320 | 91.242 | 1.00 | 28.77 |
| ATOM | 3709 | O | ARG | 602 | 102.019 | 55.479 | 91.565 | 1.00 | 31.68 |
| ATOM | 3710 | N | PHE | 603 | 100.535 | 53.817 | 91.310 | 1.00 | 24.79 |
| ATOM | 3711 | CA | PHE | 603 | 99.447 | 54.617 | 91.866 | 1.00 | 24.91 |
| ATOM | 3712 | CB | PHE | 603 | 98.093 | 54.067 | 91.462 | 1.00 | 22.69 |
| ATOM | 3713 | CG | PHE | 603 | 97.694 | 54.432 | 90.081 | 1.00 | 24.90 |
| ATOM | 3714 | CD1 | PHE | 603 | 97.075 | 53.500 | 89.256 | 1.00 | 26.47 |
| ATOM | 3715 | CD2 | PHE | 603 | 97.944 | 55.712 | 89.592 | 1.00 | 24.64 |
| ATOM | 3716 | CE1 | PHE | 603 | 96.714 | 53.836 | 87.956 | 1.00 | 26.13 |
| ATOM | 3717 | CE2 | PHE | 603 | 97.589 | 56.063 | 88.303 | 1.00 | 25.98 |
| ATOM | 3718 | CZ | PHE | 603 | 96.973 | 55.127 | 87.477 | 1.00 | 27.62 |
| ATOM | 3719 | C | PHE | 603 | 99.592 | 54.545 | 93.360 | 1.00 | 28.18 |
| ATOM | 3720 | O | PHE | 603 | 99.990 | 53.522 | 93.886 | 1.00 | 36.34 |
| ATOM | 3721 | N | SER | 604 | 99.265 | 55.614 | 94.063 | 1.00 | 30.79 |
| ATOM | 3722 | CA | SER | 604 | 99.438 | 55.595 | 95.504 | 1.00 | 32.85 |
| ATOM | 3723 | CB | SER | 604 | 99.376 | 57.002 | 96.079 | 1.00 | 37.22 |
| ATOM | 3724 | OG | SER | 604 | 99.339 | 56.920 | 97.494 | 1.00 | 40.36 |
| ATOM | 3725 | C | SER | 604 | 98.457 | 54.754 | 96.252 | 1.00 | 32.28 |

107

| ATOM | 3726 | O | SER | 604 | 97.264 | 54.816 | 95.993 | 1.00 | 38.05 |
| ATOM | 3727 | N | GLU | 605 | 98.953 | 53.976 | 97.199 | 1.00 | 31.78 |
| ATOM | 3728 | CA | GLU | 605 | 98.053 | 53.161 | 97.988 | 1.00 | 33.97 |
| ATOM | 3729 | CB | GLU | 605 | 98.727 | 51.888 | 98.498 | 1.00 | 33.46 |
| ATOM | 3730 | CG | GLU | 605 | 98.908 | 50.777 | 97.485 | 1.00 | 35.98 |
| ATOM | 3731 | CD | GLU | 605 | 99.242 | 49.467 | 98.176 | 1.00 | 36.66 |
| ATOM | 3732 | OE1 | GLU | 605 | 99.276 | 48.412 | 97.508 | 1.00 | 36.99 |
| ATOM | 3733 | OE2 | GLU | 605 | 99.468 | 49.504 | 99.405 | 1.00 | 36.14 |
| ATOM | 3734 | C | GLU | 605 | 97.536 | 53.925 | 99.189 | 1.00 | 35.04 |
| ATOM | 3735 | O | GLU | 605 | 96.586 | 53.493 | 99.821 | 1.00 | 38.91 |
| ATOM | 3736 | N | SER | 606 | 98.131 | 55.066 | 99.503 | 1.00 | 33.30 |
| ATOM | 3737 | CA | SER | 606 | 97.699 | 55.803 | 100.683 | 1.00 | 35.29 |
| ATOM | 3738 | CB | SER | 606 | 98.911 | 56.474 | 101.313 | 1.00 | 33.44 |
| ATOM | 3739 | OG | SER | 606 | 99.858 | 55.482 | 101.668 | 1.00 | 35.64 |
| ATOM | 3740 | C | SER | 606 | 96.572 | 56.825 | 100.541 | 1.00 | 40.82 |
| ATOM | 3741 | O | SER | 606 | 95.673 | 56.875 | 101.379 | 1.00 | 42.70 |
| ATOM | 3742 | N | SER | 607 | 96.609 | 57.630 | 99.484 | 1.00 | 42.58 |
| ATOM | 3743 | CA | SER | 607 | 95.608 | 58.668 | 99.278 | 1.00 | 41.68 |
| ATOM | 3744 | CB | SER | 607 | 95.983 | 59.461 | 98.033 | 1.00 | 40.06 |
| ATOM | 3745 | OG | SER | 607 | 97.220 | 60.119 | 98.270 | 1.00 | 46.77 |
| ATOM | 3746 | C | SER | 607 | 94.158 | 58.222 | 99.218 | 1.00 | 41.07 |
| ATOM | 3747 | O | SER | 607 | 93.745 | 57.598 | 98.254 | 1.00 | 40.36 |
| ATOM | 3748 | N | ARG | 608 | 93.315 | 59.304 | 99.885 | 1.00 | 42.17 |
| ATOM | 3749 | CA | ARG | 608 | 91.877 | 59.243 | 99.766 | 1.00 | 47.94 |
| ATOM | 3750 | CB | ARG | 608 | 91.209 | 60.260 | 100.824 | 1.00 | 57.00 |
| ATOM | 3757 | C | ARG | 608 | 91.541 | 59.608 | 98.433 | 1.00 | 47.36 |
| ATOM | 3758 | O | ARG | 608 | 90.503 | 59.047 | 97.966 | 1.00 | 47.16 |
| ATOM | 3759 | N | GLU | 609 | 92.322 | 60.012 | 97.737 | 1.00 | 54.18 |
| ATOM | 3760 | CA | GLU | 609 | 92.021 | 60.915 | 96.620 | 1.00 | 47.87 |
| ATOM | 3761 | CB | GLU | 609 | 92.682 | 62.286 | 96.807 | 1.00 | 42.27 |
| ATOM | 3762 | CG | GLU | 609 | 92.108 | 63.101 | 97.933 | 1.00 | 48.36 |
| ATOM | 3763 | CD | GLU | 609 | 93.034 | 63.153 | 99.125 | 1.00 | 56.54 |
| ATOM | 3764 | OE1 | GLU | 609 | 93.465 | 62.070 | 99.603 | 1.00 | 53.56 |
| ATOM | 3765 | OE2 | GLU | 609 | 93.329 | 64.285 | 99.578 | 1.00 | 61.81 |
| ATOM | 3766 | C | GLU | 609 | 92.448 | 60.378 | 95.265 | 1.00 | 44.88 |
| ATOM | 3767 | O | GLU | 609 | 91.720 | 60.473 | 94.274 | 1.00 | 36.86 |
| ATOM | 3768 | N | GLY | 610 | 93.641 | 59.814 | 95.223 | 1.00 | 39.86 |
| ATOM | 3769 | CA | GLY | 610 | 94.122 | 59.282 | 93.974 | 1.00 | 36.86 |
| ATOM | 3770 | C | GLY | 610 | 95.281 | 60.149 | 93.606 | 1.00 | 35.18 |
| ATOM | 3771 | O | GLY | 610 | 95.097 | 61.319 | 93.282 | 1.00 | 39.16 |
| ATOM | 3772 | N | ALA | 611 | 96.470 | 59.562 | 93.667 | 1.00 | 34.88 |
| ATOM | 3773 | CA | ALA | 611 | 97.712 | 60.259 | 93.380 | 1.00 | 31.62 |
| ATOM | 3774 | CB | ALA | 611 | 98.283 | 60.785 | 94.704 | 1.00 | 23.34 |
| ATOM | 3775 | C | ALA | 611 | 98.716 | 59.311 | 92.681 | 1.00 | 30.61 |
| ATOM | 3776 | O | ALA | 611 | 98.521 | 58.096 | 92.700 | 1.00 | 28.22 |
| ATOM | 3777 | N | ILE | 612 | 99.772 | 59.857 | 92.064 | 1.00 | 30.88 |
| ATOM | 3778 | CA | ILE | 612 | 100.780 | 59.015 | 91.403 | 1.00 | 30.91 |
| ATOM | 3779 | CB | ILE | 612 | 100.812 | 59.141 | 89.843 | 1.00 | 29.78 |
| ATOM | 3780 | CG2 | ILE | 612 | 101.316 | 57.851 | 89.246 | 1.00 | 24.45 |
| ATOM | 3781 | CG1 | ILE | 612 | 99.422 | 59.343 | 89.251 | 1.00 | 33.00 |
| ATOM | 3782 | CD1 | ILE | 612 | 98.902 | 60.719 | 89.443 | 1.00 | 36.95 |
| ATOM | 3783 | C | ILE | 612 | 102.191 | 59.358 | 91.861 | 1.00 | 33.00 |
| ATOM | 3784 | O | ILE | 612 | 102.529 | 60.529 | 92.038 | 1.00 | 32.48 |
| ATOM | 3785 | N | THR | 613 | 103.010 | 58.321 | 92.037 | 1.00 | 35.65 |
| ATOM | 3786 | CA | THR | 613 | 104.404 | 58.462 | 92.448 | 1.00 | 34.92 |
| ATOM | 3787 | CB | THR | 613 | 104.683 | 57.803 | 93.783 | 1.00 | 33.67 |
| ATOM | 3788 | OG1 | THR | 613 | 103.833 | 58.361 | 94.771 | 1.00 | 44.71 |
| ATOM | 3789 | CG2 | THR | 613 | 106.102 | 58.039 | 94.200 | 1.00 | 34.52 |
| ATOM | 3790 | C | THR | 613 | 105.258 | 57.692 | 91.479 | 1.00 | 37.40 |
| ATOM | 3791 | O | THR | 613 | 104.756 | 56.845 | 90.744 | 1.00 | 39.25 |
| ATOM | 3792 | N | PHE | 614 | 106.549 | 58.006 | 91.468 | 1.00 | 40.84 |
| ATOM | 3793 | CA | PHE | 614 | 107.513 | 57.255 | 90.670 | 1.00 | 41.17 |
| ATOM | 3794 | CB | PHE | 614 | 108.151 | 58.071 | 89.522 | 1.00 | 39.16 |
| ATOM | 3795 | CG | PHE | 614 | 108.666 | 59.428 | 89.917 | 1.00 | 38.22 |
| ATOM | 3796 | CD1 | PHE | 614 | 109.526 | 59.593 | 90.993 | 1.00 | 38.17 |
| ATOM | 3797 | CD2 | PHE | 614 | 108.316 | 60.548 | 89.170 | 1.00 | 34.13 |
| ATOM | 3798 | CE1 | PHE | 614 | 110.028 | 60.852 | 91.311 | 1.00 | 36.15 |
| ATOM | 3799 | CE2 | PHE | 614 | 108.816 | 61.800 | 89.492 | 1.00 | 35.11 |
| ATOM | 3800 | CZ | PHE | 614 | 109.672 | 61.953 | 90.561 | 1.00 | 28.45 |
| ATOM | 3801 | C | PHE | 614 | 108.569 | 56.817 | 91.659 | 1.00 | 41.95 |

108

| ATOM | 3802 | O | PHE | 614 | 108.691 | 57.403 | 92.741 | 1.00 | 34.94 |
| ATOM | 3803 | N | THR | 615 | 109.287 | 55.753 | 91.323 | 1.00 | 48.43 |
| ATOM | 3804 | CA | THR | 615 | 110.336 | 55.308 | 92.198 | 1.00 | 56.15 |
| ATOM | 3805 | CB | THR | 615 | 110.044 | 53.948 | 92.800 | 1.00 | 57.74 |
| ATOM | 3806 | OG1 | THR | 615 | 108.864 | 54.043 | 93.607 | 1.00 | 55.10 |
| ATOM | 3807 | CG2 | THR | 615 | 111.188 | 53.538 | 93.704 | 1.00 | 60.34 |
| ATOM | 3808 | C | THR | 615 | 111.710 | 55.367 | 91.546 | 1.00 | 61.76 |
| ATOM | 3809 | O | THR | 615 | 111.922 | 55.066 | 90.372 | 1.00 | 60.82 |
| ATOM | 3810 | N | TRP | 616 | 112.621 | 55.791 | 92.404 | 1.00 | 70.82 |
| ATOM | 3811 | CA | TRP | 616 | 114.029 | 56.092 | 92.186 | 1.00 | 75.75 |
| ATOM | 3812 | CB | TRP | 616 | 114.325 | 57.219 | 93.141 | 1.00 | 78.95 |
| ATOM | 3813 | CG | TRP | 616 | 115.035 | 58.390 | 92.728 | 1.00 | 81.96 |
| ATOM | 3814 | CD2 | TRP | 616 | 114.887 | 59.652 | 93.346 | 1.00 | 84.52 |
| ATOM | 3815 | CE2 | TRP | 616 | 115.935 | 60.476 | 92.881 | 1.00 | 85.43 |
| ATOM | 3816 | CE3 | TRP | 616 | 113.973 | 60.183 | 94.262 | 1.00 | 86.43 |
| ATOM | 3817 | CD1 | TRP | 616 | 116.123 | 58.472 | 91.915 | 1.00 | 80.20 |
| ATOM | 3818 | NE1 | TRP | 616 | 116.677 | 59.723 | 92.003 | 1.00 | 83.09 |
| ATOM | 3819 | CZ2 | TRP | 616 | 116.093 | 61.800 | 93.302 | 1.00 | 88.36 |
| ATOM | 3820 | CZ3 | TRP | 616 | 114.124 | 61.493 | 94.686 | 1.00 | 89.25 |
| ATOM | 3821 | CH2 | TRP | 616 | 115.180 | 62.291 | 94.205 | 1.00 | 89.86 |
| ATOM | 3822 | C | TRP | 616 | 115.027 | 54.966 | 92.534 | 1.00 | 76.72 |
| ATOM | 3823 | O | TRP | 616 | 114.921 | 54.376 | 93.608 | 1.00 | 77.61 |
| ATOM | 3824 | N | VAL | 617 | 116.018 | 54.780 | 91.663 | 1.00 | 77.66 |
| ATOM | 3825 | CA | VAL | 617 | 117.118 | 53.842 | 91.932 | 1.00 | 77.44 |
| ATOM | 3826 | CB | VAL | 617 | 116.796 | 52.387 | 91.546 | 1.00 | 77.64 |
| ATOM | 3827 | CG1 | VAL | 617 | 117.954 | 51.493 | 91.946 | 1.00 | 77.78 |
| ATOM | 3828 | CG2 | VAL | 617 | 115.548 | 51.916 | 92.258 | 1.00 | 79.77 |
| ATOM | 3829 | C | VAL | 617 | 118.418 | 54.244 | 91.223 | 1.00 | 77.11 |
| ATOM | 3830 | O | VAL | 617 | 118.559 | 54.073 | 90.017 | 1.00 | 73.14 |
| ATOM | 3831 | N | GLU | 618 | 119.349 | 54.822 | 91.976 | 1.00 | 82.25 |
| ATOM | 3832 | CA | GLU | 618 | 120.655 | 55.199 | 91.429 | 1.00 | 90.78 |
| ATOM | 3833 | CB | GLU | 618 | 120.915 | 56.694 | 91.604 | 1.00 | 90.69 |
| ATOM | 3834 | CG | GLU | 618 | 119.825 | 57.559 | 90.982 | 1.00 | 94.33 |
| ATOM | 3835 | CD | GLU | 618 | 120.290 | 58.971 | 90.690 | 1.00 | 96.51 |
| ATOM | 3836 | OE1 | GLU | 618 | 120.959 | 59.572 | 91.558 | 1.00 | 97.94 |
| ATOM | 3837 | OE2 | GLU | 618 | 119.973 | 59.488 | 89.595 | 1.00 | 97.48 |
| ATOM | 3838 | C | GLU | 618 | 121.622 | 54.340 | 92.249 | 1.00 | 94.43 |
| ATOM | 3839 | O | GLU | 618 | 121.209 | 53.283 | 92.700 | 1.00 | 96.13 |
| ATOM | 3840 | N | ARG | 619 | 122.884 | 54.713 | 92.442 | 1.00 | 97.30 |
| ATOM | 3841 | CA | ARG | 619 | 123.711 | 53.818 | 93.260 | 1.00 | 100.48 |
| ATOM | 3842 | CB | ARG | 619 | 124.983 | 53.375 | 92.523 | 1.00 | 102.71 |
| ATOM | 3843 | CG | ARG | 619 | 124.716 | 52.118 | 91.664 | 1.00 | 107.54 |
| ATOM | 3844 | CD | ARG | 619 | 125.645 | 50.935 | 92.000 | 1.00 | 110.65 |
| ATOM | 3845 | NE | ARG | 619 | 125.084 | 49.662 | 91.531 | 1.00 | 113.74 |
| ATOM | 3846 | CZ | ARG | 619 | 125.711 | 48.484 | 91.566 | 1.00 | 114.75 |
| ATOM | 3847 | NH1 | ARG | 619 | 126.945 | 48.393 | 92.051 | 1.00 | 114.91 |
| ATOM | 3848 | NH2 | ARG | 619 | 125.096 | 47.389 | 91.124 | 1.00 | 113.45 |
| ATOM | 3849 | C | ARG | 619 | 124.027 | 54.293 | 94.661 | 1.00 | 101.41 |
| ATOM | 3850 | O | ARG | 619 | 124.054 | 55.494 | 94.926 | 1.00 | 102.41 |
| ATOM | 3851 | N | SER | 620 | 124.250 | 53.326 | 95.554 | 1.00 | 101.65 |
| ATOM | 3852 | CA | SER | 620 | 124.501 | 53.590 | 96.969 | 1.00 | 102.46 |
| ATOM | 3853 | CB | SER | 620 | 124.140 | 52.350 | 97.793 | 1.00 | 104.46 |
| ATOM | 3854 | OG | SER | 620 | 124.097 | 52.652 | 99.182 | 1.00 | 104.59 |
| ATOM | 3855 | C | SER | 620 | 125.885 | 54.080 | 97.385 | 1.00 | 102.03 |
| ATOM | 3856 | O | SER | 620 | 126.106 | 54.370 | 98.563 | 1.00 | 101.02 |
| ATOM | 3857 | N | GLN | 621 | 126.816 | 54.152 | 96.437 | 1.00 | 102.13 |
| ATOM | 3858 | CA | GLN | 621 | 128.161 | 54.651 | 96.734 | 1.00 | 104.01 |
| ATOM | 3859 | CB | GLN | 621 | 128.084 | 56.082 | 97.285 | 1.00 | 103.89 |
| ATOM | 3860 | CG | GLN | 621 | 127.037 | 56.954 | 96.612 | 1.00 | 103.35 |
| ATOM | 3861 | CD | GLN | 621 | 127.006 | 58.351 | 97.184 | 1.00 | 102.99 |
| ATOM | 3862 | OE1 | GLN | 621 | 127.098 | 58.532 | 98.405 | 1.00 | 100.19 |
| ATOM | 3863 | NE2 | GLN | 621 | 126.848 | 59.354 | 96.309 | 1.00 | 102.01 |
| ATOM | 3864 | C | GLN | 621 | 128.870 | 53.783 | 97.770 | 1.00 | 104.92 |
| ATOM | 3865 | O | GLN | 621 | 129.976 | 54.108 | 98.214 | 1.00 | 104.64 |
| ATOM | 3866 | N | ASN | 622 | 128.218 | 52.656 | 98.175 | 1.00 | 106.33 |
| ATOM | 3867 | CA | ASN | 622 | 128.789 | 51.781 | 99.161 | 1.00 | 106.75 |
| ATOM | 3868 | CB | ASN | 622 | 128.497 | 52.273 | 100.599 | 1.00 | 105.78 |
| ATOM | 3869 | CG | ASN | 622 | 129.186 | 53.607 | 100.926 | 1.00 | 104.16 |
| ATOM | 3870 | OD1 | ASN | 622 | 130.422 | 53.727 | 100.894 | 1.00 | 100.85 |
| ATOM | 3871 | ND2 | ASN | 622 | 128.377 | 54.614 | 101.241 | 1.00 | 102.13 |

109

| ATOM | 3872 | C | ASN | 622 | 128.272 | 50.344 | 98.980 | 1.00 | 108.22 |
| ATOM | 3873 | O | ASN | 622 | 128.167 | 49.585 | 99.944 | 1.00 | 109.11 |
| ATOM | 3874 | N | GLY | 623 | 127.953 | 49.955 | 97.751 | 1.00 | 108.69 |
| ATOM | 3875 | CA | GLY | 623 | 127.483 | 48.597 | 97.553 | 1.00 | 108.01 |
| ATOM | 3876 | C | GLY | 623 | 126.204 | 48.346 | 98.311 | 1.00 | 109.32 |
| ATOM | 3877 | O | GLY | 623 | 126.148 | 47.669 | 99.319 | 1.00 | 109.46 |
| ATOM | 3878 | N | GLY | 624 | 125.551 | 48.787 | 97.867 | 1.00 | 110.01 |
| ATOM | 3879 | CA | GLY | 624 | 124.175 | 48.696 | 98.298 | 1.00 | 110.30 |
| ATOM | 3880 | C | GLY | 624 | 123.322 | 49.577 | 97.367 | 1.00 | 111.48 |
| ATOM | 3881 | O | GLY | 624 | 123.512 | 50.785 | 97.274 | 1.00 | 112.59 |
| ATOM | 3882 | N | GLU | 625 | 122.366 | 48.953 | 96.676 | 1.00 | 111.56 |
| ATOM | 3883 | CA | GLU | 625 | 121.525 | 49.749 | 95.774 | 1.00 | 110.87 |
| ATOM | 3884 | CB | GLU | 625 | 120.402 | 49.033 | 95.042 | 1.00 | 109.15 |
| ATOM | 3889 | C | GLU | 625 | 120.949 | 50.806 | 96.691 | 1.00 | 110.75 |
| ATOM | 3890 | O | GLU | 625 | 120.491 | 50.517 | 97.772 | 1.00 | 111.52 |
| ATOM | 3891 | N | PRO | 626 | 120.987 | 52.051 | 96.340 | 1.00 | 110.88 |
| ATOM | 3892 | CD | PRO | 626 | 121.219 | 52.445 | 94.957 | 1.00 | 111.67 |
| ATOM | 3893 | CA | PRO | 626 | 120.436 | 53.174 | 97.101 | 1.00 | 111.66 |
| ATOM | 3894 | CB | PRO | 626 | 120.797 | 54.397 | 96.251 | 1.00 | 111.55 |
| ATOM | 3895 | CG | PRO | 626 | 120.819 | 53.891 | 94.862 | 1.00 | 112.10 |
| ATOM | 3896 | C | PRO | 626 | 118.904 | 53.135 | 97.185 | 1.00 | 112.54 |
| ATOM | 3897 | O | PRO | 626 | 118.216 | 52.878 | 96.172 | 1.00 | 112.80 |
| ATOM | 3898 | N | ASP | 627 | 118.577 | 53.453 | 98.313 | 1.00 | 113.67 |
| ATOM | 3899 | CA | ASP | 627 | 117.435 | 53.267 | 99.150 | 1.00 | 113.10 |
| ATOM | 3900 | CB | ASP | 627 | 117.508 | 54.330 | 100.237 | 1.00 | 116.27 |
| ATOM | 3901 | CG | ASP | 627 | 118.777 | 54.181 | 101.066 | 1.00 | 119.96 |
| ATOM | 3902 | OD1 | ASP | 627 | 119.398 | 53.049 | 101.081 | 1.00 | 122.47 |
| ATOM | 3903 | OD2 | ASP | 627 | 119.227 | 55.178 | 101.739 | 1.00 | 122.21 |
| ATOM | 3904 | C | ASP | 627 | 116.052 | 53.405 | 98.564 | 1.00 | 110.12 |
| ATOM | 3905 | O | ASP | 627 | 115.033 | 53.403 | 99.261 | 1.00 | 111.21 |
| ATOM | 3906 | N | PHE | 628 | 116.098 | 53.380 | 97.284 | 1.00 | 105.23 |
| ATOM | 3907 | CA | PHE | 628 | 114.785 | 53.063 | 96.739 | 1.00 | 98.26 |
| ATOM | 3908 | CB | PHE | 628 | 114.171 | 51.907 | 95.951 | 1.00 | 98.77 |
| ATOM | 3909 | CG | PHE | 628 | 115.186 | 51.010 | 95.311 | 1.00 | 99.24 |
| ATOM | 3910 | CD1 | PHE | 628 | 115.674 | 49.905 | 95.987 | 1.00 | 100.63 |
| ATOM | 3911 | CD2 | PHE | 628 | 115.652 | 51.276 | 94.037 | 1.00 | 100.78 |
| ATOM | 3912 | CE1 | PHE | 628 | 116.612 | 49.077 | 95.399 | 1.00 | 104.52 |
| ATOM | 3913 | CE2 | PHE | 628 | 116.590 | 50.453 | 93.443 | 1.00 | 103.37 |
| ATOM | 3914 | CZ | PHE | 628 | 117.070 | 49.351 | 94.125 | 1.00 | 106.12 |
| ATOM | 3915 | C | PHE | 628 | 113.743 | 54.050 | 97.239 | 1.00 | 94.33 |
| ATOM | 3916 | O | PHE | 628 | 112.984 | 53.795 | 98.036 | 1.00 | 93.76 |
| ATOM | 3917 | N | HIS | 629 | 114.320 | 55.295 | 97.025 | 1.00 | 87.40 |
| ATOM | 3918 | CA | HIS | 629 | 113.468 | 56.498 | 96.393 | 1.00 | 81.59 |
| ATOM | 3919 | CB | HIS | 629 | 114.461 | 57.595 | 96.095 | 1.00 | 81.19 |
| ATOM | 3920 | CG | HIS | 629 | 115.675 | 57.525 | 96.953 | 1.00 | 82.12 |
| ATOM | 3921 | CD2 | HIS | 629 | 115.997 | 56.666 | 97.950 | 1.00 | 81.82 |
| ATOM | 3922 | ND1 | HIS | 629 | 116.700 | 58.433 | 96.871 | 1.00 | 82.70 |
| ATOM | 3923 | CE1 | HIS | 629 | 117.612 | 58.142 | 97.785 | 1.00 | 83.29 |
| ATOM | 3924 | NE2 | HIS | 629 | 117.210 | 57.078 | 98.450 | 1.00 | 83.85 |
| ATOM | 3925 | C | HIS | 629 | 112.147 | 56.776 | 95.693 | 1.00 | 76.31 |
| ATOM | 3926 | O | HIS | 629 | 112.048 | 56.659 | 94.484 | 1.00 | 72.69 |
| ATOM | 3927 | N | ALA | 630 | 111.135 | 57.136 | 96.485 | 1.00 | 71.92 |
| ATOM | 3928 | CA | ALA | 630 | 109.796 | 57.453 | 95.975 | 1.00 | 65.91 |
| ATOM | 3929 | CB | ALA | 630 | 108.852 | 56.299 | 96.247 | 1.00 | 68.60 |
| ATOM | 3930 | C | ALA | 630 | 109.216 | 58.755 | 96.555 | 1.00 | 61.75 |
| ATOM | 3931 | O | ALA | 630 | 109.005 | 58.889 | 97.773 | 1.00 | 61.63 |
| ATOM | 3932 | N | VAL | 631 | 108.981 | 59.704 | 95.652 | 1.00 | 55.24 |
| ATOM | 3933 | CA | VAL | 631 | 108.428 | 61.020 | 95.933 | 1.00 | 50.04 |
| ATOM | 3934 | CB | VAL | 631 | 108.331 | 61.775 | 94.650 | 1.00 | 50.21 |
| ATOM | 3935 | CG1 | VAL | 631 | 107.503 | 63.024 | 94.844 | 1.00 | 53.11 |
| ATOM | 3936 | CG2 | VAL | 631 | 109.700 | 62.081 | 94.158 | 1.00 | 50.53 |
| ATOM | 3937 | C | VAL | 631 | 107.015 | 60.968 | 96.489 | 1.00 | 49.70 |
| ATOM | 3938 | O | VAL | 631 | 106.266 | 60.056 | 96.149 | 1.00 | 53.06 |
| ATOM | 3939 | N | GLU | 632 | 106.620 | 61.939 | 97.308 | 1.00 | 44.89 |
| ATOM | 3940 | CA | GLU | 632 | 105.244 | 61.943 | 97.820 | 1.00 | 45.47 |
| ATOM | 3941 | CB | GLU | 632 | 104.976 | 63.153 | 98.709 | 1.00 | 48.28 |
| ATOM | 3942 | CG | GLU | 632 | 105.455 | 64.469 | 98.086 | 1.00 | 54.22 |
| ATOM | 3943 | CD | GLU | 632 | 105.242 | 65.646 | 99.013 | 1.00 | 54.08 |
| ATOM | 3944 | OE1 | GLU | 632 | 105.325 | 65.398 | 100.235 | 1.00 | 52.52 |
| ATOM | 3945 | OE2 | GLU | 632 | 105.024 | 66.794 | 98.533 | 1.00 | 53.23 |

110

```
ATOM   3946  C    GLU   632     104.334  62.010  96.610  1.00 44.41
ATOM   3947  O    GLU   632     104.621  62.742  95.660  1.00 46.48
ATOM   3948  N    PRO   633     103.204  61.289  96.643  1.00 42.91
ATOM   3949  CD   PRO   633     102.705  60.508  97.781  1.00 43.53
ATOM   3950  CA   PRO   633     102.226  61.226  95.559  1.00 43.42
ATOM   3951  CB   PRO   633     101.134  60.349  96.146  1.00 44.44
ATOM   3952  CG   PRO   633     101.922  59.437  97.076  1.00 44.32
ATOM   3953  C    PRO   633     101.694  62.555  95.110  1.00 44.61
ATOM   3954  O    PRO   633     101.683  63.523  95.862  1.00 50.56
ATOM   3955  N    TYR   634     101.245  62.598  93.875  1.00 42.65
ATOM   3956  CA   TYR   634     100.709  63.820  93.351  1.00 43.96
ATOM   3957  CB   TYR   634     101.320  64.112  91.973  1.00 47.31
ATOM   3958  CG   TYR   634     102.817  64.379  92.015  1.00 47.80
ATOM   3959  CD1  TYR   634     103.745  63.382  91.696  1.00 45.92
ATOM   3960  CE1  TYR   634     105.122  63.646  91.756  1.00 48.31
ATOM   3961  CD2  TYR   634     103.301  65.680  92.401  1.00 47.28
ATOM   3962  CE2  TYR   634     104.653  65.913  92.468  1.00 46.54
ATOM   3963  CZ   TYR   634     105.566  64.925  92.143  1.00 49.01
ATOM   3964  OH   TYR   634     106.910  65.258  92.155  1.00 51.58
ATOM   3965  C    TYR   634      99.204  63.659  93.261  1.00 46.29
ATOM   3966  O    TYR   634      98.706  62.681  92.707  1.00 46.06
ATOM   3967  N    THR   635      98.468  64.607  93.821  1.00 46.17
ATOM   3968  CA   THR   635      97.028  64.507  93.778  1.00 47.44
ATOM   3969  CB   THR   635      96.488  64.967  95.121  1.00 48.54
ATOM   3970  OG1  THR   635      95.065  64.782  95.153  1.00 54.67
ATOM   3971  CG2  THR   635      96.890  66.428  95.364  1.00 48.08
ATOM   3972  C    THR   635      96.533  65.360  92.584  1.00 46.95
ATOM   3973  O    THR   635      97.354  65.821  91.794  1.00 45.11
ATOM   3974  N    LYS   636      95.227  65.557  92.411  1.00 45.66
ATOM   3975  CA   LYS   636      94.783  66.366  91.279  1.00 46.22
ATOM   3976  CB   LYS   636      93.273  66.547  91.267  1.00 49.59
ATOM   3977  CG   LYS   636      92.488  65.349  91.703  1.00 58.41
ATOM   3978  CD   LYS   636      92.444  65.335  93.211  1.00 63.61
ATOM   3979  CE   LYS   636      91.813  64.071  93.758  1.00 64.75
ATOM   3980  NZ   LYS   636      91.858  64.126  95.246  1.00 63.08
ATOM   3981  C    LYS   636      95.416  67.761  91.331  1.00 46.13
ATOM   3982  O    LYS   636      95.806  68.316  90.295  1.00 44.17
ATOM   3983  N    LYS   637      95.512  68.325  92.536  1.00 45.16
ATOM   3984  CA   LYS   637      96.073  69.663  92.726  1.00 42.39
ATOM   3985  CB   LYS   637      96.356  69.923  94.204  1.00 41.94
ATOM   3986  CG   LYS   637      96.749  71.373  94.496  1.00 42.90
ATOM   3987  CD   LYS   637      97.054  71.592  95.978  1.00 39.48
ATOM   3988  CE   LYS   637      97.414  73.045  96.283  1.00 42.37
ATOM   3989  NZ   LYS   637      97.664  73.326  97.746  1.00 42.06
ATOM   3990  C    LYS   637      97.354  69.825  91.928  1.00 43.63
ATOM   3991  O    LYS   637      97.329  70.264  90.785  1.00 46.04
ATOM   3992  N    GLU   638      98.480  69.450  92.515  1.00 43.35
ATOM   3993  CA   GLU   638      99.748  69.583  91.818  1.00 44.20
ATOM   3994  CB   GLU   638     100.847  68.751  92.484  1.00 49.03
ATOM   3995  CG   GLU   638     100.983  68.980  93.959  1.00 57.25
ATOM   3996  CD   GLU   638     100.182  67.991  94.789  1.00 61.56
ATOM   3997  OE1  GLU   638      98.982  67.744  94.481  1.00 60.68
ATOM   3998  OE2  GLU   638     100.775  67.477  95.772  1.00 66.97
ATOM   3999  C    GLU   638      99.687  69.199  90.344  1.00 42.13
ATOM   4000  O    GLU   638     100.441  69.770  89.549  1.00 43.44
ATOM   4001  N    LEU   639      98.829  68.239  89.972  1.00 38.33
ATOM   4002  CA   LEU   639      98.717  67.821  88.558  1.00 34.52
ATOM   4003  CB   LEU   639      98.067  66.457  88.401  1.00 29.90
ATOM   4004  CG   LEU   639      98.998  65.278  88.183  1.00 25.29
ATOM   4005  CD1  LEU   639      99.987  65.183  89.345  1.00 26.21
ATOM   4006  CD2  LEU   639      98.151  64.005  88.035  1.00 18.61
ATOM   4007  C    LEU   639      97.945  68.783  87.688  1.00 34.10
ATOM   4008  O    LEU   639      98.242  68.919  86.521  1.00 31.23
ATOM   4009  N    SER   640      96.949  69.449  88.247  1.00 35.74
ATOM   4010  CA   SER   640      96.173  70.391  87.456  1.00 37.99
ATOM   4011  CB   SER   640      94.869  70.672  88.177  1.00 42.88
ATOM   4012  OG   SER   640      95.159  70.860  89.545  1.00 53.35
ATOM   4013  C    SER   640      96.984  71.663  87.189  1.00 34.13
ATOM   4014  O    SER   640      96.785  72.367  86.201  1.00 28.15
ATOM   4015  N    ALA   641      97.919  71.965  88.066  1.00 34.79
```

[1]

```
ATOM   4016  CA  ALA   641      98.753  73.120  87.781  1.00 38.76
ATOM   4017  CB  ALA   641      99.221  73.771  89.086  1.00 39.47
ATOM   4018  C   ALA   641      99.977  72.694  86.890  1.00 37.57
ATOM   4019  O   ALA   641     100.695  73.539  86.351  1.00 34.07
ATOM   4020  N   VAL   642     100.203  71.388  86.732  1.00 35.92
ATOM   4021  CA  VAL   642     101.324  70.898  85.928  1.00 35.21
ATOM   4022  CB  VAL   642     102.614  70.869  86.737  1.00 32.98
ATOM   4023  CG1 VAL   642     103.754  70.593  85.848  1.00 33.35
ATOM   4024  CG2 VAL   642     102.836  72.159  87.410  1.00 37.25
ATOM   4025  C   VAL   642     101.065  69.472  85.452  1.00 36.40
ATOM   4026  O   VAL   642     100.724  68.607  86.250  1.00 38.79
ATOM   4027  N   THR   643     101.237  69.219  84.159  1.00 35.16
ATOM   4028  CA  THR   643     101.014  67.877  83.609  1.00 34.37
ATOM   4029  CB  THR   643     101.453  67.823  82.148  1.00 36.18
ATOM   4030  OG1 THR   643     100.858  68.907  81.443  1.00 42.10
ATOM   4031  CG2 THR   643     100.978  66.585  81.496  1.00 41.54
ATOM   4032  C   THR   643     101.890  66.929  84.400  1.00 30.99
ATOM   4033  O   THR   643     102.723  67.381  85.147  1.00 32.00
ATOM   4034  N   PHE   644     101.711  65.625  84.274  1.00 31.09
ATOM   4035  CA  PHE   644     102.591  64.710  85.009  1.00 33.72
ATOM   4036  CB  PHE   644     101.925  63.368  85.250  1.00 30.79
ATOM   4037  CG  PHE   644     102.666  62.487  86.181  1.00 27.97
ATOM   4038  CD1 PHE   644     102.989  62.934  87.462  1.00 22.47
ATOM   4039  CD2 PHE   644     103.006  61.176  85.805  1.00 30.26
ATOM   4040  CE1 PHE   644     103.649  62.078  88.390  1.00 24.39
ATOM   4041  CE2 PHE   644     103.668  60.300  86.719  1.00 29.74
ATOM   4042  CZ  PHE   644     103.990  60.760  88.022  1.00 24.81
ATOM   4043  C   PHE   644     103.862  64.528  84.185  1.00 37.91
ATOM   4044  O   PHE   644     104.952  64.538  84.725  1.00 40.41
ATOM   4045  N   PRO   645     103.745  64.341  82.861  1.00 41.74
ATOM   4046  CD  PRO   645     102.579  64.237  81.958  1.00 41.54
ATOM   4047  CA  PRO   645     104.988  64.192  82.099  1.00 43.94
ATOM   4048  CB  PRO   645     104.491  64.237  80.650  1.00 42.33
ATOM   4049  CG  PRO   645     103.149  63.507  80.762  1.00 40.24
ATOM   4050  C   PRO   645     105.954  65.343  82.399  1.00 47.65
ATOM   4051  O   PRO   645     107.113  65.105  82.758  1.00 49.95
ATOM   4052  N   ASP   646     105.450  66.578  82.265  1.00 49.27
ATOM   4053  CA  ASP   646     106.240  67.790  82.462  1.00 49.42
ATOM   4054  CB  ASP   646     105.369  69.039  82.265  1.00 50.78
ATOM   4055  CG  ASP   646     104.960  69.247  80.810  1.00 53.45
ATOM   4056  OD1 ASP   646     105.836  69.443  79.941  1.00 55.58
ATOM   4057  OD2 ASP   646     103.753  69.204  80.527  1.00 56.44
ATOM   4058  C   ASP   646     106.955  67.849  83.796  1.00 49.91
ATOM   4059  O   ASP   646     108.032  68.447  83.913  1.00 50.63
ATOM   4060  N   ILE   647     106.372  67.225  84.811  1.00 50.66
ATOM   4061  CA  ILE   647     107.006  67.210  86.132  1.00 50.04
ATOM   4062  CB  ILE   647     105.907  67.079  87.282  1.00 46.28
ATOM   4063  CG2 ILE   647     104.662  66.459  86.777  1.00 40.54
ATOM   4064  CG1 ILE   647     106.452  66.295  88.463  1.00 48.02
ATOM   4065  CD1 ILE   647     105.456  66.124  89.503  1.00 44.61
ATOM   4066  C   ILE   647     108.108  66.117  86.191  1.00 49.26
ATOM   4067  O   ILE   647     109.037  66.184  86.991  1.00 49.17
ATOM   4068  N   ILE   648     107.995  65.143  85.294  1.00 48.35
ATOM   4069  CA  ILE   648     108.935  64.046  85.157  1.00 47.50
ATOM   4070  CB  ILE   648     108.316  62.912  84.312  1.00 49.50
ATOM   4071  CG2 ILE   648     109.377  61.983  83.789  1.00 48.18
ATOM   4072  CG1 ILE   648     107.311  62.147  85.156  1.00 53.31
ATOM   4073  CD1 ILE   648     106.679  61.027  84.422  1.00 59.09
ATOM   4074  C   ILE   648     110.154  64.578  84.434  1.00 46.19
ATOM   4075  O   ILE   648     111.289  64.248  84.771  1.00 43.87
ATOM   4076  N   ARG   649     109.905  65.397  83.421  1.00 46.04
ATOM   4077  CA  ARG   649     110.987  65.997  82.639  1.00 46.14
ATOM   4078  CB  ARG   649     110.429  66.925  81.562  1.00 45.63
ATOM   4079  CG  ARG   649     111.388  67.497  80.517  1.00 43.42
ATOM   4080  CD  ARG   649     110.560  68.368  79.553  1.00 47.47
ATOM   4081  NE  ARG   649     111.293  69.029  78.473  1.00 56.63
ATOM   4082  CZ  ARG   649     110.735  69.890  77.610  1.00 60.08
ATOM   4083  NH1 ARG   649     109.445  70.199  77.711  1.00 62.22
ATOM   4084  NH2 ARG   649     111.453  70.449  76.640  1.00 61.83
ATOM   4085  C   ARG   649     111.853  66.807  83.561  1.00 45.30
```

112

| ATOM | 4086 | O | ARG | 649 | 113.075 | 66.670 | 83.554 | 1.00 | 50.56 |
|---|---|---|---|---|---|---|---|---|---|
| ATOM | 4087 | N | ASN | 650 | 111.227 | 67.622 | 84.392 | 1.00 | 41.68 |
| ATOM | 4088 | CA | ASN | 650 | 112.006 | 68.484 | 85.244 | 1.00 | 39.65 |
| ATOM | 4089 | CB | ASN | 650 | 111.510 | 69.929 | 85.099 | 1.00 | 38.88 |
| ATOM | 4090 | CG | ASN | 650 | 111.334 | 70.366 | 83.630 | 1.00 | 40.12 |
| ATOM | 4091 | OD1 | ASN | 650 | 112.272 | 70.349 | 82.823 | 1.00 | 44.30 |
| ATOM | 4092 | ND2 | ASN | 650 | 110.130 | 70.765 | 83.294 | 1.00 | 36.11 |
| ATOM | 4093 | C | ASN | 650 | 112.053 | 68.142 | 86.704 | 1.00 | 39.44 |
| ATOM | 4094 | O | ASN | 650 | 112.057 | 69.050 | 87.494 | 1.00 | 40.66 |
| ATOM | 4095 | N | TYR | 651 | 112.088 | 66.882 | 87.111 | 1.00 | 39.16 |
| ATOM | 4096 | CA | TYR | 651 | 112.159 | 66.634 | 88.550 | 1.00 | 44.93 |
| ATOM | 4097 | CB | TYR | 651 | 111.860 | 65.175 | 88.877 | 1.00 | 41.57 |
| ATOM | 4098 | CG | TYR | 651 | 112.018 | 64.898 | 90.368 | 1.00 | 44.18 |
| ATOM | 4099 | CD1 | TYR | 651 | 111.463 | 65.768 | 91.304 | 1.00 | 44.32 |
| ATOM | 4100 | CE1 | TYR | 651 | 111.637 | 65.574 | 92.672 | 1.00 | 46.20 |
| ATOM | 4101 | CD2 | TYR | 651 | 112.758 | 63.804 | 90.852 | 1.00 | 43.56 |
| ATOM | 4102 | CE2 | TYR | 651 | 112.938 | 63.597 | 92.249 | 1.00 | 41.15 |
| ATOM | 4103 | CZ | TYR | 651 | 112.372 | 64.494 | 93.152 | 1.00 | 42.87 |
| ATOM | 4104 | OH | TYR | 651 | 112.531 | 64.368 | 94.527 | 1.00 | 37.07 |
| ATOM | 4105 | C | TYR | 651 | 113.533 | 66.980 | 89.151 | 1.00 | 53.29 |
| ATOM | 4106 | O | TYR | 651 | 113.851 | 66.591 | 90.250 | 1.00 | 56.19 |
| ATOM | 4107 | N | LYS | 652 | 114.365 | 67.739 | 88.452 | 1.00 | 59.06 |
| ATOM | 4108 | CA | LYS | 652 | 115.706 | 68.067 | 88.916 | 1.00 | 67.93 |
| ATOM | 4109 | CB | LYS | 652 | 116.020 | 69.494 | 88.442 | 1.00 | 68.19 |
| ATOM | 4110 | CG | LYS | 652 | 115.794 | 69.579 | 86.952 | 1.00 | 72.04 |
| ATOM | 4111 | CD | LYS | 652 | 116.203 | 70.884 | 86.352 | 1.00 | 76.68 |
| ATOM | 4112 | CE | LYS | 652 | 115.884 | 70.952 | 84.873 | 1.00 | 81.35 |
| ATOM | 4113 | NZ | LYS | 652 | 116.375 | 72.180 | 84.182 | 1.00 | 85.71 |
| ATOM | 4114 | C | LYS | 652 | 116.140 | 67.783 | 90.390 | 1.00 | 73.68 |
| ATOM | 4115 | O | LYS | 652 | 117.292 | 67.418 | 90.622 | 1.00 | 78.21 |
| ATOM | 4116 | N | VAL | 653 | 115.282 | 67.924 | 91.397 | 1.00 | 76.90 |
| ATOM | 4117 | CA | VAL | 653 | 115.616 | 67.594 | 92.805 | 1.00 | 83.16 |
| ATOM | 4118 | CB | VAL | 653 | 115.333 | 66.135 | 93.032 | 1.00 | 85.69 |
| ATOM | 4121 | C | VAL | 653 | 116.991 | 67.903 | 93.460 | 1.00 | 87.35 |
| ATOM | 4122 | O | VAL | 653 | 117.737 | 66.963 | 93.789 | 1.00 | 84.54 |
| ATOM | 4123 | N | MET | 654 | 117.269 | 69.192 | 93.715 | 1.00 | 92.58 |
| ATOM | 4124 | CA | MET | 654 | 118.531 | 69.659 | 94.315 | 1.00 | 98.56 |
| ATOM | 4125 | CB | MET | 654 | 118.664 | 69.142 | 95.791 | 1.00 | 95.93 |
| ATOM | 4129 | C | MET | 654 | 119.651 | 69.101 | 93.405 | 1.00 | 103.27 |
| ATOM | 4130 | O | MET | 654 | 120.195 | 68.027 | 93.651 | 1.00 | 104.92 |
| ATOM | 4131 | N | ALA | 655 | 119.945 | 69.822 | 92.316 | 1.00 | 106.63 |
| ATOM | 4132 | CA | ALA | 655 | 120.950 | 69.391 | 91.336 | 1.00 | 107.58 |
| ATOM | 4133 | CB | ALA | 655 | 120.261 | 68.967 | 90.050 | 1.00 | 105.85 |
| ATOM | 4134 | C | ALA | 655 | 121.987 | 70.466 | 91.014 | 1.00 | 109.47 |
| ATOM | 4135 | O | ALA | 655 | 121.713 | 71.380 | 90.249 | 1.00 | 111.43 |
| ATOM | 4136 | N | ALA | 656 | 123.157 | 70.316 | 91.647 | 1.00 | 110.13 |
| ATOM | 4137 | CA | ALA | 656 | 124.293 | 71.231 | 91.513 | 1.00 | 111.00 |
| ATOM | 4138 | CB | ALA | 656 | 125.476 | 70.719 | 92.403 | 1.00 | 107.47 |
| ATOM | 4139 | C | ALA | 656 | 124.694 | 71.307 | 90.033 | 1.00 | 112.01 |
| ATOM | 4140 | O | ALA | 656 | 125.201 | 70.322 | 89.494 | 1.00 | 113.27 |
| ATOM | 4141 | N | GLU | 657 | 124.468 | 72.440 | 89.357 | 1.00 | 112.92 |
| ATOM | 4142 | CA | GLU | 657 | 124.841 | 72.476 | 87.935 | 1.00 | 115.18 |
| ATOM | 4143 | CB | GLU | 657 | 124.039 | 71.377 | 87.188 | 1.00 | 115.02 |
| ATOM | 4148 | C | GLU | 657 | 124.823 | 73.773 | 87.088 | 1.00 | 116.28 |
| ATOM | 4149 | O | GLU | 657 | 125.242 | 74.862 | 87.514 | 1.00 | 116.94 |
| ATOM | 4150 | N | ASN | 658 | 124.367 | 73.615 | 85.849 | 1.00 | 116.83 |
| ATOM | 4151 | CA | ASN | 658 | 124.297 | 74.719 | 84.917 | 1.00 | 117.10 |
| ATOM | 4152 | CB | ASN | 658 | 125.624 | 75.521 | 84.937 | 1.00 | 115.37 |
| ATOM | 4156 | C | ASN | 658 | 124.011 | 74.194 | 83.512 | 1.00 | 117.58 |
| ATOM | 4157 | O | ASN | 658 | 124.593 | 74.689 | 82.552 | 1.00 | 118.16 |
| ATOM | 4158 | N | ILE | 659 | 123.131 | 73.197 | 83.386 | 1.00 | 117.59 |
| ATOM | 4159 | CA | ILE | 659 | 122.778 | 72.652 | 82.066 | 1.00 | 118.09 |
| ATOM | 4160 | CB | ILE | 659 | 124.025 | 72.243 | 81.293 | 1.00 | 117.77 |
| ATOM | 4164 | C | ILE | 659 | 121.815 | 71.476 | 82.130 | 1.00 | 119.13 |
| ATOM | 4165 | O | ILE | 659 | 120.677 | 71.612 | 81.684 | 1.00 | 120.29 |
| ATOM | 4166 | N | PRO | 660 | 122.282 | 70.322 | 82.639 | 1.00 | 119.45 |
| ATOM | 4168 | CA | PRO | 660 | 121.462 | 69.092 | 82.803 | 1.00 | 117.66 |
| ATOM | 4169 | CB | PRO | 660 | 122.005 | 67.944 | 81.912 | 1.00 | 116.75 |
| ATOM | 4171 | C | PRO | 660 | 121.510 | 68.679 | 84.291 | 1.00 | 116.67 |
| ATOM | 4172 | O | PRO | 660 | 122.462 | 69.026 | 84.993 | 1.00 | 118.59 |

113

```
ATOM  4173  N    GLU  661   120.481  67.976  84.770  1.00113.91
ATOM  4174  CA   GLU  661   120.393  67.496  86.163  1.00110.08
ATOM  4175  CB   GLU  661   120.209  68.687  87.118  1.00110.28
ATOM  4180  C    GLU  661   119.166  66.552  86.176  1.00107.23
ATOM  4181  O    GLU  661   118.250  66.736  85.367  1.00108.80
ATOM  4182  N    ASN  662   119.138  65.540  87.043  1.00101.97
ATOM  4183  CA   ASN  662   118.023  64.584  87.048  1.00 95.96
ATOM  4184  CB   ASN  662   118.359  63.398  86.233  1.00 94.10
ATOM  4188  C    ASN  662   117.767  64.178  88.451  1.00 92.76
ATOM  4189  O    ASN  662   117.983  65.009  89.335  1.00 94.84
ATOM  4190  N    PRO  663   117.506  62.877  88.736  1.00 88.27
ATOM  4191  CD   PRO  663   117.124  62.990  90.144  1.00 85.26
ATOM  4192  CA   PRO  663   117.264  61.471  88.337  1.00 85.48
ATOM  4193  CB   PRO  663   117.003  60.832  89.650  1.00 84.44
ATOM  4194  CG   PRO  663   116.179  61.918  90.247  1.00 84.32
ATOM  4195  C    PRO  663   116.165  61.064  87.377  1.00 84.49
ATOM  4196  O    PRO  663   115.093  60.624  87.773  1.00 81.80
ATOM  4197  N    LEU  664   116.435  61.125  86.105  1.00 85.41
ATOM  4198  CA   LEU  664   115.413  60.773  85.164  1.00 86.37
ATOM  4199  CB   LEU  664   115.043  62.098  84.459  1.00 86.63
ATOM  4200  CG   LEU  664   115.166  63.386  85.359  1.00 87.96
ATOM  4201  CD1  LEU  664   115.032  64.652  84.519  1.00 86.43
ATOM  4202  CD2  LEU  664   114.149  63.415  86.521  1.00 87.79
ATOM  4203  C    LEU  664   116.201  59.787  84.269  1.00 88.61
ATOM  4204  O    LEU  664   117.321  59.464  84.596  1.00 89.98
ATOM  4205  N    LYS  665   115.587  59.251  83.227  1.00 90.57
ATOM  4206  CA   LYS  665   116.304  58.438  82.216  1.00 89.30
ATOM  4207  CB   LYS  665   117.630  58.986  81.845  1.00 93.28
ATOM  4208  CG   LYS  665   117.540  60.267  80.983  1.00 96.25
ATOM  4209  CD   LYS  665   118.948  60.777  80.615  1.00 97.31
ATOM  4210  CE   LYS  665   118.893  62.008  79.686  1.00 98.74
ATOM  4211  NZ   LYS  665   120.243  62.521  79.247  1.00 97.41
ATOM  4212  C    LYS  665   116.419  56.963  82.034  1.00 87.92
ATOM  4213  O    LYS  665   117.430  56.381  81.738  1.00 89.66
ATOM  4214  N    TYR  666   115.337  56.387  82.481  1.00 86.50
ATOM  4215  CA   TYR  666   114.978  55.071  81.964  1.00 84.67
ATOM  4216  CB   TYR  666   116.253  53.934  81.710  1.00 84.35
ATOM  4224  C    TYR  666   113.767  54.616  82.703  1.00 82.50
ATOM  4225  O    TYR  666   113.635  54.551  83.933  1.00 82.68
ATOM  4226  N    LEU  667   112.845  54.644  81.792  1.00 82.06
ATOM  4227  CA   LEU  667   111.495  54.492  82.015  1.00 84.35
ATOM  4228  CB   LEU  667   110.688  54.934  80.832  1.00 81.52
ATOM  4229  CG   LEU  667   109.245  55.168  81.172  1.00 79.70
ATOM  4230  CD1  LEU  667   109.288  56.315  82.104  1.00 84.50
ATOM  4231  CD2  LEU  667   108.429  55.554  79.951  1.00 79.13
ATOM  4232  C    LEU  667   110.955  53.189  82.606  1.00 86.36
ATOM  4233  O    LEU  667   110.251  53.198  83.564  1.00 89.33
ATOM  4234  N    TYR  668   111.288  52.119  81.981  1.00 86.95
ATOM  4235  CA   TYR  668   111.055  50.883  82.645  1.00 90.83
ATOM  4236  CB   TYR  668   109.764  50.154  82.385  1.00 88.10
ATOM  4237  CG   TYR  668   109.876  48.848  83.216  1.00 89.12
ATOM  4238  CD1  TYR  668   110.844  48.726  84.259  1.00 86.86
ATOM  4239  CE1  TYR  668   111.142  47.465  84.834  1.00 85.92
ATOM  4240  CD2  TYR  668   109.220  47.674  82.824  1.00 89.60
ATOM  4241  CE2  TYR  668   109.509  46.455  83.390  1.00 86.94
ATOM  4242  CZ   TYR  668   110.463  46.347  84.359  1.00 85.95
ATOM  4243  OH   TYR  668   110.744  45.076  84.759  1.00 86.44
ATOM  4244  C    TYR  668   112.334  50.250  82.157  1.00 97.04
ATOM  4245  O    TYR  668   113.285  51.009  82.108  1.00 99.76
ATOM  4246  N    PRO  669   112.425  48.967  81.704  1.00100.60
ATOM  4247  CD   PRO  669   111.736  47.637  81.382  1.00100.42
ATOM  4248  CA   PRO  669   113.855  48.837  81.383  1.00102.56
ATOM  4249  CB   PRO  669   114.066  47.331  81.352  1.00103.77
ATOM  4250  CG   PRO  669   112.820  46.927  80.612  1.00103.14
ATOM  4251  C    PRO  669   114.373  49.496  80.127  1.00103.61
ATOM  4252  O    PRO  669   114.274  48.987  79.005  1.00102.61
ATOM  4253  N    ASN  670   114.932  50.657  80.335  1.00105.05
ATOM  4254  CA   ASN  670   115.493  51.388  79.260  1.00108.50
ATOM  4255  CB   ASN  670   116.765  50.715  78.763  1.00114.46
ATOM  4256  CG   ASN  670   117.905  50.883  79.745  1.00120.58
```

114

| ATOM | 4257 | OD1 | ASN | 670 | 117.824 | 50.400 | 80.880 | 1.00 | 125.10 |
| ATOM | 4258 | ND2 | ASN | 670 | 118.959 | 51.599 | 79.337 | 1.00 | 121.21 |
| ATOM | 4259 | C | ASN | 670 | 114.664 | 51.773 | 78.094 | 1.00 | 107.12 |
| ATOM | 4260 | O | ASN | 670 | 114.903 | 51.337 | 76.962 | 1.00 | 109.13 |
| ATOM | 4261 | N | ILE | 671 | 113.618 | 52.517 | 78.376 | 1.00 | 103.12 |
| ATOM | 4262 | CA | ILE | 671 | 112.962 | 53.120 | 77.270 | 1.00 | 100.54 |
| ATOM | 4263 | CB | ILE | 671 | 111.427 | 52.939 | 77.233 | 1.00 | 100.11 |
| ATOM | 4264 | CG2 | ILE | 671 | 110.769 | 54.210 | 76.829 | 1.00 | 100.95 |
| ATOM | 4265 | CG1 | ILE | 671 | 111.062 | 51.952 | 76.107 | 1.00 | 100.07 |
| ATOM | 4266 | CD1 | ILE | 671 | 109.557 | 51.833 | 75.783 | 1.00 | 99.19 |
| ATOM | 4267 | C | ILE | 671 | 113.531 | 54.437 | 77.845 | 1.00 | 98.88 |
| ATOM | 4268 | O | ILE | 671 | 113.489 | 54.668 | 79.059 | 1.00 | 97.92 |
| ATOM | 4269 | N | ASP | 672 | 114.204 | 55.193 | 76.967 | 1.00 | 97.62 |
| ATOM | 4270 | CA | ASP | 672 | 114.918 | 56.461 | 77.247 | 1.00 | 93.57 |
| ATOM | 4271 | CB | ASP | 672 | 115.651 | 56.944 | 75.973 | 1.00 | 96.75 |
| ATOM | 4272 | CG | ASP | 672 | 116.512 | 55.835 | 75.333 | 1.00 | 100.41 |
| ATOM | 4273 | OD1 | ASP | 672 | 117.551 | 55.463 | 75.921 | 1.00 | 102.22 |
| ATOM | 4274 | OD2 | ASP | 672 | 116.139 | 55.305 | 74.253 | 1.00 | 103.25 |
| ATOM | 4275 | C | ASP | 672 | 114.016 | 57.547 | 77.735 | 1.00 | 87.08 |
| ATOM | 4276 | O | ASP | 672 | 113.211 | 58.060 | 76.972 | 1.00 | 84.48 |
| ATOM | 4277 | N | LYS | 673 | 114.185 | 57.923 | 78.995 | 1.00 | 80.82 |
| ATOM | 4278 | CA | LYS | 673 | 113.322 | 58.928 | 79.537 | 1.00 | 75.65 |
| ATOM | 4279 | CB | LYS | 673 | 114.021 | 59.907 | 80.408 | 1.00 | 68.11 |
| ATOM | 4280 | CG | LYS | 673 | 113.025 | 60.991 | 80.746 | 1.00 | 57.65 |
| ATOM | 4281 | CD | LYS | 673 | 113.517 | 61.911 | 81.760 | 1.00 | 50.56 |
| ATOM | 4282 | CE | LYS | 673 | 113.015 | 63.223 | 81.407 | 1.00 | 48.57 |
| ATOM | 4283 | NZ | LYS | 673 | 113.962 | 64.297 | 81.759 | 1.00 | 50.47 |
| ATOM | 4284 | C | LYS | 673 | 112.609 | 59.732 | 78.510 | 1.00 | 77.07 |
| ATOM | 4285 | O | LYS | 673 | 111.415 | 59.562 | 78.330 | 1.00 | 79.72 |
| ATOM | 4286 | N | ASP | 674 | 113.318 | 60.619 | 77.833 | 1.00 | 76.86 |
| ATOM | 4287 | CA | ASP | 674 | 112.645 | 61.430 | 76.838 | 1.00 | 78.77 |
| ATOM | 4288 | CB | ASP | 674 | 113.603 | 62.450 | 76.224 | 1.00 | 78.85 |
| ATOM | 4289 | CG | ASP | 674 | 114.016 | 63.541 | 77.232 | 1.00 | 80.32 |
| ATOM | 4290 | OD1 | ASP | 674 | 113.089 | 64.082 | 77.859 | 1.00 | 78.06 |
| ATOM | 4291 | OD2 | ASP | 674 | 115.229 | 63.868 | 77.404 | 1.00 | 80.17 |
| ATOM | 4292 | C | ASP | 674 | 111.911 | 60.639 | 75.756 | 1.00 | 80.67 |
| ATOM | 4293 | O | ASP | 674 | 110.720 | 60.889 | 75.564 | 1.00 | 81.85 |
| ATOM | 4294 | N | HIS | 675 | 112.587 | 59.691 | 75.083 | 1.00 | 81.96 |
| ATOM | 4295 | CA | HIS | 675 | 112.000 | 58.841 | 74.016 | 1.00 | 81.72 |
| ATOM | 4296 | CB | HIS | 675 | 113.040 | 57.776 | 73.579 | 1.00 | 86.60 |
| ATOM | 4297 | CG | HIS | 675 | 112.587 | 56.840 | 72.489 | 1.00 | 91.81 |
| ATOM | 4298 | CD2 | HIS | 675 | 112.929 | 56.766 | 71.178 | 1.00 | 93.66 |
| ATOM | 4299 | ND1 | HIS | 675 | 111.694 | 55.801 | 72.699 | 1.00 | 94.62 |
| ATOM | 4300 | CE1 | HIS | 675 | 111.507 | 55.136 | 71.574 | 1.00 | 95.03 |
| ATOM | 4301 | NE2 | HIS | 675 | 112.246 | 55.703 | 70.632 | 1.00 | 96.14 |
| ATOM | 4302 | C | HIS | 675 | 110.735 | 58.210 | 74.611 | 1.00 | 80.22 |
| ATOM | 4303 | O | HIS | 675 | 109.719 | 57.979 | 73.936 | 1.00 | 81.48 |
| ATOM | 4304 | N | ALA | 676 | 110.798 | 57.962 | 75.907 | 1.00 | 76.79 |
| ATOM | 4305 | CA | ALA | 676 | 109.667 | 57.414 | 76.624 | 1.00 | 72.68 |
| ATOM | 4306 | CB | ALA | 676 | 110.049 | 57.192 | 78.032 | 1.00 | 71.74 |
| ATOM | 4307 | C | ALA | 676 | 108.520 | 58.399 | 76.576 | 1.00 | 70.56 |
| ATOM | 4308 | O | ALA | 676 | 107.504 | 58.114 | 75.957 | 1.00 | 71.42 |
| ATOM | 4309 | N | PHE | 677 | 108.728 | 59.560 | 77.225 | 1.00 | 66.81 |
| ATOM | 4310 | CA | PHE | 677 | 107.745 | 60.625 | 77.353 | 1.00 | 60.76 |
| ATOM | 4311 | CB | PHE | 677 | 107.771 | 61.195 | 78.729 | 1.00 | 55.41 |
| ATOM | 4312 | CG | PHE | 677 | 107.720 | 60.197 | 79.786 | 1.00 | 54.15 |
| ATOM | 4313 | CD1 | PHE | 677 | 108.872 | 59.730 | 80.320 | 1.00 | 51.57 |
| ATOM | 4314 | CD2 | PHE | 677 | 106.503 | 59.824 | 80.368 | 1.00 | 55.50 |
| ATOM | 4315 | CE1 | PHE | 677 | 108.819 | 58.921 | 81.403 | 1.00 | 52.25 |
| ATOM | 4316 | CE2 | PHE | 677 | 106.455 | 58.974 | 81.485 | 1.00 | 54.80 |
| ATOM | 4317 | CZ | PHE | 677 | 107.608 | 58.545 | 82.031 | 1.00 | 49.63 |
| ATOM | 4318 | C | PHE | 677 | 107.848 | 61.800 | 76.418 | 1.00 | 60.49 |
| ATOM | 4319 | O | PHE | 677 | 107.444 | 62.929 | 76.774 | 1.00 | 60.80 |
| ATOM | 4320 | N | GLY | 678 | 108.346 | 61.557 | 75.216 | 1.00 | 58.16 |
| ATOM | 4321 | CA | GLY | 678 | 108.454 | 62.648 | 74.279 | 1.00 | 54.18 |
| ATOM | 4322 | C | GLY | 678 | 107.124 | 63.274 | 73.878 | 1.00 | 52.79 |
| ATOM | 4323 | O | GLY | 678 | 107.047 | 64.514 | 73.762 | 1.00 | 52.32 |
| ATOM | 4324 | N | LYS | 679 | 106.076 | 62.462 | 73.678 | 1.00 | 50.97 |
| ATOM | 4325 | CA | LYS | 679 | 104.787 | 63.012 | 73.239 | 1.00 | 49.34 |
| ATOM | 4326 | CB | LYS | 679 | 103.738 | 61.927 | 73.002 | 1.00 | 50.77 |

| ATOM | 4327 | CG | LYS | 679 | 104.109 | 60.747 | 72.160 | 1.00 | 55.06 |
|------|------|-----|-----|-----|---------|--------|--------|------|-------|
| ATOM | 4328 | CD | LYS | 679 | 102.941 | 59.758 | 72.011 | 1.00 | 56.48 |
| ATOM | 4329 | CE | LYS | 679 | 103.340 | 58.625 | 71.020 | 1.00 | 60.36 |
| ATOM | 4330 | NZ | LYS | 679 | 102.332 | 57.517 | 70.796 | 1.00 | 60.15 |
| ATOM | 4331 | C | LYS | 679 | 104.138 | 63.966 | 74.212 | 1.00 | 49.25 |
| ATOM | 4332 | O | LYS | 679 | 103.688 | 65.023 | 73.847 | 1.00 | 51.13 |
| ATOM | 4333 | N | TYR | 680 | 104.120 | 63.577 | 75.464 | 1.00 | 48.20 |
| ATOM | 4334 | CA | TYR | 680 | 103.422 | 64.244 | 76.533 | 1.00 | 49.66 |
| ATOM | 4335 | CB | TYR | 680 | 103.334 | 63.240 | 77.669 | 1.00 | 51.02 |
| ATOM | 4336 | CG | TYR | 680 | 103.083 | 61.825 | 77.174 | 1.00 | 46.78 |
| ATOM | 4337 | CD1 | TYR | 680 | 103.958 | 60.801 | 77.502 | 1.00 | 47.06 |
| ATOM | 4338 | CE1 | TYR | 680 | 103.757 | 59.508 | 77.053 | 1.00 | 49.14 |
| ATOM | 4339 | CD2 | TYR | 680 | 101.980 | 61.520 | 76.372 | 1.00 | 43.28 |
| ATOM | 4340 | CE2 | TYR | 680 | 101.764 | 60.226 | 75.915 | 1.00 | 45.50 |
| ATOM | 4341 | CZ | TYR | 680 | 102.665 | 59.218 | 76.262 | 1.00 | 49.60 |
| ATOM | 4342 | OH | TYR | 680 | 102.527 | 57.916 | 75.815 | 1.00 | 52.21 |
| ATOM | 4343 | C | TYR | 680 | 103.859 | 65.617 | 77.046 | 1.00 | 52.56 |
| ATOM | 4344 | O | TYR | 680 | 103.074 | 66.299 | 77.708 | 1.00 | 52.67 |
| ATOM | 4345 | N | TYR | 681 | 105.081 | 66.042 | 76.744 | 1.00 | 56.34 |
| ATOM | 4346 | CA | TYR | 681 | 105.564 | 67.344 | 77.225 | 1.00 | 59.62 |
| ATOM | 4347 | CB | TYR | 681 | 107.026 | 67.516 | 76.862 | 1.00 | 61.22 |
| ATOM | 4348 | CG | TYR | 681 | 107.940 | 66.529 | 77.528 | 1.00 | 62.83 |
| ATOM | 4349 | CD1 | TYR | 681 | 107.921 | 66.360 | 78.917 | 1.00 | 62.81 |
| ATOM | 4350 | CE1 | TYR | 681 | 108.832 | 65.533 | 79.547 | 1.00 | 60.26 |
| ATOM | 4351 | CD2 | TYR | 681 | 108.891 | 65.833 | 76.787 | 1.00 | 61.93 |
| ATOM | 4352 | CE2 | TYR | 681 | 109.811 | 65.004 | 77.408 | 1.00 | 61.21 |
| ATOM | 4353 | CZ | TYR | 681 | 109.782 | 64.862 | 78.790 | 1.00 | 61.53 |
| ATOM | 4354 | OH | TYR | 681 | 110.732 | 64.083 | 79.409 | 1.00 | 59.66 |
| ATOM | 4355 | C | TYR | 681 | 104.798 | 68.565 | 76.723 | 1.00 | 61.60 |
| ATOM | 4356 | O | TYR | 681 | 104.198 | 68.531 | 75.652 | 1.00 | 62.26 |
| ATOM | 4357 | N | SER | 682 | 104.846 | 69.658 | 77.483 | 1.00 | 63.83 |
| ATOM | 4358 | CA | SER | 682 | 104.135 | 70.873 | 77.094 | 1.00 | 65.85 |
| ATOM | 4359 | CB | SER | 682 | 103.657 | 71.608 | 78.331 | 1.00 | 63.25 |
| ATOM | 4361 | C | SER | 682 | 104.984 | 71.797 | 76.225 | 1.00 | 68.62 |
| ATOM | 4362 | O | SER | 682 | 104.900 | 73.019 | 76.330 | 1.00 | 68.66 |
| ATOM | 4363 | N | ARG | 683 | 105.798 | 71.208 | 75.355 | 1.00 | 72.69 |
| ATOM | 4364 | CA | ARG | 683 | 106.658 | 71.990 | 74.465 | 1.00 | 75.42 |
| ATOM | 4365 | CB | ARG | 683 | 108.038 | 71.315 | 74.335 | 1.00 | 72.75 |
| ATOM | 4372 | C | ARG | 683 | 106.007 | 72.146 | 73.084 | 1.00 | 76.66 |
| ATOM | 4373 | O | ARG | 683 | 106.078 | 73.261 | 72.518 | 1.00 | 76.33 |
| ATOM | 4374 | N | GLY | 700 | 107.405 | 92.134 | 77.181 | 1.00 | 60.39 |
| ATOM | 4375 | CA | GLY | 700 | 107.939 | 90.742 | 77.022 | 1.00 | 60.37 |
| ATOM | 4376 | C | GLY | 700 | 108.309 | 90.246 | 78.405 | 1.00 | 57.86 |
| ATOM | 4377 | O | GLY | 700 | 109.114 | 90.862 | 79.102 | 1.00 | 59.95 |
| ATOM | 4378 | N | PTR | 701 | 107.725 | 89.135 | 78.818 | 1.00 | 54.50 |
| ATOM | 4379 | CA | PTR | 701 | 108.020 | 88.641 | 80.158 | 1.00 | 53.47 |
| ATOM | 4380 | C | PTR | 701 | 109.127 | 87.603 | 80.168 | 1.00 | 52.73 |
| ATOM | 4381 | O | PTR | 701 | 109.710 | 87.307 | 79.137 | 1.00 | 57.14 |
| ATOM | 4382 | CB | PTR | 701 | 106.723 | 88.080 | 80.812 | 1.00 | 47.42 |
| ATOM | 4383 | CG | PTR | 701 | 105.798 | 89.209 | 81.278 | 1.00 | 36.85 |
| ATOM | 4384 | CD1 | PTR | 701 | 104.781 | 89.720 | 80.433 | 1.00 | 35.05 |
| ATOM | 4385 | CD2 | PTR | 701 | 105.961 | 89.759 | 82.563 | 1.00 | 30.90 |
| ATOM | 4386 | CE1 | PTR | 701 | 103.958 | 90.769 | 80.899 | 1.00 | 26.61 |
| ATOM | 4387 | CE2 | PTR | 701 | 105.155 | 90.800 | 83.047 | 1.00 | 30.11 |
| ATOM | 4388 | CZ | PTR | 701 | 104.165 | 91.285 | 82.193 | 1.00 | 29.27 |
| ATOM | 4389 | OH | PTR | 701 | 103.378 | 92.348 | 82.733 | 1.00 | 28.67 |
| ATOM | 4390 | P | PTR | 701 | 102.080 | 92.990 | 82.014 | 1.00 | 27.47 |
| ATOM | 4391 | O1P | PTR | 701 | 101.051 | 91.954 | 81.971 | 1.00 | 30.05 |
| ATOM | 4392 | O2P | PTR | 701 | 102.420 | 93.403 | 80.638 | 1.00 | 29.05 |
| ATOM | 4393 | O3P | PTR | 701 | 101.549 | 94.152 | 82.829 | 1.00 | 20.42 |
| ATOM | 4394 | N | ILE | 702 | 109.411 | 87.074 | 81.348 | 1.00 | 51.35 |
| ATOM | 4395 | CA | ILE | 702 | 110.431 | 86.051 | 81.554 | 1.00 | 54.14 |
| ATOM | 4396 | CB | ILE | 702 | 111.199 | 86.365 | 82.835 | 1.00 | 54.51 |
| ATOM | 4397 | CG2 | ILE | 702 | 112.157 | 85.231 | 83.194 | 1.00 | 51.61 |
| ATOM | 4398 | CG1 | ILE | 702 | 111.896 | 87.708 | 82.672 | 1.00 | 55.27 |
| ATOM | 4399 | CD1 | ILE | 702 | 112.526 | 88.199 | 83.949 | 1.00 | 57.01 |
| ATOM | 4400 | C | ILE | 702 | 109.743 | 84.693 | 81.743 | 1.00 | 57.93 |
| ATOM | 4401 | O | ILE | 702 | 109.584 | 84.250 | 82.884 | 1.00 | 60.54 |
| ATOM | 4402 | N | LYS | 703 | 109.354 | 84.018 | 80.654 | 1.00 | 58.61 |
| ATOM | 4403 | CA | LYS | 703 | 108.646 | 82.741 | 80.775 | 1.00 | 58.43 |

| | | | | | | | |
|---|---|---|---|---|---|---|---|
| ATOM | 4404 | CB | LYS | 703 | 108.541 | 82.060 | 79.408 | 1.00 60.54 |
| ATOM | 4405 | CG | LYS | 703 | 107.606 | 82.838 | 78.456 | 1.00 69.04 |
| ATOM | 4406 | CD | LYS | 703 | 107.184 | 82.032 | 77.211 | 1.00 75.32 |
| ATOM | 4407 | CE | LYS | 703 | 106.154 | 82.800 | 76.349 | 1.00 77.04 |
| ATOM | 4408 | NZ | LYS | 703 | 105.609 | 82.006 | 75.194 | 1.00 75.01 |
| ATOM | 4409 | C | LYS | 703 | 109.180 | 81.785 | 81.845 | 1.00 58.12 |
| ATOM | 4410 | O | LYS | 703 | 110.394 | 81.679 | 82.043 | 1.00 60.28 |
| ATOM | 4411 | N | THR | 704 | 108.256 | 81.129 | 82.559 | 1.00 56.04 |
| ATOM | 4412 | CA | THR | 704 | 108.584 | 80.193 | 83.642 | 1.00 54.20 |
| ATOM | 4413 | CB | THR | 704 | 108.246 | 80.784 | 85.038 | 1.00 53.94 |
| ATOM | 4414 | OG1 | THR | 704 | 106.849 | 81.101 | 85.116 | 1.00 53.52 |
| ATOM | 4415 | CG2 | THR | 704 | 109.065 | 82.030 | 85.288 | 1.00 50.25 |
| ATOM | 4416 | C | THR | 704 | 107.880 | 78.845 | 83.525 | 1.00 52.62 |
| ATOM | 4417 | O | THR | 704 | 107.191 | 78.584 | 82.538 | 1.00 52.66 |
| ATOM | 4418 | N | GLU | 705 | 108.065 | 77.999 | 84.541 | 1.00 50.20 |
| ATOM | 4419 | CA | GLU | 705 | 107.470 | 76.661 | 84.581 | 1.00 51.43 |
| ATOM | 4420 | CB | GLU | 705 | 108.338 | 75.647 | 83.838 | 1.00 54.92 |
| ATOM | 4421 | CG | GLU | 705 | 108.657 | 75.930 | 82.392 | 1.00 63.72 |
| ATOM | 4422 | CD | GLU | 705 | 109.599 | 74.876 | 81.819 | 1.00 68.53 |
| ATOM | 4423 | OE1 | GLU | 705 | 110.669 | 74.661 | 82.439 | 1.00 67.20 |
| ATOM | 4424 | OE2 | GLU | 705 | 109.276 | 74.270 | 80.764 | 1.00 68.67 |
| ATOM | 4425 | C | GLU | 705 | 107.393 | 76.173 | 86.021 | 1.00 50.20 |
| ATOM | 4426 | O | GLU | 705 | 108.237 | 76.518 | 86.831 | 1.00 52.76 |
| ATOM | 4427 | N | LEU | 706 | 106.392 | 75.371 | 86.353 | 1.00 48.92 |
| ATOM | 4428 | CA | LEU | 706 | 106.337 | 74.844 | 87.706 | 1.00 48.60 |
| ATOM | 4429 | CB | LEU | 706 | 104.909 | 74.575 | 88.171 | 1.00 50.44 |
| ATOM | 4430 | CG | LEU | 706 | 103.962 | 75.718 | 88.517 | 1.00 51.88 |
| ATOM | 4431 | CD1 | LEU | 706 | 102.603 | 75.140 | 88.905 | 1.00 55.57 |
| ATOM | 4432 | CD2 | LEU | 706 | 104.520 | 76.514 | 89.665 | 1.00 51.66 |
| ATOM | 4433 | C | LEU | 706 | 107.087 | 73.533 | 87.641 | 1.00 50.37 |
| ATOM | 4434 | O | LEU | 706 | 107.131 | 72.870 | 86.587 | 1.00 50.03 |
| ATOM | 4435 | N | ILE | 707 | 107.660 | 73.147 | 88.769 | 1.00 48.25 |
| ATOM | 4436 | CA | ILE | 707 | 108.439 | 71.933 | 88.821 | 1.00 49.68 |
| ATOM | 4437 | CB | ILE | 707 | 109.876 | 72.243 | 88.402 | 1.00 53.06 |
| ATOM | 4438 | CG2 | ILE | 707 | 110.786 | 71.104 | 88.790 | 1.00 55.15 |
| ATOM | 4439 | CG1 | ILE | 707 | 109.903 | 72.568 | 36.905 | 1.00 53.95 |
| ATOM | 4440 | CD1 | ILE | 707 | 111.228 | 73.058 | 86.391 | 1.00 52.75 |
| ATOM | 4441 | C | ILE | 707 | 108.440 | 71.335 | 90.211 | 1.00 49.68 |
| ATOM | 4442 | O | ILE | 707 | 108.416 | 72.050 | 91.207 | 1.00 47.24 |
| ATOM | 4443 | N | SER | 708 | 108.455 | 70.018 | 90.291 | 1.00 51.52 |
| ATOM | 4444 | CA | SER | 708 | 108.468 | 69.416 | 91.600 | 1.00 56.03 |
| ATOM | 4445 | CB | SER | 708 | 107.835 | 68.021 | 91.574 | 1.00 58.20 |
| ATOM | 4446 | OG | SER | 708 | 107.605 | 67.545 | 92.895 | 1.00 59.05 |
| ATOM | 4447 | C | SER | 708 | 109.942 | 69.338 | 91.957 | 1.00 59.31 |
| ATOM | 4448 | O | SER | 708 | 110.787 | 69.153 | 91.078 | 1.00 58.96 |
| ATOM | 4449 | N | VAL | 709 | 110.246 | 69.492 | 93.241 | 1.00 61.49 |
| ATOM | 4450 | CA | VAL | 709 | 111.620 | 69.460 | 93.713 | 1.00 63.10 |
| ATOM | 4451 | CB | VAL | 709 | 112.194 | 70.887 | 93.783 | 1.00 60.94 |
| ATOM | 4452 | CG1 | VAL | 709 | 113.505 | 70.891 | 94.554 | 1.00 61.77 |
| ATOM | 4453 | CG2 | VAL | 709 | 112.408 | 71.425 | 92.373 | 1.00 53.62 |
| ATOM | 4454 | C | VAL | 709 | 111.694 | 68.811 | 95.082 | 1.00 66.28 |
| ATOM | 4455 | O | VAL | 709 | 110.728 | 68.862 | 95.836 | 1.00 64.78 |
| ATOM | 4456 | N | SER | 710 | 112.845 | 68.206 | 95.385 | 1.00 71.27 |
| ATOM | 4457 | CA | SER | 710 | 113.083 | 67.520 | 96.659 | 1.00 76.97 |
| ATOM | 4458 | CB | SER | 710 | 114.571 | 67.220 | 96.833 | 1.00 77.45 |
| ATOM | 4459 | OG | SER | 710 | 115.290 | 68.415 | 97.083 | 1.00 78.82 |
| ATOM | 4460 | C | SER | 710 | 112.621 | 68.350 | 97.855 | 1.00 79.32 |
| ATOM | 4461 | O | SER | 710 | 113.188 | 68.125 | 98.949 | 1.00 81.77 |
| ATOM | 1 | CB | LEU | 4136 | 75.391 | 115.883 | 116.832 | 1.00 78.90 |
| ATOM | 2 | CG | LEU | 4136 | 76.404 | 114.759 | 116.746 | 1.00 80.10 |
| ATOM | 3 | CD1 | LEU | 4136 | 76.714 | 114.240 | 118.157 | 1.00 76.67 |
| ATOM | 4 | CD2 | LEU | 4136 | 75.840 | 113.607 | 115.889 | 1.00 78.56 |
| ATOM | 5 | C | LEU | 4136 | 73.863 | 117.590 | 115.874 | 1.00 78.60 |
| ATOM | 6 | O | LEU | 4136 | 72.741 | 117.345 | 116.318 | 1.00 78.79 |
| ATOM | 7 | N | LEU | 4136 | 75.936 | 116.978 | 114.671 | 1.00 76.89 |
| ATOM | 8 | CA | LEU | 4136 | 74.831 | 116.469 | 115.531 | 1.00 78.14 |
| ATOM | 9 | N | ASP | 4137 | 74.312 | 118.821 | 115.669 | 1.00 80.35 |
| ATOM | 10 | CA | ASP | 4137 | 73.508 | 120.003 | 115.961 | 1.00 80.53 |
| ATOM | 11 | CB | ASP | 4137 | 74.149 | 121.236 | 115.326 | 1.00 81.03 |
| ATOM | 12 | CG | ASP | 4137 | 73.305 | 122.471 | 115.495 | 1.00 81.50 |

117

| | | | | | | | |
|---|---|---|---|---|---|---|---|
| ATOM | 13 | OD1 ASP | 4137 | 73.048 | 122.859 | 116.653 | 1.00 83.62 |
| ATOM | 14 | OD2 ASP | 4137 | 72.890 | 123.048 | 114.468 | 1.00 82.58 |
| ATOM | 15 | C ASP | 4137 | 72.057 | 119.889 | 115.499 | 1.00 79.98 |
| ATOM | 16 | O ASP | 4137 | 71.141 | 119.861 | 116.323 | 1.00 81.29 |
| ATOM | 17 | N LYS | 4138 | 71.852 | 119.834 | 114.184 | 1.00 77.77 |
| ATOM | 18 | CA LYS | 4138 | 70.509 | 119.723 | 113.624 | 1.00 74.77 |
| ATOM | 19 | CB LYS | 4138 | 70.556 | 119.486 | 112.108 | 1.00 78.12 |
| ATOM | 20 | CG LYS | 4138 | 71.041 | 120.681 | 111.292 | 1.00 80.83 |
| ATOM | 21 | CD LYS | 4138 | 70.876 | 120.439 | 109.795 | 1.00 81.18 |
| ATOM | 22 | CE LYS | 4138 | 71.282 | 121.667 | 108.989 | 1.00 82.16 |
| ATOM | 23 | NZ LYS | 4138 | 71.086 | 121.457 | 107.528 | 1.00 82.40 |
| ATOM | 24 | C LYS | 4138 | 69.721 | 118.603 | 114.279 | 1.00 71.05 |
| ATOM | 25 | O LYS | 4138 | 68.535 | 118.755 | 114.561 | 1.00 70.94 |
| ATOM | 26 | N GLN | 4139 | 70.374 | 117.475 | 114.517 | 1.00 66.84 |
| ATOM | 27 | CA GLN | 4139 | 69.692 | 116.360 | 115.152 | 1.00 65.35 |
| ATOM | 28 | CB GLN | 4139 | 70.655 | 115.186 | 115.340 | 1.00 64.57 |
| ATOM | 29 | CG GLN | 4139 | 71.302 | 114.712 | 114.047 | 1.00 63.28 |
| ATOM | 30 | CD GLN | 4139 | 71.936 | 113.340 | 114.180 | 1.00 64.52 |
| ATOM | 31 | OE1 GLN | 4139 | 72.808 | 113.118 | 115.022 | 1.00 61.50 |
| ATOM | 32 | NE2 GLN | 4139 | 71.498 | 112.408 | 113.340 | 1.00 63.79 |
| ATOM | 33 | C GLN | 4139 | 69.142 | 116.814 | 116.503 | 1.00 64.51 |
| ATOM | 34 | O GLN | 4139 | 67.934 | 116.778 | 116.748 | 1.00 63.29 |
| ATOM | 35 | N LYS | 4140 | 70.048 | 117.259 | 117.366 | 1.00 64.02 |
| ATOM | 36 | CA LYS | 4140 | 69.704 | 117.745 | 118.698 | 1.00 62.28 |
| ATOM | 37 | CB LYS | 4140 | 70.937 | 118.395 | 119.314 | 1.00 66.09 |
| ATOM | 38 | CG LYS | 4140 | 72.163 | 117.481 | 119.288 | 1.00 72.92 |
| ATOM | 39 | CD LYS | 4140 | 73.440 | 118.178 | 119.761 | 1.00 75.96 |
| ATOM | 40 | CE LYS | 4140 | 74.647 | 117.235 | 119.671 | 1.00 77.62 |
| ATOM | 41 | NZ LYS | 4140 | 75.937 | 117.867 | 120.088 | 1.00 74.46 |
| ATOM | 42 | C LYS | 4140 | 68.528 | 118.712 | 118.687 | 1.00 59.26 |
| ATOM | 43 | O LYS | 4140 | 67.693 | 118.697 | 119.586 | 1.00 55.98 |
| ATOM | 44 | N GLU | 4141 | 68.454 | 119.555 | 117.667 | 1.00 58.71 |
| ATOM | 45 | CA GLU | 4141 | 67.369 | 120.522 | 117.582 | 1.00 61.13 |
| ATOM | 46 | CB GLU | 4141 | 67.705 | 121.620 | 116.571 | 1.00 67.33 |
| ATOM | 47 | CG GLU | 4141 | 66.652 | 122.723 | 116.493 | 1.00 75.25 |
| ATOM | 48 | CD GLU | 4141 | 67.086 | 123.894 | 115.628 | 1.00 80.17 |
| ATOM | 49 | OE1 GLU | 4141 | 67.310 | 123.697 | 114.414 | 1.00 84.23 |
| ATOM | 50 | OE2 GLU | 4141 | 67.209 | 125.015 | 116.167 | 1.00 81.08 |
| ATOM | 51 | C GLU | 4141 | 66.051 | 119.867 | 117.204 | 1.00 59.26 |
| ATOM | 52 | O GLU | 4141 | 64.987 | 120.302 | 117.636 | 1.00 60.74 |
| ATOM | 53 | N LEU | 4142 | 66.117 | 118.830 | 116.383 | 1.00 56.93 |
| ATOM | 54 | CA LEU | 4142 | 64.909 | 118.128 | 115.979 | 1.00 53.72 |
| ATOM | 55 | CB LEU | 4142 | 65.204 | 117.188 | 114.810 | 1.00 51.75 |
| ATOM | 56 | CG LEU | 4142 | 64.114 | 116.176 | 114.463 | 1.00 48.29 |
| ATOM | 57 | CD1 LEU | 4142 | 62.808 | 116.878 | 114.147 | 1.00 43.64 |
| ATOM | 58 | CD2 LEU | 4142 | 64.583 | 115.345 | 113.297 | 1.00 47.35 |
| ATOM | 59 | C LEU | 4142 | 64.433 | 117.325 | 117.170 | 1.00 53.73 |
| ATOM | 60 | O LEU | 4142 | 63.261 | 116.979 | 117.282 | 1.00 53.89 |
| ATOM | 61 | N ASP | 4143 | 65.359 | 117.036 | 118.071 | 1.00 54.01 |
| ATOM | 62 | CA ASP | 4143 | 65.038 | 116.260 | 119.256 | 1.00 54.22 |
| ATOM | 63 | CB ASP | 4143 | 66.322 | 115.923 | 120.005 | 1.00 56.24 |
| ATOM | 64 | CG ASP | 4143 | 66.326 | 114.516 | 120.526 | 1.00 59.81 |
| ATOM | 65 | OD1 ASP | 4143 | 65.446 | 114.175 | 121.345 | 1.00 64.14 |
| ATOM | 66 | OD2 ASP | 4143 | 67.212 | 113.747 | 120.102 | 1.00 65.27 |
| ATOM | 67 | C ASP | 4143 | 64.089 | 117.039 | 120.168 | 1.00 52.41 |
| ATOM | 68 | O ASP | 4143 | 63.178 | 116.471 | 120.768 | 1.00 51.12 |
| ATOM | 69 | N SER | 4144 | 64.306 | 118.345 | 120.265 | 1.00 50.96 |
| ATOM | 70 | CA SER | 4144 | 63.466 | 119.178 | 121.103 | 1.00 48.47 |
| ATOM | 71 | CB SER | 4144 | 64.148 | 120.516 | 121.396 | 1.00 49.53 |
| ATOM | 72 | OG SER | 4144 | 64.211 | 121.326 | 120.235 | 1.00 53.41 |
| ATOM | 73 | C SER | 4144 | 62.127 | 119.422 | 120.422 | 1.00 46.34 |
| ATOM | 74 | O SER | 4144 | 61.096 | 119.486 | 121.083 | 1.00 49.82 |
| ATOM | 75 | N LYS | 4145 | 62.130 | 119.571 | 119.103 | 1.00 42.15 |
| ATOM | 76 | CA LYS | 4145 | 60.873 | 119.797 | 118.414 | 1.00 38.82 |
| ATOM | 77 | CB LYS | 4145 | 61.069 | 119.925 | 116.906 | 1.00 40.16 |
| ATOM | 78 | CG LYS | 4145 | 61.670 | 121.219 | 116.439 | 1.00 41.21 |
| ATOM | 79 | CD LYS | 4145 | 61.642 | 121.231 | 114.924 | 1.00 50.07 |
| ATOM | 80 | CE LYS | 4145 | 62.154 | 122.536 | 114.343 | 1.00 53.11 |
| ATOM | 81 | NZ LYS | 4145 | 62.104 | 122.505 | 112.852 | 1.00 54.84 |
| ATOM | 82 | C LYS | 4145 | 59.943 | 118.637 | 118.697 | 1.00 35.62 |

118

| ATOM | 83 | O | LYS | 4145 | 58.732 | 118.827 | 118.801 | 1.00 | 36.54 |
| --- | --- | --- | --- | --- | --- | --- | --- | --- | --- |
| ATOM | 84 | N | VAL | 4146 | 60.507 | 117.436 | 118.819 | 1.00 | 31.82 |
| ATOM | 85 | CA | VAL | 4146 | 59.699 | 116.256 | 119.100 | 1.00 | 32.33 |
| ATOM | 86 | CB | VAL | 4146 | 60.455 | 114.956 | 118.783 | 1.00 | 28.44 |
| ATOM | 87 | CG1 | VAL | 4146 | 59.680 | 113.763 | 119.299 | 1.00 | 27.77 |
| ATOM | 88 | CG2 | VAL | 4146 | 60.634 | 114.826 | 117.286 | 1.00 | 25.92 |
| ATOM | 89 | C | VAL | 4146 | 59.252 | 116.244 | 120.556 | 1.00 | 34.07 |
| ATOM | 90 | O | VAL | 4146 | 58.100 | 115.951 | 120.843 | 1.00 | 33.32 |
| ATOM | 91 | N | ARG | 4147 | 60.152 | 116.549 | 121.481 | 1.00 | 36.78 |
| ATOM | 92 | CA | ARG | 4147 | 59.749 | 116.599 | 122.878 | 1.00 | 44.42 |
| ATOM | 93 | CB | ARG | 4147 | 60.942 | 116.937 | 123.779 | 1.00 | 50.03 |
| ATOM | 94 | CG | ARG | 4147 | 61.784 | 115.711 | 124.148 | 1.00 | 60.30 |
| ATOM | 95 | CD | ARG | 4147 | 62.150 | 114.867 | 122.925 | 1.00 | 66.59 |
| ATOM | 96 | NE | ARG | 4147 | 62.776 | 113.599 | 123.300 | 1.00 | 75.47 |
| ATOM | 97 | CZ | ARG | 4147 | 63.121 | 112.642 | 122.438 | 1.00 | 77.95 |
| ATOM | 98 | NH1 | ARG | 4147 | 62.897 | 112.804 | 121.140 | 1.00 | 78.19 |
| ATOM | 99 | NH2 | ARG | 4147 | 63.681 | 111.517 | 122.875 | 1.00 | 77.84 |
| ATOM | 100 | C | ARG | 4147 | 58.658 | 117.653 | 122.999 | 1.00 | 44.14 |
| ATOM | 101 | O | ARG | 4147 | 57.668 | 117.456 | 123.700 | 1.00 | 45.79 |
| ATOM | 102 | N | ASN | 4148 | 58.826 | 118.762 | 122.286 | 1.00 | 43.39 |
| ATOM | 103 | CA | ASN | 4148 | 57.837 | 119.835 | 122.305 | 1.00 | 43.36 |
| ATOM | 104 | CB | ASN | 4148 | 58.231 | 120.967 | 121.362 | 1.00 | 45.08 |
| ATOM | 105 | CG | ASN | 4148 | 57.236 | 122.103 | 121.391 | 1.00 | 45.85 |
| ATOM | 106 | OD1 | ASN | 4148 | 57.066 | 122.753 | 122.416 | 1.00 | 51.32 |
| ATOM | 107 | ND2 | ASN | 4148 | 56.558 | 122.337 | 120.274 | 1.00 | 45.98 |
| ATOM | 108 | C | ASN | 4148 | 56.471 | 119.314 | 121.887 | 1.00 | 40.02 |
| ATOM | 109 | O | ASN | 4148 | 55.462 | 119.639 | 122.503 | 1.00 | 40.50 |
| ATOM | 110 | N | VAL | 4149 | 56.437 | 118.520 | 120.824 | 1.00 | 36.79 |
| ATOM | 111 | CA | VAL | 4149 | 55.181 | 117.959 | 120.363 | 1.00 | 36.35 |
| ATOM | 112 | CB | VAL | 4149 | 55.370 | 117.066 | 119.101 | 1.00 | 34.77 |
| ATOM | 113 | CG1 | VAL | 4149 | 54.035 | 116.427 | 118.700 | 1.00 | 32.94 |
| ATOM | 114 | CG2 | VAL | 4149 | 55.906 | 117.905 | 117.949 | 1.00 | 33.68 |
| ATOM | 115 | C | VAL | 4149 | 54.564 | 117.132 | 121.485 | 1.00 | 37.24 |
| ATOM | 116 | O | VAL | 4149 | 53.409 | 117.357 | 121.846 | 1.00 | 40.54 |
| ATOM | 117 | N | LYS | 4150 | 55.328 | 116.192 | 122.046 | 1.00 | 35.32 |
| ATOM | 118 | CA | LYS | 4150 | 54.817 | 115.354 | 123.129 | 1.00 | 34.77 |
| ATOM | 119 | CB | LYS | 4150 | 55.894 | 114.408 | 123.674 | 1.00 | 37.25 |
| ATOM | 120 | CG | LYS | 4150 | 55.381 | 113.573 | 124.864 | 1.00 | 47.77 |
| ATOM | 121 | CD | LYS | 4150 | 56.432 | 112.665 | 125.517 | 1.00 | 50.00 |
| ATOM | 122 | CE | LYS | 4150 | 56.816 | 111.483 | 124.639 | 1.00 | 50.86 |
| ATOM | 123 | NZ | LYS | 4150 | 57.809 | 110.596 | 125.313 | 1.00 | 51.16 |
| ATOM | 124 | C | LYS | 4150 | 54.266 | 116.208 | 124.274 | 1.00 | 35.60 |
| ATOM | 125 | O | LYS | 4150 | 53.170 | 115.942 | 124.763 | 1.00 | 35.76 |
| ATOM | 126 | N | ASP | 4151 | 55.012 | 117.225 | 124.709 | 1.00 | 34.33 |
| ATOM | 127 | CA | ASP | 4151 | 54.513 | 118.081 | 125.777 | 1.00 | 36.68 |
| ATOM | 128 | CB | ASP | 4151 | 55.434 | 119.276 | 126.047 | 1.00 | 40.49 |
| ATOM | 129 | CG | ASP | 4151 | 56.786 | 118.869 | 126.607 | 1.00 | 46.68 |
| ATOM | 130 | OD1 | ASP | 4151 | 56.854 | 117.827 | 127.302 | 1.00 | 43.58 |
| ATOM | 131 | OD2 | ASP | 4151 | 57.772 | 119.612 | 126.378 | 1.00 | 47.75 |
| ATOM | 132 | C | ASP | 4151 | 53.136 | 118.612 | 125.406 | 1.00 | 37.74 |
| ATOM | 133 | O | ASP | 4151 | 52.155 | 118.320 | 126.085 | 1.00 | 40.86 |
| ATOM | 134 | N | LYS | 4152 | 53.058 | 119.380 | 124.322 | 1.00 | 37.37 |
| ATOM | 135 | CA | LYS | 4152 | 51.782 | 119.947 | 123.893 | 1.00 | 35.11 |
| ATOM | 136 | CB | LYS | 4152 | 51.895 | 120.616 | 122.521 | 1.00 | 34.51 |
| ATOM | 137 | CG | LYS | 4152 | 52.754 | 121.860 | 122.494 | 1.00 | 35.87 |
| ATOM | 138 | CD | LYS | 4152 | 52.334 | 122.800 | 121.374 | 1.00 | 36.70 |
| ATOM | 139 | CE | LYS | 4152 | 53.149 | 124.087 | 121.412 | 1.00 | 42.21 |
| ATOM | 140 | NZ | LYS | 4152 | 52.617 | 125.143 | 120.490 | 1.00 | 46.74 |
| ATOM | 141 | C | LYS | 4152 | 50.615 | 118.972 | 123.854 | 1.00 | 35.71 |
| ATOM | 142 | O | LYS | 4152 | 49.484 | 119.367 | 124.100 | 1.00 | 36.33 |
| ATOM | 143 | N | VAL | 4153 | 50.869 | 117.707 | 123.544 | 1.00 | 33.21 |
| ATOM | 144 | CA | VAL | 4153 | 49.778 | 116.741 | 123.480 | 1.00 | 33.70 |
| ATOM | 145 | CB | VAL | 4153 | 50.209 | 115.447 | 122.759 | 1.00 | 36.62 |
| ATOM | 146 | CG1 | VAL | 4153 | 48.987 | 114.569 | 122.493 | 1.00 | 36.64 |
| ATOM | 147 | CG2 | VAL | 4153 | 50.908 | 115.784 | 121.468 | 1.00 | 38.90 |
| ATOM | 148 | C | VAL | 4153 | 49.271 | 116.376 | 124.877 | 1.00 | 32.20 |
| ATOM | 149 | O | VAL | 4153 | 48.059 | 116.238 | 125.091 | 1.00 | 28.40 |
| ATOM | 150 | N | MET | 4154 | 50.199 | 116.206 | 125.816 | 1.00 | 30.18 |
| ATOM | 151 | CA | MET | 4154 | 49.833 | 115.876 | 127.184 | 1.00 | 31.44 |
| ATOM | 152 | CB | MET | 4154 | 51.059 | 115.413 | 127.974 | 1.00 | 30.24 |

119

| ATOM | 153 | CG | MET | 4154 | 51.596 | 114.077 | 127.487 | 1.00 | 43.57 |
| ATOM | 154 | SD | MET | 4154 | 53.057 | 113.453 | 128.360 | 1.00 | 58.55 |
| ATOM | 155 | CE | MET | 4154 | 54.267 | 114.735 | 128.064 | 1.00 | 52.24 |
| ATOM | 156 | C | MET | 4154 | 49.220 | 117.112 | 127.813 | 1.00 | 30.49 |
| ATOM | 157 | O | MET | 4154 | 48.182 | 117.043 | 128.470 | 1.00 | 30.45 |
| ATOM | 158 | N | CYS | 4155 | 49.854 | 118.253 | 127.583 | 1.00 | 29.98 |
| ATOM | 159 | CA | CYS | 4155 | 49.352 | 119.493 | 128.124 | 1.00 | 31.39 |
| ATOM | 160 | CB | CYS | 4155 | 50.181 | 120.665 | 127.610 | 1.00 | 36.24 |
| ATOM | 161 | SG | CYS | 4155 | 49.769 | 122.266 | 128.367 | 1.00 | 58.18 |
| ATOM | 162 | C | CYS | 4155 | 47.909 | 119.616 | 127.667 | 1.00 | 29.83 |
| ATOM | 163 | O | CYS | 4155 | 47.027 | 119.937 | 128.448 | 1.00 | 34.32 |
| ATOM | 164 | N | ILE | 4156 | 47.663 | 119.330 | 126.399 | 1.00 | 31.51 |
| ATOM | 165 | CA | ILE | 4156 | 46.314 | 119.415 | 125.862 | 1.00 | 31.07 |
| ATOM | 166 | CB | ILE | 4156 | 46.291 | 119.256 | 124.325 | 1.00 | 28.44 |
| ATOM | 167 | CG2 | ILE | 4156 | 44.858 | 119.209 | 123.827 | 1.00 | 25.04 |
| ATOM | 168 | CG1 | ILE | 4156 | 47.018 | 120.433 | 123.671 | 1.00 | 30.51 |
| ATOM | 169 | CD1 | ILE | 4156 | 47.071 | 120.358 | 122.166 | 1.00 | 34.46 |
| ATOM | 170 | C | ILE | 4156 | 45.360 | 118.389 | 126.447 | 1.00 | 32.31 |
| ATOM | 171 | O | ILE | 4156 | 44.167 | 118.658 | 126.568 | 1.00 | 34.94 |
| ATOM | 172 | N | GLU | 4157 | 45.846 | 117.214 | 126.816 | 1.00 | 35.80 |
| ATOM | 173 | CA | GLU | 4157 | 44.902 | 116.247 | 127.355 | 1.00 | 41.03 |
| ATOM | 174 | CB | GLU | 4157 | 45.477 | 114.827 | 127.341 | 1.00 | 45.85 |
| ATOM | 175 | CG | GLU | 4157 | 44.425 | 113.757 | 127.654 | 1.00 | 53.60 |
| ATOM | 176 | CD | GLU | 4157 | 44.846 | 112.369 | 127.195 | 1.00 | 61.45 |
| ATOM | 177 | OE1 | GLU | 4157 | 44.083 | 111.401 | 127.429 | 1.00 | 63.05 |
| ATOM | 178 | OE2 | GLU | 4157 | 45.937 | 112.252 | 126.590 | 1.00 | 62.31 |
| ATOM | 179 | C | GLU | 4157 | 44.443 | 116.637 | 128.753 | 1.00 | 40.56 |
| ATOM | 180 | O | GLU | 4157 | 43.324 | 116.309 | 129.150 | 1.00 | 42.93 |
| ATOM | 181 | N | HIS | 4158 | 45.300 | 117.341 | 129.493 | 1.00 | 38.68 |
| ATOM | 182 | CA | HIS | 4158 | 44.942 | 117.791 | 130.836 | 1.00 | 33.97 |
| ATOM | 183 | CB | HIS | 4158 | 46.118 | 118.475 | 131.527 | 1.00 | 28.31 |
| ATOM | 184 | CG | HIS | 4158 | 47.147 | 117.525 | 132.044 | 1.00 | 29.87 |
| ATOM | 185 | CD2 | HIS | 4158 | 48.476 | 117.434 | 131.812 | 1.00 | 30.45 |
| ATOM | 186 | ND1 | HIS | 4158 | 46.842 | 116.517 | 132.933 | 1.00 | 30.53 |
| ATOM | 187 | CE1 | HIS | 4158 | 47.940 | 115.845 | 133.226 | 1.00 | 31.17 |
| ATOM | 188 | NE2 | HIS | 4158 | 48.946 | 116.381 | 132.559 | 1.00 | 33.12 |
| ATOM | 189 | C | HIS | 4158 | 43.797 | 118.776 | 130.730 | 1.00 | 34.66 |
| ATOM | 190 | O | HIS | 4158 | 42.756 | 118.600 | 131.356 | 1.00 | 36.53 |
| ATOM | 191 | N | GLU | 4159 | 43.990 | 119.811 | 129.926 | 1.00 | 31.59 |
| ATOM | 192 | CA | GLU | 4159 | 42.960 | 120.813 | 129.753 | 1.00 | 34.13 |
| ATOM | 193 | CB | GLU | 4159 | 43.405 | 121.863 | 128.734 | 1.00 | 39.12 |
| ATOM | 194 | CG | GLU | 4159 | 44.619 | 122.667 | 129.161 | 1.00 | 47.51 |
| ATOM | 195 | CD | GLU | 4159 | 44.969 | 123.753 | 128.165 | 1.00 | 55.28 |
| ATOM | 196 | OE1 | GLU | 4159 | 44.097 | 124.614 | 127.906 | 1.00 | 57.63 |
| ATOM | 197 | OE2 | GLU | 4159 | 46.111 | 123.744 | 127.645 | 1.00 | 60.95 |
| ATOM | 198 | C | GLU | 4159 | 41.629 | 120.218 | 129.317 | 1.00 | 33.97 |
| ATOM | 199 | O | GLU | 4159 | 40.581 | 120.835 | 129.506 | 1.00 | 34.45 |
| ATOM | 200 | N | ILE | 4160 | 41.655 | 119.025 | 128.736 | 1.00 | 33.50 |
| ATOM | 201 | CA | ILE | 4160 | 40.413 | 118.417 | 128.282 | 1.00 | 33.77 |
| ATOM | 202 | CB | ILE | 4160 | 40.660 | 117.502 | 127.061 | 1.00 | 33.81 |
| ATOM | 203 | CG2 | ILE | 4160 | 39.476 | 116.573 | 126.818 | 1.00 | 33.51 |
| ATOM | 204 | CG1 | ILE | 4160 | 40.912 | 118.390 | 125.837 | 1.00 | 33.36 |
| ATOM | 205 | CD1 | ILE | 4160 | 41.059 | 117.650 | 124.547 | 1.00 | 39.69 |
| ATOM | 206 | C | ILE | 4160 | 39.642 | 117.701 | 129.378 | 1.00 | 34.77 |
| ATOM | 207 | O | ILE | 4160 | 38.413 | 117.756 | 129.395 | 1.00 | 36.67 |
| ATOM | 208 | N | LYS | 4161 | 40.338 | 117.034 | 130.297 | 1.00 | 35.79 |
| ATOM | 209 | CA | LYS | 4161 | 39.640 | 116.378 | 131.400 | 1.00 | 32.72 |
| ATOM | 210 | CB | LYS | 4161 | 40.612 | 115.625 | 132.312 | 1.00 | 34.10 |
| ATOM | 211 | CG | LYS | 4161 | 41.289 | 114.492 | 131.592 | 1.00 | 43.45 |
| ATOM | 212 | CD | LYS | 4161 | 42.075 | 113.547 | 132.480 | 1.00 | 48.40 |
| ATOM | 213 | CE | LYS | 4161 | 42.613 | 112.419 | 131.595 | 1.00 | 54.45 |
| ATOM | 214 | NZ | LYS | 4161 | 43.338 | 111.335 | 132.304 | 1.00 | 58.40 |
| ATOM | 215 | C | LYS | 4161 | 39.000 | 117.523 | 132.151 | 1.00 | 31.33 |
| ATOM | 216 | O | LYS | 4161 | 37.828 | 117.469 | 132.508 | 1.00 | 32.86 |
| ATOM | 217 | N | SER | 4162 | 39.785 | 118.579 | 132.344 | 1.00 | 27.67 |
| ATOM | 218 | CA | SER | 4162 | 39.338 | 119.776 | 133.037 | 1.00 | 28.87 |
| ATOM | 219 | CB | SER | 4162 | 40.482 | 120.777 | 133.140 | 1.00 | 25.30 |
| ATOM | 220 | OG | SER | 4162 | 41.603 | 120.174 | 133.753 | 1.00 | 29.25 |
| ATOM | 221 | C | SER | 4162 | 38.171 | 120.434 | 132.327 | 1.00 | 32.12 |
| ATOM | 222 | O | SER | 4162 | 37.420 | 121.190 | 132.925 | 1.00 | 38.83 |

120

| ATOM | 223 | N | LEU | 4163 | 38.019 | 120.162 | 131.043 | 1.00 | 34.61 |
| --- | --- | --- | --- | --- | --- | --- | --- | --- | --- |
| ATOM | 224 | CA | LEU | 4163 | 36.925 | 120.761 | 130.305 | 1.00 | 35.03 |
| ATOM | 225 | CB | LEU | 4163 | 37.272 | 120.833 | 128.818 | 1.00 | 38.37 |
| ATOM | 226 | CG | LEU | 4163 | 36.517 | 121.828 | 127.932 | 1.00 | 38.57 |
| ATOM | 227 | CD1 | LEU | 4163 | 36.777 | 121.452 | 126.492 | 1.00 | 40.24 |
| ATOM | 228 | CD2 | LEU | 4163 | 35.018 | 121.794 | 128.193 | 1.00 | 45.38 |
| ATOM | 229 | C | LEU | 4163 | 35.718 | 119.859 | 130.523 | 1.00 | 34.24 |
| ATOM | 230 | O | LEU | 4163 | 34.616 | 120.336 | 130.767 | 1.00 | 31.18 |
| ATOM | 231 | N | GLU | 4164 | 35.951 | 118.550 | 130.444 | 1.00 | 38.30 |
| ATOM | 232 | CA | GLU | 4164 | 34.905 | 117.543 | 130.629 | 1.00 | 44.78 |
| ATOM | 233 | CB | GLU | 4164 | 35.466 | 116.139 | 130.406 | 1.00 | 44.04 |
| ATOM | 234 | CG | GLU | 4164 | 35.945 | 115.895 | 129.001 | 1.00 | 52.45 |
| ATOM | 235 | CD | GLU | 4164 | 36.380 | 114.463 | 128.773 | 1.00 | 58.43 |
| ATOM | 236 | OE1 | GLU | 4164 | 37.335 | 114.013 | 129.447 | 1.00 | 60.52 |
| ATOM | 237 | OE2 | GLU | 4164 | 35.761 | 113.790 | 127.916 | 1.00 | 60.51 |
| ATOM | 238 | C | GLU | 4164 | 34.258 | 117.596 | 132.007 | 1.00 | 47.43 |
| ATOM | 239 | O | GLU | 4164 | 33.033 | 117.652 | 132.126 | 1.00 | 49.24 |
| ATOM | 240 | N | ASP | 4165 | 35.076 | 117.564 | 133.050 | 1.00 | 49.08 |
| ATOM | 241 | CA | ASP | 4165 | 34.543 | 117.615 | 134.398 | 1.00 | 50.66 |
| ATOM | 242 | CB | ASP | 4165 | 35.655 | 117.412 | 135.428 | 1.00 | 52.68 |
| ATOM | 243 | CG | ASP | 4165 | 36.414 | 116.123 | 135.214 | 1.00 | 56.95 |
| ATOM | 244 | OD1 | ASP | 4165 | 35.771 | 115.056 | 135.073 | 1.00 | 56.77 |
| ATOM | 245 | OD2 | ASP | 4165 | 37.660 | 116.177 | 135.199 | 1.00 | 59.48 |
| ATOM | 246 | C | ASP | 4165 | 33.877 | 118.961 | 134.635 | 1.00 | 50.27 |
| ATOM | 247 | O | ASP | 4165 | 32.714 | 119.027 | 135.028 | 1.00 | 51.73 |
| ATOM | 248 | N | LEU | 4166 | 34.614 | 120.035 | 134.378 | 1.00 | 47.88 |
| ATOM | 249 | CA | LEU | 4166 | 34.089 | 121.371 | 134.597 | 1.00 | 48.17 |
| ATOM | 250 | CB | LEU | 4166 | 35.124 | 122.410 | 134.166 | 1.00 | 49.54 |
| ATOM | 251 | CG | LEU | 4166 | 34.920 | 123.885 | 134.520 | 1.00 | 51.03 |
| ATOM | 252 | CD1 | LEU | 4166 | 36.247 | 124.608 | 134.376 | 1.00 | 52.85 |
| ATOM | 253 | CD2 | LEU | 4166 | 33.861 | 124.522 | 133.638 | 1.00 | 51.91 |
| ATOM | 254 | C | LEU | 4166 | 32.764 | 121.600 | 133.888 | 1.00 | 50.26 |
| ATOM | 255 | O | LEU | 4166 | 32.044 | 122.536 | 134.210 | 1.00 | 50.62 |
| ATOM | 256 | N | GLN | 4167 | 32.422 | 120.743 | 132.933 | 1.00 | 53.90 |
| ATOM | 257 | CA | GLN | 4167 | 31.153 | 120.917 | 132.232 | 1.00 | 56.44 |
| ATOM | 258 | CB | GLN | 4167 | 31.245 | 120.454 | 130.777 | 1.00 | 58.07 |
| ATOM | 259 | CG | GLN | 4167 | 29.984 | 120.776 | 129.987 | 1.00 | 61.99 |
| ATOM | 260 | CD | GLN | 4167 | 30.005 | 120.246 | 128.567 | 1.00 | 63.54 |
| ATOM | 261 | OE1 | GLN | 4167 | 30.028 | 119.036 | 128.340 | 1.00 | 63.55 |
| ATOM | 262 | NE2 | GLN | 4167 | 29.996 | 121.156 | 127.601 | 1.00 | 66.37 |
| ATOM | 263 | C | GLN | 4167 | 30.048 | 120.145 | 132.940 | 1.00 | 56.68 |
| ATOM | 264 | O | GLN | 4167 | 28.957 | 120.676 | 133.150 | 1.00 | 57.48 |
| ATOM | 265 | N | ASP | 4168 | 30.325 | 118.893 | 133.303 | 1.00 | 55.93 |
| ATOM | 266 | CA | ASP | 4168 | 29.337 | 118.082 | 134.009 | 1.00 | 57.13 |
| ATOM | 267 | CB | ASP | 4168 | 29.843 | 116.646 | 134.209 | 1.00 | 62.02 |
| ATOM | 268 | CG | ASP | 4168 | 30.133 | 115.934 | 132.889 | 1.00 | 71.07 |
| ATOM | 269 | OD1 | ASP | 4168 | 29.243 | 115.882 | 132.010 | 1.00 | 74.06 |
| ATOM | 270 | OD2 | ASP | 4168 | 31.256 | 115.411 | 132.729 | 1.00 | 77.41 |
| ATOM | 271 | C | ASP | 4168 | 29.032 | 118.725 | 135.365 | 1.00 | 55.08 |
| ATOM | 272 | O | ASP | 4168 | 28.079 | 118.348 | 136.038 | 1.00 | 54.17 |
| ATOM | 273 | N | GLU | 4169 | 29.856 | 119.695 | 135.756 | 1.00 | 53.00 |
| ATOM | 274 | CA | GLU | 4169 | 29.671 | 120.421 | 137.007 | 1.00 | 51.20 |
| ATOM | 275 | CB | GLU | 4169 | 30.967 | 121.122 | 137.425 | 1.00 | 48.94 |
| ATOM | 276 | CG | GLU | 4169 | 30.873 | 121.876 | 138.748 | 1.00 | 43.86 |
| ATOM | 277 | CD | GLU | 4169 | 32.089 | 122.749 | 139.025 | 1.00 | 45.23 |
| ATOM | 278 | OE1 | GLU | 4169 | 33.228 | 122.251 | 138.914 | 1.00 | 46.47 |
| ATOM | 279 | OE2 | GLU | 4169 | 31.910 | 123.937 | 139.369 | 1.00 | 42.32 |
| ATOM | 280 | C | GLU | 4169 | 28.608 | 121.472 | 136.728 | 1.00 | 52.23 |
| ATOM | 281 | O | GLU | 4169 | 27.562 | 121.510 | 137.371 | 1.00 | 52.91 |
| ATOM | 282 | N | TYR | 4170 | 28.897 | 122.325 | 135.753 | 1.00 | 53.92 |
| ATOM | 283 | CA | TYR | 4170 | 27.983 | 123.381 | 135.344 | 1.00 | 55.91 |
| ATOM | 284 | CB | TYR | 4170 | 28.622 | 124.223 | 134.241 | 1.00 | 58.27 |
| ATOM | 285 | CG | TYR | 4170 | 29.680 | 125.202 | 134.713 | 1.00 | 62.28 |
| ATOM | 286 | CD1 | TYR | 4170 | 30.670 | 124.826 | 135.624 | 1.00 | 61.31 |
| ATOM | 287 | CE1 | TYR | 4170 | 31.690 | 125.715 | 135.990 | 1.00 | 61.41 |
| ATOM | 288 | CD2 | TYR | 4170 | 29.733 | 126.488 | 134.187 | 1.00 | 63.83 |
| ATOM | 289 | CE2 | TYR | 4170 | 30.743 | 127.381 | 134.542 | 1.00 | 65.13 |
| ATOM | 290 | CZ | TYR | 4170 | 31.720 | 126.992 | 135.439 | 1.00 | 64.58 |
| ATOM | 291 | OH | TYR | 4170 | 32.731 | 127.877 | 135.755 | 1.00 | 61.68 |
| ATOM | 292 | C | TYR | 4170 | 26.650 | 122.824 | 134.852 | 1.00 | 55.20 |

121

| ATOM | 293 | O | TYR | 4170 | 25.607 | 123.434 | 135.065 | 1.00 | 53.55 |
| --- | --- | --- | --- | --- | --- | --- | --- | --- | --- |
| ATOM | 294 | N | ASP | 4171 | 26.679 | 121.670 | 134.192 | 1.00 | 56.30 |
| ATOM | 295 | CA | ASP | 4171 | 25.442 | 121.081 | 133.695 | 1.00 | 60.40 |
| ATOM | 296 | CB | ASP | 4171 | 25.724 | 119.896 | 132.770 | 1.00 | 66.08 |
| ATOM | 297 | CG | ASP | 4171 | 24.449 | 119.319 | 132.158 | 1.00 | 71.70 |
| ATOM | 298 | OD1 | ASP | 4171 | 23.780 | 120.041 | 131.381 | 1.00 | 71.00 |
| ATOM | 299 | OD2 | ASP | 4171 | 24.113 | 118.149 | 132.459 | 1.00 | 74.51 |
| ATOM | 300 | C | ASP | 4171 | 24.592 | 120.615 | 134.869 | 1.00 | 60.50 |
| ATOM | 301 | O | ASP | 4171 | 23.367 | 120.769 | 134.861 | 1.00 | 59.90 |
| ATOM | 302 | N | PHE | 4172 | 25.245 | 120.039 | 135.875 | 1.00 | 59.52 |
| ATOM | 303 | CA | PHE | 4172 | 24.546 | 119.563 | 137.063 | 1.00 | 58.11 |
| ATOM | 304 | CB | PHE | 4172 | 25.519 | 118.865 | 138.010 | 1.00 | 57.74 |
| ATOM | 305 | CG | PHE | 4172 | 24.860 | 118.256 | 139.214 | 1.00 | 58.18 |
| ATOM | 306 | CD1 | PHE | 4172 | 24.077 | 117.114 | 139.091 | 1.00 | 57.84 |
| ATOM | 307 | CD2 | PHE | 4172 | 25.012 | 118.832 | 140.471 | 1.00 | 57.54 |
| ATOM | 308 | CE1 | PHE | 4172 | 23.459 | 116.553 | 140.202 | 1.00 | 55.18 |
| ATOM | 309 | CE2 | PHE | 4172 | 24.397 | 118.281 | 141.585 | 1.00 | 55.67 |
| ATOM | 310 | CZ | PHE | 4172 | 23.620 | 117.137 | 141.451 | 1.00 | 56.82 |
| ATOM | 311 | C | PHE | 4172 | 23.926 | 120.762 | 137.778 | 1.00 | 57.85 |
| ATOM | 312 | O | PHE | 4172 | 22.754 | 120.738 | 138.154 | 1.00 | 57.10 |
| ATOM | 313 | N | LYS | 4173 | 24.720 | 121.812 | 137.963 | 1.00 | 54.82 |
| ATOM | 314 | CA | LYS | 4173 | 24.230 | 123.005 | 138.629 | 1.00 | 54.64 |
| ATOM | 315 | CB | LYS | 4173 | 25.350 | 124.034 | 138.782 | 1.00 | 49.04 |
| ATOM | 316 | CG | LYS | 4173 | 26.517 | 123.531 | 139.607 | 1.00 | 46.83 |
| ATOM | 317 | CD | LYS | 4173 | 27.494 | 124.642 | 139.937 | 1.00 | 48.12 |
| ATOM | 318 | CE | LYS | 4173 | 28.634 | 124.130 | 140.813 | 1.00 | 50.32 |
| ATOM | 319 | NZ | LYS | 4173 | 29.562 | 125.226 | 141.236 | 1.00 | 47.21 |
| ATOM | 320 | C | LYS | 4173 | 23.055 | 123.614 | 137.876 | 1.00 | 59.04 |
| ATOM | 321 | O | LYS | 4173 | 22.240 | 124.318 | 138.462 | 1.00 | 62.42 |
| ATOM | 322 | N | CYS | 4174 | 22.963 | 123.349 | 136.577 | 1.00 | 62.37 |
| ATOM | 323 | CA | CYS | 4174 | 21.856 | 123.880 | 135.790 | 1.00 | 65.61 |
| ATOM | 324 | CB | CYS | 4174 | 22.153 | 123.812 | 134.290 | 1.00 | 71.42 |
| ATOM | 325 | SG | CYS | 4174 | 23.373 | 125.002 | 133.678 | 1.00 | 81.22 |
| ATOM | 326 | C | CYS | 4174 | 20.594 | 123.096 | 136.078 | 1.00 | 65.22 |
| ATOM | 327 | O | CYS | 4174 | 19.585 | 123.667 | 136.479 | 1.00 | 64.31 |
| ATOM | 328 | N | LYS | 4175 | 20.648 | 121.785 | 135.873 | 1.00 | 65.77 |
| ATOM | 329 | CA | LYS | 4175 | 19.483 | 120.950 | 136.119 | 1.00 | 69.68 |
| ATOM | 330 | CB | LYS | 4175 | 19.846 | 119.463 | 136.051 | 1.00 | 68.45 |
| ATOM | 331 | CG | LYS | 4175 | 18.658 | 118.549 | 136.344 | 1.00 | 70.19 |
| ATOM | 332 | CD | LYS | 4175 | 19.040 | 117.078 | 136.415 | 1.00 | 71.48 |
| ATOM | 333 | CE | LYS | 4175 | 17.837 | 116.242 | 136.839 | 1.00 | 73.98 |
| ATOM | 334 | NZ | LYS | 4175 | 18.167 | 114.805 | 137.005 | 1.00 | 74.17 |
| ATOM | 335 | C | LYS | 4175 | 18.857 | 121.254 | 137.478 | 1.00 | 72.93 |
| ATOM | 336 | O | LYS | 4175 | 17.649 | 121.473 | 137.574 | 1.00 | 73.15 |
| ATOM | 337 | N | THR | 4176 | 19.675 | 121.273 | 138.527 | 1.00 | 76.15 |
| ATOM | 338 | CA | THR | 4176 | 19.158 | 121.547 | 139.862 | 1.00 | 78.83 |
| ATOM | 339 | CB | THR | 4176 | 20.282 | 121.562 | 140.931 | 1.00 | 79.52 |
| ATOM | 340 | OG1 | THR | 4176 | 21.233 | 122.586 | 140.619 | 1.00 | 84.06 |
| ATOM | 341 | CG2 | THR | 4176 | 20.985 | 120.210 | 140.989 | 1.00 | 77.87 |
| ATOM | 342 | C | THR | 4176 | 18.411 | 122.878 | 139.892 | 1.00 | 80.20 |
| ATOM | 343 | O | THR | 4176 | 17.204 | 122.896 | 140.117 | 1.00 | 83.46 |
| ATOM | 344 | N | LEU | 4177 | 19.111 | 123.985 | 139.654 | 1.00 | 79.17 |
| ATOM | 345 | CA | LEU | 4177 | 18.467 | 125.297 | 139.669 | 1.00 | 78.30 |
| ATOM | 346 | CB | LEU | 4177 | 19.409 | 126.370 | 139.111 | 1.00 | 78.05 |
| ATOM | 347 | CG | LEU | 4177 | 20.482 | 126.959 | 140.039 | 1.00 | 77.56 |
| ATOM | 348 | CD1 | LEU | 4177 | 21.336 | 125.870 | 140.662 | 1.00 | 77.06 |
| ATOM | 349 | CD2 | LEU | 4177 | 21.340 | 127.926 | 139.240 | 1.00 | 76.82 |
| ATOM | 350 | C | LEU | 4177 | 17.138 | 125.339 | 138.920 | 1.00 | 79.80 |
| ATOM | 351 | O | LEU | 4177 | 16.307 | 126.197 | 139.194 | 1.00 | 77.60 |
| ATOM | 352 | N | GLN | 4178 | 16.932 | 124.416 | 137.982 | 1.00 | 84.01 |
| ATOM | 353 | CA | GLN | 4178 | 15.680 | 124.367 | 137.226 | 1.00 | 89.15 |
| ATOM | 354 | CB | GLN | 4178 | 15.868 | 123.623 | 135.902 | 1.00 | 90.44 |
| ATOM | 355 | CG | GLN | 4178 | 16.711 | 124.378 | 134.889 | 1.00 | 96.59 |
| ATOM | 356 | CD | GLN | 4178 | 16.777 | 123.676 | 133.545 | 1.00 | 99.76 |
| ATOM | 357 | OE1 | GLN | 4178 | 15.747 | 123.394 | 132.929 | 1.00 | 102.75 |
| ATOM | 358 | NE2 | GLN | 4178 | 17.991 | 123.399 | 133.079 | 1.00 | 100.55 |
| ATOM | 359 | C | GLN | 4178 | 14.564 | 123.704 | 138.024 | 1.00 | 91.62 |
| ATOM | 360 | O | GLN | 4178 | 13.427 | 124.179 | 138.035 | 1.00 | 92.05 |
| ATOM | 361 | N | ASN | 4179 | 14.886 | 122.600 | 138.687 | 1.00 | 94.74 |
| ATOM | 362 | CA | ASN | 4179 | 13.897 | 121.906 | 139.498 | 1.00 | 97.73 |

```
ATOM   363  CB   ASN  4179      14.210 120.409 139.563  1.00  98.06
ATOM   364  CG   ASN  4179      14.170 119.751 138.192  1.00  98.79
ATOM   365  OD1  ASN  4179      13.173 119.851 137.473  1.00  97.71
ATOM   366  ND2  ASN  4179      15.254 119.073 137.824  1.00  98.47
ATOM   367  C    ASN  4179      13.846 122.519 140.897  1.00  99.54
ATOM   368  O    ASN  4179      12.861 122.350 141.614  1.00 100.58
ATOM   369  N    ARG  4180      14.908 123.229 141.283  1.00 101.87
ATOM   370  CA   ARG  4180      14.947 123.906 142.580  1.00 103.70
ATOM   371  CB   ARG  4180      16.391 124.121 143.080  1.00 104.10
ATOM   372  CG   ARG  4180      17.038 122.887 143.719  1.00 106.21
ATOM   373  CD   ARG  4180      18.368 123.191 144.442  1.00 109.06
ATOM   374  NE   ARG  4180      19.477 123.535 143.547  1.00 111.46
ATOM   375  CZ   ARG  4180      20.734 123.730 143.949  1.00 110.99
ATOM   376  NH1  ARG  4180      21.051 123.615 145.233  1.00 110.57
ATOM   377  NH2  ARG  4180      21.682 124.028 143.067  1.00 108.06
ATOM   378  C    ARG  4180      14.240 125.252 142.430  1.00 104.86
ATOM   379  O    ARG  4180      14.654 126.263 143.001  1.00 103.98
ATOM   380  N    GLU  4181      13.171 125.243 141.640  1.00 106.61
ATOM   381  CA   GLU  4181      12.363 126.428 141.388  1.00 108.71
ATOM   382  CB   GLU  4181      12.843 127.140 140.119  1.00 109.87
ATOM   383  CG   GLU  4181      14.200 127.822 140.267  1.00 112.25
ATOM   384  CD   GLU  4181      14.680 128.477 138.980  1.00 113.31
ATOM   385  OE1  GLU  4181      15.733 129.155 139.011  1.00 112.54
ATOM   386  OE2  GLU  4181      14.009 128.308 137.938  1.00 114.07
ATOM   387  C    GLU  4181      10.894 126.042 141.250  1.00 109.38
ATOM   388  O    GLU  4181      10.080 126.350 142.125  1.00 108.91
ATOM   389  N    HIS  4182      10.564 125.359 140.156  1.00 110.53
ATOM   390  CA   HIS  4182       9.192 124.927 139.897  1.00 111.09
ATOM   391  CB   HIS  4182       9.155 123.910 138.747  1.00 112.09
ATOM   392  CG   HIS  4182       9.615 124.459 137.430  1.00 112.78
ATOM   393  CD2  HIS  4182      10.570 124.029 136.569  1.00 112.20
ATOM   394  ND1  HIS  4182       9.043 125.566 136.842  1.00 112.38
ATOM   395  CE1  HIS  4182       9.624 125.796 135.677  1.00 112.09
ATOM   396  NE2  HIS  4182      10.554 124.876 135.489  1.00 112.22
ATOM   397  C    HIS  4182       8.551 124.312 141.140  1.00 110.27
ATOM   398  O    HIS  4182       8.633 123.073 141.274  1.00 108.96
ATOM   399  N    LEU  4197      27.706 133.978 139.769  1.00 102.45
ATOM   400  CA   LEU  4197      26.585 134.203 138.828  1.00 102.82
ATOM   401  CB   LEU  4197      26.893 135.309 137.924  1.00 100.97
ATOM   402  C    LEU  4197      26.385 132.944 137.964  1.00 102.70
ATOM   403  O    LEU  4197      27.183 132.717 137.052  1.00 104.63
ATOM   404  N    LEU  4198      25.359 132.133 138.260  1.00 101.78
ATOM   405  CA   LEU  4198      24.988 130.937 137.517  1.00 101.64
ATOM   406  CB   LEU  4198      23.558 130.576 137.829  1.00 102.31
ATOM   407  C    LEU  4198      25.150 131.108 136.013  1.00 101.60
ATOM   408  O    LEU  4198      26.017 130.460 135.376  1.00 101.14
ATOM   409  N    LEU  4199      24.289 131.970 135.459  1.00 101.22
ATOM   410  CA   LEU  4199      24.231 132.226 134.028  1.00 100.20
ATOM   411  CB   LEU  4199      23.206 133.325 133.717  1.00 100.68
ATOM   412  C    LEU  4199      25.590 132.572 133.434  1.00  99.95
ATOM   413  O    LEU  4199      26.047 131.881 132.521  1.00  99.72
ATOM   414  N    LYS  4200      26.220 133.639 133.926  1.00  99.53
ATOM   415  CA   LYS  4200      27.502 134.075 133.410  1.00  97.60
ATOM   416  CB   LYS  4200      28.040 135.246 134.219  1.00  98.24
ATOM   417  CG   LYS  4200      27.236 136.526 134.057  1.00 100.55
ATOM   418  CD   LYS  4200      27.926 137.725 134.686  1.00 101.35
ATOM   419  CE   LYS  4200      27.135 138.995 134.414  1.00 102.29
ATOM   420  NZ   LYS  4200      27.818 140.221 134.906  1.00 101.38
ATOM   421  C    LYS  4200      28.555 132.976 133.347  1.00  95.79
ATOM   422  O    LYS  4200      29.084 132.690 132.280  1.00  95.57
ATOM   423  N    LYS  4201      28.868 132.380 134.493  1.00  94.70
ATOM   424  CA   LYS  4201      29.874 131.323 134.550  1.00  94.46
ATOM   425  CB   LYS  4201      29.784 130.5.0 135.869  1.00  97.08
ATOM   426  CG   LYS  4201      30.178 131.310 137.122  1.00  98.09
ATOM   427  CD   LYS  4201      30.164 130.396 138.342  1.00  97.68
ATOM   428  CE   LYS  4201      30.618 131.128 139.598  1.00  98.51
ATOM   429  NZ   LYS  4201      30.629 130.231 140.790  1.00  98.01
ATOM   430  C    LYS  4201      29.749 130.348 133.387  1.00  92.03
ATOM   431  O    LYS  4201      30.588 130.328 132.487  1.00  90.97
ATOM   432  N    MET  4202      28.696 129.538 133.425  1.00  89.18
```

123

| | | | | | | | | |
|---|---|---|---|---|---|---|---|---|
| ATOM | 433 | CA | MET | 4202 | 28.429 | 128.544 | 132.389 | 1.00 86.67 |
| ATOM | 434 | CB | MET | 4202 | 26.944 | 128.131 | 132.429 | 1.00 82.65 |
| ATOM | 435 | CG | MET | 4202 | 26.665 | 126.731 | 132.994 | 1.00 77.06 |
| ATOM | 436 | SD | MET | 4202 | 26.745 | 125.3.1 | 131.812 | 1.00 69.57 |
| ATOM | 437 | CE | MET | 4202 | 25.240 | 125.557 | 130.887 | 1.00 66.97 |
| ATOM | 438 | C | MET | 4202 | 28.784 | 129.013 | 130.988 | 1.00 86.80 |
| ATOM | 439 | O | MET | 4202 | 29.944 | 128.985 | 130.579 | 1.00 88.33 |
| ATOM | 440 | N | TYR | 4203 | 27.761 | 129.453 | 130.271 | 1.00 85.72 |
| ATOM | 441 | CA | TYR | 4203 | 27.877 | 129.903 | 128.900 | 1.00 84.20 |
| ATOM | 442 | CB | TYR | 4203 | 26.570 | 130.587 | 128.518 | 1.00 87.98 |
| ATOM | 443 | CG | TYR | 4203 | 25.366 | 129.742 | 128.879 | 1.00 92.68 |
| ATOM | 444 | CD1 | TYR | 4203 | 25.235 | 128.442 | 128.392 | 1.00 94.71 |
| ATOM | 445 | CE1 | TYR | 4203 | 24.150 | 127.642 | 128.743 | 1.00 95.63 |
| ATOM | 446 | CD2 | TYR | 4203 | 24.371 | 130.229 | 129.729 | 1.00 95.53 |
| ATOM | 447 | CE2 | TYR | 4203 | 23.278 | 129.434 | 130.088 | 1.00 97.27 |
| ATOM | 448 | CZ | TYR | 4203 | 23.178 | 128.142 | 129.589 | 1.00 97.38 |
| ATOM | 449 | OH | TYR | 4203 | 22.112 | 127.345 | 129.940 | 1.00 98.13 |
| ATOM | 450 | C | TYR | 4203 | 29.069 | 130.782 | 128.525 | 1.00 82.26 |
| ATOM | 451 | O | TYR | 4203 | 29.316 | 130.997 | 127.341 | 1.00 83.66 |
| ATOM | 452 | N | LEU | 4204 | 29.820 | 131.285 | 129.500 | 1.00 78.88 |
| ATOM | 453 | CA | LEU | 4204 | 30.955 | 132.131 | 129.153 | 1.00 75.00 |
| ATOM | 454 | CB | LEU | 4204 | 30.904 | 133.463 | 129.904 | 1.00 76.04 |
| ATOM | 455 | CG | LEU | 4204 | 32.085 | 134.402 | 129.599 | 1.00 77.21 |
| ATOM | 456 | CD1 | LEU | 4204 | 32.139 | 134.695 | 128.100 | 1.00 75.86 |
| ATOM | 457 | CD2 | LEU | 4204 | 31.953 | 135.696 | 130.397 | 1.00 76.84 |
| ATOM | 458 | C | LEU | 4204 | 32.332 | 131.520 | 129.341 | 1.00 72.47 |
| ATOM | 459 | O | LEU | 4204 | 33.193 | 131.692 | 128.485 | 1.00 72.78 |
| ATOM | 460 | N | MET | 4205 | 32.574 | 130.817 | 130.440 | 1.00 70.46 |
| ATOM | 461 | CA | MET | 4205 | 33.905 | 130.256 | 130.602 | 1.00 69.43 |
| ATOM | 462 | CB | MET | 4205 | 34.244 | 130.003 | 132.064 | 1.00 71.51 |
| ATOM | 463 | CG | MET | 4205 | 35.708 | 129.644 | 132.231 | 1.00 77.83 |
| ATOM | 464 | SD | MET | 4205 | 36.234 | 129.450 | 133.924 | 1.00 87.99 |
| ATOM | 465 | CE | MET | 4205 | 35.789 | 131.053 | 134.598 | 1.00 86.47 |
| ATOM | 466 | C | MET | 4205 | 34.100 | 128.982 | 129.809 | 1.00 67.12 |
| ATOM | 467 | O | MET | 4205 | 35.153 | 128.792 | 129.205 | 1.00 67.42 |
| ATOM | 468 | N | LEU | 4206 | 33.101 | 128.105 | 129.809 | 1.00 64.45 |
| ATOM | 469 | CA | LEU | 4206 | 33.203 | 126.867 | 129.039 | 1.00 63.33 |
| ATOM | 470 | CB | LEU | 4206 | 31.861 | 126.133 | 128.980 | 1.00 60.81 |
| ATOM | 471 | CG | LEU | 4206 | 31.264 | 125.532 | 130.248 | 1.00 60.06 |
| ATOM | 472 | CD1 | LEU | 4206 | 29.969 | 124.817 | 129.894 | 1.00 61.25 |
| ATOM | 473 | CD2 | LEU | 4206 | 32.241 | 124.553 | 130.865 | 1.00 60.13 |
| ATOM | 474 | C | LEU | 4206 | 33.624 | 127.223 | 127.618 | 1.00 63.39 |
| ATOM | 475 | O | LEU | 4206 | 34.491 | 126.579 | 127.030 | 1.00 63.88 |
| ATOM | 476 | N | ASP | 4207 | 32.994 | 128.262 | 127.080 | 1.00 64.17 |
| ATOM | 477 | CA | ASP | 4207 | 33.275 | 128.737 | 125.734 | 1.00 62.35 |
| ATOM | 478 | CB | ASP | 4207 | 32.386 | 129.945 | 125.426 | 1.00 67.59 |
| ATOM | 479 | CG | ASP | 4207 | 32.410 | 130.336 | 123.962 | 1.00 72.93 |
| ATOM | 480 | OD1 | ASP | 4207 | 31.979 | 129.513 | 123.127 | 1.00 74.92 |
| ATOM | 481 | OD2 | ASP | 4207 | 32.854 | 131.465 | 123.645 | 1.00 73.67 |
| ATOM | 482 | C | ASP | 4207 | 34.750 | 129.124 | 125.649 | 1.00 59.66 |
| ATOM | 483 | O | ASP | 4207 | 35.463 | 123.6`0 | 124.755 | 1.00 59.80 |
| ATOM | 484 | N | ASN | 4208 | 35.207 | 129.951 | 126.585 | 1.00 56.54 |
| ATOM | 485 | CA | ASN | 4208 | 36.604 | 130.367 | 126.602 | 1.00 53.72 |
| ATOM | 486 | CB | ASN | 4208 | 36.873 | 131.327 | 127.754 | 1.00 54.57 |
| ATOM | 487 | CG | ASN | 4208 | 36.546 | 132.758 | 127.396 | 1.00 59.31 |
| ATOM | 488 | OD1 | ASN | 4208 | 35.442 | 133.066 | 126.935 | 1.00 58.75 |
| ATOM | 489 | ND2 | ASN | 4208 | 37.511 | 133.648 | 127.604 | 1.00 62.01 |
| ATOM | 490 | C | ASN | 4208 | 37.516 | 129.176 | 126.717 | 1.00 52.25 |
| ATOM | 491 | O | ASN | 4208 | 38.632 | 129.199 | 126.216 | 1.00 52.47 |
| ATOM | 492 | N | LYS | 4209 | 37.035 | 128.134 | 127.384 | 1.00 51.81 |
| ATOM | 493 | CA | LYS | 4209 | 37.808 | 126.914 | 127.548 | 1.00 48.31 |
| ATOM | 494 | CB | LYS | 4209 | 37.312 | 126.132 | 128.764 | 1.00 45.89 |
| ATOM | 495 | CG | LYS | 4209 | 37.765 | 126.741 | 130.071 | 1.00 48.85 |
| ATOM | 496 | CD | LYS | 4209 | 39.284 | 126.782 | 130.109 | 1.00 58.03 |
| ATOM | 497 | CE | LYS | 4209 | 39.821 | 127.312 | 131.425 | 1.00 62.03 |
| ATOM | 498 | NZ | LYS | 4209 | 41.314 | 127.361 | 131.394 | 1.00 67.26 |
| ATOM | 499 | C | LYS | 4209 | 37.766 | 126.053 | 126.286 | 1.00 46.17 |
| ATOM | 500 | O | LYS | 4209 | 38.775 | 125.452 | 125.910 | 1.00 44.93 |
| ATOM | 501 | N | ARG | 4210 | 36.610 | 125.990 | 125.630 | 1.00 41.19 |
| ATOM | 502 | CA | ARG | 4210 | 36.511 | 125.223 | 124.400 | 1.00 37.52 |

| ATOM | 503 | CB   | ARG | 4210 | 35.079 125.222 123.851 | 1.00 38.78 |
| ATOM | 504 | CG   | ARG | 4210 | 34.087 124.462 124.710 | 1.00 42.81 |
| ATOM | 505 | CD   | ARG | 4210 | 32.759 124.223 123.993 | 1.00 43.77 |
| ATOM | 506 | NE   | ARG | 4210 | 31.991 123.183 124.677 | 1.00 47.57 |
| ATOM | 507 | CZ   | ARG | 4210 | 30.940 122.553 124.160 | 1.00 45.02 |
| ATOM | 508 | NH1  | ARG | 4210 | 30.514 122.853 122.947 | 1.00 49.15 |
| ATOM | 509 | NH2  | ARG | 4210 | 30.330 121.598 124.846 | 1.00 47.84 |
| ATOM | 510 | C    | ARG | 4210 | 37.445 125.895 123.406 | 1.00 35.99 |
| ATOM | 511 | O    | ARG | 4210 | 38.401 125.287 122.926 | 1.00 35.36 |
| ATOM | 512 | N    | LYS | 4211 | 37.171 127.160 123.114 | 1.00 35.56 |
| ATOM | 513 | CA   | LYS | 4211 | 38.003 127.913 122.195 | 1.00 38.38 |
| ATOM | 514 | CB   | LYS | 4211 | 37.632 129.393 122.228 | 1.00 36.29 |
| ATOM | 515 | CG   | LYS | 4211 | 36.233 129.689 121.746 | 1.00 41.09 |
| ATOM | 516 | CD   | LYS | 4211 | 36.016 131.188 121.637 | 1.00 44.11 |
| ATOM | 517 | CE   | LYS | 4211 | 34.666 131.510 121.024 | 1.00 43.20 |
| ATOM | 518 | NZ   | LYS | 4211 | 34.536 132.972 120.788 | 1.00 48.32 |
| ATOM | 519 | C    | LYS | 4211 | 39.466 127.756 122.579 | 1.00 40.38 |
| ATOM | 520 | O    | LYS | 4211 | 40.324 127.532 121.728 | 1.00 43.38 |
| ATOM | 521 | N    | GLU | 4212 | 39.744 127.864 123.869 | 1.00 40.10 |
| ATOM | 522 | CA   | GLU | 4212 | 41.107 127.742 124.348 | 1.00 42.53 |
| ATOM | 523 | CB   | GLU | 4212 | 41.143 127.757 125.878 | 1.00 50.94 |
| ATOM | 524 | CG   | GLU | 4212 | 42.242 128.636 126.474 | 1.00 55.66 |
| ATOM | 525 | CD   | GLU | 4212 | 43.608 128.360 125.878 | 1.00 60.12 |
| ATOM | 526 | OE1  | GLU | 4212 | 43.784 128.584 124.661 | 1.00 62.48 |
| ATOM | 527 | OE2  | GLU | 4212 | 44.508 127.918 126.623 | 1.00 66.37 |
| ATOM | 528 | C    | GLU | 4212 | 41.712 126.442 123.848 | 1.00 40.06 |
| ATOM | 529 | O    | GLU | 4212 | 42.751 126.443 123.198 | 1.00 41.22 |
| ATOM | 530 | N    | VAL | 4213 | 41.061 125.327 124.150 | 1.00 39.20 |
| ATOM | 531 | CA   | VAL | 4213 | 41.580 124.039 123.717 | 1.00 41.29 |
| ATOM | 532 | CB   | VAL | 4213 | 40.681 122.863 124.172 | 1.00 42.26 |
| ATOM | 533 | CG1  | VAL | 4213 | 41.186 121.566 123.570 | 1.00 47.91 |
| ATOM | 534 | CG2  | VAL | 4213 | 40.718 122.734 125.677 | 1.00 42.17 |
| ATOM | 535 | C    | VAL | 4213 | 41.748 123.981 122.209 | 1.00 40.12 |
| ATOM | 536 | O    | VAL | 4213 | 42.858 123.792 121.725 | 1.00 39.94 |
| ATOM | 537 | N    | VAL | 4214 | 40.654 124.146 121.470 | 1.00 38.93 |
| ATOM | 538 | CA   | VAL | 4214 | 40.720 124.101 120.010 | 1.00 38.47 |
| ATOM | 539 | CB   | VAL | 4214 | 39.457 124.699 119.360 | 1.00 35.05 |
| ATOM | 540 | CG1  | VAL | 4214 | 39.719 124.998 117.904 | 1.00 31.34 |
| ATOM | 541 | CG2  | VAL | 4214 | 38.313 123.713 119.465 | 1.00 29.44 |
| ATOM | 542 | C    | VAL | 4214 | 41.941 124.842 119.488 | 1.00 39.58 |
| ATOM | 543 | O    | VAL | 4214 | 42.756 124.281 118.748 | 1.00 40.95 |
| ATOM | 544 | N    | HIS | 4215 | 42.069 126.102 119.874 | 1.00 39.71 |
| ATOM | 545 | CA   | HIS | 4215 | 43.210 126.861 119.440 | 1.00 40.81 |
| ATOM | 546 | CB   | HIS | 4215 | 43.226 128.227 120.169 | 1.00 43.75 |
| ATOM | 547 | CG   | HIS | 4215 | 44.451 129.047 119.911 | 1.00 48.64 |
| ATOM | 548 | CD2  | HIS | 4215 | 44.633 130.170 119.176 | 1.00 52.38 |
| ATOM | 549 | ND1  | HIS | 4215 | 45.684 128.729 120.439 | 1.00 49.91 |
| ATOM | 550 | CE1  | HIS | 4215 | 46.574 129.622 120.043 | 1.00 49.29 |
| ATOM | 551 | NE2  | HIS | 4215 | 45.963 130.507 119.275 | 1.00 54.44 |
| ATOM | 552 | C    | HIS | 4215 | 44.489 126.083 119.705 | 1.00 40.50 |
| ATOM | 553 | O    | HIS | 4215 | 45.292 125.879 118.799 | 1.00 40.60 |
| ATOM | 554 | N    | LYS | 4216 | 44.665 125.601 120.931 | 1.00 37.85 |
| ATOM | 555 | CA   | LYS | 4216 | 45.860 124.830 121.256 | 1.00 35.62 |
| ATOM | 556 | CB   | LYS | 4216 | 45.914 124.495 122.746 | 1.00 34.81 |
| ATOM | 557 | CG   | LYS | 4216 | 46.538 125.586 123.581 | 1.00 38.79 |
| ATOM | 558 | CD   | LYS | 4216 | 47.005 125.015 124.891 | 1.00 40.33 |
| ATOM | 559 | CE   | LYS | 4216 | 47.926 125.975 125.600 | 1.00 45.99 |
| ATOM | 560 | NZ   | LYS | 4216 | 48.497 125.354 126.833 | 1.00 51.76 |
| ATOM | 561 | C    | LYS | 4216 | 46.084 123.553 120.453 | 1.00 33.87 |
| ATOM | 562 | O    | LYS | 4216 | 47.224 123.124 120.287 | 1.00 31.70 |
| ATOM | 563 | N    | ILE | 4217 | 45.015 122.928 119.974 | 1.00 30.80 |
| ATOM | 564 | CA   | ILE | 4217 | 45.176 121.722 119.172 | 1.00 32.33 |
| ATOM | 565 | CB   | ILE | 4217 | 43.832 120.911 118.957 | 1.00 33.66 |
| ATOM | 566 | CG2  | ILE | 4217 | 43.972 119.927 117.858 | 1.00 31.33 |
| ATOM | 567 | CG1  | ILE | 4217 | 43.383 120.339 120.270 | 1.00 35.35 |
| ATOM | 568 | CD1  | ILE | 4217 | 42.039 119.637 120.184 | 1.00 39.43 |
| ATOM | 569 | C    | ILE | 4217 | 45.708 122.198 117.832 | 1.00 33.62 |
| ATOM | 570 | O    | ILE | 4217 | 46.693 121.669 117.318 | 1.00 31.48 |
| ATOM | 571 | N    | ILE | 4218 | 45.044 123.211 117.281 | 1.00 32.18 |
| ATOM | 572 | CA   | ILE | 4218 | 45.440 123.800 116.010 | 1.00 29.82 |

125

| | | | | | | | | |
|---|---|---|---|---|---|---|---|---|
| ATOM | 573 | CB | ILE | 4218 | 44.623 | 125.056 | 115.707 | 1.00 25.16 |
| ATOM | 574 | CG2 | ILE | 4218 | 45.262 | 125.835 | 114.592 | 1.00 15.90 |
| ATOM | 575 | CG1 | ILE | 4218 | 43.190 | 124.669 | 115.378 | 1.00 25.93 |
| ATOM | 576 | CD1 | ILE | 4218 | 42.283 | 125.848 | 115.174 | 1.00 27.70 |
| ATOM | 577 | C | ILE | 4218 | 46.900 | 124.205 | 116.056 | 1.00 32.59 |
| ATOM | 578 | O | ILE | 4218 | 47.587 | 124.189 | 115.043 | 1.00 36.79 |
| ATOM | 579 | N | GLU | 4219 | 47.374 | 124.560 | 117.239 | 1.00 35.00 |
| ATOM | 580 | CA | GLU | 4219 | 48.748 | 124.990 | 117.382 | 1.00 38.94 |
| ATOM | 581 | CB | GLU | 4219 | 48.879 | 125.875 | 118.618 | 1.00 46.30 |
| ATOM | 582 | CG | GLU | 4219 | 49.851 | 127.024 | 118.440 | 1.00 58.14 |
| ATOM | 583 | CD | GLU | 4219 | 49.619 | 128.139 | 119.444 | 1.00 67.39 |
| ATOM | 584 | OE1 | GLU | 4219 | 50.218 | 129.225 | 119.278 | 1.00 72.57 |
| ATOM | 585 | OE2 | GLU | 4219 | 48.840 | 127.932 | 120.402 | 1.00 73.48 |
| ATOM | 586 | C | GLU | 4219 | 49.697 | 123.811 | 117.463 | 1.00 37.29 |
| ATOM | 587 | O | GLU | 4219 | 50.853 | 123.920 | 117.065 | 1.00 36.67 |
| ATOM | 588 | N | LEU | 4220 | 49.201 | 122.684 | 117.970 | 1.00 38.39 |
| ATOM | 589 | CA | LEU | 4220 | 50.004 | 121.462 | 118.108 | 1.00 36.23 |
| ATOM | 590 | CB | LEU | 4220 | 49.279 | 120.443 | 118.995 | 1.00 35.63 |
| ATOM | 591 | CG | LEU | 4220 | 50.068 | 119.296 | 119.641 | 1.00 35.00 |
| ATOM | 592 | CD1 | LEU | 4220 | 49.079 | 118.350 | 120.317 | 1.00 36.26 |
| ATOM | 593 | CD2 | LEU | 4220 | 50.893 | 118.540 | 118.620 | 1.00 31.56 |
| ATOM | 594 | C | LEU | 4220 | 50.205 | 120.866 | 116.716 | 1.00 34.88 |
| ATOM | 595 | O | LEU | 4220 | 51.315 | 120.478 | 116.341 | 1.00 35.93 |
| ATOM | 596 | N | LEU | 4221 | 49.119 | 120.793 | 115.955 | 1.00 30.59 |
| ATOM | 597 | CA | LEU | 4221 | 49.189 | 120.268 | 114.607 | 1.00 27.66 |
| ATOM | 598 | CB | LEU | 4221 | 47.813 | 120.286 | 113.946 | 1.00 21.88 |
| ATOM | 599 | CG | LEU | 4221 | 46.820 | 119.310 | 114.576 | 1.00 25.44 |
| ATOM | 600 | CD1 | LEU | 4221 | 45.484 | 119.338 | 113.837 | 1.00 25.33 |
| ATOM | 601 | CD2 | LEU | 4221 | 47.411 | 117.916 | 114.526 | 1.00 24.29 |
| ATOM | 602 | C | LEU | 4221 | 50.178 | 121.067 | 113.771 | 1.00 32.90 |
| ATOM | 603 | O | LEU | 4221 | 50.919 | 120.490 | 112.977 | 1.00 39.66 |
| ATOM | 604 | N | ASN | 4222 | 50.207 | 122.387 | 113.936 | 1.00 33.56 |
| ATOM | 605 | CA | ASN | 4222 | 51.156 | 123.177 | 113.158 | 1.00 34.88 |
| ATOM | 606 | CB | ASN | 4222 | 51.050 | 124.680 | 113.463 | 1.00 34.83 |
| ATOM | 607 | CG | ASN | 4222 | 49.693 | 125.264 | 113.127 | 1.00 34.15 |
| ATOM | 608 | OD1 | ASN | 4222 | 49.058 | 124.886 | 112.145 | 1.00 30.54 |
| ATOM | 609 | ND2 | ASN | 4222 | 49.261 | 126.227 | 113.930 | 1.00 40.22 |
| ATOM | 610 | C | ASN | 4222 | 52.579 | 122.713 | 113.472 | 1.00 34.03 |
| ATOM | 611 | O | ASN | 4222 | 53.333 | 122.330 | 112.578 | 1.00 37.86 |
| ATOM | 612 | N | VAL | 4223 | 52.944 | 122.754 | 114.746 | 1.00 30.07 |
| ATOM | 613 | CA | VAL | 4223 | 54.271 | 122.345 | 115.168 | 1.00 28.48 |
| ATOM | 614 | CB | VAL | 4223 | 54.415 | 122.466 | 116.696 | 1.00 26.36 |
| ATOM | 615 | CG1 | VAL | 4223 | 55.794 | 122.016 | 117.137 | 1.00 27.80 |
| ATOM | 616 | CG2 | VAL | 4223 | 54.176 | 123.889 | 117.111 | 1.00 30.05 |
| ATOM | 617 | C | VAL | 4223 | 54.550 | 120.906 | 114.748 | 1.00 30.60 |
| ATOM | 618 | O | VAL | 4223 | 55.689 | 120.559 | 114.430 | 1.00 29.20 |
| ATOM | 619 | N | THR | 4224 | 53.521 | 120.064 | 114.751 | 1.00 28.91 |
| ATOM | 620 | CA | THR | 4224 | 53.717 | 118.673 | 114.357 | 1.00 32.64 |
| ATOM | 621 | CB | THR | 4224 | 52.419 | 117.868 | 114.435 | 1.00 33.32 |
| ATOM | 622 | OG1 | THR | 4224 | 51.887 | 117.954 | 115.758 | 1.00 36.51 |
| ATOM | 623 | CG2 | THR | 4224 | 52.687 | 115.472 | 114.117 | 1.00 33.90 |
| ATOM | 624 | C | THR | 4224 | 54.210 | 118.655 | 112.922 | 1.00 31.57 |
| ATOM | 625 | O | THR | 4224 | 55.116 | 117.905 | 112.577 | 1.00 32.32 |
| ATOM | 626 | N | GLU | 4225 | 53.600 | 119.494 | 112.093 | 1.00 31.14 |
| ATOM | 627 | CA | GLU | 4225 | 53.974 | 119.614 | 110.696 | 1.00 31.18 |
| ATOM | 628 | CB | GLU | 4225 | 53.116 | 120.681 | 110.028 | 1.00 36.51 |
| ATOM | 629 | CG | GLU | 4225 | 53.455 | 120.888 | 108.583 | 1.00 50.34 |
| ATOM | 630 | CD | GLU | 4225 | 53.411 | 119.591 | 107.810 | 1.00 60.77 |
| ATOM | 631 | OE1 | GLU | 4225 | 52.337 | 118.951 | 107.803 | 1.00 62.50 |
| ATOM | 632 | OE2 | GLU | 4225 | 54.448 | 119.214 | 107.216 | 1.00 69.42 |
| ATOM | 633 | C | GLU | 4225 | 55.458 | 119.974 | 110.583 | 1.00 29.76 |
| ATOM | 634 | O | GLU | 4225 | 56.228 | 119.238 | 109.973 | 1.00 30.47 |
| ATOM | 635 | N | LEU | 4226 | 55.860 | 121.100 | 111.168 | 1.00 27.58 |
| ATOM | 636 | CA | LEU | 4226 | 57.264 | 121.515 | 111.138 | 1.00 28.56 |
| ATOM | 637 | CB | LEU | 4226 | 57.521 | 122.691 | 112.080 | 1.00 31.03 |
| ATOM | 638 | CG | LEU | 4226 | 57.167 | 124.120 | 111.697 | 1.00 33.55 |
| ATOM | 639 | CD1 | LEU | 4226 | 57.619 | 125.066 | 112.800 | 1.00 39.71 |
| ATOM | 640 | CD2 | LEU | 4226 | 57.876 | 124.482 | 110.433 | 1.00 31.73 |
| ATOM | 641 | C | LEU | 4226 | 58.200 | 120.393 | 111.560 | 1.00 29.87 |
| ATOM | 642 | O | LEU | 4226 | 59.258 | 120.198 | 110.969 | 1.00 34.20 |

```
ATOM  643  N    THR  4227     57.818 119.677 112.607  1.00 27.74
ATOM  644  CA   THR  4227     58.630 118.587 113.121  1.00 25.52
ATOM  645  CB   THR  4227     58.039 118.052 114.435  1.00 26.99
ATOM  646  OG1  THR  4227     57.812 119.147 115.326  1.00 26.00
ATOM  647  CG2  THR  4227     58.988 117.063 115.092  1.00 17.48
ATOM  648  C    THR  4227     58.672 117.451 112.109  1.00 25.17
ATOM  649  O    THR  4227     59.742 117.019 111.675  1.00 23.44
ATOM  650  N    GLN  4228     57.487 116.984 111.733  1.00 23.92
ATOM  651  CA   GLN  4228     57.346 115.886 110.791  1.00 26.12
ATOM  652  CB   GLN  4228     55.879 115.728 110.399  1.00 19.67
ATOM  653  CG   GLN  4228     55.399 114.299 110.443  1.00 19.87
ATOM  654  CD   GLN  4228     53.915 114.159 110.158  1.00 24.68
ATOM  655  OE1  GLN  4228     53.437 114.529 109.092  1.00 26.90
ATOM  656  NE2  GLN  4228     53.184 113.617 111.113  1.00 22.55
ATOM  657  C    GLN  4228     58.205 116.149 109.570  1.00 25.91
ATOM  658  O    GLN  4228     59.085 115.359 109.241  1.00 26.06
ATOM  659  N    ASN  4229     57.961 117.271 108.908  1.00 27.79
ATOM  660  CA   ASN  4229     58.733 117.625 107.730  1.00 29.44
ATOM  661  CB   ASN  4229     58.373 119.042 107.264  1.00 37.01
ATOM  662  CG   ASN  4229     59.397 119.615 106.286  1.00 45.60
ATOM  663  OD1  ASN  4229     60.534 119.928 106.666  1.00 41.84
ATOM  664  ND2  ASN  4229     59.006 119.737 105.020  1.00 51.47
ATOM  665  C    ASN  4229     60.246 117.510 107.923  1.00 23.90
ATOM  666  O    ASN  4229     60.956 117.171 106.990  1.00 22.56
ATOM  667  N    ALA  4230     60.750 117.799 109.114  1.00 19.65
ATOM  668  CA   ALA  4230     62.190 117.698 109.338  1.00 21.38
ATOM  669  CB   ALA  4230     62.578 118.420 110.613  1.00 23.67
ATOM  670  C    ALA  4230     62.537 116.223 109.448  1.00 23.45
ATOM  671  O    ALA  4230     63.570 115.753 108.964  1.00 20.60
ATOM  672  N    LEU  4231     61.650 115.496 110.104  1.00 24.75
ATOM  673  CA   LEU  4231     61.818 114.076 110.278  1.00 25.02
ATOM  674  CB   LEU  4231     60.646 113.540 111.090  1.00 25.42
ATOM  675  CG   LEU  4231     60.675 112.058 111.407  1.00 25.84
ATOM  676  CD1  LEU  4231     61.973 111.746 112.127  1.00 24.29
ATOM  677  CD2  LEU  4231     59.463 111.682 112.253  1.00 26.07
ATOM  678  C    LEU  4231     61.856 113.421 108.890  1.00 31.15
ATOM  679  O    LEU  4231     62.919 113.004 108.418  1.00 32.01
ATOM  680  N    ILE  4232     60.693 113.367 108.237  1.00 31.34
ATOM  681  CA   ILE  4232     60.544 112.761 106.914  1.00 29.73
ATOM  682  CB   ILE  4232     59.095 112.902 106.397  1.00 26.16
ATOM  683  CG2  ILE  4232     58.961 112.239 105.043  1.00 27.46
ATOM  684  CG1  ILE  4232     58.118 112.231 107.368  1.00 23.94
ATOM  685  CD1  ILE  4232     56.671 112.309 106.926  1.00 16.77
ATOM  686  C    ILE  4232     61.476 113.281 105.817  1.00 34.77
ATOM  687  O    ILE  4232     62.301 112.525 105.292  1.00 39.59
ATOM  688  N    ASN  4233     61.354 114.562 105.471  1.00 36.31
ATOM  689  CA   ASN  4233     62.167 115.149 104.397  1.00 33.23
ATOM  690  CB   ASN  4233     61.552 116.456 103.935  1.00 27.79
ATOM  691  CG   ASN  4233     60.132 116.292 103.502  1.00 30.93
ATOM  692  OD1  ASN  4233     59.802 115.377 102.750  1.00 35.73
ATOM  693  ND2  ASN  4233     59.271 117.187 103.959  1.00 35.50
ATOM  694  C    ASN  4233     63.665 115.379 104.569  1.00 34.17
ATOM  695  O    ASN  4233     64.380 115.435 103.579  1.00 40.81
ATOM  696  N    ASP  4234     64.162 115.537 105.784  1.00 35.33
ATOM  697  CA   ASP  4234     65.592 115.753 105.926  1.00 38.16
ATOM  698  CB   ASP  4234     65.871 117.031 106.722  1.00 42.22
ATOM  699  CG   ASP  4234     67.365 117.272 106.948  1.00 50.98
ATOM  700  OD1  ASP  4234     68.043 116.371 107.493  1.00 55.41
ATOM  701  OD2  ASP  4234     67.866 118.366 106.593  1.00 57.31
ATOM  702  C    ASP  4234     66.278 114.566 106.592  1.00 40.03
ATOM  703  O    ASP  4234     67.278 114.067 106.089  1.00 43.70
ATOM  704  N    GLU  4235     65.750 114.106 107.720  1.00 37.89
ATOM  705  CA   GLU  4235     66.375 112.956 108.409  1.00 36.19
ATOM  706  CB   GLU  4235     65.844 112.861 109.839  1.00 41.28
ATOM  707  CG   GLU  4235     66.309 113.962 110.765  1.00 45.65
ATOM  708  CD   GLU  4235     67.819 113.996 110.916  1.00 51.95
ATOM  709  OE1  GLU  4235     68.400 112.981 111.363  1.00 55.11
ATOM  710  OE2  GLU  4235     68.426 115.040 110.587  1.00 54.63
ATOM  711  C    GLU  4235     66.237 111.646 107.701  1.00 31.92
ATOM  712  O    GLU  4235     67.226 110.941 107.535  1.00 29.05
```

| | | | | | | | | |
|---|---|---|---|---|---|---|---|---|
| ATOM | 713 | N | LEU | 4236 | 65.026 | 111.283 | 107.286 | 1.00 29.07 |
| ATOM | 714 | CA | LEU | 4236 | 64.847 | 110.003 | 106.615 | 1.00 23.14 |
| ATOM | 715 | CB | LEU | 4236 | 63.375 | 109.703 | 106.360 | 1.00 20.01 |
| ATOM | 716 | CG | LEU | 4236 | 62.971 | 108.212 | 106.294 | 1.00 23.50 |
| ATOM | 717 | CD1 | LEU | 4236 | 61.582 | 108.138 | 105.679 | 1.00 23.51 |
| ATOM | 718 | CD2 | LEU | 4236 | 63.939 | 107.412 | 105.461 | 1.00 22.21 |
| ATOM | 719 | C | LEU | 4236 | 65.568 | 110.108 | 105.290 | 1.00 24.11 |
| ATOM | 720 | O | LEU | 4236 | 66.413 | 109.278 | 104.971 | 1.00 26.68 |
| ATOM | 721 | N | VAL | 4237 | 65.244 | 111.141 | 104.518 | 1.00 22.14 |
| ATOM | 722 | CA | VAL | 4237 | 65.885 | 111.335 | 103.223 | 1.00 18.63 |
| ATOM | 723 | CB | VAL | 4237 | 65.429 | 112.643 | 102.580 | 1.00 13.56 |
| ATOM | 724 | CG1 | VAL | 4237 | 66.247 | 112.935 | 101.356 | 1.00 7.56 |
| ATOM | 725 | CG2 | VAL | 4237 | 63.972 | 112.520 | 102.190 | 1.00 13.70 |
| ATOM | 726 | C | VAL | 4237 | 67.406 | 111.304 | 103.326 | 1.00 19.25 |
| ATOM | 727 | O | VAL | 4237 | 68.084 | 110.779 | 102.451 | 1.00 21.33 |
| ATOM | 728 | N | GLU | 4238 | 67.953 | 111.843 | 104.402 | 1.00 21.11 |
| ATOM | 729 | CA | GLU | 4238 | 69.391 | 111.817 | 104.557 | 1.00 23.82 |
| ATOM | 730 | CB | GLU | 4238 | 69.820 | 112.806 | 105.636 | 1.00 28.31 |
| ATOM | 731 | CG | GLU | 4238 | 71.303 | 113.096 | 105.644 | 1.00 42.03 |
| ATOM | 732 | CD | GLU | 4238 | 71.697 | 114.050 | 106.760 | 1.00 53.11 |
| ATOM | 733 | OE1 | GLU | 4238 | 71.666 | 113.661 | 107.955 | 1.00 54.64 |
| ATOM | 734 | OE2 | GLU | 4238 | 72.029 | 115.208 | 106.433 | 1.00 64.50 |
| ATOM | 735 | C | GLU | 4238 | 69.839 | 110.387 | 104.914 | 1.00 23.45 |
| ATOM | 736 | O | GLU | 4238 | 70.827 | 109.886 | 104.378 | 1.00 26.06 |
| ATOM | 737 | N | TRP | 4239 | 69.109 | 109.717 | 105.800 | 1.00 18.69 |
| ATOM | 738 | CA | TRP | 4239 | 69.478 | 108.361 | 106.167 | 1.00 17.31 |
| ATOM | 739 | CB | TRP | 4239 | 68.453 | 107.738 | 107.110 | 1.00 17.97 |
| ATOM | 740 | CG | TRP | 4239 | 68.893 | 106.401 | 107.617 | 1.00 15.86 |
| ATOM | 741 | CD2 | TRP | 4239 | 68.524 | 105.120 | 107.087 | 1.00 14.64 |
| ATOM | 742 | CE2 | TRP | 4239 | 69.271 | 104.152 | 107.789 | 1.00 17.23 |
| ATOM | 743 | CE3 | TRP | 4239 | 67.636 | 104.700 | 106.087 | 1.00 15.89 |
| ATOM | 744 | CD1 | TRP | 4239 | 69.817 | 106.160 | 108.591 | 1.00 12.12 |
| ATOM | 745 | NE1 | TRP | 4239 | 70.050 | 104.815 | 108.699 | 1.00 17.41 |
| ATOM | 746 | CZ2 | TRP | 4239 | 69.157 | 102.779 | 107.520 | 1.00 17.49 |
| ATOM | 747 | CZ3 | TRP | 4239 | 67.524 | 103.338 | 105.821 | 1.00 17.19 |
| ATOM | 748 | CH2 | TRP | 4239 | 68.280 | 102.395 | 106.534 | 1.00 16.55 |
| ATOM | 749 | C | TRP | 4239 | 69.549 | 107.511 | 104.905 | 1.00 22.10 |
| ATOM | 750 | O | TRP | 4239 | 70.454 | 106.684 | 104.739 | 1.00 23.47 |
| ATOM | 751 | N | LYS | 4240 | 68.584 | 107.710 | 104.014 | 1.00 21.51 |
| ATOM | 752 | CA | LYS | 4240 | 68.559 | 106.964 | 102.774 | 1.00 20.13 |
| ATOM | 753 | CB | LYS | 4240 | 67.277 | 107.245 | 102.004 | 1.00 16.93 |
| ATOM | 754 | CG | LYS | 4240 | 66.030 | 106.758 | 102.692 | 1.00 10.86 |
| ATOM | 755 | CD | LYS | 4240 | 64.941 | 106.528 | 101.673 | 1.00 4.21 |
| ATOM | 756 | CE | LYS | 4240 | 63.765 | 105.846 | 102.312 | 1.00 19.29 |
| ATOM | 757 | NZ | LYS | 4240 | 62.833 | 105.261 | 101.318 | 1.00 26.58 |
| ATOM | 758 | C | LYS | 4240 | 69.773 | 107.256 | 101.889 | 1.00 25.62 |
| ATOM | 759 | O | LYS | 4240 | 70.382 | 106.321 | 101.357 | 1.00 26.77 |
| ATOM | 760 | N | ARG | 4241 | 70.138 | 108.527 | 101.718 | 1.00 23.86 |
| ATOM | 761 | CA | ARG | 4241 | 71.308 | 108.818 | 100.892 | 1.00 26.60 |
| ATOM | 762 | CB | ARG | 4241 | 71.628 | 110.318 | 100.853 | 1.00 26.03 |
| ATOM | 763 | CG | ARG | 4241 | 70.579 | 111.101 | 100.158 | 1.00 34.52 |
| ATOM | 764 | CD | ARG | 4241 | 70.440 | 110.849 | 98.678 | 1.00 38.22 |
| ATOM | 765 | NE | ARG | 4241 | 69.300 | 111.534 | 98.063 | 1.00 41.98 |
| ATOM | 766 | CZ | ARG | 4241 | 68.021 | 111.312 | 98.376 | 1.00 45.51 |
| ATOM | 767 | NH1 | ARG | 4241 | 67.695 | 110.419 | 99.309 | 1.00 44.01 |
| ATOM | 768 | NH2 | ARG | 4241 | 67.057 | 111.980 | 97.748 | 1.00 44.45 |
| ATOM | 769 | C | ARG | 4241 | 72.515 | 108.059 | 101.434 | 1.00 29.11 |
| ATOM | 770 | O | ARG | 4241 | 73.260 | 107.440 | 100.673 | 1.00 31.10 |
| ATOM | 771 | N | ARG | 4242 | 72.709 | 108.088 | 102.749 | 1.00 27.92 |
| ATOM | 772 | CA | ARG | 4242 | 73.845 | 107.389 | 103.329 | 1.00 26.83 |
| ATOM | 773 | CB | ARG | 4242 | 73.940 | 107.658 | 104.822 | 1.00 28.49 |
| ATOM | 774 | CG | ARG | 4242 | 74.224 | 109.087 | 105.167 | 1.00 31.61 |
| ATOM | 775 | CD | ARG | 4242 | 74.210 | 109.222 | 106.666 | 1.00 46.69 |
| ATOM | 776 | NE | ARG | 4242 | 74.139 | 110.611 | 107.106 | 1.00 60.12 |
| ATOM | 777 | CZ | ARG | 4242 | 73.779 | 110.976 | 108.334 | 1.00 66.42 |
| ATOM | 778 | NH1 | ARG | 4242 | 73.463 | 110.046 | 109.234 | 1.00 69.02 |
| ATOM | 779 | NH2 | ARG | 4242 | 73.720 | 112.266 | 108.658 | 1.00 68.04 |
| ATOM | 780 | C | ARG | 4242 | 73.765 | 105.891 | 103.082 | 1.00 26.93 |
| ATOM | 781 | O | ARG | 4242 | 74.796 | 105.225 | 102.960 | 1.00 30.81 |
| ATOM | 782 | N | GLN | 4243 | 72.547 | 105.355 | 103.017 | 1.00 23.38 |

128

| | | | | | | | | |
|---|---|---|---|---|---|---|---|---|
| ATOM | 783 | CA | GLN | 4243 | 72.373 | 103.925 | 102.759 | 1.00 17.91 |
| ATOM | 784 | CB | GLN | 4243 | 70.891 | 103.544 | 102.852 | 1.00 6.83 |
| ATOM | 785 | CG | GLN | 4243 | 70.608 | 102.097 | 102.583 | 1.00 4.06 |
| ATOM | 786 | CD | GLN | 4243 | 69.138 | 101.738 | 102.731 | 1.00 10.99 |
| ATOM | 787 | OE1 | GLN | 4243 | 68.264 | 102.365 | 102.141 | 1.00 15.68 |
| ATOM | 788 | NE2 | GLN | 4243 | 68.863 | 100.709 | 103.513 | 1.00 14.12 |
| ATOM | 789 | C | GLN | 4243 | 72.943 | 103.631 | 101.364 | 1.00 18.76 |
| ATOM | 790 | O | GLN | 4243 | 73.749 | 102.711 | 101.195 | 1.00 12.38 |
| ATOM | 791 | N | GLN | 4244 | 72.543 | 104.430 | 100.372 | 1.00 16.93 |
| ATOM | 792 | CA | GLN | 4244 | 73.058 | 104.241 | 99.023 | 1.00 16.61 |
| ATOM | 793 | CB | GLN | 4244 | 72.743 | 105.428 | 98.100 | 1.00 16.76 |
| ATOM | 794 | CG | GLN | 4244 | 71.278 | 105.614 | 97.759 | 1.00 24.00 |
| ATOM | 795 | CD | GLN | 4244 | 71.063 | 106.669 | 96.693 | 1.00 24.92 |
| ATOM | 796 | OE1 | GLN | 4244 | 71.629 | 106.571 | 95.617 | 1.00 30.66 |
| ATOM | 797 | NE2 | GLN | 4244 | 70.236 | 107.673 | 96.983 | 1.00 24.31 |
| ATOM | 798 | C | GLN | 4244 | 74.558 | 104.103 | 99.098 | 1.00 15.57 |
| ATOM | 799 | O | GLN | 4244 | 75.117 | 103.087 | 98.707 | 1.00 21.96 |
| ATOM | 800 | N | SER | 4245 | 75.211 | 105.126 | 99.624 | 1.00 9.97 |
| ATOM | 801 | CA | SER | 4245 | 76.653 | 105.103 | 99.703 | 1.00 9.59 |
| ATOM | 802 | CB | SER | 4245 | 77.155 | 106.383 | 100.332 | 1.00 7.59 |
| ATOM | 803 | OG | SER | 4245 | 78.563 | 106.383 | 100.310 | 1.00 13.51 |
| ATOM | 804 | C | SER | 4245 | 77.221 | 103.913 | 100.458 | 1.00 12.38 |
| ATOM | 805 | O | SER | 4245 | 78.325 | 103.460 | 100.183 | 1.00 10.90 |
| ATOM | 806 | N | ALA | 4246 | 76.472 | 103.399 | 101.417 | 1.00 14.99 |
| ATOM | 807 | CA | ALA | 4246 | 76.957 | 102.262 | 102.181 | 1.00 15.16 |
| ATOM | 808 | CB | ALA | 4246 | 76.041 | 102.006 | 103.361 | 1.00 17.67 |
| ATOM | 809 | C | ALA | 4246 | 77.021 | 101.035 | 101.274 | 1.00 14.92 |
| ATOM | 810 | O | ALA | 4246 | 78.028 | 100.336 | 101.253 | 1.00 18.29 |
| ATOM | 811 | N | CYS | 4247 | 75.946 | 100.788 | 100.525 | 1.00 12.05 |
| ATOM | 812 | CA | CYS | 4247 | 75.871 | 99.657 | 99.610 | 1.00 10.68 |
| ATOM | 813 | CB | CYS | 4247 | 74.588 | 99.718 | 98.776 | 1.00 13.62 |
| ATOM | 814 | SG | CYS | 4247 | 73.043 | 99.509 | 99.704 | 1.00 23.51 |
| ATOM | 815 | C | CYS | 4247 | 77.054 | 99.583 | 98.665 | 1.00 9.59 |
| ATOM | 816 | O | CYS | 4247 | 77.477 | 98.494 | 98.283 | 1.00 14.75 |
| ATOM | 817 | N | ILE | 4248 | 77.594 | 100.725 | 98.262 | 1.00 7.77 |
| ATOM | 818 | CA | ILE | 4248 | 78.730 | 100.670 | 97.355 | 1.00 9.41 |
| ATOM | 819 | CB | ILE | 4248 | 78.609 | 101.691 | 96.195 | 1.00 8.01 |
| ATOM | 820 | CG2 | ILE | 4248 | 77.494 | 101.266 | 95.237 | 1.00 5.66 |
| ATOM | 821 | CG1 | ILE | 4248 | 78.352 | 103.092 | 96.748 | 1.00 8.56 |
| ATOM | 822 | CD1 | ILE | 4248 | 78.201 | 104.119 | 95.695 | 1.00 6.71 |
| ATOM | 823 | C | ILE | 4248 | 80.072 | 100.827 | 98.061 | 1.00 11.69 |
| ATOM | 824 | O | ILE | 4248 | 81.051 | 101.243 | 97.456 | 1.00 15.86 |
| ATOM | 825 | N | GLY | 4249 | 80.110 | 100.458 | 99.349 | 1.00 9.77 |
| ATOM | 826 | CA | GLY | 4249 | 81.356 | 100.538 | 100.091 | 1.00 4.22 |
| ATOM | 827 | C | GLY | 4249 | 81.788 | 101.788 | 100.812 | 1.00 9.80 |
| ATOM | 828 | O | GLY | 4249 | 82.944 | 101.870 | 101.221 | 1.00 13.59 |
| ATOM | 829 | N | GLY | 4250 | 80.893 | 102.755 | 100.979 | 1.00 11.42 |
| ATOM | 830 | CA | GLY | 4250 | 81.256 | 103.979 | 101.675 | 1.00 12.90 |
| ATOM | 831 | C | GLY | 4250 | 81.129 | 103.834 | 103.181 | 1.00 14.31 |
| ATOM | 832 | O | GLY | 4250 | 81.204 | 102.718 | 103.701 | 1.00 13.11 |
| ATOM | 833 | N | PRO | 4251 | 80.930 | 104.938 | 103.920 | 1.00 15.35 |
| ATOM | 834 | CD | PRO | 4251 | 80.785 | 106.341 | 103.506 | 1.00 9.56 |
| ATOM | 835 | CA | PRO | 4251 | 80.801 | 104.845 | 105.374 | 1.00 17.19 |
| ATOM | 836 | CB | PRO | 4251 | 80.633 | 106.300 | 105.782 | 1.00 10.14 |
| ATOM | 837 | CG | PRO | 4251 | 81.355 | 107.032 | 104.690 | 1.00 3.82 |
| ATOM | 838 | C | PRO | 4251 | 79.593 | 103.985 | 105.748 | 1.00 23.21 |
| ATOM | 839 | O | PRO | 4251 | 78.642 | 103.875 | 104.978 | 1.00 28.63 |
| ATOM | 840 | N | PRO | 4252 | 79.615 | 103.366 | 106.939 | 1.00 28.61 |
| ATOM | 841 | CD | PRO | 4252 | 80.696 | 103.412 | 107.941 | 1.00 34.98 |
| ATOM | 842 | CA | PRO | 4252 | 78.535 | 102.508 | 107.427 | 1.00 32.69 |
| ATOM | 843 | CB | PRO | 4252 | 79.203 | 101.789 | 108.583 | 1.00 32.18 |
| ATOM | 844 | CG | PRO | 4252 | 79.983 | 102.927 | 109.193 | 1.00 34.05 |
| ATOM | 845 | C | PRO | 4252 | 77.313 | 103.303 | 107.883 | 1.00 36.23 |
| ATOM | 846 | O | PRO | 4252 | 77.444 | 104.348 | 108.533 | 1.00 35.51 |
| ATOM | 847 | N | ASN | 4253 | 76.127 | 102.819 | 107.537 | 1.00 36.93 |
| ATOM | 848 | CA | ASN | 4253 | 74.897 | 103.484 | 107.932 | 1.00 40.43 |
| ATOM | 849 | CB | ASN | 4253 | 73.675 | 102.716 | 107.423 | 1.00 46.95 |
| ATOM | 850 | CG | ASN | 4253 | 72.891 | 103.482 | 106.380 | 1.00 58.55 |
| ATOM | 851 | OD1 | ASN | 4253 | 72.658 | 104.696 | 106.511 | 1.00 58.85 |
| ATOM | 852 | ND2 | ASN | 4253 | 72.443 | 102.769 | 105.344 | 1.00 61.95 |

| | | | | | | | | |
|---|---|---|---|---|---|---|---|---|
| ATOM | 853 | C | ASN | 4253 | 74.793 | 103.561 | 109.449 | 1.00 40.82 |
| ATOM | 854 | O | ASN | 4253 | 75.258 | 102.670 | 110.169 | 1.00 39.37 |
| ATOM | 855 | N | ALA | 4254 | 74.177 | 104.629 | 109.935 | 1.00 39.77 |
| ATOM | 856 | CA | ALA | 4254 | 73.968 | 104.710 | 111.359 | 1.00 35.09 |
| ATOM | 857 | CB | ALA | 4254 | 73.694 | 106.229 | 111.698 | 1.00 38.63 |
| ATOM | 858 | C | ALA | 4254 | 72.745 | 103.923 | 111.656 | 1.00 32.69 |
| ATOM | 859 | O | ALA | 4254 | 71.955 | 103.632 | 110.771 | 1.00 28.43 |
| ATOM | 860 | N | CYS | 4255 | 72.603 | 103.504 | 112.901 | 1.00 33.12 |
| ATOM | 861 | CA | CYS | 4255 | 71.476 | 102.687 | 113.305 | 1.00 34.09 |
| ATOM | 862 | CB | CYS | 4255 | 71.682 | 102.243 | 114.752 | 1.00 38.05 |
| ATOM | 863 | SG | CYS | 4255 | 70.307 | 101.346 | 115.477 | 1.00 44.25 |
| ATOM | 864 | C | CYS | 4255 | 70.203 | 103.516 | 113.189 | 1.00 34.22 |
| ATOM | 865 | O | CYS | 4255 | 70.223 | 104.718 | 113.442 | 1.00 38.32 |
| ATOM | 866 | N | LEU | 4256 | 69.100 | 102.876 | 112.813 | 1.00 31.19 |
| ATOM | 867 | CA | LEU | 4256 | 67.819 | 103.561 | 112.687 | 1.00 30.86 |
| ATOM | 868 | CB | LEU | 4256 | 66.875 | 102.784 | 111.771 | 1.00 31.13 |
| ATOM | 869 | CG | LEU | 4256 | 66.948 | 102.823 | 110.248 | 1.00 30.14 |
| ATOM | 870 | CD1 | LEU | 4256 | 65.830 | 101.963 | 109.704 | 1.00 23.16 |
| ATOM | 871 | CD2 | LEU | 4256 | 66.782 | 104.241 | 109.750 | 1.00 27.45 |
| ATOM | 872 | C | LEU | 4256 | 67.075 | 103.790 | 114.003 | 1.00 34.88 |
| ATOM | 873 | O | LEU | 4256 | 65.926 | 104.228 | 113.980 | 1.00 37.02 |
| ATOM | 874 | N | ASP | 4257 | 67.688 | 103.488 | 115.146 | 1.00 37.67 |
| ATOM | 875 | CA | ASP | 4257 | 66.991 | 103.690 | 116.414 | 1.00 35.09 |
| ATOM | 876 | CB | ASP | 4257 | 67.773 | 103.119 | 117.592 | 1.00 37.14 |
| ATOM | 877 | CG | ASP | 4257 | 67.764 | 101.610 | 117.612 | 1.00 47.17 |
| ATOM | 878 | OD1 | ASP | 4257 | 66.708 | 101.013 | 117.305 | 1.00 46.78 |
| ATOM | 879 | OD2 | ASP | 4257 | 68.803 | 101.016 | 117.961 | 1.00 51.54 |
| ATOM | 880 | C | ASP | 4257 | 66.695 | 105.146 | 116.670 | 1.00 32.00 |
| ATOM | 881 | O | ASP | 4257 | 65.579 | 105.500 | 117.058 | 1.00 30.45 |
| ATOM | 882 | N | GLN | 4258 | 67.686 | 105.998 | 116.453 | 1.00 28.83 |
| ATOM | 883 | CA | GLN | 4258 | 67.463 | 107.411 | 116.670 | 1.00 28.39 |
| ATOM | 884 | CB | GLN | 4258 | 68.645 | 108.218 | 116.153 | 1.00 30.08 |
| ATOM | 885 | CG | GLN | 4258 | 68.531 | 109.695 | 116.436 | 1.00 39.12 |
| ATOM | 886 | CD | GLN | 4258 | 69.730 | 110.470 | 115.935 | 1.00 46.31 |
| ATOM | 887 | OE1 | GLN | 4258 | 70.041 | 110.458 | 114.738 | 1.00 47.18 |
| ATOM | 888 | NE2 | GLN | 4258 | 70.416 | 111.153 | 116.851 | 1.00 48.63 |
| ATOM | 889 | C | GLN | 4258 | 66.178 | 107.792 | 115.928 | 1.00 28.43 |
| ATOM | 890 | O | GLN | 4258 | 65.233 | 108.310 | 116.535 | 1.00 30.75 |
| ATOM | 891 | N | LEU | 4259 | 66.142 | 107.504 | 114.625 | 1.00 23.97 |
| ATOM | 892 | CA | LEU | 4259 | 64.979 | 107.796 | 113.786 | 1.00 17.77 |
| ATOM | 893 | CB | LEU | 4259 | 65.186 | 107.269 | 112.365 | 1.00 16.83 |
| ATOM | 894 | CG | LEU | 4259 | 65.861 | 108.181 | 111.357 | 1.00 16.56 |
| ATOM | 895 | CD1 | LEU | 4259 | 66.011 | 107.462 | 110.036 | 1.00 18.10 |
| ATOM | 896 | CD2 | LEU | 4259 | 65.016 | 109.425 | 111.183 | 1.00 12.88 |
| ATOM | 897 | C | LEU | 4259 | 63.676 | 107.219 | 114.307 | 1.00 16.86 |
| ATOM | 898 | O | LEU | 4259 | 62.643 | 107.893 | 114.326 | 1.00 15.26 |
| ATOM | 899 | N | GLN | 4260 | 63.721 | 105.958 | 114.704 | 1.00 16.83 |
| ATOM | 900 | CA | GLN | 4260 | 62.537 | 105.293 | 115.201 | 1.00 18.12 |
| ATOM | 901 | CB | GLN | 4260 | 62.868 | 103.860 | 115.557 | 1.00 14.58 |
| ATOM | 902 | CG | GLN | 4260 | 61.681 | 103.037 | 115.897 | 1.00 21.89 |
| ATOM | 903 | CD | GLN | 4260 | 62.044 | 101.526 | 115.918 | 1.00 31.24 |
| ATOM | 904 | OE1 | GLN | 4260 | 62.930 | 101.171 | 116.672 | 1.00 35.38 |
| ATOM | 905 | NE2 | GLN | 4260 | 61.377 | 100.793 | 115.081 | 1.00 34.50 |
| ATOM | 906 | C | GLN | 4260 | 61.966 | 106.009 | 116.412 | 1.00 21.13 |
| ATOM | 907 | O | GLN | 4260 | 60.746 | 106.139 | 116.553 | 1.00 19.79 |
| ATOM | 908 | N | ASN | 4261 | 62.835 | 106.496 | 117.285 | 1.00 21.58 |
| ATOM | 909 | CA | ASN | 4261 | 62.326 | 107.178 | 118.455 | 1.00 26.76 |
| ATOM | 910 | CB | ASN | 4261 | 63.454 | 107.601 | 119.377 | 1.00 34.20 |
| ATOM | 911 | CG | ASN | 4261 | 62.933 | 108.101 | 120.696 | 1.00 37.70 |
| ATOM | 912 | OD1 | ASN | 4261 | 62.160 | 107.401 | 121.361 | 1.00 41.37 |
| ATOM | 913 | ND2 | ASN | 4261 | 63.334 | 109.308 | 121.086 | 1.00 40.06 |
| ATOM | 914 | C | ASN | 4261 | 61.507 | 108.399 | 118.068 | 1.00 25.98 |
| ATOM | 915 | O | ASN | 4261 | 60.372 | 108.566 | 118.506 | 1.00 23.66 |
| ATOM | 916 | N | TRP | 4262 | 62.091 | 109.263 | 117.248 | 1.00 28.58 |
| ATOM | 917 | CA | TRP | 4262 | 61.381 | 110.448 | 116.804 | 1.00 28.27 |
| ATOM | 918 | CB | TRP | 4262 | 62.235 | 111.215 | 115.796 | 1.00 25.55 |
| ATOM | 919 | CG | TRP | 4262 | 63.495 | 111.675 | 116.415 | 1.00 28.40 |
| ATOM | 920 | CD2 | TRP | 4262 | 64.680 | 112.120 | 115.748 | 1.00 34.05 |
| ATOM | 921 | CE2 | TRP | 4262 | 65.585 | 112.546 | 116.743 | 1.00 35.88 |
| ATOM | 922 | CE3 | TRP | 4262 | 65.069 | 112.176 | 114.410 | 1.00 38.07 |

130

| ATOM | 923 | CD1 | TRP | 4262 | 63.721 | 111.857 | 117.748 | 1.00 | 35.97 |
|------|-----|-----|-----|------|--------|---------|---------|------|-------|
| ATOM | 924 | NE1 | TRP | 4262 | 64.973 | 112.381 | 117.955 | 1.00 | 37.26 |
| ATOM | 925 | CZ2 | TRP | 4262 | 66.850 | 113.042 | 116.439 | 1.00 | 32.17 |
| ATOM | 926 | CZ3 | TRP | 4262 | 66.331 | 112.669 | 114.109 | 1.00 | 42.33 |
| ATOM | 927 | CH2 | TRP | 4262 | 67.206 | 113.094 | 115.122 | 1.00 | 34.45 |
| ATOM | 928 | C | TRP | 4262 | 60.029 | 110.062 | 116.207 | 1.00 | 27.63 |
| ATOM | 929 | O | TRP | 4262 | 58.980 | 110.521 | 116.671 | 1.00 | 31.14 |
| ATOM | 930 | N | PHE | 4263 | 60.052 | 109.201 | 115.196 | 1.00 | 23.56 |
| ATOM | 931 | CA | PHE | 4263 | 58.823 | 108.760 | 114.566 | 1.00 | 19.80 |
| ATOM | 932 | CB | PHE | 4263 | 59.097 | 107.648 | 113.547 | 1.00 | 19.87 |
| ATOM | 933 | CG | PHE | 4263 | 59.390 | 108.143 | 112.155 | 1.00 | 18.61 |
| ATOM | 934 | CD1 | PHE | 4263 | 60.654 | 108.595 | 111.804 | 1.00 | 18.39 |
| ATOM | 935 | CD2 | PHE | 4263 | 58.384 | 108.160 | 111.194 | 1.00 | 13.65 |
| ATOM | 936 | CE1 | PHE | 4263 | 60.911 | 109.057 | 110.511 | 1.00 | 19.90 |
| ATOM | 937 | CE2 | PHE | 4263 | 58.626 | 108.619 | 109.904 | 1.00 | 13.16 |
| ATOM | 938 | CZ | PHE | 4263 | 59.891 | 109.068 | 109.560 | 1.00 | 19.24 |
| ATOM | 939 | C | PHE | 4263 | 57.736 | 108.284 | 115.533 | 1.00 | 20.14 |
| ATOM | 940 | O | PHE | 4263 | 56.658 | 108.875 | 115.572 | 1.00 | 17.90 |
| ATOM | 941 | N | THR | 4264 | 57.994 | 107.241 | 116.325 | 1.00 | 19.21 |
| ATOM | 942 | CA | THR | 4264 | 56.924 | 106.754 | 117.207 | 1.00 | 19.63 |
| ATOM | 943 | CB | THR | 4264 | 57.314 | 105.452 | 117.993 | 1.00 | 17.63 |
| ATOM | 944 | OG1 | THR | 4264 | 57.571 | 105.769 | 119.357 | 1.00 | 26.32 |
| ATOM | 945 | CG2 | THR | 4264 | 58.535 | 104.788 | 117.396 | 1.00 | 9.38 |
| ATOM | 946 | C | THR | 4264 | 56.419 | 107.809 | 118.194 | 1.00 | 16.21 |
| ATOM | 947 | O | THR | 4264 | 55.230 | 107.881 | 118.479 | 1.00 | 15.01 |
| ATOM | 948 | N | ILE | 4265 | 57.312 | 108.641 | 118.700 | 1.00 | 14.05 |
| ATOM | 949 | CA | ILE | 4265 | 56.906 | 109.670 | 119.640 | 1.00 | 20.91 |
| ATOM | 950 | CB | ILE | 4265 | 58.105 | 110.480 | 120.114 | 1.00 | 24.10 |
| ATOM | 951 | CG2 | ILE | 4265 | 57.632 | 111.713 | 120.862 | 1.00 | 22.40 |
| ATOM | 952 | CG1 | ILE | 4265 | 59.017 | 109.590 | 120.956 | 1.00 | 27.02 |
| ATOM | 953 | CD1 | ILE | 4265 | 60.328 | 110.256 | 121.320 | 1.00 | 36.93 |
| ATOM | 954 | C | ILE | 4265 | 55.897 | 110.634 | 119.029 | 1.00 | 22.62 |
| ATOM | 955 | O | ILE | 4265 | 54.963 | 111.083 | 119.704 | 1.00 | 24.37 |
| ATOM | 956 | N | VAL | 4266 | 56.097 | 110.977 | 117.761 | 1.00 | 22.40 |
| ATOM | 957 | CA | VAL | 4266 | 55.174 | 111.882 | 117.105 | 1.00 | 23.32 |
| ATOM | 958 | CB | VAL | 4266 | 55.860 | 112.606 | 115.917 | 1.00 | 20.75 |
| ATOM | 959 | CG1 | VAL | 4266 | 56.390 | 111.602 | 114.944 | 1.00 | 28.47 |
| ATOM | 960 | CG2 | VAL | 4266 | 54.882 | 113.537 | 115.223 | 1.00 | 21.30 |
| ATOM | 961 | C | VAL | 4266 | 53.977 | 111.016 | 116.642 | 1.00 | 22.96 |
| ATOM | 962 | O | VAL | 4266 | 52.855 | 111.542 | 116.527 | 1.00 | 25.37 |
| ATOM | 963 | N | ALA | 4267 | 54.220 | 109.762 | 116.411 | 1.00 | 21.40 |
| ATOM | 964 | CA | ALA | 4267 | 53.166 | 108.855 | 115.977 | 1.00 | 22.46 |
| ATOM | 965 | CB | ALA | 4267 | 53.774 | 107.511 | 115.577 | 1.00 | 24.76 |
| ATOM | 966 | C | ALA | 4267 | 52.139 | 108.661 | 117.096 | 1.00 | 24.77 |
| ATOM | 967 | O | ALA | 4267 | 50.941 | 108.506 | 116.848 | 1.00 | 24.94 |
| ATOM | 968 | N | GLU | 4268 | 52.618 | 108.665 | 118.333 | 1.00 | 29.65 |
| ATOM | 969 | CA | GLU | 4268 | 51.744 | 108.492 | 119.490 | 1.00 | 32.38 |
| ATOM | 970 | CB | GLU | 4268 | 52.579 | 108.070 | 120.701 | 1.00 | 31.97 |
| ATOM | 971 | CG | GLU | 4268 | 53.391 | 106.809 | 120.451 | 1.00 | 36.14 |
| ATOM | 972 | CD | GLU | 4268 | 54.290 | 106.435 | 121.619 | 1.00 | 40.44 |
| ATOM | 973 | OE1 | GLU | 4268 | 55.009 | 107.320 | 122.133 | 1.00 | 44.50 |
| ATOM | 974 | OE2 | GLU | 4268 | 54.297 | 105.251 | 122.011 | 1.00 | 42.27 |
| ATOM | 975 | C | GLU | 4268 | 50.970 | 109.794 | 119.778 | 1.00 | 32.22 |
| ATOM | 976 | O | GLU | 4268 | 49.796 | 109.768 | 120.162 | 1.00 | 33.27 |
| ATOM | 977 | N | SER | 4269 | 51.625 | 110.931 | 119.580 | 1.00 | 27.06 |
| ATOM | 978 | CA | SER | 4269 | 50.967 | 112.203 | 119.799 | 1.00 | 24.86 |
| ATOM | 979 | CB | SER | 4269 | 51.948 | 113.350 | 119.602 | 1.00 | 27.07 |
| ATOM | 980 | OG | SER | 4269 | 52.963 | 113.289 | 120.586 | 1.00 | 35.50 |
| ATOM | 981 | C | SER | 4269 | 49.781 | 112.365 | 118.866 | 1.00 | 23.07 |
| ATOM | 982 | O | SER | 4269 | 48.712 | 112.766 | 119.294 | 1.00 | 27.29 |
| ATOM | 983 | N | LEU | 4270 | 49.949 | 112.067 | 117.587 | 1.00 | 26.85 |
| ATOM | 984 | CA | LEU | 4270 | 48.814 | 112.206 | 116.692 | 1.00 | 28.53 |
| ATOM | 985 | CB | LEU | 4270 | 49.218 | 111.913 | 115.232 | 1.00 | 32.73 |
| ATOM | 986 | CG | LEU | 4270 | 49.865 | 113.171 | 114.504 | 1.00 | 31.19 |
| ATOM | 987 | CD1 | LEU | 4270 | 51.119 | 113.621 | 115.209 | 1.00 | 36.64 |
| ATOM | 988 | CD2 | LEU | 4270 | 50.197 | 112.743 | 113.105 | 1.00 | 36.90 |
| ATOM | 989 | C | LEU | 4270 | 47.722 | 111.227 | 117.089 | 1.00 | 27.53 |
| ATOM | 990 | O | LEU | 4270 | 46.546 | 111.583 | 117.076 | 1.00 | 26.35 |
| ATOM | 991 | N | GLN | 4271 | 48.088 | 110.000 | 117.449 | 1.00 | 28.39 |
| ATOM | 992 | CA | GLN | 4271 | 47.056 | 109.050 | 117.851 | 1.00 | 34.57 |

131

| | | | | | | | | |
|---|---|---|---|---|---|---|---|---|
| ATOM | 993 | CB | GLN | 4271 | 47.640 | 107.694 | 118.259 | 1.00 39.19 |
| ATOM | 994 | CG | GLN | 4271 | 48.185 | 106.862 | 117.124 | 1.00 43.77 |
| ATOM | 995 | CD | GLN | 4271 | 48.526 | 105.458 | 117.576 | 1.00 48.50 |
| ATOM | 996 | OE1 | GLN | 4271 | 49.293 | 105.269 | 118.521 | 1.00 54.27 |
| ATOM | 997 | NE2 | GLN | 4271 | 47.960 | 104.461 | 116.901 | 1.00 46.44 |
| ATOM | 998 | C | GLN | 4271 | 46.291 | 109.622 | 119.031 | 1.00 32.21 |
| ATOM | 999 | O | GLN | 4271 | 45.092 | 109.391 | 119.184 | 1.00 28.44 |
| ATOM | 1000 | N | GLN | 4272 | 46.998 | 110.380 | 119.857 | 1.00 32.40 |
| ATOM | 1001 | CA | GLN | 4272 | 46.402 | 110.976 | 121.036 | 1.00 32.65 |
| ATOM | 1002 | CB | GLN | 4272 | 47.508 | 111.488 | 121.955 | 1.00 34.39 |
| ATOM | 1003 | CG | GLN | 4272 | 47.120 | 111.529 | 123.411 | 1.00 42.31 |
| ATOM | 1004 | CD | GLN | 4272 | 48.291 | 111.867 | 124.312 | 1.00 49.15 |
| ATOM | 1005 | OE1 | GLN | 4272 | 49.335 | 111.201 | 124.283 | 1.00 44.87 |
| ATOM | 1006 | NE2 | GLN | 4272 | 48.122 | 112.903 | 125.131 | 1.00 56.41 |
| ATOM | 1007 | C | GLN | 4272 | 45.441 | 112.102 | 120.641 | 1.00 31.95 |
| ATOM | 1008 | O | GLN | 4272 | 44.271 | 112.090 | 121.027 | 1.00 32.84 |
| ATOM | 1009 | N | VAL | 4273 | 45.923 | 113.068 | 119.865 | 1.00 28.72 |
| ATOM | 1010 | CA | VAL | 4273 | 45.071 | 114.170 | 119.430 | 1.00 29.08 |
| ATOM | 1011 | CB | VAL | 4273 | 45.739 | 115.001 | 118.323 | 1.00 20.32 |
| ATOM | 1012 | CG1 | VAL | 4273 | 44.778 | 116.038 | 117.804 | 1.00 10.59 |
| ATOM | 1013 | CG2 | VAL | 4273 | 46.973 | 115.673 | 118.863 | 1.00 21.82 |
| ATOM | 1014 | C | VAL | 4273 | 43.754 | 113.627 | 118.889 | 1.00 34.63 |
| ATOM | 1015 | O | VAL | 4273 | 42.695 | 114.242 | 119.039 | 1.00 35.61 |
| ATOM | 1016 | N | ARG | 4274 | 43.829 | 112.455 | 118.272 | 1.00 39.11 |
| ATOM | 1017 | CA | ARG | 4274 | 42.658 | 111.821 | 117.687 | 1.00 42.58 |
| ATOM | 1018 | CB | ARG | 4274 | 43.081 | 110.545 | 116.965 | 1.00 46.56 |
| ATOM | 1019 | CG | ARG | 4274 | 42.100 | 110.067 | 115.935 | 1.00 55.63 |
| ATOM | 1020 | CD | ARG | 4274 | 42.609 | 108.806 | 115.278 | 1.00 65.50 |
| ATOM | 1021 | NE | ARG | 4274 | 41.663 | 108.311 | 114.286 | 1.00 72.14 |
| ATOM | 1022 | CZ | ARG | 4274 | 41.610 | 107.048 | 113.882 | 1.00 73.62 |
| ATOM | 1023 | NH1 | ARG | 4274 | 42.453 | 106.159 | 114.392 | 1.00 74.54 |
| ATOM | 1024 | NH2 | ARG | 4274 | 40.708 | 106.672 | 112.984 | 1.00 73.76 |
| ATOM | 1025 | C | ARG | 4274 | 41.637 | 111.512 | 118.773 | 1.00 42.27 |
| ATOM | 1026 | O | ARG | 4274 | 40.450 | 111.770 | 118.598 | 1.00 37.56 |
| ATOM | 1027 | N | GLN | 4275 | 42.119 | 110.972 | 119.897 | 1.00 46.69 |
| ATOM | 1028 | CA | GLN | 4275 | 41.280 | 110.623 | 121.053 | 1.00 45.79 |
| ATOM | 1029 | CB | GLN | 4275 | 42.112 | 109.952 | 122.149 | 1.00 48.14 |
| ATOM | 1030 | CG | GLN | 4275 | 43.044 | 108.866 | 121.663 | 1.00 57.45 |
| ATOM | 1031 | CD | GLN | 4275 | 42.321 | 107.745 | 120.952 | 1.00 64.73 |
| ATOM | 1032 | OE1 | GLN | 4275 | 41.583 | 107.975 | 119.985 | 1.00 66.02 |
| ATOM | 1033 | NE2 | GLN | 4275 | 42.535 | 106.516 | 121.420 | 1.00 67.93 |
| ATOM | 1034 | C | GLN | 4275 | 40.708 | 111.912 | 121.618 | 1.00 44.45 |
| ATOM | 1035 | O | GLN | 4275 | 39.497 | 112.054 | 121.777 | 1.00 45.72 |
| ATOM | 1036 | N | GLN | 4276 | 41.601 | 112.846 | 121.934 | 1.00 42.91 |
| ATOM | 1037 | CA | GLN | 4276 | 41.200 | 114.138 | 122.467 | 1.00 42.79 |
| ATOM | 1038 | CB | GLN | 4276 | 42.409 | 115.069 | 122.518 | 1.00 44.87 |
| ATOM | 1039 | CG | GLN | 4276 | 43.505 | 114.538 | 123.423 | 1.00 50.88 |
| ATOM | 1040 | CD | GLN | 4276 | 44.818 | 115.271 | 123.249 | 1.00 56.17 |
| ATOM | 1041 | OE1 | GLN | 4276 | 45.362 | 115.334 | 122.146 | 1.00 56.88 |
| ATOM | 1042 | NE2 | GLN | 4276 | 45.344 | 115.820 | 124.342 | 1.00 58.75 |
| ATOM | 1043 | C | GLN | 4276 | 40.115 | 114.701 | 121.563 | 1.00 40.96 |
| ATOM | 1044 | O | GLN | 4276 | 39.169 | 115.331 | 122.030 | 1.00 36.31 |
| ATOM | 1045 | N | LEU | 4277 | 40.245 | 114.451 | 120.263 | 1.00 42.71 |
| ATOM | 1046 | CA | LEU | 4277 | 39.247 | 114.917 | 119.311 | 1.00 44.26 |
| ATOM | 1047 | CB | LEU | 4277 | 39.757 | 114.775 | 117.877 | 1.00 43.55 |
| ATOM | 1048 | CG | LEU | 4277 | 40.689 | 115.913 | 117.447 | 1.00 43.77 |
| ATOM | 1049 | CD1 | LEU | 4277 | 41.258 | 115.651 | 116.057 | 1.00 44.35 |
| ATOM | 1050 | CD2 | LEU | 4277 | 39.905 | 117.216 | 117.476 | 1.00 39.07 |
| ATOM | 1051 | C | LEU | 4277 | 37.926 | 114.182 | 119.484 | 1.00 43.83 |
| ATOM | 1052 | O | LEU | 4277 | 36.860 | 114.776 | 119.301 | 1.00 43.53 |
| ATOM | 1053 | N | LYS | 4278 | 37.994 | 112.898 | 119.836 | 1.00 43.08 |
| ATOM | 1054 | CA | LYS | 4278 | 36.787 | 112.105 | 120.067 | 1.00 44.18 |
| ATOM | 1055 | CB | LYS | 4278 | 37.125 | 110.625 | 120.261 | 1.00 48.32 |
| ATOM | 1056 | CG | LYS | 4278 | 37.738 | 109.927 | 119.056 | 1.00 55.31 |
| ATOM | 1057 | CD | LYS | 4278 | 38.023 | 108.455 | 119.372 | 1.00 59.91 |
| ATOM | 1058 | CE | LYS | 4278 | 38.650 | 107.725 | 118.191 | 1.00 63.40 |
| ATOM | 1059 | NZ | LYS | 4278 | 38.923 | 106.296 | 118.512 | 1.00 64.87 |
| ATOM | 1060 | C | LYS | 4278 | 36.101 | 112.630 | 121.330 | 1.00 42.39 |
| ATOM | 1061 | O | LYS | 4278 | 34.877 | 112.766 | 121.368 | 1.00 39.17 |
| ATOM | 1062 | N | LYS | 4279 | 36.898 | 112.924 | 122.358 | 1.00 39.67 |

```
ATOM  1063  CA   LYS  4279      36.364 113.451 123.610  1.00 38.21
ATOM  1064  CB   LYS  4279      37.477 113.716 124.629  1.00 36.85
ATOM  1065  CG   LYS  4279      38.122 112.475 125.215  1.00 41.29
ATOM  1066  CD   LYS  4279      39.035 112.857 126.378  1.00 48.66
ATOM  1067  CE   LYS  4279      39.588 111.640 127.127  1.00 48.48
ATOM  1068  NZ   LYS  4279      40.305 112.028 128.395  1.00 45.47
ATOM  1069  C    LYS  4279      35.604 114.745 123.364  1.00 37.99
ATOM  1070  O    LYS  4279      34.478 114.908 123.839  1.00 39.89
ATOM  1071  N    LEU  4280      36.217 115.668 122.628  1.00 36.65
ATOM  1072  CA   LEU  4280      35.560 116.934 122.344  1.00 37.27
ATOM  1073  CB   LEU  4280      36.429 117.824 121.462  1.00 32.83
ATOM  1074  CG   LEU  4280      37.680 118.400 122.122  1.00 32.26
ATOM  1075  CD1  LEU  4280      38.306 119.438 121.208  1.00 32.06
ATOM  1076  CD2  LEU  4280      37.312 119.051 123.426  1.00 27.52
ATOM  1077  C    LEU  4280      34.214 116.724 121.680  1.00 39.68
ATOM  1078  O    LEU  4280      33.234 117.365 122.040  1.00 39.84
ATOM  1079  N    GLU  4281      34.147 115.830 120.705  1.00 44.46
ATOM  1080  CA   GLU  4281      32.866 115.611 120.072  1.00 50.60
ATOM  1081  CB   GLU  4281      32.990 114.640 118.889  1.00 51.66
ATOM  1082  CG   GLU  4281      33.699 115.276 117.689  1.00 58.50
ATOM  1083  CD   GLU  4281      33.557 114.480 116.401  1.00 61.34
ATOM  1084  OE1  GLU  4281      32.405 114.253 115.972  1.00 62.78
ATOM  1085  OE2  GLU  4281      34.593 114.093 115.811  1.00 61.12
ATOM  1086  C    GLU  4281      31.874 115.113 121.114  1.00 52.45
ATOM  1087  O    GLU  4281      30.705 115.499 121.104  1.00 50.47
ATOM  1088  N    GLU  4282      32.347 114.285 122.040  1.00 57.39
ATOM  1089  CA   GLU  4282      31.466 113.769 123.080  1.00 59.19
ATOM  1090  CB   GLU  4282      32.212 112.786 123.999  1.00 61.86
ATOM  1091  CG   GLU  4282      32.548 111.439 123.323  1.00 69.91
ATOM  1092  CD   GLU  4282      33.182 110.411 124.269  1.00 71.52
ATOM  1093  OE1  GLU  4282      32.556 110.072 125.298  1.00 71.14
ATOM  1094  OE2  GLU  4282      34.302 109.933 123.977  1.00 70.65
ATOM  1095  C    GLU  4282      30.843 114.900 123.894  1.00 57.33
ATOM  1096  O    GLU  4282      29.708 114.776 124.355  1.00 57.47
ATOM  1097  N    LEU  4283      31.568 116.007 124.053  1.00 54.00
ATOM  1098  CA   LEU  4283      31.044 117.135 124.811  1.00 51.80
ATOM  1099  CB   LEU  4283      32.142 118.119 125.211  1.00 49.82
ATOM  1100  CG   LEU  4283      33.306 117.706 126.107  1.00 52.56
ATOM  1101  CD1  LEU  4283      33.997 118.984 126.574  1.00 49.11
ATOM  1102  CD2  LEU  4283      32.820 116.916 127.314  1.00 51.58
ATOM  1103  C    LEU  4283      29.988 117.907 124.049  1.00 53.49
ATOM  1104  O    LEU  4283      29.058 118.430 124.654  1.00 55.33
ATOM  1105  N    GLU  4284      30.118 118.001 122.729  1.00 55.71
ATOM  1106  CA   GLU  4284      29.120 118.752 121.976  1.00 55.38
ATOM  1107  CB   GLU  4284      29.569 119.014 120.537  1.00 54.03
ATOM  1108  CG   GLU  4284      29.444 117.833 119.608  1.00 59.81
ATOM  1109  CD   GLU  4284      29.762 118.203 118.173  1.00 62.29
ATOM  1110  OE1  GLU  4284      29.112 119.133 117.643  1.00 59.90
ATOM  1111  OE2  GLU  4284      30.657 117.563 117.578  1.00 61.42
ATOM  1112  C    GLU  4284      27.798 117.996 121.981  1.00 55.09
ATOM  1113  O    GLU  4284      26.736 118.606 122.010  1.00 54.36
ATOM  1114  N    GLN  4285      27.854 116.669 121.954  1.00 55.63
ATOM  1115  CA   GLN  4285      26.625 115.891 121.991  1.00 58.23
ATOM  1116  CB   GLN  4285      26.913 114.394 121.830  1.00 60.15
ATOM  1117  CG   GLN  4285      27.279 113.992 120.402  1.00 67.28
ATOM  1118  CD   GLN  4285      27.480 112.489 120.240  1.00 74.12
ATOM  1119  OE1  GLN  4285      26.594 111.694 120.555  1.00 74.60
ATOM  1120  NE2  GLN  4285      28.647 112.097 119.736  1.00 78.26
ATOM  1121  C    GLN  4285      25.909 116.165 123.310  1.00 57.70
ATOM  1122  O    GLN  4285      24.677 116.189 123.365  1.00 57.35
ATOM  1123  N    LYS  4286      26.685 116.376 124.370  1.00 56.09
ATOM  1124  CA   LYS  4286      26.112 116.664 125.676  1.00 54.68
ATOM  1125  CB   LYS  4286      27.113 116.413 126.806  1.00 54.58
ATOM  1126  CG   LYS  4286      27.448 114.946 127.014  1.00 55.54
ATOM  1127  CD   LYS  4286      28.496 114.760 128.102  1.00 56.56
ATOM  1128  CE   LYS  4286      28.886 113.294 128.236  1.00 57.05
ATOM  1129  NZ   LYS  4286      29.992 113.094 129.208  1.00 57.24
ATOM  1130  C    LYS  4286      25.717 118.150 125.702  1.00 53.45
ATOM  1131  O    LYS  4286      24.761 118.525 126.369  1.00 55.29
ATOM  1132  N    TYR  4287      26.453 118.981 124.974  1.00 54.61
```

133

```
ATOM   1133  CA   TYR  4287      26.146 120.404 124.931  1.00 57.52
ATOM   1134  CB   TYR  4287      26.581 121.075 126.238  1.00 54.70
ATOM   1135  CG   TYR  4287      26.311 122.559 126.256  1.00 54.09
ATOM   1136  CD1  TYR  4287      25.036 123.049 125.982  1.00 51.95
ATOM   1137  CE1  TYR  4287      24.786 124.408 125.943  1.00 54.94
ATOM   1138  CD2  TYR  4287      27.335 123.475 126.503  1.00 52.31
ATOM   1139  CE2  TYR  4287      27.096 124.841 126.467  1.00 53.29
ATOM   1140  CZ   TYR  4287      25.817 125.301 126.181  1.00 56.41
ATOM   1141  OH   TYR  4287      25.567 126.650 126.089  1.00 58.71
ATOM   1142  C    TYR  4287      26.770 121.142 123.745  1.00 60.67
ATOM   1143  O    TYR  4287      27.965 121.006 123.470  1.00 61.53
ATOM   1144  N    THR  4288      25.948 121.932 123.054  1.00 61.23
ATOM   1145  CA   THR  4288      26.400 122.703 121.900  1.00 61.97
ATOM   1146  CB   THR  4288      26.030 122.013 120.590  1.00 59.99
ATOM   1147  OG1  THR  4288      26.420 120.641 120.660  1.00 65.21
ATOM   1148  CG2  THR  4288      26.763 122.665 119.424  1.00 62.23
ATOM   1149  C    THR  4288      25.762 124.087 121.897  1.00 61.64
ATOM   1150  O    THR  4288      25.033 124.448 122.822  1.00 60.84
ATOM   1151  N    TYR  4289      26.037 124.859 120.849  1.00 61.94
ATOM   1152  CA   TYR  4289      25.490 126.199 120.743  1.00 61.03
ATOM   1153  CB   TYR  4289      25.773 126.960 122.042  1.00 54.72
ATOM   1154  CG   TYR  4289      27.233 127.041 122.415  1.00 51.15
ATOM   1155  CD1  TYR  4289      28.032 128.091 121.967  1.00 51.78
ATOM   1156  CE1  TYR  4289      29.377 128.170 122.315  1.00 51.28
ATOM   1157  CD2  TYR  4289      27.820 126.066 123.219  1.00 48.79
ATOM   1158  CE2  TYR  4289      29.162 126.114 123.569  1.00 47.85
ATOM   1159  CZ   TYR  4289      29.932 127.191 123.117  1.00 50.10
ATOM   1160  OH   TYR  4289      31.255 127.282 123.483  1.00 51.14
ATOM   1161  C    TYR  4289      26.023 126.959 119.536  1.00 63.74
ATOM   1162  O    TYR  4289      27.117 126.691 119.048  1.00 62.92
ATOM   1163  N    GLU  4290      25.217 127.907 119.069  1.00 69.67
ATOM   1164  CA   GLU  4290      25.511 128.751 117.911  1.00 75.22
ATOM   1165  CB   GLU  4290      24.869 130.130 118.111  1.00 79.97
ATOM   1166  CG   GLU  4290      23.346 130.090 118.004  1.00 89.27
ATOM   1167  CD   GLU  4290      22.675 131.418 118.316  1.00 93.57
ATOM   1168  OE1  GLU  4290      23.020 132.437 117.674  1.00 95.68
ATOM   1169  OE2  GLU  4290      21.790 131.433 119.202  1.00 94.24
ATOM   1170  C    GLU  4290      26.961 128.923 117.465  1.00 73.60
ATOM   1171  O    GLU  4290      27.287 128.635 116.311  1.00 74.26
ATOM   1172  N    HIS  4291      27.826 129.400 118.352  1.00 71.52
ATOM   1173  CA   HIS  4291      29.218 129.602 117.974  1.00 71.29
ATOM   1174  CB   HIS  4291      29.601 131.066 118.148  1.00 73.52
ATOM   1175  CG   HIS  4291      28.672 131.999 117.447  1.00 75.86
ATOM   1176  CD2  HIS  4291      28.025 133.108 117.875  1.00 76.81
ATOM   1177  ND1  HIS  4291      28.285 131.809 116.138  1.00 77.44
ATOM   1178  CE1  HIS  4291      27.438 132.760 115.791  1.00 79.81
ATOM   1179  NE2  HIS  4291      27.263 133.561 116.827  1.00 80.07
ATOM   1180  C    HIS  4291      30.153 128.706 118.752  1.00 69.94
ATOM   1181  O    HIS  4291      31.217 129.171 119.224  1.00 68.71
ATOM   1182  N    ASP  4292      29.725 127.459 118.876  1.00 67.87
ATOM   1183  CA   ASP  4292      30.486 126.438 119.564  1.00 64.42
ATOM   1184  CB   ASP  4292      29.566 125.250 119.861  1.00 65.32
ATOM   1185  CG   ASP  4292      30.320 124.015 120.258  1.00 67.16
ATOM   1186  OD1  ASP  4292      31.349 124.150 120.952  1.00 69.00
ATOM   1187  OD2  ASP  4292      29.869 122.909 119.893  1.00 67.27
ATOM   1188  C    ASP  4292      31.663 126.042 118.675  1.00 59.74
ATOM   1189  O    ASP  4292      31.490 125.388 117.645  1.00 56.46
ATOM   1190  N    PRO  4293      32.880 126.458 119.066  1.00 55.91
ATOM   1191  CD   PRO  4293      33.162 127.225 120.288  1.00 54.69
ATOM   1192  CA   PRO  4293      34.137 126.194 118.361  1.00 56.99
ATOM   1193  CB   PRO  4293      35.178 126.824 119.290  1.00 55.86
ATOM   1194  CG   PRO  4293      34.525 126.692 120.647  1.00 55.06
ATOM   1195  C    PRO  4293      34.382 124.712 118.144  1.00 57.25
ATOM   1196  O    PRO  4293      34.892 124.283 117.106  1.00 59.39
ATOM   1197  N    ILE  4294      33.999 123.933 119.142  1.00 55.40
ATOM   1198  CA   ILE  4294      34.170 122.496 119.107  1.00 52.29
ATOM   1199  CB   ILE  4294      33.732 121.898 120.477  1.00 51.13
ATOM   1200  CG2  ILE  4294      32.303 121.396 120.410  1.00 54.38
ATOM   1201  CG1  ILE  4294      34.642 120.746 120.873  1.00 46.91
ATOM   1202  CD1  ILE  4294      34.387 120.273 122.278  1.00 47.38
```

134

```
ATOM   1203  C    ILE  4294    33.351 121.923 117.944  1.00 49.76
ATOM   1204  O    ILE  4294    33.360 120.726 117.700  1.00 50.69
ATOM   1205  N    THR  4295    32.653 122.793 117.221  1.00 49.07
ATOM   1206  CA   THR  4295    31.833 122.367 116.086  1.00 51.16
ATOM   1207  CB   THR  4295    30.367 122.815 116.249  1.00 50.59
ATOM   1208  OG1  THR  4295    29.822 122.253 117.446  1.00 51.83
ATOM   1209  CG2  THR  4295    29.541 122.340 115.072  1.00 48.78
ATOM   1210  C    THR  4295    32.346 122.903 114.743  1.00 49.90
ATOM   1211  O    THR  4295    32.281 122.216 113.727  1.00 48.03
ATOM   1212  N    LYS  4296    32.840 124.134 114.738  1.00 49.13
ATOM   1213  CA   LYS  4296    33.360 124.722 113.522  1.00 51.93
ATOM   1214  CB   LYS  4296    33.472 126.244 113.682  1.00 52.82
ATOM   1215  CG   LYS  4296    32.104 126.814 113.971  1.00 59.11
ATOM   1216  CD   LYS  4296    32.114 128.436 114.051  1.00 55.65
ATOM   1217  CE   LYS  4296    30.687 128.987 114.271  1.00 45.24
ATOM   1218  NZ   LYS  4296    30.590 130.474 114.254  1.00 37.02
ATOM   1219  C    LYS  4296    34.714 124.077 113.236  1.00 55.06
ATOM   1220  O    LYS  4296    34.872 123.382 112.227  1.00 56.63
ATOM   1221  N    ASN  4297    35.681 124.280 114.128  1.00 53.08
ATOM   1222  CA   ASN  4297    37.008 123.690 113.952  1.00 52.15
ATOM   1223  CB   ASN  4297    37.945 124.183 115.049  1.00 53.86
ATOM   1224  CG   ASN  4297    38.093 125.685 115.059  1.00 55.78
ATOM   1225  OD1  ASN  4297    38.561 126.280 114.091  1.00 61.09
ATOM   1226  ND2  ASN  4297    37.699 126.311 116.162  1.00 59.41
ATOM   1227  C    ASN  4297    36.920 122.158 114.010  1.00 51.83
ATOM   1228  O    ASN  4297    37.849 121.439 113.633  1.00 50.24
ATOM   1229  N    LYS  4298    35.787 121.679 114.502  1.00 49.72
ATOM   1230  CA   LYS  4298    35.510 120.259 114.649  1.00 47.90
ATOM   1231  CB   LYS  4298    33.997 120.074 114.742  1.00 48.66
ATOM   1232  CG   LYS  4298    33.485 118.663 114.859  1.00 44.51
ATOM   1233  CD   LYS  4298    31.964 118.711 114.872  1.00 45.88
ATOM   1234  CE   LYS  4298    31.341 117.328 114.826  1.00 47.28
ATOM   1235  NZ   LYS  4298    29.853 117.418 114.737  1.00 47.12
ATOM   1236  C    LYS  4298    36.074 119.420 113.512  1.00 47.79
ATOM   1237  O    LYS  4298    37.046 118.692 113.696  1.00 42.57
ATOM   1238  N    GLN  4299    35.464 119.540 112.335  1.00 51.79
ATOM   1239  CA   GLN  4299    35.876 118.769 111.156  1.00 51.88
ATOM   1240  CB   GLN  4299    34.891 118.980 110.020  1.00 51.10
ATOM   1241  CG   GLN  4299    35.163 118.067 108.850  1.00 50.56
ATOM   1242  CD   GLN  4299    34.856 116.625 109.173  1.00 50.22
ATOM   1243  OE1  GLN  4299    33.708 116.274 109.454  1.00 53.87
ATOM   1244  NE2  GLN  4299    35.875 115.779 109.142  1.00 51.50
ATOM   1245  C    GLN  4299    37.280 119.045 110.618  1.00 49.96
ATOM   1246  O    GLN  4299    38.013 118.121 110.285  1.00 49.68
ATOM   1247  N    VAL  4300    37.642 120.315 110.502  1.00 47.84
ATOM   1248  CA   VAL  4300    38.963 120.676 110.007  1.00 44.58
ATOM   1249  CB   VAL  4300    39.241 122.174 110.215  1.00 45.76
ATOM   1250  CG1  VAL  4300    40.581 122.534 109.612  1.00 48.32
ATOM   1251  CG2  VAL  4300    38.131 123.003 109.612  1.00 49.81
ATOM   1252  C    VAL  4300    40.073 119.906 110.726  1.00 41.93
ATOM   1253  O    VAL  4300    40.872 119.216 110.101  1.00 38.98
ATOM   1254  N    LEU  4301    40.104 120.045 112.048  1.00 41.05
ATOM   1255  CA   LEU  4301    41.105 119.413 112.899  1.00 38.62
ATOM   1256  CB   LEU  4301    40.837 119.754 114.363  1.00 43.99
ATOM   1257  CG   LEU  4301    40.949 121.221 114.768  1.00 49.80
ATOM   1258  CD1  LEU  4301    40.626 121.362 116.253  1.00 53.48
ATOM   1259  CD2  LEU  4301    42.360 121.723 114.468  1.00 49.99
ATOM   1260  C    LEU  4301    41.215 117.909 112.772  1.00 35.75
ATOM   1261  O    LEU  4301    42.310 117.353 112.848  1.00 34.40
ATOM   1262  N    TRP  4302    40.087 117.278 112.602  1.00 34.20
ATOM   1263  CA   TRP  4302    40.140 115.793 112.487  1.00 35.36
ATOM   1264  CB   TRP  4302    38.740 115.198 112.366  1.00 39.06
ATOM   1265  CG   TRP  4302    38.714 113.777 112.803  1.00 48.72
ATOM   1266  CD2  TRP  4302    38.762 112.613 111.962  1.00 52.89
ATOM   1267  CE2  TRP  4302    38.824 111.489 112.807  1.00 56.67
ATOM   1268  CE3  TRP  4302    38.763 112.433 110.575  1.00 57.89
ATOM   1269  CD1  TRP  4302    38.743 113.313 114.094  1.00 51.22
ATOM   1270  NE1  TRP  4302    38.809 111.940 114.104  1.00 54.53
ATOM   1271  CZ2  TRP  4302    38.885 110.187 112.311  1.00 59.53
ATOM   1272  CZ3  TRP  4302    38.825 111.138 110.079  1.00 62.01
```

135

```
ATOM   1273  CH2 TRP  4302      38.884 110.030 110.948  1.00 63.70
ATOM   1274  C   TRP  4302      40.948 115.449 111.240  1.00 32.82
ATOM   1275  O   TRP  4302      42.032 114.857 111.329  1.00 32.64
ATOM   1276  N   ASP  4303      40.414 115.844 110.084  1.00 28.45
ATOM   1277  CA  ASP  4303      41.055 115.594 108.804  1.00 25.59
ATOM   1278  CB  ASP  4303      40.352 116.355 107.687  1.00 26.25
ATOM   1279  CG  ASP  4303      38.930 115.901 107.478  1.00 29.72
ATOM   1280  OD1 ASP  4303      38.665 114.686 107.595  1.00 36.14
ATOM   1281  OD2 ASP  4303      38.079 116.753 107.162  1.00 35.81
ATOM   1282  C   ASP  4303      42.520 115.964 108.790  1.00 21.28
ATOM   1283  O   ASP  4303      43.350 115.219 108.291  1.00 19.18
ATOM   1284  N   ARG  4304      42.839 117.124 109.332  1.00 20.05
ATOM   1285  CA  ARG  4304      44.218 117.551 109.361  1.00 23.99
ATOM   1286  CB  ARG  4304      44.328 118.947 109.960  1.00 22.62
ATOM   1287  CG  ARG  4304      45.729 119.492 109.872  1.00 31.09
ATOM   1288  CD  ARG  4304      45.848 120.861 110.492  1.00 31.88
ATOM   1289  NE  ARG  4304      47.242 121.279 110.502  1.00 36.98
ATOM   1290  CZ  ARG  4304      47.702 122.336 111.157  1.00 37.21
ATOM   1291  NH1 ARG  4304      46.878 123.093 111.867  1.00 36.05
ATOM   1292  NH2 ARG  4304      48.993 122.629 111.103  1.00 41.44
ATOM   1293  C   ARG  4304      45.088 116.571 110.153  1.00 28.59
ATOM   1294  O   ARG  4304      46.292 116.468 109.906  1.00 31.48
ATOM   1295  N   THR  4305      44.486 115.845 111.098  1.00 29.81
ATOM   1296  CA  THR  4305      45.242 114.862 111.903  1.00 24.21
ATOM   1297  CB  THR  4305      44.622 114.673 113.308  1.00 24.88
ATOM   1298  OG1 THR  4305      44.696 115.898 114.050  1.00 27.85
ATOM   1299  CG2 THR  4305      45.388 113.606 114.074  1.00 25.54
ATOM   1300  C   THR  4305      45.352 113.544 111.202  1.00 18.37
ATOM   1301  O   THR  4305      46.128 112.693 111.605  1.00 16.94
ATOM   1302  N   PHE  4306      44.570 113.352 110.150  1.00 15.94
ATOM   1303  CA  PHE  4306      44.657 112.114 109.403  1.00 12.60
ATOM   1304  CB  PHE  4306      43.398 111.894 108.577  1.00 15.38
ATOM   1305  CG  PHE  4306      43.445 110.650 107.747  1.00 21.76
ATOM   1306  CD1 PHE  4306      43.363 109.400 108.345  1.00 20.33
ATOM   1307  CD2 PHE  4306      43.650 110.726 106.365  1.00 24.10
ATOM   1308  CE1 PHE  4306      43.489 108.248 107.585  1.00 23.91
ATOM   1309  CE2 PHE  4306      43.778 109.581 105.597  1.00 23.52
ATOM   1310  CZ  PHE  4306      43.699 108.337 106.208  1.00 29.73
ATOM   1311  C   PHE  4306      45.873 112.271 108.480  1.00 17.73
ATOM   1312  O   PHE  4306      46.724 111.370 108.381  1.00 16.46
ATOM   1313  N   SER  4307      45.959 113.429 107.824  1.00 15.11
ATOM   1314  CA  SER  4307      47.074 113.732 106.936  1.00 19.06
ATOM   1315  CB  SER  4307      46.977 115.167 106.436  1.00 20.89
ATOM   1316  OG  SER  4307      45.818 115.345 105.652  1.00 36.23
ATOM   1317  C   SER  4307      48.429 113.546 107.620  1.00 22.29
ATOM   1318  O   SER  4307      49.188 112.634 107.270  1.00 26.36
ATOM   1319  N   LEU  4308      48.739 114.424 108.580  1.00 20.60
ATOM   1320  CA  LEU  4308      50.002 114.340 109.300  1.00 15.77
ATOM   1321  CB  LEU  4308      49.974 115.129 110.604  1.00 15.80
ATOM   1322  CG  LEU  4308      50.096 116.646 110.744  1.00 21.98
ATOM   1323  CD1 LEU  4308      51.462 117.088 110.261  1.00 26.62
ATOM   1324  CD2 LEU  4308      48.985 117.340 109.998  1.00 28.90
ATOM   1325  C   LEU  4308      50.291 112.901 109.654  1.00 18.96
ATOM   1326  O   LEU  4308      51.421 112.435 109.496  1.00 22.93
ATOM   1327  N   PHE  4309      49.270 112.194 110.131  1.00 16.59
ATOM   1328  CA  PHE  4309      49.452 110.810 110.544  1.00 20.11
ATOM   1329  CB  PHE  4309      48.283 110.337 111.398  1.00 19.00
ATOM   1330  CG  PHE  4309      48.475 108.960 111.944  1.00 15.63
ATOM   1331  CD1 PHE  4309      49.401 108.730 112.955  1.00 17.24
ATOM   1332  CD2 PHE  4309      47.794 107.875 111.388  1.00 12.36
ATOM   1333  CE1 PHE  4309      49.654 107.431 113.406  1.00 16.15
ATOM   1334  CE2 PHE  4309      48.033 106.583 111.826  1.00 15.43
ATOM   1335  CZ  PHE  4309      48.968 106.357 112.837  1.00 17.87
ATOM   1336  C   PHE  4309      49.642 109.847 109.384  1.00 20.97
ATOM   1337  O   PHE  4309      50.449 108.906 109.464  1.00 17.52
ATOM   1338  N   GLN  4310      48.890 110.065 108.312  1.00 22.10
ATOM   1339  CA  GLN  4310      49.031 109.297 107.136  1.00 23.33
ATOM   1340  CB  GLN  4310      48.036 109.580 106.047  1.00 22.77
ATOM   1341  CG  GLN  4310      48.283 108.824 104.774  1.00 18.76
ATOM   1342  CD  GLN  4310      47.731 109.542 103.580  1.00 23.39
```

```
ATOM  1343  OE1 GLN  4310    46.525 109.776 103.482  1.00 26.24
ATOM  1344  NE2 GLN  4310    48.612 109.911 102.659  1.00 25.99
ATOM  1345  C   GLN  4310    50.425 109.404 106.577  1.00 17.79
ATOM  1346  O   GLN  4310    51.175 108.462 106.386  1.00 14.86
ATOM  1347  N   GLN  4311    50.759 110.656 106.321  1.00 17.15
ATOM  1348  CA  GLN  4311    52.059 110.985 105.777  1.00 21.88
ATOM  1349  CB  GLN  4311    52.254 112.496 105.786  1.00 18.60
ATOM  1350  CG  GLN  4311    53.470 112.935 105.035  1.00 25.56
ATOM  1351  CD  GLN  4311    53.565 114.436 104.960  1.00 35.33
ATOM  1352  OE1 GLN  4311    53.793 115.115 105.972  1.00 34.54
ATOM  1353  NE2 GLN  4311    53.372 114.9 7 103.755  1.00 36.66
ATOM  1354  C   GLN  4311    53.150 110.320 106.591  1.00 21.31
ATOM  1355  O   GLN  4311    53.939 109.530 106.068  1.00 20.60
ATOM  1356  N   LEU  4312    53.170 110.650 107.879  1.00 25.30
ATOM  1357  CA  LEU  4312    54.143 110.125 108.817  1.00 24.96
ATOM  1358  CB  LEU  4312    53.801 110.588 110.236  1.00 21.27
ATOM  1359  CG  LEU  4312    54.647 109.988 111.368  1.00 24.65
ATOM  1360  CD1 LEU  4312    56.075 110.486 111.265  1.00 21.92
ATOM  1361  CD2 LEU  4312    54.064 110.372 112.714  1.00 19.02
ATOM  1362  C   LEU  4312    54.246 108.603 108.785  1.00 25.75
ATOM  1363  O   LEU  4312    55.342 108.057 108.746  1.00 27.98
ATOM  1364  N   ILE  4313    53.122 107.902 108.791  1.00 26.58
ATOM  1365  CA  ILE  4313    53.212 106.450 108.794  1.00 29.08
ATOM  1366  CB  ILE  4313    51.876 105.795 109.138  1.00 32.07
ATOM  1367  CG2 ILE  4313    50.801 106.284 108.193  1.00 33.25
ATOM  1368  CG1 ILE  4313    52.048 104.274 109.095  1.00 34.12
ATOM  1369  CD1 ILE  4313    50.776 103.496 109.252  1.00 44.95
ATOM  1370  C   ILE  4313    53.715 105.868 107.483  1.00 25.17
ATOM  1371  O   ILE  4313    54.443 104.882 107.476  1.00 25.38
ATOM  1372  N   GLN  4314    53.321 106.468 106.369  1.00 26.88
ATOM  1373  CA  GLN  4314    53.771 105.983 105.073  1.00 25.48
ATOM  1374  CB  GLN  4314    53.015 106.687 103.947  1.00 25.30
ATOM  1375  CG  GLN  4314    51.515 106.509 104.037  1.00 29.08
ATOM  1376  CD  GLN  4314    50.776 107.138 102.880  1.00 33.89
ATOM  1377  OE1 GLN  4314    50.999 108.298 102.539  1.00 37.04
ATOM  1378  NE2 GLN  4314    49.871 106.380 102.282  1.00 37.72
ATOM  1379  C   GLN  4314    55.270 106.221 104.935  1.00 23.31
ATOM  1380  O   GLN  4314    55.992 105.384 104.395  1.00 25.97
ATOM  1381  N   SER  4315    55.746 107.356 105.431  1.00 16.45
ATOM  1382  CA  SER  4315    57.167 107.644 105.353  1.00 17.76
ATOM  1383  CB  SER  4315    57.444 109.100 105.724  1.00 17.64
ATOM  1384  OG  SER  4315    56.862 109.991 104.796  1.00 22.55
ATOM  1385  C   SER  4315    57.990 106.737 106.261  1.00 19.65
ATOM  1386  O   SER  4315    59.136 106.432 105.947  1.00 20.54
ATOM  1387  N   SER  4316    57.408 106.304 107.380  1.00 20.68
ATOM  1388  CA  SER  4316    58.107 105.447 108.345  1.00 19.70
ATOM  1389  CB  SER  4316    57.307 105.334 109.642  1.00 23.63
ATOM  1390  OG  SER  4316    56.097 104.624 109.435  1.00 27.17
ATOM  1391  C   SER  4316    58.416 104.036 107.849  1.00 19.03
ATOM  1392  O   SER  4316    59.306 103.376 108.393  1.00 17.75
ATOM  1393  N   PHE  4317    57.661 103.572 106.850  1.00 15.52
ATOM  1394  CA  PHE  4317    57.852 102.251 106.245  1.00 12.66
ATOM  1395  CB  PHE  4317    56.709 101.957 105.287  1.00 11.88
ATOM  1396  CG  PHE  4317    56.647 100.532 104.818  1.00 10.16
ATOM  1397  CD1 PHE  4317    56.099 100.228 103.588  1.00  9.59
ATOM  1398  CD2 PHE  4317    57.018  99.487 105.654  1.00  6.40
ATOM  1399  CE1 PHE  4317    55.916  98.902 103.203  1.00 14.26
ATOM  1400  CE2 PHE  4317    56.830  99.176 105.268  1.00  6.42
ATOM  1401  CZ  PHE  4317    56.280  97.867 104.051  1.00  6.01
ATOM  1402  C   PHE  4317    59.128 102.336 105.414  1.00 14.67
ATOM  1403  O   PHE  4317    59.147 103.017 104.392  1.00 15.55
ATOM  1404  N   VAL  4318    60.187 101.651 105.815  1.00 11.03
ATOM  1405  CA  VAL  4318    61.417 101.739 105.040  1.00  9.10
ATOM  1406  CB  VAL  4318    62.420 102.689 105.702  1.00  5.34
ATOM  1407  CG1 VAL  4318    63.001 102.040 106.948  1.00  3.09
ATOM  1408  CG2 VAL  4318    63.510 103.060 104.717  1.00 11.83
ATOM  1409  C   VAL  4318    62.127 100.415 104.822  1.00 10.78
ATOM  1410  O   VAL  4318    61.901  99.432 105.528  1.00 16.70
ATOM  1411  N   VAL  4319    62.994 100.394 103.824  1.00 10.44
ATOM  1412  CA  VAL  4319    63.754  99.198 103.535  1.00 13.74
```

| ATOM | 1413 | CB | VAL | 4319 | 64.033 | 99.067 | 102.042 | 1.00 | 14.50 |
| --- | --- | --- | --- | --- | --- | --- | --- | --- | --- |
| ATOM | 1414 | CG1 | VAL | 4319 | 64.956 | 97.898 | 101.794 | 1.00 | 7.96 |
| ATOM | 1415 | CG2 | VAL | 4319 | 62.719 | 98.880 | 101.304 | 1.00 | 14.78 |
| ATOM | 1416 | C | VAL | 4319 | 65.052 | 99.313 | 104.294 | 1.00 | 14.67 |
| ATOM | 1417 | O | VAL | 4319 | 66.021 | 99.857 | 103.791 | 1.00 | 18.28 |
| ATOM | 1418 | N | GLU | 4320 | 65.042 | 98.808 | 105.523 | 1.00 | 20.34 |
| ATOM | 1419 | CA | GLU | 4320 | 66.199 | 98.839 | 106.399 | 1.00 | 20.70 |
| ATOM | 1420 | CB | GLU | 4320 | 65.865 | 98.173 | 107.728 | 1.00 | 23.22 |
| ATOM | 1421 | CG | GLU | 4320 | 67.069 | 97.888 | 108.579 | 1.00 | 31.29 |
| ATOM | 1422 | CD | GLU | 4320 | 66.689 | 97.573 | 109.997 | 1.00 | 37.84 |
| ATOM | 1423 | OE1 | GLU | 4320 | 65.721 | 96.813 | 110.198 | 1.00 | 42.42 |
| ATOM | 1424 | OE2 | GLU | 4320 | 67.368 | 98.077 | 110.913 | 1.00 | 41.32 |
| ATOM | 1425 | C | GLU | 4320 | 67.411 | 98.189 | 105.772 | 1.00 | 20.66 |
| ATOM | 1426 | O | GLU | 4320 | 68.486 | 98.785 | 105.744 | 1.00 | 23.40 |
| ATOM | 1427 | N | ARG | 4321 | 67.271 | 96.959 | 105.298 | 1.00 | 18.81 |
| ATOM | 1428 | CA | ARG | 4321 | 68.408 | 96.364 | 104.631 | 1.00 | 18.32 |
| ATOM | 1429 | CB | ARG | 4321 | 68.967 | 95.149 | 105.377 | 1.00 | 15.82 |
| ATOM | 1430 | CG | ARG | 4321 | 70.346 | 94.838 | 104.832 | 1.00 | 31.43 |
| ATOM | 1431 | CD | ARG | 4321 | 70.931 | 96.208 | 104.401 | 1.00 | 45.04 |
| ATOM | 1432 | NE | ARG | 4321 | 72.152 | 96.211 | 103.601 | 1.00 | 53.48 |
| ATOM | 1433 | CZ | ARG | 4321 | 72.499 | 97.228 | 102.812 | 1.00 | 49.21 |
| ATOM | 1434 | NH1 | ARG | 4321 | 71.707 | 98.231 | 102.721 | 1.00 | 31.36 |
| ATOM | 1435 | NH2 | ARG | 4321 | 73.642 | 97.193 | 102.134 | 1.00 | 51.91 |
| ATOM | 1436 | C | ARG | 4321 | 68.092 | 96.007 | 103.183 | 1.00 | 18.19 |
| ATOM | 1437 | O | ARG | 4321 | 67.304 | 95.107 | 102.908 | 1.00 | 18.03 |
| ATOM | 1438 | N | GLN | 4322 | 68.704 | 96.742 | 102.260 | 1.00 | 13.67 |
| ATOM | 1439 | CA | GLN | 4322 | 68.481 | 96.524 | 100.840 | 1.00 | 14.31 |
| ATOM | 1440 | CB | GLN | 4322 | 69.454 | 97.362 | 100.016 | 1.00 | 20.99 |
| ATOM | 1441 | CG | GLN | 4322 | 69.185 | 98.865 | 100.051 | 1.00 | 19.96 |
| ATOM | 1442 | CD | GLN | 4322 | 67.775 | 99.184 | 99.617 | 1.00 | 18.89 |
| ATOM | 1443 | OE1 | GLN | 4322 | 67.287 | 98.659 | 98.608 | 1.00 | 17.94 |
| ATOM | 1444 | NE2 | GLN | 4322 | 67.110 | 100.050 | 100.367 | 1.00 | 22.92 |
| ATOM | 1445 | C | GLN | 4322 | 68.607 | 95.070 | 100.440 | 1.00 | 12.66 |
| ATOM | 1446 | O | GLN | 4322 | 69.260 | 94.282 | 101.132 | 1.00 | 15.23 |
| ATOM | 1447 | N | PRO | 4323 | 67.983 | 94.692 | 99.308 | 1.00 | 12.52 |
| ATOM | 1448 | CD | PRO | 4323 | 67.231 | 95.564 | 98.396 | 1.00 | 13.20 |
| ATOM | 1449 | CA | PRO | 4323 | 67.998 | 93.324 | 98.776 | 1.00 | 14.43 |
| ATOM | 1450 | CB | PRO | 4323 | 67.310 | 93.478 | 97.428 | 1.00 | 8.87 |
| ATOM | 1451 | CG | PRO | 4323 | 66.319 | 94.556 | 97.732 | 1.00 | 15.57 |
| ATOM | 1452 | C | PRO | 4323 | 69.434 | 92.919 | 98.637 | 1.00 | 15.26 |
| ATOM | 1453 | O | PRO | 4323 | 70.279 | 93.773 | 98.513 | 1.00 | 19.74 |
| ATOM | 1454 | N | CYS | 4324 | 69.716 | 91.628 | 98.679 | 1.00 | 18.60 |
| ATOM | 1455 | CA | CYS | 4324 | 71.084 | 91.157 | 98.566 | 1.00 | 17.16 |
| ATOM | 1456 | CB | CYS | 4324 | 71.928 | 91.767 | 99.682 | 1.00 | 11.98 |
| ATOM | 1457 | SG | CYS | 4324 | 73.688 | 91.430 | 99.534 | 1.00 | 25.84 |
| ATOM | 1458 | C | CYS | 4324 | 71.172 | 89.631 | 98.647 | 1.00 | 18.58 |
| ATOM | 1459 | O | CYS | 4324 | 70.306 | 89.974 | 99.239 | 1.00 | 18.19 |
| ATOM | 1460 | N | MET | 4325 | 72.208 | 89.071 | 98.024 | 1.00 | 22.00 |
| ATOM | 1461 | CA | MET | 4325 | 72.435 | 87.630 | 98.080 | 1.00 | 20.26 |
| ATOM | 1462 | CB | MET | 4325 | 73.067 | 87.146 | 96.782 | 1.00 | 12.79 |
| ATOM | 1463 | CG | MET | 4325 | 72.170 | 87.390 | 95.608 | 1.00 | 18.48 |
| ATOM | 1464 | SD | MET | 4325 | 72.735 | 86.700 | 94.073 | 1.00 | 18.16 |
| ATOM | 1465 | CE | MET | 4325 | 72.857 | 85.048 | 94.514 | 1.00 | 26.16 |
| ATOM | 1466 | C | MET | 4325 | 73.367 | 87.400 | 99.271 | 1.00 | 21.05 |
| ATOM | 1467 | O | MET | 4325 | 74.395 | 88.060 | 99.399 | 1.00 | 24.07 |
| ATOM | 1468 | N | PRO | 4326 | 72.994 | 86.481 | 100.179 | 1.00 | 19.98 |
| ATOM | 1469 | CD | PRO | 4326 | 71.765 | 85.672 | 100.133 | 1.00 | 22.16 |
| ATOM | 1470 | CA | PRO | 4326 | 73.762 | 86.133 | 101.377 | 1.00 | 14.08 |
| ATOM | 1471 | CB | PRO | 4326 | 72.919 | 85.035 | 101.997 | 1.00 | 15.91 |
| ATOM | 1472 | CG | PRO | 4326 | 71.518 | 85.455 | 101.588 | 1.00 | 21.82 |
| ATOM | 1473 | C | PRO | 4326 | 75.172 | 85.673 | 101.075 | 1.00 | 11.07 |
| ATOM | 1474 | O | PRO | 4326 | 76.029 | 85.728 | 101.932 | 1.00 | 10.10 |
| ATOM | 1475 | N | THR | 4327 | 75.406 | 85.225 | 99.849 | 1.00 | 12.84 |
| ATOM | 1476 | CA | THR | 4327 | 76.726 | 84.764 | 99.442 | 1.00 | 16.26 |
| ATOM | 1477 | CB | THR | 4327 | 76.633 | 83.739 | 98.270 | 1.00 | 23.95 |
| ATOM | 1478 | OG1 | THR | 4327 | 75.784 | 82.645 | 98.634 | 1.00 | 31.77 |
| ATOM | 1479 | CG2 | THR | 4327 | 78.013 | 83.188 | 97.933 | 1.00 | 30.49 |
| ATOM | 1480 | C | THR | 4327 | 77.545 | 85.953 | 98.952 | 1.00 | 14.38 |
| ATOM | 1481 | O | THR | 4327 | 78.727 | 85.805 | 98.651 | 1.00 | 13.07 |
| ATOM | 1482 | N | HIS | 4328 | 76.904 | 87.110 | 98.866 | 1.00 | 13.70 |

| | | | | | | | | |
|---|---|---|---|---|---|---|---|---|
| ATOM | 1483 | CA | HIS | 4328 | 77.551 | 88.322 | 98.374 | 1.00 18.04 |
| ATOM | 1484 | CB | HIS | 4328 | 77.045 | 88.619 | 96.967 | 1.00 16.17 |
| ATOM | 1485 | CG | HIS | 4328 | 77.405 | 87.566 | 95.976 | 1.00 14.08 |
| ATOM | 1486 | CD2 | HIS | 4328 | 76.671 | 86.572 | 95.427 | 1.00 17.57 |
| ATOM | 1487 | ND1 | HIS | 4328 | 78.690 | 87.403 | 95.506 | 1.00 14.41 |
| ATOM | 1488 | CE1 | HIS | 4328 | 78.730 | 86.351 | 94.709 | 1.00 19.23 |
| ATOM | 1489 | NE2 | HIS | 4328 | 77.519 | 85.830 | 94.645 | 1.00 19.92 |
| ATOM | 1490 | C | HIS | 4328 | 77.288 | 89.522 | 99.263 | 1.00 21.79 |
| ATOM | 1491 | O | HIS | 4328 | 76.810 | 90.553 | 98.802 | 1.00 26.54 |
| ATOM | 1492 | N | PRO | 4329 | 77.602 | 89.400 | 100.555 | 1.00 23.69 |
| ATOM | 1493 | CD | PRO | 4329 | 78.206 | 88.254 | 101.246 | 1.00 22.07 |
| ATOM | 1494 | CA | PRO | 4329 | 77.388 | 90.492 | 101.503 | 1.00 21.25 |
| ATOM | 1495 | CB | PRO | 4329 | 78.072 | 89.964 | 102.769 | 1.00 26.68 |
| ATOM | 1496 | CG | PRO | 4329 | 79.108 | 88.966 | 102.208 | 1.00 22.05 |
| ATOM | 1497 | C | PRO | 4329 | 77.918 | 91.852 | 101.056 | 1.00 15.61 |
| ATOM | 1498 | O | PRO | 4329 | 77.415 | 92.878 | 101.496 | 1.00 16.90 |
| ATOM | 1499 | N | GLN | 4330 | 78.927 | 91.865 | 100.189 | 1.00 14.91 |
| ATOM | 1500 | CA | GLN | 4330 | 79.480 | 93.132 | 99.715 | 1.00 16.77 |
| ATOM | 1501 | CB | GLN | 4330 | 81.014 | 93.132 | 99.774 | 1.00 23.52 |
| ATOM | 1502 | CG | GLN | 4330 | 81.565 | 93.320 | 101.183 | 1.00 30.89 |
| ATOM | 1503 | CD | GLN | 4330 | 81.024 | 92.295 | 102.147 | 1.00 35.36 |
| ATOM | 1504 | OE1 | GLN | 4330 | 81.393 | 91.123 | 102.101 | 1.00 37.43 |
| ATOM | 1505 | NE2 | GLN | 4330 | 80.112 | 92.726 | 103.011 | 1.00 39.25 |
| ATOM | 1506 | C | GLN | 4330 | 79.039 | 93.558 | 98.330 | 1.00 14.39 |
| ATOM | 1507 | O | GLN | 4330 | 79.661 | 94.423 | 97.730 | 1.00 12.12 |
| ATOM | 1508 | N | ARG | 4331 | 77.972 | 92.942 | 97.827 | 1.00 14.51 |
| ATOM | 1509 | CA | ARG | 4331 | 77.419 | 93.271 | 96.519 | 1.00 13.34 |
| ATOM | 1510 | CB | ARG | 4331 | 78.102 | 92.458 | 95.427 | 1.00 5.87 |
| ATOM | 1511 | CG | ARG | 4331 | 79.510 | 92.971 | 95.293 | 1.00 9.37 |
| ATOM | 1512 | CD | ARG | 4331 | 80.226 | 92.549 | 94.073 | 1.00 14.50 |
| ATOM | 1513 | NE | ARG | 4331 | 81.588 | 93.069 | 94.105 | 1.00 21.06 |
| ATOM | 1514 | CZ | ARG | 4331 | 82.524 | 92.753 | 93.216 | 1.00 31.08 |
| ATOM | 1515 | NH1 | ARG | 4331 | 82.251 | 91.913 | 92.209 | 1.00 29.86 |
| ATOM | 1516 | NH2 | ARG | 4331 | 83.741 | 93.266 | 93.341 | 1.00 30.75 |
| ATOM | 1517 | C | ARG | 4331 | 75.921 | 93.074 | 96.535 | 1.00 15.33 |
| ATOM | 1518 | O | ARG | 4331 | 75.379 | 92.156 | 95.914 | 1.00 18.05 |
| ATOM | 1519 | N | PRO | 4332 | 75.230 | 93.964 | 97.268 | 1.00 14.69 |
| ATOM | 1520 | CD | PRO | 4332 | 75.921 | 95.018 | 98.037 | 1.00 12.19 |
| ATOM | 1521 | CA | PRO | 4332 | 73.792 | 94.057 | 97.509 | 1.00 11.26 |
| ATOM | 1522 | CB | PRO | 4332 | 73.716 | 95.090 | 98.632 | 1.00 9.21 |
| ATOM | 1523 | CG | PRO | 4332 | 74.811 | 96.032 | 98.252 | 1.00 12.86 |
| ATOM | 1524 | C | PRO | 4332 | 72.738 | 94.333 | 96.428 | 1.00 9.94 |
| ATOM | 1525 | O | PRO | 4332 | 71.589 | 93.920 | 96.585 | 1.00 23.57 |
| ATOM | 1526 | N | LEU | 4333 | 72.991 | 94.988 | 95.327 | 1.00 2.99 |
| ATOM | 1527 | CA | LEU | 4333 | 71.758 | 95.120 | 94.570 | 1.00 8.02 |
| ATOM | 1528 | CB | LEU | 4333 | 71.507 | 96.603 | 94.290 | 1.00 11.16 |
| ATOM | 1529 | CG | LEU | 4333 | 71.246 | 97.401 | 95.583 | 1.00 10.53 |
| ATOM | 1530 | CD1 | LEU | 4333 | 71.486 | 98.867 | 95.363 | 1.00 14.50 |
| ATOM | 1531 | CD2 | LEU | 4333 | 69.845 | 97.181 | 96.066 | 1.00 6.72 |
| ATOM | 1532 | C | LEU | 4333 | 71.662 | 94.224 | 93.333 | 1.00 11.16 |
| ATOM | 1533 | O | LEU | 4333 | 70.778 | 94.382 | 92.481 | 1.00 9.95 |
| ATOM | 1534 | N | VAL | 4334 | 72.569 | 93.247 | 93.284 | 1.00 8.01 |
| ATOM | 1535 | CA | VAL | 4334 | 72.642 | 92.300 | 92.193 | 1.00 5.93 |
| ATOM | 1536 | CB | VAL | 4334 | 74.063 | 92.183 | 91.727 | 1.00 2.99 |
| ATOM | 1537 | CG1 | VAL | 4334 | 74.161 | 91.233 | 90.547 | 1.00 2.99 |
| ATOM | 1538 | CG2 | VAL | 4334 | 74.552 | 93.555 | 91.378 | 1.00 2.99 |
| ATOM | 1539 | C | VAL | 4334 | 72.116 | 90.926 | 92.589 | 1.00 8.65 |
| ATOM | 1540 | O | VAL | 4334 | 72.802 | 90.137 | 93.233 | 1.00 2.99 |
| ATOM | 1541 | N | LEU | 4335 | 70.880 | 90.665 | 92.173 | 1.00 9.14 |
| ATOM | 1542 | CA | LEU | 4335 | 70.175 | 89.427 | 92.448 | 1.00 7.34 |
| ATOM | 1543 | CB | LEU | 4335 | 68.716 | 89.744 | 92.706 | 1.00 6.12 |
| ATOM | 1544 | CG | LEU | 4335 | 68.562 | 90.814 | 93.772 | 1.00 8.54 |
| ATOM | 1545 | CD1 | LEU | 4335 | 67.080 | 91.058 | 94.033 | 1.00 5.51 |
| ATOM | 1546 | CD2 | LEU | 4335 | 69.285 | 90.364 | 95.045 | 1.00 6.66 |
| ATOM | 1547 | C | LEU | 4335 | 70.263 | 88.424 | 91.312 | 1.00 10.02 |
| ATOM | 1548 | O | LEU | 4335 | 69.981 | 88.737 | 90.154 | 1.00 13.30 |
| ATOM | 1549 | N | LYS | 4336 | 70.641 | 87.202 | 91.645 | 1.00 13.10 |
| ATOM | 1550 | CA | LYS | 4336 | 70.742 | 86.174 | 90.628 | 1.00 15.85 |
| ATOM | 1551 | CB | LYS | 4336 | 72.034 | 85.378 | 90.762 | 1.00 14.82 |
| ATOM | 1552 | CG | LYS | 4336 | 72.036 | 84.119 | 89.926 | 1.00 15.90 |

139

```
ATOM   1553  CD   LYS  4336    73.230  83.261  90.271  1.00 26.88
ATOM   1554  CE   LYS  4336    73.100  81.844  89.732  1.00 25.68
ATOM   1555  NZ   LYS  4336    74.276  81.017  90.153  1.00 25.22
ATOM   1556  C    LYS  4336    69.583  85.218  90.707  1.00 14.65
ATOM   1557  O    LYS  4336    69.234  84.711  91.778  1.00 18.98
ATOM   1558  N    THR  4337    69.001  84.978  89.544  1.00 13.01
ATOM   1559  CA   THR  4337    67.887  84.066  89.375  1.00 11.01
ATOM   1560  CB   THR  4337    67.648  83.881  87.883  1.00  5.42
ATOM   1561  OG1  THR  4337    66.758  84.900  87.441  1.00 13.87
ATOM   1562  CG2  THR  4337    67.091  82.527  87.566  1.00 16.08
ATOM   1563  C    THR  4337    68.145  82.721  90.050  1.00 11.71
ATOM   1564  O    THR  4337    69.282  82.258  90.116  1.00 14.89
ATOM   1565  N    GLY  4338    67.091  82.102  90.566  1.00 13.28
ATOM   1566  CA   GLY  4338    67.250  80.811  91.202  1.00 18.27
ATOM   1567  C    GLY  4338    67.725  80.867  92.637  1.00 23.39
ATOM   1568  O    GLY  4338    67.233  80.107  93.472  1.00 29.63
ATOM   1569  N    VAL  4339    68.686  81.746  92.923  1.00 26.48
ATOM   1570  CA   VAL  4339    69.218  81.916  94.278  1.00 26.27
ATOM   1571  CB   VAL  4339    70.568  82.652  94.261  1.00 28.07
ATOM   1572  CG1  VAL  4339    71.170  82.610  95.638  1.00 25.58
ATOM   1573  CG2  VAL  4339    71.513  82.026  93.246  1.00 27.61
ATOM   1574  C    VAL  4339    68.226  82.776  95.068  1.00 27.29
ATOM   1575  O    VAL  4339    67.527  83.613  94.489  1.00 31.21
ATOM   1576  N    GLN  4340    68.160  82.588  96.383  1.00 28.29
ATOM   1577  CA   GLN  4340    67.213  83.370  97.185  1.00 31.56
ATOM   1578  CB   GLN  4340    66.362  82.448  98.076  1.00 30.25
ATOM   1579  CG   GLN  4340    67.121  81.480  98.950  1.00 34.97
ATOM   1580  CD   GLN  4340    66.197  80.423  99.572  1.00 40.83
ATOM   1581  OE1  GLN  4340    65.463  79.725  98.866  1.00 36.53
ATOM   1582  NE2  GLN  4340    66.243  80.298 100.894  1.00 42.24
ATOM   1583  C    GLN  4340    67.848  84.469  98.015  1.00 30.61
ATOM   1584  O    GLN  4340    68.654  84.207  98.901  1.00 38.09
ATOM   1585  N    PHE  4341    67.463  85.707  97.728  1.00 22.02
ATOM   1586  CA   PHE  4341    68.014  86.851  98.429  1.00 17.36
ATOM   1587  CB   PHE  4341    68.030  88.066  97.498  1.00 19.30
ATOM   1588  CG   PHE  4341    66.692  88.379  96.904  1.00 17.64
ATOM   1589  CD1  PHE  4341    65.864  89.321  97.484  1.00 16.16
ATOM   1590  CD2  PHE  4341    66.232  87.670  95.802  1.00 17.37
ATOM   1591  CE1  PHE  4341    64.594  89.552  96.980  1.00 19.86
ATOM   1592  CE2  PHE  4341    64.974  87.894  95.296  1.00 18.07
ATOM   1593  CZ   PHE  4341    64.148  88.837  95.886  1.00 21.56
ATOM   1594  C    PHE  4341    67.263  87.177  99.695  1.00 14.47
ATOM   1595  O    PHE  4341    66.226  86.583  99.990  1.00  6.78
ATOM   1596  N    THR  4342    67.799  88.155 100.419  1.00 13.34
ATOM   1597  CA   THR  4342    67.248  88.612 101.684  1.00 14.79
ATOM   1598  CB   THR  4342    68.178  88.238 102.833  1.00 16.93
ATOM   1599  OG1  THR  4342    68.238  86.813 102.951  1.00 30.91
ATOM   1600  CG2  THR  4342    67.694  88.835 104.121  1.00 26.33
ATOM   1601  C    THR  4342    67.083  90.120 101.719  1.00 15.95
ATOM   1602  O    THR  4342    68.019  90.864 101.402  1.00 17.12
ATOM   1603  N    VAL  4343    65.901  90.576 102.112  1.00  9.97
ATOM   1604  CA   VAL  4343    65.675  92.002 102.211  1.00  8.23
ATOM   1605  CB   VAL  4343    64.634  92.481 101.228  1.00  6.73
ATOM   1606  CG1  VAL  4343    64.733  93.983 101.087  1.00  4.54
ATOM   1607  CG2  VAL  4343    64.807  91.781  99.909  1.00 10.57
ATOM   1608  C    VAL  4343    65.123  92.216 103.596  1.00  9.38
ATOM   1609  O    VAL  4343    64.559  91.290 104.168  1.00 12.92
ATOM   1610  N    LYS  4344    65.291  93.412 104.155  1.00  9.18
ATOM   1611  CA   LYS  4344    64.735  93.667 105.474  1.00 11.90
ATOM   1612  CB   LYS  4344    65.814  93.734 106.554  1.00 10.50
ATOM   1613  CG   LYS  4344    65.193  93.703 107.957  1.00 14.67
ATOM   1614  CD   LYS  4344    66.184  93.912 109.074  1.00 12.69
ATOM   1615  CE   LYS  4344    65.461  93.923 110.412  1.00 22.94
ATOM   1616  NZ   LYS  4344    66.288  91.407 111.565  1.00 23.90
ATOM   1617  C    LYS  4344    63.934  94.959 105.497  1.00 17.52
ATOM   1618  O    LYS  4344    64.460  96.038 105.192  1.00 14.12
ATOM   1619  N    LEU  4345    62.658  94.878 105.860  1.00 17.99
ATOM   1620  CA   LEU  4345    61.766  95.991 105.936  1.00 20.73
ATOM   1621  CB   LEU  4345    60.401  95.657 105.334  1.00 21.64
ATOM   1622  CG   LEU  4345    60.416  95.184 103.880  1.00 24.52
```

140

```
ATOM   1623  CD1 LEU  4345     58.986  94.991 103.451  1.00 26.85
ATOM   1624  CD2 LEU  4345     61.118  96.190 102.971  1.00 26.03
ATOM   1625  C   LEU  4345     61.586  96.403 107.383  1.00 20.69
ATOM   1626  O   LEU  4345     61.937  95.660 108.287  1.00 24.69
ATOM   1627  N   ARG  4346     61.028  97.583 107.600  1.00 17.11
ATOM   1628  CA  ARG  4346     60.825  98.064 108.947  1.00 17.28
ATOM   1629  CB  ARG  4346     62.168  98.393 109.574  1.00 22.31
ATOM   1630  CG  ARG  4346     62.066  99.047 110.935  1.00 22.31
ATOM   1631  CD  ARG  4346     63.447  99.121 111.519  1.00 22.62
ATOM   1632  NE  ARG  4346     63.474  99.714 112.841  1.00 23.75
ATOM   1633  CZ  ARG  4346     64.597  99.923 113.512  1.00 30.44
ATOM   1634  NH1 ARG  4346     65.760  99.581 112.973  1.00 26.88
ATOM   1635  NH2 ARG  4346     64.566 100.500 114.706  1.00 39.09
ATOM   1636  C   ARG  4346     59.923  99.277 109.044  1.00 18.61
ATOM   1637  O   ARG  4346     59.997 100.189 108.229  1.00 21.79
ATOM   1638  N   LEU  4347     59.070  99.289 110.057  1.00 19.26
ATOM   1639  CA  LEU  4347     58.166 100.406 110.246  1.00 25.09
ATOM   1640  CB  LEU  4347     56.755  99.899 110.545  1.00 17.62
ATOM   1641  CG  LEU  4347     55.649 100.937 110.376  1.00 16.64
ATOM   1642  CD1 LEU  4347     55.711 101.527 108.985  1.00 13.31
ATOM   1643  CD2 LEU  4347     54.309 100.286 110.600  1.00 17.42
ATOM   1644  C   LEU  4347     58.726 101.187 111.420  1.00 29.76
ATOM   1645  O   LEU  4347     58.734 100.695 112.553  1.00 38.29
ATOM   1646  N   LEU  4348     59.202 102.398 111.147  1.00 28.09
ATOM   1647  CA  LEU  4348     59.812 103.230 112.178  1.00 28.01
ATOM   1648  CB  LEU  4348     60.593 104.367 111.521  1.00 23.79
ATOM   1649  CG  LEU  4348     61.731 103.968 110.581  1.00 19.13
ATOM   1650  CD1 LEU  4348     62.225 105.174 109.837  1.00 22.21
ATOM   1651  CD2 LEU  4348     62.855 103.331 111.369  1.00 19.26
ATOM   1652  C   LEU  4348     58.822 103.807 113.168  1.00 31.91
ATOM   1653  O   LEU  4348     59.183 101.655 113.976  1.00 33.58
ATOM   1654  N   VAL  4349     57.580 103.336 113.116  1.00 39.93
ATOM   1655  CA  VAL  4349     56.539 103.844 114.000  1.00 46.27
ATOM   1656  CB  VAL  4349     55.199 103.939 113.249  1.00 45.89
ATOM   1657  CG1 VAL  4349     54.067 104.232 114.206  1.00 44.52
ATOM   1658  CG2 VAL  4349     55.278 105.065 112.231  1.00 47.72
ATOM   1659  C   VAL  4349     56.309 103.161 115.349  1.00 50.99
ATOM   1660  O   VAL  4349     55.866 103.817 116.285  1.00 59.93
ATOM   1661  N   LYS  4350     56.595 101.874 115.485  1.00 52.31
ATOM   1662  CA  LYS  4350     56.385 101.222 116.783  1.00 54.71
ATOM   1663  CB  LYS  4350     57.466 101.624 117.788  1.00 56.20
ATOM   1664  CG  LYS  4350     58.796 100.925 117.677  1.00 62.56
ATOM   1665  CD  LYS  4350     59.692 101.446 118.786  1.00 71.44
ATOM   1666  CE  LYS  4350     61.049 100.777 118.801  1.00 76.32
ATOM   1667  NZ  LYS  4350     61.957 101.356 119.843  1.00 79.68
ATOM   1668  C   LYS  4350     55.044 101.520 117.450  1.00 54.60
ATOM   1669  O   LYS  4350     54.939 102.429 118.266  1.00 55.66
ATOM   1670  N   LEU  4351     54.018 100.762 117.114  1.00 54.06
ATOM   1671  CA  LEU  4351     52.736 100.962 117.753  1.00 56.28
ATOM   1672  CB  LEU  4351     51.749 101.632 116.797  1.00 55.45
ATOM   1673  CG  LEU  4351     52.084 103.095 116.489  1.00 52.96
ATOM   1674  CD1 LEU  4351     50.974 103.707 115.661  1.00 51.94
ATOM   1675  CD2 LEU  4351     52.244 103.872 117.784  1.00 52.53
ATOM   1676  C   LEU  4351     52.245  99.600 118.209  1.00 59.74
ATOM   1677  O   LEU  4351     51.863  98.707 117.400  1.00 60.51
ATOM   1678  N   GLN  4352     52.286  99.380 119.518  1.00 64.18
ATOM   1679  CA  GLN  4352     51.880  98.114 120.112  1.00 68.94
ATOM   1680  CB  GLN  4352     51.502  98.331 121.585  1.00 74.42
ATOM   1681  CG  GLN  4352     51.284  97.045 122.378  1.00 78.27
ATOM   1682  CD  GLN  4352     52.526  96.170 122.416  1.00 80.26
ATOM   1683  OE1 GLN  4352     53.572  96.575 122.930  1.00 82.60
ATOM   1684  NE2 GLN  4352     52.417  94.966 121.863  1.00 81.28
ATOM   1685  C   GLN  4352     50.725  97.452 119.359  1.00 69.59
ATOM   1686  O   GLN  4352     50.874  96.357 118.816  1.00 69.75
ATOM   1687  N   GLU  4353     49.578  98.122 119.322  1.00 68.82
ATOM   1688  CA  GLU  4353     48.409  97.586 118.638  1.00 69.95
ATOM   1689  CB  GLU  4353     47.159  98.395 119.018  1.00 73.68
ATOM   1690  CG  GLU  4353     47.363  99.909 119.120  1.00 77.45
ATOM   1691  CD  GLU  4353     47.877 100.544 117.838  1.00 77.47
ATOM   1692  OE1 GLU  4353     47.200 100.423 116.793  1.00 75.56
```

|41|

| ATOM | 1693 | OE2 | GLU | 4353 | 48.957 | 101.174 | 117.882 | 1.00 | 77.93 |
| ATOM | 1694 | C | GLU | 4353 | 48.561 | 97.529 | 117.124 | 1.00 | 68.69 |
| ATOM | 1695 | O | GLU | 4353 | 47.575 | 97.595 | 116.388 | 1.00 | 72.13 |
| ATOM | 1696 | N | LEU | 4354 | 49.799 | 97.380 | 116.665 | 1.00 | 65.01 |
| ATOM | 1697 | CA | LEU | 4354 | 50.101 | 97.324 | 115.234 | 1.00 | 60.44 |
| ATOM | 1698 | CB | LEU | 4354 | 50.836 | 98.602 | 114.807 | 1.00 | 56.77 |
| ATOM | 1699 | CG | LEU | 4354 | 51.112 | 98.862 | 113.332 | 1.00 | 50.13 |
| ATOM | 1700 | CD1 | LEU | 4354 | 49.804 | 98.979 | 112.593 | 1.00 | 50.28 |
| ATOM | 1701 | CD2 | LEU | 4354 | 51.897 | 100.140 | 113.183 | 1.00 | 48.83 |
| ATOM | 1702 | C | LEU | 4354 | 50.978 | 96.110 | 114.950 | 1.00 | 59.94 |
| ATOM | 1703 | O | LEU | 4354 | 51.461 | 95.926 | 113.839 | 1.00 | 60.64 |
| ATOM | 1704 | N | ASN | 4355 | 51.180 | 95.286 | 115.969 | 1.00 | 58.76 |
| ATOM | 1705 | CA | ASN | 4355 | 51.993 | 94.088 | 115.841 | 1.00 | 55.53 |
| ATOM | 1706 | CB | ASN | 4355 | 52.627 | 93.792 | 117.205 | 1.00 | 57.49 |
| ATOM | 1707 | CG | ASN | 4355 | 53.597 | 92.629 | 117.178 | 1.00 | 59.14 |
| ATOM | 1708 | OD1 | ASN | 4355 | 54.389 | 92.470 | 116.247 | 1.00 | 61.95 |
| ATOM | 1709 | ND2 | ASN | 4355 | 53.568 | 91.829 | 118.231 | 1.00 | 59.56 |
| ATOM | 1710 | C | ASN | 4355 | 51.097 | 92.947 | 115.335 | 1.00 | 53.11 |
| ATOM | 1711 | O | ASN | 4355 | 49.979 | 92.708 | 115.805 | 1.00 | 53.96 |
| ATOM | 1712 | N | TYR | 4356 | 51.597 | 92.215 | 114.346 | 1.00 | 54.40 |
| ATOM | 1713 | CA | TYR | 4356 | 50.881 | 91.111 | 113.703 | 1.00 | 55.90 |
| ATOM | 1714 | CB | TYR | 4356 | 50.474 | 90.024 | 114.709 | 1.00 | 56.40 |
| ATOM | 1715 | CG | TYR | 4356 | 51.635 | 89.349 | 115.402 | 1.00 | 59.31 |
| ATOM | 1716 | CD1 | TYR | 4356 | 52.304 | 89.980 | 116.444 | 1.00 | 61.31 |
| ATOM | 1717 | CE1 | TYR | 4356 | 53.388 | 89.382 | 117.078 | 1.00 | 57.61 |
| ATOM | 1718 | CD2 | TYR | 4356 | 52.082 | 88.090 | 115.001 | 1.00 | 59.91 |
| ATOM | 1719 | CE2 | TYR | 4356 | 53.172 | 87.480 | 115.630 | 1.00 | 59.50 |
| ATOM | 1720 | CZ | TYR | 4356 | 53.817 | 88.139 | 116.673 | 1.00 | 58.37 |
| ATOM | 1721 | OH | TYR | 4356 | 54.879 | 87.564 | 117.333 | 1.00 | 57.81 |
| ATOM | 1722 | C | TYR | 4356 | 49.643 | 91.558 | 112.926 | 1.00 | 53.74 |
| ATOM | 1723 | O | TYR | 4356 | 48.705 | 90.781 | 112.757 | 1.00 | 54.38 |
| ATOM | 1724 | N | ASN | 4357 | 49.642 | 92.801 | 112.451 | 1.00 | 50.64 |
| ATOM | 1725 | CA | ASN | 4357 | 48.512 | 93.313 | 111.680 | 1.00 | 52.33 |
| ATOM | 1726 | CB | ASN | 4357 | 47.907 | 94.541 | 112.355 | 1.00 | 52.50 |
| ATOM | 1727 | CG | ASN | 4357 | 47.102 | 94.188 | 113.574 | 1.00 | 52.86 |
| ATOM | 1728 | OD1 | ASN | 4357 | 46.155 | 93.409 | 113.495 | 1.00 | 51.37 |
| ATOM | 1729 | ND2 | ASN | 4357 | 47.464 | 94.762 | 114.711 | 1.00 | 55.42 |
| ATOM | 1730 | C | ASN | 4357 | 48.886 | 93.664 | 110.249 | 1.00 | 52.73 |
| ATOM | 1731 | O | ASN | 4357 | 48.108 | 93.437 | 109.313 | 1.00 | 51.42 |
| ATOM | 1732 | N | LEU | 4358 | 50.080 | 94.222 | 110.082 | 1.00 | 49.89 |
| ATOM | 1733 | CA | LEU | 4358 | 50.550 | 94.605 | 108.762 | 1.00 | 44.67 |
| ATOM | 1734 | CB | LEU | 4358 | 51.626 | 95.673 | 108.889 | 1.00 | 43.24 |
| ATOM | 1735 | CG | LEU | 4358 | 51.130 | 96.909 | 109.625 | 1.00 | 41.27 |
| ATOM | 1736 | CD1 | LEU | 4358 | 52.279 | 97.868 | 109.844 | 1.00 | 43.21 |
| ATOM | 1737 | CD2 | LEU | 4358 | 50.017 | 97.557 | 108.825 | 1.00 | 44.97 |
| ATOM | 1738 | C | LEU | 4358 | 51.092 | 93.413 | 107.993 | 1.00 | 41.77 |
| ATOM | 1739 | O | LEU | 4358 | 52.091 | 92.809 | 108.371 | 1.00 | 43.56 |
| ATOM | 1740 | N | LYS | 4359 | 50.412 | 93.076 | 106.910 | 1.00 | 41.02 |
| ATOM | 1741 | CA | LYS | 4359 | 50.818 | 91.969 | 106.072 | 1.00 | 38.85 |
| ATOM | 1742 | CB | LYS | 4359 | 49.572 | 91.237 | 105.587 | 1.00 | 42.51 |
| ATOM | 1743 | CG | LYS | 4359 | 49.818 | 89.929 | 104.875 | 1.00 | 51.75 |
| ATOM | 1744 | CD | LYS | 4359 | 48.490 | 89.259 | 104.581 | 1.00 | 57.82 |
| ATOM | 1745 | CE | LYS | 4359 | 48.675 | 87.884 | 103.980 | 1.00 | 62.48 |
| ATOM | 1746 | NZ | LYS | 4359 | 47.350 | 87.249 | 103.734 | 1.00 | 68.22 |
| ATOM | 1747 | C | LYS | 4359 | 51.584 | 92.585 | 104.900 | 1.00 | 39.79 |
| ATOM | 1748 | O | LYS | 4359 | 51.042 | 93.420 | 104.168 | 1.00 | 44.17 |
| ATOM | 1749 | N | VAL | 4360 | 52.848 | 92.200 | 104.736 | 1.00 | 34.84 |
| ATOM | 1750 | CA | VAL | 4360 | 53.652 | 92.742 | 103.655 | 1.00 | 26.87 |
| ATOM | 1751 | CB | VAL | 4360 | 55.077 | 92.993 | 104.107 | 1.00 | 22.94 |
| ATOM | 1752 | CG1 | VAL | 4360 | 55.892 | 93.572 | 102.953 | 1.00 | 16.57 |
| ATOM | 1753 | CG2 | VAL | 4360 | 55.074 | 93.931 | 105.297 | 1.00 | 18.83 |
| ATOM | 1754 | C | VAL | 4360 | 53.688 | 91.800 | 102.470 | 1.00 | 27.93 |
| ATOM | 1755 | O | VAL | 4360 | 53.816 | 90.591 | 102.641 | 1.00 | 29.28 |
| ATOM | 1756 | N | LYS | 4361 | 53.579 | 92.364 | 101.269 | 1.00 | 28.24 |
| ATOM | 1757 | CA | LYS | 4361 | 53.594 | 91.588 | 100.033 | 1.00 | 26.64 |
| ATOM | 1758 | CB | LYS | 4361 | 52.279 | 91.737 | 99.281 | 1.00 | 33.43 |
| ATOM | 1759 | CG | LYS | 4361 | 51.077 | 92.021 | 100.161 | 1.00 | 46.46 |
| ATOM | 1760 | CD | LYS | 4361 | 49.942 | 92.568 | 99.315 | 1.00 | 51.10 |
| ATOM | 1761 | CE | LYS | 4361 | 48.803 | 93.106 | 100.162 | 1.00 | 54.54 |
| ATOM | 1762 | NZ | LYS | 4361 | 47.780 | 93.764 | 99.292 | 1.00 | 56.08 |

142

| | | | | | | | | |
|---|---|---|---|---|---|---|---|---|
| ATOM | 1763 | C | LYS | 4361 | 54.701 | 92.169 | 99.167 | 1.00 21.39 |
| ATOM | 1764 | O | LYS | 4361 | 54.753 | 93.389 | 98.982 | 1.00 20.87 |
| ATOM | 1765 | N | VAL | 4362 | 55.565 | 91.308 | 98.625 | 1.00 18.92 |
| ATOM | 1766 | CA | VAL | 4362 | 56.666 | 91.752 | 97.763 | 1.00 10.25 |
| ATOM | 1767 | CB | VAL | 4362 | 57.888 | 90.842 | 97.863 | 1.00 5.35 |
| ATOM | 1768 | CG1 | VAL | 4362 | 59.035 | 91.480 | 97.163 | 1.00 11.99 |
| ATOM | 1769 | CG2 | VAL | 4362 | 58.247 | 90.521 | 99.289 | 1.00 8.53 |
| ATOM | 1770 | C | VAL | 4362 | 56.223 | 91.683 | 96.319 | 1.00 9.21 |
| ATOM | 1771 | O | VAL | 4362 | 55.725 | 90.660 | 95.884 | 1.00 12.58 |
| ATOM | 1772 | N | LEU | 4363 | 56.398 | 92.772 | 95.578 | 1.00 13.08 |
| ATOM | 1773 | CA | LEU | 4363 | 56.029 | 92.813 | 94.158 | 1.00 13.14 |
| ATOM | 1774 | CB | LEU | 4363 | 54.977 | 93.878 | 93.892 | 1.00 14.01 |
| ATOM | 1775 | CG | LEU | 4363 | 53.566 | 93.509 | 94.328 | 1.00 20.44 |
| ATOM | 1776 | CD1 | LEU | 4363 | 53.526 | 93.221 | 95.811 | 1.00 19.51 |
| ATOM | 1777 | CD2 | LEU | 4363 | 52.635 | 94.646 | 93.976 | 1.00 25.52 |
| ATOM | 1778 | C | LEU | 4363 | 57.235 | 93.114 | 93.302 | 1.00 17.48 |
| ATOM | 1779 | O | LEU | 4363 | 58.190 | 93.738 | 93.770 | 1.00 15.89 |
| ATOM | 1780 | N | PHE | 4364 | 57.211 | 92.667 | 92.049 | 1.00 21.53 |
| ATOM | 1781 | CA | PHE | 4364 | 58.343 | 92.946 | 91.180 | 1.00 23.17 |
| ATOM | 1782 | CB | PHE | 4364 | 58.909 | 91.672 | 90.592 | 1.00 18.87 |
| ATOM | 1783 | CG | PHE | 4364 | 60.354 | 91.788 | 90.232 | 1.00 16.83 |
| ATOM | 1784 | CD1 | PHE | 4364 | 61.305 | 92.003 | 91.225 | 1.00 14.05 |
| ATOM | 1785 | CD2 | PHE | 4364 | 60.777 | 91.671 | 88.918 | 1.00 12.42 |
| ATOM | 1786 | CE1 | PHE | 4364 | 62.651 | 92.092 | 90.914 | 1.00 13.05 |
| ATOM | 1787 | CE2 | PHE | 4364 | 62.128 | 91.762 | 88.599 | 1.00 15.07 |
| ATOM | 1788 | CZ | PHE | 4364 | 63.064 | 91.970 | 89.598 | 1.00 9.70 |
| ATOM | 1789 | C | PHE | 4364 | 57.982 | 93.908 | 90.060 | 1.00 25.21 |
| ATOM | 1790 | O | PHE | 4364 | 56.925 | 93.796 | 89.449 | 1.00 28.66 |
| ATOM | 1791 | N | ASP | 4365 | 58.880 | 94.853 | 89.803 | 1.00 28.53 |
| ATOM | 1792 | CA | ASP | 4365 | 58.691 | 95.886 | 88.785 | 1.00 31.89 |
| ATOM | 1793 | CB | ASP | 4365 | 59.001 | 95.349 | 87.382 | 1.00 31.91 |
| ATOM | 1794 | CG | ASP | 4365 | 60.457 | 94.929 | 87.220 | 1.00 37.15 |
| ATOM | 1795 | OD1 | ASP | 4365 | 61.348 | 95.651 | 87.724 | 1.00 32.82 |
| ATOM | 1796 | OD2 | ASP | 4365 | 60.712 | 93.887 | 86.566 | 1.00 42.62 |
| ATOM | 1797 | C | ASP | 4365 | 57.315 | 96.567 | 88.784 | 1.00 32.21 |
| ATOM | 1798 | O | ASP | 4365 | 56.742 | 96.822 | 87.727 | 1.00 31.36 |
| ATOM | 1799 | N | LYS | 4366 | 56.794 | 96.872 | 89.970 | 1.00 34.07 |
| ATOM | 1800 | CA | LYS | 4366 | 55.509 | 97.553 | 90.083 | 1.00 35.19 |
| ATOM | 1801 | CB | LYS | 4366 | 55.075 | 97.645 | 91.546 | 1.00 32.45 |
| ATOM | 1802 | CG | LYS | 4366 | 53.786 | 98.426 | 91.755 | 1.00 26.06 |
| ATOM | 1803 | CD | LYS | 4366 | 53.534 | 98.735 | 93.224 | 1.00 30.87 |
| ATOM | 1804 | CE | LYS | 4366 | 52.314 | 99.631 | 93.397 | 1.00 30.66 |
| ATOM | 1805 | NZ | LYS | 4366 | 52.048 | 99.938 | 94.826 | 1.00 36.42 |
| ATOM | 1806 | C | LYS | 4366 | 55.681 | 98.966 | 89.528 | 1.00 42.03 |
| ATOM | 1807 | O | LYS | 4366 | 56.609 | 99.677 | 89.919 | 1.00 44.46 |
| ATOM | 1808 | N | ASP | 4367 | 54.792 | 99.375 | 88.624 | 1.00 46.03 |
| ATOM | 1809 | CA | ASP | 4367 | 54.866 | 100.708 | 88.031 | 1.00 48.28 |
| ATOM | 1810 | CB | ASP | 4367 | 54.656 | 101.789 | 89.096 | 1.00 46.87 |
| ATOM | 1811 | CG | ASP | 4367 | 53.334 | 101.649 | 89.820 | 1.00 47.26 |
| ATOM | 1812 | OD1 | ASP | 4367 | 52.279 | 101.571 | 89.153 | 1.00 45.49 |
| ATOM | 1813 | OD2 | ASP | 4367 | 53.356 | 101.634 | 91.069 | 1.00 48.05 |
| ATOM | 1814 | C | ASP | 4367 | 56.220 | 100.933 | 87.361 | 1.00 50.33 |
| ATOM | 1815 | O | ASP | 4367 | 56.924 | 101.905 | 87.649 | 1.00 53.11 |
| ATOM | 1816 | N | VAL | 4368 | 56.590 | 100.003 | 86.474 | 1.00 50.69 |
| ATOM | 1817 | CA | VAL | 4368 | 57.852 | 100.138 | 85.774 | 1.00 50.06 |
| ATOM | 1818 | CB | VAL | 4368 | 58.770 | 98.943 | 86.086 | 1.00 46.12 |
| ATOM | 1819 | CG1 | VAL | 4368 | 60.007 | 98.991 | 85.209 | 1.00 47.56 |
| ATOM | 1820 | CG2 | VAL | 4368 | 59.177 | 98.983 | 87.544 | 1.00 39.85 |
| ATOM | 1821 | C | VAL | 4368 | 57.556 | 100.203 | 84.291 | 1.00 53.94 |
| ATOM | 1822 | O | VAL | 4368 | 57.358 | 99.184 | 83.634 | 1.00 54.08 |
| ATOM | 1823 | N | ASN | 4369 | 57.516 | 101.422 | 83.773 | 1.00 58.96 |
| ATOM | 1824 | CA | ASN | 4369 | 57.225 | 101.645 | 82.370 | 1.00 62.71 |
| ATOM | 1825 | CB | ASN | 4369 | 57.103 | 103.146 | 82.114 | 1.00 64.34 |
| ATOM | 1826 | CG | ASN | 4369 | 55.998 | 103.778 | 82.940 | 1.00 69.13 |
| ATOM | 1827 | OD1 | ASN | 4369 | 54.821 | 103.440 | 82.784 | 1.00 72.28 |
| ATOM | 1828 | ND2 | ASN | 4369 | 56.371 | 104.687 | 83.836 | 1.00 70.37 |
| ATOM | 1829 | C | ASN | 4369 | 58.253 | 101.018 | 81.437 | 1.00 63.40 |
| ATOM | 1830 | O | ASN | 4369 | 57.928 | 100.656 | 80.307 | 1.00 65.70 |
| ATOM | 1831 | N | GLU | 4370 | 59.488 | 100.879 | 81.910 | 1.00 62.50 |
| ATOM | 1832 | CA | GLU | 4370 | 60.541 | 100.286 | 81.096 | 1.00 62.56 |

143

| | | | | | | | | |
|---|---|---|---|---|---|---|---|---|
| ATOM | 1833 | CB   | GLU | 4370 | 61.820 | 100.106 | 81.918 | 1.00 61.79 |
| ATOM | 1834 | CG   | GLU | 4370 | 62.580 | 101.393 | 82.236 | 1.00 64.67 |
| ATOM | 1835 | CD   | GLU | 4370 | 61.749 | 102.442 | 82.966 | 1.00 65.82 |
| ATOM | 1836 | OE1  | GLU | 4370 | 61.104 | 102.104 | 83.980 | 1.00 67.32 |
| ATOM | 1837 | OE2  | GLU | 4370 | 61.758 | 103.617 | 82.536 | 1.00 64.04 |
| ATOM | 1838 | C    | GLU | 4370 | 60.089 | 98.938  | 80.539 | 1.00 62.89 |
| ATOM | 1839 | O    | GLU | 4370 | 60.674 | 98.426  | 79.586 | 1.00 60.42 |
| ATOM | 1840 | N    | ARG | 4371 | 59.048 | 98.371  | 81.142 | 1.00 64.29 |
| ATOM | 1841 | CA   | ARG | 4371 | 58.501 | 97.089  | 80.702 | 1.00 65.30 |
| ATOM | 1842 | CB   | ARG | 4371 | 57.295 | 96.690  | 81.551 | 1.00 67.73 |
| ATOM | 1843 | CG   | ARG | 4371 | 57.548 | 96.367  | 83.008 | 1.00 67.61 |
| ATOM | 1844 | CD   | ARG | 4371 | 56.209 | 96.037  | 83.630 | 1.00 72.25 |
| ATOM | 1845 | NE   | ARG | 4371 | 56.292 | 95.565  | 85.003 | 1.00 81.24 |
| ATOM | 1846 | CZ   | ARG | 4371 | 55.244 | 95.128  | 85.700 | 1.00 87.21 |
| ATOM | 1847 | NH1  | ARG | 4371 | 54.037 | 95.108  | 85.145 | 1.00 88.15 |
| ATOM | 1848 | NH2  | ARG | 4371 | 55.401 | 94.701  | 86.948 | 1.00 91.06 |
| ATOM | 1849 | C    | ARG | 4371 | 58.036 | 97.197  | 79.257 | 1.00 64.60 |
| ATOM | 1850 | O    | ARG | 4371 | 58.336 | 96.339  | 78.426 | 1.00 63.97 |
| ATOM | 1851 | N    | ASN | 4372 | 57.282 | 98.255  | 78.975 | 1.00 62.72 |
| ATOM | 1852 | CA   | ASN | 4372 | 56.759 | 98.499  | 77.637 | 1.00 61.95 |
| ATOM | 1853 | CB   | ASN | 4372 | 55.442 | 99.268  | 77.722 | 1.00 63.07 |
| ATOM | 1854 | CG   | ASN | 4372 | 54.474 | 98.641  | 78.691 | 1.00 63.91 |
| ATOM | 1855 | OD1  | ASN | 4372 | 54.125 | 97.471  | 78.554 | 1.00 64.48 |
| ATOM | 1856 | ND2  | ASN | 4372 | 54.035 | 99.416  | 79.684 | 1.00 61.34 |
| ATOM | 1857 | C    | ASN | 4372 | 57.765 | 99.327  | 76.850 | 1.00 60.95 |
| ATOM | 1858 | O    | ASN | 4372 | 58.301 | 98.883  | 75.830 | 1.00 63.68 |
| ATOM | 1859 | N    | THR | 4373 | 58.017 | 100.533 | 77.346 | 1.00 57.61 |
| ATOM | 1860 | CA   | THR | 4373 | 58.941 | 101.459 | 76.714 | 1.00 53.62 |
| ATOM | 1861 | CB   | THR | 4373 | 59.198 | 102.666 | 77.625 | 1.00 53.88 |
| ATOM | 1862 | OG1  | THR | 4373 | 57.998 | 103.447 | 77.713 | 1.00 54.31 |
| ATOM | 1863 | CG2  | THR | 4373 | 60.343 | 103.521 | 77.087 | 1.00 54.97 |
| ATOM | 1864 | C    | THR | 4373 | 60.275 | 100.870 | 76.283 | 1.00 48.96 |
| ATOM | 1865 | O    | THR | 4373 | 60.778 | 101.208 | 75.218 | 1.00 51.44 |
| ATOM | 1866 | N    | VAL | 4374 | 60.859 | 99.994  | 77.088 | 1.00 43.88 |
| ATOM | 1867 | CA   | VAL | 4374 | 62.140 | 99.426  | 76.698 | 1.00 40.92 |
| ATOM | 1868 | CB   | VAL | 4374 | 63.079 | 99.251  | 77.910 | 1.00 41.09 |
| ATOM | 1869 | CG1  | VAL | 4374 | 64.449 | 98.753  | 77.439 | 1.00 37.84 |
| ATOM | 1870 | CG2  | VAL | 4374 | 63.220 | 100.573 | 78.653 | 1.00 37.11 |
| ATOM | 1871 | C    | VAL | 4374 | 62.021 | 98.096  | 75.955 | 1.00 39.43 |
| ATOM | 1872 | O    | VAL | 4374 | 61.318 | 97.177  | 76.381 | 1.00 36.07 |
| ATOM | 1873 | N    | LYS | 4375 | 62.728 | 98.020  | 74.833 | 1.00 37.35 |
| ATOM | 1874 | CA   | LYS | 4375 | 62.740 | 96.814  | 73.980 | 1.00 36.81 |
| ATOM | 1875 | CB   | LYS | 4375 | 63.281 | 97.242  | 72.607 | 1.00 40.06 |
| ATOM | 1876 | CG   | LYS | 4375 | 63.255 | 96.168  | 71.528 | 1.00 42.28 |
| ATOM | 1877 | CD   | LYS | 4375 | 63.764 | 96.776  | 70.228 | 1.00 47.85 |
| ATOM | 1878 | CE   | LYS | 4375 | 63.795 | 95.804  | 69.065 | 1.00 50.57 |
| ATOM | 1879 | NZ   | LYS | 4375 | 64.338 | 96.486  | 67.846 | 1.00 51.16 |
| ATOM | 1880 | C    | LYS | 4375 | 63.612 | 95.773  | 74.616 | 1.00 35.26 |
| ATOM | 1881 | O    | LYS | 4375 | 64.551 | 96.092  | 75.334 | 1.00 36.20 |
| ATOM | 1882 | N    | GLY | 4376 | 63.287 | 94.509  | 74.360 | 1.00 35.25 |
| ATOM | 1883 | CA   | GLY | 4376 | 64.047 | 93.401  | 74.912 | 1.00 32.11 |
| ATOM | 1884 | C    | GLY | 4376 | 63.913 | 93.214  | 76.416 | 1.00 33.07 |
| ATOM | 1885 | O    | GLY | 4376 | 64.199 | 92.139  | 76.938 | 1.00 36.31 |
| ATOM | 1886 | N    | PHE | 4377 | 63.477 | 94.263  | 77.105 | 1.00 30.18 |
| ATOM | 1887 | CA   | PHE | 4377 | 63.298 | 94.272  | 78.558 | 1.00 29.04 |
| ATOM | 1888 | CB   | PHE | 4377 | 62.401 | 95.453  | 78.918 | 1.00 29.63 |
| ATOM | 1889 | CG   | PHE | 4377 | 62.509 | 95.894  | 80.341 | 1.00 29.50 |
| ATOM | 1890 | CD1  | PHE | 4377 | 63.661 | 96.522  | 80.797 | 1.00 21.28 |
| ATOM | 1891 | CD2  | PHE | 4377 | 61.449 | 95.695  | 81.229 | 1.00 31.91 |
| ATOM | 1892 | CE1  | PHE | 4377 | 63.756 | 96.946  | 82.113 | 1.00 27.42 |
| ATOM | 1893 | CE2  | PHE | 4377 | 61.534 | 96.115  | 82.559 | 1.00 28.74 |
| ATOM | 1894 | CZ   | PHE | 4377 | 62.689 | 96.742  | 82.999 | 1.00 28.78 |
| ATOM | 1895 | C    | PHE | 4377 | 62.666 | 92.969  | 79.074 | 1.00 32.87 |
| ATOM | 1896 | O    | PHE | 4377 | 61.566 | 92.606  | 78.646 | 1.00 35.87 |
| ATOM | 1897 | N    | ARG | 4378 | 63.338 | 92.273  | 79.996 | 1.00 29.24 |
| ATOM | 1898 | CA   | ARG | 4378 | 62.803 | 91.016  | 80.540 | 1.00 27.11 |
| ATOM | 1899 | CB   | ARG | 4378 | 63.941 | 90.035  | 80.789 | 1.00 22.72 |
| ATOM | 1900 | CG   | ARG | 4378 | 65.182 | 90.720  | 81.214 | 1.00 28.51 |
| ATOM | 1901 | CD   | ARG | 4378 | 66.314 | 89.788  | 81.543 | 1.00 28.35 |
| ATOM | 1902 | NE   | ARG | 4378 | 67.387 | 90.599  | 82.096 | 1.00 38.26 |

```
ATOM  1903  CZ   ARG  4378    68.374  90.137  82.845  1.00 43.91
ATOM  1904  NH1  ARG  4378    68.439  88.851  83.142  1.00 46.76
ATOM  1905  NH2  ARG  4378    69.281  90.973  83.327  1.00 50.80
ATOM  1906  C    ARG  4378    61.948  91.167  81.799  1.00 25.36
ATOM  1907  O    ARG  4378    62.092  92.134  82.529  1.00 24.57
ATOM  1908  N    LYS  4379    61.047  90.217  82.020  1.00 28.34
ATOM  1909  CA   LYS  4379    60.121  90.190  83.159  1.00 26.00
ATOM  1910  CB   LYS  4379    58.697  89.953  82.690  1.00 27.01
ATOM  1911  CG   LYS  4379    58.156  90.874  81.631  1.00 34.28
ATOM  1912  CD   LYS  4379    56.738  90.384  81.296  1.00 46.71
ATOM  1913  CE   LYS  4379    55.962  91.307  80.353  1.00 54.74
ATOM  1914  NZ   LYS  4379    54.564  90.805  80.149  1.00 50.35
ATOM  1915  C    LYS  4379    60.435  89.042  84.101  1.00 26.76
ATOM  1916  O    LYS  4379    60.823  87.968  83.662  1.00 29.98
ATOM  1917  N    PHE  4380    60.247  89.242  85.396  1.00 26.63
ATOM  1918  CA   PHE  4380    60.501  88.150  86.330  1.00 26.29
ATOM  1919  CB   PHE  4380    61.834  88.329  87.063  1.00 18.88
ATOM  1920  CG   PHE  4380    63.014  88.476  86.159  1.00 13.37
ATOM  1921  CD1  PHE  4380    63.233  89.655  85.463  1.00 11.67
ATOM  1922  CD2  PHE  4380    63.924  87.433  86.012  1.00 16.55
ATOM  1923  CE1  PHE  4380    64.348  89.796  84.633  1.00 12.69
ATOM  1924  CE2  PHE  4380    65.043  87.565  85.184  1.00 11.78
ATOM  1925  CZ   PHE  4380    65.252  88.754  84.494  1.00 11.17
ATOM  1926  C    PHE  4380    59.387  88.041  87.361  1.00 28.67
ATOM  1927  O    PHE  4380    58.580  88.953  87.525  1.00 31.55
ATOM  1928  N    ASN  4381    59.343  86.914  88.053  1.00 30.25
ATOM  1929  CA   ASN  4381    58.343  86.706  89.078  1.00 31.33
ATOM  1930  CB   ASN  4381    57.470  85.510  88.745  1.00 33.57
ATOM  1931  CG   ASN  4381    56.725  85.676  87.465  1.00 38.93
ATOM  1932  OD1  ASN  4381    55.884  86.567  87.336  1.00 36.52
ATOM  1933  ND2  ASN  4381    57.020  84.812  86.496  1.00 40.24
ATOM  1934  C    ASN  4381    59.077  86.390  90.354  1.00 33.90
ATOM  1935  O    ASN  4381    60.089  85.685  90.328  1.00 36.66
ATOM  1936  N    ILE  4382    58.582  86.909  91.473  1.00 36.07
ATOM  1937  CA   ILE  4382    59.197  86.596  92.749  1.00 36.19
ATOM  1938  CB   ILE  4382    58.669  87.482  93.854  1.00 33.46
ATOM  1939  CG2  ILE  4382    59.435  87.215  95.120  1.00 32.20
ATOM  1940  CG1  ILE  4382    58.867  88.942  93.452  1.00 32.92
ATOM  1941  CD1  ILE  4382    58.217  89.929  94.366  1.00 38.75
ATOM  1942  C    ILE  4382    58.705  85.171  92.894  1.00 38.26
ATOM  1943  O    ILE  4382    57.838  84.746  92.135  1.00 39.98
ATOM  1944  N    LEU  4383    59.209  84.411  93.848  1.00 39.32
ATOM  1945  CA   LEU  4383    58.761  83.032  93.866  1.00 39.96
ATOM  1946  CB   LEU  4383    59.793  82.202  93.111  1.00 35.43
ATOM  1947  CG   LEU  4383    59.476  80.839  92.542  1.00 28.20
ATOM  1948  CD1  LEU  4383    58.457  80.997  91.449  1.00 30.05
ATOM  1949  CD2  LEU  4383    60.745  80.239  91.977  1.00 25.53
ATOM  1950  C    LEU  4383    58.521  82.438  95.235  1.00 45.09
ATOM  1951  O    LEU  4383    57.413  81.970  95.513  1.00 48.97
ATOM  1952  N    GLY  4384    59.559  82.459  96.074  1.00 46.02
ATOM  1953  CA   GLY  4384    59.487  81.899  97.420  1.00 50.15
ATOM  1954  C    GLY  4384    58.280  82.257  98.272  1.00 53.37
ATOM  1955  O    GLY  4384    57.182  81.705  98.077  1.00 55.71
ATOM  1956  N    THR  4385    58.478  83.142  99.241  1.00 53.98
ATOM  1957  CA   THR  4385    57.378  83.564 100.102  1.00 58.55
ATOM  1958  CB   THR  4385    57.742  83.352 101.602  1.00 57.59
ATOM  1959  OG1  THR  4385    57.957  81.954 101.855  1.00 53.16
ATOM  1960  CG2  THR  4385    56.621  83.833 102.494  1.00 59.42
ATOM  1961  C    THR  4385    57.024  85.037  99.822  1.00 61.02
ATOM  1962  O    THR  4385    57.591  85.951 100.416  1.00 60.96
ATOM  1963  N    HIS  4386    56.081  85.253  98.907  1.00 61.46
ATOM  1964  CA   HIS  4386    55.671  86.599  98.517  1.00 61.45
ATOM  1965  CB   HIS  4386    54.494  86.550  97.545  1.00 68.04
ATOM  1966  CG   HIS  4386    54.674  85.616  96.394  1.00 77.37
ATOM  1967  CD2  HIS  4386    55.698  84.800  96.047  1.00 81.75
ATOM  1968  ND1  HIS  4386    53.687  85.410  95.449  1.00 82.22
ATOM  1969  CE1  HIS  4386    54.094  84.510  94.577  1.00 83.92
ATOM  1970  NE2  HIS  4386    55.312  84.121  94.914  1.00 85.42
ATOM  1971  C    HIS  4386    55.228  87.468  99.690  1.00 59.77
ATOM  1972  O    HIS  4386    55.257  89.698  99.596  1.00 59.09
```

145

| | | | | | | | | |
|---|---|---|---|---|---|---|---|---|
| ATOM | 1973 | N | THR | 4387 | 54.797 | 86.836 | 100.781 | 1.00 55.81 |
| ATOM | 1974 | CA | THR | 4387 | 54.289 | 87.577 | 101.937 | 1.00 51.63 |
| ATOM | 1975 | CB | THR | 4387 | 52.773 | 87.369 | 102.100 | 1.00 51.51 |
| ATOM | 1976 | OG1 | THR | 4387 | 52.095 | 87.810 | 100.919 | 1.00 54.34 |
| ATOM | 1977 | CG2 | THR | 4387 | 52.255 | 88.148 | 103.291 | 1.00 55.32 |
| ATOM | 1978 | C | THR | 4387 | 54.915 | 87.199 | 103.260 | 1.00 48.89 |
| ATOM | 1979 | O | THR | 4387 | 55.344 | 86.068 | 103.443 | 1.00 52.20 |
| ATOM | 1980 | N | LYS | 4388 | 54.942 | 88.150 | 104.189 | 1.00 46.57 |
| ATOM | 1981 | CA | LYS | 4388 | 55.490 | 87.911 | 105.519 | 1.00 45.76 |
| ATOM | 1982 | CB | LYS | 4388 | 57.015 | 87.882 | 105.471 | 1.00 41.96 |
| ATOM | 1983 | CG | LYS | 4388 | 57.664 | 87.206 | 106.663 | 1.00 35.19 |
| ATOM | 1984 | CD | LYS | 4388 | 59.150 | 87.042 | 106.414 | 1.00 34.53 |
| ATOM | 1985 | CE | LYS | 4388 | 59.769 | 86.065 | 107.387 | 1.00 37.59 |
| ATOM | 1986 | NZ | LYS | 4388 | 59.583 | 86.494 | 108.795 | 1.00 42.90 |
| ATOM | 1987 | C | LYS | 4388 | 55.019 | 89.008 | 106.467 | 1.00 48.59 |
| ATOM | 1988 | O | LYS | 4388 | 55.283 | 90.190 | 106.245 | 1.00 53.42 |
| ATOM | 1989 | N | VAL | 4389 | 54.310 | 88.601 | 107.517 | 1.00 46.90 |
| ATOM | 1990 | CA | VAL | 4389 | 53.771 | 89.510 | 108.526 | 1.00 42.32 |
| ATOM | 1991 | CB | VAL | 4389 | 52.837 | 88.749 | 109.474 | 1.00 41.35 |
| ATOM | 1992 | CG1 | VAL | 4389 | 52.186 | 89.710 | 110.442 | 1.00 43.11 |
| ATOM | 1993 | CG2 | VAL | 4389 | 51.800 | 87.985 | 108.670 | 1.00 41.17 |
| ATOM | 1994 | C | VAL | 4389 | 54.861 | 90.176 | 109.367 | 1.00 41.51 |
| ATOM | 1995 | O | VAL | 4389 | 55.852 | 89.546 | 109.734 | 1.00 43.60 |
| ATOM | 1996 | N | MET | 4390 | 54.679 | 91.452 | 109.684 | 1.00 38.14 |
| ATOM | 1997 | CA | MET | 4390 | 55.669 | 92.149 | 110.484 | 1.00 39.84 |
| ATOM | 1998 | CB | MET | 4390 | 55.632 | 93.644 | 110.185 | 1.00 39.79 |
| ATOM | 1999 | CG | MET | 4390 | 56.259 | 93.994 | 108.844 | 1.00 42.83 |
| ATOM | 2000 | SD | MET | 4390 | 56.520 | 95.758 | 108.572 | 1.00 39.18 |
| ATOM | 2001 | CE | MET | 4390 | 54.848 | 96.311 | 108.521 | 1.00 34.80 |
| ATOM | 2002 | C | MET | 4390 | 55.504 | 91.912 | 111.973 | 1.00 41.88 |
| ATOM | 2003 | O | MET | 4390 | 54.393 | 91.960 | 112.489 | 1.00 45.14 |
| ATOM | 2004 | N | ASN | 4391 | 56.619 | 91.650 | 112.653 | 1.00 44.60 |
| ATOM | 2005 | CA | ASN | 4391 | 56.630 | 91.397 | 114.094 | 1.00 48.82 |
| ATOM | 2006 | CB | ASN | 4391 | 57.211 | 90.021 | 114.421 | 1.00 54.79 |
| ATOM | 2007 | CG | ASN | 4391 | 56.590 | 88.907 | 113.631 | 1.00 60.64 |
| ATOM | 2008 | OD1 | ASN | 4391 | 55.379 | 88.678 | 113.688 | 1.00 65.87 |
| ATOM | 2009 | ND2 | ASN | 4391 | 57.425 | 88.183 | 112.892 | 1.00 61.10 |
| ATOM | 2010 | C | ASN | 4391 | 57.558 | 92.379 | 114.774 | 1.00 50.32 |
| ATOM | 2011 | O | ASN | 4391 | 58.079 | 93.307 | 114.163 | 1.00 50.01 |
| ATOM | 2012 | N | MET | 4392 | 57.766 | 92.132 | 116.060 | 1.00 54.16 |
| ATOM | 2013 | CA | MET | 4392 | 58.689 | 92.896 | 116.883 | 1.00 60.31 |
| ATOM | 2014 | CB | MET | 4392 | 57.959 | 93.692 | 117.969 | 1.00 56.19 |
| ATOM | 2015 | CG | MET | 4392 | 57.230 | 94.911 | 117.436 | 1.00 56.19 |
| ATOM | 2016 | SD | MET | 4392 | 56.598 | 95.995 | 118.717 | 1.00 52.44 |
| ATOM | 2017 | CE | MET | 4392 | 55.515 | 94.850 | 119.564 | 1.00 56.97 |
| ATOM | 2018 | C | MET | 4392 | 59.563 | 91.820 | 117.507 | 1.00 64.97 |
| ATOM | 2019 | O | MET | 4392 | 60.567 | 92.099 | 118.160 | 1.00 65.93 |
| ATOM | 2020 | N | GLU | 4393 | 59.164 | 90.575 | 117.262 | 1.00 73.18 |
| ATOM | 2021 | CA | GLU | 4393 | 59.861 | 89.404 | 117.771 | 1.00 80.67 |
| ATOM | 2022 | CB | GLU | 4393 | 58.918 | 88.194 | 117.759 | 1.00 80.78 |
| ATOM | 2023 | CG | GLU | 4393 | 58.507 | 87.742 | 116.364 | 1.00 86.43 |
| ATOM | 2024 | CD | GLU | 4393 | 57.511 | 86.593 | 116.369 | 1.00 89.63 |
| ATOM | 2025 | OE1 | GLU | 4393 | 57.777 | 85.557 | 117.019 | 1.00 92.89 |
| ATOM | 2026 | OE2 | GLU | 4393 | 56.461 | 86.721 | 115.706 | 1.00 90.77 |
| ATOM | 2027 | C | GLU | 4393 | 61.105 | 89.103 | 116.935 | 1.00 85.11 |
| ATOM | 2028 | O | GLU | 4393 | 62.183 | 88.867 | 117.483 | 1.00 86.94 |
| ATOM | 2029 | N | GLU | 4394 | 60.954 | 89.118 | 115.611 | 1.00 90.05 |
| ATOM | 2030 | CA | GLU | 4394 | 62.067 | 88.835 | 114.704 | 1.00 94.23 |
| ATOM | 2031 | CB | GLU | 4394 | 61.709 | 89.224 | 113.262 | 1.00 98.44 |
| ATOM | 2032 | CG | GLU | 4394 | 60.713 | 88.295 | 112.577 | 1.00101.69 |
| ATOM | 2033 | CD | GLU | 4394 | 60.553 | 88.601 | 111.095 | 1.00102.20 |
| ATOM | 2034 | OE1 | GLU | 4394 | 60.021 | 89.679 | 110.752 | 1.00103.73 |
| ATOM | 2035 | OE2 | GLU | 4394 | 60.974 | 87.763 | 110.271 | 1.00101.48 |
| ATOM | 2036 | C | GLU | 4394 | 63.382 | 89.511 | 115.083 | 1.00 94.97 |
| ATOM | 2037 | O | GLU | 4394 | 64.416 | 88.851 | 115.197 | 1.00 93.34 |
| ATOM | 2038 | N | SER | 4395 | 63.342 | 90.827 | 115.270 | 1.00 96.41 |
| ATOM | 2039 | CA | SER | 4395 | 64.541 | 91.580 | 115.616 | 1.00 96.15 |
| ATOM | 2040 | CB | SER | 4395 | 64.554 | 92.912 | 114.858 | 1.00 97.26 |
| ATOM | 2041 | OG | SER | 4395 | 64.564 | 92.693 | 113.455 | 1.00 96.01 |
| ATOM | 2042 | C | SER | 4395 | 64.689 | 91.830 | 117.113 | 1.00 94.96 |

```
ATOM  2043  O    SER  4395     63.831  92.459 117.738  1.00 92.90
ATOM  2044  N    THR  4396     65.789  91.328 117.675  1.00 95.40
ATOM  2045  CA   THR  4396     66.090  91.484 119.097  1.00 94.03
ATOM  2046  CB   THR  4396     67.533  91.070 119.384  1.00 92.59
ATOM  2047  C    THR  4396     65.885  92.944 119.468  1.00 92.43
ATOM  2048  O    THR  4396     65.397  93.266 120.556  1.00 92.62
ATOM  2049  N    ASN  4397     66.268  93.824 118.550  1.00 90.08
ATOM  2050  CA   ASN  4397     66.095  95.246 118.762  1.00 87.52
ATOM  2051  CB   ASN  4397     66.661  96.024 117.579  1.00 84.94
ATOM  2052  C    ASN  4397     64.586  95.451 118.865  1.00 86.47
ATOM  2053  O    ASN  4397     63.847  95.097 117.943  1.00 86.04
ATOM  2054  N    GLY  4398     64.130  95.983 119.998  1.00 84.13
ATOM  2055  CA   GLY  4398     62.706  96.240 120.203  1.00 80.51
ATOM  2056  C    GLY  4398     62.252  97.151 119.072  1.00 79.00
ATOM  2057  O    GLY  4398     62.274  98.375 119.218  1.00 82.87
ATOM  2058  N    SER  4399     61.855  96.553 117.949  1.00 70.42
ATOM  2059  CA   SER  4399     61.423  97.314 116.778  1.00 58.90
ATOM  2060  CB   SER  4399     62.651  97.814 116.004  1.00 52.07
ATOM  2061  C    SER  4399     60.538  96.465 115.868  1.00 51.76
ATOM  2062  O    SER  4399     60.676  95.243 115.807  1.00 48.55
ATOM  2063  N    LEU  4400     59.628  97.120 115.158  1.00 43.97
ATOM  2064  CA   LEU  4400     58.729  96.407 114.260  1.00 36.40
ATOM  2065  CB   LEU  4400     57.435  97.198 114.091  1.00 30.85
ATOM  2066  CG   LEU  4400     56.315  96.427 113.407  1.00 22.35
ATOM  2067  CD1  LEU  4400     55.780  95.400 114.365  1.00 23.86
ATOM  2068  CD2  LEU  4400     55.206  97.371 113.014  1.00 25.54
ATOM  2069  C    LEU  4400     59.418  96.231 112.904  1.00 33.63
ATOM  2070  O    LEU  4400     59.835  97.212 112.287  1.00 34.51
ATOM  2071  N    ALA  4401     59.539  94.987 112.445  1.00 29.44
ATOM  2072  CA   ALA  4401     60.199  94.701 111.172  1.00 24.05
ATOM  2073  CB   ALA  4401     61.698  94.545 111.396  1.00 16.73
ATOM  2074  C    ALA  4401     59.658  93.480 110.421  1.00 23.24
ATOM  2075  O    ALA  4401     58.623  92.929 110.763  1.00 27.02
ATOM  2076  N    ALA  4402     60.371  93.081 109.377  1.00 25.82
ATOM  2077  CA   ALA  4402     59.999  91.932 108.551  1.00 26.79
ATOM  2078  CB   ALA  4402     58.747  92.236 107.730  1.00 23.55
ATOM  2079  C    ALA  4402     61.177  91.631 107.629  1.00 27.15
ATOM  2080  O    ALA  4402     61.571  92.453 106.796  1.00 27.53
ATOM  2081  N    GLU  4403     61.752  90.452 107.796  1.00 29.72
ATOM  2082  CA   GLU  4403     62.890  90.090 106.989  1.00 31.33
ATOM  2083  CB   GLU  4403     64.082  89.703 107.863  1.00 33.23
ATOM  2084  CG   GLU  4403     65.375  89.583 107.082  1.00 37.15
ATOM  2085  CD   GLU  4403     66.549  89.175 107.941  1.00 42.62
ATOM  2086  OE1  GLU  4403     66.772  89.816 108.988  1.00 49.23
ATOM  2087  OE2  GLU  4403     67.261  88.220 107.566  1.00 46.03
ATOM  2088  C    GLU  4403     62.529  86.936 106.101  1.00 32.67
ATOM  2089  O    GLU  4403     62.013  87.923 106.560  1.00 34.12
ATOM  2090  N    PHE  4404     62.790  83.109 104.814  1.00 34.31
ATOM  2091  CA   PHE  4404     62.516  88.069 103.856  1.00 30.64
ATOM  2092  CB   PHE  4404     61.921  88.630 102.565  1.00 25.42
ATOM  2093  CG   PHE  4404     60.633  89.353 102.763  1.00 21.09
ATOM  2094  CD1  PHE  4404     60.612  90.605 103.367  1.00 20.91
ATOM  2095  CD2  PHE  4404     59.432  88.759 102.399  1.00 10.39
ATOM  2096  CE1  PHE  4404     59.399  91.255 103.609  1.00 15.51
ATOM  2097  CE2  PHE  4404     58.228  89.388 102.632  1.00 14.07
ATOM  2098  CZ   PHE  4404     58.203  90.641 103.240  1.00 19.09
ATOM  2099  C    PHE  4404     63.803  87.367 103.529  1.00 33.68
ATOM  2100  O    PHE  4404     64.877  87.971 103.421  1.00 31.58
ATOM  2101  N    ARG  4405     63.664  86.063 103.395  1.00 37.56
ATOM  2102  CA   ARG  4405     64.740  85.166 103.031  1.00 36.57
ATOM  2103  CB   ARG  4405     65.243  84.452 104.273  1.00 31.06
ATOM  2104  CG   ARG  4405     65.820  85.435 105.277  1.00 31.70
ATOM  2105  CD   ARG  4405     66.020  84.803 106.628  1.00 37.04
ATOM  2106  NE   ARG  4405     66.510  85.757 107.618  1.00 44.10
ATOM  2107  CZ   ARG  4405     66.112  85.774 108.891  1.00 50.59
ATOM  2108  NH1  ARG  4405     65.223  84.882 109.320  1.00 49.49
ATOM  2109  NH2  ARG  4405     66.598  86.682 109.738  1.00 48.92
ATOM  2110  C    ARG  4405     63.955  84.253 102.112  1.00 36.23
ATOM  2111  O    ARG  4405     62.720  84.256 102.148  1.00 42.67
ATOM  2112  N    HIS  4406     64.632  83.508 101.264  1.00 32.61
```

| | | | | | | | | |
|---|---|---|---|---|---|---|---|---|
| ATOM | 2113 | CA | HIS | 4406 | 63.921 | 82.621 | 100.357 | 1.00 37.89 |
| ATOM | 2114 | CB | HIS | 4406 | 62.835 | 81.836 | 101.115 | 1.00 36.24 |
| ATOM | 2115 | CG | HIS | 4406 | 63.249 | 81.432 | 102.498 | 1.00 37.87 |
| ATOM | 2116 | CD2 | HIS | 4406 | 62.648 | 81.614 | 103.697 | 1.00 35.78 |
| ATOM | 2117 | ND1 | HIS | 4406 | 64.463 | 80.835 | 102.765 | 1.00 37.50 |
| ATOM | 2118 | CE1 | HIS | 4406 | 64.595 | 80.672 | 104.070 | 1.00 33.63 |
| ATOM | 2119 | NE2 | HIS | 4406 | 63.508 | 81.137 | 104.657 | 1.00 33.52 |
| ATOM | 2120 | C | HIS | 4406 | 63.305 | 83.372 | 99.164 | 1.00 39.83 |
| ATOM | 2121 | O | HIS | 4406 | 62.456 | 82.809 | 98.466 | 1.00 45.48 |
| ATOM | 2122 | N | LEU | 4407 | 63.702 | 84.627 | 98.922 | 1.00 37.15 |
| ATOM | 2123 | CA | LEU | 4407 | 62.714 | 85.449 | 98.058 | 1.00 28.54 |
| ATOM | 2124 | CB | LEU | 4407 | 62.935 | 86.943 | 98.199 | 1.00 26.43 |
| ATOM | 2125 | CG | LEU | 4407 | 61.933 | 87.734 | 99.018 | 1.00 27.62 |
| ATOM | 2126 | CD1 | LEU | 4407 | 62.466 | 89.128 | 99.208 | 1.00 27.73 |
| ATOM | 2127 | CD2 | LEU | 4407 | 60.583 | 87.772 | 98.314 | 1.00 28.36 |
| ATOM | 2128 | C | LEU | 4407 | 63.516 | 84.946 | 96.877 | 1.00 29.36 |
| ATOM | 2129 | O | LEU | 4407 | 64.705 | 84.671 | 97.003 | 1.00 30.18 |
| ATOM | 2130 | N | GLN | 4408 | 62.899 | 84.852 | 95.715 | 1.00 26.44 |
| ATOM | 2131 | CA | GLN | 4408 | 63.636 | 84.296 | 94.607 | 1.00 24.32 |
| ATOM | 2132 | CB | GLN | 4408 | 63.637 | 82.799 | 94.839 | 1.00 22.71 |
| ATOM | 2133 | CG | GLN | 4408 | 64.374 | 81.930 | 93.891 | 1.00 23.57 |
| ATOM | 2134 | CD | GLN | 4408 | 64.192 | 80.494 | 94.302 | 1.00 21.23 |
| ATOM | 2135 | OE1 | GLN | 4408 | 64.601 | 80.099 | 95.395 | 1.00 18.17 |
| ATOM | 2136 | NE2 | GLN | 4408 | 63.544 | 79.710 | 93.451 | 1.00 22.44 |
| ATOM | 2137 | C | GLN | 4408 | 63.042 | 84.673 | 93.254 | 1.00 24.35 |
| ATOM | 2138 | O | GLN | 4408 | 61.830 | 84.665 | 93.070 | 1.00 24.75 |
| ATOM | 2139 | N | LEU | 4409 | 63.901 | 85.006 | 92.302 | 1.00 24.67 |
| ATOM | 2140 | CA | LEU | 4409 | 63.433 | 85.403 | 90.982 | 1.00 26.17 |
| ATOM | 2141 | CB | LEU | 4409 | 64.122 | 86.710 | 90.569 | 1.00 24.46 |
| ATOM | 2142 | CG | LEU | 4409 | 63.638 | 88.047 | 91.138 | 1.00 25.49 |
| ATOM | 2143 | CD1 | LEU | 4409 | 63.049 | 87.884 | 92.517 | 1.00 28.34 |
| ATOM | 2144 | CD2 | LEU | 4409 | 64.807 | 89.021 | 91.138 | 1.00 30.52 |
| ATOM | 2145 | C | LEU | 4409 | 63.631 | 84.363 | 89.884 | 1.00 26.03 |
| ATOM | 2146 | O | LEU | 4409 | 64.647 | 83.661 | 89.840 | 1.00 21.11 |
| ATOM | 2147 | N | LYS | 4410 | 62.647 | 84.276 | 88.996 | 1.00 28.79 |
| ATOM | 2148 | CA | LYS | 4410 | 62.711 | 83.361 | 87.860 | 1.00 33.51 |
| ATOM | 2149 | CB | LYS | 4410 | 61.908 | 82.088 | 88.140 | 1.00 33.69 |
| ATOM | 2150 | CG | LYS | 4410 | 62.017 | 81.063 | 87.032 | 1.00 39.52 |
| ATOM | 2151 | CD | LYS | 4410 | 61.243 | 79.804 | 87.349 | 1.00 43.40 |
| ATOM | 2152 | CE | LYS | 4410 | 61.459 | 78.721 | 86.285 | 1.00 45.99 |
| ATOM | 2153 | NZ | LYS | 4410 | 62.879 | 78.245 | 86.200 | 1.00 45.95 |
| ATOM | 2154 | C | LYS | 4410 | 62.123 | 84.099 | 86.656 | 1.00 33.40 |
| ATOM | 2155 | O | LYS | 4410 | 61.199 | 84.901 | 86.822 | 1.00 30.07 |
| ATOM | 2156 | N | GLU | 4411 | 62.663 | 83.858 | 85.460 | 1.00 33.27 |
| ATOM | 2157 | CA | GLU | 4411 | 62.142 | 84.520 | 84.259 | 1.00 37.76 |
| ATOM | 2158 | CB | GLU | 4411 | 62.984 | 84.243 | 83.026 | 1.00 33.42 |
| ATOM | 2159 | CG | GLU | 4411 | 64.102 | 85.182 | 82.787 | 1.00 35.86 |
| ATOM | 2160 | CD | GLU | 4411 | 64.209 | 85.509 | 81.330 | 1.00 37.11 |
| ATOM | 2161 | OE1 | GLU | 4411 | 63.310 | 86.212 | 80.814 | 1.00 33.84 |
| ATOM | 2162 | OE2 | GLU | 4411 | 65.178 | 85.051 | 80.699 | 1.00 44.21 |
| ATOM | 2163 | C | GLU | 4411 | 60.750 | 84.098 | 83.883 | 1.00 43.64 |
| ATOM | 2164 | O | GLU | 4411 | 60.343 | 82.961 | 84.127 | 1.00 48.12 |
| ATOM | 2165 | N | GLN | 4412 | 60.033 | 85.018 | 83.251 | 1.00 48.96 |
| ATOM | 2166 | CA | GLN | 4412 | 58.694 | 84.737 | 82.782 | 1.00 55.18 |
| ATOM | 2167 | CB | GLN | 4412 | 57.782 | 85.931 | 83.038 | 1.00 57.76 |
| ATOM | 2168 | CG | GLN | 4412 | 56.308 | 85.618 | 82.865 | 1.00 66.63 |
| ATOM | 2169 | CD | GLN | 4412 | 55.424 | 86.847 | 83.008 | 1.00 70.64 |
| ATOM | 2170 | OE1 | GLN | 4412 | 55.463 | 87.760 | 82.174 | 1.00 69.65 |
| ATOM | 2171 | NE2 | GLN | 4412 | 54.624 | 86.879 | 84.073 | 1.00 71.58 |
| ATOM | 2172 | C | GLN | 4412 | 58.872 | 84.502 | 81.280 | 1.00 61.73 |
| ATOM | 2173 | O | GLN | 4412 | 58.340 | 85.239 | 80.445 | 1.00 61.03 |
| ATOM | 2174 | N | LYS | 4413 | 59.667 | 83.481 | 80.958 | 1.00 68.95 |
| ATOM | 2175 | CA | LYS | 4413 | 59.968 | 83.089 | 79.578 | 1.00 74.24 |
| ATOM | 2176 | CB | LYS | 4413 | 60.552 | 81.675 | 79.556 | 1.00 72.95 |
| ATOM | 2177 | CG | LYS | 4413 | 61.811 | 81.462 | 80.373 | 1.00 69.38 |
| ATOM | 2178 | CD | LYS | 4413 | 62.998 | 82.163 | 79.748 | 1.00 69.79 |
| ATOM | 2179 | CE | LYS | 4413 | 64.275 | 81.807 | 80.477 | 1.00 65.82 |
| ATOM | 2180 | NZ | LYS | 4413 | 65.464 | 82.407 | 79.834 | 1.00 63.52 |
| ATOM | 2181 | C | LYS | 4413 | 58.685 | 83.084 | 78.759 | 1.00 80.17 |
| ATOM | 2182 | O | LYS | 4413 | 57.793 | 82.278 | 79.025 | 1.00 81.79 |

| | | | | | | | |
|---|---|---|---|---|---|---|---|
| ATOM | 2183 | N | ASN | 4414 | 58.586 | 83.955 | 77.761 | 1.00 87.09 |
| ATOM | 2184 | CA | ASN | 4414 | 57.375 | 84.003 | 76.946 | 1.00 95.52 |
| ATOM | 2185 | CB | ASN | 4414 | 56.267 | 84.755 | 77.692 | 1.00 100.40 |
| ATOM | 2186 | CG | ASN | 4414 | 55.695 | 83.962 | 78.851 | 1.00 104.68 |
| ATOM | 2187 | OD1 | ASN | 4414 | 55.143 | 82.873 | 78.662 | 1.00 106.92 |
| ATOM | 2188 | ND2 | ASN | 4414 | 55.819 | 84.503 | 80.059 | 1.00 106.48 |
| ATOM | 2189 | C | ASN | 4414 | 57.515 | 84.611 | 75.558 | 1.00 98.71 |
| ATOM | 2190 | O | ASN | 4414 | 58.604 | 84.986 | 75.120 | 1.00 98.34 |
| ATOM | 2191 | N | ALA | 4415 | 56.377 | 84.699 | 74.877 | 1.00 102.54 |
| ATOM | 2192 | CA | ALA | 4415 | 56.301 | 85.264 | 73.541 | 1.00 106.90 |
| ATOM | 2193 | CB | ALA | 4415 | 55.309 | 84.468 | 72.695 | 1.00 105.30 |
| ATOM | 2194 | C | ALA | 4415 | 55.853 | 86.720 | 73.651 | 1.00 110.34 |
| ATOM | 2195 | O | ALA | 4415 | 56.150 | 87.535 | 72.775 | 1.00 111.70 |
| ATOM | 2196 | N | GLY | 4416 | 55.142 | 87.035 | 74.736 | 1.00 114.20 |
| ATOM | 2197 | CA | GLY | 4416 | 54.635 | 88.390 | 74.992 | 1.00 117.21 |
| ATOM | 2198 | C | GLY | 4416 | 55.755 | 89.425 | 74.886 | 1.00 118.21 |
| ATOM | 2199 | O | GLY | 4416 | 55.625 | 90.435 | 74.187 | 1.00 118.02 |
| ATOM | 2200 | N | THR | 4417 | 56.851 | 89.164 | 75.594 | 1.00 118.19 |
| ATOM | 2201 | CA | THR | 4417 | 58.012 | 90.043 | 75.584 | 1.00 117.02 |
| ATOM | 2202 | CB | THR | 4417 | 58.298 | 90.552 | 76.996 | 1.00 115.07 |
| ATOM | 2203 | C | THR | 4417 | 59.199 | 89.244 | 75.051 | 1.00 116.53 |
| ATOM | 2204 | O | THR | 4417 | 60.183 | 89.022 | 75.761 | 1.00 117.74 |
| ATOM | 2205 | N | ARG | 4418 | 59.092 | 88.805 | 73.798 | 1.00 114.62 |
| ATOM | 2206 | CA | ARG | 4418 | 60.142 | 88.018 | 73.158 | 1.00 112.22 |
| ATOM | 2207 | CB | ARG | 4418 | 59.797 | 87.796 | 71.686 | 1.00 109.92 |
| ATOM | 2208 | C | ARG | 4418 | 61.509 | 88.692 | 73.283 | 1.00 110.79 |
| ATOM | 2209 | O | ARG | 4418 | 61.611 | 89.919 | 73.278 | 1.00 111.08 |
| ATOM | 2210 | N | THR | 4419 | 62.558 | 87.884 | 73.402 | 1.00 109.21 |
| ATOM | 2211 | CA | THR | 4419 | 63.916 | 88.402 | 73.519 | 1.00 107.88 |
| ATOM | 2212 | CB | THR | 4419 | 64.894 | 87.257 | 73.752 | 1.00 106.18 |
| ATOM | 2213 | C | THR | 4419 | 64.294 | 89.170 | 72.259 | 1.00 108.21 |
| ATOM | 2214 | O | THR | 4419 | 63.684 | 88.989 | 71.204 | 1.00 109.97 |
| ATOM | 2215 | N | ASN | 4420 | 65.304 | 90.025 | 72.365 | 1.00 107.63 |
| ATOM | 2216 | CA | ASN | 4420 | 65.756 | 90.818 | 71.227 | 1.00 106.37 |
| ATOM | 2217 | CB | ASN | 4420 | 65.252 | 92.254 | 71.347 | 1.00 106.51 |
| ATOM | 2218 | C | ASN | 4420 | 67.280 | 90.798 | 71.181 | 1.00 105.90 |
| ATOM | 2219 | O | ASN | 4420 | 67.879 | 91.094 | 70.149 | 1.00 105.84 |
| ATOM | 2220 | N | GLU | 4421 | 67.887 | 90.452 | 72.323 | 1.00 105.25 |
| ATOM | 2221 | CA | GLU | 4421 | 69.347 | 90.362 | 72.499 | 1.00 104.83 |
| ATOM | 2222 | CB | GLU | 4421 | 69.903 | 89.102 | 71.860 | 1.00 106.61 |
| ATOM | 2223 | CG | GLU | 4421 | 69.693 | 89.041 | 70.357 | 1.00 109.77 |
| ATOM | 2224 | CD | GLU | 4421 | 70.321 | 87.821 | 69.763 | 1.00 110.95 |
| ATOM | 2225 | OE1 | GLU | 4421 | 71.544 | 87.652 | 69.937 | 1.00 111.97 |
| ATOM | 2226 | OE2 | GLU | 4421 | 69.584 | 87.046 | 69.140 | 1.00 112.24 |
| ATOM | 2227 | C | GLU | 4421 | 70.089 | 91.549 | 71.894 | 1.00 103.23 |
| ATOM | 2228 | O | GLU | 4421 | 71.189 | 91.392 | 71.320 | 1.00 105.43 |
| ATOM | 2229 | N | GLY | 4422 | 69.476 | 92.714 | 71.980 | 1.00 99.96 |
| ATOM | 2230 | CA | GLY | 4422 | 69.939 | 93.546 | 70.597 | 1.00 93.92 |
| ATOM | 2231 | C | GLY | 4422 | 69.086 | 94.734 | 70.957 | 1.00 90.85 |
| ATOM | 2232 | O | GLY | 4422 | 69.177 | 95.715 | 70.289 | 1.00 90.27 |
| ATOM | 2233 | N | PRO | 4423 | 68.206 | 94.589 | 71.978 | 1.00 87.96 |
| ATOM | 2234 | CD | PRO | 4423 | 67.823 | 93.428 | 72.813 | 1.00 87.40 |
| ATOM | 2235 | CA | PRO | 4423 | 67.387 | 95.741 | 72.340 | 1.00 81.12 |
| ATOM | 2236 | CB | PRO | 4423 | 66.407 | 95.154 | 73.346 | 1.00 84.06 |
| ATOM | 2237 | CG | PRO | 4423 | 67.219 | 94.106 | 74.041 | 1.00 86.90 |
| ATOM | 2238 | C | PRO | 4423 | 68.225 | 96.858 | 72.940 | 1.00 73.80 |
| ATOM | 2239 | O | PRO | 4423 | 69.440 | 96.749 | 73.131 | 1.00 72.15 |
| ATOM | 2240 | N | LEU | 4424 | 67.525 | 97.926 | 73.266 | 1.00 64.98 |
| ATOM | 2241 | CA | LEU | 4424 | 68.103 | 99.132 | 73.820 | 1.00 57.94 |
| ATOM | 2242 | CB | LEU | 4424 | 66.971 | 99.944 | 74.450 | 1.00 60.84 |
| ATOM | 2243 | CG | LEU | 4424 | 65.753 | 99.967 | 73.507 | 1.00 64.48 |
| ATOM | 2244 | CD1 | LEU | 4424 | 64.595 | 100.739 | 74.157 | 1.00 68.52 |
| ATOM | 2245 | CD2 | LEU | 4424 | 66.142 | 100.636 | 72.176 | 1.00 69.23 |
| ATOM | 2246 | C | LEU | 4424 | 69.279 | 99.007 | 74.803 | 1.00 52.33 |
| ATOM | 2247 | O | LEU | 4424 | 70.154 | 99.871 | 74.821 | 1.00 52.98 |
| ATOM | 2248 | N | ILE | 4425 | 69.330 | 97.941 | 75.597 | 1.00 45.49 |
| ATOM | 2249 | CA | ILE | 4425 | 70.412 | 97.816 | 76.578 | 1.00 38.92 |
| ATOM | 2250 | CB | ILE | 4425 | 70.045 | 98.595 | 77.877 | 1.00 39.10 |
| ATOM | 2251 | CG2 | ILE | 4425 | 70.129 | 100.100 | 77.651 | 1.00 43.38 |
| ATOM | 2252 | CG1 | ILE | 4425 | 68.636 | 98.203 | 78.335 | 1.00 34.56 |

| ATOM | 2253 | CD1 | ILE | 4425 | 68.132 | 99.007 | 79.511 | 1.00 | 21.80 |
| ATOM | 2254 | C | ILE | 4425 | 70.824 | 96.397 | 76.991 | 1.00 | 34.34 |
| ATOM | 2255 | O | ILE | 4425 | 70.013 | 95.479 | 76.982 | 1.00 | 35.19 |
| ATOM | 2256 | N | VAL | 4426 | 72.095 | 96.242 | 77.354 | 1.00 | 28.78 |
| ATOM | 2257 | CA | VAL | 4426 | 72.658 | 94.973 | 77.821 | 1.00 | 27.42 |
| ATOM | 2258 | CB | VAL | 4426 | 74.129 | 95.185 | 78.284 | 1.00 | 24.91 |
| ATOM | 2259 | CG1 | VAL | 4426 | 74.654 | 93.966 | 79.007 | 1.00 | 35.41 |
| ATOM | 2260 | CG2 | VAL | 4426 | 74.996 | 95.479 | 77.094 | 1.00 | 26.66 |
| ATOM | 2261 | C | VAL | 4426 | 71.787 | 94.543 | 79.008 | 1.00 | 28.82 |
| ATOM | 2262 | O | VAL | 4426 | 71.054 | 95.380 | 79.543 | 1.00 | 30.49 |
| ATOM | 2263 | N | THR | 4427 | 71.854 | 93.277 | 79.438 | 1.00 | 22.96 |
| ATOM | 2264 | CA | THR | 4427 | 71.005 | 92.845 | 80.546 | 1.00 | 20.32 |
| ATOM | 2265 | CB | THR | 4427 | 71.087 | 91.316 | 80.832 | 1.00 | 19.13 |
| ATOM | 2266 | OG1 | THR | 4427 | 72.435 | 90.944 | 81.105 | 1.00 | 30.96 |
| ATOM | 2267 | CG2 | THR | 4427 | 70.575 | 90.521 | 79.673 | 1.00 | 11.08 |
| ATOM | 2268 | C | THR | 4427 | 71.196 | 93.607 | 81.855 | 1.00 | 23.55 |
| ATOM | 2269 | O | THR | 4427 | 70.658 | 93.196 | 82.891 | 1.00 | 22.45 |
| ATOM | 2270 | N | GLU | 4428 | 71.971 | 94.699 | 81.821 | 1.00 | 28.67 |
| ATOM | 2271 | CA | GLU | 4428 | 72.129 | 95.569 | 83.002 | 1.00 | 28.03 |
| ATOM | 2272 | CB | GLU | 4428 | 73.571 | 95.999 | 83.224 | 1.00 | 22.20 |
| ATOM | 2273 | CG | GLU | 4428 | 74.399 | 94.952 | 83.951 | 1.00 | 29.62 |
| ATOM | 2274 | CD | GLU | 4428 | 74.437 | 93.615 | 83.237 | 1.00 | 25.78 |
| ATOM | 2275 | OE1 | GLU | 4428 | 73.370 | 92.986 | 83.108 | 1.00 | 24.10 |
| ATOM | 2276 | OE2 | GLU | 4428 | 75.534 | 93.198 | 82.802 | 1.00 | 29.09 |
| ATOM | 2277 | C | GLU | 4428 | 71.199 | 96.790 | 82.856 | 1.00 | 27.16 |
| ATOM | 2278 | O | GLU | 4428 | 71.590 | 97.915 | 82.551 | 1.00 | 27.25 |
| ATOM | 2279 | N | GLU | 4429 | 69.935 | 96.462 | 83.067 | 1.00 | 27.46 |
| ATOM | 2280 | CA | GLU | 4429 | 68.769 | 97.306 | 83.042 | 1.00 | 24.68 |
| ATOM | 2281 | CB | GLU | 4429 | 67.712 | 96.576 | 82.236 | 1.00 | 25.82 |
| ATOM | 2282 | CG | GLU | 4429 | 67.788 | 95.086 | 82.534 | 1.00 | 27.46 |
| ATOM | 2283 | CD | GLU | 4429 | 66.854 | 94.240 | 81.711 | 1.00 | 32.85 |
| ATOM | 2284 | OE1 | GLU | 4429 | 66.829 | 94.401 | 80.474 | 1.00 | 30.36 |
| ATOM | 2285 | OE2 | GLU | 4429 | 66.162 | 93.391 | 82.309 | 1.00 | 28.94 |
| ATOM | 2286 | C | GLU | 4429 | 68.411 | 97.268 | 84.516 | 1.00 | 26.74 |
| ATOM | 2287 | O | GLU | 4429 | 68.774 | 96.321 | 85.210 | 1.00 | 30.95 |
| ATOM | 2288 | N | LEU | 4430 | 67.681 | 98.253 | 85.004 | 1.00 | 23.65 |
| ATOM | 2289 | CA | LEU | 4430 | 67.370 | 98.215 | 86.417 | 1.00 | 19.05 |
| ATOM | 2290 | CB | LEU | 4430 | 67.717 | 99.631 | 86.977 | 1.00 | 12.62 |
| ATOM | 2291 | CG | LEU | 4430 | 69.150 | 100.041 | 86.635 | 1.00 | 9.85 |
| ATOM | 2292 | CD1 | LEU | 4430 | 69.308 | 101.524 | 86.885 | 1.00 | 7.62 |
| ATOM | 2293 | CD2 | LEU | 4430 | 70.162 | 99.211 | 87.425 | 1.00 | 7.97 |
| ATOM | 2294 | C | LEU | 4430 | 65.920 | 97.927 | 86.710 | 1.00 | 24.17 |
| ATOM | 2295 | O | LEU | 4430 | 65.010 | 98.379 | 86.018 | 1.00 | 24.79 |
| ATOM | 2296 | N | HIS | 4431 | 65.729 | 97.119 | 87.748 | 1.00 | 21.35 |
| ATOM | 2297 | CA | HIS | 4431 | 64.417 | 96.696 | 88.198 | 1.00 | 18.35 |
| ATOM | 2298 | CB | HIS | 4431 | 64.357 | 95.182 | 88.198 | 1.00 | 18.74 |
| ATOM | 2299 | CG | HIS | 4431 | 64.408 | 94.586 | 86.832 | 1.00 | 21.07 |
| ATOM | 2300 | CD2 | HIS | 4431 | 65.415 | 93.980 | 86.160 | 1.00 | 21.32 |
| ATOM | 2301 | ND1 | HIS | 4431 | 63.339 | 94.626 | 85.966 | 1.00 | 26.33 |
| ATOM | 2302 | CE1 | HIS | 4431 | 63.683 | 94.069 | 84.819 | 1.00 | 23.42 |
| ATOM | 2303 | NE2 | HIS | 4431 | 64.938 | 93.670 | 84.911 | 1.00 | 18.11 |
| ATOM | 2304 | C | HIS | 4431 | 64.194 | 97.221 | 89.610 | 1.00 | 18.73 |
| ATOM | 2305 | O | HIS | 4431 | 65.081 | 97.847 | 90.184 | 1.00 | 16.10 |
| ATOM | 2306 | N | SER | 4432 | 63.005 | 96.982 | 90.163 | 1.00 | 19.42 |
| ATOM | 2307 | CA | SER | 4432 | 62.710 | 97.424 | 91.519 | 1.00 | 18.24 |
| ATOM | 2308 | CB | SER | 4432 | 61.922 | 98.741 | 91.521 | 1.00 | 16.89 |
| ATOM | 2309 | OG | SER | 4432 | 60.559 | 98.534 | 91.177 | 1.00 | 14.21 |
| ATOM | 2310 | C | SER | 4432 | 61.891 | 96.367 | 92.241 | 1.00 | 19.37 |
| ATOM | 2311 | O | SER | 4432 | 61.162 | 95.597 | 91.614 | 1.00 | 22.52 |
| ATOM | 2312 | N | LEU | 4433 | 62.043 | 96.330 | 93.561 | 1.00 | 20.78 |
| ATOM | 2313 | CA | LEU | 4433 | 61.300 | 95.424 | 94.429 | 1.00 | 19.96 |
| ATOM | 2314 | CB | LEU | 4433 | 62.240 | 94.681 | 95.363 | 1.00 | 21.54 |
| ATOM | 2315 | CG | LEU | 4433 | 63.122 | 93.571 | 94.822 | 1.00 | 27.14 |
| ATOM | 2316 | CD1 | LEU | 4433 | 64.296 | 93.427 | 95.751 | 1.00 | 26.40 |
| ATOM | 2317 | CD2 | LEU | 4433 | 62.330 | 92.259 | 94.690 | 1.00 | 24.72 |
| ATOM | 2318 | C | LEU | 4433 | 60.443 | 96.352 | 95.263 | 1.00 | 22.93 |
| ATOM | 2319 | O | LEU | 4433 | 60.967 | 97.149 | 96.032 | 1.00 | 30.49 |
| ATOM | 2320 | N | SER | 4434 | 59.133 | 96.274 | 95.110 | 1.00 | 24.71 |
| ATOM | 2321 | CA | SER | 4434 | 58.258 | 97.142 | 95.881 | 1.00 | 20.49 |
| ATOM | 2322 | CB | SER | 4434 | 57.156 | 97.707 | 94.986 | 1.00 | 24.34 |

150

| ATOM | 2323 | OG | SER | 4434 | 57.692 | 98.220 | 95.773 | 1.00 | 35.39 |
| ATOM | 2324 | C | SER | 4434 | 57.652 | 96.305 | 96.993 | 1.00 | 20.33 |
| ATOM | 2325 | O | SER | 4434 | 57.433 | 95.102 | 96.839 | 1.00 | 24.04 |
| ATOM | 2326 | N | PHE | 4435 | 57.396 | 96.946 | 98.122 | 1.00 | 20.71 |
| ATOM | 2327 | CA | PHE | 4435 | 56.813 | 96.284 | 99.283 | 1.00 | 14.99 |
| ATOM | 2328 | CB | PHE | 4435 | 57.811 | 96.313 | 100.427 | 1.00 | 7.92 |
| ATOM | 2329 | CG | PHE | 4435 | 59.088 | 95.623 | 100.082 | 1.00 | 8.03 |
| ATOM | 2330 | CD1 | PHE | 4435 | 59.180 | 94.240 | 100.147 | 1.00 | 12.20 |
| ATOM | 2331 | CD2 | PHE | 4435 | 60.153 | 96.338 | 99.562 | 1.00 | 2.99 |
| ATOM | 2332 | CE1 | PHE | 4435 | 60.311 | 93.579 | 99.696 | 1.00 | 11.05 |
| ATOM | 2333 | CE2 | PHE | 4435 | 61.282 | 95.694 | 99.107 | 1.00 | 5.78 |
| ATOM | 2334 | CZ | PHE | 4435 | 61.365 | 94.306 | 99.173 | 1.00 | 11.62 |
| ATOM | 2335 | C | PHE | 4435 | 55.571 | 97.057 | 99.592 | 1.00 | 15.41 |
| ATOM | 2336 | O | PHE | 4435 | 55.596 | 98.275 | 99.731 | 1.00 | 14.60 |
| ATOM | 2337 | N | GLU | 4436 | 54.474 | 96.329 | 99.675 | 1.00 | 19.88 |
| ATOM | 2338 | CA | GLU | 4436 | 53.182 | 96.931 | 99.902 | 1.00 | 23.43 |
| ATOM | 2339 | CB | GLU | 4436 | 52.364 | 96.741 | 98.635 | 1.00 | 23.87 |
| ATOM | 2340 | CG | GLU | 4436 | 51.125 | 97.555 | 98.518 | 1.00 | 29.77 |
| ATOM | 2341 | CD | GLU | 4436 | 50.556 | 97.441 | 97.128 | 1.00 | 38.96 |
| ATOM | 2342 | OE1 | GLU | 4436 | 50.147 | 96.320 | 96.758 | 1.00 | 40.11 |
| ATOM | 2343 | OE2 | GLU | 4436 | 50.540 | 98.459 | 96.401 | 1.00 | 40.64 |
| ATOM | 2344 | C | GLU | 4436 | 52.465 | 96.308 | 101.078 | 1.00 | 22.62 |
| ATOM | 2345 | O | GLU | 4436 | 52.488 | 95.096 | 101.258 | 1.00 | 23.51 |
| ATOM | 2346 | N | THR | 4437 | 51.848 | 97.144 | 101.896 | 1.00 | 23.27 |
| ATOM | 2347 | CA | THR | 4437 | 51.078 | 96.644 | 103.026 | 1.00 | 26.10 |
| ATOM | 2348 | CB | THR | 4437 | 51.938 | 96.434 | 104.293 | 1.00 | 30.22 |
| ATOM | 2349 | OG1 | THR | 4437 | 51.115 | 95.909 | 105.342 | 1.00 | 22.74 |
| ATOM | 2350 | CG2 | THR | 4437 | 52.571 | 97.747 | 104.744 | 1.00 | 30.56 |
| ATOM | 2351 | C | THR | 4437 | 49.980 | 97.641 | 103.318 | 1.00 | 25.90 |
| ATOM | 2352 | O | THR | 4437 | 49.935 | 98.721 | 102.723 | 1.00 | 24.31 |
| ATOM | 2353 | N | GLN | 4438 | 49.091 | 97.289 | 104.231 | 1.00 | 25.40 |
| ATOM | 2354 | CA | GLN | 4438 | 47.994 | 98.184 | 104.539 | 1.00 | 29.19 |
| ATOM | 2355 | CB | GLN | 4438 | 46.845 | 97.913 | 103.565 | 1.00 | 27.69 |
| ATOM | 2356 | CG | GLN | 4438 | 45.534 | 98.512 | 103.980 | 1.00 | 35.65 |
| ATOM | 2357 | CD | GLN | 4438 | 44.453 | 98.327 | 102.936 | 1.00 | 41.29 |
| ATOM | 2358 | OE1 | GLN | 4438 | 44.273 | 97.233 | 102.380 | 1.00 | 44.99 |
| ATOM | 2359 | NE2 | GLN | 4438 | 43.706 | 99.394 | 102.677 | 1.00 | 43.69 |
| ATOM | 2360 | C | GLN | 4438 | 47.499 | 98.151 | 105.981 | 1.00 | 28.67 |
| ATOM | 2361 | O | GLN | 4438 | 47.115 | 97.108 | 106.514 | 1.00 | 28.27 |
| ATOM | 2362 | N | LEU | 4439 | 47.526 | 99.320 | 106.606 | 1.00 | 30.10 |
| ATOM | 2363 | CA | LEU | 4439 | 47.065 | 99.477 | 107.973 | 1.00 | 32.18 |
| ATOM | 2364 | CB | LEU | 4439 | 47.656 | 100.752 | 108.575 | 1.00 | 27.24 |
| ATOM | 2365 | CG | LEU | 4439 | 47.091 | 101.123 | 109.936 | 1.00 | 24.61 |
| ATOM | 2366 | CD1 | LEU | 4439 | 47.178 | 99.931 | 110.843 | 1.00 | 30.43 |
| ATOM | 2367 | CD2 | LEU | 4439 | 47.830 | 102.304 | 110.503 | 1.00 | 23.82 |
| ATOM | 2368 | C | LEU | 4439 | 45.542 | 99.555 | 107.963 | 1.00 | 35.48 |
| ATOM | 2369 | O | LEU | 4439 | 44.956 | 100.576 | 107.597 | 1.00 | 34.80 |
| ATOM | 2370 | N | CYS | 4440 | 44.894 | 98.418 | 108.355 | 1.00 | 42.32 |
| ATOM | 2371 | CA | CYS | 4440 | 43.445 | 98.458 | 108.366 | 1.00 | 47.98 |
| ATOM | 2372 | CB | CYS | 4440 | 42.900 | 97.205 | 107.686 | 1.00 | 49.90 |
| ATOM | 2373 | SG | CYS | 4440 | 41.087 | 97.182 | 107.607 | 1.00 | 63.76 |
| ATOM | 2374 | C | CYS | 4440 | 42.901 | 98.536 | 109.772 | 1.00 | 47.45 |
| ATOM | 2375 | O | CYS | 4440 | 43.156 | 97.658 | 110.590 | 1.00 | 45.50 |
| ATOM | 2376 | N | GLN | 4441 | 42.144 | 99.597 | 110.030 | 1.00 | 50.88 |
| ATOM | 2377 | CA | GLN | 4441 | 41.522 | 99.841 | 111.326 | 1.00 | 54.22 |
| ATOM | 2378 | CB | GLN | 4441 | 42.454 | 100.688 | 112.202 | 1.00 | 54.30 |
| ATOM | 2379 | CG | GLN | 4441 | 43.386 | 99.865 | 113.083 | 1.00 | 52.75 |
| ATOM | 2380 | CD | GLN | 4441 | 44.453 | 100.701 | 113.765 | 1.00 | 52.28 |
| ATOM | 2381 | OE1 | GLN | 4441 | 44.213 | 101.844 | 114.161 | 1.00 | 53.22 |
| ATOM | 2382 | NE2 | GLN | 4441 | 45.634 | 100.122 | 113.932 | 1.00 | 52.50 |
| ATOM | 2383 | C | GLN | 4441 | 40.164 | 100.531 | 111.173 | 1.00 | 55.33 |
| ATOM | 2384 | O | GLN | 4441 | 39.865 | 101.105 | 110.125 | 1.00 | 55.43 |
| ATOM | 2385 | N | PRO | 4442 | 39.309 | 100.454 | 112.212 | 1.00 | 57.84 |
| ATOM | 2386 | CD | PRO | 4442 | 39.497 | 99.755 | 113.496 | 1.00 | 58.02 |
| ATOM | 2387 | CA | PRO | 4442 | 37.981 | 101.079 | 112.182 | 1.00 | 56.57 |
| ATOM | 2388 | CB | PRO | 4442 | 37.357 | 100.579 | 113.478 | 1.00 | 56.69 |
| ATOM | 2389 | CG | PRO | 4442 | 38.566 | 100.537 | 114.402 | 1.00 | 56.85 |
| ATOM | 2390 | C | PRO | 4442 | 38.114 | 102.605 | 112.148 | 1.00 | 56.52 |
| ATOM | 2391 | O | PRO | 4442 | 38.599 | 103.218 | 113.105 | 1.00 | 56.90 |
| ATOM | 2392 | N | GLY | 4443 | 37.692 | 103.214 | 111.044 | 1.00 | 56.31 |

151

| ATOM | 2393 | CA | GLY | 4443 | 37.798 | 104.657 | 110.927 | 1.00 | 54.86 |
| ATOM | 2394 | C | GLY | 4443 | 39.146 | 105.069 | 110.364 | 1.00 | 53.06 |
| ATOM | 2395 | O | GLY | 4443 | 39.381 | 106.248 | 110.097 | 1.00 | 54.62 |
| ATOM | 2396 | N | LEU | 4444 | 40.035 | 104.090 | 110.204 | 1.00 | 49.03 |
| ATOM | 2397 | CA | LEU | 4444 | 41.368 | 104.312 | 109.646 | 1.00 | 44.32 |
| ATOM | 2398 | CB | LEU | 4444 | 42.467 | 104.210 | 110.703 | 1.00 | 40.97 |
| ATOM | 2399 | CG | LEU | 4444 | 43.070 | 105.456 | 111.338 | 1.00 | 36.92 |
| ATOM | 2400 | CD1 | LEU | 4444 | 44.221 | 105.005 | 112.209 | 1.00 | 40.25 |
| ATOM | 2401 | CD2 | LEU | 4444 | 43.577 | 106.419 | 110.289 | 1.00 | 33.69 |
| ATOM | 2402 | C | LEU | 4444 | 41.685 | 103.282 | 108.594 | 1.00 | 42.42 |
| ATOM | 2403 | O | LEU | 4444 | 41.287 | 102.133 | 108.696 | 1.00 | 43.94 |
| ATOM | 2404 | N | VAL | 4445 | 42.419 | 103.704 | 107.582 | 1.00 | 41.36 |
| ATOM | 2405 | CA | VAL | 4445 | 42.834 | 102.817 | 106.514 | 1.00 | 38.38 |
| ATOM | 2406 | CB | VAL | 4445 | 41.742 | 102.584 | 105.451 | 1.00 | 33.59 |
| ATOM | 2407 | CG1 | VAL | 4445 | 42.133 | 101.413 | 104.587 | 1.00 | 30.85 |
| ATOM | 2408 | CG2 | VAL | 4445 | 40.407 | 102.352 | 106.091 | 1.00 | 35.52 |
| ATOM | 2409 | C | VAL | 4445 | 43.966 | 103.549 | 105.833 | 1.00 | 37.27 |
| ATOM | 2410 | O | VAL | 4445 | 43.806 | 104.695 | 105.398 | 1.00 | 40.30 |
| ATOM | 2411 | N | ILE | 4446 | 45.119 | 102.911 | 105.754 | 1.00 | 31.70 |
| ATOM | 2412 | CA | ILE | 4446 | 46.230 | 103.548 | 105.092 | 1.00 | 28.68 |
| ATOM | 2413 | CB | ILE | 4446 | 47.164 | 104.260 | 106.090 | 1.00 | 26.97 |
| ATOM | 2414 | CG2 | ILE | 4446 | 48.173 | 105.089 | 105.316 | 1.00 | 26.27 |
| ATOM | 2415 | CG1 | ILE | 4446 | 46.363 | 105.174 | 107.027 | 1.00 | 25.44 |
| ATOM | 2416 | CD1 | ILE | 4446 | 47.210 | 105.859 | 108.076 | 1.00 | 20.66 |
| ATOM | 2417 | C | ILE | 4446 | 47.010 | 102.467 | 104.380 | 1.00 | 28.63 |
| ATOM | 2418 | O | ILE | 4446 | 47.129 | 101.350 | 104.880 | 1.00 | 29.22 |
| ATOM | 2419 | N | ASP | 4447 | 47.521 | 102.787 | 103.199 | 1.00 | 28.33 |
| ATOM | 2420 | CA | ASP | 4447 | 48.319 | 101.823 | 102.458 | 1.00 | 27.00 |
| ATOM | 2421 | CB | ASP | 4447 | 47.870 | 101.737 | 101.000 | 1.00 | 31.71 |
| ATOM | 2422 | CG | ASP | 4447 | 46.418 | 101.322 | 100.859 | 1.00 | 34.84 |
| ATOM | 2423 | OD1 | ASP | 4447 | 46.066 | 100.219 | 101.331 | 1.00 | 38.90 |
| ATOM | 2424 | OD2 | ASP | 4447 | 45.633 | 102.101 | 100.275 | 1.00 | 37.39 |
| ATOM | 2425 | C | ASP | 4447 | 49.745 | 102.317 | 102.519 | 1.00 | 23.98 |
| ATOM | 2426 | O | ASP | 4447 | 50.015 | 103.470 | 102.197 | 1.00 | 23.21 |
| ATOM | 2427 | N | LEU | 4448 | 50.650 | 101.454 | 102.958 | 1.00 | 20.39 |
| ATOM | 2428 | CA | LEU | 4448 | 52.058 | 101.806 | 103.052 | 1.00 | 19.56 |
| ATOM | 2429 | CB | LEU | 4448 | 52.621 | 101.321 | 104.387 | 1.00 | 16.66 |
| ATOM | 2430 | CG | LEU | 4448 | 51.820 | 101.780 | 105.607 | 1.00 | 21.42 |
| ATOM | 2431 | CD1 | LEU | 4448 | 52.180 | 100.959 | 106.822 | 1.00 | 28.41 |
| ATOM | 2432 | CD2 | LEU | 4448 | 52.070 | 103.252 | 105.860 | 1.00 | 27.98 |
| ATOM | 2433 | C | LEU | 4448 | 52.789 | 101.120 | 101.895 | 1.00 | 21.05 |
| ATOM | 2434 | O | LEU | 4448 | 52.502 | 99.969 | 101.547 | 1.00 | 21.65 |
| ATOM | 2435 | N | GLU | 4449 | 53.729 | 101.829 | 101.295 | 1.00 | 18.78 |
| ATOM | 2436 | CA | GLU | 4449 | 54.496 | 101.284 | 100.191 | 1.00 | 18.21 |
| ATOM | 2437 | CB | GLU | 4449 | 53.795 | 101.597 | 98.870 | 1.00 | 21.06 |
| ATOM | 2438 | CG | GLU | 4449 | 54.602 | 101.230 | 97.637 | 1.00 | 34.45 |
| ATOM | 2439 | CD | GLU | 4449 | 53.875 | 101.596 | 96.360 | 1.00 | 42.97 |
| ATOM | 2440 | OE1 | GLU | 4449 | 54.435 | 101.360 | 95.265 | 1.00 | 45.69 |
| ATOM | 2441 | OE2 | GLU | 4449 | 52.738 | 102.121 | 96.453 | 1.00 | 43.49 |
| ATOM | 2442 | C | GLU | 4449 | 55.892 | 101.883 | 100.183 | 1.00 | 14.54 |
| ATOM | 2443 | O | GLU | 4449 | 56.083 | 103.051 | 100.536 | 1.00 | 15.86 |
| ATOM | 2444 | N | THR | 4450 | 56.867 | 101.084 | 99.786 | 1.00 | 8.28 |
| ATOM | 2445 | CA | THR | 4450 | 58.244 | 101.558 | 99.721 | 1.00 | 10.97 |
| ATOM | 2446 | CB | THR | 4450 | 58.926 | 101.542 | 101.114 | 1.00 | 12.50 |
| ATOM | 2447 | OG1 | THR | 4450 | 60.300 | 101.909 | 100.984 | 1.00 | 9.41 |
| ATOM | 2448 | CG2 | THR | 4450 | 58.859 | 100.166 | 101.731 | 1.00 | 17.23 |
| ATOM | 2449 | C | THR | 4450 | 58.971 | 100.616 | 98.792 | 1.00 | 9.84 |
| ATOM | 2450 | O | THR | 4450 | 58.573 | 99.470 | 98.659 | 1.00 | 14.29 |
| ATOM | 2451 | N | THR | 4451 | 60.016 | 101.072 | 98.121 | 1.00 | 3.94 |
| ATOM | 2452 | CA | THR | 4451 | 60.698 | 100.150 | 97.241 | 1.00 | 5.14 |
| ATOM | 2453 | CB | THR | 4451 | 60.393 | 100.439 | 95.738 | 1.00 | 11.97 |
| ATOM | 2454 | OG1 | THR | 4451 | 61.164 | 101.555 | 95.290 | 1.00 | 8.83 |
| ATOM | 2455 | CG2 | THR | 4451 | 58.913 | 100.754 | 95.545 | 1.00 | 9.56 |
| ATOM | 2456 | C | THR | 4451 | 62.197 | 100.174 | 97.462 | 1.00 | 5.03 |
| ATOM | 2457 | O | THR | 4451 | 62.755 | 101.134 | 97.993 | 1.00 | 4.94 |
| ATOM | 2458 | N | SER | 4452 | 62.850 | 99.090 | 97.074 | 1.00 | 7.72 |
| ATOM | 2459 | CA | SER | 4452 | 64.287 | 99.010 | 97.218 | 1.00 | 7.53 |
| ATOM | 2460 | CB | SER | 4452 | 64.759 | 97.590 | 96.988 | 1.00 | 2.99 |
| ATOM | 2461 | OG | SER | 4452 | 64.402 | 97.190 | 95.677 | 1.00 | 7.13 |
| ATOM | 2462 | C | SER | 4452 | 64.885 | 99.893 | 96.143 | 1.00 | 6.89 |

152

```
ATOM   2463  O    SER  4452      64.177 100.391  95.260  1.00  8.33
ATOM   2464  N    LEU  4453      66.190 100.101  96.240  1.00  5.76
ATOM   2465  CA   LEU  4453      66.898 100.876  95.250  1.00  5.54
ATOM   2466  CB   LEU  4453      68.346 101.087  95.693  1.00  7.29
ATOM   2467  CG   LEU  4453      68.681 101.902  96.941  1.00  2.99
ATOM   2468  CD1  LEU  4453      70.077 101.560  97.409  1.00  2.99
ATOM   2469  CD2  LEU  4453      68.570 103.380  96.636  1.00  2.99
ATOM   2470  C    LEU  4453      66.860  99.958  94.020  1.00 10.51
ATOM   2471  O    LEU  4453      66.633  98.749  94.130  1.00  9.59
ATOM   2472  N    PRO  4454      67.070 100.514  92.831  1.00 13.03
ATOM   2473  CD   PRO  4454      67.373 101.890  92.430  1.00 16.37
ATOM   2474  CA   PRO  4454      67.040  99.646  91.659  1.00 13.53
ATOM   2475  CB   PRO  4454      67.491 100.581  90.543  1.00 19.76
ATOM   2476  CG   PRO  4454      68.326 101.620  91.299  1.00 24.39
ATOM   2477  C    PRO  4454      67.961  98.444  91.818  1.00  9.03
ATOM   2478  O    PRO  4454      69.066  98.552  92.348  1.00 10.84
ATOM   2479  N    VAL  4455      67.478  97.309  91.332  1.00 13.10
ATOM   2480  CA   VAL  4455      68.159  96.014  91.363  1.00 11.90
ATOM   2481  CB   VAL  4455      67.161  94.944  91.909  1.00 10.38
ATOM   2482  CG1  VAL  4455      67.604  93.552  91.563  1.00 20.03
ATOM   2483  CG2  VAL  4455      67.051  95.073  93.410  1.00 18.72
ATOM   2484  C    VAL  4455      68.662  95.597  89.963  1.00  8.60
ATOM   2485  O    VAL  4455      68.222  96.152  88.948  1.00 10.89
ATOM   2486  N    VAL  4456      69.600  94.662  89.918  1.00  6.74
ATOM   2487  CA   VAL  4456      70.122  94.134  88.659  1.00  8.39
ATOM   2488  CB   VAL  4456      71.627  94.466  88.481  1.00  6.61
ATOM   2489  CG1  VAL  4456      72.257  93.599  87.387  1.00  2.99
ATOM   2490  CG2  VAL  4456      71.769  95.915  88.117  1.00  4.38
ATOM   2491  C    VAL  4456      69.945  92.619  88.704  1.00  9.81
ATOM   2492  O    VAL  4456      70.521  91.961  89.566  1.00 13.27
ATOM   2493  N    VAL  4457      69.158  92.055  87.789  1.00  9.21
ATOM   2494  CA   VAL  4457      68.938  90.606  87.808  1.00  8.57
ATOM   2495  CB   VAL  4457      67.462  90.260  87.452  1.00  6.82
ATOM   2496  CG1  VAL  4457      67.242  88.765  87.530  1.00  5.32
ATOM   2497  CG2  VAL  4457      66.503  90.982  88.400  1.00  9.52
ATOM   2498  C    VAL  4457      69.859  89.842  86.864  1.00  7.61
ATOM   2499  O    VAL  4457      69.891  90.136  85.675  1.00  8.74
ATOM   2500  N    ILE  4458      70.607  88.868  87.386  1.00  8.04
ATOM   2501  CA   ILE  4458      71.500  88.062  86.538  1.00 10.91
ATOM   2502  CB   ILE  4458      72.976  88.195  86.933  1.00 10.01
ATOM   2503  CG2  ILE  4458      73.487  89.574  86.581  1.00  6.77
ATOM   2504  CG1  ILE  4458      73.149  87.813  88.402  1.00  9.10
ATOM   2505  CD1  ILE  4458      74.599  87.754  88.818  1.00  5.34
ATOM   2506  C    ILE  4458      71.179  86.567  86.587  1.00 13.93
ATOM   2507  O    ILE  4458      70.474  86.117  87.490  1.00 21.61
ATOM   2508  N    SER  4459      71.697  85.794  85.630  1.00 13.16
ATOM   2509  CA   SER  4459      71.439  84.356  85.632  1.00 13.83
ATOM   2510  CB   SER  4459      70.878  83.884  84.284  1.00 16.68
ATOM   2511  OG   SER  4459      71.827  84.008  83.246  1.00 17.40
ATOM   2512  C    SER  4459      72.686  83.558  85.963  1.00 12.46
ATOM   2513  O    SER  4459      72.603  82.399  86.334  1.00 14.57
ATOM   2514  N    ASN  4460      73.848  84.175  85.831  1.00 14.66
ATOM   2515  CA   ASN  4460      75.088  83.484  86.139  1.00 18.40
ATOM   2516  CB   ASN  4460      75.737  82.984  84.859  1.00 17.64
ATOM   2517  CG   ASN  4460      76.798  81.942  85.129  1.00 25.74
ATOM   2518  OD1  ASN  4460      77.793  82.199  85.828  1.00 26.74
ATOM   2519  ND2  ASN  4460      76.586  80.742  84.588  1.00 25.46
ATOM   2520  C    ASN  4460      76.059  84.399  86.893  1.00 19.49
ATOM   2521  O    ASN  4460      76.253  85.559  86.526  1.00 18.25
ATOM   2522  N    VAL  4461      76.685  83.877  87.940  1.00 19.41
ATOM   2523  CA   VAL  4461      77.590  84.695  88.725  1.00 20.99
ATOM   2524  CB   VAL  4461      78.245  83.893  89.871  1.00 21.32
ATOM   2525  CG1  VAL  4461      78.935  84.842  90.828  1.00 26.23
ATOM   2526  CG2  VAL  4461      77.189  83.097  90.635  1.00 34.86
ATOM   2527  C    VAL  4461      78.672  85.298  87.854  1.00 18.92
ATOM   2528  O    VAL  4461      79.446  86.142  88.309  1.00 22.30
ATOM   2529  N    SER  4462      78.731  84.887  86.592  1.00 16.27
ATOM   2530  CA   SER  4462      79.755  85.437  85.708  1.00 17.66
ATOM   2531  CB   SER  4462      79.921  84.577  84.476  1.00 14.55
ATOM   2532  OG   SER  4462      78.730  84.653  83.723  1.00 24.91
```

153

```
ATOM   2533  C    SER  4462      79.315  86.816  85.284  1.00  16.50
ATOM   2534  O    SER  4462      80.113  87.624  84.830  1.00  22.25
ATOM   2535  N    GLN  4463      78.024  87.072  85.440  1.00  19.76
ATOM   2536  CA   GLN  4463      77.433  88.353  85.088  1.00  18.42
ATOM   2537  CB   GLN  4463      75.996  88.150  84.621  1.00   8.90
ATOM   2538  CG   GLN  4463      75.842  87.166  83.517  1.00   8.83
ATOM   2539  CD   GLN  4463      74.426  87.126  83.004  1.00  14.77
ATOM   2540  OE1  GLN  4463      73.492  86.884  83.774  1.00  12.51
ATOM   2541  NE2  GLN  4463      74.248  87.367  81.693  1.00  14.36
ATOM   2542  C    GLN  4463      77.400  89.219  86.295  1.00  20.75
ATOM   2543  O    GLN  4463      76.786  90.350  86.240  1.00  24.19
ATOM   2544  N    LEU  4464      78.045  88.906  87.387  1.00  20.05
ATOM   2545  CA   LEU  4464      77.988  89.738  88.569  1.00  19.85
ATOM   2546  CB   LEU  4464      78.155  88.860  89.811  1.00  21.18
ATOM   2547  CG   LEU  4464      78.237  89.491  91.198  1.00  23.31
ATOM   2548  CD1  LEU  4464      77.848  88.457  92.234  1.00  23.93
ATOM   2549  CD2  LEU  4464      79.658  90.012  91.451  1.00  26.18
ATOM   2550  C    LEU  4464      78.958  90.914  88.553  1.00  20.90
ATOM   2551  O    LEU  4464      78.574  92.049  88.857  1.00  22.06
ATOM   2552  N    PRO  4465      80.225  90.674  88.195  1.00  19.34
ATOM   2553  CD   PRO  4465      80.938  89.463  87.783  1.00  19.16
ATOM   2554  CA   PRO  4465      81.141  91.808  88.176  1.00  16.62
ATOM   2555  CB   PRO  4465      82.428  91.187  87.645  1.00   4.24
ATOM   2556  CG   PRO  4465      81.918  90.062  86.804  1.00  18.18
ATOM   2557  C    PRO  4465      80.603  92.922  87.282  1.00  18.12
ATOM   2558  O    PRO  4465      80.751  94.104  87.591  1.00  23.17
ATOM   2559  N    SER  4466      79.953  92.552  86.188  1.00  19.30
ATOM   2560  CA   SER  4466      79.421  93.562  85.281  1.00  21.24
ATOM   2561  CB   SER  4466      79.062  92.919  83.943  1.00  21.39
ATOM   2562  OG   SER  4466      78.644  93.898  83.014  1.00  30.76
ATOM   2563  C    SER  4466      78.195  94.243  85.897  1.00  20.72
ATOM   2564  O    SER  4466      77.988  95.458  85.759  1.00  19.04
ATOM   2565  N    GLY  4467      77.381  93.449  86.577  1.00  20.30
ATOM   2566  CA   GLY  4467      76.202  93.989  87.216  1.00  18.36
ATOM   2567  C    GLY  4467      76.602  94.960  88.311  1.00  16.20
ATOM   2568  O    GLY  4467      75.980  96.016  88.478  1.00  17.52
ATOM   2569  N    TRP  4468      77.648  94.615  89.056  1.00  11.82
ATOM   2570  CA   TRP  4468      78.098  95.475  90.134  1.00  11.12
ATOM   2571  CB   TRP  4468      79.284  94.839  90.855  1.00  12.38
ATOM   2572  CG   TRP  4468      79.745  95.623  92.049  1.00  12.58
ATOM   2573  CD2  TRP  4468      78.963  95.989  93.183  1.00  11.82
ATOM   2574  CE2  TRP  4468      79.793  96.738  94.040  1.00  13.53
ATOM   2575  CE3  TRP  4468      77.638  95.762  93.561  1.00  13.59
ATOM   2576  CD1  TRP  4468      80.988  96.148  92.256  1.00   7.83
ATOM   2577  NE1  TRP  4468      81.026  96.818  93.445  1.00   8.07
ATOM   2578  CZ2  TRP  4468      79.342  97.263  95.260  1.00  14.54
ATOM   2579  CZ3  TRP  4468      77.189  96.284  94.775  1.00  18.05
ATOM   2580  CH2  TRP  4468      78.041  97.026  95.607  1.00  14.64
ATOM   2581  C    TRP  4468      78.493  96.822  89.554  1.00  10.44
ATOM   2582  O    TRP  4468      78.132  97.875  90.077  1.00  14.09
ATOM   2583  N    ALA  4469      79.237  96.789  88.459  1.00  13.55
ATOM   2584  CA   ALA  4469      79.664  98.023  87.822  1.00  15.28
ATOM   2585  CB   ALA  4469      80.238  97.731  86.442  1.00   9.42
ATOM   2586  C    ALA  4469      78.497  98.999  87.706  1.00  12.95
ATOM   2587  O    ALA  4469      78.640 100.174  88.014  1.00  13.69
ATOM   2588  N    SER  4470      77.341  98.496  87.282  1.00  12.21
ATOM   2589  CA   SER  4470      76.153  99.306  87.091  1.00  10.10
ATOM   2590  CB   SER  4470      75.041  98.513  86.437  1.00   7.12
ATOM   2591  OG   SER  4470      75.390  98.156  85.112  1.00  16.69
ATOM   2592  C    SER  4470      75.622  99.961  88.356  1.00  11.73
ATOM   2593  O    SER  4470      75.195 101.115  88.344  1.00   9.84
ATOM   2594  N    ILE  4471      75.637  99.201  89.444  1.00  15.27
ATOM   2595  CA   ILE  4471      75.158  99.686  90.731  1.00  13.31
ATOM   2596  CB   ILE  4471      74.870  98.492  91.655  1.00  10.04
ATOM   2597  CG2  ILE  4471      74.496  98.941  93.048  1.00   9.87
ATOM   2598  CG1  ILE  4471      73.716  97.711  91.054  1.00  11.74
ATOM   2599  CD1  ILE  4471      73.308  96.536  91.832  1.00  20.79
ATOM   2600  C    ILE  4471      76.145 100.681  91.356  1.00  17.11
ATOM   2601  O    ILE  4471      75.744 101.557  92.140  1.00  22.71
ATOM   2602  N    LEU  4472      77.429 100.561  91.019  1.00  15.66
```

| ATOM | 2603 | CA | LEU | 4472 | 78.389 | 101.526 | 91.535 | 1.00 | 19.04 |
| ATOM | 2604 | CB | LEU | 4472 | 79.829 | 101.167 | 91.165 | 1.00 | 18.23 |
| ATOM | 2605 | CG | LEU | 4472 | 80.512 | 99.925 | 91.727 | 1.00 | 23.42 |
| ATOM | 2606 | CD1 | LEU | 4472 | 81.981 | 99.934 | 91.298 | 1.00 | 23.19 |
| ATOM | 2607 | CD2 | LEU | 4472 | 80.428 | 99.927 | 93.241 | 1.00 | 26.02 |
| ATOM | 2608 | C | LEU | 4472 | 78.039 | 102.823 | 90.824 | 1.00 | 20.24 |
| ATOM | 2609 | O | LEU | 4472 | 77.856 | 103.868 | 91.437 | 1.00 | 25.84 |
| ATOM | 2610 | N | TRP | 4473 | 77.918 | 102.718 | 89.508 | 1.00 | 17.57 |
| ATOM | 2611 | CA | TRP | 4473 | 77.638 | 103.848 | 88.651 | 1.00 | 14.10 |
| ATOM | 2612 | CB | TRP | 4473 | 77.713 | 103.389 | 87.208 | 1.00 | 9.58 |
| ATOM | 2613 | CG | TRP | 4473 | 78.047 | 104.463 | 86.264 | 1.00 | 11.53 |
| ATOM | 2614 | CD2 | TRP | 4473 | 79.359 | 104.900 | 85.916 | 1.00 | 9.32 |
| ATOM | 2615 | CE2 | TRP | 4473 | 79.220 | 105.930 | 84.956 | 1.00 | 7.60 |
| ATOM | 2616 | CE3 | TRP | 4473 | 80.645 | 104.517 | 86.319 | 1.00 | 5.25 |
| ATOM | 2617 | CD1 | TRP | 4473 | 77.182 | 105.224 | 85.538 | 1.00 | 14.14 |
| ATOM | 2618 | NE1 | TRP | 4473 | 77.877 | 106.110 | 84.744 | 1.00 | 15.87 |
| ATOM | 2619 | CZ2 | TRP | 4473 | 80.316 | 106.585 | 84.387 | 1.00 | 6.93 |
| ATOM | 2620 | CZ3 | TRP | 4473 | 81.736 | 105.162 | 85.757 | 1.00 | 8.03 |
| ATOM | 2621 | CH2 | TRP | 4473 | 81.565 | 106.187 | 84.798 | 1.00 | 6.63 |
| ATOM | 2622 | C | TRP | 4473 | 76.293 | 104.468 | 88.943 | 1.00 | 16.96 |
| ATOM | 2623 | O | TRP | 4473 | 76.114 | 105.670 | 88.886 | 1.00 | 20.32 |
| ATOM | 2624 | N | TYR | 4474 | 75.332 | 103.632 | 89.274 | 1.00 | 18.22 |
| ATOM | 2625 | CA | TYR | 4474 | 74.023 | 104.166 | 89.568 | 1.00 | 18.53 |
| ATOM | 2626 | CB | TYR | 4474 | 73.031 | 103.055 | 89.822 | 1.00 | 22.21 |
| ATOM | 2627 | CG | TYR | 4474 | 71.660 | 103.611 | 89.988 | 1.00 | 22.29 |
| ATOM | 2628 | CD1 | TYR | 4474 | 70.958 | 104.055 | 88.885 | 1.00 | 23.56 |
| ATOM | 2629 | CE1 | TYR | 4474 | 69.740 | 104.650 | 89.024 | 1.00 | 26.50 |
| ATOM | 2630 | CD2 | TYR | 4474 | 71.100 | 103.781 | 91.254 | 1.00 | 19.61 |
| ATOM | 2631 | CE2 | TYR | 4474 | 69.874 | 104.382 | 91.412 | 1.00 | 16.55 |
| ATOM | 2632 | CZ | TYR | 4474 | 69.206 | 104.816 | 90.288 | 1.00 | 25.96 |
| ATOM | 2633 | OH | TYR | 4474 | 68.012 | 105.444 | 90.387 | 1.00 | 25.10 |
| ATOM | 2634 | C | TYR | 4474 | 74.075 | 105.026 | 90.814 | 1.00 | 19.18 |
| ATOM | 2635 | O | TYR | 4474 | 73.887 | 106.238 | 90.756 | 1.00 | 22.90 |
| ATOM | 2636 | N | ASN | 4475 | 74.334 | 104.372 | 91.942 | 1.00 | 15.02 |
| ATOM | 2637 | CA | ASN | 4475 | 74.394 | 105.026 | 93.239 | 1.00 | 14.76 |
| ATOM | 2638 | CB | ASN | 4475 | 74.592 | 103.963 | 94.302 | 1.00 | 16.93 |
| ATOM | 2639 | CG | ASN | 4475 | 73.459 | 102.965 | 94.327 | 1.00 | 16.74 |
| ATOM | 2640 | OD1 | ASN | 4475 | 72.391 | 103.244 | 94.861 | 1.00 | 17.75 |
| ATOM | 2641 | ND2 | ASN | 4475 | 73.674 | 101.805 | 93.718 | 1.00 | 13.07 |
| ATOM | 2642 | C | ASN | 4475 | 75.476 | 106.092 | 93.344 | 1.00 | 19.28 |
| ATOM | 2643 | O | ASN | 4475 | 75.405 | 106.991 | 94.181 | 1.00 | 15.61 |
| ATOM | 2644 | N | MET | 4476 | 76.485 | 105.995 | 92.493 | 1.00 | 20.59 |
| ATOM | 2645 | CA | MET | 4476 | 77.537 | 106.977 | 92.515 | 1.00 | 18.15 |
| ATOM | 2646 | CB | MET | 4476 | 78.731 | 106.496 | 91.704 | 1.00 | 18.72 |
| ATOM | 2647 | CG | MET | 4476 | 79.997 | 107.271 | 91.989 | 1.00 | 24.27 |
| ATOM | 2648 | SD | MET | 4476 | 81.292 | 106.951 | 90.794 | 1.00 | 34.28 |
| ATOM | 2649 | CE | MET | 4476 | 81.311 | 105.162 | 90.804 | 1.00 | 28.63 |
| ATOM | 2650 | C | MET | 4476 | 76.966 | 108.251 | 91.893 | 1.00 | 20.87 |
| ATOM | 2651 | O | MET | 4476 | 77.350 | 109.357 | 92.265 | 1.00 | 22.54 |
| ATOM | 2652 | N | LEU | 4477 | 76.026 | 108.111 | 90.965 | 1.00 | 22.91 |
| ATOM | 2653 | CA | LEU | 4477 | 75.479 | 109.301 | 90.323 | 1.00 | 28.10 |
| ATOM | 2654 | CB | LEU | 4477 | 75.886 | 109.316 | 88.849 | 1.00 | 24.65 |
| ATOM | 2655 | CG | LEU | 4477 | 77.396 | 109.282 | 88.605 | 1.00 | 24.07 |
| ATOM | 2656 | CD1 | LEU | 4477 | 77.697 | 109.286 | 87.123 | 1.00 | 21.65 |
| ATOM | 2657 | CD2 | LEU | 4477 | 78.029 | 110.469 | 89.269 | 1.00 | 19.29 |
| ATOM | 2658 | C | LEU | 4477 | 73.983 | 109.571 | 90.422 | 1.00 | 32.48 |
| ATOM | 2659 | O | LEU | 4477 | 73.459 | 110.351 | 89.634 | 1.00 | 32.84 |
| ATOM | 2660 | N | VAL | 4478 | 73.291 | 108.954 | 91.378 | 1.00 | 39.03 |
| ATOM | 2661 | CA | VAL | 4478 | 71.846 | 109.175 | 91.536 | 1.00 | 44.63 |
| ATOM | 2662 | CB | VAL | 4478 | 71.048 | 108.039 | 90.874 | 1.00 | 40.69 |
| ATOM | 2663 | CG1 | VAL | 4478 | 69.561 | 108.257 | 91.065 | 1.00 | 40.11 |
| ATOM | 2664 | CG2 | VAL | 4478 | 71.374 | 107.980 | 89.403 | 1.00 | 36.70 |
| ATOM | 2665 | C | VAL | 4478 | 71.435 | 109.292 | 93.012 | 1.00 | 50.69 |
| ATOM | 2666 | O | VAL | 4478 | 72.178 | 108.879 | 93.896 | 1.00 | 53.37 |
| ATOM | 2667 | N | ALA | 4479 | 70.262 | 109.868 | 93.275 | 1.00 | 57.24 |
| ATOM | 2668 | CA | ALA | 4479 | 69.765 | 110.038 | 94.644 | 1.00 | 63.60 |
| ATOM | 2669 | CB | ALA | 4479 | 70.207 | 111.381 | 95.192 | 1.00 | 58.03 |
| ATOM | 2670 | C | ALA | 4479 | 68.244 | 109.940 | 94.703 | 1.00 | 70.27 |
| ATOM | 2671 | O | ALA | 4479 | 67.655 | 109.848 | 95.777 | 1.00 | 74.30 |
| ATOM | 2672 | N | GLU | 4480 | 67.621 | 109.968 | 93.534 | 1.00 | 77.20 |

```
ATOM   2673  CA   GLU  4480      66.483 111.454  93.304  1.00 81.95
ATOM   2674  CB   GLU  4480      66.437 112.198  91.967  1.00 83.92
ATOM   2675  CG   GLU  4480      67.827 112.584  91.485  1.00 87.80
ATOM   2676  CD   GLU  4480      67.837 113.148  90.091  1.00 90.76
ATOM   2677  OE1  GLU  4480      67.263 112.501  89.186  1.00 92.09
ATOM   2678  OE2  GLU  4480      68.436 114.228  89.898  1.00 92.61
ATOM   2679  C    GLU  4480      65.539 110.260  93.236  1.00 83.13
ATOM   2680  O    GLU  4480      65.984 109.117  93.377  1.00 83.93
ATOM   2681  N    PRO  4481      64.218 110.501  93.058  1.00 83.98
ATOM   2682  CD   PRO  4481      63.422 111.726  92.898  1.00 83.97
ATOM   2683  CA   PRO  4481      63.342 109.327  92.968  1.00 82.98
ATOM   2684  CB   PRO  4481      61.991 109.946  92.599  1.00 83.21
ATOM   2685  CG   PRO  4481      62.399 111.251  91.908  1.00 84.59
ATOM   2686  C    PRO  4481      64.051 108.642  91.804  1.00 80.27
ATOM   2687  O    PRO  4481      64.472 109.316  90.856  1.00 80.00
ATOM   2688  N    ARG  4482      64.203 107.330  91.840  1.00 74.38
ATOM   2689  CA   ARG  4482      65.021 106.771  90.794  1.00 68.21
ATOM   2690  CB   ARG  4482      66.094 105.882  91.428  1.00 74.75
ATOM   2691  CG   ARG  4482      65.778 105.116  92.699  1.00 75.98
ATOM   2692  CD   ARG  4482      65.643 106.044  93.885  1.00 76.94
ATOM   2693  NE   ARG  4482      66.107 105.409  95.111  1.00 80.59
ATOM   2694  CZ   ARG  4482      66.030 105.962  96.319  1.00 83.27
ATOM   2695  NH1  ARG  4482      65.500 107.171  96.468  1.00 85.13
ATOM   2696  NH2  ARG  4482      66.510 105.320  97.379  1.00 83.46
ATOM   2697  C    ARG  4482      64.592 106.165  89.479  1.00 61.78
ATOM   2698  O    ARG  4482      63.682 105.336  89.377  1.00 65.17
ATOM   2699  N    ASN  4483      65.369 106.614  88.492  1.00 50.99
ATOM   2700  CA   ASN  4483      65.312 106.324  87.063  1.00 42.36
ATOM   2701  CB   ASN  4483      66.133 107.400  86.356  1.00 43.27
ATOM   2702  CG   ASN  4483      66.282 107.161  84.869  1.00 46.70
ATOM   2703  OD1  ASN  4483      67.069 107.845  84.212  1.00 50.86
ATOM   2704  ND2  ASN  4483      65.524 106.213  84.325  1.00 43.91
ATOM   2705  C    ASN  4483      65.808 104.958  86.601  1.00 34.50
ATOM   2706  O    ASN  4483      67.009 104.756  86.440  1.00 32.10
ATOM   2707  N    LEU  4484      64.881 104.049  86.325  1.00 28.52
ATOM   2708  CA   LEU  4484      65.237 102.711  85.873  1.00 24.56
ATOM   2709  CB   LEU  4484      64.058 101.766  86.055  1.00 23.03
ATOM   2710  CG   LEU  4484      63.433 101.661  87.442  1.00 18.83
ATOM   2711  CD1  LEU  4484      62.331 100.595  87.443  1.00 11.34
ATOM   2712  CD2  LEU  4484      64.505 101.305  88.427  1.00 22.14
ATOM   2713  C    LEU  4484      65.681 102.665  84.410  1.00 24.68
ATOM   2714  O    LEU  4484      65.890 101.585  83.855  1.00 21.85
ATOM   2715  N    SER  4485      65.805 103.832  83.781  1.00 26.46
ATOM   2716  CA   SER  4485      66.247 103.925  82.378  1.00 24.10
ATOM   2717  CB   SER  4485      65.259 104.725  81.523  1.00 26.60
ATOM   2718  OG   SER  4485      63.976 104.133  81.520  1.00 24.78
ATOM   2719  C    SER  4485      67.588 104.640  82.385  1.00 21.38
ATOM   2720  O    SER  4485      68.079 105.088  81.357  1.00 18.51
ATOM   2721  N    PHE  4486      68.160 104.738  83.577  1.00 19.23
ATOM   2722  CA   PHE  4486      69.440 105.379  83.788  1.00 18.70
ATOM   2723  CB   PHE  4486      70.035 104.922  85.109  1.00 14.88
ATOM   2724  CG   PHE  4486      71.313 105.617  85.478  1.00 12.45
ATOM   2725  CD1  PHE  4486      71.295 106.911  85.990  1.00  2.99
ATOM   2726  CD2  PHE  4486      72.529 104.952  85.378  1.00  9.82
ATOM   2727  CE1  PHE  4486      72.456 107.526  86.411  1.00  2.99
ATOM   2728  CE2  PHE  4486      73.707 105.564  85.799  1.00 10.70
ATOM   2729  CZ   PHE  4486      73.667 106.852  86.320  1.00  9.95
ATOM   2730  C    PHE  4486      70.434 105.066  82.687  1.00 20.87
ATOM   2731  O    PHE  4486      70.981 105.982  82.078  1.00 24.94
ATOM   2732  N    PHE  4487      70.669 103.784  82.417  1.00 22.81
ATOM   2733  CA   PHE  4487      71.649 103.428  81.389  1.00 25.79
ATOM   2734  CB   PHE  4487      72.132 101.982  81.579  1.00 17.94
ATOM   2735  CG   PHE  4487      72.868 101.787  82.857  1.00 20.22
ATOM   2736  CD1  PHE  4487      72.232 101.266  83.974  1.00 19.37
ATOM   2737  CD2  PHE  4487      74.172 102.252  82.989  1.00 22.89
ATOM   2738  CE1  PHE  4487      72.880 101.215  85.212  1.00 21.04
ATOM   2739  CE2  PHE  4487      74.829 102.207  84.220  1.00 19.94
ATOM   2740  CZ   PHE  4487      74.176 101.686  85.334  1.00 20.07
ATOM   2741  C    PHE  4487      71.307 103.699  79.925  1.00 23.78
ATOM   2742  O    PHE  4487      72.107 103.406  79.040  1.00 21.23
```

156

| ATOM | 2743 | N | LEU | 4488 | 70.135 | 104.256 | 79.656 | 1.00 | 20.84 |
| ATOM | 2744 | CA | LEU | 4488 | 69.829 | 104.594 | 78.280 | 1.00 | 24.73 |
| ATOM | 2745 | CB | LEU | 4488 | 68.349 | 104.902 | 78.105 | 1.00 | 17.11 |
| ATOM | 2746 | CG | LEU | 4488 | 67.467 | 103.663 | 78.070 | 1.00 | 17.56 |
| ATOM | 2747 | CD1 | LEU | 4488 | 66.024 | 104.110 | 78.108 | 1.00 | 19.95 |
| ATOM | 2748 | CD2 | LEU | 4488 | 67.782 | 102.809 | 76.820 | 1.00 | 9.73 |
| ATOM | 2749 | C | LEU | 4488 | 70.658 | 105.829 | 77.947 | 1.00 | 28.27 |
| ATOM | 2750 | O | LEU | 4488 | 70.859 | 106.170 | 76.779 | 1.00 | 29.34 |
| ATOM | 2751 | N | THR | 4489 | 71.151 | 106.483 | 78.992 | 1.00 | 31.30 |
| ATOM | 2752 | CA | THR | 4489 | 71.950 | 107.687 | 78.855 | 1.00 | 33.91 |
| ATOM | 2753 | CB | THR | 4489 | 71.050 | 108.909 | 78.710 | 1.00 | 37.88 |
| ATOM | 2754 | OG1 | THR | 4489 | 70.362 | 108.836 | 77.454 | 1.00 | 40.91 |
| ATOM | 2755 | CG2 | THR | 4489 | 71.870 | 110.196 | 78.784 | 1.00 | 44.83 |
| ATOM | 2756 | C | THR | 4489 | 72.814 | 107.842 | 80.090 | 1.00 | 34.22 |
| ATOM | 2757 | O | THR | 4489 | 72.593 | 108.734 | 80.914 | 1.00 | 37.77 |
| ATOM | 2758 | N | PRO | 4490 | 73.815 | 106.963 | 80.235 | 1.00 | 32.24 |
| ATOM | 2759 | CD | PRO | 4490 | 74.155 | 105.876 | 79.308 | 1.00 | 33.46 |
| ATOM | 2760 | CA | PRO | 4490 | 74.746 | 106.945 | 81.355 | 1.00 | 30.98 |
| ATOM | 2761 | CB | PRO | 4490 | 75.591 | 105.7.4 | 81.057 | 1.00 | 32.33 |
| ATOM | 2762 | CG | PRO | 4490 | 75.637 | 105.734 | 79.558 | 1.00 | 32.30 |
| ATOM | 2763 | C | PRO | 4490 | 75.578 | 108.204 | 81.452 | 1.00 | 29.67 |
| ATOM | 2764 | O | PRO | 4490 | 76.497 | 108.415 | 80.660 | 1.00 | 31.94 |
| ATOM | 2765 | N | PRO | 4491 | 75.266 | 109.063 | 82.427 | 1.00 | 27.50 |
| ATOM | 2766 | CD | PRO | 4491 | 74.203 | 108.939 | 83.427 | 1.00 | 25.89 |
| ATOM | 2767 | CA | PRO | 4491 | 75.990 | 110.312 | 82.640 | 1.00 | 27.98 |
| ATOM | 2768 | CB | PRO | 4491 | 75.265 | 110.901 | 83.836 | 1.00 | 28.82 |
| ATOM | 2769 | CG | PRO | 4491 | 74.820 | 109.670 | 84.566 | 1.00 | 27.12 |
| ATOM | 2770 | C | PRO | 4491 | 77.443 | 109.977 | 82.949 | 1.00 | 30.90 |
| ATOM | 2771 | O | PRO | 4491 | 77.722 | 108.931 | 83.531 | 1.00 | 35.20 |
| ATOM | 2772 | N | CYS | 4492 | 78.371 | 110.842 | 82.554 | 1.00 | 30.10 |
| ATOM | 2773 | CA | CYS | 4492 | 79.780 | 110.578 | 82.814 | 1.00 | 25.57 |
| ATOM | 2774 | CB | CYS | 4492 | 80.653 | 111.609 | 82.099 | 1.00 | 33.58 |
| ATOM | 2775 | SG | CYS | 4492 | 80.363 | 111.739 | 80.313 | 1.00 | 50.28 |
| ATOM | 2776 | C | CYS | 4492 | 79.991 | 110.663 | 84.316 | 1.00 | 22.84 |
| ATOM | 2777 | O | CYS | 4492 | 79.078 | 111.053 | 85.045 | 1.00 | 23.93 |
| ATOM | 2778 | N | ALA | 4493 | 81.183 | 110.290 | 84.779 | 1.00 | 19.09 |
| ATOM | 2779 | CA | ALA | 4493 | 81.510 | 110.339 | 86.200 | 1.00 | 15.11 |
| ATOM | 2780 | CB | ALA | 4493 | 81.703 | 108.948 | 86.737 | 1.00 | 9.51 |
| ATOM | 2781 | C | ALA | 4493 | 82.777 | 111.143 | 86.413 | 1.00 | 17.34 |
| ATOM | 2782 | O | ALA | 4493 | 83.765 | 110.952 | 85.702 | 1.00 | 18.16 |
| ATOM | 2783 | N | ARG | 4494 | 82.761 | 112.035 | 87.397 | 1.00 | 23.22 |
| ATOM | 2784 | CA | ARG | 4494 | 83.941 | 112.849 | 87.693 | 1.00 | 27.33 |
| ATOM | 2785 | CB | ARG | 4494 | 83.520 | 114.015 | 88.566 | 1.00 | 34.43 |
| ATOM | 2786 | CG | ARG | 4494 | 84.593 | 115.010 | 88.835 | 1.00 | 48.98 |
| ATOM | 2787 | CD | ARG | 4494 | 84.021 | 116.081 | 89.712 | 1.00 | 56.03 |
| ATOM | 2788 | NE | ARG | 4494 | 85.064 | 116.869 | 90.345 | 1.00 | 65.90 |
| ATOM | 2789 | CZ | ARG | 4494 | 84.820 | 117.774 | 91.282 | 1.00 | 76.49 |
| ATOM | 2790 | NH1 | ARG | 4494 | 83.569 | 117.993 | 91.674 | 1.00 | 80.94 |
| ATOM | 2791 | NH2 | ARG | 4494 | 85.820 | 118.455 | 91.828 | 1.00 | 83.01 |
| ATOM | 2792 | C | ARG | 4494 | 84.984 | 111.954 | 88.383 | 1.00 | 22.71 |
| ATOM | 2793 | O | ARG | 4494 | 84.637 | 111.082 | 89.175 | 1.00 | 21.71 |
| ATOM | 2794 | N | TRP | 4495 | 86.263 | 112.152 | 88.102 | 1.00 | 21.21 |
| ATOM | 2795 | CA | TRP | 4495 | 87.229 | 111.233 | 88.680 | 1.00 | 22.62 |
| ATOM | 2796 | CB | TRP | 4495 | 88.534 | 111.222 | 87.895 | 1.00 | 26.65 |
| ATOM | 2797 | CG | TRP | 4495 | 89.352 | 110.021 | 88.278 | 1.00 | 35.87 |
| ATOM | 2798 | CD2 | TRP | 4495 | 90.694 | 110.014 | 88.741 | 1.00 | 32.98 |
| ATOM | 2799 | CE2 | TRP | 4495 | 91.041 | 108.670 | 89.016 | 1.00 | 38.42 |
| ATOM | 2800 | CE3 | TRP | 4495 | 91.643 | 111.013 | 88.960 | 1.00 | 37.62 |
| ATOM | 2801 | CD1 | TRP | 4495 | 88.939 | 108.706 | 88.279 | 1.00 | 38.63 |
| ATOM | 2802 | NE1 | TRP | 4495 | 89.951 | 107.888 | 88.722 | 1.00 | 37.12 |
| ATOM | 2803 | CZ2 | TRP | 4495 | 92.296 | 108.304 | 89.490 | 1.00 | 45.27 |
| ATOM | 2804 | CZ3 | TRP | 4495 | 92.895 | 110.652 | 89.433 | 1.00 | 46.34 |
| ATOM | 2805 | CH2 | TRP | 4495 | 93.210 | 109.310 | 89.696 | 1.00 | 49.63 |
| ATOM | 2806 | C | TRP | 4495 | 87.544 | 111.365 | 90.144 | 1.00 | 18.98 |
| ATOM | 2807 | O | TRP | 4495 | 87.928 | 110.395 | 90.788 | 1.00 | 16.68 |
| ATOM | 2808 | N | ALA | 4496 | 87.400 | 112.556 | 90.682 | 1.00 | 16.97 |
| ATOM | 2809 | CA | ALA | 4496 | 87.651 | 112.716 | 92.096 | 1.00 | 21.54 |
| ATOM | 2810 | CB | ALA | 4496 | 87.383 | 114.152 | 92.495 | 1.00 | 22.40 |
| ATOM | 2811 | C | ALA | 4496 | 86.679 | 111.756 | 92.812 | 1.00 | 24.63 |
| ATOM | 2812 | O | ALA | 4496 | 86.962 | 111.211 | 93.883 | 1.00 | 24.91 |

| | | | | | | | | |
|---|---|---|---|---|---|---|---|---|
| ATOM | 2813 | N | GLN | 4497 | 85.536 | 111.529 | 92.181 | 1.00 24.31 |
| ATOM | 2814 | CA | GLN | 4497 | 84.521 | 110.655 | 92.730 | 1.00 22.55 |
| ATOM | 2815 | CB | GLN | 4497 | 83.157 | 111.145 | 92.260 | 1.00 21.74 |
| ATOM | 2816 | CG | GLN | 4497 | 82.014 | 110.225 | 92.581 | 1.00 32.36 |
| ATOM | 2817 | CD | GLN | 4497 | 80.712 | 110.749 | 92.029 | 1.00 42.04 |
| ATOM | 2818 | OE1 | GLN | 4497 | 80.643 | 111.167 | 90.864 | 1.00 47.49 |
| ATOM | 2819 | NE2 | GLN | 4497 | 79.660 | 110.723 | 92.852 | 1.00 44.24 |
| ATOM | 2820 | C | GLN | 4497 | 84.702 | 109.160 | 92.402 | 1.00 26.25 |
| ATOM | 2821 | O | GLN | 4497 | 84.509 | 108.302 | 93.272 | 1.00 27.25 |
| ATOM | 2822 | N | LEU | 4498 | 85.074 | 108.836 | 91.165 | 1.00 23.97 |
| ATOM | 2823 | CA | LEU | 4498 | 85.250 | 107.427 | 90.792 | 1.00 19.85 |
| ATOM | 2824 | CB | LEU | 4498 | 85.432 | 107.297 | 89.281 | 1.00 13.34 |
| ATOM | 2825 | CG | LEU | 4498 | 85.112 | 105.972 | 88.593 | 1.00 7.91 |
| ATOM | 2826 | CD1 | LEU | 4498 | 85.651 | 106.047 | 87.185 | 1.00 7.38 |
| ATOM | 2827 | CD2 | LEU | 4498 | 85.743 | 104.811 | 89.302 | 1.00 7.59 |
| ATOM | 2828 | C | LEU | 4498 | 86.474 | 106.837 | 91.508 | 1.00 20.34 |
| ATOM | 2829 | O | LEU | 4498 | 86.417 | 105.737 | 92.070 | 1.00 23.49 |
| ATOM | 2830 | N | SER | 4499 | 87.586 | 107.565 | 91.475 | 1.00 18.97 |
| ATOM | 2831 | CA | SER | 4499 | 88.808 | 107.117 | 92.136 | 1.00 17.08 |
| ATOM | 2832 | CB | SER | 4499 | 89.801 | 108.259 | 92.191 | 1.00 9.85 |
| ATOM | 2833 | OG | SER | 4499 | 89.173 | 109.368 | 92.791 | 1.00 15.60 |
| ATOM | 2834 | C | SER | 4499 | 88.495 | 106.665 | 93.562 | 1.00 18.66 |
| ATOM | 2835 | O | SER | 4499 | 88.972 | 105.628 | 94.023 | 1.00 17.98 |
| ATOM | 2836 | N | GLU | 4500 | 87.687 | 107.459 | 94.257 | 1.00 17.37 |
| ATOM | 2837 | CA | GLU | 4500 | 87.312 | 107.144 | 95.619 | 1.00 13.88 |
| ATOM | 2838 | CB | GLU | 4500 | 86.437 | 108.250 | 96.182 | 1.00 18.52 |
| ATOM | 2839 | CG | GLU | 4500 | 86.149 | 108.071 | 97.652 | 1.00 31.79 |
| ATOM | 2840 | CD | GLU | 4500 | 85.400 | 109.240 | 98.237 | 1.00 39.48 |
| ATOM | 2841 | OE1 | GLU | 4500 | 84.311 | 109.566 | 97.718 | 1.00 50.72 |
| ATOM | 2842 | OE2 | GLU | 4500 | 85.898 | 109.871 | 99.216 | 1.00 42.38 |
| ATOM | 2843 | C | GLU | 4500 | 86.581 | 105.818 | 95.651 | 1.00 11.99 |
| ATOM | 2844 | O | GLU | 4500 | 87.037 | 104.865 | 96.264 | 1.00 13.68 |
| ATOM | 2845 | N | VAL | 4501 | 85.445 | 105.767 | 94.994 | 1.00 14.41 |
| ATOM | 2846 | CA | VAL | 4501 | 84.695 | 104.526 | 94.932 | 1.00 12.58 |
| ATOM | 2847 | CB | VAL | 4501 | 83.552 | 104.624 | 93.906 | 1.00 8.10 |
| ATOM | 2848 | CG1 | VAL | 4501 | 83.011 | 103.256 | 93.631 | 1.00 2.99 |
| ATOM | 2849 | CG2 | VAL | 4501 | 82.405 | 105.563 | 94.461 | 1.00 6.71 |
| ATOM | 2850 | C | VAL | 4501 | 85.624 | 103.371 | 94.548 | 1.00 14.63 |
| ATOM | 2851 | O | VAL | 4501 | 85.486 | 102.263 | 95.058 | 1.00 14.80 |
| ATOM | 2852 | N | LEU | 4502 | 86.574 | 103.606 | 93.651 | 1.00 13.92 |
| ATOM | 2853 | CA | LEU | 4502 | 87.442 | 102.515 | 93.322 | 1.00 20.31 |
| ATOM | 2854 | CB | LEU | 4502 | 88.468 | 102.907 | 92.276 | 1.00 22.10 |
| ATOM | 2855 | CG | LEU | 4502 | 87.754 | 103.016 | 90.917 | 1.00 26.90 |
| ATOM | 2856 | CD1 | LEU | 4502 | 88.740 | 103.329 | 89.831 | 1.00 31.51 |
| ATOM | 2857 | CD2 | LEU | 4502 | 87.104 | 101.710 | 90.564 | 1.00 27.47 |
| ATOM | 2858 | C | LEU | 4502 | 88.089 | 102.047 | 94.599 | 1.00 23.21 |
| ATOM | 2859 | O | LEU | 4502 | 87.960 | 100.876 | 94.974 | 1.00 29.47 |
| ATOM | 2860 | N | SER | 4503 | 88.738 | 102.950 | 95.306 | 1.00 20.82 |
| ATOM | 2861 | CA | SER | 4503 | 89.380 | 102.570 | 96.547 | 1.00 21.69 |
| ATOM | 2862 | CB | SER | 4503 | 89.959 | 103.813 | 97.216 | 1.00 20.75 |
| ATOM | 2863 | OG | SER | 4503 | 90.778 | 103.449 | 98.301 | 1.00 27.50 |
| ATOM | 2864 | C | SER | 4503 | 88.387 | 101.846 | 97.495 | 1.00 20.79 |
| ATOM | 2865 | O | SER | 4503 | 88.731 | 100.832 | 98.129 | 1.00 19.45 |
| ATOM | 2866 | N | TRP | 4504 | 87.159 | 102.319 | 97.599 | 1.00 17.20 |
| ATOM | 2867 | CA | TRP | 4504 | 86.202 | 101.682 | 98.466 | 1.00 14.16 |
| ATOM | 2868 | CB | TRP | 4504 | 84.789 | 102.251 | 98.327 | 1.00 7.81 |
| ATOM | 2869 | CG | TRP | 4504 | 84.659 | 103.635 | 98.843 | 1.00 7.87 |
| ATOM | 2870 | CD2 | TRP | 4504 | 83.477 | 104.463 | 98.846 | 1.00 7.23 |
| ATOM | 2871 | CE2 | TRP | 4504 | 83.792 | 105.648 | 99.563 | 1.00 5.70 |
| ATOM | 2872 | CE3 | TRP | 4504 | 82.175 | 104.318 | 98.317 | 1.00 11.63 |
| ATOM | 2873 | CD1 | TRP | 4504 | 85.609 | 104.330 | 99.523 | 1.00 7.56 |
| ATOM | 2874 | NE1 | TRP | 4504 | 85.098 | 105.539 | 99.962 | 1.00 7.99 |
| ATOM | 2875 | CZ2 | TRP | 4504 | 82.871 | 106.692 | 99.765 | 1.00 2.99 |
| ATOM | 2876 | CZ3 | TRP | 4504 | 81.233 | 105.366 | 98.514 | 1.00 9.00 |
| ATOM | 2877 | CH2 | TRP | 4504 | 81.603 | 106.538 | 99.241 | 1.00 7.59 |
| ATOM | 2878 | C | TRP | 4504 | 86.173 | 100.225 | 98.087 | 1.00 15.20 |
| ATOM | 2879 | O | TRP | 4504 | 86.292 | 99.366 | 98.932 | 1.00 20.75 |
| ATOM | 2880 | N | GLN | 4505 | 86.049 | 99.932 | 96.806 | 1.00 15.02 |
| ATOM | 2881 | CA | GLN | 4505 | 85.950 | 98.554 | 96.410 | 1.00 12.05 |
| ATOM | 2882 | CB | GLN | 4505 | 86.022 | 98.426 | 94.905 | 1.00 10.86 |

158

| ATOM | 2883 | CG | GLN | 4505 | 84.905 | 99.192 | 94.231 | 1.00 | 15.10 |
| ATOM | 2884 | CD | GLN | 4505 | 83.617 | 99.222 | 95.079 | 1.00 | 17.04 |
| ATOM | 2885 | OE1 | GLN | 4505 | 83.352 | 100.217 | 95.730 | 1.00 | 16.48 |
| ATOM | 2886 | NE2 | GLN | 4505 | 82.850 | 98.123 | 95.095 | 1.00 | 9.06 |
| ATOM | 2887 | C | GLN | 4505 | 86.966 | 97.697 | 97.085 | 1.00 | 14.64 |
| ATOM | 2888 | O | GLN | 4505 | 86.602 | 96.671 | 97.627 | 1.00 | 16.27 |
| ATOM | 2889 | N | PHE | 4506 | 88.235 | 98.106 | 97.066 | 1.00 | 15.74 |
| ATOM | 2890 | CA | PHE | 4506 | 89.296 | 97.361 | 97.743 | 1.00 | 12.60 |
| ATOM | 2891 | CB | PHE | 4506 | 90.640 | 97.951 | 97.404 | 1.00 | 11.05 |
| ATOM | 2892 | CG | PHE | 4506 | 91.067 | 97.665 | 96.010 | 1.00 | 20.20 |
| ATOM | 2893 | CD1 | PHE | 4506 | 90.431 | 98.270 | 94.932 | 1.00 | 18.84 |
| ATOM | 2894 | CD2 | PHE | 4506 | 92.089 | 96.729 | 95.756 | 1.00 | 19.41 |
| ATOM | 2895 | CE1 | PHE | 4506 | 90.817 | 97.943 | 93.608 | 1.00 | 19.60 |
| ATOM | 2896 | CE2 | PHE | 4506 | 92.470 | 96.403 | 94.444 | 1.00 | 12.39 |
| ATOM | 2897 | CZ | PHE | 4506 | 91.839 | 97.007 | 93.375 | 1.00 | 13.45 |
| ATOM | 2898 | C | PHE | 4506 | 89.114 | 97.404 | 99.255 | 1.00 | 13.80 |
| ATOM | 2899 | O | PHE | 4506 | 89.299 | 96.433 | 99.965 | 1.00 | 13.49 |
| ATOM | 2900 | N | SER | 4507 | 88.736 | 98.539 | 99.786 | 1.00 | 15.47 |
| ATOM | 2901 | CA | SER | 4507 | 88.590 | 98.504 | 101.206 | 1.00 | 19.24 |
| ATOM | 2902 | CB | SER | 4507 | 88.686 | 99.907 | 101.844 | 1.00 | 13.66 |
| ATOM | 2903 | OG | SER | 4507 | 87.860 | 100.823 | 101.218 | 1.00 | 22.24 |
| ATOM | 2904 | C | SER | 4507 | 87.345 | 97.783 | 101.628 | 1.00 | 20.25 |
| ATOM | 2905 | O | SER | 4507 | 87.017 | 97.795 | 102.817 | 1.00 | 27.99 |
| ATOM | 2906 | N | SER | 4508 | 86.675 | 97.114 | 100.690 | 1.00 | 19.51 |
| ATOM | 2907 | CA | SER | 4508 | 85.439 | 96.386 | 101.010 | 1.00 | 22.13 |
| ATOM | 2908 | CB | SER | 4508 | 84.341 | 96.791 | 100.063 | 1.00 | 26.57 |
| ATOM | 2909 | OG | SER | 4508 | 84.236 | 98.202 | 100.078 | 1.00 | 44.13 |
| ATOM | 2910 | C | SER | 4508 | 85.628 | 94.879 | 100.949 | 1.00 | 26.02 |
| ATOM | 2911 | O | SER | 4508 | 84.927 | 94.130 | 101.621 | 1.00 | 30.85 |
| ATOM | 2912 | N | VAL | 4509 | 86.574 | 94.424 | 100.133 | 1.00 | 27.32 |
| ATOM | 2913 | CA | VAL | 4509 | 86.895 | 93.014 | 100.034 | 1.00 | 21.98 |
| ATOM | 2914 | CB | VAL | 4509 | 87.093 | 92.638 | 98.613 | 1.00 | 17.99 |
| ATOM | 2915 | CG1 | VAL | 4509 | 87.392 | 91.157 | 98.462 | 1.00 | 14.86 |
| ATOM | 2916 | CG2 | VAL | 4509 | 85.860 | 92.981 | 97.904 | 1.00 | 17.66 |
| ATOM | 2917 | C | VAL | 4509 | 88.171 | 92.712 | 100.814 | 1.00 | 23.50 |
| ATOM | 2918 | O | VAL | 4509 | 88.488 | 91.545 | 101.026 | 1.00 | 26.47 |
| ATOM | 2919 | N | THR | 4510 | 88.883 | 93.757 | 101.244 | 1.00 | 21.43 |
| ATOM | 2920 | CA | THR | 4510 | 90.125 | 93.617 | 101.995 | 1.00 | 18.80 |
| ATOM | 2921 | CB | THR | 4510 | 91.362 | 93.865 | 101.168 | 1.00 | 18.71 |
| ATOM | 2922 | OG1 | THR | 4510 | 91.453 | 95.268 | 100.847 | 1.00 | 10.43 |
| ATOM | 2923 | CG2 | THR | 4510 | 91.323 | 92.918 | 99.908 | 1.00 | 15.16 |
| ATOM | 2924 | C | THR | 4510 | 90.196 | 94.634 | 103.064 | 1.00 | 20.92 |
| ATOM | 2925 | O | THR | 4510 | 89.238 | 95.350 | 103.304 | 1.00 | 24.65 |
| ATOM | 2926 | N | LYS | 4511 | 91.378 | 94.732 | 103.661 | 1.00 | 25.14 |
| ATOM | 2927 | CA | LYS | 4511 | 91.654 | 95.634 | 104.787 | 1.00 | 28.07 |
| ATOM | 2928 | CB | LYS | 4511 | 92.535 | 94.909 | 105.825 | 1.00 | 30.82 |
| ATOM | 2929 | CG | LYS | 4511 | 92.067 | 93.539 | 106.354 | 1.00 | 36.78 |
| ATOM | 2930 | CD | LYS | 4511 | 93.187 | 92.947 | 107.219 | 1.00 | 46.24 |
| ATOM | 2931 | CE | LYS | 4511 | 92.860 | 91.585 | 107.819 | 1.00 | 54.23 |
| ATOM | 2932 | NZ | LYS | 4511 | 94.055 | 91.000 | 108.523 | 1.00 | 54.82 |
| ATOM | 2933 | C | LYS | 4511 | 92.333 | 96.974 | 104.439 | 1.00 | 28.17 |
| ATOM | 2934 | O | LYS | 4511 | 92.571 | 97.795 | 105.330 | 1.00 | 28.97 |
| ATOM | 2935 | N | ARG | 4512 | 92.694 | 97.188 | 103.175 | 1.00 | 28.53 |
| ATOM | 2936 | CA | ARG | 4512 | 93.301 | 98.462 | 102.797 | 1.00 | 27.04 |
| ATOM | 2937 | CB | ARG | 4512 | 94.804 | 98.412 | 102.932 | 1.00 | 23.09 |
| ATOM | 2938 | CG | ARG | 4512 | 95.499 | 97.761 | 101.816 | 1.00 | 30.57 |
| ATOM | 2939 | CD | ARG | 4512 | 96.916 | 97.479 | 102.212 | 1.00 | 30.40 |
| ATOM | 2940 | NE | ARG | 4512 | 97.604 | 98.717 | 102.484 | 1.00 | 34.55 |
| ATOM | 2941 | CZ | ARG | 4512 | 98.616 | 98.828 | 103.333 | 1.00 | 37.28 |
| ATOM | 2942 | NH1 | ARG | 4512 | 99.054 | 97.767 | 103.991 | 1.00 | 31.86 |
| ATOM | 2943 | NH2 | ARG | 4512 | 99.173 | 100.019 | 103.537 | 1.00 | 44.11 |
| ATOM | 2944 | C | ARG | 4512 | 92.905 | 98.856 | 101.383 | 1.00 | 25.71 |
| ATOM | 2945 | O | ARG | 4512 | 92.926 | 98.029 | 100.472 | 1.00 | 27.58 |
| ATOM | 2946 | N | GLY | 4513 | 92.513 | 100.123 | 101.232 | 1.00 | 24.86 |
| ATOM | 2947 | CA | GLY | 4513 | 92.069 | 100.644 | 99.957 | 1.00 | 19.29 |
| ATOM | 2948 | C | GLY | 4513 | 93.240 | 100.914 | 99.064 | 1.00 | 19.73 |
| ATOM | 2949 | O | GLY | 4513 | 94.296 | 100.280 | 99.101 | 1.00 | 16.98 |
| ATOM | 2950 | N | LEU | 4514 | 93.053 | 101.966 | 98.247 | 1.00 | 20.54 |
| ATOM | 2951 | CA | LEU | 4514 | 94.079 | 102.366 | 97.320 | 1.00 | 23.37 |
| ATOM | 2952 | CB | LEU | 4514 | 93.462 | 102.641 | 95.952 | 1.00 | 23.53 |

| | | | | | | | |
|---|---|---|---|---|---|---|---|
|ATOM|2953|CG  |LEU|4514| 92.748|101.501|95.239|1.00 21.53|
|ATOM|2954|CD1 |LEU|4514| 92.299|101.956|93.859|1.00 11.24|
|ATOM|2955|CD2 |LEU|4514| 93.732|100.309|95.171|1.00 16.80|
|ATOM|2956|C   |LEU|4514| 94.590|103.648|97.872|1.00 26.45|
|ATOM|2957|O   |LEU|4514| 93.797|104.406|98.408|1.00 26.37|
|ATOM|2958|N   |ASN|4515| 95.897|103.895|97.741|1.00 28.94|
|ATOM|2959|CA  |ASN|4515| 96.516|105.139|98.211|1.00 28.53|
|ATOM|2960|CB  |ASN|4515| 97.935|104.871|98.681|1.00 28.65|
|ATOM|2961|CG  |ASN|4515| 98.826|104.343|97.550|1.00 28.10|
|ATOM|2962|OD1 |ASN|4515| 98.816|104.862|96.441|1.00 25.58|
|ATOM|2963|ND2 |ASN|4515| 99.600|103.324|97.840|1.00 31.85|
|ATOM|2964|C   |ASN|4515| 96.602|106.033|96.977|1.00 32.26|
|ATOM|2965|O   |ASN|4515| 96.182|105.632|95.880|1.00 34.24|
|ATOM|2966|N   |VAL|4516| 97.180|107.220|97.135|1.00 31.17|
|ATOM|2967|CA  |VAL|4516| 97.341|108.112|96.006|1.00 31.12|
|ATOM|2968|CB  |VAL|4516| 97.823|109.485|96.513|1.00 31.42|
|ATOM|2969|CG1 |VAL|4516| 98.199|110.403|95.363|1.00 34.40|
|ATOM|2970|CG2 |VAL|4516| 96.690|110.143|97.244|1.00 34.04|
|ATOM|2971|C   |VAL|4516| 98.230|107.587|94.824|1.00 33.16|
|ATOM|2972|O   |VAL|4516| 97.869|107.767|93.669|1.00 34.62|
|ATOM|2973|N   |ASP|4517| 99.358|106.928|95.060|1.00 34.19|
|ATOM|2974|CA  |ASP|4517|100.155|106.465|93.907|1.00 38.41|
|ATOM|2975|CB  |ASP|4517|101.437|105.750|94.335|1.00 43.24|
|ATOM|2976|CG  |ASP|4517|102.384|106.656|95.096|1.00 50.92|
|ATOM|2977|OD1 |ASP|4517|102.928|107.565|94.437|1.00 55.11|
|ATOM|2978|OD2 |ASP|4517|102.579|106.474|96.338|1.00 52.69|
|ATOM|2979|C   |ASP|4517| 99.398|105.510|93.023|1.00 36.86|
|ATOM|2980|O   |ASP|4517| 99.459|105.595|91.800|1.00 38.49|
|ATOM|2981|N   |GLN|4518| 98.712|104.581|93.659|1.00 35.50|
|ATOM|2982|CA  |GLN|4518| 97.939|103.582|92.956|1.00 34.33|
|ATOM|2983|CB  |GLN|4518| 97.387|102.600|93.983|1.00 34.56|
|ATOM|2984|CG  |GLN|4518| 98.529|102.006|94.763|1.00 34.52|
|ATOM|2985|CD  |GLN|4518| 98.126|101.097|95.890|1.00 34.14|
|ATOM|2986|OE1 |GLN|4518| 97.435|101.506|96.857|1.00 31.83|
|ATOM|2987|NE2 |GLN|4518| 98.572| 99.837|95.790|1.00 33.92|
|ATOM|2988|C   |GLN|4518| 96.823|104.276|92.173|1.00 34.07|
|ATOM|2989|O   |GLN|4518| 96.549|103.973|91.004|1.00 34.11|
|ATOM|2990|N   |LEU|4519| 96.186|105.230|92.815|1.00 31.41|
|ATOM|2991|CA  |LEU|4519| 95.128|105.931|92.148|1.00 30.24|
|ATOM|2992|CB  |LEU|4519| 94.372|106.799|93.131|1.00 25.38|
|ATOM|2993|CG  |LEU|4519| 93.639|105.961|94.148|1.00 20.93|
|ATOM|2994|CD1 |LEU|4519| 92.944|106.883|95.059|1.00 16.15|
|ATOM|2995|CD2 |LEU|4519| 92.650|105.020|93.440|1.00 15.83|
|ATOM|2996|C   |LEU|4519| 95.577|106.779|90.983|1.00 32.22|
|ATOM|2997|O   |LEU|4519| 94.787|106.965|90.070|1.00 38.55|
|ATOM|2998|N   |ASN|4520| 96.801|107.305|90.978|1.00 31.01|
|ATOM|2999|CA  |ASN|4520| 97.203|108.145|89.836|1.00 34.46|
|ATOM|3000|CB  |ASN|4520| 98.428|109.033|90.151|1.00 35.43|
|ATOM|3001|CG  |ASN|4520| 98.174|110.079|91.281|1.00 40.99|
|ATOM|3002|OD1 |ASN|4520| 97.139|110.766|91.321|1.00 34.28|
|ATOM|3003|ND2 |ASN|4520| 99.163|110.221|92.181|1.00 41.37|
|ATOM|3004|C   |ASN|4520| 97.550|107.254|88.640|1.00 34.60|
|ATOM|3005|O   |ASN|4520| 97.417|107.664|87.482|1.00 32.29|
|ATOM|3006|N   |MET|4521| 97.991|106.030|88.954|1.00 32.92|
|ATOM|3007|CA  |MET|4521| 98.401|105.025|87.974|1.00 27.06|
|ATOM|3008|CB  |MET|4521| 99.027|103.847|88.719|1.00 27.89|
|ATOM|3009|CG  |MET|4521| 99.411|102.650|87.883|1.00 30.72|
|ATOM|3010|SD  |MET|4521| 98.028|101.706|87.199|1.00 38.43|
|ATOM|3011|CE  |MET|4521| 98.920|100.318|86.582|1.00 28.87|
|ATOM|3012|C   |MET|4521| 97.163|104.606|87.227|1.00 24.60|
|ATOM|3013|O   |MET|4521| 97.164|104.476|86.012|1.00 23.37|
|ATOM|3014|N   |LEU|4522| 96.093|104.401|87.974|1.00 22.69|
|ATOM|3015|CA  |LEU|4522| 94.833|104.037|87.381|1.00 21.37|
|ATOM|3016|CB  |LEU|4522| 93.874|103.549|88.451|1.00 17.76|
|ATOM|3017|CG  |LEU|4522| 94.252|102.229|89.137|1.00 20.29|
|ATOM|3018|CD1 |LEU|4522| 93.273|101.985|90.254|1.00 15.93|
|ATOM|3019|CD2 |LEU|4522| 94.274|101.029|88.141|1.00 14.50|
|ATOM|3020|C   |LEU|4522| 94.265|105.255|86.673|1.00 22.37|
|ATOM|3021|O   |LEU|4522| 93.649|105.146|85.616|1.00 26.13|
|ATOM|3022|N   |GLY|4523| 94.473|106.422|87.254|1.00 23.71|

160

```
ATOM  3023  CA   GLY  4523    93.983 107.641  86.646  1.00 25.05
ATOM  3024  C    GLY  4523    94.582 107.947  85.288  1.00 28.15
ATOM  3025  O    GLY  4523    93.857 108.284  84.381  1.00 30.48
ATOM  3026  N    GLU  4524    95.888 107.831  85.105  1.00 32.20
ATOM  3027  CA   GLU  4524    96.430 108.168  83.798  1.00 37.80
ATOM  3028  CB   GLU  4524    97.950 108.415  83.874  1.00 46.32
ATOM  3029  CG   GLU  4524    98.309 109.720  84.646  1.00 60.81
ATOM  3030  CD   GLU  4524    99.836 109.980  84.829  1.00 69.00
ATOM  3031  OE1  GLU  4524   100.570 109.106  85.371  1.00 74.99
ATOM  3032  OE2  GLU  4524   100.302 111.082  84.449  1.00 68.23
ATOM  3033  C    GLU  4524    96.103 107.043  82.850  1.00 36.94
ATOM  3034  O    GLU  4524    96.552 106.991  81.701  1.00 42.11
ATOM  3035  N    LYS  4525    95.288 106.136  83.342  1.00 33.36
ATOM  3036  CA   LYS  4525    94.912 104.983  82.558  1.00 29.49
ATOM  3037  CB   LYS  4525    95.046 103.746  83.433  1.00 30.54
ATOM  3038  CG   LYS  4525    94.833 102.462  82.714  1.00 35.97
ATOM  3039  CD   LYS  4525    95.509 101.341  83.447  1.00 39.11
ATOM  3040  CE   LYS  4525    95.313 100.068  82.657  1.00 42.69
ATOM  3041  NZ   LYS  4525    96.308  99.082  83.082  1.00 52.57
ATOM  3042  C    LYS  4525    93.500 105.146  82.042  1.00 25.91
ATOM  3043  O    LYS  4525    93.104 104.492  81.103  1.00 24.13
ATOM  3044  N    LEU  4526    92.762 106.054  82.659  1.00 21.67
ATOM  3045  CA   LEU  4526    91.398 106.317  82.295  1.00 21.03
ATOM  3046  CB   LEU  4526    90.492 106.215  83.517  1.00 24.10
ATOM  3047  CG   LEU  4526    90.167 104.849  84.107  1.00 28.95
ATOM  3048  CD1  LEU  4526    89.232 105.021  85.283  1.00 27.89
ATOM  3049  CD2  LEU  4526    89.494 103.974  83.029  1.00 29.55
ATOM  3050  C    LEU  4526    91.261 107.702  81.725  1.00 22.60
ATOM  3051  O    LEU  4526    90.297 108.014  81.035  1.00 27.01
ATOM  3052  N    LEU  4527    92.214 108.559  82.019  1.00 19.41
ATOM  3053  CA   LEU  4527    92.097 109.887  81.508  1.00 17.02
ATOM  3054  CB   LEU  4527    91.777 110.818  82.629  1.00 19.69
ATOM  3055  CG   LEU  4527    90.460 110.665  83.358  1.00 26.99
ATOM  3056  CD1  LEU  4527    90.491 111.562  84.654  1.00 28.28
ATOM  3057  CD2  LEU  4527    89.316 111.063  82.423  1.00 24.50
ATOM  3058  C    LEU  4527    93.378 110.316  80.857  1.00 18.46
ATOM  3059  O    LEU  4527    93.429 111.360  80.218  1.00 24.77
ATOM  3060  N    GLY  4528    94.426 109.529  81.017  1.00 15.65
ATOM  3061  CA   GLY  4528    95.677 109.923  80.411  1.00 17.90
ATOM  3062  C    GLY  4528    96.430 110.985  81.203  1.00 20.93
ATOM  3063  O    GLY  4528    96.029 111.380  82.313  1.00 16.96
ATOM  3064  N    PRO  4529    97.568 111.435  80.664  1.00 19.80
ATOM  3065  CD   PRO  4529    98.176 110.936  79.430  1.00 23.68
ATOM  3066  CA   PRO  4529    98.440 112.446  81.240  1.00 18.74
ATOM  3067  CB   PRO  4529    99.431 112.714  80.107  1.00 19.83
ATOM  3068  CG   PRO  4529    98.723 112.195  78.885  1.00 25.57
ATOM  3069  C    PRO  4529    97.795 113.709  81.816  1.00 17.05
ATOM  3070  O    PRO  4529    98.324 114.297  82.747  1.00 21.62
ATOM  3071  N    ASN  4530    96.683 114.161  81.282  1.00 13.32
ATOM  3072  CA   ASN  4530    96.077 115.318  81.893  1.00 10.40
ATOM  3073  CB   ASN  4530    95.406 116.217  80.843  1.00 12.78
ATOM  3074  CG   ASN  4530    96.399 116.886  79.929  1.00 16.08
ATOM  3075  OD1  ASN  4530    97.446 117.375  80.365  1.00 15.39
ATOM  3076  ND2  ASN  4530    96.060 116.952  78.656  1.00 20.34
ATOM  3077  C    ASN  4530    95.036 114.820  82.898  1.00  9.36
ATOM  3078  O    ASN  4530    94.032 115.485  83.142  1.00 12.07
ATOM  3079  N    ALA  4531    95.244 113.631  83.444  1.00  9.11
ATOM  3080  CA   ALA  4531    94.312 113.087  84.430  1.00 16.24
ATOM  3081  CB   ALA  4531    94.884 111.820  85.035  1.00 15.66
ATOM  3082  C    ALA  4531    94.137 114.175  85.500  1.00 20.32
ATOM  3083  O    ALA  4531    95.126 114.783  85.934  1.00 23.70
ATOM  3084  N    SER  4532    92.900 114.398  85.929  1.00 20.26
ATOM  3085  CA   SER  4532    92.562 115.413  86.852  1.00 23.52
ATOM  3086  CB   SER  4532    92.271 116.735  86.005  1.00 20.83
ATOM  3087  OG   SER  4532    91.618 117.782  86.717  1.00 21.44
ATOM  3088  C    SER  4532    91.318 115.108  87.660  1.00 29.15
ATOM  3089  O    SER  4532    90.414 114.478  87.140  1.00 33.79
ATOM  3090  N    PRO  4533    91.225 115.526  88.931  1.00 30.94
ATOM  3091  CD   PRO  4533    92.102 116.368  89.738  1.00 31.79
ATOM  3092  CA   PRO  4533    90.042 115.194  89.726  1.00 30.69
```

| ATOM | 3093 | CB | PRO | 4533 | 90.267 | 115.981 | 90.998 | 1.00 | 30.00 |
|------|------|-----|-----|------|--------|---------|--------|------|-------|
| ATOM | 3094 | CG | PRO | 4533 | 91.045 | 117.121 | 90.501 | 1.00 | 32.94 |
| ATOM | 3095 | C | PRO | 4533 | 88.756 | 115.576 | 89.030 | 1.00 | 29.74 |
| ATOM | 3096 | O | PRO | 4533 | 87.755 | 114.863 | 89.108 | 1.00 | 32.67 |
| ATOM | 3097 | N | ASP | 4534 | 88.786 | 116.700 | 88.334 | 1.00 | 30.43 |
| ATOM | 3098 | CA | ASP | 4534 | 87.605 | 117.151 | 87.588 | 1.00 | 28.51 |
| ATOM | 3099 | CB | ASP | 4534 | 87.709 | 118.657 | 87.308 | 1.00 | 33.67 |
| ATOM | 3100 | CG | ASP | 4534 | 87.462 | 119.483 | 88.544 | 1.00 | 41.12 |
| ATOM | 3101 | OD1 | ASP | 4534 | 86.350 | 119.371 | 89.096 | 1.00 | 47.49 |
| ATOM | 3102 | OD2 | ASP | 4534 | 88.357 | 120.238 | 88.976 | 1.00 | 46.20 |
| ATOM | 3103 | C | ASP | 4534 | 87.352 | 116.402 | 86.273 | 1.00 | 17.83 |
| ATOM | 3104 | O | ASP | 4534 | 86.281 | 116.460 | 85.722 | 1.00 | 13.32 |
| ATOM | 3105 | N | GLY | 4535 | 88.332 | 115.694 | 85.771 | 1.00 | 12.79 |
| ATOM | 3106 | CA | GLY | 4535 | 88.105 | 115.006 | 84.516 | 1.00 | 16.58 |
| ATOM | 3107 | C | GLY | 4535 | 86.890 | 114.099 | 84.411 | 1.00 | 17.53 |
| ATOM | 3108 | O | GLY | 4535 | 86.615 | 113.330 | 85.315 | 1.00 | 21.34 |
| ATOM | 3109 | N | LEU | 4536 | 86.154 | 114.169 | 83.306 | 1.00 | 14.15 |
| ATOM | 3110 | CA | LEU | 4536 | 85.004 | 113.291 | 83.159 | 1.00 | 13.54 |
| ATOM | 3111 | CB | LEU | 4536 | 83.924 | 114.010 | 82.367 | 1.00 | 9.02 |
| ATOM | 3112 | CG | LEU | 4536 | 83.178 | 115.061 | 83.181 | 1.00 | 2.99 |
| ATOM | 3113 | CD1 | LEU | 4536 | 82.166 | 115.687 | 82.337 | 1.00 | 2.99 |
| ATOM | 3114 | CD2 | LEU | 4536 | 82.506 | 114.441 | 84.387 | 1.00 | 7.27 |
| ATOM | 3115 | C | LEU | 4536 | 85.345 | 111.909 | 82.534 | 1.00 | 17.67 |
| ATOM | 3116 | O | LEU | 4536 | 86.195 | 111.799 | 81.655 | 1.00 | 21.34 |
| ATOM | 3117 | N | ILE | 4537 | 84.690 | 110.857 | 83.006 | 1.00 | 16.53 |
| ATOM | 3118 | CA | ILE | 4537 | 84.966 | 109.492 | 82.545 | 1.00 | 16.70 |
| ATOM | 3119 | CB | ILE | 4537 | 85.533 | 108.613 | 83.701 | 1.00 | 9.12 |
| ATOM | 3120 | CG2 | ILE | 4537 | 85.847 | 107.266 | 83.212 | 1.00 | 6.56 |
| ATOM | 3121 | CG1 | ILE | 4537 | 86.750 | 109.319 | 84.300 | 1.00 | 12.41 |
| ATOM | 3122 | CD1 | ILE | 4537 | 87.638 | 108.433 | 85.192 | 1.00 | 12.78 |
| ATOM | 3123 | C | ILE | 4537 | 83.704 | 108.777 | 82.023 | 1.00 | 19.54 |
| ATOM | 3124 | O | ILE | 4537 | 82.898 | 108.273 | 82.780 | 1.00 | 17.95 |
| ATOM | 3125 | N | PRO | 4538 | 83.548 | 108.684 | 80.715 | 1.00 | 21.87 |
| ATOM | 3126 | CD | PRO | 4538 | 84.404 | 109.093 | 79.594 | 1.00 | 25.30 |
| ATOM | 3127 | CA | PRO | 4538 | 82.363 | 108.007 | 80.220 | 1.00 | 19.92 |
| ATOM | 3128 | CB | PRO | 4538 | 82.590 | 108.024 | 78.724 | 1.00 | 23.53 |
| ATOM | 3129 | CG | PRO | 4538 | 83.370 | 109.312 | 78.538 | 1.00 | 24.29 |
| ATOM | 3130 | C | PRO | 4538 | 82.166 | 106.571 | 80.753 | 1.00 | 19.86 |
| ATOM | 3131 | O | PRO | 4538 | 83.124 | 105.806 | 80.971 | 1.00 | 15.94 |
| ATOM | 3132 | N | TRP | 4539 | 80.890 | 106.238 | 80.961 | 1.00 | 20.34 |
| ATOM | 3133 | CA | TRP | 4539 | 80.454 | 104.927 | 81.413 | 1.00 | 17.93 |
| ATOM | 3134 | CB | TRP | 4539 | 78.939 | 104.843 | 81.242 | 1.00 | 14.96 |
| ATOM | 3135 | CG | TRP | 4539 | 78.373 | 103.483 | 81.284 | 1.00 | 17.80 |
| ATOM | 3136 | CD2 | TRP | 4539 | 78.481 | 102.514 | 82.340 | 1.00 | 23.05 |
| ATOM | 3137 | CE2 | TRP | 4539 | 77.693 | 101.401 | 81.979 | 1.00 | 20.91 |
| ATOM | 3138 | CE3 | TRP | 4539 | 79.161 | 102.480 | 83.563 | 1.00 | 20.35 |
| ATOM | 3139 | CD1 | TRP | 4539 | 77.551 | 102.919 | 80.353 | 1.00 | 20.91 |
| ATOM | 3140 | NE1 | TRP | 4539 | 77.136 | 101.674 | 80.757 | 1.00 | 16.86 |
| ATOM | 3141 | CZ2 | TRP | 4539 | 77.572 | 100.288 | 82.773 | 1.00 | 20.78 |
| ATOM | 3142 | CZ3 | TRP | 4539 | 79.034 | 101.386 | 84.340 | 1.00 | 22.02 |
| ATOM | 3143 | CH2 | TRP | 4539 | 78.246 | 100.300 | 83.953 | 1.00 | 21.44 |
| ATOM | 3144 | C | TRP | 4539 | 81.189 | 103.970 | 80.489 | 1.00 | 18.97 |
| ATOM | 3145 | O | TRP | 4539 | 81.889 | 103.049 | 80.908 | 1.00 | 20.76 |
| ATOM | 3146 | N | THR | 4540 | 81.056 | 104.251 | 79.209 | 1.00 | 22.49 |
| ATOM | 3147 | CA | THR | 4540 | 81.704 | 103.515 | 78.144 | 1.00 | 24.76 |
| ATOM | 3148 | CB | THR | 4540 | 81.512 | 104.318 | 76.893 | 1.00 | 25.48 |
| ATOM | 3149 | OG1 | THR | 4540 | 80.159 | 104.805 | 76.924 | 1.00 | 30.38 |
| ATOM | 3150 | CG2 | THR | 4540 | 81.758 | 103.474 | 75.641 | 1.00 | 18.07 |
| ATOM | 3151 | C | THR | 4540 | 83.204 | 103.248 | 78.387 | 1.00 | 24.53 |
| ATOM | 3152 | O | THR | 4540 | 83.648 | 102.126 | 78.318 | 1.00 | 22.92 |
| ATOM | 3153 | N | ARG | 4541 | 84.014 | 104.267 | 78.679 | 1.00 | 26.20 |
| ATOM | 3154 | CA | ARG | 4541 | 85.427 | 104.022 | 78.918 | 1.00 | 24.35 |
| ATOM | 3155 | CB | ARG | 4541 | 86.226 | 105.343 | 79.094 | 1.00 | 26.91 |
| ATOM | 3156 | CG | ARG | 4541 | 87.763 | 105.197 | 78.788 | 1.00 | 28.98 |
| ATOM | 3157 | CD | ARG | 4541 | 88.445 | 106.506 | 78.715 | 1.00 | 33.22 |
| ATOM | 3158 | NE | ARG | 4541 | 87.828 | 107.378 | 77.720 | 1.00 | 45.72 |
| ATOM | 3159 | CZ | ARG | 4541 | 88.054 | 108.701 | 77.605 | 1.00 | 50.69 |
| ATOM | 3160 | NH1 | ARG | 4541 | 88.914 | 109.331 | 78.417 | 1.00 | 49.15 |
| ATOM | 3161 | NH2 | ARG | 4541 | 87.439 | 109.409 | 76.643 | 1.00 | 50.60 |
| ATOM | 3162 | C | ARG | 4541 | 85.584 | 103.176 | 80.153 | 1.00 | 24.31 |

| | | | | | | | | |
|---|---|---|---|---|---|---|---|---|
| ATOM | 3163 | O | ARG | 4541 | 86.618 | 102.576 | 80.359 | 1.00 24.09 |
| ATOM | 3164 | N | PHE | 4542 | 84.537 | 103.060 | 80.959 | 1.00 23.81 |
| ATOM | 3165 | CA | PHE | 4542 | 84.662 | 102.319 | 82.188 | 1.00 22.27 |
| ATOM | 3166 | CB | PHE | 4542 | 83.786 | 102.992 | 83.232 | 1.00 18.66 |
| ATOM | 3167 | CG | PHE | 4542 | 83.938 | 102.451 | 84.637 | 1.00 20.13 |
| ATOM | 3168 | CD1 | PHE | 4542 | 85.112 | 102.599 | 85.347 | 1.00 17.86 |
| ATOM | 3169 | CD2 | PHE | 4542 | 82.900 | 101.730 | 85.243 | 1.00 16.68 |
| ATOM | 3170 | CE1 | PHE | 4542 | 85.213 | 102.014 | 86.631 | 1.00 17.80 |
| ATOM | 3171 | CE2 | PHE | 4542 | 83.036 | 101.171 | 86.493 | 1.00 11.59 |
| ATOM | 3172 | CZ | PHE | 4542 | 84.190 | 101.304 | 87.182 | 1.00  8.87 |
| ATOM | 3173 | C | PHE | 4542 | 84.362 | 100.852 | 82.133 | 1.00 27.35 |
| ATOM | 3174 | O | PHE | 4542 | 85.135 | 100.087 | 82.677 | 1.00 28.66 |
| ATOM | 3175 | N | CYS | 4543 | 83.242 | 100.449 | 81.494 | 1.00 32.72 |
| ATOM | 3176 | CA | CYS | 4543 | 82.770 | 99.012 | 81.461 | 1.00 34.68 |
| ATOM | 3177 | CB | CYS | 4543 | 81.431 | 98.868 | 82.302 | 1.00 35.45 |
| ATOM | 3178 | SG | CYS | 4543 | 80.742 | 96.964 | 82.759 | 1.00 57.09 |
| ATOM | 3179 | C | CYS | 4543 | 82.570 | 98.531 | 80.026 | 1.00 34.86 |
| ATOM | 3180 | O | CYS | 4543 | 82.102 | 97.430 | 79.826 | 1.00 37.10 |
| ATOM | 3181 | N | LYS | 4544 | 82.956 | 99.293 | 79.019 | 1.00 35.70 |
| ATOM | 3182 | CA | LYS | 4544 | 82.766 | 98.853 | 77.641 | 1.00 34.21 |
| ATOM | 3183 | CB | LYS | 4544 | 81.618 | 99.633 | 77.036 | 1.00 28.25 |
| ATOM | 3184 | CG | LYS | 4544 | 80.421 | 99.377 | 77.790 | 1.00 29.41 |
| ATOM | 3185 | CD | LYS | 4544 | 79.244 | 99.891 | 77.065 | 1.00 31.35 |
| ATOM | 3186 | CE | LYS | 4544 | 78.032 | 99.297 | 77.686 | 1.00 30.59 |
| ATOM | 3187 | NZ | LYS | 4544 | 76.944 | 99.503 | 76.781 | 1.00 30.23 |
| ATOM | 3188 | C | LYS | 4544 | 83.980 | 98.921 | 76.717 | 1.00 37.46 |
| ATOM | 3189 | O | LYS | 4544 | 84.323 | 97.959 | 76.050 | 1.00 38.19 |
| ATOM | 3190 | N | GLU | 4545 | 84.634 | 100.062 | 76.651 | 1.00 43.22 |
| ATOM | 3191 | CA | GLU | 4545 | 85.784 | 100.206 | 75.788 | 1.00 51.22 |
| ATOM | 3192 | CB | GLU | 4545 | 86.294 | 101.617 | 75.919 | 1.00 53.28 |
| ATOM | 3193 | CG | GLU | 4545 | 87.217 | 102.042 | 74.867 | 1.00 63.18 |
| ATOM | 3194 | CD | GLU | 4545 | 88.065 | 103.204 | 75.355 | 1.00 70.60 |
| ATOM | 3195 | OE1 | GLU | 4545 | 89.071 | 102.953 | 76.102 | 1.00 71.06 |
| ATOM | 3196 | OE2 | GLU | 4545 | 87.701 | 104.372 | 75.020 | 1.00 74.69 |
| ATOM | 3197 | C | GLU | 4545 | 86.805 | 99.183 | 76.297 | 1.00 55.82 |
| ATOM | 3198 | O | GLU | 4545 | 86.727 | 98.745 | 77.435 | 1.00 62.58 |
| ATOM | 3199 | N | ASN | 4546 | 87.752 | 98.788 | 75.464 | 1.00 57.63 |
| ATOM | 3200 | CA | ASN | 4546 | 88.754 | 97.797 | 75.804 | 1.00 57.40 |
| ATOM | 3201 | CB | ASN | 4546 | 89.170 | 97.178 | 74.522 | 1.00 59.88 |
| ATOM | 3202 | CG | ASN | 4546 | 90.239 | 96.169 | 74.678 | 1.00 65.28 |
| ATOM | 3203 | OD1 | ASN | 4546 | 90.030 | 95.070 | 75.202 | 1.00 66.76 |
| ATOM | 3204 | ND2 | ASN | 4546 | 91.424 | 96.520 | 74.179 | 1.00 66.15 |
| ATOM | 3205 | C | ASN | 4546 | 89.746 | 98.776 | 76.305 | 1.00 58.23 |
| ATOM | 3206 | O | ASN | 4546 | 89.755 | 99.880 | 75.838 | 1.00 58.91 |
| ATOM | 3207 | N | ILE | 4547 | 90.616 | 98.434 | 77.251 | 1.00 62.18 |
| ATOM | 3208 | CA | ILE | 4547 | 91.466 | 99.542 | 77.740 | 1.00 63.55 |
| ATOM | 3209 | CB | ILE | 4547 | 91.119 | 99.906 | 79.247 | 1.00 63.13 |
| ATOM | 3210 | CG2 | ILE | 4547 | 91.563 | 98.847 | 80.207 | 1.00 58.54 |
| ATOM | 3211 | CG1 | ILE | 4547 | 91.601 | 101.320 | 79.629 | 1.00 66.35 |
| ATOM | 3212 | CD1 | ILE | 4547 | 90.730 | 101.913 | 80.777 | 1.00 70.43 |
| ATOM | 3213 | C | ILE | 4547 | 92.935 | 99.703 | 77.154 | 1.00 65.14 |
| ATOM | 3214 | O | ILE | 4547 | 93.263 | 99.200 | 76.134 | 1.00 69.33 |
| ATOM | 3215 | N | ASN | 4548 | 93.826 | 100.398 | 77.811 | 1.00 68.68 |
| ATOM | 3216 | CA | ASN | 4548 | 95.169 | 100.762 | 77.181 | 1.00 70.68 |
| ATOM | 3217 | CB | ASN | 4548 | 96.226 | 100.943 | 78.281 | 1.00 64.95 |
| ATOM | 3218 | CG | ASN | 4548 | 95.686 | 101.766 | 79.356 | 1.00 62.95 |
| ATOM | 3219 | OD1 | ASN | 4548 | 94.906 | 102.709 | 79.091 | 1.00 66.19 |
| ATOM | 3220 | ND2 | ASN | 4548 | 95.910 | 101.350 | 80.547 | 1.00 65.73 |
| ATOM | 3221 | C | ASN | 4548 | 95.698 | 100.015 | 75.844 | 1.00 72.35 |
| ATOM | 3222 | O | ASN | 4548 | 96.071 | 100.744 | 74.924 | 1.00 77.17 |
| ATOM | 3223 | N | ASP | 4549 | 95.579 | 98.709 | 75.653 | 1.00 70.24 |
| ATOM | 3224 | CA | ASP | 4549 | 96.049 | 98.166 | 74.361 | 1.00 66.17 |
| ATOM | 3225 | CB | ASP | 4549 | 97.581 | 98.156 | 74.270 | 1.00 67.12 |
| ATOM | 3226 | CG | ASP | 4549 | 98.238 | 97.003 | 75.009 | 1.00 73.35 |
| ATOM | 3227 | OD1 | ASP | 4549 | 97.692 | 96.648 | 76.049 | 1.00 83.98 |
| ATOM | 3228 | OD2 | ASP | 4549 | 99.283 | 96.450 | 74.557 | 1.00 74.95 |
| ATOM | 3229 | C | ASP | 4549 | 95.520 | 96.679 | 74.388 | 1.00 65.37 |
| ATOM | 3230 | O | ASP | 4549 | 95.883 | 95.900 | 73.533 | 1.00 65.29 |
| ATOM | 3231 | N | LYS | 4550 | 94.684 | 96.391 | 75.345 | 1.00 63.59 |
| ATOM | 3232 | CA | LYS | 4550 | 94.099 | 95.001 | 75.562 | 1.00 61.93 |

163

| ATOM | 3233 | CB | LYS | 4550 | 93.931 | 94.932 | 77.063 | 1.00 | 61.71 |
| ATOM | 3234 | CG | LYS | 4550 | 95.151 | 95.567 | 77.737 | 1.00 | 63.31 |
| ATOM | 3235 | CD | LYS | 4550 | 94.724 | 95.941 | 79.145 | 1.00 | 69.77 |
| ATOM | 3236 | CE | LYS | 4550 | 95.767 | 96.608 | 80.127 | 1.00 | 69.50 |
| ATOM | 3237 | NZ | LYS | 4550 | 95.241 | 96.729 | 81.609 | 1.00 | 61.63 |
| ATOM | 3238 | C | LYS | 4550 | 92.808 | 94.365 | 74.869 | 1.00 | 61.84 |
| ATOM | 3239 | O | LYS | 4550 | 92.477 | 94.571 | 73.734 | 1.00 | 63.76 |
| ATOM | 3240 | N | ASN | 4551 | 92.200 | 93.379 | 75.570 | 1.00 | 61.82 |
| ATOM | 3241 | CA | ASN | 4551 | 90.987 | 92.663 | 75.074 | 1.00 | 60.51 |
| ATOM | 3242 | CB | ASN | 4551 | 91.294 | 91.228 | 74.655 | 1.00 | 66.42 |
| ATOM | 3243 | CG | ASN | 4551 | 92.211 | 91.184 | 73.541 | 1.00 | 72.41 |
| ATOM | 3244 | OD1 | ASN | 4551 | 91.926 | 91.724 | 72.463 | 1.00 | 76.65 |
| ATOM | 3245 | ND2 | ASN | 4551 | 93.361 | 90.577 | 73.764 | 1.00 | 76.33 |
| ATOM | 3246 | C | ASN | 4551 | 89.953 | 92.539 | 76.182 | 1.00 | 56.75 |
| ATOM | 3247 | O | ASN | 4551 | 89.244 | 91.493 | 76.266 | 1.00 | 57.11 |
| ATOM | 3248 | N | PHE | 4552 | 89.912 | 93.566 | 77.050 | 1.00 | 48.02 |
| ATOM | 3249 | CA | PHE | 4552 | 88.960 | 93.663 | 78.169 | 1.00 | 38.19 |
| ATOM | 3250 | CB | PHE | 4552 | 89.409 | 92.803 | 79.351 | 1.00 | 39.00 |
| ATOM | 3251 | CG | PHE | 4552 | 90.887 | 92.863 | 79.630 | 1.00 | 41.98 |
| ATOM | 3252 | CD1 | PHE | 4552 | 91.420 | 92.866 | 80.443 | 1.00 | 42.87 |
| ATOM | 3253 | CD2 | PHE | 4552 | 91.764 | 92.024 | 78.944 | 1.00 | 39.73 |
| ATOM | 3254 | CE1 | PHE | 4552 | 92.778 | 94.019 | 80.549 | 1.00 | 42.60 |
| ATOM | 3255 | CE2 | PHE | 4552 | 93.141 | 92.168 | 79.043 | 1.00 | 39.57 |
| ATOM | 3256 | CZ | PHE | 4552 | 93.654 | 93.159 | 79.826 | 1.00 | 41.84 |
| ATOM | 3257 | C | PHE | 4552 | 88.901 | 95.0.7 | 78.556 | 1.00 | 31.48 |
| ATOM | 3258 | O | PHE | 4552 | 89.843 | 95.826 | 78.262 | 1.00 | 30.14 |
| ATOM | 3259 | N | PRO | 4553 | 87.778 | 95.527 | 79.158 | 1.00 | 25.59 |
| ATOM | 3260 | CD | PRO | 4553 | 86.618 | 94.666 | 79.419 | 1.00 | 24.90 |
| ATOM | 3261 | CA | PRO | 4553 | 87.488 | 96.877 | 79.647 | 1.00 | 20.27 |
| ATOM | 3262 | CB | PRO | 4553 | 85.960 | 96.862 | 79.888 | 1.00 | 17.37 |
| ATOM | 3263 | CG | PRO | 4553 | 85.505 | 95.651 | 79.245 | 1.00 | 21.71 |
| ATOM | 3264 | C | PRO | 4553 | 88.228 | 97.102 | 80.991 | 1.00 | 16.68 |
| ATOM | 3265 | O | PRO | 4553 | 88.615 | 96.174 | 81.660 | 1.00 | 9.69 |
| ATOM | 3266 | N | PHE | 4554 | 88.348 | 98.367 | 81.376 | 1.00 | 19.06 |
| ATOM | 3267 | CA | PHE | 4554 | 88.974 | 98.764 | 82.586 | 1.00 | 16.66 |
| ATOM | 3268 | CB | PHE | 4554 | 88.764 | 100.220 | 82.775 | 1.00 | 14.57 |
| ATOM | 3269 | CG | PHE | 4554 | 89.288 | 100.744 | 84.090 | 1.00 | 23.60 |
| ATOM | 3270 | CD1 | PHE | 4554 | 90.662 | 100.797 | 84.337 | 1.00 | 23.97 |
| ATOM | 3271 | CD2 | PHE | 4554 | 88.408 | 101.216 | 85.097 | 1.00 | 23.65 |
| ATOM | 3272 | CE1 | PHE | 4554 | 91.187 | 101.309 | 85.542 | 1.00 | 21.44 |
| ATOM | 3273 | CE2 | PHE | 4554 | 88.919 | 101.726 | 86.308 | 1.00 | 24.09 |
| ATOM | 3274 | CZ | PHE | 4554 | 90.319 | 101.772 | 86.531 | 1.00 | 21.53 |
| ATOM | 3275 | C | PHE | 4554 | 88.339 | 98.030 | 83.740 | 1.00 | 18.69 |
| ATOM | 3276 | O | PHE | 4554 | 89.012 | 97.320 | 84.495 | 1.00 | 18.91 |
| ATOM | 3277 | N | TRP | 4555 | 87.024 | 98.141 | 83.860 | 1.00 | 18.51 |
| ATOM | 3278 | CA | TRP | 4555 | 86.395 | 97.557 | 85.051 | 1.00 | 20.70 |
| ATOM | 3279 | CB | TRP | 4555 | 84.885 | 97.937 | 85.181 | 1.00 | 18.54 |
| ATOM | 3280 | CG | TRP | 4555 | 84.254 | 97.257 | 86.378 | 1.00 | 15.36 |
| ATOM | 3281 | CD2 | TRP | 4555 | 84.585 | 97.439 | 87.751 | 1.00 | 17.70 |
| ATOM | 3282 | CE2 | TRP | 4555 | 83.860 | 96.507 | 88.459 | 1.00 | 22.49 |
| ATOM | 3283 | CE3 | TRP | 4555 | 85.448 | 98.305 | 88.448 | 1.00 | 21.95 |
| ATOM | 3284 | CD1 | TRP | 4555 | 83.375 | 96.280 | 86.334 | 1.00 | 15.17 |
| ATOM | 3285 | NE1 | TRP | 4555 | 83.115 | 95.819 | 87.550 | 1.00 | 20.97 |
| ATOM | 3286 | CZ2 | TRP | 4555 | 83.944 | 96.387 | 89.861 | 1.00 | 24.57 |
| ATOM | 3287 | CZ3 | TRP | 4555 | 85.551 | 98.208 | 89.800 | 1.00 | 20.00 |
| ATOM | 3288 | CH2 | TRP | 4555 | 84.804 | 97.248 | 90.505 | 1.00 | 23.36 |
| ATOM | 3289 | C | TRP | 4555 | 86.596 | 96.073 | 85.326 | 1.00 | 22.83 |
| ATOM | 3290 | O | TRP | 4555 | 86.896 | 95.700 | 86.470 | 1.00 | 23.95 |
| ATOM | 3291 | N | LEU | 4556 | 86.477 | 95.235 | 84.300 | 1.00 | 21.86 |
| ATOM | 3292 | CA | LEU | 4556 | 86.652 | 93.829 | 84.523 | 1.00 | 20.24 |
| ATOM | 3293 | CB | LEU | 4556 | 86.241 | 93.047 | 83.302 | 1.00 | 28.70 |
| ATOM | 3294 | CG | LEU | 4556 | 84.850 | 93.561 | 82.818 | 1.00 | 37.28 |
| ATOM | 3295 | CD1 | LEU | 4556 | 84.705 | 93.087 | 81.349 | 1.00 | 38.52 |
| ATOM | 3296 | CD2 | LEU | 4556 | 83.625 | 93.135 | 83.753 | 1.00 | 33.03 |
| ATOM | 3297 | C | LEU | 4556 | 88.047 | 93.537 | 84.877 | 1.00 | 18.28 |
| ATOM | 3298 | O | LEU | 4556 | 88.297 | 92.521 | 85.518 | 1.00 | 22.74 |
| ATOM | 3299 | N | TRP | 4557 | 88.983 | 94.396 | 84.496 | 1.00 | 15.99 |
| ATOM | 3300 | CA | TRP | 4557 | 90.418 | 94.167 | 84.845 | 1.00 | 14.69 |
| ATOM | 3301 | CB | TRP | 4557 | 91.308 | 95.113 | 84.022 | 1.00 | 13.79 |
| ATOM | 3302 | CG | TRP | 4557 | 92.702 | 95.264 | 84.424 | 1.00 | 15.32 |

| ATOM | 3303 | CD2 | TRP | 4557 | 93.271 | 96.418 | 84.993 | 1.00 | 17.15 |
| ATOM | 3304 | CE2 | TRP | 4557 | 94.657 | 96.155 | 85.189 | 1.00 | 19.14 |
| ATOM | 3305 | CE3 | TRP | 4557 | 92.750 | 97.667 | 85.369 | 1.00 | 18.98 |
| ATOM | 3306 | CD1 | TRP | 4557 | 93.739 | 94.347 | 84.305 | 1.00 | 18.59 |
| ATOM | 3307 | NE1 | TRP | 4557 | 94.920 | 94.880 | 84.765 | 1.00 | 12.98 |
| ATOM | 3308 | CZ2 | TRP | 4557 | 95.502 | 97.097 | 85.726 | 1.00 | 19.30 |
| ATOM | 3309 | CZ3 | TRP | 4557 | 93.583 | 98.594 | 85.901 | 1.00 | 18.38 |
| ATOM | 3310 | CH2 | TRP | 4557 | 94.951 | 98.311 | 86.076 | 1.00 | 22.88 |
| ATOM | 3311 | C | TRP | 4557 | 90.568 | 94.428 | 86.362 | 1.00 | 15.98 |
| ATOM | 3312 | O | TRP | 4557 | 91.120 | 93.632 | 87.081 | 1.00 | 13.10 |
| ATOM | 3313 | N | ILE | 4558 | 90.059 | 95.549 | 86.843 | 1.00 | 14.66 |
| ATOM | 3314 | CA | ILE | 4558 | 90.126 | 95.767 | 88.222 | 1.00 | 15.31 |
| ATOM | 3315 | CB | ILE | 4558 | 89.652 | 97.168 | 88.564 | 1.00 | 14.44 |
| ATOM | 3316 | CG2 | ILE | 4558 | 88.991 | 97.226 | 89.880 | 1.00 | 11.57 |
| ATOM | 3317 | CG1 | ILE | 4558 | 90.864 | 98.009 | 88.820 | 1.00 | 17.32 |
| ATOM | 3318 | CD1 | ILE | 4558 | 90.635 | 99.479 | 88.642 | 1.00 | 21.17 |
| ATOM | 3319 | C | ILE | 4558 | 89.294 | 94.675 | 88.918 | 1.00 | 15.98 |
| ATOM | 3320 | O | ILE | 4558 | 89.741 | 94.082 | 89.909 | 1.00 | 20.25 |
| ATOM | 3321 | N | GLU | 4559 | 88.125 | 94.343 | 88.398 | 1.00 | 14.89 |
| ATOM | 3322 | CA | GLU | 4559 | 87.331 | 93.318 | 89.104 | 1.00 | 18.27 |
| ATOM | 3323 | CB | GLU | 4559 | 86.004 | 92.953 | 88.456 | 1.00 | 23.11 |
| ATOM | 3324 | CG | GLU | 4559 | 84.747 | 93.169 | 89.282 | 1.00 | 33.51 |
| ATOM | 3325 | CD | GLU | 4559 | 84.800 | 92.399 | 90.574 | 1.00 | 43.95 |
| ATOM | 3326 | OE1 | GLU | 4559 | 85.069 | 93.107 | 91.583 | 1.00 | 48.11 |
| ATOM | 3327 | OE2 | GLU | 4559 | 84.611 | 91.131 | 90.574 | 1.00 | 44.84 |
| ATOM | 3328 | C | GLU | 4559 | 88.022 | 92.054 | 89.188 | 1.00 | 16.22 |
| ATOM | 3329 | O | GLU | 4559 | 87.752 | 91.312 | 90.069 | 1.00 | 16.29 |
| ATOM | 3330 | N | SER | 4560 | 88.929 | 91.786 | 88.282 | 1.00 | 15.24 |
| ATOM | 3331 | CA | SER | 4560 | 89.537 | 90.513 | 88.379 | 1.00 | 18.10 |
| ATOM | 3332 | CB | SER | 4560 | 89.806 | 89.986 | 86.973 | 1.00 | 15.45 |
| ATOM | 3333 | OG | SER | 4560 | 90.779 | 90.756 | 86.341 | 1.00 | 27.44 |
| ATOM | 3334 | C | SER | 4560 | 90.765 | 90.518 | 89.283 | 1.00 | 18.35 |
| ATOM | 3335 | O | SER | 4560 | 91.210 | 89.474 | 89.761 | 1.00 | 20.60 |
| ATOM | 3336 | N | ILE | 4561 | 91.317 | 91.688 | 89.542 | 1.00 | 16.98 |
| ATOM | 3337 | CA | ILE | 4561 | 92.456 | 91.723 | 90.385 | 1.00 | 17.36 |
| ATOM | 3338 | CB | ILE | 4561 | 93.194 | 93.012 | 90.258 | 1.00 | 21.77 |
| ATOM | 3339 | CG2 | ILE | 4561 | 94.179 | 93.268 | 91.435 | 1.00 | 18.44 |
| ATOM | 3340 | CG1 | ILE | 4561 | 93.890 | 93.101 | 88.915 | 1.00 | 18.15 |
| ATOM | 3341 | CD1 | ILE | 4561 | 94.729 | 94.341 | 88.647 | 1.00 | 25.08 |
| ATOM | 3342 | C | ILE | 4561 | 91.860 | 91.557 | 91.759 | 1.00 | 18.32 |
| ATOM | 3343 | O | ILE | 4561 | 92.408 | 90.833 | 92.596 | 1.00 | 17.23 |
| ATOM | 3344 | N | LEU | 4562 | 90.734 | 92.229 | 91.988 | 1.00 | 16.68 |
| ATOM | 3345 | CA | LEU | 4562 | 90.065 | 92.091 | 93.264 | 1.00 | 17.63 |
| ATOM | 3346 | CB | LEU | 4562 | 88.731 | 92.821 | 93.280 | 1.00 | 10.34 |
| ATOM | 3347 | CG | LEU | 4562 | 88.590 | 94.237 | 93.783 | 1.00 | 10.62 |
| ATOM | 3348 | CD1 | LEU | 4562 | 87.277 | 94.084 | 94.384 | 1.00 | 18.40 |
| ATOM | 3349 | CD2 | LEU | 4562 | 89.491 | 94.710 | 94.869 | 1.00 | 7.89 |
| ATOM | 3350 | C | LEU | 4562 | 89.806 | 90.604 | 93.518 | 1.00 | 20.04 |
| ATOM | 3351 | O | LEU | 4562 | 90.104 | 90.047 | 94.582 | 1.00 | 21.18 |
| ATOM | 3352 | N | GLU | 4563 | 89.216 | 89.961 | 92.535 | 1.00 | 22.52 |
| ATOM | 3353 | CA | GLU | 4563 | 88.927 | 88.599 | 92.732 | 1.00 | 25.41 |
| ATOM | 3354 | CB | GLU | 4563 | 88.209 | 88.031 | 91.524 | 1.00 | 31.72 |
| ATOM | 3355 | CG | GLU | 4563 | 86.665 | 88.229 | 91.635 | 1.00 | 44.56 |
| ATOM | 3356 | CD | GLU | 4563 | 85.826 | 87.430 | 90.571 | 1.00 | 51.48 |
| ATOM | 3357 | OE1 | GLU | 4563 | 86.029 | 86.156 | 90.455 | 1.00 | 54.55 |
| ATOM | 3358 | OE2 | GLU | 4563 | 84.966 | 88.100 | 89.894 | 1.00 | 48.03 |
| ATOM | 3359 | C | GLU | 4563 | 90.207 | 87.897 | 92.978 | 1.00 | 25.52 |
| ATOM | 3360 | O | GLU | 4563 | 90.226 | 86.913 | 93.662 | 1.00 | 26.81 |
| ATOM | 3361 | N | LEU | 4564 | 91.299 | 88.409 | 92.430 | 1.00 | 26.30 |
| ATOM | 3362 | CA | LEU | 4564 | 92.585 | 87.735 | 92.618 | 1.00 | 26.55 |
| ATOM | 3363 | CB | LEU | 4564 | 93.594 | 88.131 | 91.540 | 1.00 | 22.99 |
| ATOM | 3364 | CG | LEU | 4564 | 94.922 | 87.507 | 91.925 | 1.00 | 23.73 |
| ATOM | 3365 | CD1 | LEU | 4564 | 94.857 | 86.002 | 91.550 | 1.00 | 25.89 |
| ATOM | 3366 | CD2 | LEU | 4564 | 96.064 | 88.229 | 91.239 | 1.00 | 22.00 |
| ATOM | 3367 | C | LEU | 4564 | 93.158 | 87.955 | 94.026 | 1.00 | 24.51 |
| ATOM | 3368 | O | LEU | 4564 | 93.736 | 87.047 | 94.618 | 1.00 | 24.95 |
| ATOM | 3369 | N | ILE | 4565 | 92.975 | 89.155 | 94.546 | 1.00 | 22.72 |
| ATOM | 3370 | CA | ILE | 4565 | 93.405 | 89.498 | 95.905 | 1.00 | 22.30 |
| ATOM | 3371 | CB | ILE | 4565 | 93.134 | 90.964 | 96.227 | 1.00 | 15.85 |
| ATOM | 3372 | CG2 | ILE | 4565 | 93.370 | 91.235 | 97.684 | 1.00 | 13.00 |

165

| | | | | | | | | |
|---|---|---|---|---|---|---|---|---|
| ATOM | 3373 | CG1 | ILE | 4565 | 94.051 | 91.781 | 95.365 | 1.00 12.16 |
| ATOM | 3374 | CD1 | ILE | 4565 | 93.646 | 93.082 | 95.201 | 1.00 20.64 |
| ATOM | 3375 | C | ILE | 4565 | 92.671 | 88.660 | 96.920 | 1.00 24.08 |
| ATOM | 3376 | O | ILE | 4565 | 93.326 | 87.953 | 97.691 | 1.00 26.27 |
| ATOM | 3377 | N | LYS | 4566 | 91.333 | 88.754 | 96.883 | 1.00 24.44 |
| ATOM | 3378 | CA | LYS | 4566 | 90.396 | 88.063 | 97.763 | 1.00 26.09 |
| ATOM | 3379 | CB | LYS | 4566 | 88.950 | 88.362 | 97.345 | 1.00 31.14 |
| ATOM | 3380 | CG | LYS | 4566 | 87.867 | 87.702 | 98.159 | 1.00 30.15 |
| ATOM | 3381 | CD | LYS | 4566 | 86.471 | 87.868 | 97.510 | 1.00 37.38 |
| ATOM | 3382 | CE | LYS | 4566 | 85.431 | 86.864 | 98.216 | 1.00 42.47 |
| ATOM | 3383 | NZ | LYS | 4566 | 83.929 | 86.825 | 97.902 | 1.00 39.57 |
| ATOM | 3384 | C | LYS | 4566 | 90.571 | 86.569 | 97.882 | 1.00 26.81 |
| ATOM | 3385 | O | LYS | 4566 | 90.270 | 86.043 | 98.927 | 1.00 27.37 |
| ATOM | 3386 | N | LYS | 4567 | 91.035 | 85.880 | 96.838 | 1.00 26.95 |
| ATOM | 3387 | CA | LYS | 4567 | 91.283 | 84.424 | 96.902 | 1.00 27.90 |
| ATOM | 3388 | CB | LYS | 4567 | 90.714 | 83.692 | 95.684 | 1.00 29.88 |
| ATOM | 3389 | CG | LYS | 4567 | 89.255 | 83.885 | 95.317 | 1.00 38.26 |
| ATOM | 3390 | CD | LYS | 4567 | 89.171 | 83.491 | 93.823 | 1.00 47.74 |
| ATOM | 3391 | CE | LYS | 4567 | 87.783 | 83.575 | 93.136 | 1.00 50.15 |
| ATOM | 3392 | NZ | LYS | 4567 | 87.815 | 82.689 | 91.873 | 1.00 44.36 |
| ATOM | 3393 | C | LYS | 4567 | 92.790 | 84.006 | 96.949 | 1.00 30.15 |
| ATOM | 3394 | O | LYS | 4567 | 93.081 | 82.805 | 96.907 | 1.00 31.17 |
| ATOM | 3395 | N | HIS | 4568 | 93.766 | 84.923 | 97.038 | 1.00 29.59 |
| ATOM | 3396 | CA | HIS | 4568 | 95.165 | 84.460 | 96.993 | 1.00 26.57 |
| ATOM | 3397 | CB | HIS | 4568 | 95.594 | 84.080 | 95.572 | 1.00 25.77 |
| ATOM | 3398 | CG | HIS | 4568 | 94.837 | 82.961 | 94.958 | 1.00 22.03 |
| ATOM | 3399 | CD2 | HIS | 4568 | 93.865 | 82.957 | 94.014 | 1.00 21.98 |
| ATOM | 3400 | ND1 | HIS | 4568 | 95.096 | 81.646 | 95.259 | 1.00 23.44 |
| ATOM | 3401 | CE1 | HIS | 4568 | 94.315 | 80.878 | 94.514 | 1.00 26.47 |
| ATOM | 3402 | NE2 | HIS | 4568 | 93.559 | 81.652 | 93.749 | 1.00 20.39 |
| ATOM | 3403 | C | HIS | 4568 | 96.211 | 85.450 | 97.435 | 1.00 26.51 |
| ATOM | 3404 | O | HIS | 4568 | 97.411 | 85.134 | 97.405 | 1.00 26.87 |
| ATOM | 3405 | N | LEU | 4569 | 95.816 | 86.665 | 97.771 | 1.00 24.93 |
| ATOM | 3406 | CA | LEU | 4569 | 96.856 | 87.576 | 98.211 | 1.00 23.36 |
| ATOM | 3407 | CB | LEU | 4569 | 97.197 | 88.488 | 97.065 | 1.00 17.29 |
| ATOM | 3408 | CG | LEU | 4569 | 97.526 | 87.772 | 95.779 | 1.00 13.67 |
| ATOM | 3409 | CD1 | LEU | 4569 | 97.559 | 88.795 | 94.559 | 1.00 7.24 |
| ATOM | 3410 | CD2 | LEU | 4569 | 98.844 | 87.000 | 96.005 | 1.00 10.46 |
| ATOM | 3411 | C | LEU | 4569 | 96.500 | 88.425 | 99.447 | 1.00 25.58 |
| ATOM | 3412 | O | LEU | 4569 | 97.297 | 89.309 | 99.834 | 1.00 27.82 |
| ATOM | 3413 | N | LEU | 4570 | 95.361 | 88.143 | 100.092 | 1.00 24.66 |
| ATOM | 3414 | CA | LEU | 4570 | 94.929 | 88.992 | 101.186 | 1.00 24.53 |
| ATOM | 3415 | CB | LEU | 4570 | 93.753 | 88.425 | 101.926 | 1.00 23.12 |
| ATOM | 3416 | CG | LEU | 4570 | 92.420 | 88.923 | 101.407 | 1.00 20.59 |
| ATOM | 3417 | CD1 | LEU | 4570 | 91.346 | 88.213 | 102.111 | 1.00 16.74 |
| ATOM | 3418 | CD2 | LEU | 4570 | 92.296 | 90.407 | 101.583 | 1.00 18.05 |
| ATOM | 3419 | C | LEU | 4570 | 95.967 | 89.401 | 102.167 | 1.00 26.99 |
| ATOM | 3420 | O | LEU | 4570 | 96.191 | 90.621 | 102.409 | 1.00 28.67 |
| ATOM | 3421 | N | PRO | 4571 | 96.593 | 88.413 | 102.809 | 1.00 26.85 |
| ATOM | 3422 | CD | PRO | 4571 | 96.379 | 86.969 | 102.834 | 1.00 23.77 |
| ATOM | 3423 | CA | PRO | 4571 | 97.633 | 88.805 | 103.769 | 1.00 25.58 |
| ATOM | 3424 | CB | PRO | 4571 | 98.116 | 87.470 | 104.283 | 1.00 21.80 |
| ATOM | 3425 | CG | PRO | 4571 | 97.715 | 86.549 | 103.129 | 1.00 24.73 |
| ATOM | 3426 | C | PRO | 4571 | 98.732 | 89.729 | 103.155 | 1.00 24.46 |
| ATOM | 3427 | O | PRO | 4571 | 98.977 | 90.839 | 103.701 | 1.00 19.72 |
| ATOM | 3428 | N | LEU | 4572 | 99.336 | 89.326 | 102.024 | 1.00 24.04 |
| ATOM | 3429 | CA | LEU | 4572 | 100.374 | 90.167 | 101.407 | 1.00 24.92 |
| ATOM | 3430 | CB | LEU | 4572 | 100.829 | 89.653 | 100.054 | 1.00 25.01 |
| ATOM | 3431 | CG | LEU | 4572 | 101.328 | 88.272 | 99.792 | 1.00 22.76 |
| ATOM | 3432 | CD1 | LEU | 4572 | 101.702 | 88.290 | 98.349 | 1.00 18.35 |
| ATOM | 3433 | CD2 | LEU | 4572 | 102.494 | 87.906 | 100.675 | 1.00 22.35 |
| ATOM | 3434 | C | LEU | 4572 | 99.782 | 91.531 | 101.110 | 1.00 26.81 |
| ATOM | 3435 | O | LEU | 4572 | 100.434 | 92.605 | 101.380 | 1.00 25.43 |
| ATOM | 3436 | N | TRP | 4573 | 98.561 | 91.484 | 100.524 | 1.00 24.17 |
| ATOM | 3437 | CA | TRP | 4573 | 97.881 | 92.728 | 100.117 | 1.00 24.15 |
| ATOM | 3438 | CB | TRP | 4573 | 96.534 | 92.504 | 99.435 | 1.00 18.70 |
| ATOM | 3439 | CG | TRP | 4573 | 95.757 | 93.773 | 99.228 | 1.00 9.45 |
| ATOM | 3440 | CD2 | TRP | 4573 | 96.068 | 94.839 | 98.345 | 1.00 3.81 |
| ATOM | 3441 | CE2 | TRP | 4573 | 95.178 | 95.903 | 98.631 | 1.00 3.68 |
| ATOM | 3442 | CE3 | TRP | 4573 | 97.001 | 95.013 | 97.356 | 1.00 6.58 |

166

| ATOM | 3443 | CD1 | TRP | 4573 | 94.727 | 94.203 | 99.982 | 1.00 | 8.55 |
| ATOM | 3444 | NE1 | TRP | 4573 | 94.367 | 95.487 | 99.648 | 1.00 | 5.71 |
| ATOM | 3445 | CZ2 | TRP | 4573 | 95.194 | 97.111 | 97.951 | 1.00 | 2.99 |
| ATOM | 3446 | CZ3 | TRP | 4573 | 97.029 | 96.272 | 96.664 | 1.00 | 10.21 |
| ATOM | 3447 | CH2 | TRP | 4573 | 96.134 | 97.277 | 96.971 | 1.00 | 5.63 |
| ATOM | 3448 | C | TRP | 4573 | 97.637 | 93.606 | 101.262 | 1.00 | 25.90 |
| ATOM | 3449 | O | TRP | 4573 | 98.070 | 94.742 | 101.276 | 1.00 | 24.35 |
| ATOM | 3450 | N | ASN | 4574 | 96.913 | 93.066 | 102.221 | 1.00 | 29.35 |
| ATOM | 3451 | CA | ASN | 4574 | 96.629 | 93.837 | 103.394 | 1.00 | 34.97 |
| ATOM | 3452 | CB | ASN | 4574 | 95.900 | 93.039 | 104.453 | 1.00 | 36.78 |
| ATOM | 3453 | CG | ASN | 4574 | 94.516 | 92.621 | 104.022 | 1.00 | 36.43 |
| ATOM | 3454 | OD1 | ASN | 4574 | 93.795 | 93.408 | 103.388 | 1.00 | 34.44 |
| ATOM | 3455 | ND2 | ASN | 4574 | 94.115 | 91.395 | 104.397 | 1.00 | 34.02 |
| ATOM | 3456 | C | ASN | 4574 | 97.886 | 94.376 | 103.990 | 1.00 | 36.99 |
| ATOM | 3457 | O | ASN | 4574 | 97.921 | 95.576 | 104.182 | 1.00 | 40.76 |
| ATOM | 3458 | N | ASP | 4575 | 98.910 | 93.554 | 104.286 | 1.00 | 36.98 |
| ATOM | 3459 | CA | ASP | 4575 | 100.155 | 94.125 | 104.873 | 1.00 | 38.81 |
| ATOM | 3460 | CB | ASP | 4575 | 101.007 | 93.085 | 105.644 | 1.00 | 39.37 |
| ATOM | 3461 | CG | ASP | 4575 | 100.200 | 92.208 | 106.593 | 1.00 | 38.82 |
| ATOM | 3462 | OD1 | ASP | 4575 | 99.294 | 92.709 | 107.263 | 1.00 | 39.09 |
| ATOM | 3463 | OD2 | ASP | 4575 | 100.491 | 90.996 | 106.692 | 1.00 | 40.02 |
| ATOM | 3464 | C | ASP | 4575 | 101.084 | 94.819 | 103.853 | 1.00 | 38.65 |
| ATOM | 3465 | O | ASP | 4575 | 102.287 | 94.607 | 103.862 | 1.00 | 38.81 |
| ATOM | 3466 | N | GLY | 4576 | 100.492 | 95.640 | 102.985 | 1.00 | 40.50 |
| ATOM | 3467 | CA | GLY | 4576 | 101.176 | 96.445 | 101.964 | 1.00 | 38.10 |
| ATOM | 3468 | C | GLY | 4576 | 102.465 | 96.008 | 101.300 | 1.00 | 37.23 |
| ATOM | 3469 | O | GLY | 4576 | 103.370 | 96.803 | 101.141 | 1.00 | 34.47 |
| ATOM | 3470 | N | CYS | 4577 | 102.537 | 94.760 | 100.873 | 1.00 | 39.92 |
| ATOM | 3471 | CA | CYS | 4577 | 103.741 | 94.238 | 100.236 | 1.00 | 38.82 |
| ATOM | 3472 | CB | CYS | 4577 | 104.019 | 92.803 | 100.766 | 1.00 | 36.66 |
| ATOM | 3473 | SG | CYS | 4577 | 103.663 | 92.500 | 102.599 | 1.00 | 43.25 |
| ATOM | 3474 | C | CYS | 4577 | 103.448 | 94.262 | 98.701 | 1.00 | 40.69 |
| ATOM | 3475 | O | CYS | 4577 | 104.282 | 93.850 | 97.879 | 1.00 | 40.40 |
| ATOM | 3476 | N | ILE | 4578 | 102.267 | 94.744 | 98.289 | 1.00 | 40.27 |
| ATOM | 3477 | CA | ILE | 4578 | 101.985 | 94.769 | 96.852 | 1.00 | 38.34 |
| ATOM | 3478 | CB | ILE | 4578 | 100.735 | 94.042 | 96.485 | 1.00 | 34.86 |
| ATOM | 3479 | CG2 | ILE | 4578 | 100.598 | 94.006 | 95.047 | 1.00 | 28.64 |
| ATOM | 3480 | CG1 | ILE | 4578 | 100.756 | 92.640 | 97.069 | 1.00 | 35.63 |
| ATOM | 3481 | CD1 | ILE | 4578 | 99.430 | 91.922 | 97.043 | 1.00 | 28.97 |
| ATOM | 3482 | C | ILE | 4578 | 101.706 | 96.178 | 96.550 | 1.00 | 42.26 |
| ATOM | 3483 | O | ILE | 4578 | 100.953 | 96.817 | 97.273 | 1.00 | 44.13 |
| ATOM | 3484 | N | MET | 4579 | 102.325 | 96.656 | 95.483 | 1.00 | 45.96 |
| ATOM | 3485 | CA | MET | 4579 | 102.183 | 98.005 | 94.980 | 1.00 | 47.73 |
| ATOM | 3486 | CB | MET | 4579 | 103.549 | 98.576 | 94.708 | 1.00 | 49.49 |
| ATOM | 3487 | CG | MET | 4579 | 104.164 | 99.051 | 95.991 | 1.00 | 57.86 |
| ATOM | 3488 | SD | MET | 4579 | 105.674 | 100.045 | 95.963 | 1.00 | 59.50 |
| ATOM | 3489 | CE | MET | 4579 | 105.633 | 100.488 | 98.022 | 1.00 | 48.98 |
| ATOM | 3490 | C | MET | 4579 | 101.511 | 97.862 | 93.680 | 1.00 | 49.56 |
| ATOM | 3491 | O | MET | 4579 | 101.655 | 98.712 | 92.856 | 1.00 | 55.19 |
| ATOM | 3492 | N | GLY | 4580 | 100.823 | 96.741 | 93.490 | 1.00 | 50.38 |
| ATOM | 3493 | CA | GLY | 4580 | 100.143 | 96.370 | 92.245 | 1.00 | 46.04 |
| ATOM | 3494 | C | GLY | 4580 | 99.980 | 97.315 | 91.083 | 1.00 | 44.50 |
| ATOM | 3495 | O | GLY | 4580 | 100.277 | 96.993 | 89.939 | 1.00 | 45.20 |
| ATOM | 3496 | N | PHE | 4581 | 99.497 | 98.500 | 91.346 | 1.00 | 41.55 |
| ATOM | 3497 | CA | PHE | 4581 | 99.318 | 99.361 | 90.245 | 1.00 | 41.39 |
| ATOM | 3498 | CB | PHE | 4581 | 98.039 | 100.090 | 90.448 | 1.00 | 42.54 |
| ATOM | 3499 | CG | PHE | 4581 | 96.875 | 99.201 | 90.709 | 1.00 | 39.74 |
| ATOM | 3500 | CD1 | PHE | 4581 | 96.648 | 98.716 | 91.955 | 1.00 | 37.08 |
| ATOM | 3501 | CD2 | PHE | 4581 | 95.941 | 98.960 | 89.719 | 1.00 | 40.16 |
| ATOM | 3502 | CE1 | PHE | 4581 | 95.531 | 97.997 | 92.209 | 1.00 | 34.99 |
| ATOM | 3503 | CE2 | PHE | 4581 | 94.826 | 98.250 | 89.979 | 1.00 | 38.52 |
| ATOM | 3504 | CZ | PHE | 4581 | 94.616 | 97.776 | 91.234 | 1.00 | 36.68 |
| ATOM | 3505 | C | PHE | 4581 | 100.447 | 100.338 | 90.016 | 1.00 | 42.95 |
| ATOM | 3506 | O | PHE | 4581 | 100.430 | 101.469 | 90.501 | 1.00 | 40.91 |
| ATOM | 3507 | N | ILE | 4582 | 101.446 | 99.897 | 89.270 | 1.00 | 46.89 |
| ATOM | 3508 | CA | ILE | 4582 | 102.563 | 100.776 | 88.959 | 1.00 | 50.28 |
| ATOM | 3509 | CB | ILE | 4582 | 103.863 | 100.397 | 89.609 | 1.00 | 49.03 |
| ATOM | 3510 | CG2 | ILE | 4582 | 104.859 | 101.512 | 89.359 | 1.00 | 47.83 |
| ATOM | 3511 | CG1 | ILE | 4582 | 103.727 | 100.331 | 91.109 | 1.00 | 51.15 |
| ATOM | 3512 | CD1 | ILE | 4582 | 105.068 | 100.223 | 91.782 | 1.00 | 52.88 |

```
ATOM   3513  C    ILE  4582     102.908 100.879  87.495  1.00 52.98
ATOM   3514  O    ILE  4582     103.256  99.886  86.829  1.00 54.41
ATOM   3515  N    SER  4583     102.843 102.119  87.040  1.00 53.36
ATOM   3516  CA   SER  4583     103.149 102.529  85.694  1.00 55.22
ATOM   3517  CB   SER  4583     103.478 104.024  85.830  1.00 57.27
ATOM   3518  OG   SER  4583     103.465 104.729  84.616  1.00 62.93
ATOM   3519  C    SER  4583     104.368 101.678  85.448  1.00 55.20
ATOM   3520  O    SER  4583     105.060 101.470  86.397  1.00 55.16
ATOM   3521  N    LYS  4584     104.641 101.132  84.254  1.00 59.07
ATOM   3522  CA   LYS  4584     105.907 100.322  84.071  1.00 59.61
ATOM   3523  CB   LYS  4584     105.940  99.510  82.769  1.00 57.32
ATOM   3524  CG   LYS  4584     104.884  98.467  82.678  1.00 61.01
ATOM   3525  CD   LYS  4584     105.327  97.304  81.795  1.00 64.39
ATOM   3526  CE   LYS  4584     104.196  96.281  81.526  1.00 64.69
ATOM   3527  NZ   LYS  4584     104.663  95.192  80.621  1.00 64.59
ATOM   3528  C    LYS  4584     107.165 101.216  84.096  1.00 61.21
ATOM   3529  O    LYS  4584     108.277 100.745  84.327  1.00 60.52
ATOM   3530  N    GLU  4585     106.970 102.510  83.824  1.00 63.34
ATOM   3531  CA   GLU  4585     108.035 103.481  83.876  1.00 62.62
ATOM   3532  CB   GLU  4585     107.534 104.852  83.592  1.00 64.94
ATOM   3533  CG   GLU  4585     107.025 105.023  82.272  1.00 70.80
ATOM   3534  CD   GLU  4585     106.964 106.497  81.982  1.00 76.32
ATOM   3535  OE1  GLU  4585     107.826 107.287  82.522  1.00 70.90
ATOM   3536  OE2  GLU  4585     106.052 106.830  81.193  1.00 79.84
ATOM   3537  C    GLU  4585     108.513 103.542  85.274  1.00 61.32
ATOM   3538  O    GLU  4585     109.580 103.096  85.557  1.00 61.30
ATOM   3539  N    ARG  4586     107.691 104.120  86.142  1.00 61.92
ATOM   3540  CA   ARG  4586     108.049 104.298  87.522  1.00 61.55
ATOM   3541  CB   ARG  4586     106.922 104.891  88.337  1.00 64.40
ATOM   3542  CG   ARG  4586     107.430 105.266  89.722  1.00 67.33
ATOM   3543  CD   ARG  4586     106.398 105.125  90.841  1.00 68.76
ATOM   3544  NE   ARG  4586     105.259 105.997  90.690  1.00 70.50
ATOM   3545  CZ   ARG  4586     104.362 106.196  91.647  1.00 75.50
ATOM   3546  NH1  ARG  4586     104.483 105.575  92.813  1.00 72.10
ATOM   3547  NH2  ARG  4586     103.341 107.029  91.434  1.00 80.24
ATOM   3548  C    ARG  4586     108.521 103.044  88.163  1.00 61.66
ATOM   3549  O    ARG  4586     109.281 103.124  89.125  1.00 63.22
ATOM   3550  N    GLU  4587     108.078 101.887  87.681  1.00 61.75
ATOM   3551  CA   GLU  4587     108.606 100.621  88.216  1.00 64.12
ATOM   3552  CB   GLU  4587     108.094  99.421  87.415  1.00 63.94
ATOM   3553  CG   GLU  4587     108.798  98.104  87.719  1.00 67.04
ATOM   3554  CD   GLU  4587     108.311  96.927  86.880  1.00 67.88
ATOM   3555  OE1  GLU  4587     108.299  96.994  85.619  1.00 69.40
ATOM   3556  OE2  GLU  4587     107.960  95.917  87.500  1.00 67.44
ATOM   3557  C    GLU  4587     110.122 100.725  87.996  1.00 67.19
ATOM   3558  O    GLU  4587     110.850 101.064  88.935  1.00 67.95
ATOM   3559  N    ARG  4588     110.578 100.680  86.745  1.00 70.16
ATOM   3560  CA   ARG  4588     111.974 100.915  86.348  1.00 71.97
ATOM   3561  CB   ARG  4588     112.004 101.406  84.878  1.00 75.25
ATOM   3562  CG   ARG  4588     111.332 100.510  83.805  1.00 78.25
ATOM   3563  CD   ARG  4588     111.378 101.137  82.357  1.00 79.69
ATOM   3564  NE   ARG  4588     111.172 100.107  81.322  1.00 81.26
ATOM   3565  CZ   ARG  4588     111.496 100.236  80.030  1.00 83.00
ATOM   3566  NH1  ARG  4588     112.054 101.356  79.589  1.00 83.21
ATOM   3567  NH2  ARG  4588     111.301  99.230  79.177  1.00 82.76
ATOM   3568  C    ARG  4588     112.635 102.016  87.246  1.00 72.13
ATOM   3569  O    ARG  4588     113.567 101.735  88.023  1.00 72.00
ATOM   3570  N    ALA  4589     112.151 103.259  87.103  1.00 71.62
ATOM   3571  CA   ALA  4589     112.622 104.437  87.845  1.00 72.59
ATOM   3572  CB   ALA  4589     111.594 105.518  87.794  1.00 73.21
ATOM   3573  C    ALA  4589     112.986 104.195  89.283  1.00 73.38
ATOM   3574  O    ALA  4589     114.069 104.564  89.736  1.00 73.26
ATOM   3575  N    LEU  4590     112.083 103.578  90.011  1.00 74.19
ATOM   3576  CA   LEU  4590     112.373 103.330  91.385  1.00 77.99
ATOM   3577  CB   LEU  4590     111.092 103.080  92.135  1.00 79.14
ATOM   3578  CG   LEU  4590     111.156 102.652  93.609  1.00 79.98
ATOM   3579  CD1  LEU  4590     112.349 103.272  94.431  1.00 78.22
ATOM   3580  CD2  LEU  4590     109.761 103.044  94.145  1.00 77.30
ATOM   3581  C    LEU  4590     113.322 102.105  91.643  1.00 80.76
ATOM   3582  O    LEU  4590     113.701 101.953  92.794  1.00 80.36
```

168

```
ATOM   3583  N   LEU 4591     113.758 101.506  90.600  1.00 84.85
ATOM   3584  CA  LEU 4591     114.610 100.372  90.900  1.00 89.58
ATOM   3585  CB  LEU 4591     114.131  99.094  90.195  1.00 89.75
ATOM   3586  CG  LEU 4591     112.819  98.534  90.792  1.00 88.63
ATOM   3587  CD1 LEU 4591     112.441  97.251  90.097  1.00 91.20
ATOM   3588  CD2 LEU 4591     112.963  98.291  92.266  1.00 86.04
ATOM   3589  C   LEU 4591     116.098 100.488  90.821  1.00 92.12
ATOM   3590  O   LEU 4591     116.786  99.497  90.962  1.00 93.19
ATOM   3591  N   LYS 4592     116.621 101.673  90.573  1.00 94.82
ATOM   3592  CA  LYS 4592     118.049 101.777  90.691  1.00 96.18
ATOM   3593  CB  LYS 4592     118.594 102.937  89.889  1.00 97.72
ATOM   3594  CG  LYS 4592     118.513 102.702  88.383  1.00 98.39
ATOM   3595  CD  LYS 4592     119.317 103.786  87.693  1.00 99.59
ATOM   3596  CE  LYS 4592     119.709 103.419  86.275  1.00100.32
ATOM   3597  NZ  LYS 4592     120.673 104.401  85.692  1.00 99.60
ATOM   3598  C   LYS 4592     118.008 102.099  92.170  1.00 97.07
ATOM   3599  O   LYS 4592     117.964 103.253  92.550  1.00 96.96
ATOM   3600  N   ASP 4593     117.854 101.048  92.974  1.00 98.38
ATOM   3601  CA  ASP 4593     117.823 101.111  94.436  1.00 99.07
ATOM   3602  CB  ASP 4593     116.575 100.476  95.031  1.00 94.43
ATOM   3603  CG  ASP 4593     116.393 100.842  96.470  1.00 90.60
ATOM   3604  OD1 ASP 4593     116.714 101.999  96.771  1.00 86.87
ATOM   3605  OD2 ASP 4593     115.909 100.024  97.284  1.00 88.75
ATOM   3606  C   ASP 4593     118.981 100.192  94.652  1.00102.18
ATOM   3607  O   ASP 4593     119.385  99.916  95.767  1.00103.40
ATOM   3608  N   GLN 4594     119.472  99.701  93.518  1.00105.49
ATOM   3609  CA  GLN 4594     120.633  98.846  93.452  1.00109.29
ATOM   3610  CB  GLN 4594     121.828  99.693  93.000  1.00112.41
ATOM   3611  CG  GLN 4594     123.193  99.091  93.337  1.00114.35
ATOM   3612  CD  GLN 4594     124.226 100.131  93.775  1.00115.68
ATOM   3613  OE1 GLN 4594     123.922 101.077  94.533  1.00113.90
ATOM   3614  NE2 GLN 4594     125.470  99.935  93.327  1.00116.89
ATOM   3615  C   GLN 4594     120.955  98.145  94.760  1.00110.02
ATOM   3616  O   GLN 4594     122.074  98.176  95.257  1.00112.42
ATOM   3617  N   GLN 4595     119.955  97.578  95.375  1.00109.21
ATOM   3618  CA  GLN 4595     120.207  96.805  96.553  1.00109.77
ATOM   3619  CB  GLN 4595     119.363  97.359  97.680  1.00109.74
ATOM   3620  CG  GLN 4595     119.805  98.762  97.962  1.00110.79
ATOM   3621  CD  GLN 4595     118.929  99.505  98.913  1.00111.93
ATOM   3622  OE1 GLN 4595     117.713  99.616  98.718  1.00114.95
ATOM   3623  NE2 GLN 4595     119.538 100.048  99.951  1.00111.61
ATOM   3624  C   GLN 4595     119.584  95.717  95.730  1.00110.27
ATOM   3625  O   GLN 4595     118.368  95.486  95.801  1.00111.25
ATOM   3626  N   PRO 4596     120.425  95.064  94.883  1.00109.67
ATOM   3627  CD  PRO 4596     121.887  95.253  94.945  1.00110.11
ATOM   3628  CA  PRO 4596     120.141  93.989  93.930  1.00108.52
ATOM   3629  CB  PRO 4596     121.510  93.366  93.729  1.00109.39
ATOM   3630  CG  PRO 4596     122.351  94.591  93.654  1.00109.50
ATOM   3631  C   PRO 4596     119.037  92.988  94.213  1.00107.19
ATOM   3632  O   PRO 4596     118.698  92.217  93.318  1.00106.40
ATOM   3633  N   GLY 4597     118.482  93.023  95.436  1.00105.83
ATOM   3634  CA  GLY 4597     117.376  92.163  95.852  1.00101.00
ATOM   3635  C   GLY 4597     116.298  93.136  95.526  1.00 98.36
ATOM   3636  O   GLY 4597     115.718  93.810  96.349  1.00 97.98
ATOM   3637  N   THR 4598     116.095  93.269  94.244  1.00 96.76
ATOM   3638  CA  THR 4598     115.118  94.207  93.784  1.00 94.35
ATOM   3639  CB  THR 4598     115.642  94.969  92.564  1.00 96.85
ATOM   3640  OG1 THR 4598     116.743  95.815  92.957  1.00 96.70
ATOM   3641  CG2 THR 4598     114.533  95.794  91.982  1.00 98.37
ATOM   3642  C   THR 4598     113.745  93.619  93.505  1.00 90.12
ATOM   3643  O   THR 4598     113.434  93.165  92.403  1.00 90.84
ATOM   3644  N   PHE 4599     112.930  93.664  94.548  1.00 84.26
ATOM   3645  CA  PHE 4599     111.566  93.193  94.548  1.00 75.24
ATOM   3646  CB  PHE 4599     111.302  92.515  95.853  1.00 79.32
ATOM   3647  CG  PHE 4599     111.364  91.091  95.783  1.00 82.12
ATOM   3648  CD1 PHE 4599     112.110  90.475  94.798  1.00 86.02
ATOM   3649  CD2 PHE 4599     110.667  90.341  96.696  1.00 84.26
ATOM   3650  CE1 PHE 4599     112.172  89.068  94.717  1.00 90.74
ATOM   3651  CE2 PHE 4599     110.703  88.973  96.652  1.00 90.38
ATOM   3652  CZ  PHE 4599     111.458  88.309  95.648  1.00 92.07
```

169

```
ATOM   3653  C    PHE  4599    110.526  94.292  94.390  1.00 68.29
ATOM   3654  O    PHE  4599    110.596  95.366  95.005  1.00 62.77
ATOM   3655  N    LEU  4600    109.528  93.947  93.590  1.00 62.22
ATOM   3656  CA   LEU  4600    108.367  94.782  93.298  1.00 55.02
ATOM   3657  CB   LEU  4600    108.730  95.879  92.308  1.00 56.98
ATOM   3658  CG   LEU  4600    107.577  96.830  92.009  1.00 54.45
ATOM   3659  CD1  LEU  4600    107.379  97.711  93.218  1.00 56.85
ATOM   3660  CD2  LEU  4600    107.876  97.678  90.797  1.00 55.06
ATOM   3661  C    LEU  4600    107.231  93.953  92.703  1.00 50.57
ATOM   3662  O    LEU  4600    107.282  93.573  91.528  1.00 52.08
ATOM   3663  N    LEU  4601    106.210  93.686  93.510  1.00 41.07
ATOM   3664  CA   LEU  4601    105.049  92.913  93.079  1.00 30.95
ATOM   3665  CB   LEU  4601    104.412  92.248  94.291  1.00 21.58
ATOM   3666  CG   LEU  4601    105.385  91.572  95.271  1.00 16.19
ATOM   3667  CD1  LEU  4601    104.618  91.033  96.449  1.00 10.48
ATOM   3668  CD2  LEU  4601    106.167  90.479  94.601  1.00 14.08
ATOM   3669  C    LEU  4601    104.061  93.894  92.449  1.00 30.95
ATOM   3670  O    LEU  4601    103.562  94.781  93.121  1.00 31.11
ATOM   3671  N    ARG  4602    103.808  93.755  91.151  1.00 33.37
ATOM   3672  CA   ARG  4602    102.882  94.6`4  90.416  1.00 31.57
ATOM   3673  CB   ARG  4602    103.593  95.310  89.228  1.00 26.78
ATOM   3674  CG   ARG  4602    102.652  96.167  88.398  1.00 37.34
ATOM   3675  CD   ARG  4602    103.262  96.905  87.170  1.00 41.62
ATOM   3676  NE   ARG  4602    103.319  96.120  85.936  1.00 40.96
ATOM   3677  CZ   ARG  4602    104.170  95.121  85.719  1.00 44.17
ATOM   3678  NH1  ARG  4602    105.046  94.785  86.660  1.00 44.25
ATOM   3679  NH2  ARG  4602    104.159  94.464  84.557  1.00 40.54
ATOM   3680  C    ARG  4602    101.765  93.740  89.878  1.00 28.77
ATOM   3681  O    ARG  4602    102.019  92.581  89.555  1.00 31.68
ATOM   3682  N    PHE  4603    100.535  94.243  89.810  1.00 24.79
ATOM   3683  CA   PHE  4603     99.447  93.443  89.254  1.00 24.91
ATOM   3684  CB   PHE  4603     98.093  93.993  89.658  1.00 22.69
ATOM   3685  CG   PHE  4603     97.694  93.628  91.039  1.00 24.90
ATOM   3686  CD1  PHE  4603     97.075  94.560  91.864  1.00 26.47
ATOM   3687  CD2  PHE  4603     97.944  92.349  91.528  1.00 24.64
ATOM   3688  CE1  PHE  4603     96.714  94.224  93.164  1.00 26.13
ATOM   3689  CE2  PHE  4603     97.589  91.997  92.817  1.00 25.98
ATOM   3690  CZ   PHE  4603     96.973  92.933  93.643  1.00 27.62
ATOM   3691  C    PHE  4603     99.592  93.515  87.760  1.00 28.18
ATOM   3692  O    PHE  4603     99.990  94.538  87.234  1.00 36.34
ATOM   3693  N    SER  4604     99.265  92.446  87.057  1.00 30.79
ATOM   3694  CA   SER  4604     99.438  92.465  85.616  1.00 32.85
ATOM   3695  CB   SER  4604     99.376  91.058  85.041  1.00 37.22
ATOM   3696  OG   SER  4604     99.339  91.140  83.626  1.00 40.36
ATOM   3697  C    SER  4604     98.457  93.306  84.868  1.00 32.28
ATOM   3698  O    SER  4604     97.264  93.244  85.127  1.00 38.05
ATOM   3699  N    GLU  4605     98.953  94.084  83.921  1.00 31.78
ATOM   3700  CA   GLU  4605     98.053  94.899  83.132  1.00 33.97
ATOM   3701  CB   GLU  4605     98.727  96.172  82.622  1.00 33.46
ATOM   3702  CG   GLU  4605     98.908  97.283  83.635  1.00 35.98
ATOM   3703  CD   GLU  4605     99.242  98.593  82.944  1.00 36.66
ATOM   3704  OE1  GLU  4605     99.276  99.648  83.612  1.00 36.99
ATOM   3705  OE2  GLU  4605     99.468  98.556  81.715  1.00 36.14
ATOM   3706  C    GLU  4605     97.536  94.135  81.931  1.00 35.04
ATOM   3707  O    GLU  4605     96.586  94.567  81.299  1.00 38.91
ATOM   3708  N    SER  4606     98.131  92.994  81.617  1.00 33.30
ATOM   3709  CA   SER  4606     97.699  92.257  80.437  1.00 35.29
ATOM   3710  CB   SER  4606     98.911  91.586  79.807  1.00 33.44
ATOM   3711  OG   SER  4606     99.858  92.578  79.452  1.00 35.64
ATOM   3712  C    SER  4606     96.572  91.235  80.579  1.00 40.82
ATOM   3713  O    SER  4606     95.673  91.185  79.741  1.00 42.70
ATOM   3714  N    SER  4607     96.609  90.430  81.636  1.00 42.58
ATOM   3715  CA   SER  4607     95.608  89.392  81.842  1.00 41.68
ATOM   3716  CB   SER  4607     95.983  88.599  83.087  1.00 40.06
ATOM   3717  OG   SER  4607     97.220  87.941  82.850  1.00 46.77
ATOM   3718  C    SER  4607     94.158  89.838  81.902  1.00 41.07
ATOM   3719  O    SER  4607     93.745  90.4`2  82.866  1.00 40.36
ATOM   3720  N    ARG  4608     93.315  88.756  81.235  1.00 42.17
ATOM   3721  CA   ARG  4608     91.877  88.817  81.354  1.00 47.94
ATOM   3722  CB   ARG  4608     91.209  87.800  80.296  1.00 57.00
```

| ATOM | 3723 | C | ARG | 4608 | 91.541 | 88.452 | 82.687 | 1.00 | 47.36 |
| ATOM | 3724 | O | ARG | 4608 | 90.503 | 89.013 | 83.154 | 1.00 | 47.16 |
| ATOM | 3725 | N | GLU | 4609 | 92.322 | 88.048 | 83.383 | 1.00 | 54.18 |
| ATOM | 3726 | CA | GLU | 4609 | 92.021 | 87.141 | 84.500 | 1.00 | 47.87 |
| ATOM | 3727 | CB | GLU | 4609 | 92.682 | 85.774 | 84.313 | 1.00 | 42.27 |
| ATOM | 3728 | CG | GLU | 4609 | 92.108 | 84.959 | 83.187 | 1.00 | 48.36 |
| ATOM | 3729 | CD | GLU | 4609 | 93.034 | 84.917 | 81.995 | 1.00 | 56.54 |
| ATOM | 3730 | OE1 | GLU | 4609 | 93.465 | 85.990 | 81.517 | 1.00 | 53.56 |
| ATOM | 3731 | OE2 | GLU | 4609 | 93.329 | 83.775 | 81.542 | 1.00 | 61.81 |
| ATOM | 3732 | C | GLU | 4609 | 92.448 | 87.682 | 85.855 | 1.00 | 44.88 |
| ATOM | 3733 | O | GLU | 4609 | 91.720 | 87.587 | 86.846 | 1.00 | 36.86 |
| ATOM | 3734 | N | GLY | 4610 | 93.641 | 88.246 | 85.897 | 1.00 | 39.86 |
| ATOM | 3735 | CA | GLY | 4610 | 94.122 | 88.778 | 87.146 | 1.00 | 36.86 |
| ATOM | 3736 | C | GLY | 4610 | 95.281 | 87.911 | 87.514 | 1.00 | 35.18 |
| ATOM | 3737 | O | GLY | 4610 | 95.097 | 86.741 | 87.838 | 1.00 | 39.16 |
| ATOM | 3738 | N | ALA | 4611 | 96.470 | 88.498 | 87.453 | 1.00 | 34.88 |
| ATOM | 3739 | CA | ALA | 4611 | 97.712 | 87.801 | 87.740 | 1.00 | 31.62 |
| ATOM | 3740 | CB | ALA | 4611 | 98.283 | 87.275 | 86.416 | 1.00 | 23.34 |
| ATOM | 3741 | C | ALA | 4611 | 98.716 | 88.749 | 88.439 | 1.00 | 30.61 |
| ATOM | 3742 | O | ALA | 4611 | 98.521 | 89.964 | 88.420 | 1.00 | 28.22 |
| ATOM | 3743 | N | ILE | 4612 | 99.772 | 88.203 | 89.056 | 1.00 | 30.88 |
| ATOM | 3744 | CA | ILE | 4612 | 100.780 | 89.045 | 89.717 | 1.00 | 30.91 |
| ATOM | 3745 | CB | ILE | 4612 | 100.812 | 88.919 | 91.277 | 1.00 | 29.78 |
| ATOM | 3746 | CG2 | ILE | 4612 | 101.316 | 90.209 | 91.874 | 1.00 | 24.45 |
| ATOM | 3747 | CG1 | ILE | 4612 | 99.422 | 88.717 | 91.869 | 1.00 | 33.00 |
| ATOM | 3748 | CD1 | ILE | 4612 | 98.902 | 87.341 | 91.677 | 1.00 | 36.95 |
| ATOM | 3749 | C | ILE | 4612 | 102.191 | 88.702 | 89.259 | 1.00 | 33.00 |
| ATOM | 3750 | O | ILE | 4612 | 102.529 | 87.531 | 89.082 | 1.00 | 32.48 |
| ATOM | 3751 | N | THR | 4613 | 103.010 | 89.739 | 89.083 | 1.00 | 35.65 |
| ATOM | 3752 | CA | THR | 4613 | 104.404 | 89.598 | 88.672 | 1.00 | 34.92 |
| ATOM | 3753 | CB | THR | 4613 | 104.683 | 90.257 | 87.337 | 1.00 | 33.67 |
| ATOM | 3754 | OG1 | THR | 4613 | 103.833 | 89.699 | 86.349 | 1.00 | 44.71 |
| ATOM | 3755 | CG2 | THR | 4613 | 106.102 | 90.021 | 86.920 | 1.00 | 34.52 |
| ATOM | 3756 | C | THR | 4613 | 105.258 | 90.368 | 89.641 | 1.00 | 37.40 |
| ATOM | 3757 | O | THR | 4613 | 104.756 | 91.215 | 90.376 | 1.00 | 39.25 |
| ATOM | 3758 | N | PHE | 4614 | 106.549 | 90.054 | 89.652 | 1.00 | 40.84 |
| ATOM | 3759 | CA | PHE | 4614 | 107.513 | 90.805 | 90.450 | 1.00 | 41.17 |
| ATOM | 3760 | CB | PHE | 4614 | 108.151 | 89.989 | 91.598 | 1.00 | 39.16 |
| ATOM | 3761 | CG | PHE | 4614 | 108.666 | 88.632 | 91.203 | 1.00 | 38.22 |
| ATOM | 3762 | CD1 | PHE | 4614 | 109.526 | 88.467 | 90.127 | 1.00 | 38.17 |
| ATOM | 3763 | CD2 | PHE | 4614 | 108.316 | 87.512 | 91.950 | 1.00 | 34.13 |
| ATOM | 3764 | CE1 | PHE | 4614 | 110.028 | 87.208 | 89.809 | 1.00 | 36.15 |
| ATOM | 3765 | CE2 | PHE | 4614 | 108.816 | 86.260 | 91.628 | 1.00 | 35.11 |
| ATOM | 3766 | CZ | PHE | 4614 | 109.672 | 86.107 | 90.559 | 1.00 | 28.45 |
| ATOM | 3767 | C | PHE | 4614 | 108.569 | 91.243 | 89.461 | 1.00 | 41.95 |
| ATOM | 3768 | O | PHE | 4614 | 108.691 | 90.657 | 88.379 | 1.00 | 34.94 |
| ATOM | 3769 | N | THR | 4615 | 109.287 | 92.307 | 89.797 | 1.00 | 48.43 |
| ATOM | 3770 | CA | THR | 4615 | 110.336 | 92.752 | 88.922 | 1.00 | 56.15 |
| ATOM | 3771 | CB | THR | 4615 | 110.044 | 94.112 | 88.320 | 1.00 | 57.74 |
| ATOM | 3772 | OG1 | THR | 4615 | 108.864 | 94.017 | 87.513 | 1.00 | 55.10 |
| ATOM | 3773 | CG2 | THR | 4615 | 111.188 | 94.522 | 87.416 | 1.00 | 60.34 |
| ATOM | 3774 | C | THR | 4615 | 111.710 | 92.693 | 89.574 | 1.00 | 61.76 |
| ATOM | 3775 | O | THR | 4615 | 111.922 | 92.994 | 90.748 | 1.00 | 60.82 |
| ATOM | 3776 | N | TRP | 4616 | 112.621 | 92.209 | 88.716 | 1.00 | 70.82 |
| ATOM | 3777 | CA | TRP | 4616 | 114.029 | 91.968 | 88.934 | 1.00 | 75.75 |
| ATOM | 3778 | CB | TRP | 4616 | 114.325 | 90.841 | 87.979 | 1.00 | 78.95 |
| ATOM | 3779 | CG | TRP | 4616 | 115.035 | 89.670 | 88.392 | 1.00 | 81.96 |
| ATOM | 3780 | CD2 | TRP | 4616 | 114.887 | 88.408 | 87.774 | 1.00 | 84.52 |
| ATOM | 3781 | CE2 | TRP | 4616 | 115.935 | 87.584 | 88.239 | 1.00 | 85.43 |
| ATOM | 3782 | CE3 | TRP | 4616 | 113.973 | 87.877 | 86.858 | 1.00 | 86.43 |
| ATOM | 3783 | CD1 | TRP | 4616 | 116.123 | 89.588 | 89.205 | 1.00 | 80.20 |
| ATOM | 3784 | NE1 | TRP | 4616 | 116.677 | 88.337 | 89.117 | 1.00 | 83.09 |
| ATOM | 3785 | CZ2 | TRP | 4616 | 116.093 | 86.260 | 87.818 | 1.00 | 88.36 |
| ATOM | 3786 | CZ3 | TRP | 4616 | 114.124 | 86.567 | 86.434 | 1.00 | 89.25 |
| ATOM | 3787 | CH2 | TRP | 4616 | 115.180 | 85.769 | 86.915 | 1.00 | 89.86 |
| ATOM | 3788 | C | TRP | 4616 | 115.027 | 93.074 | 88.586 | 1.00 | 76.72 |
| ATOM | 3789 | O | TRP | 4616 | 114.921 | 93.684 | 87.512 | 1.00 | 77.61 |
| ATOM | 3790 | N | VAL | 4617 | 116.018 | 93.280 | 89.457 | 1.00 | 77.66 |
| ATOM | 3791 | CA | VAL | 4617 | 117.118 | 94.218 | 89.188 | 1.00 | 77.44 |
| ATOM | 3792 | CB | VAL | 4617 | 116.796 | 95.673 | 89.574 | 1.00 | 77.64 |

171

| ATOM | 3793 | CG1 | VAL | 4617 | 117.954 | 96.567 | 89.174 | 1.00 | 77.78 |
| ATOM | 3794 | CG2 | VAL | 4617 | 115.548 | 96.144 | 88.862 | 1.00 | 79.77 |
| ATOM | 3795 | C | VAL | 4617 | 118.418 | 93.816 | 89.897 | 1.00 | 77.11 |
| ATOM | 3796 | O | VAL | 4617 | 118.559 | 93.987 | 91.103 | 1.00 | 73.14 |
| ATOM | 3797 | N | GLU | 4618 | 119.349 | 93.238 | 89.144 | 1.00 | 82.25 |
| ATOM | 3798 | CA | GLU | 4618 | 120.655 | 92.861 | 89.691 | 1.00 | 90.78 |
| ATOM | 3799 | CB | GLU | 4618 | 120.915 | 91.366 | 89.516 | 1.00 | 90.69 |
| ATOM | 3800 | CG | GLU | 4618 | 119.825 | 90.501 | 90.138 | 1.00 | 94.33 |
| ATOM | 3801 | CD | GLU | 4618 | 120.290 | 89.089 | 90.430 | 1.00 | 96.51 |
| ATOM | 3802 | OE1 | GLU | 4618 | 120.959 | 88.488 | 89.562 | 1.00 | 97.94 |
| ATOM | 3803 | OE2 | GLU | 4618 | 119.973 | 88.572 | 91.525 | 1.00 | 97.48 |
| ATOM | 3804 | C | GLU | 4618 | 121.622 | 93.720 | 88.871 | 1.00 | 94.43 |
| ATOM | 3805 | O | GLU | 4618 | 121.209 | 94.777 | 88.420 | 1.00 | 96.13 |
| ATOM | 3806 | N | ARG | 4619 | 122.884 | 93.347 | 88.678 | 1.00 | 97.30 |
| ATOM | 3807 | CA | ARG | 4619 | 123.711 | 94.242 | 87.860 | 1.00 | 100.48 |
| ATOM | 3808 | CB | ARG | 4619 | 124.983 | 94.685 | 88.597 | 1.00 | 102.71 |
| ATOM | 3809 | CG | ARG | 4619 | 124.716 | 95.942 | 89.456 | 1.00 | 107.54 |
| ATOM | 3810 | CD | ARG | 4619 | 125.645 | 97.125 | 89.120 | 1.00 | 110.65 |
| ATOM | 3811 | NE | ARG | 4619 | 125.084 | 98.398 | 89.589 | 1.00 | 113.74 |
| ATOM | 3812 | CZ | ARG | 4619 | 125.711 | 99.576 | 89.554 | 1.00 | 114.75 |
| ATOM | 3813 | NH1 | ARG | 4619 | 126.945 | 99.667 | 89.069 | 1.00 | 114.91 |
| ATOM | 3814 | NH2 | ARG | 4619 | 125.096 | 100.671 | 89.996 | 1.00 | 113.45 |
| ATOM | 3815 | C | ARG | 4619 | 124.027 | 93.767 | 86.459 | 1.00 | 101.41 |
| ATOM | 3816 | O | ARG | 4619 | 124.054 | 92.566 | 86.194 | 1.00 | 102.41 |
| ATOM | 3817 | N | SER | 4620 | 124.250 | 94.734 | 85.566 | 1.00 | 101.65 |
| ATOM | 3818 | CA | SER | 4620 | 124.501 | 94.470 | 84.151 | 1.00 | 102.46 |
| ATOM | 3819 | CB | SER | 4620 | 124.140 | 95.710 | 83.327 | 1.00 | 104.46 |
| ATOM | 3820 | OG | SER | 4620 | 124.097 | 95.408 | 81.938 | 1.00 | 104.59 |
| ATOM | 3821 | C | SER | 4620 | 125.885 | 93.980 | 83.735 | 1.00 | 102.03 |
| ATOM | 3822 | O | SER | 4620 | 126.106 | 93.690 | 82.557 | 1.00 | 101.02 |
| ATOM | 3823 | N | GLN | 4621 | 126.816 | 93.908 | 84.683 | 1.00 | 102.13 |
| ATOM | 3824 | CA | GLN | 4621 | 128.161 | 93.409 | 84.386 | 1.00 | 104.01 |
| ATOM | 3825 | CB | GLN | 4621 | 128.084 | 91.978 | 83.835 | 1.00 | 103.89 |
| ATOM | 3826 | CG | GLN | 4621 | 127.037 | 91.106 | 84.508 | 1.00 | 103.35 |
| ATOM | 3827 | CD | GLN | 4621 | 127.006 | 89.709 | 83.936 | 1.00 | 102.99 |
| ATOM | 3828 | OE1 | GLN | 4621 | 127.098 | 89.528 | 82.715 | 1.00 | 100.19 |
| ATOM | 3829 | NE2 | GLN | 4621 | 126.848 | 88.706 | 84.811 | 1.00 | 102.01 |
| ATOM | 3830 | C | GLN | 4621 | 128.870 | 94.277 | 83.350 | 1.00 | 104.92 |
| ATOM | 3831 | O | GLN | 4621 | 129.976 | 93.952 | 82.906 | 1.00 | 104.64 |
| ATOM | 3832 | N | ASN | 4622 | 128.218 | 95.364 | 82.945 | 1.00 | 106.33 |
| ATOM | 3833 | CA | ASN | 4622 | 128.789 | 96.279 | 81.959 | 1.00 | 106.75 |
| ATOM | 3834 | CB | ASN | 4622 | 128.437 | 95.717 | 80.521 | 1.00 | 105.78 |
| ATOM | 3835 | CG | ASN | 4622 | 129.186 | 94.453 | 80.194 | 1.00 | 104.16 |
| ATOM | 3836 | OD1 | ASN | 4622 | 130.422 | 94.333 | 80.226 | 1.00 | 100.85 |
| ATOM | 3837 | ND2 | ASN | 4622 | 128.377 | 93.446 | 79.879 | 1.00 | 102.13 |
| ATOM | 3838 | C | ASN | 4622 | 128.272 | 97.716 | 82.140 | 1.00 | 108.22 |
| ATOM | 3839 | O | ASN | 4622 | 128.167 | 98.475 | 81.176 | 1.00 | 109.11 |
| ATOM | 3840 | N | GLY | 4623 | 127.953 | 98.105 | 83.369 | 1.00 | 108.69 |
| ATOM | 3841 | CA | GLY | 4623 | 127.483 | 99.463 | 83.567 | 1.00 | 108.01 |
| ATOM | 3842 | C | GLY | 4623 | 126.204 | 99.714 | 82.809 | 1.00 | 109.32 |
| ATOM | 3843 | O | GLY | 4623 | 126.148 | 100.391 | 81.801 | 1.00 | 109.46 |
| ATOM | 3844 | N | GLY | 4624 | 125.551 | 99.273 | 83.253 | 1.00 | 110.01 |
| ATOM | 3845 | CA | GLY | 4624 | 124.175 | 99.364 | 82.822 | 1.00 | 110.30 |
| ATOM | 3846 | C | GLY | 4624 | 123.322 | 98.483 | 83.753 | 1.00 | 111.48 |
| ATOM | 3847 | O | GLY | 4624 | 123.512 | 97.275 | 83.846 | 1.00 | 112.59 |
| ATOM | 3848 | N | GLU | 4625 | 122.366 | 99.107 | 84.444 | 1.00 | 111.56 |
| ATOM | 3849 | CA | GLU | 4625 | 121.525 | 98.311 | 85.346 | 1.00 | 110.87 |
| ATOM | 3850 | CB | GLU | 4625 | 120.402 | 99.027 | 86.078 | 1.00 | 109.15 |
| ATOM | 3851 | C | GLU | 4625 | 120.949 | 97.254 | 84.429 | 1.00 | 110.75 |
| ATOM | 3852 | O | GLU | 4625 | 120.491 | 97.543 | 83.348 | 1.00 | 111.52 |
| ATOM | 3853 | N | PRO | 4626 | 120.987 | 96.009 | 84.780 | 1.00 | 110.88 |
| ATOM | 3854 | CD | PRO | 4626 | 121.219 | 95.615 | 86.163 | 1.00 | 111.67 |
| ATOM | 3855 | CA | PRO | 4626 | 120.436 | 94.886 | 84.019 | 1.00 | 111.66 |
| ATOM | 3856 | CB | PRO | 4626 | 120.797 | 93.663 | 84.869 | 1.00 | 111.55 |
| ATOM | 3857 | CG | PRO | 4626 | 120.819 | 94.169 | 86.258 | 1.00 | 112.10 |
| ATOM | 3858 | C | PRO | 4626 | 118.904 | 94.925 | 83.935 | 1.00 | 112.54 |
| ATOM | 3859 | O | PRO | 4626 | 118.216 | 95.182 | 84.948 | 1.00 | 112.80 |
| ATOM | 3860 | N | ASP | 4627 | 118.577 | 94.607 | 82.807 | 1.00 | 113.67 |
| ATOM | 3861 | CA | ASP | 4627 | 117.435 | 94.703 | 81.970 | 1.00 | 113.10 |
| ATOM | 3862 | CB | ASP | 4627 | 117.508 | 93.730 | 80.883 | 1.00 | 116.27 |

172

| ATOM | 3863 | CG | ASP | 4627 | 118.777 | 95.879 | 80.054 | 1.00 | 119.96 |
|---|---|---|---|---|---|---|---|---|---|
| ATOM | 3864 | OD1 | ASP | 4627 | 119.398 | 95.011 | 80.039 | 1.00 | 122.47 |
| ATOM | 3865 | OD2 | ASP | 4627 | 119.227 | 92.882 | 79.381 | 1.00 | 122.21 |
| ATOM | 3866 | C | ASP | 4627 | 116.052 | 94.655 | 82.556 | 1.00 | 110.12 |
| ATOM | 3867 | O | ASP | 4627 | 115.033 | 94.657 | 81.859 | 1.00 | 111.21 |
| ATOM | 3868 | N | PHE | 4628 | 116.098 | 94.680 | 83.836 | 1.00 | 105.23 |
| ATOM | 3869 | CA | PHE | 4628 | 114.785 | 94.997 | 84.381 | 1.00 | 98.26 |
| ATOM | 3870 | CB | PHE | 4628 | 114.171 | 96.153 | 85.169 | 1.00 | 98.77 |
| ATOM | 3871 | CG | PHE | 4628 | 115.186 | 97.050 | 85.809 | 1.00 | 99.24 |
| ATOM | 3872 | CD1 | PHE | 4628 | 115.674 | 98.155 | 85.133 | 1.00 | 100.63 |
| ATOM | 3873 | CD2 | PHE | 4628 | 115.652 | 96.784 | 87.083 | 1.00 | 100.78 |
| ATOM | 3874 | CE1 | PHE | 4628 | 116.612 | 98.983 | 85.721 | 1.00 | 104.52 |
| ATOM | 3875 | CE2 | PHE | 4628 | 116.590 | 97.607 | 87.677 | 1.00 | 103.37 |
| ATOM | 3876 | CZ | PHE | 4628 | 117.070 | 98.709 | 86.995 | 1.00 | 106.12 |
| ATOM | 3877 | C | PHE | 4628 | 113.743 | 94.010 | 83.881 | 1.00 | 94.33 |
| ATOM | 3878 | O | PHE | 4628 | 112.984 | 94.265 | 83.084 | 1.00 | 93.76 |
| ATOM | 3879 | N | HIS | 4629 | 114.320 | 92.765 | 84.095 | 1.00 | 87.40 |
| ATOM | 3880 | CA | HIS | 4629 | 113.468 | 91.562 | 84.727 | 1.00 | 81.59 |
| ATOM | 3881 | CB | HIS | 4629 | 114.461 | 90.465 | 85.025 | 1.00 | 81.19 |
| ATOM | 3882 | CG | HIS | 4629 | 115.675 | 90.535 | 84.167 | 1.00 | 82.12 |
| ATOM | 3883 | CD2 | HIS | 4629 | 115.997 | 91.394 | 83.170 | 1.00 | 81.82 |
| ATOM | 3884 | ND1 | HIS | 4629 | 116.700 | 89.627 | 84.249 | 1.00 | 82.70 |
| ATOM | 3885 | CE1 | HIS | 4629 | 117.612 | 89.918 | 83.335 | 1.00 | 83.29 |
| ATOM | 3886 | NE2 | HIS | 4629 | 117.210 | 90.982 | 82.670 | 1.00 | 83.85 |
| ATOM | 3887 | C | HIS | 4629 | 112.147 | 91.284 | 85.427 | 1.00 | 76.31 |
| ATOM | 3888 | O | HIS | 4629 | 112.048 | 91.401 | 86.636 | 1.00 | 72.69 |
| ATOM | 3889 | N | ALA | 4630 | 111.135 | 90.924 | 84.635 | 1.00 | 71.92 |
| ATOM | 3890 | CA | ALA | 4630 | 109.796 | 90.607 | 85.145 | 1.00 | 65.91 |
| ATOM | 3891 | CB | ALA | 4630 | 108.852 | 91.771 | 84.873 | 1.00 | 68.60 |
| ATOM | 3892 | C | ALA | 4630 | 109.216 | 89.305 | 84.565 | 1.00 | 61.75 |
| ATOM | 3893 | O | ALA | 4630 | 109.005 | 89.171 | 83.347 | 1.00 | 61.63 |
| ATOM | 3894 | N | VAL | 4631 | 108.981 | 88.356 | 85.468 | 1.00 | 55.24 |
| ATOM | 3895 | CA | VAL | 4631 | 108.428 | 87.040 | 85.187 | 1.00 | 50.04 |
| ATOM | 3896 | CB | VAL | 4631 | 108.331 | 86.285 | 86.470 | 1.00 | 50.21 |
| ATOM | 3897 | CG1 | VAL | 4631 | 107.503 | 85.036 | 86.276 | 1.00 | 53.11 |
| ATOM | 3898 | CG2 | VAL | 4631 | 109.700 | 85.979 | 86.962 | 1.00 | 50.53 |
| ATOM | 3899 | C | VAL | 4631 | 107.015 | 87.092 | 84.631 | 1.00 | 49.70 |
| ATOM | 3900 | O | VAL | 4631 | 106.266 | 88.004 | 84.971 | 1.00 | 53.06 |
| ATOM | 3901 | N | GLU | 4632 | 106.620 | 86.121 | 83.812 | 1.00 | 44.89 |
| ATOM | 3902 | CA | GLU | 4632 | 105.244 | 86.117 | 83.300 | 1.00 | 45.47 |
| ATOM | 3903 | CB | GLU | 4632 | 104.976 | 84.907 | 82.411 | 1.00 | 48.28 |
| ATOM | 3904 | CG | GLU | 4632 | 105.455 | 83.591 | 83.034 | 1.00 | 54.22 |
| ATOM | 3905 | CD | GLU | 4632 | 105.242 | 82.414 | 82.107 | 1.00 | 54.08 |
| ATOM | 3906 | OE1 | GLU | 4632 | 105.325 | 82.662 | 80.885 | 1.00 | 52.52 |
| ATOM | 3907 | OE2 | GLU | 4632 | 105.024 | 81.266 | 82.587 | 1.00 | 53.23 |
| ATOM | 3908 | C | GLU | 4632 | 104.334 | 86.050 | 84.510 | 1.00 | 44.41 |
| ATOM | 3909 | O | GLU | 4632 | 104.621 | 85.318 | 85.460 | 1.00 | 46.48 |
| ATOM | 3910 | N | PRO | 4633 | 103.204 | 86.771 | 84.477 | 1.00 | 42.91 |
| ATOM | 3911 | CD | PRO | 4633 | 102.705 | 87.552 | 83.339 | 1.00 | 43.53 |
| ATOM | 3912 | CA | PRO | 4633 | 102.226 | 86.834 | 85.561 | 1.00 | 43.42 |
| ATOM | 3913 | CB | PRO | 4633 | 101.134 | 87.711 | 84.974 | 1.00 | 44.44 |
| ATOM | 3914 | CG | PRO | 4633 | 101.922 | 88.623 | 84.044 | 1.00 | 44.32 |
| ATOM | 3915 | C | PRO | 4633 | 101.694 | 85.505 | 86.010 | 1.00 | 44.61 |
| ATOM | 3916 | O | PRO | 4633 | 101.683 | 84.537 | 85.258 | 1.00 | 50.56 |
| ATOM | 3917 | N | TYR | 4634 | 101.245 | 85.462 | 87.245 | 1.00 | 42.65 |
| ATOM | 3918 | CA | TYR | 4634 | 100.709 | 84.240 | 87.769 | 1.00 | 43.96 |
| ATOM | 3919 | CB | TYR | 4634 | 101.320 | 83.948 | 89.147 | 1.00 | 47.31 |
| ATOM | 3920 | CG | TYR | 4634 | 102.817 | 83.681 | 89.105 | 1.00 | 47.80 |
| ATOM | 3921 | CD1 | TYR | 4634 | 103.745 | 84.678 | 89.424 | 1.00 | 45.92 |
| ATOM | 3922 | CE1 | TYR | 4634 | 105.122 | 84.414 | 89.364 | 1.00 | 48.31 |
| ATOM | 3923 | CD2 | TYR | 4634 | 103.301 | 82.420 | 88.719 | 1.00 | 47.28 |
| ATOM | 3924 | CE2 | TYR | 4634 | 104.653 | 82.147 | 88.652 | 1.00 | 46.54 |
| ATOM | 3925 | CZ | TYR | 4634 | 105.566 | 83.135 | 88.977 | 1.00 | 49.01 |
| ATOM | 3926 | OH | TYR | 4634 | 106.910 | 82.802 | 88.965 | 1.00 | 51.58 |
| ATOM | 3927 | C | TYR | 4634 | 99.204 | 84.401 | 87.859 | 1.00 | 46.29 |
| ATOM | 3928 | O | TYR | 4634 | 98.706 | 85.379 | 88.413 | 1.00 | 46.06 |
| ATOM | 3929 | N | THR | 4635 | 98.468 | 83.453 | 87.299 | 1.00 | 46.17 |
| ATOM | 3930 | CA | THR | 4635 | 97.028 | 83.553 | 87.342 | 1.00 | 47.44 |
| ATOM | 3931 | CB | THR | 4635 | 96.488 | 83.093 | 85.999 | 1.00 | 48.54 |
| ATOM | 3932 | OG1 | THR | 4635 | 95.065 | 83.278 | 85.967 | 1.00 | 54.67 |

173

| ATOM | 3933 | CG2 | THR | 4635 | 96.890 | 81.632 | 85.756 | 1.00 | 48.08 |
| ATOM | 3934 | C | THR | 4635 | 96.533 | 82.700 | 88.536 | 1.00 | 46.95 |
| ATOM | 3935 | O | THR | 4635 | 97.354 | 82.239 | 89.326 | 1.00 | 45.11 |
| ATOM | 3936 | N | LYS | 4636 | 95.227 | 82.503 | 88.709 | 1.00 | 45.66 |
| ATOM | 3937 | CA | LYS | 4636 | 94.783 | 81.694 | 89.841 | 1.00 | 46.22 |
| ATOM | 3938 | CB | LYS | 4636 | 93.273 | 81.513 | 89.853 | 1.00 | 49.59 |
| ATOM | 3939 | CG | LYS | 4636 | 92.488 | 82.711 | 89.417 | 1.00 | 58.41 |
| ATOM | 3940 | CD | LYS | 4636 | 92.444 | 82.725 | 87.909 | 1.00 | 63.61 |
| ATOM | 3941 | CE | LYS | 4636 | 91.813 | 83.989 | 87.362 | 1.00 | 64.75 |
| ATOM | 3942 | NZ | LYS | 4636 | 91.858 | 83.934 | 85.874 | 1.00 | 63.08 |
| ATOM | 3943 | C | LYS | 4636 | 95.416 | 80.299 | 89.789 | 1.00 | 46.13 |
| ATOM | 3944 | O | LYS | 4636 | 95.806 | 79.744 | 90.825 | 1.00 | 44.17 |
| ATOM | 3945 | N | LYS | 4637 | 95.512 | 79.735 | 88.584 | 1.00 | 45.16 |
| ATOM | 3946 | CA | LYS | 4637 | 96.073 | 78.397 | 88.394 | 1.00 | 42.39 |
| ATOM | 3947 | CB | LYS | 4637 | 96.356 | 78.137 | 86.916 | 1.00 | 41.94 |
| ATOM | 3948 | CG | LYS | 4637 | 96.749 | 76.687 | 86.624 | 1.00 | 42.90 |
| ATOM | 3949 | CD | LYS | 4637 | 97.054 | 76.468 | 85.142 | 1.00 | 39.48 |
| ATOM | 3950 | CE | LYS | 4637 | 97.414 | 75.015 | 84.837 | 1.00 | 42.37 |
| ATOM | 3951 | NZ | LYS | 4637 | 97.664 | 74.734 | 83.374 | 1.00 | 42.06 |
| ATOM | 3952 | C | LYS | 4637 | 97.354 | 78.235 | 89.192 | 1.00 | 43.63 |
| ATOM | 3953 | O | LYS | 4637 | 97.329 | 77.796 | 90.335 | 1.00 | 46.04 |
| ATOM | 3954 | N | GLU | 4638 | 98.480 | 78.610 | 88.605 | 1.00 | 43.35 |
| ATOM | 3955 | CA | GLU | 4638 | 99.748 | 78.477 | 89.302 | 1.00 | 44.20 |
| ATOM | 3956 | CB | GLU | 4638 | 100.847 | 79.309 | 88.636 | 1.00 | 49.03 |
| ATOM | 3957 | CG | GLU | 4638 | 100.983 | 79.080 | 87.161 | 1.00 | 57.25 |
| ATOM | 3958 | CD | GLU | 4638 | 100.182 | 80.069 | 86.331 | 1.00 | 61.56 |
| ATOM | 3959 | OE1 | GLU | 4638 | 98.982 | 80.316 | 86.639 | 1.00 | 60.68 |
| ATOM | 3960 | OE2 | GLU | 4638 | 100.775 | 80.583 | 85.348 | 1.00 | 66.97 |
| ATOM | 3961 | C | GLU | 4638 | 99.687 | 78.861 | 90.776 | 1.00 | 42.13 |
| ATOM | 3962 | O | GLU | 4638 | 100.441 | 78.290 | 91.571 | 1.00 | 43.44 |
| ATOM | 3963 | N | LEU | 4639 | 98.829 | 79.821 | 91.148 | 1.00 | 38.33 |
| ATOM | 3964 | CA | LEU | 4639 | 98.717 | 80.239 | 92.562 | 1.00 | 34.52 |
| ATOM | 3965 | CB | LEU | 4639 | 98.067 | 81.603 | 92.719 | 1.00 | 29.90 |
| ATOM | 3966 | CG | LEU | 4639 | 98.998 | 82.782 | 92.937 | 1.00 | 25.29 |
| ATOM | 3967 | CD1 | LEU | 4639 | 99.987 | 82.877 | 91.775 | 1.00 | 26.21 |
| ATOM | 3968 | CD2 | LEU | 4639 | 98.151 | 84.055 | 93.085 | 1.00 | 18.61 |
| ATOM | 3969 | C | LEU | 4639 | 97.945 | 79.277 | 93.432 | 1.00 | 34.10 |
| ATOM | 3970 | O | LEU | 4639 | 98.242 | 79.141 | 94.599 | 1.00 | 31.23 |
| ATOM | 3971 | N | SER | 4640 | 96.949 | 78.611 | 92.873 | 1.00 | 35.74 |
| ATOM | 3972 | CA | SER | 4640 | 96.173 | 77.669 | 93.664 | 1.00 | 37.99 |
| ATOM | 3973 | CB | SER | 4640 | 94.869 | 77.388 | 92.943 | 1.00 | 42.88 |
| ATOM | 3974 | OG | SER | 4640 | 95.159 | 77.197 | 91.575 | 1.00 | 53.35 |
| ATOM | 3975 | C | SER | 4640 | 96.984 | 76.397 | 93.931 | 1.00 | 34.13 |
| ATOM | 3976 | O | SER | 4640 | 96.785 | 75.693 | 94.919 | 1.00 | 28.15 |
| ATOM | 3977 | N | ALA | 4641 | 97.919 | 76.095 | 93.054 | 1.00 | 34.79 |
| ATOM | 3978 | CA | ALA | 4641 | 98.753 | 74.940 | 93.339 | 1.00 | 38.76 |
| ATOM | 3979 | CB | ALA | 4641 | 99.221 | 74.289 | 92.034 | 1.00 | 39.47 |
| ATOM | 3980 | C | ALA | 4641 | 99.977 | 75.366 | 94.230 | 1.00 | 37.57 |
| ATOM | 3981 | O | ALA | 4641 | 100.695 | 74.521 | 94.769 | 1.00 | 34.07 |
| ATOM | 3982 | N | VAL | 4642 | 100.203 | 76.672 | 94.388 | 1.00 | 35.92 |
| ATOM | 3983 | CA | VAL | 4642 | 101.324 | 77.162 | 95.192 | 1.00 | 35.21 |
| ATOM | 3984 | CB | VAL | 4642 | 102.614 | 77.191 | 94.383 | 1.00 | 32.98 |
| ATOM | 3985 | CG1 | VAL | 4642 | 103.754 | 77.467 | 95.272 | 1.00 | 33.35 |
| ATOM | 3986 | CG2 | VAL | 4642 | 102.836 | 75.901 | 93.710 | 1.00 | 37.25 |
| ATOM | 3987 | C | VAL | 4642 | 101.065 | 78.588 | 95.668 | 1.00 | 36.40 |
| ATOM | 3988 | O | VAL | 4642 | 100.724 | 79.453 | 94.870 | 1.00 | 38.79 |
| ATOM | 3989 | N | THR | 4643 | 101.237 | 78.841 | 96.961 | 1.00 | 35.16 |
| ATOM | 3990 | CA | THR | 4643 | 101.014 | 80.183 | 97.511 | 1.00 | 34.37 |
| ATOM | 3991 | CB | THR | 4643 | 101.453 | 80.237 | 98.972 | 1.00 | 36.18 |
| ATOM | 3992 | OG1 | THR | 4643 | 100.858 | 79.153 | 99.677 | 1.00 | 42.10 |
| ATOM | 3993 | CG2 | THR | 4643 | 100.978 | 81.475 | 99.624 | 1.00 | 41.54 |
| ATOM | 3994 | C | THR | 4643 | 101.890 | 81.131 | 96.720 | 1.00 | 30.99 |
| ATOM | 3995 | O | THR | 4643 | 102.723 | 80.679 | 95.973 | 1.00 | 32.00 |
| ATOM | 3996 | N | PHE | 4644 | 101.711 | 82.415 | 96.846 | 1.00 | 31.09 |
| ATOM | 3997 | CA | PHE | 4644 | 102.591 | 83.350 | 96.111 | 1.00 | 33.72 |
| ATOM | 3998 | CB | PHE | 4644 | 101.925 | 84.692 | 95.870 | 1.00 | 30.79 |
| ATOM | 3999 | CG | PHE | 4644 | 102.666 | 85.573 | 94.939 | 1.00 | 27.97 |
| ATOM | 4000 | CD1 | PHE | 4644 | 102.989 | 85.126 | 93.658 | 1.00 | 22.47 |
| ATOM | 4001 | CD2 | PHE | 4644 | 103.006 | 86.884 | 95.315 | 1.00 | 30.26 |
| ATOM | 4002 | CE1 | PHE | 4644 | 103.649 | 85.982 | 92.730 | 1.00 | 24.39 |

| | | | | | | | | |
|---|---|---|---|---|---|---|---|---|
| ATOM | 4003 | CE2 | PHE | 4644 | 103.668 | 87.760 | 94.401 | 1.00 29.74 |
| ATOM | 4004 | CZ | PHE | 4644 | 103.990 | 87.300 | 93.098 | 1.00 24.81 |
| ATOM | 4005 | C | PHE | 4644 | 103.862 | 83.532 | 96.935 | 1.00 37.91 |
| ATOM | 4006 | O | PHE | 4644 | 104.952 | 83.522 | 96.395 | 1.00 40.41 |
| ATOM | 4007 | N | PRO | 4645 | 103.745 | 83.719 | 98.259 | 1.00 41.74 |
| ATOM | 4008 | CD | PRO | 4645 | 102.579 | 83.823 | 99.162 | 1.00 41.54 |
| ATOM | 4009 | CA | PRO | 4645 | 104.988 | 83.868 | 99.021 | 1.00 43.94 |
| ATOM | 4010 | CB | PRO | 4645 | 104.491 | 83.823 | 100.470 | 1.00 42.33 |
| ATOM | 4011 | CG | PRO | 4645 | 103.149 | 84.553 | 100.358 | 1.00 40.24 |
| ATOM | 4012 | C | PRO | 4645 | 105.954 | 82.717 | 98.721 | 1.00 47.65 |
| ATOM | 4013 | O | PRO | 4645 | 107.113 | 82.955 | 98.362 | 1.00 49.95 |
| ATOM | 4014 | N | ASP | 4646 | 105.450 | 81.482 | 98.855 | 1.00 49.27 |
| ATOM | 4015 | CA | ASP | 4646 | 106.240 | 80.270 | 98.658 | 1.00 49.42 |
| ATOM | 4016 | CB | ASP | 4646 | 105.369 | 79.021 | 98.855 | 1.00 50.78 |
| ATOM | 4017 | CG | ASP | 4646 | 104.960 | 78.813 | 100.310 | 1.00 53.45 |
| ATOM | 4018 | OD1 | ASP | 4646 | 105.836 | 78.617 | 101.179 | 1.00 55.58 |
| ATOM | 4019 | OD2 | ASP | 4646 | 103.753 | 78.856 | 100.593 | 1.00 56.44 |
| ATOM | 4020 | C | ASP | 4646 | 106.955 | 80.211 | 97.324 | 1.00 49.91 |
| ATOM | 4021 | O | ASP | 4646 | 108.032 | 79.613 | 97.207 | 1.00 50.63 |
| ATOM | 4022 | N | ILE | 4647 | 106.372 | 80.835 | 96.309 | 1.00 50.66 |
| ATOM | 4023 | CA | ILE | 4647 | 107.006 | 80.850 | 94.988 | 1.00 50.04 |
| ATOM | 4024 | CB | ILE | 4647 | 105.907 | 80.981 | 93.838 | 1.00 46.28 |
| ATOM | 4025 | CG2 | ILE | 4647 | 104.662 | 81.601 | 94.343 | 1.00 40.54 |
| ATOM | 4026 | CG1 | ILE | 4647 | 106.452 | 81.765 | 92.657 | 1.00 48.02 |
| ATOM | 4027 | CD1 | ILE | 4647 | 105.456 | 81.936 | 91.617 | 1.00 44.61 |
| ATOM | 4028 | C | ILE | 4647 | 108.108 | 81.943 | 94.929 | 1.00 49.26 |
| ATOM | 4029 | O | ILE | 4647 | 109.037 | 81.876 | 94.129 | 1.00 49.17 |
| ATOM | 4030 | N | ILE | 4648 | 107.995 | 82.917 | 95.826 | 1.00 48.35 |
| ATOM | 4031 | CA | ILE | 4648 | 108.935 | 84.014 | 95.963 | 1.00 47.50 |
| ATOM | 4032 | CB | ILE | 4648 | 108.316 | 85.148 | 96.808 | 1.00 49.50 |
| ATOM | 4033 | CG2 | ILE | 4648 | 109.377 | 86.077 | 97.331 | 1.00 48.18 |
| ATOM | 4034 | CG1 | ILE | 4648 | 107.311 | 85.913 | 95.964 | 1.00 53.31 |
| ATOM | 4035 | CD1 | ILE | 4648 | 106.679 | 87.033 | 96.698 | 1.00 59.09 |
| ATOM | 4036 | C | ILE | 4648 | 110.154 | 83.482 | 96.686 | 1.00 46.19 |
| ATOM | 4037 | O | ILE | 4648 | 111.289 | 83.812 | 96.349 | 1.00 43.87 |
| ATOM | 4038 | N | ARG | 4649 | 109.905 | 82.663 | 97.699 | 1.00 46.04 |
| ATOM | 4039 | CA | ARG | 4649 | 110.987 | 82.063 | 98.481 | 1.00 46.14 |
| ATOM | 4040 | CB | ARG | 4649 | 110.429 | 81.135 | 99.558 | 1.00 45.63 |
| ATOM | 4041 | CG | ARG | 4649 | 111.388 | 80.563 | 100.603 | 1.00 43.42 |
| ATOM | 4042 | CD | ARG | 4649 | 110.560 | 79.692 | 101.567 | 1.00 47.47 |
| ATOM | 4043 | NE | ARG | 4649 | 111.293 | 79.031 | 102.647 | 1.00 56.63 |
| ATOM | 4044 | CZ | ARG | 4649 | 110.735 | 78.170 | 103.510 | 1.00 60.08 |
| ATOM | 4045 | NH1 | ARG | 4649 | 109.445 | 77.861 | 103.409 | 1.00 62.22 |
| ATOM | 4046 | NH2 | ARG | 4649 | 111.453 | 77.611 | 104.480 | 1.00 61.83 |
| ATOM | 4047 | C | ARG | 4649 | 111.853 | 81.253 | 97.559 | 1.00 45.30 |
| ATOM | 4048 | O | ARG | 4649 | 113.075 | 81.390 | 97.566 | 1.00 50.56 |
| ATOM | 4049 | N | ASN | 4650 | 111.227 | 80.438 | 96.728 | 1.00 41.68 |
| ATOM | 4050 | CA | ASN | 4650 | 112.006 | 79.576 | 95.876 | 1.00 39.65 |
| ATOM | 4051 | CB | ASN | 4650 | 111.510 | 78.131 | 96.021 | 1.00 38.88 |
| ATOM | 4052 | CG | ASN | 4650 | 111.334 | 77.694 | 97.490 | 1.00 40.12 |
| ATOM | 4053 | OD1 | ASN | 4650 | 112.272 | 77.711 | 98.297 | 1.00 44.30 |
| ATOM | 4054 | ND2 | ASN | 4650 | 110.130 | 77.295 | 97.826 | 1.00 36.11 |
| ATOM | 4055 | C | ASN | 4650 | 112.053 | 79.918 | 94.416 | 1.00 39.44 |
| ATOM | 4056 | O | ASN | 4650 | 112.057 | 79.010 | 93.626 | 1.00 40.66 |
| ATOM | 4057 | N | TYR | 4651 | 112.088 | 81.178 | 94.009 | 1.00 39.16 |
| ATOM | 4058 | CA | TYR | 4651 | 112.159 | 81.426 | 92.570 | 1.00 44.93 |
| ATOM | 4059 | CB | TYR | 4651 | 111.860 | 82.885 | 92.243 | 1.00 41.57 |
| ATOM | 4060 | CG | TYR | 4651 | 112.018 | 83.162 | 90.752 | 1.00 44.18 |
| ATOM | 4061 | CD1 | TYR | 4651 | 111.463 | 82.292 | 89.816 | 1.00 44.32 |
| ATOM | 4062 | CE1 | TYR | 4651 | 111.637 | 82.486 | 88.448 | 1.00 46.20 |
| ATOM | 4063 | CD2 | TYR | 4651 | 112.758 | 84.256 | 90.268 | 1.00 43.56 |
| ATOM | 4064 | CE2 | TYR | 4651 | 112.938 | 84.463 | 88.871 | 1.00 41.15 |
| ATOM | 4065 | CZ | TYR | 4651 | 112.372 | 83.566 | 87.968 | 1.00 42.87 |
| ATOM | 4066 | OH | TYR | 4651 | 112.531 | 83.692 | 86.593 | 1.00 37.07 |
| ATOM | 4067 | C | TYR | 4651 | 113.533 | 81.080 | 91.969 | 1.00 53.29 |
| ATOM | 4068 | O | TYR | 4651 | 113.851 | 81.469 | 90.870 | 1.00 56.19 |
| ATOM | 4069 | N | LYS | 4652 | 114.365 | 80.321 | 92.668 | 1.00 59.06 |
| ATOM | 4070 | CA | LYS | 4652 | 115.706 | 79.993 | 92.204 | 1.00 67.93 |
| ATOM | 4071 | CB | LYS | 4652 | 116.020 | 78.566 | 92.678 | 1.00 68.19 |
| ATOM | 4072 | CG | LYS | 4652 | 115.794 | 78.481 | 94.168 | 1.00 72.04 |

175

```
ATOM  4073  CD   LYS  4652   116.203  77.176  94.768  1.00 76.68
ATOM  4074  CE   LYS  4652   115.884  77.108  96.247  1.00 81.35
ATOM  4075  NZ   LYS  4652   116.375  75.880  96.938  1.00 85.71
ATOM  4076  C    LYS  4652   116.140  80.277  90.730  1.00 73.68
ATOM  4077  O    LYS  4652   117.292  80.642  90.498  1.00 78.21
ATOM  4078  N    VAL  4653   115.282  80.136  89.723  1.00 76.90
ATOM  4079  CA   VAL  4653   115.616  80.466  88.315  1.00 83.16
ATOM  4080  CB   VAL  4653   115.333  81.925  88.088  1.00 85.69
ATOM  4081  C    VAL  4653   116.991  80.157  87.660  1.00 87.35
ATOM  4082  O    VAL  4653   117.737  81.097  87.331  1.00 84.54
ATOM  4083  N    MET  4654   117.269  78.868  87.405  1.00 92.58
ATOM  4084  CA   MET  4654   118.531  78.401  86.805  1.00 98.56
ATOM  4085  CB   MET  4654   118.664  78.918  85.329  1.00 95.93
ATOM  4086  C    MET  4654   119.651  78.959  87.715  1.00103.27
ATOM  4087  O    MET  4654   120.195  80.033  87.469  1.00104.92
ATOM  4088  N    ALA  4655   119.945  78.238  88.804  1.00106.63
ATOM  4089  CA   ALA  4655   120.950  78.669  89.784  1.00107.58
ATOM  4090  CB   ALA  4655   120.261  79.093  91.070  1.00105.85
ATOM  4091  C    ALA  4655   121.987  77.594  90.106  1.00109.47
ATOM  4092  O    ALA  4655   121.713  76.680  90.871  1.00111.43
ATOM  4093  N    ALA  4656   123.157  77.744  89.473  1.00110.13
ATOM  4094  CA   ALA  4656   124.293  76.829  89.607  1.00111.00
ATOM  4095  CB   ALA  4656   125.476  77.341  88.717  1.00107.47
ATOM  4096  C    ALA  4656   124.694  76.753  91.087  1.00112.01
ATOM  4097  O    ALA  4656   125.201  77.738  91.626  1.00113.27
ATOM  4098  N    GLU  4657   124.468  75.620  91.763  1.00112.92
ATOM  4099  CA   GLU  4657   124.841  75.584  93.185  1.00115.18
ATOM  4100  CB   GLU  4657   124.039  76.683  93.932  1.00115.02
ATOM  4101  C    GLU  4657   124.823  74.287  94.032  1.00116.28
ATOM  4102  O    GLU  4657   125.242  73.198  93.606  1.00116.94
ATOM  4103  N    ASN  4658   124.367  74.445  95.271  1.00116.83
ATOM  4104  CA   ASN  4658   124.297  73.341  96.203  1.00117.10
ATOM  4105  CB   ASN  4658   125.624  72.539  96.183  1.00115.37
ATOM  4106  C    ASN  4658   124.011  73.866  97.608  1.00117.58
ATOM  4107  O    ASN  4658   124.593  73.371  98.568  1.00118.16
ATOM  4108  N    ILE  4659   123.131  74.863  97.734  1.00117.59
ATOM  4109  CA   ILE  4659   122.778  75.408  99.054  1.00118.70
ATOM  4110  CB   ILE  4659   124.025  75.817  99.827  1.00117.77
ATOM  4111  C    ILE  4659   121.815  76.584  98.990  1.00119.13
ATOM  4112  O    ILE  4659   120.677  76.448  99.436  1.00120.29
ATOM  4113  N    PRO  4660   122.282  77.738  98.481  1.00119.45
ATOM  4114  CA   PRO  4660   121.462  78.968  98.317  1.00117.66
ATOM  4115  CB   PRO  4660   122.005  80.116  99.208  1.00116.75
ATOM  4116  C    PRO  4660   121.510  79.381  96.829  1.00116.67
ATOM  4117  O    PRO  4660   122.462  79.034  96.127  1.00118.59
ATOM  4118  N    GLU  4661   120.481  80.084  96.350  1.00113.91
ATOM  4119  CA   GLU  4661   120.393  80.564  94.957  1.00110.08
ATOM  4120  CB   GLU  4661   120.209  79.373  94.002  1.00110.28
ATOM  4121  C    GLU  4661   119.166  81.508  94.944  1.00107.23
ATOM  4122  O    GLU  4661   118.250  81.324  95.753  1.00108.80
ATOM  4123  N    ASN  4662   119.138  82.520  94.077  1.00101.97
ATOM  4124  CA   ASN  4662   118.023  83.476  94.072  1.00 95.96
ATOM  4125  CB   ASN  4662   118.359  84.662  94.887  1.00 94.10
ATOM  4126  C    ASN  4662   117.767  83.882  92.669  1.00 92.76
ATOM  4127  O    ASN  4662   117.983  83.051  91.785  1.00 94.84
ATOM  4128  N    PRO  4663   117.506  85.183  92.384  1.00 88.27
ATOM  4129  CD   PRO  4663   117.124  85.070  90.976  1.00 85.26
ATOM  4130  CA   PRO  4663   117.264  86.589  92.783  1.00 85.48
ATOM  4131  CB   PRO  4663   117.003  87.228  91.470  1.00 84.44
ATOM  4132  CG   PRO  4663   116.179  86.142  90.873  1.00 84.32
ATOM  4133  C    PRO  4663   116.165  86.996  93.743  1.00 84.49
ATOM  4134  O    PRO  4663   115.093  87.436  93.347  1.00 81.80
ATOM  4135  N    LEU  4664   116.435  86.935  95.015  1.00 85.41
ATOM  4136  CA   LEU  4664   115.413  87.287  95.956  1.00 86.37
ATOM  4137  CB   LEU  4664   115.043  85.962  96.661  1.00 86.63
ATOM  4138  CG   LEU  4664   115.166  84.674  95.761  1.00 87.96
ATOM  4139  CD1  LEU  4664   115.032  83.408  96.601  1.00 86.43
ATOM  4140  CD2  LEU  4664   114.149  84.645  94.599  1.00 87.79
ATOM  4141  C    LEU  4664   116.201  88.273  96.851  1.00 88.61
ATOM  4142  O    LEU  4664   117.321  88.596  96.524  1.00 89.98
```

176

| | | | | | | | | |
|---|---|---|---|---|---|---|---|---|
| ATOM | 4143 | N | LYS | 4665 | 115.587 | 88.805 | 97.893 | 1.00 90.57 |
| ATOM | 4144 | CA | LYS | 4665 | 116.304 | 89.612 | 98.904 | 1.00 89.30 |
| ATOM | 4145 | CB | LYS | 4665 | 117.630 | 89.074 | 99.275 | 1.00 93.28 |
| ATOM | 4146 | CG | LYS | 4665 | 117.540 | 87.793 | 100.137 | 1.00 96.25 |
| ATOM | 4147 | CD | LYS | 4665 | 118.948 | 87.283 | 100.505 | 1.00 97.31 |
| ATOM | 4148 | CE | LYS | 4665 | 118.893 | 86.052 | 101.434 | 1.00 98.74 |
| ATOM | 4149 | NZ | LYS | 4665 | 120.243 | 85.539 | 101.873 | 1.00 97.41 |
| ATOM | 4150 | C | LYS | 4665 | 116.419 | 91.097 | 99.086 | 1.00 87.92 |
| ATOM | 4151 | O | LYS | 4665 | 117.430 | 91.679 | 99.382 | 1.00 89.66 |
| ATOM | 4152 | N | TYR | 4666 | 115.337 | 91.673 | 98.639 | 1.00 86.50 |
| ATOM | 4153 | CA | TYR | 4666 | 114.978 | 92.989 | 99.156 | 1.00 84.67 |
| ATOM | 4154 | CB | TYR | 4666 | 116.253 | 94.126 | 99.410 | 1.00 84.35 |
| ATOM | 4155 | C | TYR | 4666 | 113.767 | 93.444 | 98.417 | 1.00 82.50 |
| ATOM | 4156 | O | TYR | 4666 | 113.635 | 93.509 | 97.187 | 1.00 82.68 |
| ATOM | 4157 | N | LEU | 4667 | 112.845 | 93.416 | 99.328 | 1.00 82.06 |
| ATOM | 4158 | CA | LEU | 4667 | 111.495 | 93.568 | 99.105 | 1.00 84.35 |
| ATOM | 4159 | CB | LEU | 4667 | 110.688 | 93.126 | 100.288 | 1.00 81.52 |
| ATOM | 4160 | CG | LEU | 4667 | 109.245 | 92.872 | 99.948 | 1.00 79.70 |
| ATOM | 4161 | CD1 | LEU | 4667 | 109.288 | 91.745 | 99.016 | 1.00 84.50 |
| ATOM | 4162 | CD2 | LEU | 4667 | 108.429 | 92.506 | 101.169 | 1.00 79.13 |
| ATOM | 4163 | C | LEU | 4667 | 110.955 | 94.871 | 98.514 | 1.00 86.36 |
| ATOM | 4164 | O | LEU | 4667 | 110.251 | 94.862 | 97.556 | 1.00 89.33 |
| ATOM | 4165 | N | TYR | 4668 | 111.288 | 95.941 | 99.139 | 1.00 86.95 |
| ATOM | 4166 | CA | TYR | 4668 | 111.055 | 97.177 | 98.475 | 1.00 90.83 |
| ATOM | 4167 | CB | TYR | 4668 | 109.764 | 97.906 | 98.735 | 1.00 88.10 |
| ATOM | 4168 | CG | TYR | 4668 | 109.876 | 99.212 | 97.904 | 1.00 89.12 |
| ATOM | 4169 | CD1 | TYR | 4668 | 110.844 | 99.334 | 96.861 | 1.00 86.86 |
| ATOM | 4170 | CE1 | TYR | 4668 | 111.142 | 100.595 | 96.286 | 1.00 85.92 |
| ATOM | 4171 | CD2 | TYR | 4668 | 109.220 | 100.386 | 98.296 | 1.00 89.60 |
| ATOM | 4172 | CE2 | TYR | 4668 | 109.509 | 101.605 | 97.730 | 1.00 86.94 |
| ATOM | 4173 | CZ | TYR | 4668 | 110.463 | 101.713 | 96.761 | 1.00 85.95 |
| ATOM | 4174 | OH | TYR | 4668 | 110.744 | 102.984 | 96.361 | 1.00 86.44 |
| ATOM | 4175 | C | TYR | 4668 | 112.334 | 97.810 | 98.963 | 1.00 97.04 |
| ATOM | 4176 | O | TYR | 4668 | 113.285 | 97.051 | 99.012 | 1.00 99.76 |
| ATOM | 4177 | N | PRO | 4669 | 112.425 | 99.093 | 99.416 | 1.00 100.60 |
| ATOM | 4178 | CD | PRO | 4669 | 111.736 | 100.363 | 99.738 | 1.00 100.42 |
| ATOM | 4179 | CA | PRO | 4669 | 113.855 | 99.223 | 99.737 | 1.00 102.56 |
| ATOM | 4180 | CB | PRO | 4669 | 114.066 | 100.729 | 99.768 | 1.00 103.77 |
| ATOM | 4181 | CG | PRO | 4669 | 112.820 | 101.133 | 100.508 | 1.00 103.14 |
| ATOM | 4182 | C | PRO | 4669 | 114.373 | 98.564 | 100.993 | 1.00 103.61 |
| ATOM | 4183 | O | PRO | 4669 | 114.274 | 99.073 | 102.115 | 1.00 102.62 |
| ATOM | 4184 | N | ASN | 4670 | 114.932 | 97.403 | 100.785 | 1.00 105.05 |
| ATOM | 4185 | CA | ASN | 4670 | 115.493 | 96.672 | 101.860 | 1.00 108.50 |
| ATOM | 4186 | CB | ASN | 4670 | 116.765 | 97.345 | 102.357 | 1.00 114.46 |
| ATOM | 4187 | CG | ASN | 4670 | 117.905 | 97.177 | 101.375 | 1.00 120.58 |
| ATOM | 4188 | OD1 | ASN | 4670 | 117.824 | 97.660 | 100.240 | 1.00 125.10 |
| ATOM | 4189 | ND2 | ASN | 4670 | 118.959 | 96.461 | 101.783 | 1.00 121.21 |
| ATOM | 4190 | C | ASN | 4670 | 114.664 | 96.287 | 103.026 | 1.00 107.12 |
| ATOM | 4191 | O | ASN | 4670 | 114.903 | 96.703 | 104.158 | 1.00 109.13 |
| ATOM | 4192 | N | ILE | 4671 | 113.618 | 95.543 | 102.744 | 1.00 103.12 |
| ATOM | 4193 | CA | ILE | 4671 | 112.962 | 94.940 | 103.850 | 1.00 100.54 |
| ATOM | 4194 | CB | ILE | 4671 | 111.427 | 95.121 | 103.887 | 1.00 100.11 |
| ATOM | 4195 | CG2 | ILE | 4671 | 110.769 | 93.850 | 104.291 | 1.00 100.95 |
| ATOM | 4196 | CG1 | ILE | 4671 | 111.062 | 96.108 | 105.013 | 1.00 100.07 |
| ATOM | 4197 | CD1 | ILE | 4671 | 109.557 | 96.227 | 105.337 | 1.00 99.19 |
| ATOM | 4198 | C | ILE | 4671 | 113.531 | 93.623 | 103.275 | 1.00 98.88 |
| ATOM | 4199 | O | ILE | 4671 | 113.489 | 93.392 | 102.061 | 1.00 97.92 |
| ATOM | 4200 | N | ASP | 4672 | 114.204 | 92.867 | 104.153 | 1.00 97.62 |
| ATOM | 4201 | CA | ASP | 4672 | 114.918 | 91.599 | 103.873 | 1.00 93.57 |
| ATOM | 4202 | CB | ASP | 4672 | 115.651 | 91.116 | 105.147 | 1.00 96.75 |
| ATOM | 4203 | CG | ASP | 4672 | 116.512 | 92.225 | 105.787 | 1.00 100.41 |
| ATOM | 4204 | OD1 | ASP | 4672 | 117.551 | 92.597 | 105.199 | 1.00 102.22 |
| ATOM | 4205 | OD2 | ASP | 4672 | 116.139 | 92.755 | 106.867 | 1.00 103.25 |
| ATOM | 4206 | C | ASP | 4672 | 114.016 | 90.513 | 103.385 | 1.00 87.08 |
| ATOM | 4207 | O | ASP | 4672 | 113.211 | 90.000 | 104.148 | 1.00 84.48 |
| ATOM | 4208 | N | LYS | 4673 | 114.185 | 90.137 | 102.125 | 1.00 80.82 |
| ATOM | 4209 | CA | LYS | 4673 | 113.322 | 89.132 | 101.583 | 1.00 75.65 |
| ATOM | 4210 | CB | LYS | 4673 | 114.021 | 88.153 | 100.712 | 1.00 68.11 |
| ATOM | 4211 | CG | LYS | 4673 | 113.025 | 87.069 | 100.374 | 1.00 57.65 |
| ATOM | 4212 | CD | LYS | 4673 | 113.517 | 86.149 | 99.360 | 1.00 50.56 |

```
ATOM   4213  CE   LYS  4673     113.015  84.837  99.713  1.00 48.57
ATOM   4214  NZ   LYS  4673     113.962  83.763  99.361  1.00 50.47
ATOM   4215  C    LYS  4673     112.609  88.328 102.610  1.00 77.07
ATOM   4216  O    LYS  4673     111.415  88.498 102.790  1.00 79.72
ATOM   4217  N    ASP  4674     113.318  87.441 103.287  1.00 76.86
ATOM   4218  CA   ASP  4674     112.645  86.630 104.282  1.00 78.77
ATOM   4219  CB   ASP  4674     113.603  85.610 104.896  1.00 78.85
ATOM   4220  CG   ASP  4674     114.016  84.519 103.888  1.00 80.32
ATOM   4221  OD1  ASP  4674     113.089  83.978 103.261  1.00 78.06
ATOM   4222  OD2  ASP  4674     115.229  84.192 103.716  1.00 80.17
ATOM   4223  C    ASP  4674     111.911  87.421 105.364  1.00 80.67
ATOM   4224  O    ASP  4674     110.720  87.171 105.556  1.00 81.85
ATOM   4225  N    HIS  4675     112.587  88.369 106.037  1.00 81.96
ATOM   4226  CA   HIS  4675     112.000  89.219 107.104  1.00 81.72
ATOM   4227  CB   HIS  4675     113.040  90.284 107.541  1.00 86.60
ATOM   4228  CG   HIS  4675     112.587  91.220 108.631  1.00 91.81
ATOM   4229  CD2  HIS  4675     112.929  91.294 109.942  1.00 93.66
ATOM   4230  ND1  HIS  4675     111.694  92.259 108.421  1.00 94.62
ATOM   4231  CE1  HIS  4675     111.507  92.924 109.546  1.00 95.03
ATOM   4232  NE2  HIS  4675     112.246  92.357 110.488  1.00 96.14
ATOM   4233  C    HIS  4675     110.735  89.850 106.509  1.00 80.22
ATOM   4234  O    HIS  4675     109.719  90.081 107.184  1.00 81.48
ATOM   4235  N    ALA  4676     110.798  90.098 105.213  1.00 76.79
ATOM   4236  CA   ALA  4676     109.667  90.646 104.496  1.00 72.68
ATOM   4237  CB   ALA  4676     110.049  90.868 103.088  1.00 71.74
ATOM   4238  C    ALA  4676     108.520  89.661 104.544  1.00 70.56
ATOM   4239  O    ALA  4676     107.504  89.946 105.163  1.00 71.42
ATOM   4240  N    PHE  4677     108.728  88.500 103.895  1.00 66.81
ATOM   4241  CA   PHE  4677     107.745  87.435 103.767  1.00 60.76
ATOM   4242  CB   PHE  4677     107.771  86.865 102.391  1.00 55.41
ATOM   4243  CG   PHE  4677     107.720  87.863 101.334  1.00 54.15
ATOM   4244  CD1  PHE  4677     108.872  88.330 100.800  1.00 51.57
ATOM   4245  CD2  PHE  4677     106.503  88.236 100.752  1.00 55.50
ATOM   4246  CE1  PHE  4677     108.819  89.139  99.717  1.00 52.25
ATOM   4247  CE2  PHE  4677     106.455  89.086  99.635  1.00 54.80
ATOM   4248  CZ   PHE  4677     107.608  89.575  99.119  1.00 49.63
ATOM   4249  C    PHE  4677     107.848  86.260 104.702  1.00 60.49
ATOM   4250  O    PHE  4677     107.444  85.131 104.346  1.00 60.80
ATOM   4251  N    GLY  4678     108.346  86.503 105.904  1.00 58.16
ATOM   4252  CA   GLY  4678     108.454  85.412 106.841  1.00 54.18
ATOM   4253  C    GLY  4678     107.124  84.786 107.242  1.00 52.79
ATOM   4254  O    GLY  4678     107.047  83.546 107.358  1.00 52.32
ATOM   4255  N    LYS  4679     106.076  85.598 107.442  1.00 50.97
ATOM   4256  CA   LYS  4679     104.787  85.048 107.881  1.00 49.34
ATOM   4257  CB   LYS  4679     103.738  86.133 108.118  1.00 50.77
ATOM   4258  CG   LYS  4679     104.109  87.313 108.960  1.00 55.06
ATOM   4259  CD   LYS  4679     102.941  88.302 109.109  1.00 56.48
ATOM   4260  CE   LYS  4679     103.340  89.435 110.100  1.00 60.36
ATOM   4261  NZ   LYS  4679     102.332  90.543 110.324  1.00 60.15
ATOM   4262  C    LYS  4679     104.138  84.094 106.908  1.00 49.25
ATOM   4263  O    LYS  4679     103.688  83.037 107.273  1.00 51.13
ATOM   4264  N    TYR  4680     104.120  84.483 105.656  1.00 48.20
ATOM   4265  CA   TYR  4680     103.422  83.826 104.587  1.00 49.66
ATOM   4266  CB   TYR  4680     103.334  84.820 103.451  1.00 51.02
ATOM   4267  CG   TYR  4680     103.083  86.235 103.946  1.00 46.78
ATOM   4268  CD1  TYR  4680     103.958  87.259 103.618  1.00 47.06
ATOM   4269  CE1  TYR  4680     103.757  88.552 104.067  1.00 49.14
ATOM   4270  CD2  TYR  4680     101.980  86.540 104.748  1.00 43.28
ATOM   4271  CE2  TYR  4680     101.764  87.834 105.205  1.00 45.50
ATOM   4272  CZ   TYR  4680     102.665  88.842 104.858  1.00 49.60
ATOM   4273  OH   TYR  4680     102.527  90.144 105.305  1.00 52.21
ATOM   4274  C    TYR  4680     103.859  82.443 104.074  1.00 52.56
ATOM   4275  O    TYR  4680     103.074  81.767 103.412  1.00 52.67
ATOM   4276  N    TYR  4681     105.081  82.018 104.376  1.00 56.34
ATOM   4277  CA   TYR  4681     105.564  80.716 103.895  1.00 59.62
ATOM   4278  CB   TYR  4681     107.026  80.544 104.258  1.00 61.22
ATOM   4279  CG   TYR  4681     107.940  81.531 103.592  1.00 62.83
ATOM   4280  CD1  TYR  4681     107.921  81.700 102.203  1.00 62.81
ATOM   4281  CE1  TYR  4681     108.832  82.527 101.573  1.00 60.26
ATOM   4282  CD2  TYR  4681     108.891  82.227 104.333  1.00 61.93
```

| ATOM | 4283 | CE2 | TYR | 4681 | 109.811 | 83.056 | 103.712 | 1.00 | 61.21 |
| ATOM | 4284 | CZ | TYR | 4681 | 109.782 | 83.198 | 102.330 | 1.00 | 61.53 |
| ATOM | 4285 | OH | TYR | 4681 | 110.732 | 83.977 | 101.711 | 1.00 | 59.66 |
| ATOM | 4286 | C | TYR | 4681 | 104.798 | 79.495 | 104.397 | 1.00 | 61.60 |
| ATOM | 4287 | O | TYR | 4681 | 104.198 | 79.529 | 105.468 | 1.00 | 62.26 |
| ATOM | 4288 | N | SER | 4682 | 104.846 | 78.402 | 103.637 | 1.00 | 63.83 |
| ATOM | 4289 | CA | SER | 4682 | 104.135 | 77.187 | 104.026 | 1.00 | 65.85 |
| ATOM | 4290 | CB | SER | 4682 | 103.657 | 76.452 | 102.789 | 1.00 | 63.25 |
| ATOM | 4291 | C | SER | 4682 | 104.984 | 76.263 | 104.895 | 1.00 | 68.62 |
| ATOM | 4292 | O | SER | 4682 | 104.900 | 75.041 | 104.790 | 1.00 | 68.66 |
| ATOM | 4293 | N | ARG | 4683 | 105.798 | 76.852 | 105.765 | 1.00 | 72.69 |
| ATOM | 4294 | CA | ARG | 4683 | 106.658 | 76.070 | 106.655 | 1.00 | 75.42 |
| ATOM | 4295 | CB | ARG | 4683 | 108.038 | 76.745 | 106.785 | 1.00 | 72.75 |
| ATOM | 4296 | C | ARG | 4683 | 106.007 | 75.914 | 108.036 | 1.00 | 76.66 |
| ATOM | 4297 | O | ARG | 4683 | 106.078 | 74.799 | 108.602 | 1.00 | 76.33 |
| ATOM | 4298 | N | GLY | 4700 | 107.405 | 55.926 | 103.939 | 1.00 | 60.39 |
| ATOM | 4299 | CA | GLY | 4700 | 107.939 | 57.318 | 104.098 | 1.00 | 60.37 |
| ATOM | 4300 | C | GLY | 4700 | 108.309 | 57.814 | 102.715 | 1.00 | 57.86 |
| ATOM | 4301 | O | GLY | 4700 | 109.114 | 57.198 | 102.018 | 1.00 | 59.95 |
| ATOM | 4302 | N | PTR | 4701 | 107.725 | 58.925 | 102.302 | 1.00 | 54.50 |
| ATOM | 4303 | CA | PTR | 4701 | 108.020 | 59.419 | 100.962 | 1.00 | 53.47 |
| ATOM | 4304 | C | PTR | 4701 | 109.127 | 60.457 | 100.952 | 1.00 | 52.73 |
| ATOM | 4305 | O | PTR | 4701 | 109.710 | 60.753 | 101.983 | 1.00 | 57.14 |
| ATOM | 4306 | CB | PTR | 4701 | 106.723 | 59.980 | 100.308 | 1.00 | 47.42 |
| ATOM | 4307 | CG | PTR | 4701 | 105.798 | 58.851 | 99.842 | 1.00 | 36.85 |
| ATOM | 4308 | CD1 | PTR | 4701 | 104.781 | 58.340 | 100.687 | 1.00 | 35.05 |
| ATOM | 4309 | CD2 | PTR | 4701 | 105.961 | 58.301 | 98.557 | 1.00 | 30.90 |
| ATOM | 4310 | CE1 | PTR | 4701 | 103.958 | 57.291 | 100.221 | 1.00 | 26.61 |
| ATOM | 4311 | CE2 | PTR | 4701 | 105.155 | 57.260 | 98.073 | 1.00 | 30.11 |
| ATOM | 4312 | CZ | PTR | 4701 | 104.165 | 56.775 | 98.927 | 1.00 | 29.27 |
| ATOM | 4313 | OH | PTR | 4701 | 103.378 | 55.712 | 98.387 | 1.00 | 28.67 |
| ATOM | 4314 | P | PTR | 4701 | 102.080 | 55.070 | 99.106 | 1.00 | 27.47 |
| ATOM | 4315 | O1P | PTR | 4701 | 101.051 | 56.106 | 99.149 | 1.00 | 30.05 |
| ATOM | 4316 | O2P | PTR | 4701 | 102.420 | 54.657 | 100.482 | 1.00 | 29.05 |
| ATOM | 4317 | O3P | PTR | 4701 | 101.549 | 53.908 | 98.291 | 1.00 | 20.42 |
| ATOM | 4318 | N | ILE | 4702 | 109.411 | 60.986 | 99.772 | 1.00 | 51.35 |
| ATOM | 4319 | CA | ILE | 4702 | 110.431 | 62.009 | 99.566 | 1.00 | 54.14 |
| ATOM | 4320 | CB | ILE | 4702 | 111.199 | 61.695 | 98.285 | 1.00 | 54.51 |
| ATOM | 4321 | CG2 | ILE | 4702 | 112.157 | 62.829 | 97.926 | 1.00 | 51.61 |
| ATOM | 4322 | CG1 | ILE | 4702 | 111.896 | 60.352 | 98.448 | 1.00 | 55.27 |
| ATOM | 4323 | CD1 | ILE | 4702 | 112.526 | 59.861 | 97.171 | 1.00 | 57.01 |
| ATOM | 4324 | C | ILE | 4702 | 109.743 | 62.369 | 99.377 | 1.00 | 57.93 |
| ATOM | 4325 | O | ILE | 4702 | 109.584 | 63.810 | 98.236 | 1.00 | 60.54 |
| ATOM | 4326 | N | LYS | 4703 | 109.354 | 64.042 | 100.466 | 1.00 | 58.61 |
| ATOM | 4327 | CA | LYS | 4703 | 108.646 | 65.319 | 100.345 | 1.00 | 58.43 |
| ATOM | 4328 | CB | LYS | 4703 | 108.541 | 66.000 | 101.712 | 1.00 | 60.54 |
| ATOM | 4329 | CG | LYS | 4703 | 107.606 | 65.212 | 102.664 | 1.00 | 69.04 |
| ATOM | 4330 | CD | LYS | 4703 | 107.184 | 66.028 | 103.909 | 1.00 | 75.32 |
| ATOM | 4331 | CE | LYS | 4703 | 106.154 | 65.260 | 104.771 | 1.00 | 77.04 |
| ATOM | 4332 | NZ | LYS | 4703 | 105.609 | 66.054 | 105.926 | 1.00 | 75.01 |
| ATOM | 4333 | C | LYS | 4703 | 109.180 | 66.275 | 99.275 | 1.00 | 58.12 |
| ATOM | 4334 | O | LYS | 4703 | 110.394 | 66.381 | 99.077 | 1.00 | 60.28 |
| ATOM | 4335 | N | THR | 4704 | 108.256 | 66.931 | 98.561 | 1.00 | 56.04 |
| ATOM | 4336 | CA | THR | 4704 | 108.584 | 67.867 | 97.478 | 1.00 | 54.20 |
| ATOM | 4337 | CB | THR | 4704 | 108.246 | 67.276 | 96.082 | 1.00 | 53.94 |
| ATOM | 4338 | OG1 | THR | 4704 | 106.849 | 66.959 | 96.004 | 1.00 | 53.52 |
| ATOM | 4339 | CG2 | THR | 4704 | 109.065 | 66.030 | 95.832 | 1.00 | 50.25 |
| ATOM | 4340 | C | THR | 4704 | 107.880 | 69.215 | 97.595 | 1.00 | 52.62 |
| ATOM | 4341 | O | THR | 4704 | 107.191 | 69.476 | 98.582 | 1.00 | 52.66 |
| ATOM | 4342 | N | GLU | 4705 | 108.065 | 70.061 | 96.579 | 1.00 | 50.20 |
| ATOM | 4343 | CA | GLU | 4705 | 107.470 | 71.399 | 96.539 | 1.00 | 51.43 |
| ATOM | 4344 | CB | GLU | 4705 | 108.338 | 72.413 | 97.282 | 1.00 | 54.92 |
| ATOM | 4345 | CG | GLU | 4705 | 108.657 | 72.130 | 98.728 | 1.00 | 63.72 |
| ATOM | 4346 | CD | GLU | 4705 | 109.599 | 73.184 | 99.301 | 1.00 | 68.53 |
| ATOM | 4347 | OE1 | GLU | 4705 | 110.669 | 72.399 | 98.681 | 1.00 | 67.20 |
| ATOM | 4348 | OE2 | GLU | 4705 | 109.276 | 72.790 | 100.356 | 1.00 | 68.67 |
| ATOM | 4349 | C | GLU | 4705 | 107.393 | 71.887 | 95.099 | 1.00 | 50.20 |
| ATOM | 4350 | O | GLU | 4705 | 108.237 | 71.542 | 94.289 | 1.00 | 52.76 |
| ATOM | 4351 | N | LEU | 4706 | 106.392 | 72.689 | 94.767 | 1.00 | 48.92 |
| ATOM | 4352 | CA | LEU | 4706 | 106.337 | 73.216 | 93.414 | 1.00 | 48.60 |

| | | | | | | | | |
|---|---|---|---|---|---|---|---|---|
| ATOM | 4353 | CB | LEU | 4706 | 104.909 | 73.485 | 92.949 | 1.00 50.44 |
| ATOM | 4354 | CG | LEU | 4706 | 103.962 | 72.342 | 92.603 | 1.00 51.88 |
| ATOM | 4355 | CD1 | LEU | 4706 | 102.603 | 72.920 | 92.215 | 1.00 55.57 |
| ATOM | 4356 | CD2 | LEU | 4706 | 104.520 | 71.546 | 91.455 | 1.00 51.66 |
| ATOM | 4357 | C | LEU | 4706 | 107.087 | 74.527 | 93.479 | 1.00 50.37 |
| ATOM | 4358 | O | LEU | 4706 | 107.131 | 75.190 | 94.533 | 1.00 50.03 |
| ATOM | 4359 | N | ILE | 4707 | 107.660 | 74.913 | 92.351 | 1.00 48.25 |
| ATOM | 4360 | CA | ILE | 4707 | 108.439 | 76.127 | 92.299 | 1.00 49.68 |
| ATOM | 4361 | CB | ILE | 4707 | 109.876 | 75.817 | 92.718 | 1.00 53.06 |
| ATOM | 4362 | CG2 | ILE | 4707 | 110.786 | 76.956 | 92.330 | 1.00 55.15 |
| ATOM | 4363 | CG1 | ILE | 4707 | 109.903 | 75.472 | 94.215 | 1.00 53.95 |
| ATOM | 4364 | CD1 | ILE | 4707 | 111.228 | 75.002 | 94.729 | 1.00 52.75 |
| ATOM | 4365 | C | ILE | 4707 | 108.440 | 76.725 | 90.909 | 1.00 49.68 |
| ATOM | 4366 | O | ILE | 4707 | 108.416 | 76.010 | 89.913 | 1.00 47.24 |
| ATOM | 4367 | N | SER | 4708 | 108.455 | 78.042 | 90.829 | 1.00 51.52 |
| ATOM | 4368 | CA | SER | 4708 | 108.468 | 78.644 | 89.520 | 1.00 56.03 |
| ATOM | 4369 | CB | SER | 4708 | 107.835 | 80.039 | 89.546 | 1.00 58.20 |
| ATOM | 4370 | OG | SER | 4708 | 107.605 | 80.515 | 88.225 | 1.00 59.05 |
| ATOM | 4371 | C | SER | 4708 | 109.942 | 78.722 | 89.163 | 1.00 59.31 |
| ATOM | 4372 | O | SER | 4708 | 110.787 | 78.907 | 90.042 | 1.00 58.96 |
| ATOM | 4373 | N | VAL | 4709 | 110.246 | 78.568 | 87.879 | 1.00 61.49 |
| ATOM | 4374 | CA | VAL | 4709 | 111.620 | 78.600 | 87.407 | 1.00 63.10 |
| ATOM | 4375 | CB | VAL | 4709 | 112.194 | 77.173 | 87.337 | 1.00 60.94 |
| ATOM | 4376 | CG1 | VAL | 4709 | 113.505 | 77.169 | 86.566 | 1.00 61.77 |
| ATOM | 4377 | CG2 | VAL | 4709 | 112.408 | 76.635 | 88.747 | 1.00 53.62 |
| ATOM | 4378 | C | VAL | 4709 | 111.694 | 79.249 | 86.038 | 1.00 66.28 |
| ATOM | 4379 | O | VAL | 4709 | 110.728 | 79.198 | 85.284 | 1.00 64.78 |
| ATOM | 4380 | N | SER | 4710 | 112.845 | 79.854 | 85.735 | 1.00 71.27 |
| ATOM | 4381 | CA | SER | 4710 | 113.083 | 80.540 | 84.461 | 1.00 76.97 |
| ATOM | 4382 | CB | SER | 4710 | 114.571 | 80.840 | 84.287 | 1.00 77.45 |
| ATOM | 4383 | OG | SER | 4710 | 115.290 | 79.645 | 84.037 | 1.00 78.82 |
| ATOM | 4384 | C | SER | 4710 | 112.621 | 79.710 | 83.265 | 1.00 79.32 |
| ATOM | 4385 | O | SER | 4710 | 113.188 | 79.935 | 82.171 | 1.00 81.77 |
| ATOM | 4463 | O5' | ADE | 1001 | 79.935 | 84.916 | 58.730 | 0.50 61.68 |
| ATOM | 4464 | N9 | ADE | 1001 | 75.989 | 83.053 | 62.156 | 0.50 55.18 |
| ATOM | 4465 | C4 | ADE | 1001 | 74.817 | 83.634 | 62.597 | 0.50 51.40 |
| ATOM | 4466 | N3 | ADE | 1001 | 74.656 | 84.877 | 63.094 | 0.50 48.96 |
| ATOM | 4467 | C2 | ADE | 1001 | 73.381 | 85.086 | 63.438 | 0.50 48.30 |
| ATOM | 4468 | N1 | ADE | 1001 | 72.330 | 84.254 | 63.358 | 0.50 48.13 |
| ATOM | 4469 | C6 | ADE | 1001 | 72.525 | 83.007 | 62.868 | 0.50 48.40 |
| ATOM | 4470 | N6 | ADE | 1001 | 71.487 | 82.170 | 62.829 | 0.50 45.05 |
| ATOM | 4471 | C5 | ADE | 1001 | 73.830 | 82.665 | 62.441 | 0.50 49.82 |
| ATOM | 4472 | N7 | ADE | 1001 | 74.358 | 81.506 | 61.879 | 0.50 51.64 |
| ATOM | 4473 | C8 | ADE | 1001 | 75.635 | 81.784 | 61.725 | 0.50 53.55 |
| ATOM | 4474 | C2' | ADE | 1001 | 78.504 | 82.820 | 61.765 | 0.50 61.56 |
| ATOM | 4475 | C5' | ADE | 1001 | 78.614 | 84.988 | 59.270 | 0.50 63.05 |
| ATOM | 4476 | C4' | ADE | 1001 | 78.666 | 84.989 | 60.781 | 0.50 63.42 |
| ATOM | 4477 | O4' | ADE | 1001 | 77.329 | 84.801 | 61.322 | 0.50 62.47 |
| ATOM | 4478 | C1' | ADE | 1001 | 77.321 | 83.681 | 62.197 | 0.50 59.07 |
| ATOM | 4479 | C3' | ADE | 1001 | 79.531 | 83.873 | 61.375 | 0.50 64.05 |
| ATOM | 4480 | O3' | ADE | 1001 | 80.228 | 84.362 | 62.540 | 0.50 68.12 |
| ATOM | 4481 | P | CYT | 1002 | 81.727 | 83.852 | 62.876 | 0.50 70.49 |
| ATOM | 4482 | O1P | CYT | 1002 | 82.628 | 84.973 | 62.474 | 0.50 70.74 |
| ATOM | 4483 | O2P | CYT | 1002 | 81.949 | 82.485 | 62.315 | 0.50 69.44 |
| ATOM | 4484 | O5' | CYT | 1002 | 81.753 | 83.742 | 64.475 | 0.50 69.42 |
| ATOM | 4485 | N1 | CYT | 1002 | 76.639 | 82.298 | 66.592 | 0.50 61.72 |
| ATOM | 4486 | C6 | CYT | 1002 | 77.220 | 81.062 | 66.698 | 0.50 61.58 |
| ATOM | 4487 | C2 | CYT | 1002 | 75.224 | 82.472 | 66.610 | 0.50 61.68 |
| ATOM | 4488 | O2 | CYT | 1002 | 74.708 | 83.556 | 66.591 | 0.50 61.23 |
| ATOM | 4489 | N3 | CYT | 1002 | 74.463 | 81.296 | 66.662 | 0.50 60.73 |
| ATOM | 4490 | C4 | CYT | 1002 | 75.051 | 80.094 | 66.728 | 0.50 59.76 |
| ATOM | 4491 | N4 | CYT | 1002 | 74.271 | 79.015 | 66.756 | 0.50 56.99 |
| ATOM | 4492 | C5 | CYT | 1002 | 76.473 | 79.947 | 66.765 | 0.50 60.45 |
| ATOM | 4493 | C2' | CYT | 1002 | 78.432 | 83.899 | 67.527 | 0.50 62.21 |
| ATOM | 4494 | C5' | CYT | 1002 | 80.720 | 83.042 | 65.185 | 0.50 66.50 |
| ATOM | 4495 | C4' | CYT | 1002 | 79.550 | 83.970 | 65.433 | 0.50 65.71 |
| ATOM | 4496 | O4' | CYT | 1002 | 78.288 | 83.273 | 65.285 | 0.50 63.74 |
| ATOM | 4497 | C1' | CYT | 1002 | 77.469 | 83.506 | 66.411 | 0.50 61.45 |
| ATOM | 4498 | C3' | CYT | 1002 | 79.495 | 84.697 | 66.778 | 0.50 64.32 |
| ATOM | 4499 | O3' | CYT | 1002 | 79.077 | 86.070 | 66.565 | 0.50 64.08 |

180

```
ATOM   4500  P    ADE  1003     80.152  87.289  66.682  0.50 64.71
ATOM   4501  O1P  ADE  1003     79.749  88.315  65.677  0.50 62.06
ATOM   4502  O2P  ADE  1003     81.563  86.792  66.696  0.50 61.83
ATOM   4503  O5'  ADE  1003     79.877  87.909  68.123  0.50 61.25
ATOM   4504  N9   ADE  1003     77.620  85.479  70.634  0.50 38.90
ATOM   4505  C4   ADE  1003     76.389  84.926  70.364  0.50 37.10
ATOM   4506  N3   ADE  1003     75.207  85.562  70.294  0.50 32.97
ATOM   4507  C2   ADE  1003     74.228  84.709  69.993  0.50 32.67
ATOM   4508  N1   ADE  1003     74.289  83.392  69.764  0.50 34.17
ATOM   4509  C6   ADE  1003     75.492  82.778  69.844  0.50 37.27
ATOM   4510  N6   ADE  1003     75.557  81.464  69.611  0.50 36.69
ATOM   4511  C5   ADE  1003     76.615  83.572  70.167  0.50 37.90
ATOM   4512  N7   ADE  1003     77.962  83.268  70.331  0.50 38.69
ATOM   4513  C8   ADE  1003     78.514  84.429  70.607  0.50 40.06
ATOM   4514  C2'  ADE  1003     79.305  87.320  71.193  0.50 44.23
ATOM   4515  C5'  ADE  1003     78.942  88.969  68.306  0.50 53.39
ATOM   4516  C4'  ADE  1003     78.297  88.858  69.667  0.50 48.24
ATOM   4517  O4'  ADE  1003     77.505  87.640  69.724  0.50 45.62
ATOM   4518  C1'  ADE  1003     77.871  86.902  70.887  0.50 43.00
ATOM   4519  C3'  ADE  1003     79.249  88.808  70.874  0.50 45.38
ATOM   4520  O3'  ADE  1003     78.637  89.578  71.936  0.50 41.52
ATOM   4521  P    GUA  1004     79.243  89.576  73.439  0.50 35.99
ATOM   4522  O1P  GUA  1004     80.182  90.726  73.604  0.50 36.53
ATOM   4523  O2P  GUA  1004     79.669  88.214  73.842  0.50 32.52
ATOM   4524  O5'  GUA  1004     77.966  89.925  74.313  0.50 32.15
ATOM   4525  N9   GUA  1004     75.943  86.663  74.475  0.50 15.63
ATOM   4526  C4   GUA  1004     75.380  85.448  74.141  0.50 16.69
ATOM   4527  N3   GUA  1004     74.061  85.169  74.086  0.50 18.19
ATOM   4528  C2   GUA  1004     73.840  83.926  73.714  0.50 15.37
ATOM   4529  N2   GUA  1004     72.588  83.464  73.633  0.50 16.41
ATOM   4530  N1   GUA  1004     74.829  83.040  73.400  0.50 14.85
ATOM   4531  C6   GUA  1004     76.190  83.311  73.435  0.50 12.29
ATOM   4532  O6   GUA  1004     76.997  82.448  73.103  0.50  9.35
ATOM   4533  C5   GUA  1004     76.444  84.618  73.855  0.50 13.65
ATOM   4534  N7   GUA  1004     77.646  85.274  74.038  0.50 15.41
ATOM   4535  C8   GUA  1004     77.303  86.479  74.412  0.50 15.85
ATOM   4536  C2'  GUA  1004     75.677  88.647  76.029  0.50 18.36
ATOM   4537  C5'  GUA  1004     76.928  90.728  73.780  0.50 24.91
ATOM   4538  C4'  GUA  1004     75.590  90.166  74.183  0.50 19.98
ATOM   4539  O4'  GUA  1004     75.475  88.807  73.699  0.50 21.46
ATOM   4540  C1'  GUA  1004     75.235  87.906  74.778  0.50 17.94
ATOM   4541  C3'  GUA  1004     75.351  90.093  75.687  0.50 16.00
ATOM   4542  O3'  GUA  1004     73.970  90.399  75.905  0.50 14.89
ATOM   4543  P    THY  1005     73.404  90.540  77.391  0.50 12.76
ATOM   4544  O1P  THY  1005     72.543  91.741  77.463  0.50 11.57
ATOM   4545  O2P  THY  1005     74.553  90.350  78.309  0.50 14.25
ATOM   4546  O5'  THY  1005     72.467  89.287  77.548  0.50  7.20
ATOM   4547  N1   THY  1005     74.051  84.298  77.561  0.50 15.10
ATOM   4548  C6   THY  1005     75.205  85.027  77.706  0.50 12.99
ATOM   4549  C2   THY  1005     74.073  83.020  77.030  0.50 15.89
ATOM   4550  O2   THY  1005     73.073  82.338  76.876  0.50 19.64
ATOM   4551  N3   THY  1005     75.320  82.563  76.687  0.50 16.25
ATOM   4552  C4   THY  1005     76.526  83.233  76.818  0.50 18.36
ATOM   4553  O4   THY  1005     77.588  82.687  76.455  0.50 14.57
ATOM   4554  C5   THY  1005     76.419  84.570  77.386  0.50 15.88
ATOM   4555  C5A  THY  1005     77.661  85.372  77.605  0.50 12.34
ATOM   4556  C2'  THY  1005     72.792  85.688  79.278  0.50 14.33
ATOM   4557  C5'  THY  1005     72.873  88.052  77.045  0.50  8.04
ATOM   4558  C4'  THY  1005     71.900  87.006  77.494  0.50 11.57
ATOM   4559  O4'  THY  1005     72.327  85.736  76.970  0.50 13.06
ATOM   4560  C1'  THY  1005     72.752  84.872  77.989  0.50 15.13
ATOM   4561  C3'  THY  1005     71.883  86.875  79.006  0.50 14.65
ATOM   4562  O3'  THY  1005     70.536  86.755  79.459  0.50 13.64
ATOM   4563  P    THY  1006     70.233  86.174  80.916  0.50 15.83
ATOM   4564  O1P  THY  1006     68.898  86.689  81.320  0.50 16.51
ATOM   4565  O2P  THY  1006     71.399  86.408  81.787  0.50 14.25
ATOM   4566  O5'  THY  1006     70.103  84.608  80.642  0.50 17.47
ATOM   4567  N1   THY  1006     72.285  81.371  80.110  0.50 15.39
ATOM   4568  C6   THY  1006     72.830  82.536  80.611  0.50 13.62
ATOM   4569  C2   THY  1006     73.093  80.406  79.522  0.50 17.37
```

181

| | | | | | | | | |
|---|---|---|---|---|---|---|---|---|
| ATOM | 4570 | O2 | THY | 1006 | 72.694 | 79.306 | 79.156 | 0.50 21.89 |
| ATOM | 4571 | N3 | THY | 1006 | 74.406 | 80.768 | 79.405 | 0.50 14.96 |
| ATOM | 4572 | C4 | THY | 1006 | 74.994 | 81.924 | 79.848 | 0.50 11.54 |
| ATOM | 4573 | O4 | THY | 1006 | 76.175 | 82.108 | 79.646 | 0.50 12.79 |
| ATOM | 4574 | C5 | THY | 1006 | 74.125 | 82.843 | 80.525 | 0.50 12.06 |
| ATOM | 4575 | C5A | THY | 1006 | 74.703 | 84.092 | 81.106 | 0.50 12.26 |
| ATOM | 4576 | C2' | THY | 1006 | 70.163 | 81.455 | 81.508 | 0.50 14.04 |
| ATOM | 4577 | C5' | THY | 1006 | 69.115 | 84.130 | 79.729 | 0.50 13.89 |
| ATOM | 4578 | C4' | THY | 1006 | 69.020 | 82.624 | 79.766 | 0.50 11.28 |
| ATOM | 4579 | O4' | THY | 1006 | 70.240 | 82.054 | 79.250 | 0.50 10.43 |
| ATOM | 4580 | C1' | THY | 1006 | 70.816 | 81.158 | 80.168 | 0.50 11.23 |
| ATOM | 4581 | C3' | THY | 1006 | 68.791 | 81.997 | 81.132 | 0.50 14.64 |
| ATOM | 4582 | O3' | THY | 1006 | 67.780 | 80.982 | 81.031 | 0.50 16.79 |
| ATOM | 4583 | P | THY | 1007 | 67.305 | 80.164 | 82.343 | 0.50 18.91 |
| ATOM | 4584 | O1P | THY | 1007 | 65.819 | 80.198 | 82.450 | 0.50 11.70 |
| ATOM | 4585 | O2P | THY | 1007 | 68.130 | 80.543 | 83.514 | 0.50 16.90 |
| ATOM | 4586 | O5' | THY | 1007 | 67.722 | 78.677 | 81.975 | 0.50 16.49 |
| ATOM | 4587 | N1 | THY | 1007 | 71.957 | 77.466 | 81.759 | 0.50 20.44 |
| ATOM | 4588 | C6 | THY | 1007 | 71.848 | 78.358 | 82.811 | 0.50 21.63 |
| ATOM | 4589 | C2 | THY | 1007 | 73.158 | 77.292 | 81.107 | 0.50 22.61 |
| ATOM | 4590 | O2 | THY | 1007 | 73.330 | 76.447 | 80.253 | 0.50 27.97 |
| ATOM | 4591 | N3 | THY | 1007 | 74.158 | 78.140 | 81.498 | 0.50 21.24 |
| ATOM | 4592 | C4 | THY | 1007 | 74.099 | 79.105 | 82.477 | 0.50 19.92 |
| ATOM | 4593 | O4 | THY | 1007 | 75.065 | 79.857 | 82.657 | 0.50 19.41 |
| ATOM | 4594 | C5 | THY | 1007 | 72.851 | 79.162 | 83.205 | 0.50 19.23 |
| ATOM | 4595 | C5A | THY | 1007 | 72.736 | 80.094 | 84.364 | 0.50 18.98 |
| ATOM | 4596 | C2' | THY | 1007 | 69.832 | 76.046 | 82.200 | 0.50 16.27 |
| ATOM | 4597 | C5' | THY | 1007 | 67.651 | 78.228 | 80.639 | 0.50 17.25 |
| ATOM | 4598 | C4' | THY | 1007 | 68.641 | 77.115 | 80.400 | 0.50 17.16 |
| ATOM | 4599 | O4' | THY | 1007 | 70.006 | 77.596 | 80.457 | 0.50 18.08 |
| ATOM | 4600 | C1' | THY | 1007 | 70.797 | 76.700 | 81.230 | 0.50 18.05 |
| ATOM | 4601 | C3' | THY | 1007 | 68.553 | 75.934 | 81.366 | 0.50 16.69 |
| ATOM | 4602 | O3' | THY | 1007 | 68.491 | 74.773 | 80.580 | 0.50 16.87 |
| ATOM | 4603 | P | CYT | 1008 | 67.707 | 73.449 | 81.130 | 0.50 16.50 |
| ATOM | 4604 | O1P | CYT | 1008 | 66.911 | 72.929 | 79.991 | 0.50 16.80 |
| ATOM | 4605 | O2P | CYT | 1008 | 67.029 | 73.810 | 82.411 | 0.50 15.56 |
| ATOM | 4606 | O5' | CYT | 1008 | 68.894 | 72.437 | 81.417 | 0.50 14.61 |
| ATOM | 4607 | N1 | CYT | 1008 | 73.443 | 73.587 | 83.717 | 0.50 24.44 |
| ATOM | 4608 | C6 | CYT | 1008 | 72.548 | 74.549 | 84.113 | 0.50 24.18 |
| ATOM | 4609 | C2 | CYT | 1008 | 74.823 | 73.838 | 83.789 | 0.50 23.10 |
| ATOM | 4610 | O2 | CYT | 1008 | 75.627 | 72.937 | 83.478 | 0.50 19.91 |
| ATOM | 4611 | N3 | CYT | 1008 | 75.244 | 75.053 | 84.207 | 0.50 21.71 |
| ATOM | 4612 | C4 | CYT | 1008 | 74.362 | 75.978 | 84.571 | 0.50 20.79 |
| ATOM | 4613 | N4 | CYT | 1008 | 74.831 | 77.147 | 84.957 | 0.50 24.43 |
| ATOM | 4614 | C5 | CYT | 1008 | 72.964 | 75.741 | 84.548 | 0.50 22.26 |
| ATOM | 4615 | C2' | CYT | 1008 | 71.835 | 71.640 | 83.977 | 0.50 27.10 |
| ATOM | 4616 | C5' | CYT | 1008 | 70.207 | 72.949 | 81.568 | 0.50 20.99 |
| ATOM | 4617 | C4' | CYT | 1008 | 71.217 | 71.839 | 81.682 | 0.50 23.20 |
| ATOM | 4618 | O4' | CYT | 1008 | 72.501 | 72.479 | 81.866 | 0.50 25.42 |
| ATOM | 4619 | C1' | CYT | 1008 | 72.978 | 72.278 | 83.196 | 0.50 26.45 |
| ATOM | 4620 | C3' | CYT | 1008 | 71.022 | 70.943 | 82.899 | 0.50 25.71 |
| ATOM | 4621 | O3' | CYT | 1008 | 71.514 | 69.636 | 82.586 | 0.50 26.75 |
| ATOM | 4622 | P | CYT | 1009 | 71.464 | 68.454 | 83.678 | 0.50 24.38 |
| ATOM | 4623 | O1P | CYT | 1009 | 71.002 | 67.260 | 82.932 | 0.50 27.69 |
| ATOM | 4624 | O2P | CYT | 1009 | 70.722 | 68.889 | 84.881 | 0.50 25.71 |
| ATOM | 4625 | O5' | CYT | 1009 | 72.996 | 68.246 | 84.053 | 0.50 21.41 |
| ATOM | 4626 | N1 | CYT | 1009 | 75.662 | 71.617 | 86.205 | 0.50 18.00 |
| ATOM | 4627 | C6 | CYT | 1009 | 74.311 | 71.681 | 86.393 | 0.50 14.45 |
| ATOM | 4628 | C2 | CYT | 1009 | 76.393 | 72.865 | 86.470 | 0.50 19.06 |
| ATOM | 4629 | O2 | CYT | 1009 | 77.595 | 72.908 | 86.178 | 0.50 23.13 |
| ATOM | 4630 | N3 | CYT | 1009 | 75.758 | 73.926 | 87.024 | 0.50 17.62 |
| ATOM | 4631 | C4 | CYT | 1009 | 74.444 | 73.864 | 87.257 | 0.50 15.43 |
| ATOM | 4632 | N4 | CYT | 1009 | 73.854 | 74.903 | 87.837 | 0.50 7.46 |
| ATOM | 4633 | C5 | CYT | 1009 | 73.676 | 72.727 | 86.912 | 0.50 14.78 |
| ATOM | 4634 | C2' | CYT | 1009 | 75.864 | 69.286 | 86.616 | 0.50 23.31 |
| ATOM | 4635 | C5' | CYT | 1009 | 73.861 | 69.365 | 84.076 | 0.50 22.81 |
| ATOM | 4636 | C4' | CYT | 1009 | 75.292 | 68.949 | 84.307 | 0.50 23.11 |
| ATOM | 4637 | O4' | CYT | 1009 | 76.028 | 70.189 | 84.427 | 0.50 24.09 |
| ATOM | 4638 | C1' | CYT | 1009 | 76.362 | 70.462 | 85.786 | 0.50 23.42 |
| ATOM | 4639 | C3' | CYT | 1009 | 75.492 | 68.210 | 85.623 | 0.50 22.98 |

```
ATOM   4640  O3'  CYT  1009     76.533  67.264  85.558  0.50 25.66
ATOM   4641  P    CYT  1010     76.680  66.181  86.734  0.50 30.31
ATOM   4642  O1P  CYT  1010     76.490  64.852  86.085  0.50 31.13
ATOM   4643  O2P  CYT  1010     75.822  66.553  87.895  0.50 26.79
ATOM   4644  O5'  CYT  1010     78.201  66.340  87.188  0.50 26.63
ATOM   4645  N1   CYT  1010     78.508  69.997  89.269  0.50 31.20
ATOM   4646  C6   CYT  1010     77.296  69.382  89.394  0.50 32.20
ATOM   4647  C2   CYT  1010     78.673  71.308  89.702  0.50 31.96
ATOM   4648  O2   CYT  1010     79.790  71.847  89.603  0.50 34.07
ATOM   4649  N3   CYT  1010     77.620  71.963  90.227  0.50 32.29
ATOM   4650  C4   CYT  1010     76.445  71.357  90.339  0.50 30.65
ATOM   4651  N4   CYT  1010     75.436  72.052  90.860  0.50 34.80
ATOM   4652  C5   CYT  1010     76.249  70.018  89.922  0.50 31.24
ATOM   4653  C2'  CYT  1010     79.970  67.942  89.311  0.50 32.62
ATOM   4654  C5'  CYT  1010     79.185  66.791  86.271  0.50 27.02
ATOM   4655  C4'  CYT  1010     80.101  67.790  86.934  0.50 28.64
ATOM   4656  O4'  CYT  1010     79.389  69.000  87.313  0.50 30.28
ATOM   4657  C1'  CYT  1010     79.664  69.288  88.685  0.50 32.90
ATOM   4658  C3'  CYT  1010     80.767  67.282  88.208  0.50 30.12
ATOM   4659  O3'  CYT  1010     82.069  67.821  88.280  0.50 30.60
ATOM   4660  P    GUA  1011     83.295  65.281  90.529  0.50 36.04
ATOM   4661  O1P  GUA  1011     84.467  65.125  89.629  0.50 35.50
ATOM   4662  O2P  GUA  1011     83.219  64.509  91.806  0.50 38.03
ATOM   4663  O5'  GUA  1011     83.109  66.825  90.854  0.50 35.34
ATOM   4664  N9   GUA  1011     80.697  68.908  93.085  0.50 32.52
ATOM   4665  C4   GUA  1011     79.787  69.937  93.137  0.50 31.58
ATOM   4666  N3   GUA  1011     80.080  71.242  93.294  0.50 32.59
ATOM   4667  C2   GUA  1011     78.990  71.996  93.333  0.50 33.31
ATOM   4668  N2   GUA  1011     79.102  73.323  93.476  0.50 31.84
ATOM   4669  N1   GUA  1011     77.709  71.508  93.233  0.50 32.91
ATOM   4670  C6   GUA  1011     77.375  70.169  93.082  0.50 34.69
ATOM   4671  O6   GUA  1011     76.172  69.835  93.024  0.50 36.23
ATOM   4672  C5   GUA  1011     78.545  69.341  93.026  0.50 33.43
ATOM   4673  N7   GUA  1011     78.669  67.961  92.889  0.50 34.01
ATOM   4674  C8   GUA  1011     79.961  67.752  92.910  0.50 33.57
ATOM   4675  C2'  GUA  1011     82.876  67.850  93.844  0.50 33.14
ATOM   4676  C5'  GUA  1011     84.201  67.738  90.808  0.50 34.06
ATOM   4677  C4'  GUA  1011     84.097  68.701  91.964  0.50 34.04
ATOM   4678  O4'  GUA  1011     82.735  69.215  91.962  0.50 35.13
ATOM   4679  C1'  GUA  1011     82.150  69.036  93.238  0.50 32.64
ATOM   4680  C3'  GUA  1011     84.296  68.045  93.333  0.50 33.92
ATOM   4681  O3'  GUA  1011     85.039  68.911  94.202  0.50 31.90
ATOM   4682  P    THY  1012     85.639  68.346  95.598  0.50 30.25
ATOM   4683  O1P  THY  1012     87.067  68.0~2  95.385  0.50 33.34
ATOM   4684  O2P  THY  1012     84.751  67.328  96.214  0.50 33.97
ATOM   4685  O5'  THY  1012     85.591  69.635  96.519  0.50 29.69
ATOM   4686  N1   THY  1012     81.489  70.904  96.895  0.50 27.63
ATOM   4687  C6   THY  1012     81.651  69.537  96.709  0.50 27.53
ATOM   4688  C2   THY  1012     80.236  71.498  96.750  0.50 24.24
ATOM   4689  O2   THY  1012     80.016  72.682  96.925  0.50 23.00
ATOM   4690  N3   THY  1012     79.240  70.637  96.388  0.50 22.58
ATOM   4691  C4   THY  1012     79.340  69.283  96.154  0.50 24.31
ATOM   4692  O4   THY  1012     78.355  68.668  95.776  0.50 20.37
ATOM   4693  C5   THY  1012     80.656  68.798  96.360  0.50 25.11
ATOM   4694  C5A  THY  1012     80.852  67.233  96.180  0.50 23.80
ATOM   4695  C2'  THY  1012     83.514  71.278  98.410  0.50 28.58
ATOM   4696  C5'  THY  1012     85.823  70.918  95.954  0.50 30.76
ATOM   4697  C4'  THY  1012     84.906  71.941  96.576  0.50 28.26
ATOM   4698  O4'  THY  1012     83.540  71.782  96.126  0.50 27.44
ATOM   4699  C1'  THY  1012     82.664  71.757  97.245  0.50 28.27
ATOM   4700  C3'  THY  1012     84.872  71.888  98.098  0.50 31.16
ATOM   4701  O3'  THY  1012     84.964  73.219  98.593  0.50 35.42
ATOM   4702  P    ADE  1013     86.113  73.602  99.639  0.50 34.91
ATOM   4703  O1P  ADE  1013     87.118  74.430  98.928  0.50 36.04
ATOM   4704  O2P  ADE  1013     86.542  72.380 100.354  0.50 36.43
ATOM   4705  O5'  ADE  1013     85.320  74.514 100.663  0.50 39.14
ATOM   4706  N9   ADE  1013     80.880  73.270 101.069  0.50 47.53
ATOM   4707  C4   ADE  1013     79.516  73.1~3 100.891  0.50 47.33
ATOM   4708  N3   ADE  1013     78.570  74.086 101.124  0.50 46.51
ATOM   4709  C2   ADE  1013     77.357  73.614 100.812  0.50 45.36
```

183

| | | | | | | | |
|---|---|---|---|---|---|---|---|
| ATOM | 4710 | N1 | ADE | 1013 | 77.014 | 72.412 | 100.324 | 0.50 41.97 |
| ATOM | 4711 | C6 | ADE | 1013 | 77.991 | 71.510 | 100.088 | 0.50 42.61 |
| ATOM | 4712 | N6 | ADE | 1013 | 77.663 | 70.328 | 99.570 | 0.50 40.21 |
| ATOM | 4713 | C5 | ADE | 1013 | 79.310 | 71.875 | 100.393 | 0.50 45.02 |
| ATOM | 4714 | N7 | ADE | 1013 | 80.513 | 71.192 | 100.280 | 0.50 46.74 |
| ATOM | 4715 | C8 | ADE | 1013 | 81.409 | 72.057 | 100.695 | 0.50 47.51 |
| ATOM | 4716 | C2' | ADE | 1013 | 82.645 | 74.266 | 102.609 | 0.50 43.44 |
| ATOM | 4717 | C5' | ADE | 1013 | 84.646 | 75.676 | 100.211 | 0.50 41.15 |
| ATOM | 4718 | C4' | ADE | 1013 | 83.357 | 75.858 | 100.976 | 0.50 44.22 |
| ATOM | 4719 | O4' | ADE | 1013 | 82.296 | 75.023 | 100.441 | 0.50 45.89 |
| ATOM | 4720 | C1' | ADE | 1013 | 81.590 | 74.462 | 101.537 | 0.50 46.13 |
| ATOM | 4721 | C3' | ADE | 1013 | 83.411 | 75.575 | 102.483 | 0.50 42.87 |
| ATOM | 4722 | O3' | ADE | 1013 | 82.738 | 76.651 | 103.162 | 0.50 41.75 |
| ATOM | 4723 | P | ADE | 1014 | 82.313 | 76.513 | 104.711 | 0.50 41.45 |
| ATOM | 4724 | O1P | ADE | 1014 | 82.284 | 77.904 | 105.274 | 0.50 41.14 |
| ATOM | 4725 | O2P | ADE | 1014 | 83.130 | 75.459 | 105.377 | 0.50 40.47 |
| ATOM | 4726 | O5' | ADE | 1014 | 80.803 | 76.016 | 104.641 | 0.50 39.07 |
| ATOM | 4727 | N9 | ADE | 1014 | 78.165 | 73.019 | 104.256 | 0.50 33.14 |
| ATOM | 4728 | C4 | ADE | 1014 | 77.417 | 72.001 | 103.690 | 0.50 30.65 |
| ATOM | 4729 | N3 | ADE | 1014 | 76.078 | 71.935 | 103.546 | 0.50 29.37 |
| ATOM | 4730 | C2 | ADE | 1014 | 75.713 | 70.764 | 103.003 | 0.50 25.20 |
| ATOM | 4731 | N1 | ADE | 1014 | 76.469 | 69.735 | 102.620 | 0.50 20.57 |
| ATOM | 4732 | C6 | ADE | 1014 | 77.806 | 69.837 | 102.754 | 0.50 25.27 |
| ATOM | 4733 | N6 | ADE | 1014 | 78.560 | 68.818 | 102.345 | 0.50 22.46 |
| ATOM | 4734 | C5 | ADE | 1014 | 78.327 | 71.028 | 103.317 | 0.50 29.02 |
| ATOM | 4735 | N7 | ADE | 1014 | 79.624 | 71.445 | 103.581 | 0.50 30.26 |
| ATOM | 4736 | C8 | ADE | 1014 | 79.476 | 72.628 | 104.124 | 0.50 30.26 |
| ATOM | 4737 | C2' | ADE | 1014 | 78.361 | 74.537 | 106.254 | 0.50 36.29 |
| ATOM | 4738 | C5' | ADE | 1014 | 79.770 | 76.924 | 104.273 | 0.50 39.90 |
| ATOM | 4739 | C4' | ADE | 1014 | 78.441 | 76.480 | 104.839 | 0.50 38.75 |
| ATOM | 4740 | O4' | ADE | 1014 | 77.947 | 75.349 | 104.073 | 0.50 37.78 |
| ATOM | 4741 | C1' | ADE | 1014 | 77.673 | 74.241 | 104.917 | 0.50 35.72 |
| ATOM | 4742 | C3' | ADE | 1014 | 78.458 | 76.055 | 106.309 | 0.50 38.29 |
| ATOM | 4743 | O3' | ADE | 1014 | 77.448 | 76.773 | 107.065 | 0.50 41.23 |
| ATOM | 4744 | P | ADE | 1015 | 76.227 | 75.999 | 107.792 | 0.50 47.54 |
| ATOM | 4745 | O1P | ADE | 1015 | 75.369 | 77.041 | 108.420 | 0.50 49.15 |
| ATOM | 4746 | O2P | ADE | 1015 | 76.715 | 74.871 | 108.635 | 0.50 44.42 |
| ATOM | 4747 | O5' | ADE | 1015 | 75.402 | 75.404 | 106.568 | 0.50 43.50 |
| ATOM | 4748 | N9 | ADE | 1015 | 74.430 | 72.232 | 106.332 | 0.50 29.38 |
| ATOM | 4749 | C4 | ADE | 1015 | 74.495 | 70.920 | 105.924 | 0.50 26.33 |
| ATOM | 4750 | N3 | ADE | 1015 | 73.499 | 70.161 | 105.436 | 0.50 24.92 |
| ATOM | 4751 | C2 | ADE | 1015 | 73.948 | 68.950 | 105.135 | 0.50 24.57 |
| ATOM | 4752 | N1 | ADE | 1015 | 75.184 | 68.450 | 105.252 | 0.50 23.21 |
| ATOM | 4753 | C6 | ADE | 1015 | 76.156 | 69.239 | 105.745 | 0.50 21.04 |
| ATOM | 4754 | N6 | ADE | 1015 | 77.382 | 68.748 | 105.861 | 0.50 19.14 |
| ATOM | 4755 | C5 | ADE | 1015 | 75.815 | 70.535 | 106.107 | 0.50 23.40 |
| ATOM | 4756 | N7 | ADE | 1015 | 76.562 | 71.574 | 106.633 | 0.50 24.86 |
| ATOM | 4757 | C8 | ADE | 1015 | 75.698 | 72.554 | 106.750 | 0.50 27.26 |
| ATOM | 4758 | C2' | ADE | 1015 | 73.015 | 73.833 | 107.634 | 0.50 34.89 |
| ATOM | 4759 | C5' | ADE | 1015 | 74.424 | 76.189 | 105.896 | 0.50 37.81 |
| ATOM | 4760 | C4' | ADE | 1015 | 73.125 | 75.427 | 105.846 | 0.50 35.59 |
| ATOM | 4761 | O4' | ADE | 1015 | 73.479 | 74.116 | 105.336 | 0.50 35.39 |
| ATOM | 4762 | C1' | ADE | 1015 | 73.255 | 73.108 | 106.317 | 0.50 33.49 |
| ATOM | 4763 | C3' | ADE | 1015 | 72.475 | 75.192 | 107.214 | 0.50 33.39 |
| ATOM | 4764 | O3' | ADE | 1015 | 71.040 | 75.211 | 107.121 | 0.50 31.52 |
| ATOM | 4765 | P | THY | 1016 | 70.129 | 74.646 | 108.338 | 0.50 35.83 |
| ATOM | 4766 | O1P | THY | 1016 | 69.297 | 75.748 | 108.864 | 0.50 37.78 |
| ATOM | 4767 | O2P | THY | 1016 | 70.922 | 73.809 | 109.299 | 0.50 33.84 |
| ATOM | 4768 | O5' | THY | 1016 | 69.094 | 73.703 | 107.586 | 0.50 38.54 |
| ATOM | 4769 | N1 | THY | 1016 | 71.831 | 69.678 | 108.172 | 0.50 31.91 |
| ATOM | 4770 | C6 | THY | 1016 | 72.460 | 70.758 | 108.759 | 0.50 31.57 |
| ATOM | 4771 | C2 | THY | 1016 | 72.516 | 68.477 | 107.965 | 0.50 31.73 |
| ATOM | 4772 | O2 | THY | 1016 | 72.022 | 67.471 | 107.457 | 0.50 26.44 |
| ATOM | 4773 | N3 | THY | 1016 | 73.825 | 68.498 | 108.393 | 0.50 30.72 |
| ATOM | 4774 | C4 | THY | 1016 | 74.497 | 69.541 | 109.002 | 0.50 29.02 |
| ATOM | 4775 | O4 | THY | 1016 | 75.664 | 69.394 | 109.343 | 0.50 25.01 |
| ATOM | 4776 | C5 | THY | 1016 | 73.729 | 70.748 | 109.187 | 0.50 31.34 |
| ATOM | 4777 | C5A | THY | 1016 | 74.371 | 71.929 | 109.852 | 0.50 34.64 |
| ATOM | 4778 | C2' | THY | 1016 | 69.503 | 70.436 | 108.816 | 0.50 37.60 |
| ATOM | 4779 | C5' | THY | 1016 | 69.500 | 72.933 | 106.458 | 0.50 38.49 |

184

| ATOM | 4780 | C4' | THY | 1016 | 69.144 | 71.484 | 106.670 | 0.50 | 38.84 |
| ATOM | 4781 | O4' | THY | 1016 | 70.352 | 70.681 | 106.644 | 0.50 | 39.12 |
| ATOM | 4782 | C1' | THY | 1016 | 70.404 | 69.805 | 107.764 | 0.50 | 35.97 |
| ATOM | 4783 | C3' | THY | 1016 | 68.463 | 71.206 | 108.008 | 0.50 | 40.47 |
| ATOM | 4784 | O3' | THY | 1016 | 67.262 | 70.470 | 107.800 | 0.50 | 43.96 |
| ATOM | 4785 | P   | GUA | 1017 | 66.369 | 70.017 | 109.059 | 0.50 | 46.98 |
| ATOM | 4786 | O1P | GUA | 1017 | 64.988 | 70.507 | 108.831 | 0.50 | 45.15 |
| ATOM | 4787 | O2P | GUA | 1017 | 67.061 | 70.369 | 110.339 | 0.50 | 45.96 |
| ATOM | 4788 | O5' | GUA | 1017 | 66.352 | 68.432 | 108.871 | 0.50 | 47.83 |
| ATOM | 4789 | N9  | GUA | 1017 | 68.752 | 66.315 | 109.993 | 0.50 | 41.78 |
| ATOM | 4790 | C4  | GUA | 1017 | 70.050 | 65.965 | 110.352 | 0.50 | 36.30 |
| ATOM | 4791 | N3  | GUA | 1017 | 70.629 | 64.765 | 110.181 | 0.50 | 29.76 |
| ATOM | 4792 | C2  | GUA | 1017 | 71.882 | 64.761 | 110.593 | 0.50 | 28.94 |
| ATOM | 4793 | N2  | GUA | 1017 | 72.613 | 63.653 | 110.493 | 0.50 | 27.14 |
| ATOM | 4794 | N1  | GUA | 1017 | 72.523 | 65.843 | 111.131 | 0.50 | 28.31 |
| ATOM | 4795 | C6  | GUA | 1017 | 71.958 | 67.094 | 111.316 | 0.50 | 33.06 |
| ATOM | 4796 | O6  | GUA | 1017 | 72.641 | 68.018 | 111.791 | 0.50 | 33.28 |
| ATOM | 4797 | C5  | GUA | 1017 | 70.604 | 67.116 | 110.888 | 0.50 | 35.53 |
| ATOM | 4798 | N7  | GUA | 1017 | 69.675 | 68.152 | 110.902 | 0.50 | 39.36 |
| ATOM | 4799 | C8  | GUA | 1017 | 68.595 | 67.633 | 110.374 | 0.50 | 40.54 |
| ATOM | 4800 | C2' | GUA | 1017 | 66.346 | 65.554 | 109.893 | 0.50 | 47.04 |
| ATOM | 4801 | C5' | GUA | 1017 | 66.226 | 67.851 | 107.559 | 0.50 | 47.96 |
| ATOM | 4802 | C4' | GUA | 1017 | 66.316 | 66.342 | 107.627 | 0.50 | 46.29 |
| ATOM | 4803 | O4' | GUA | 1017 | 67.665 | 65.961 | 107.966 | 0.50 | 42.51 |
| ATOM | 4804 | C1' | GUA | 1017 | 67.756 | 65.482 | 109.305 | 0.50 | 43.48 |
| ATOM | 4805 | C3' | GUA | 1017 | 65.420 | 65.723 | 108.693 | 0.50 | 49.54 |
| ATOM | 4806 | O3' | GUA | 1017 | 64.796 | 64.512 | 108.225 | 0.50 | 52.78 |
| ATOM | 4807 | P   | CYT | 1018 | 63.329 | 64.094 | 108.779 | 0.50 | 56.11 |
| ATOM | 4808 | O1P | CYT | 1018 | 62.758 | 65.243 | 109.533 | 0.50 | 55.03 |
| ATOM | 4809 | O2P | CYT | 1018 | 62.544 | 63.508 | 107.648 | 0.50 | 51.99 |
| ATOM | 4810 | O5' | CYT | 1018 | 63.662 | 62.963 | 109.859 | 0.50 | 53.54 |
| ATOM | 4811 | N1  | CYT | 1018 | 67.659 | 63.016 | 113.108 | 0.50 | 51.73 |
| ATOM | 4812 | C6  | CYT | 1018 | 67.263 | 64.265 | 112.729 | 0.50 | 49.20 |
| ATOM | 4813 | C2  | CYT | 1018 | 68.955 | 62.814 | 113.635 | 0.50 | 49.98 |
| ATOM | 4814 | O2  | CYT | 1018 | 69.314 | 61.669 | 113.960 | 0.50 | 50.61 |
| ATOM | 4815 | N3  | CYT | 1018 | 69.776 | 63.875 | 113.781 | 0.50 | 47.91 |
| ATOM | 4816 | C4  | CYT | 1018 | 69.357 | 65.092 | 113.436 | 0.50 | 48.14 |
| ATOM | 4817 | N4  | CYT | 1018 | 70.184 | 66.126 | 113.635 | 0.50 | 45.79 |
| ATOM | 4818 | C5  | CYT | 1018 | 68.066 | 65.316 | 112.878 | 0.50 | 49.18 |
| ATOM | 4819 | C2' | CYT | 1018 | 65.325 | 62.166 | 113.560 | 0.50 | 56.51 |
| ATOM | 4820 | C5' | CYT | 1018 | 64.942 | 62.930 | 110.487 | 0.50 | 54.23 |
| ATOM | 4821 | C4' | CYT | 1018 | 65.155 | 61.638 | 111.241 | 0.50 | 56.22 |
| ATOM | 4822 | O4' | CYT | 1018 | 66.558 | 61.586 | 111.602 | 0.50 | 55.66 |
| ATOM | 4823 | C1' | CYT | 1018 | 66.726 | 61.871 | 112.992 | 0.50 | 55.11 |
| ATOM | 4824 | C3' | CYT | 1018 | 64.383 | 61.521 | 112.558 | 0.50 | 57.56 |
| ATOM | 4825 | O3' | CYT | 1018 | 64.214 | 60.160 | 112.992 | 0.50 | 58.68 |
| ATOM | 4829 | O5' | THY | 2001 | 78.992 | 65.071 | 124.302 | 0.50 | 70.88 |
| ATOM | 4830 | N1  | THY | 2001 | 75.130 | 64.253 | 120.843 | 0.50 | 65.07 |
| ATOM | 4831 | C6  | THY | 2001 | 74.318 | 65.308 | 121.216 | 0.50 | 64.02 |
| ATOM | 4832 | C2  | THY | 2001 | 74.598 | 62.988 | 120.625 | 0.50 | 63.89 |
| ATOM | 4833 | O2  | THY | 2001 | 75.265 | 62.007 | 120.318 | 0.50 | 62.43 |
| ATOM | 4834 | N3  | THY | 2001 | 73.232 | 62.916 | 120.779 | 0.50 | 62.41 |
| ATOM | 4835 | C4  | THY | 2001 | 72.368 | 63.942 | 121.124 | 0.50 | 60.72 |
| ATOM | 4836 | O4  | THY | 2001 | 71.164 | 63.727 | 121.202 | 0.50 | 56.98 |
| ATOM | 4837 | C5  | THY | 2001 | 72.994 | 65.221 | 121.361 | 0.50 | 62.09 |
| ATOM | 4838 | C5A | THY | 2001 | 72.145 | 66.388 | 121.757 | 0.50 | 61.47 |
| ATOM | 4839 | C2' | THY | 2001 | 76.932 | 65.911 | 120.214 | 0.50 | 69.01 |
| ATOM | 4840 | C5' | THY | 2001 | 78.394 | 65.899 | 123.296 | 0.50 | 70.72 |
| ATOM | 4841 | C4' | THY | 2001 | 78.413 | 65.187 | 121.963 | 0.50 | 70.41 |
| ATOM | 4842 | O4' | THY | 2001 | 77.264 | 64.295 | 121.880 | 0.50 | 68.60 |
| ATOM | 4843 | C1' | THY | 2001 | 76.590 | 64.489 | 120.643 | 0.50 | 67.42 |
| ATOM | 4844 | C3' | THY | 2001 | 78.348 | 66.101 | 120.731 | 0.50 | 69.80 |
| ATOM | 4845 | O3' | THY | 2001 | 79.331 | 65.695 | 119.765 | 0.50 | 69.69 |
| ATOM | 4846 | P   | GUA | 2002 | 79.234 | 66.203 | 118.231 | 0.50 | 69.76 |
| ATOM | 4847 | O1P | GUA | 2002 | 80.617 | 66.584 | 117.813 | 0.50 | 69.94 |
| ATOM | 4848 | O2P | GUA | 2002 | 78.128 | 67.112 | 118.079 | 0.50 | 68.57 |
| ATOM | 4849 | O5' | GUA | 2002 | 78.808 | 64.876 | 117.438 | 0.50 | 69.50 |
| ATOM | 4850 | N9  | GUA | 2002 | 76.137 | 63.410 | 115.339 | 0.50 | 49.76 |
| ATOM | 4851 | C4  | GUA | 2002 | 74.888 | 63.106 | 114.846 | 0.50 | 46.86 |
| ATOM | 4852 | N3  | GUA | 2002 | 74.542 | 61.982 | 114.180 | 0.50 | 44.31 |

185

| | | | | | | | | |
|---|---|---|---|---|---|---|---|---|
| ATOM | 4853 | C2 | GUA | 2002 | 73.262 | 61.996 | 113.822 | 0.50 43.46 |
| ATOM | 4854 | N2 | GUA | 2002 | 72.736 | 60.943 | 113.166 | 0.50 41.74 |
| ATOM | 4855 | N1 | GUA | 2002 | 72.406 | 63.038 | 114.083 | 0.50 40.69 |
| ATOM | 4856 | C6 | GUA | 2002 | 72.754 | 64.204 | 114.754 | 0.50 43.01 |
| ATOM | 4857 | O6 | GUA | 2002 | 71.927 | 65.093 | 114.914 | 0.50 42.77 |
| ATOM | 4858 | C5 | GUA | 2002 | 74.101 | 64.193 | 115.163 | 0.50 45.36 |
| ATOM | 4859 | N7 | GUA | 2002 | 74.827 | 65.143 | 115.873 | 0.50 47.12 |
| ATOM | 4860 | C8 | GUA | 2002 | 76.024 | 64.634 | 115.961 | 0.50 48.34 |
| ATOM | 4861 | C2' | GUA | 2002 | 78.462 | 63.471 | 114.581 | 0.50 55.48 |
| ATOM | 4862 | C5' | GUA | 2002 | 79.313 | 63.576 | 117.826 | 0.50 64.17 |
| ATOM | 4863 | C4' | GUA | 2002 | 79.185 | 62.576 | 116.694 | 0.50 58.67 |
| ATOM | 4864 | O4' | GUA | 2002 | 77.787 | 62.254 | 116.502 | 0.50 55.32 |
| ATOM | 4865 | C1' | GUA | 2002 | 77.355 | 62.624 | 115.196 | 0.50 53.60 |
| ATOM | 4866 | C3' | GUA | 2002 | 79.712 | 63.066 | 115.339 | 0.50 58.10 |
| ATOM | 4867 | O3' | GUA | 2002 | 80.443 | 62.060 | 114.619 | 0.50 57.80 |
| ATOM | 4868 | P | CYT | 2003 | 81.418 | 62.498 | 113.404 | 0.50 56.31 |
| ATOM | 4869 | O1P | CYT | 2003 | 82.734 | 61.835 | 113.631 | 0.50 53.04 |
| ATOM | 4870 | O2P | CYT | 2003 | 81.339 | 63.988 | 113.270 | 0.50 52.65 |
| ATOM | 4871 | O5' | CYT | 2003 | 80.770 | 61.816 | 112.114 | 0.50 54.98 |
| ATOM | 4872 | N1 | CYT | 2003 | 77.020 | 62.976 | 111.096 | 0.50 46.76 |
| ATOM | 4873 | C6 | CYT | 2003 | 77.825 | 64.040 | 111.417 | 0.50 46.73 |
| ATOM | 4874 | C2 | CYT | 2003 | 75.621 | 63.122 | 111.100 | 0.50 44.53 |
| ATOM | 4875 | O2 | CYT | 2003 | 74.916 | 62.155 | 110.784 | 0.50 40.99 |
| ATOM | 4876 | N3 | CYT | 2003 | 75.079 | 64.314 | 111.441 | 0.50 44.93 |
| ATOM | 4877 | C4 | CYT | 2003 | 75.871 | 65.344 | 111.753 | 0.50 46.36 |
| ATOM | 4878 | N4 | CYT | 2003 | 75.284 | 66.504 | 112.070 | 0.50 46.05 |
| ATOM | 4879 | C5 | CYT | 2003 | 77.298 | 65.232 | 111.748 | 0.50 45.48 |
| ATOM | 4880 | C2' | CYT | 2003 | 78.638 | 61.567 | 109.665 | 0.50 50.23 |
| ATOM | 4881 | C5' | CYT | 2003 | 80.513 | 60.412 | 112.105 | 0.50 54.27 |
| ATOM | 4882 | C4' | CYT | 2003 | 79.176 | 60.16 | 111.465 | 0.50 52.42 |
| ATOM | 4883 | O4' | CYT | 2003 | 78.183 | 61.084 | 111.901 | 0.50 50.72 |
| ATOM | 4884 | C1' | CYT | 2003 | 77.579 | 61.652 | 110.750 | 0.50 48.45 |
| ATOM | 4885 | C3' | CYT | 2003 | 79.158 | 60.163 | 109.934 | 0.50 52.04 |
| ATOM | 4886 | O3' | CYT | 2003 | 78.163 | 59.225 | 109.468 | 0.50 51.54 |
| ATOM | 4887 | P | ADE | 2004 | 78.591 | 57.826 | 108.790 | 0.50 49.78 |
| ATOM | 4888 | O1P | ADE | 2004 | 78.655 | 56.780 | 109.852 | 0.50 46.28 |
| ATOM | 4889 | O2P | ADE | 2004 | 79.751 | 58.024 | 107.880 | 0.50 50.06 |
| ATOM | 4890 | O5' | ADE | 2004 | 77.322 | 57.502 | 107.892 | 0.50 44.06 |
| ATOM | 4891 | N9 | ADE | 2004 | 75.192 | 61.572 | 106.895 | 0.50 25.95 |
| ATOM | 4892 | C4 | ADE | 2004 | 74.292 | 62.578 | 107.161 | 0.50 25.78 |
| ATOM | 4893 | N3 | ADE | 2004 | 72.951 | 62.476 | 107.237 | 0.50 24.43 |
| ATOM | 4894 | C2 | ADE | 2004 | 72.405 | 63.663 | 107.488 | 0.50 22.88 |
| ATOM | 4895 | N1 | ADE | 2004 | 73.002 | 64.848 | 107.664 | 0.50 24.46 |
| ATOM | 4896 | C6 | ADE | 2004 | 74.350 | 64.909 | 107.602 | 0.50 24.61 |
| ATOM | 4897 | N6 | ADE | 2004 | 74.949 | 66.086 | 107.806 | 0.50 26.84 |
| ATOM | 4898 | C5 | ADE | 2004 | 75.047 | 63.725 | 107.331 | 0.50 24.16 |
| ATOM | 4899 | N7 | ADE | 2004 | 76.401 | 63.451 | 107.185 | 0.50 22.36 |
| ATOM | 4900 | C8 | ADE | 2004 | 76.434 | 62.163 | 106.930 | 0.50 24.02 |
| ATOM | 4901 | C2' | ADE | 2004 | 75.698 | 59.367 | 105.715 | 0.50 27.44 |
| ATOM | 4902 | C5' | ADE | 2004 | 76.032 | 57.406 | 108.478 | 0.50 36.06 |
| ATOM | 4903 | C4' | ADE | 2004 | 75.001 | 58.061 | 107.588 | 0.50 30.60 |
| ATOM | 4904 | O4' | ADE | 2004 | 74.830 | 59.472 | 107.876 | 0.50 30.69 |
| ATOM | 4905 | C1' | ADE | 2004 | 74.816 | 60.180 | 106.642 | 0.50 27.21 |
| ATOM | 4906 | C3' | ADE | 2004 | 75.251 | 57.962 | 106.081 | 0.50 25.84 |
| ATOM | 4907 | O3' | ADE | 2004 | 74.001 | 57.693 | 105.445 | 0.50 21.10 |
| ATOM | 4908 | P | THY | 2005 | 73.962 | 57.302 | 103.897 | 0.50 18.99 |
| ATOM | 4909 | O1P | THY | 2005 | 73.101 | 56.096 | 103.798 | 0.50 16.18 |
| ATOM | 4910 | O2P | THY | 2005 | 75.377 | 57.265 | 103.403 | 0.50 12.81 |
| ATOM | 4911 | O5' | THY | 2005 | 73.141 | 58.469 | 103.205 | 0.50 12.34 |
| ATOM | 4912 | N1 | THY | 2005 | 73.095 | 63.590 | 103.666 | 0.50 15.75 |
| ATOM | 4913 | C6 | THY | 2005 | 74.377 | 63.098 | 103.625 | 0.50 12.55 |
| ATOM | 4914 | C2 | THY | 2005 | 72.826 | 64.862 | 104.138 | 0.50 16.85 |
| ATOM | 4915 | O2 | THY | 2005 | 71.694 | 65.328 | 104.231 | 0.50 15.91 |
| ATOM | 4916 | N3 | THY | 2005 | 73.940 | 65.572 | 104.503 | 0.50 16.75 |
| ATOM | 4917 | C4 | THY | 2005 | 75.251 | 65.150 | 104.460 | 0.50 15.89 |
| ATOM | 4918 | O4 | THY | 2005 | 76.149 | 65.909 | 104.822 | 0.50 18.38 |
| ATOM | 4919 | C5 | THY | 2005 | 75.448 | 63.797 | 103.978 | 0.50 15.51 |
| ATOM | 4920 | C5A | THY | 2005 | 76.833 | 63.243 | 103.883 | 0.50 15.66 |
| ATOM | 4921 | C2' | THY | 2005 | 72.293 | 62.127 | 101.819 | 0.50 15.12 |
| ATOM | 4922 | C5' | THY | 2005 | 73.109 | 59.748 | 103.764 | 0.50 11.28 |

186

```
ATOM   4923  C4'  THY  2005    71.813  60.428 103.411  0.50 12.80
ATOM   4924  O4'  THY  2005    71.840  61.695 104.089  0.50 15.45
ATOM   4925  C1'  THY  2005    71.995  62.757 103.174  0.50 14.12
ATOM   4926  C3'  THY  2005    71.647  60.760 101.931  0.50 15.45
ATOM   4927  O3'  THY  2005    70.261  60.809 101.569  0.50 12.17
ATOM   4928  P    THY  2006    69.808  61.625 100.256  0.50 15.18
ATOM   4929  O1P  THY  2006    68.352  61.407 100.020  0.50 14.72
ATOM   4930  O2P  THY  2006    70.774  61.311  99.186  0.50 15.80
ATOM   4931  O5'  THY  2006    70.004  63.168 100.646  0.50 18.34
ATOM   4932  N1   THY  2006    72.366  66.919 101.135  0.50 19.82
ATOM   4933  C6   THY  2006    73.083  65.765 100.902  0.50 19.53
ATOM   4934  C2   THY  2006    73.018  68.129 101.370  0.50 21.47
ATOM   4935  O2   THY  2006    72.446  69.201 101.560  0.50 22.44
ATOM   4936  N3   THY  2006    74.386  68.041 101.357  0.50 22.45
ATOM   4937  C4   THY  2006    75.154  66.919 101.119  0.50 22.21
ATOM   4938  O4   THY  2006    76.376  67.015 101.102  0.50 25.32
ATOM   4939  C5   THY  2006    74.415  65.704 100.885  0.50 19.21
ATOM   4940  C5A  THY  2006    75.158  64.433 100.637  0.50 19.56
ATOM   4941  C2'  THY  2006    70.235  66.554  99.802  0.50 14.92
ATOM   4942  C5'  THY  2006    69.161  63.780 101.628  0.50 15.27
ATOM   4943  C4'  THY  2006    69.202  65.293 101.546  0.50 12.89
ATOM   4944  O4'  THY  2006    70.482  65.808 101.979  0.50 13.42
ATOM   4945  C1'  THY  2006    70.877  66.868 101.138  0.50 14.24
ATOM   4946  C3'  THY  2006    68.893  65.969 100.213  0.50 14.33
ATOM   4947  O3'  THY  2006    67.915  67.007 100.414  0.50 14.21
ATOM   4948  P    THY  2007    67.415  67.919  99.169  0.50 15.33
ATOM   4949  O1P  THY  2007    65.994  68.289  99.409  0.50  7.33
ATOM   4950  O2P  THY  2007    67.787  67.276  97.885  0.50 12.49
ATOM   4951  O5'  THY  2007    68.277  69.251  99.338  0.50 10.90
ATOM   4952  N1   THY  2007    72.253  71.120  99.185  0.50 15.00
ATOM   4953  C6   THY  2007    72.128  69.910  98.533  0.50 16.10
ATOM   4954  C2   THY  2007    73.494  71.608  99.544  0.50 17.01
ATOM   4955  O2   THY  2007    73.666  72.721 100.031  0.50 20.01
ATOM   4956  N3   THY  2007    74.538  70.743  99.301  0.50 13.22
ATOM   4957  C4   THY  2007    74.467  69.485  98.727  0.50 14.48
ATOM   4958  O4   THY  2007    75.484  68.781  98.642  0.50 16.04
ATOM   4959  C5   THY  2007    73.151  69.085  98.289  0.50 13.63
ATOM   4960  C5A  THY  2007    72.983  67.777  97.589  0.50 10.21
ATOM   4961  C2'  THY  2007    70.038  72.189  98.483  0.50 13.37
ATOM   4962  C5'  THY  2007    68.156  70.021 100.525  0.50 14.36
ATOM   4963  C4'  THY  2007    68.932  71.315 100.434  0.50 15.86
ATOM   4964  O4'  THY  2007    70.358  71.086 100.523  0.50 16.54
ATOM   4965  C1'  THY  2007    71.050  71.883  99.573  0.50 13.50
ATOM   4966  C3'  THY  2007    68.706  72.239  99.234  0.50 15.60
ATOM   4967  O3'  THY  2007    68.378  73.548  99.743  0.50 19.42
ATOM   4968  P    ADE  2008    68.197  74.795  98.748  0.50 21.97
ATOM   4969  O1P  ADE  2008    66.888  75.403  99.071  0.50 20.06
ATOM   4970  O2P  ADE  2008    68.485  74.372  97.351  0.50 20.66
ATOM   4971  O5'  ADE  2008    69.378  75.759  99.218  0.50 19.71
ATOM   4972  N9   ADE  2008    73.778  74.467  97.470  0.50 24.36
ATOM   4973  C4   ADE  2008    74.994  73.881  97.221  0.50 23.56
ATOM   4974  N3   ADE  2008    76.212  74.400  97.468  0.50 22.45
ATOM   4975  C2   ADE  2008    77.160  73.544  97.118  0.50 23.57
ATOM   4976  N1   ADE  2008    77.038  72.318  96.591  0.50 24.92
ATOM   4977  C6   ADE  2008    75.801  71.832  96.352  0.50 23.56
ATOM   4978  N6   ADE  2008    75.686  70.617  95.828  0.50 28.08
ATOM   4979  C5   ADE  2008    74.711  72.640  96.673  0.50 22.52
ATOM   4980  N7   ADE  2008    73.343  72.457  96.540  0.50 21.35
ATOM   4981  C8   ADE  2008    72.832  73.564  97.023  0.50 23.56
ATOM   4982  C2'  ADE  2008    72.644  76.717  97.353  0.50 25.74
ATOM   4983  C5'  ADE  2008    70.684  75.210  99.356  0.50 23.22
ATOM   4984  C4'  ADE  2008    71.745  76.272  99.521  0.50 23.62
ATOM   4985  O4'  ADE  2008    72.996  75.552  99.397  0.50 24.98
ATOM   4986  C1'  ADE  2008    73.581  75.778  98.110  0.50 25.59
ATOM   4987  C3'  ADE  2008    71.811  77.360  98.450  0.50 24.47
ATOM   4988  O3'  ADE  2008    72.458  76.535  98.995  0.50 25.76
ATOM   4989  P    CYT  2009    72.672  79.846  98.078  0.50 21.31
ATOM   4990  O1P  CYT  2009    72.815  81.063  98.920  0.50 14.77
ATOM   4991  O2P  CYT  2009    71.652  79.799  97.008  0.50 19.19
ATOM   4992  O5'  CYT  2009    74.079  79.629  97.409  0.50 18.16
```

| ATOM | 4993 | N1 | CYT | 2009 | 75.690 | 76.380 | 94.255 | 0.50 | 23.57 |
|------|------|------|------|------|--------|--------|--------|------|-------|
| ATOM | 4994 | C6 | CYT | 2009 | 74.387 | 75.994 | 94.376 | 0.50 | 19.83 |
| ATOM | 4995 | C2 | CYT | 2009 | 76.670 | 75.450 | 93.919 | 0.50 | 24.55 |
| ATOM | 4996 | O2 | CYT | 2009 | 77.853 | 75.827 | 93.864 | 0.50 | 27.75 |
| ATOM | 4997 | N3 | CYT | 2009 | 76.318 | 74.173 | 93.663 | 0.50 | 22.22 |
| ATOM | 4998 | C4 | CYT | 2009 | 75.040 | 73.811 | 93.743 | 0.50 | 22.88 |
| ATOM | 4999 | N4 | CYT | 2009 | 74.740 | 72.552 | 93.455 | 0.50 | 20.62 |
| ATOM | 5000 | C5 | CYT | 2009 | 74.019 | 74.750 | 94.121 | 0.50 | 21.85 |
| ATOM | 5001 | C2' | CYT | 2009 | 75.562 | 78.779 | 93.432 | 0.50 | 29.15 |
| ATOM | 5002 | C5' | CYT | 2009 | 74.311 | 80.171 | 96.146 | 0.50 | 23.44 |
| ATOM | 5003 | C4' | CYT | 2009 | 75.634 | 79.696 | 95.626 | 0.50 | 24.48 |
| ATOM | 5004 | O4' | CYT | 2009 | 75.689 | 78.252 | 95.689 | 0.50 | 27.98 |
| ATOM | 5005 | C1' | CYT | 2009 | 76.112 | 77.782 | 94.430 | 0.50 | 27.59 |
| ATOM | 5006 | C3' | CYT | 2009 | 75.827 | 80.078 | 94.163 | 0.50 | 27.57 |
| ATOM | 5007 | O3' | CYT | 2009 | 77.168 | 80.471 | 93.958 | 0.50 | 30.00 |
| ATOM | 5008 | P | GUA | 2010 | 77.784 | 81.635 | 94.850 | 0.50 | 29.98 |
| ATOM | 5009 | O1P | GUA | 2010 | 77.965 | 81.021 | 96.183 | 0.50 | 31.28 |
| ATOM | 5010 | O2P | GUA | 2010 | 76.934 | 82.847 | 94.715 | 0.50 | 35.33 |
| ATOM | 5011 | O5' | GUA | 2010 | 79.212 | 81.885 | 94.213 | 0.50 | 23.91 |
| ATOM | 5012 | N9 | GUA | 2010 | 79.747 | 78.884 | 91.747 | 0.50 | 26.03 |
| ATOM | 5013 | C4 | GUA | 2010 | 79.747 | 77.559 | 91.459 | 0.50 | 28.14 |
| ATOM | 5014 | N3 | GUA | 2010 | 80.820 | 76.755 | 91.498 | 0.50 | 31.65 |
| ATOM | 5015 | C2 | GUA | 2010 | 80.504 | 75.513 | 91.218 | 0.50 | 30.69 |
| ATOM | 5016 | N2 | GUA | 2010 | 81.455 | 74.594 | 91.192 | 0.50 | 36.88 |
| ATOM | 5017 | N1 | GUA | 2010 | 79.234 | 75.082 | 90.938 | 0.50 | 30.67 |
| ATOM | 5018 | C6 | GUA | 2010 | 78.104 | 75.900 | 90.902 | 0.50 | 30.93 |
| ATOM | 5019 | O6 | GUA | 2010 | 76.989 | 75.415 | 90.658 | 0.50 | 31.01 |
| ATOM | 5020 | C5 | GUA | 2010 | 78.435 | 77.259 | 91.180 | 0.50 | 27.21 |
| ATOM | 5021 | N7 | GUA | 2010 | 77.634 | 78.360 | 91.240 | 0.50 | 26.81 |
| ATOM | 5022 | C8 | GUA | 2010 | 78.456 | 79.319 | 91.561 | 0.50 | 28.72 |
| ATOM | 5023 | C2' | GUA | 2010 | 81.011 | 81.082 | 91.815 | 0.50 | 21.16 |
| ATOM | 5024 | C5' | GUA | 2010 | 80.363 | 81.626 | 94.980 | 0.50 | 23.25 |
| ATOM | 5025 | C4' | GUA | 2010 | 81.384 | 80.892 | 94.152 | 0.50 | 20.47 |
| ATOM | 5026 | O4' | GUA | 2010 | 80.787 | 79.684 | 93.650 | 0.50 | 20.83 |
| ATOM | 5027 | C1' | GUA | 2010 | 80.898 | 79.639 | 92.238 | 0.50 | 21.23 |
| ATOM | 5028 | C3' | GUA | 2010 | 81.871 | 81.648 | 92.928 | 0.50 | 18.64 |
| ATOM | 5029 | O3' | GUA | 2010 | 83.243 | 81.331 | 92.731 | 0.50 | 18.10 |
| ATOM | 5030 | P | GUA | 2011 | 83.748 | 81.661 | 92.462 | 0.50 | 18.19 |
| ATOM | 5031 | O1P | GUA | 2011 | 85.118 | 81.765 | 93.023 | 0.50 | 13.65 |
| ATOM | 5032 | O2P | GUA | 2011 | 82.903 | 82.855 | 92.290 | 0.50 | 12.18 |
| ATOM | 5033 | O5' | GUA | 2011 | 83.829 | 80.862 | 91.097 | 0.50 | 19.34 |
| ATOM | 5034 | N9 | GUA | 2011 | 81.030 | 78.418 | 88.431 | 0.50 | 19.44 |
| ATOM | 5035 | C4 | GUA | 2011 | 80.375 | 77.280 | 88.032 | 0.50 | 18.19 |
| ATOM | 5036 | N3 | GUA | 2011 | 80.963 | 76.141 | 87.612 | 0.50 | 17.70 |
| ATOM | 5037 | C2 | GUA | 2011 | 80.074 | 75.202 | 87.333 | 0.50 | 18.43 |
| ATOM | 5038 | N2 | GUA | 2011 | 80.483 | 73.999 | 86.918 | 0.50 | 22.83 |
| ATOM | 5039 | N1 | GUA | 2011 | 78.714 | 75.365 | 87.445 | 0.50 | 17.57 |
| ATOM | 5040 | C6 | GUA | 2011 | 78.084 | 76.529 | 87.867 | 0.50 | 15.86 |
| ATOM | 5041 | O6 | GUA | 2011 | 76.845 | 76.567 | 87.926 | 0.50 | 11.92 |
| ATOM | 5042 | C5 | GUA | 2011 | 79.037 | 77.553 | 88.182 | 0.50 | 15.30 |
| ATOM | 5043 | N7 | GUA | 2011 | 78.854 | 78.844 | 88.646 | 0.50 | 17.48 |
| ATOM | 5044 | C8 | GUA | 2011 | 80.064 | 79.319 | 88.775 | 0.50 | 17.52 |
| ATOM | 5045 | C2' | GUA | 2011 | 83.163 | 78.777 | 87.901 | 0.50 | 23.39 |
| ATOM | 5046 | C5' | GUA | 2011 | 84.683 | 79.736 | 90.995 | 0.50 | 22.86 |
| ATOM | 5047 | C4' | GUA | 2011 | 84.321 | 78.891 | 89.798 | 0.50 | 23.43 |
| ATOM | 5048 | O4' | GUA | 2011 | 82.914 | 78.544 | 89.826 | 0.50 | 25.54 |
| ATOM | 5049 | C1' | GUA | 2011 | 82.481 | 78.566 | 88.480 | 0.50 | 22.54 |
| ATOM | 5050 | C3' | GUA | 2011 | 84.569 | 79.500 | 88.413 | 0.50 | 24.06 |
| ATOM | 5051 | O3' | GUA | 2011 | 85.112 | 78.468 | 87.592 | 0.50 | 21.91 |
| ATOM | 5052 | P | GUA | 2012 | 86.600 | 78.589 | 87.029 | 0.50 | 23.02 |
| ATOM | 5053 | O1P | GUA | 2012 | 87.453 | 77.726 | 87.871 | 0.50 | 24.02 |
| ATOM | 5054 | O2P | GUA | 2012 | 86.942 | 80.016 | 86.889 | 0.50 | 29.60 |
| ATOM | 5055 | O5' | GUA | 2012 | 86.474 | 77.958 | 85.566 | 0.50 | 28.44 |
| ATOM | 5056 | N9 | GUA | 2012 | 82.683 | 76.899 | 84.086 | 0.50 | 34.12 |
| ATOM | 5057 | C4 | GUA | 2012 | 81.410 | 76.364 | 84.049 | 0.50 | 33.83 |
| ATOM | 5058 | N3 | GUA | 2012 | 81.067 | 75.150 | 83.566 | 0.50 | 34.09 |
| ATOM | 5059 | C2 | GUA | 2012 | 79.764 | 74.933 | 83.661 | 0.50 | 31.66 |
| ATOM | 5060 | N2 | GUA | 2012 | 79.250 | 73.750 | 83.279 | 0.50 | 33.03 |
| ATOM | 5061 | N1 | GUA | 2012 | 78.873 | 75.851 | 84.148 | 0.50 | 29.39 |
| ATOM | 5062 | C6 | GUA | 2012 | 79.200 | 77.111 | 84.629 | 0.50 | 29.47 |

188

| ATOM | 5063 | O6 | GUA | 2012 | 78.310 | 77.875 | 85.011 | 0.50 | 28.19 |
| ATOM | 5064 | C5 | GUA | 2012 | 80.590 | 77.339 | 84.584 | 0.50 | 31.65 |
| ATOM | 5065 | N7 | GUA | 2012 | 81.333 | 78.442 | 84.991 | 0.50 | 34.31 |
| ATOM | 5066 | C8 | GUA | 2012 | 82.567 | 78.133 | 84.687 | 0.50 | 35.53 |
| ATOM | 5067 | C2' | GUA | 2012 | 84.736 | 77.258 | 82.733 | 0.50 | 32.71 |
| ATOM | 5068 | C5' | GUA | 2012 | 86.934 | 76.627 | 85.292 | 0.50 | 29.83 |
| ATOM | 5069 | C4' | GUA | 2012 | 86.108 | 75.967 | 84.206 | 0.50 | 30.41 |
| ATOM | 5070 | O4' | GUA | 2012 | 84.719 | 75.900 | 84.621 | 0.50 | 26.94 |
| ATOM | 5071 | C1' | GUA | 2012 | 83.895 | 76.298 | 83.545 | 0.50 | 31.49 |
| ATOM | 5072 | C3' | GUA | 2012 | 86.112 | 76.626 | 82.820 | 0.50 | 32.30 |
| ATOM | 5073 | O3' | GUA | 2012 | 86.249 | 75.640 | 81.776 | 0.50 | 35.49 |
| ATOM | 5074 | P | ADE | 2013 | 86.253 | 76.101 | 80.223 | 0.50 | 40.72 |
| ATOM | 5075 | O1P | ADE | 2013 | 87.431 | 75.487 | 79.548 | 0.50 | 40.69 |
| ATOM | 5076 | O2P | ADE | 2013 | 86.051 | 77.571 | 80.142 | 0.50 | 39.73 |
| ATOM | 5077 | O5' | ADE | 2013 | 84.948 | 75.431 | 79.610 | 0.50 | 36.77 |
| ATOM | 5078 | N9 | ADE | 2013 | 81.108 | 76.578 | 80.314 | 0.50 | 43.71 |
| ATOM | 5079 | C4 | ADE | 2013 | 79.827 | 76.953 | 80.660 | 0.50 | 43.56 |
| ATOM | 5080 | N3 | ADE | 2013 | 78.688 | 76.274 | 80.437 | 0.50 | 41.50 |
| ATOM | 5081 | C2 | ADE | 2013 | 77.645 | 76.938 | 80.908 | 0.50 | 41.07 |
| ATOM | 5082 | N1 | ADE | 2013 | 77.602 | 78.126 | 81.520 | 0.50 | 41.72 |
| ATOM | 5083 | C6 | ADE | 2013 | 78.756 | 78.798 | 81.712 | 0.50 | 43.77 |
| ATOM | 5084 | N6 | ADE | 2013 | 78.706 | 80.004 | 82.284 | 0.50 | 45.49 |
| ATOM | 5085 | C5 | ADE | 2013 | 79.948 | 78.186 | 81.279 | 0.50 | 45.33 |
| ATOM | 5086 | N7 | ADE | 2013 | 81.282 | 78.581 | 81.339 | 0.50 | 46.34 |
| ATOM | 5087 | C8 | ADE | 2013 | 81.930 | 77.591 | 80.766 | 0.50 | 44.67 |
| ATOM | 5088 | C2' | ADE | 2013 | 82.197 | 75.596 | 78.274 | 0.50 | 41.75 |
| ATOM | 5089 | C5' | ADE | 2013 | 84.643 | 74.069 | 79.857 | 0.50 | 37.11 |
| ATOM | 5090 | C4' | ADE | 2013 | 83.210 | 73.802 | 79.481 | 0.50 | 37.96 |
| ATOM | 5091 | O4' | ADE | 2013 | 82.357 | 74.578 | 80.364 | 0.50 | 41.49 |
| ATOM | 5092 | C1' | ADE | 2013 | 81.466 | 75.357 | 79.578 | 0.50 | 42.43 |
| ATOM | 5093 | C3' | ADE | 2013 | 82.876 | 74.257 | 78.059 | 0.50 | 39.52 |
| ATOM | 5094 | O3' | ADE | 2013 | 81.962 | 73.356 | 77.422 | 0.50 | 40.21 |
| ATOM | 5095 | P | ADE | 2014 | 81.888 | 73.290 | 75.809 | 0.50 | 39.31 |
| ATOM | 5096 | O1P | ADE | 2014 | 83.127 | 72.618 | 75.345 | 0.50 | 38.44 |
| ATOM | 5097 | O2P | ADE | 2014 | 81.531 | 74.618 | 75.248 | 0.50 | 38.73 |
| ATOM | 5098 | O5' | ADE | 2014 | 80.639 | 72.339 | 75.536 | 0.50 | 37.41 |
| ATOM | 5099 | N9 | ADE | 2014 | 77.670 | 75.083 | 76.652 | 0.50 | 40.98 |
| ATOM | 5100 | C4 | ADE | 2014 | 76.858 | 76.047 | 77.212 | 0.50 | 39.13 |
| ATOM | 5101 | N3 | ADE | 2014 | 75.705 | 75.814 | 77.886 | 0.50 | 37.58 |
| ATOM | 5102 | C2 | ADE | 2014 | 75.181 | 77.040 | 78.248 | 0.50 | 35.42 |
| ATOM | 5103 | N1 | ADE | 2014 | 75.641 | 78.274 | 78.032 | 0.50 | 31.69 |
| ATOM | 5104 | C6 | ADE | 2014 | 76.798 | 78.420 | 77.358 | 0.50 | 34.75 |
| ATOM | 5105 | N6 | ADE | 2014 | 77.250 | 79.646 | 77.142 | 0.50 | 36.62 |
| ATOM | 5106 | C5 | ADE | 2014 | 77.456 | 77.263 | 76.919 | 0.50 | 37.51 |
| ATOM | 5107 | N7 | ADE | 2014 | 78.640 | 77.071 | 76.218 | 0.50 | 38.78 |
| ATOM | 5108 | C8 | ADE | 2014 | 78.730 | 75.768 | 76.097 | 0.50 | 39.05 |
| ATOM | 5109 | C2' | ADE | 2014 | 77.443 | 73.040 | 75.232 | 0.50 | 41.56 |
| ATOM | 5110 | C5' | ADE | 2014 | 80.160 | 71.455 | 76.542 | 0.50 | 40.64 |
| ATOM | 5111 | C4' | ADE | 2014 | 78.679 | 71.663 | 76.762 | 0.50 | 42.16 |
| ATOM | 5112 | O4' | ADE | 2014 | 78.435 | 72.971 | 77.348 | 0.50 | 42.98 |
| ATOM | 5113 | C1' | ADE | 2014 | 77.407 | 73.638 | 76.626 | 0.50 | 41.63 |
| ATOM | 5114 | C3' | ADE | 2014 | 77.825 | 71.594 | 75.492 | 0.50 | 41.81 |
| ATOM | 5115 | O3' | ADE | 2014 | 76.653 | 70.803 | 75.721 | 0.50 | 43.50 |
| ATOM | 5116 | P | ADE | 2015 | 75.649 | 70.486 | 74.501 | 0.50 | 41.89 |
| ATOM | 5117 | O1P | ADE | 2015 | 75.028 | 69.152 | 74.769 | 0.50 | 40.30 |
| ATOM | 5118 | O2P | ADE | 2015 | 76.376 | 70.725 | 73.220 | 0.50 | 41.58 |
| ATOM | 5119 | O5' | ADE | 2015 | 74.520 | 71.593 | 74.660 | 0.50 | 38.54 |
| ATOM | 5120 | N9 | ADE | 2015 | 73.996 | 75.962 | 74.411 | 0.50 | 34.89 |
| ATOM | 5121 | C4 | ADE | 2015 | 74.020 | 77.281 | 74.803 | 0.50 | 33.88 |
| ATOM | 5122 | N3 | ADE | 2015 | 73.134 | 77.913 | 75.591 | 0.50 | 32.72 |
| ATOM | 5123 | C2 | ADE | 2015 | 73.493 | 79.176 | 75.775 | 0.50 | 32.68 |
| ATOM | 5124 | N1 | ADE | 2015 | 74.559 | 79.832 | 75.305 | 0.50 | 32.48 |
| ATOM | 5125 | C6 | ADE | 2015 | 75.437 | 79.167 | 74.527 | 0.50 | 32.96 |
| ATOM | 5126 | N6 | ADE | 2015 | 76.518 | 79.814 | 74.086 | 0.50 | 34.42 |
| ATOM | 5127 | C5 | ADE | 2015 | 75.161 | 77.821 | 74.238 | 0.50 | 33.70 |
| ATOM | 5128 | N7 | ADE | 2015 | 75.827 | 76.874 | 73.472 | 0.50 | 33.13 |
| ATOM | 5129 | C8 | ADE | 2015 | 75.095 | 75.792 | 73.601 | 0.50 | 32.49 |
| ATOM | 5130 | C2' | ADE | 2015 | 72.432 | 74.036 | 73.786 | 0.50 | 36.42 |
| ATOM | 5131 | C5' | ADE | 2015 | 73.850 | 71.736 | 75.899 | 0.50 | 36.63 |
| ATOM | 5132 | C4' | ADE | 2015 | 72.875 | 72.883 | 75.841 | 0.50 | 37.18 |

189

```
ATOM   5133  O4'  ADE  2015   73.599  74.136  75.806  0.50 36.99
ATOM   5134  C1'  ADE  2015   72.997  74.979  74.838  0.50 36.59
ATOM   5135  C3'  ADE  2015   71.910  72.895  74.648  0.50 34.34
ATOM   5136  O3'  ADE  2015   70.594  73.195  75.125  0.50 33.79
ATOM   5137  P    CYT  2016   69.316  72.950  74.188  0.50 32.08
ATOM   5138  O1P  CYT  2016   68.415  72.045  74.926  0.50 32.70
ATOM   5139  O2P  CYT  2016   69.783  72.581  72.837  0.50 31.88
ATOM   5140  O5'  CYT  2016   68.640  74.391  74.088  0.50 37.15
ATOM   5141  N1   CYT  2016   70.979  79.217  72.974  0.50 38.24
ATOM   5142  C6   CYT  2016   71.518  78.346  72.065  0.50 36.59
ATOM   5143  C2   CYT  2016   71.660  80.421  73.300  0.50 37.18
ATOM   5144  O2   CYT  2016   71.123  81.246  74.056  0.50 34.75
ATOM   5145  N3   CYT  2016   72.885  80.645  72.768  0.50 37.89
ATOM   5146  C4   CYT  2016   73.422  79.754  71.919  0.50 39.42
ATOM   5147  N4   CYT  2016   74.651  79.993  71.454  0.50 38.59
ATOM   5148  C5   CYT  2016   72.725  78.571  71.521  0.50 37.27
ATOM   5149  C2'  CYT  2016   68.518  78.529  72.803  0.50 42.97
ATOM   5150  C5'  CYT  2016   69.434  75.519  73.731  0.50 40.92
ATOM   5151  C4'  CYT  2016   68.910  76.775  74.385  0.50 42.80
ATOM   5152  O4'  CYT  2016   69.987  77.735  74.471  0.50 44.99
ATOM   5153  C1'  CYT  2016   69.719  78.886  73.671  0.50 41.50
ATOM   5154  C3'  CYT  2016   67.786  77.481  73.637  0.50 44.95
ATOM   5155  O3'  CYT  2016   66.891  78.076  74.582  0.50 48.19
ATOM   5156  P    THY  2017   65.324  78.157  74.249  0.50 53.10
ATOM   5157  O1P  THY  2017   64.565  78.473  75.494  0.50 51.00
ATOM   5158  O2P  THY  2017   64.994  76.931  73.482  0.50 54.53
ATOM   5159  O5'  THY  2017   65.209  79.388  73.248  0.50 52.22
ATOM   5160  N1   THY  2017   68.087  80.536  69.803  0.50 53.29
ATOM   5161  C6   THY  2017   67.903  79.252  69.312  0.50 53.03
ATOM   5162  C2   THY  2017   69.354  81.127  69.797  0.50 53.82
ATOM   5163  O2   THY  2017   69.587  82.269  70.198  0.50 53.62
ATOM   5164  N3   THY  2017   70.351  80.322  69.291  0.50 53.36
ATOM   5165  C4   THY  2017   70.229  79.033  68.805  0.50 53.31
ATOM   5166  O4   THY  2017   71.228  78.435  68.417  0.50 53.95
ATOM   5167  C5   THY  2017   68.885  78.489  68.815  0.50 53.56
ATOM   5168  C5A  THY  2017   68.647  77.114  68.270  0.50 54.48
ATOM   5169  C2'  THY  2017   65.552  80.648  70.172  0.50 55.08
ATOM   5170  C5'  THY  2017   65.706  80.684  73.603  0.50 55.20
ATOM   5171  C4'  THY  2017   65.787  81.570  72.380  0.50 56.40
ATOM   5172  O4'  THY  2017   67.088  81.472  71.741  0.50 54.85
ATOM   5173  C1'  THY  2017   66.920  81.308  70.339  0.50 53.82
ATOM   5174  C3'  THY  2017   64.739  81.258  71.302  0.50 56.40
ATOM   5175  O3'  THY  2017   64.091  82.446  70.854  0.50 58.30
ATOM   5176  P    GUA  2018   62.596  82.367  70.270  0.50 61.87
ATOM   5177  O1P  GUA  2018   62.618  81.367  69.167  0.50 61.98
ATOM   5178  O2P  GUA  2018   61.638  82.200  71.393  0.50 59.16
ATOM   5179  O5'  GUA  2018   62.357  83.828  69.671  0.50 61.49
ATOM   5180  N9   GUA  2018   66.849  82.685  67.526  0.50 59.16
ATOM   5181  C4   GUA  2018   68.109  82.295  67.108  0.50 58.60
ATOM   5182  N3   GUA  2018   69.266  82.914  67.312  0.50 56.36
ATOM   5183  C2   GUA  2018   70.315  82.330  66.810  0.50 54.70
ATOM   5184  N2   GUA  2018   71.548  82.853  66.940  0.50 53.99
ATOM   5185  N1   GUA  2018   70.234  81.127  66.148  0.50 54.61
ATOM   5186  C6   GUA  2018   69.056  80.416  65.914  0.50 56.66
ATOM   5187  O6   GUA  2018   69.091  79.350  65.288  0.50 55.05
ATOM   5188  C5   GUA  2018   67.921  81.084  66.465  0.50 58.23
ATOM   5189  N7   GUA  2018   66.575  80.725  66.467  0.50 58.85
ATOM   5190  C8   GUA  2018   65.977  81.705  67.097  0.50 59.05
ATOM   5191  C2'  GUA  2018   66.103  85.076  67.454  0.50 61.28
ATOM   5192  C5'  GUA  2018   63.196  84.371  68.643  0.50 60.54
ATOM   5193  C4'  GUA  2018   64.544  84.747  69.214  0.50 61.16
ATOM   5194  O4'  GUA  2018   65.415  83.592  69.127  0.50 59.39
ATOM   5195  C1'  GUA  2018   66.524  83.885  68.288  0.50 59.36
ATOM   5196  C3'  GUA  2018   65.279  85.855  68.462  0.50 62.51
ATOM   5197  O3'  GUA  2018   66.206  86.474  69.387  0.50 63.58
END
```

What is claimed is:

1. A crystal comprising a portion of a Signal Transducer and Activator of Transcription (STAT) and a duplex DNA, wherein the duplex DNA consists of 24 base pairs or less and comprises the nucleotide sequences of SEQ ID NO:13, and SEQ ID NO:14; wherein the portion of the STAT consists of 582 amino acid residues or less comprising amino acid residues 136–710 of SEQ ID NO:2; wherein the crystal effectively diffracts X-rays for the determination of the atomic coordinates of the portion of the STAT and the duplex DNA to a resolution of greater than 5.0 Angstroms; and wherein said crystal has a space group of $C222_1$ with unit cell dimensions of a=76.6, b=148.2, and c=181.1 Å.

2. The crystal of claim 1 wherein the crystal effectively diffracts X-rays for the determination of the atomic coordinates of the portion of the STAT and the duplex DNA to a resolution of greater than 3.0 Angstroms.

3. The crystal of claim 1 wherein the portion of the STAT further comprises amino acid residues 132–135 of SEQ ID NO:2.

4. The crystal of claim 1 wherein the portion of the STAT further comprises amino acid residues 711–713 of SEQ ID NO:2.

5. The crystal of claim 4 wherein the portion of the STAT further comprises amino acid residues 132–135 of SEQ ID NO:2.

6. A method of making a crystal comprising a portion of a Signal Transducer and Activator of Transcription (STAT) and a duplex DNA, wherein the duplex DNA consists of 24 base pairs or less and comprises the nucleotide sequences of SEQ ID NO:13, and SEQ ID NO:14; wherein the portion of the STAT consists of 582 or less comprising amino acid residues 136–710 of SEQ ID NO:2; wherein the crystal effectively diffracts X-rays for the determination of the atomic coordinates of the portion of the STAT and the duplex DNA to a resolution of greater than 5.0 Angstroms; and wherein said crystal has a space group of $C222_1$ with unit cell dimensions of a=76.6, b=148.2, and c=181.1 Å;

said method comprising growing a crystal by vapor diffusion using a reservoir buffer that comprises 100 mM Na acetate, pH 5.0, 100 mM KCl, 20 mM $MgCl_2$, and 3% PEG400.

7. The method of claim 6 wherein said growing of the crystal by vapor diffusion is performed by placing an aliquot of the solution on a cover slip as a hanging drop above a well containing a reservoir buffer that comprises 100 mM Na acetate, pH 5.0, 100 mM KCl, 20 mM $MgCl_2$, and 3% PEG400; wherein said aliquot of said solution contains 1 part 0.10 mM protein:DNA complex and 1 part of the reservoir buffer.

8. A peptide fragment which consists of 160–190 amino acid residues comprising an amino acid sequence selected from the group consisting of SEQ ID NO:18, SEQ ID NO:24, SEQ ID NO:26, SEQ ID NO:28, SEQ ID NO:30, and SEQ ID NO:32.

9. The peptide fragment of claim 8 wherein the peptide fragment comprises the amino acid sequence of SEQ ID NO:18.

10. The peptide fragment of claim 8 that is part of a fusion peptide or protein, with the proviso that the fusion protein does not comprise a full-length naturally occurring STAT protein.

* * * * *